United States Patent
Jin et al.

(10) Patent No.: US 10,781,184 B2
(45) Date of Patent: Sep. 22, 2020

(54) SUBSTITUTED BENZAZINONES AS ANTIBACTERIAL COMPOUNDS

(71) Applicant: GlaxoSmithKline Intellectual Property Development Limited, Brentford, Middlesex (GB)

(72) Inventors: Qi Jin, Collegeville, PA (US); Denise Teotico Pohlhaus, Collegeville, PA (US); Jared T. Spletstoser, Collegeville, PA (US)

(73) Assignee: GlaxoSmithKline Intellectual Property Development Limited (GB)

( * ) Notice: Subject to any disclaimer, the term of this patent is extended or adjusted under 35 U.S.C. 154(b) by 0 days.

(21) Appl. No.: 16/060,641

(22) PCT Filed: Dec. 8, 2016

(86) PCT No.: PCT/IB2016/057451
§ 371 (c)(1),
(2) Date: Jun. 8, 2018

(87) PCT Pub. No.: WO2017/098440
PCT Pub. Date: Jun. 15, 2017

(65) Prior Publication Data
US 2018/0362474 A1 Dec. 20, 2018

Related U.S. Application Data

(60) Provisional application No. 62/264,628, filed on Dec. 8, 2015.

(51) Int. Cl.
| | | |
|---|---|---|
| C07D 239/88 | (2006.01) |
| C07D 217/24 | (2006.01) |
| C07D 401/04 | (2006.01) |
| C07D 401/10 | (2006.01) |
| C07D 403/10 | (2006.01) |
| C07D 405/04 | (2006.01) |
| C07D 409/04 | (2006.01) |
| C07D 417/04 | (2006.01) |
| C07D 253/08 | (2006.01) |
| C07D 209/46 | (2006.01) |
| A61P 31/04 | (2006.01) |
| C07D 413/10 | (2006.01) |

(52) U.S. Cl.
CPC ............ *C07D 239/88* (2013.01); *A61P 31/04* (2018.01); *C07D 209/46* (2013.01); *C07D 217/24* (2013.01); *C07D 253/08* (2013.01); *C07D 401/04* (2013.01); *C07D 401/10* (2013.01); *C07D 403/10* (2013.01); *C07D 405/04* (2013.01); *C07D 409/04* (2013.01); *C07D 413/10* (2013.01); *C07D 417/04* (2013.01)

(58) Field of Classification Search
CPC .............................. C07D 239/88; A61P 31/04
See application file for complete search history.

(56) References Cited

U.S. PATENT DOCUMENTS 9,796,686 B2 * 10/2017 Chapoux .............. A61K 31/517

FOREIGN PATENT DOCUMENTS

WO    WO 2015/173329 A1    11/2015

OTHER PUBLICATIONS

Gao et al (2014), STN International (Columbus, Ohio) HCAPLUS database, Accession No. 2014: 1582420.*
Gauvin et al (2015), STN International (Columbus, Ohio), HCAPLUS database, Accession No. 2015: 1847958.*
Gao et al., "Overexpression of Pseudomonas aeruginosa LpxC with its inhibitors in an acrB-deficient *Escherichia coli* strain", *Protein Expression and Purification*, vol. 104, pp. 57-64 (2014).

* cited by examiner

*Primary Examiner* — Golam M Shameem
(74) *Attorney, Agent, or Firm* — Hao Yin

(57) ABSTRACT

The present invention relates to LpxC antibacterial compounds of Formula (IA):

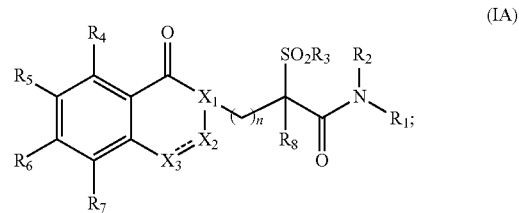

corresponding pharmaceutically acceptable salts thereof, corresponding pharmaceutical compositions, compound preparation, treatment methods and uses for bacterial infections, especially those caused by gram-negative bacteria.

4 Claims, No Drawings

SUBSTITUTED BENZAZINONES AS ANTIBACTERIAL COMPOUNDS

This application is a § 371 application of International Application No. PCT/IB2016/057451, filed 8 Dec. 2016, which claims the benefit of U.S. Provisional Application No. 62/264,628, filed 8 Dec. 2015, the disclosures of which are incorporated herein in their entireties.

FIELD OF THE INVENTION

The present invention relates to LpxC inhibitor antibacterial compounds, corresponding pharmaceutical compositions, processes and methods of compound preparation, treatment methods and uses for bacterial infections.

BACKGROUND OF THE INVENTION

Over the past several decades, the frequency of antimicrobial resistance and its association with serious infectious diseases has increased at alarming rates. For example, in the United States, the Centers for Disease Control and Prevention estimate that roughly 1.7 million hospital-associated infections, from all types of microorganisms, including bacteria, combined, cause or contribute to 99,000 deaths each year. In Europe, where hospital surveys have been conducted, the category of Gram-negative infections are estimated to account for two-thirds of the 25,000 deaths each year. Nosocomial infections can cause severe pneumonia and infections of the urinary tract, bloodstream and other parts of the body. Many types are difficult to attack with antibiotics, and antibiotic resistance is spreading to Gram-negative bacteria that can infect people outside the hospital (see, Pollack, Andrew. "Rising Threat of Infections Unfazed by Antibiotics" New York Times, Feb. 27, 2010). This high rate of resistance increases the morbidity, mortality, and costs associated with nosocomial infections. In addition, the costs and regulatory challenges associated with the development of new antibacterial agents, combined with the perception of modest future profitability, has unfortunately resulted in most major pharmaceutical companies exiting anti-infective drug research at a time when it is most needed. While it has been regularly stated that there is a great need to identify novel lead series with new antibacterial modes of action, in reality this goal remains highly elusive.

The problem of antibacterial resistance is compounded by the existence of bacterial strains resistant to multiple antibacterials. It is conventionally taught in the art that among: Gram-negative resistance includes extended-spectrum beta-lactamases (ESBLs) in *Klebsiella pneumoniae, Escherichia coli*, and *Proteus mirabilis*, high-level third-generation LpxC (Amp C) beta-lactamase resistance among *Enterobacter* species and *Citrobacter freundii*, and multidrug-resistance genes observed in *Pseudomonas aeruginosa, Acinetobacter*, and *Stenotrophomonas maltophilia*.

Drug resistant Gram-negative infections are an increasing threat to public health, especially for seriously ill, hospitalized patients. Infections arising from multidrug resistant *Pseudomonas aeruginosa* and *Acinetobacter* species as well as drug resistant *Klebsiella pneumoniae* present formidable challenges for the medical community as few treatment options remain. Unfortunately, while resistance to current therapies continues to spread, new clinical agents to treat these infections are few in number.

One of the emerging targets in Gram-negative bacteria is the biosynthetic pathway of lipid A, typically a phosphorylated, hexaacylated glucosamine disaccharide that makes up the outer leaflet of the outer membrane. The outer membrane of gram-negative bacteria is comprised of Lipopolysaccharide (LPS) that serves as the permeability barrier to protect the bacterium against antibiotics. As the membrane anchor of LPS, Lipid A is essential for LPS assembly in the outer membrane. Since lipid A is the toxic component of LPS and is required for the bacterial viability, inhibition of its biosynthesis is lethal to bacteria. Hence, inhibitors targeting the enzymes in the biosynthesis of lipid A may serve as the antibiotics selective against Gram-negative pathogens and reduce Gram-negative sepsis more effectively. Among the nine unique enzymes involved in the biosynthesis of lipid A, UDP-3-O—(R-3-hydroxymyristoyl)-N-acetylglucosamine deacetylase (LpxC), is a zinc-dependent metalloamidase, which catalyzes the first committed, second overall step in the biosynthetic pathway of lipid A. Additionally, LpxC is highly conserved among Gram-negative bacteria and shares no sequence homology with any other known zincmetalloenzymes.

Thus, LpxC has become an attractive target for the structure-based drug design, and research on LpxC inhibitors is a very promising strategy in the development of current antibiotic therapy for Gram-negative bacteria. Intensive efforts have been spent in recent years to identify LpxC inhibitors for the development of antibacterial drug design and agents targeting Gram-negative bacteria. As no inhibitors of LpxC have been approved to date, antibiotics from this new chemical class would likely overcome pre-existing class specific mechanisms of resistance such as extended-spectrum β-lactamases (ESBLs), *Klebsiella pneumonia* carbapenemases (KPCs), and the recently described New Delhi metallo-β-lactamase (NDM-1).

Thus, there is a need for new antibacterials, particularly antibacterials with novel LpxC mechanisms of action.

In light of the above, a need exists to develop compounds of the present invention, which provides LpxC compounds that exhibit potent antimicrobial spectrum against a variety of bacteria including Gram negative bacteria, corresponding pharmaceutical compositions, treatment methods and uses for bacterial infections.

The present invention is directed to overcoming these and other problems encountered in the art.

SUMMARY OF THE INVENTION

In general, the present invention relates to LpxC antibacterial compounds, corresponding pharmaceutical compositions, compound preparation, treatment methods and uses for bacterial infections, especially those caused by gram-negative bacteria and gram-positive bacteria.

In particular, the present invention relates to novel compounds of Formulas (IA), (I) to (VI), respectively, or pharmaceutically acceptable salts thereof and corresponding pharmaceutical compositions, respectively.

The present invention also relates to processes for making compounds of Formulas (IA), (I) to (VI), respectively, or pharmaceutically acceptable salt thereof.

The present invention also relates to methods and uses for treating bacterial infections, which comprises administering an effective amount of a compound of Formulas (IA), (I) to (VI), respectively, or a pharmaceutically acceptable salt thereof or a corresponding pharmaceutical composition, respectively, to a subject in need thereof.

DETAILED DESCRIPTION OF THE INVENTION

In general, the present invention relates to LpxC antibacterial compounds, corresponding pharmaceutical compositions, compound preparation, treatment methods and uses for bacterial infections, especially those caused by gram-negative bacteria and gram-positive bacteria.

Compounds

In particular, the present invention relates to novel compounds of Formulas (IA), (I) to (VI), respectively, or pharmaceutically acceptable salts thereof.

In one aspect, the present invention relates to a compound of Formula (IA):

(IA)

where:
≡≡≡ represents a double bond or is non-existent such that a single bond exists between $X_2$ and $X_3$;
each $X_1$, $X_2$ or $X_3$ independently is selected from —N or —$CR_9$; or —$C(R_9)_2$;
each $R^1$ or $R^2$ independently is selected from hydrogen, hydroxy or straight or branched $C_1$-$C_6$ alkyl;
$R^3$ is —O$^-$, -hydroxy, -straight or branched $C_1$-$C_6$ alkyl or -straight or branched $C_1$-$C_6$ alkoxy;
each $R^4$, $R^5$, $R^7$, $R^8$ or $R^9$ independently is selected from hydrogen, halogen, —OH, —$(CH_2)_x$OH, —C≡N, —$NR_aR_b$, -straight or branched $C_1$-$C_6$ alkyl, -straight or branched-$C_1$-$C_6$ haloalkyl, -straight or branched $C_1$-$C_6$ alkoxy, -straight or branched $C_1$-$C_6$ haloalkoxy, —O-straight or branched-$C_1$-$C_6$ haloalkyl;
$R^6$, is heterocyclyl, aryl, or heteroaryl;
where:
each $R^4$, $R^5$, $R^6$, $R^7$, $R^8$ or $R^9$ as defined above optionally is further substituted with one or more substituents selected from hydrogen, halogen, —OH, —$(CH_2)_x$OH, —C≡N, —$NR_cR_d$, —$(CH_2)_xNR_eR_f$, -straight or branched $C_1$-$C_6$ alkyl, -straight or branched-$C_1$-$C_6$ haloalkyl, -straight or branched $C_1$-$C_6$ alkoxy, —$(CH_2)_x$ straight or branched $C_1$-$C_6$ alkoxy, -straight or branched $C_1$-$C_6$ haloalkoxy, —O-straight or branched-$C_1$-$C_6$ haloalkyl, —$C_1$-$C_6$ cycloalkyl, —$(CH_2)_x$— cycloalkyl, -heterocyclyl, —$(CH_2)_x$— heterocyclyl, —N-heterocyclyl, —$(CH_2)_x$N-heterocyclyl, aryl, -heteroaryl, —$(CH_2)_x$-heteroaryl, —O—$(CH_2)_x$CH(OH)CH$_2$(OH), —C(O)OR$_f$, —$(CH_2)_x$—C(O)OR$_f$, —NR$_g$—NR$_h$R$_i$, —$(CH_2)_x$—NR$_g$—NR$_h$R$_i$, —O—$(CH_2)_x$—N(R$_9$)—NR$_h$R$_i$;
where:
each $R_a$, $R_b$, $R_c$, $R_d$, $R_e$, or $R_f$ as defined above independently is selected from hydrogen, -straight or branched $C_1$-$C_6$ alkyl, -straight or branched $C_1$-$C_6$ alkoxy, —$(CH_2)_x$ straight or branched $C_1$-$C_6$ alkoxy, —$(CH_2)_x$OH, -straight or branched-$C_1$-$C_6$ haloalkyl, —$C_1$-$C_6$-cycloalkyl, —$(CH_2)_xC_1$-$C_6$-cycloalkyl, heterocyclyl, —$(CH_2)_x$heterocyclyl, —N-heterocyclyl, —$(CH_2)_x$N-heterocyclyl, aryl, heteroaryl, or —$(CH_2)_x$heteroaryl, —$(CHR_g)_x$heteroaryl, —NR$_g$R$_h$, —C(O)OR$_i$, —$(CH_2)_xC(O)OR_j$;

where:
each $R_g$, $R_h$, $R_i$, or $R_1$ is hydrogen, -straight or branched $C_1$-$C_6$ alkyl or -straight or branched-$C_1$-$C_6$ haloalkyl;
n is an integer selected from 1 to 3;
x is 0 or an integer from 1 to 6; or
a pharmaceutically salt thereof.

In one aspect, the present invention relates to a compound of Formula (I):

(I)

where:
≡≡≡ represents a double bond or is non-existent such that a single bond exists between $X_2$ and $X_3$;
each $X_1$, $X_2$ or $X_3$ independently is selected from —N or —$CR_9$; or —$C(R_9)_2$;
each $R^1$ or $R^2$ independently is selected from hydrogen, hydroxy or straight or branched $C_1$-$C_6$ alkyl;
$R^3$ is —O$^-$, -hydroxy, -straight or branched $C_1$-$C_6$ alkyl or -straight or branched $C_1$-$C_6$ alkoxy;
each $R^4$, $R^5$, $R^7$, $R^6$ or $R^9$ independently is selected from hydrogen, halogen, —OH, —$(CH_2)_x$OH, —C≡N, —$NR_aR_b$, -straight or branched $C_1$-$C_6$ alkyl, -straight or branched-$C_1$-$C_6$ haloalkyl, -straight or branched $C_1$-$C_6$ alkoxy, -straight or branched $C_1$-$C_6$ haloalkoxy, —O-straight or branched-$C_1$-$C_6$ haloalkyl;
$R^6$, is heterocyclyl, aryl, or heteroaryl;
where:
each $R^4$, $R^5$, $R^6$, $R^7$, $R^8$ or $R^9$ as defined above optionally is further substituted with one or more substituents selected from hydrogen, halogen, —OH, —$(CH_2)_x$OH, —C≡N, —$NR_cR_d$, —$(CH_2)_xNR_eR_f$, -straight or branched $C_1$-$C_6$ alkyl, -straight or branched-$C_1$-$C_6$ haloalkyl, -straight or branched $C_1$-$C_6$ alkoxy, —$(CH_2)_x$ straight or branched $C_1$-$C_6$ alkoxy, -straight or branched $C_1$-$C_6$ haloalkoxy, —O-straight or branched-$C_1$-$C_6$ haloalkyl, —$C_1$-$C_6$ cycloalkyl, —$(CH_2)_x$— cycloalkyl, -heterocyclyl, —$(CH_2)_x$— heterocyclyl, —N-heterocyclyl, —$(CH_2)_x$N-heterocyclyl, aryl, -heteroaryl, —$(CH_2)_x$-heteroaryl, —O—$(CH_2)_x$CH(OH)CH$_2$(OH), —C(O)OR$_f$, —$(CH_2)_x$—C(O)OR$_f$, —NR$_g$—NR$_h$R$_i$, —$(CH_2)_x$—NR$_g$—NR$_h$R$_i$, —O—$(CH_2)_x$—N(R$_g$)—NR$_h$R$_i$;
where:
each $R_a$, $R_b$, $R_c$, $R_d$, $R_e$, or $R_f$ as defined above independently is selected from hydrogen, -straight or branched $C_1$-$C_6$ alkyl, -straight or branched $C_1$-$C_6$ alkoxy, —$(CH_2)_x$ straight or branched $C_1$-$C_6$ alkoxy, —$(CH_2)_x$OH, -straight or branched-$C_1$-$C_6$ haloalkyl, —$C_1$-$C_6$-cycloalkyl, —$(CH_2)_xC_1$-$C_6$-cycloalkyl, heterocyclyl, —$(CH_2)_x$heterocyclyl, —N-heterocyclyl, —$(CH_2)_x$N-heterocyclyl, aryl, heteroaryl, or —$(CH_2)_x$heteroaryl, —$(CHR_g)_x$heteroaryl, —NR$_g$R$_h$, —C(O)OR$_i$, —$(CH_2)_xC(O)OR_j$;
where:
each $R_g$, $R_h$, $R_i$, or $R_1$ is hydrogen, -straight or branched $C_1$-$C_6$ alkyl or -straight or branched-$C_1$-$C_6$ haloalkyl;
n is an integer selected from 1 to 3;
x is 0 or an integer from 1 to 6; or
a pharmaceutically salt thereof.

In one aspect, the present invention relates to a compound of Formula (I) where $R^6$ is selected from:

| $R_6$ | |
|---|---|
| | phenyl; |
| | 1,3-dihydroisobenzofuranyl; |
| | 1,3-benzodioxoyl; |
| | Thiophenyl; |
| | pyrrolindyl; |
| | pyridinyl; |
| | thiazoylyl; or |
| | pyrimidinyl. |

In one aspect, the present invention relates to a compound of Formula (II):

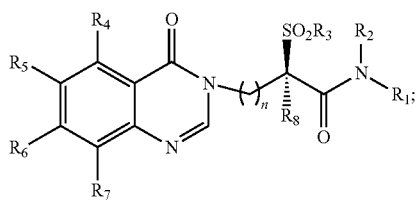

(II)

where:

each $R^1$ or $R^2$ independently is selected from hydrogen, hydroxy or straight or branched $C_1$-$C_6$ alkyl;

$R^3$ is —O⁻, -hydroxy, -straight or branched $C_1$-$C_6$ alkyl or -straight or branched $C_1$-$C_6$ alkoxy;

each $R^4$, $R^5$, $R^7$, $R^8$ or $R^9$ independently is selected from hydrogen, halogen, —OH, —(CH$_2$)$_x$OH, —C≡N, —NR$_a$R$_b$, -straight or branched $C_1$-$C_6$ alkyl, -straight or branched-$C_1$-$C_6$ haloalkyl, -straight or branched $C_1$-$C_6$ alkoxy, -straight or branched $C_1$-$C_6$ haloalkoxy, —O-straight or branched-$C_1$-$C_6$ haloalkyl;

$R^6$, is heterocyclyl, aryl, or heteroaryl;

where:

each $R^4$, $R^5$, $R^6$, $R^7$, $R^8$ or $R^9$ as defined above optionally is further substituted with one or more substituents selected from hydrogen, halogen, —OH, —(CH$_2$)$_x$OH, —C≡N, —NR$_c$R$_d$, —(CH$_2$)$_x$NR$_e$R$_f$, -straight or branched $C_1$-$C_6$ alkyl, -straight or branched-$C_1$-$C_6$ haloalkyl, -straight or branched $C_1$-$C_6$ alkoxy, —(CH$_2$)$_x$ straight or branched $C_1$-$C_6$ alkoxy, -straight or branched $C_1$-$C_6$ haloalkoxy, —O-straight or branched-$C_1$-$C_6$ haloalkyl, —$C_1$-$C_6$ cycloalkyl, —(CH$_2$)$_x$— cycloalkyl, -heterocyclyl, —(CH$_2$)$_x$— heterocyclyl, —N-heterocyclyl, —(CH$_2$)$_x$N-heterocyclyl, aryl, -heteroaryl, —(CH$_2$)$_x$-heteroaryl, —O—(CH$_2$)$_x$CH(OH)CH$_2$(OH), —C(O)OR$_f$, —(CH$_2$)$_x$— C(O)OR$_f$; —NR$_g$—NR$_h$R$_i$, —(CH$_2$)$_x$—NR$_g$—NR$_h$R$_i$, —O—(CH$_2$)$_x$—N(R$_g$)—NR$_h$R$_i$;

each R$_a$, R$_b$, R$_c$, R$_d$, R$_e$, or R$_f$ as defined above independently is selected from hydrogen, -straight or branched $C_1$-$C_6$ alkyl, -straight or branched $C_1$-$C_6$ alkoxy, —(CH$_2$)$_x$ straight or branched $C_1$-$C_6$ alkoxy, —(CH$_2$)$_x$OH, -straight or branched-$C_1$-$C_6$ haloalkyl, —$C_1$-$C_6$-cycloalkyl, —(CH$_2$)$_x$$C_1$-$C_6$-cycloalkyl, heterocyclyl, —(CH$_2$)$_x$heterocyclyl, —N-heterocyclyl, —(CH$_2$)$_x$N-heterocyclyl, aryl, heteroaryl, or —(CH$_2$)$_x$heteroaryl, —(CHR$_g$)$_x$heteroaryl, —NR$_g$R$_h$, —C(O)OR$_i$, —(CH$_2$)$_x$C(O)OR$_j$;

where:

each R$_g$, R$_h$, R$_i$, or R$_j$ is hydrogen, -straight or branched $C_1$-$C_6$ alkyl or -straight or branched-$C_1$-$C_6$ haloalkyl;

n is an integer selected from 1 to 3;

x is 0 or an integer from 1 to 6; or a pharmaceutically salt thereof.

In one aspect the present invention relates to a compound which is:

| EX. | Chemical Name | Chemical Structures |
|---|---|---|
| 1 | (2R)-N-hydroxy-2-methanesulfonyl-2-methyl-4-(4-oxo-7-phenyl-3,4-dihydroquinazolin-3-yl)butanamide | 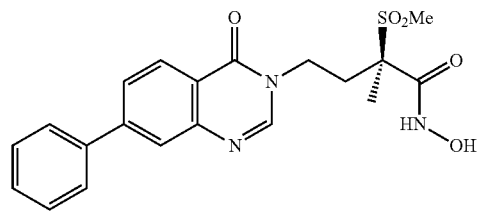 [SMILES: C[C@@](CCn1cnc2cc(-c3ccccc3)ccc2c1=O)(C(=O)NO)S(C)(=O)=O] |

-continued

| EX. | Chemical Name | Chemical Structures |
|---|---|---|
| 2 | (2R)-N-hydroxy-2-methanesulfonyl-2-methyl-4-[7-(4-methylphenyl)-4-oxo-3,4-dihydroquinazolin-3-yl]butanamide | 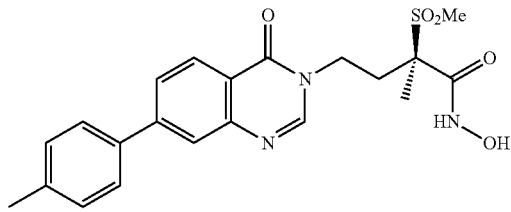 [SMILES: Cc1ccc(-c2ccc3c(=O)n(CC[C@](C)(C(=O)NO)S(C)(=O)=O)cnc3c2)cc1] |
| 3 | (2R)-N-hydroxy-2-methanesulfonyl-4-[7-(4-methoxyphenyl)-4-oxo-3,4-dihydroquinazolin-3-yl]-2-methylbutanamide | 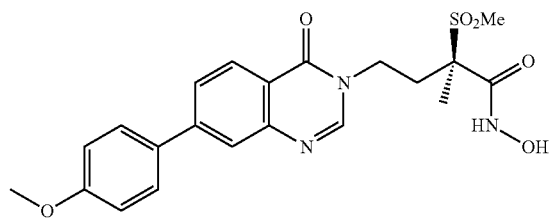 [SMILES: COc1ccc(-c2ccc3c(=O)n(CC[C@](C)(C(=O)NO)S(C)(=O)=O)cnc3c2)cc1] |
| 4 | (2R)-4-{7-[4-(dimethylamino)phenyl]-4-oxo-3,4-dihydroquinazolin-3-yl}-N-hydroxy-2-methanesulfonyl-2-methylbutanamide | 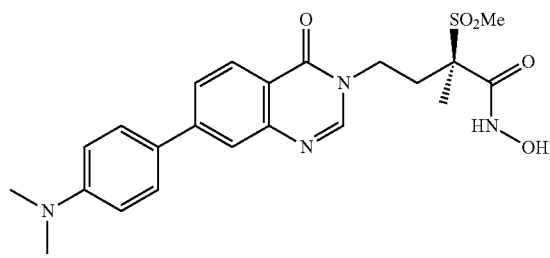 [SMILES: CN(C)c1ccc(-c2ccc3c(=O)n(CC[C@](C)(C(=O)NO)S(C)(=O)=O)cnc3c2)cc1] |
| 5 | (2R)-4-{7-[4-(difluoromethoxy)phenyl]-4-oxo-3,4-dihydroquinazolin-3-yl}-N-hydroxy-2-methanesulfonyl-2-methylbutanamide | 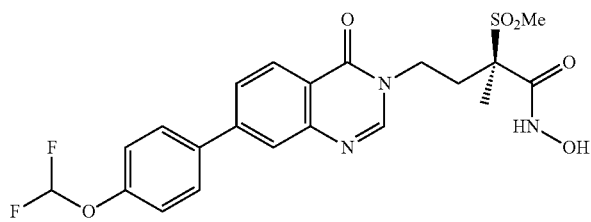 [SMILES: C[C@@](CCn1cnc2cc(-c3ccc(OC(F)F)cc3)ccc2c1=O)(C(=O)NO)S(C)(=O)=O] |
| 6 | (2R)-4-[7-(2,3-difluorophenyl)-4-oxo-3,4-dihydroquinazolin-3-yl]-N-hydroxy-2-methanesulfonyl-2-methylbutanamide | 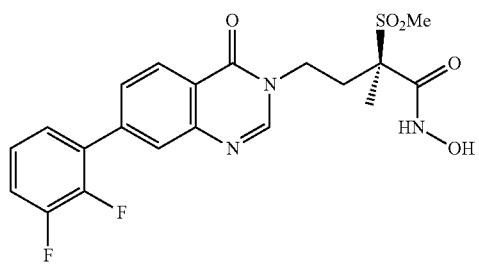 [SMILES: C[C@@](CCn1cnc2cc(-c3cccc(F)c3F)ccc2c1=O)(C(=O)NO)S(C)(=O)=O] |
| 7 | (2R)-4-[7-(2,5-difluorophenyl)-4-oxo-3,4-dihydroquinazolin-3-yl]-N-hydroxy-2-methanesulfonyl-2-methylbutanamide | 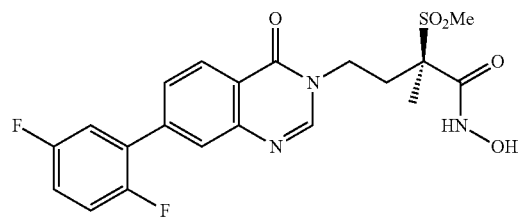 [SMILES: C[C@@](CCn1cnc2cc(-c3cc(F)ccc3F)ccc2c1=O)(C(=O)NO)S(C)(=O)=O] |

-continued

| EX. | Chemical Name | Chemical Structures |
|---|---|---|
| 8 | (2R)-4-[7-(2-fluorophenyl)-4-oxo-3,4-dihydroquinazolin-3-yl]-N-hydroxy-2-methanesulfonyl-2-methylbutanamide | 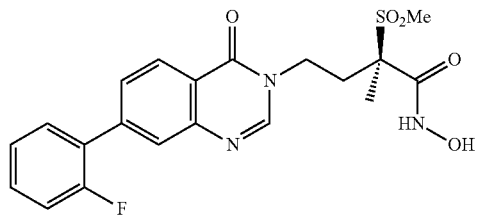 [SMILES: C[C@@](CCn1cnc2cc(-c3ccccc3F)ccc2c1=O)(C(=O)NO)S(C)(=O)=O] |
| 9 | (2R)-4-[7-(3-fluoro-4-methylphenyl)-4-oxo-3,4-dihydroquinazolin-3-yl]-N-hydroxy-2-methanesulfonyl-2-methylbutanamide | 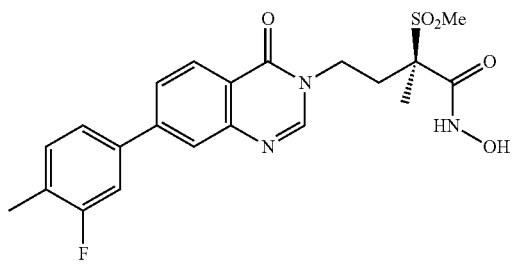 [SMILES: Cc1ccc(-c2ccc3c(=O)n(CC[C@](C)(C(=O)NO)S(C)(=O)=O)cnc3c2)cc1F] |
| 10 | (2R)-4-{7-[4-(difluoromethyl)phenyl]-4-oxo-3,4-dihydroquinazolin-3-yl}-N-hydroxy-2-methanesulfonyl-2-methylbutanamide | 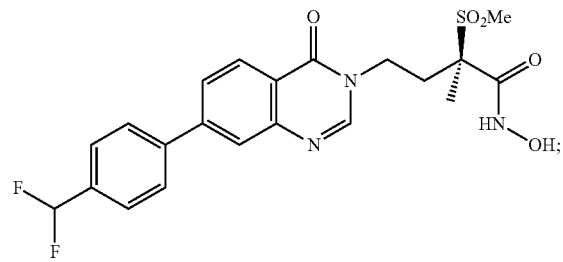 [SMILES: C[C@@](CCn1cnc2cc(-c3ccc(C(F)F)cc3)ccc2c1=O)(C(=O)NO)S(C)(=O)=O] | or
a pharmaceutically acceptable salt thereof.

In another aspect, the present invention relates to a compound which is:

| Ex. | Compound Name | Chemical Structure |
|---|---|---|
| 11 | (2R)-4-[7-(2,6-difluorophenyl)-4-oxo-3,4-dihydroquinazolin-3-yl]-N-hydroxy-2-methanesulfonyl-2-methylbutanamide | 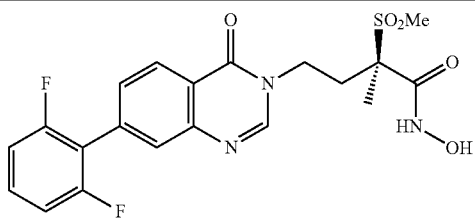 |
| 12 | (2R)-4-[7-(1,3-dihydro-2-benzofuran-5-yl)-4-oxo-3,4-dihydroquinazolin-3-yl]-N-hydroxy-2-methanesulfonyl-2-methylbutanamide | 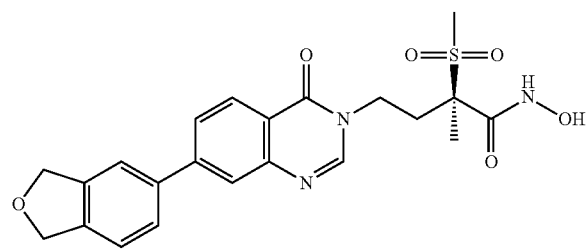 |
| 13 | (2R)-4-[6-fluoro-7-(4-methoxyphenyl)-4-oxo-3,4-dihydroquinazolin-3-yl]-N-hydroxy-2-methanesulfonyl-2-methylbutanamide | 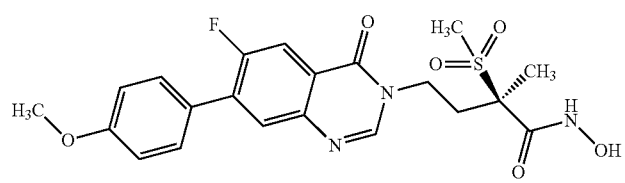 [SMILES: COc1ccc(-c2cc3ncn(CC[C@](C)(C(=O)NO)S(C)(=O)=O)c(=O)c3cc2F)cc1] |

-continued

| Ex. | Compound Name | Chemical Structure |
|---|---|---|
| 14 | (2R)-4-[8-fluoro-7-(4-methoxyphenyl)-4-oxo-3,4-dihydroquinazolin-3-yl]-N-hydroxy-2-methanesulfonyl-2-methylbutanamide | 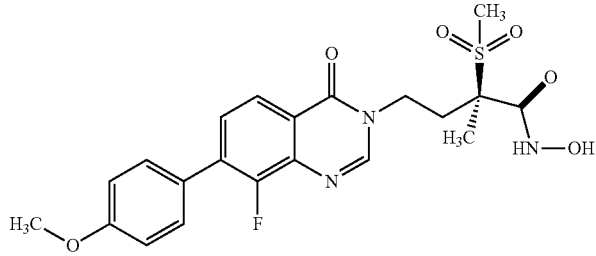 [SMILES: COc1ccc(-c2ccc3c(=O)n(CC[C@@](C)([C@@H](O)NO)S(C)(=O)=O)cnc3c2F)cc1] |
| 15 | (2R)-4-[6-fluoro-7-(4-methylphenyl)-4-oxo-3,4-dihydroquinazolin-3-yl]-N-hydroxy-2-methanesulfonyl-2-methylbutanamide | 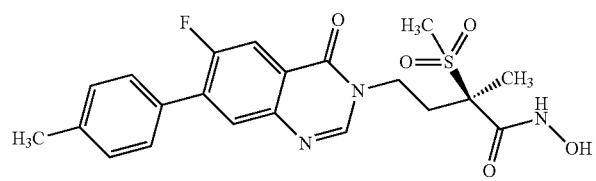 [SMILES: Cc1ccc(-c2cc3ncn(CC[C@](C)(C(=O)NO)S(C)(=O)=O)c(=O)c3cc2F)cc1] |
| 16 | (2R)-4-[5-fluoro-7-(4-methoxyphenyl)-4-oxo-3,4-dihydroquinazolin-3-yl]-N-hydroxy-2-methanesulfonyl-2-methylbutanamide | 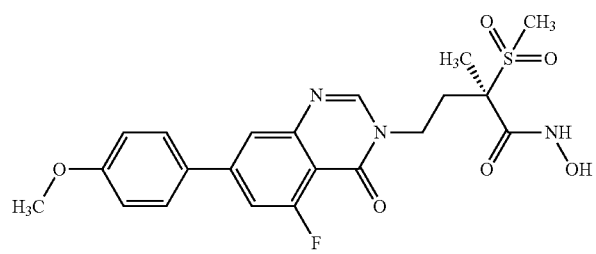 [SMILES: COc1ccc(-c2cc(F)c3c(=O)n(CC[C@](C)(C(=O)NO)S(C)(=O)=O)cnc3c2)cc1] |
| 17 | (2R)-4-[5-fluoro-7-(4-methylphenyl)-4-oxo-3,4-dihydroquinazolin-3-yl]-N-hydroxy-2-methanesulfonyl-2-methylbutanamide | 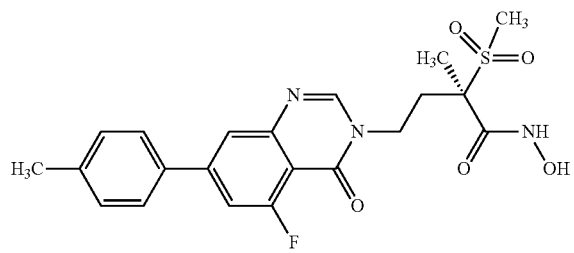 [SMILES: Cc1ccc(-c2cc(F)c3c(=O)n(CC[C@](C)(C(=O)NO)S(C)(=O)=O)cnc3c2)cc1] |
| 20 | (2R)-4-(6-fluoro-7-{4-[(morpholin-4-yl)methyl]phenyl}-4-oxo-3,4-dihydroquinazolin-3-yl)-N-hydroxy-2-methanesulfonyl-2-methylbutanamide | 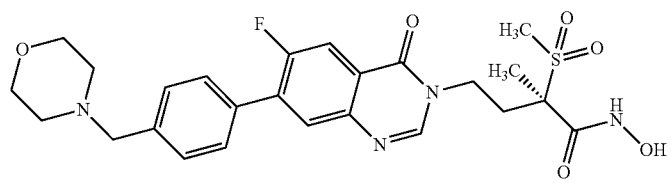 [SMILES: C[C@@](CCn1cnc2cc(-c3ccc(CN4CCOCC4)cc3)c(F)cc2c1=O)(C(=O)NO)S(C)(=O)=O] |
| 21 | (2R)-4-(6-fluoro-7-{4-[2-(morpholin-4-yl)ethyl]phenyl}-4-oxo-3,4-dihydroquinazolin-3-yl)-N-hydroxy-2-methanesulfonyl-2-methylbutanamide | 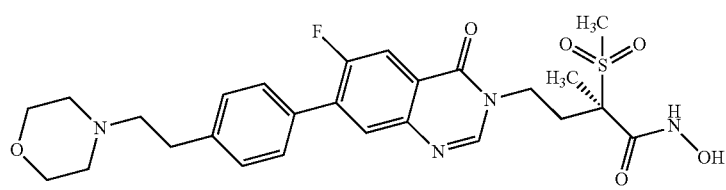 [SMILES: C[C@@](CCn1cnc2cc(-c3ccc(CCN4CCOCC4)cc3)c(F)cc2c1=O)(C(=O)NO)S(C)(=O)=O] |

-continued

| Ex. | Compound Name | Chemical Structure |
|---|---|---|
| 22 | (2R)-4-[7-(4-{[cyclopropyl(methyl)amino]methyl}phenyl)-6-fluoro-4-oxo-3,4-dihydroquinazolin-3-yl]-N-hydroxy-2-methanesulfonyl-2-methylbutanamide | 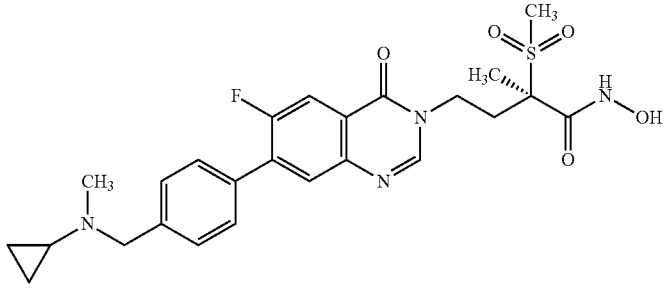 [SMILES: CN(Cc1ccc(-c2cc3ncn(CC[C@](C)(C(=O)NO)S(C)(=O)=O)c(=O)c3cc2F)cc1)C1CC1] |
| 23 | (2R)-4-[6-fluoro-7-(2-fluoro-4-{[(2-methoxyethyl)(methyl)amino]methyl}phenyl)-4-oxo-3,4-dihydroquinazolin-3-yl]-N-hydroxy-2-methanesulfonyl-2-methylbutanamide | 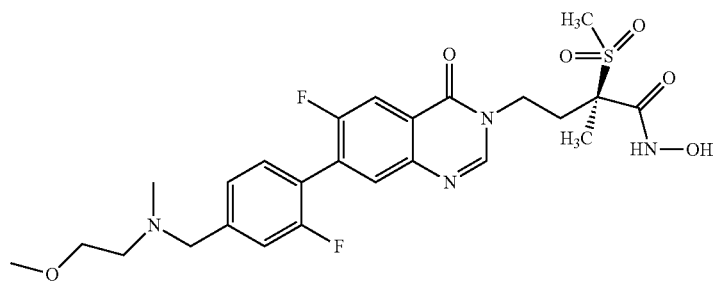 |
| 24 | (2R)-4-(7-{2,3-difluoro-4-[2-(3-methoxyazetidin-1-yl)ethyl]phenyl}-6-fluoro-4-oxo-3,4-dihydroquinazolin-3-yl)-N-hydroxy-2-methanesulfonyl-2-methylbutanamide | 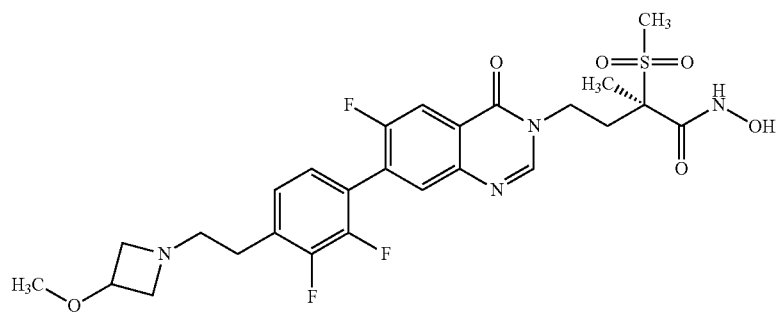 [SMILES: COC1CN(CCc2ccc(-c3cc4ncn(CC[C@](C)(C(=O)NO)S(C)(=O)=O)c(=O)c4cc3F)c(F)c2F)C1] |
| 25 | (2R)-4-(7-{4-[(cyclopropylamino)methyl]-2-fluorophenyl}-6-fluoro-4-oxo-3,4-dihydroquinazolin-3-yl)-N-hydroxy-2-methanesulfonyl-2-methylbutanamide | 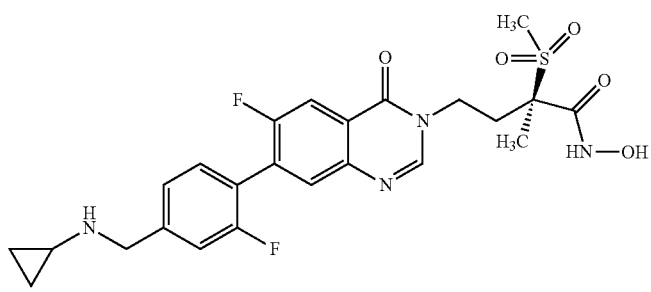 |
| 26 | (2R)-4-(6-fluoro-7-{2-fluoro-4-[(morpholin-4-yl)methyl]phenyl}-4-oxo-3,4-dihydroquinazolin-3-yl)-N-hydroxy-2-methanesulfonyl-2-methylbutanamide | 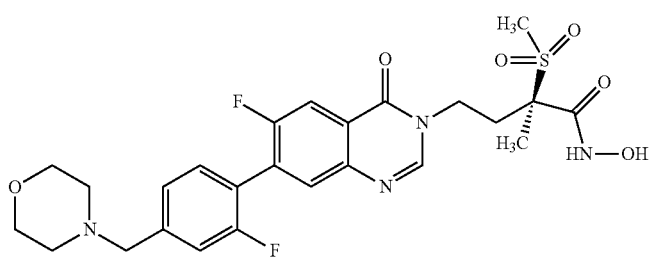 |

-continued

| Ex. | Compound Name | Chemical Structure |
|---|---|---|
| 27 | (2R)-4-{6-fluoro-7-[2-fluoro-4-(2-hydroxyethyl)phenyl]-4-oxo-3,4-dihydroquinazolin-3-yl}-N-hydroxy-2-methanesulfonyl-2-methylbutanamide | 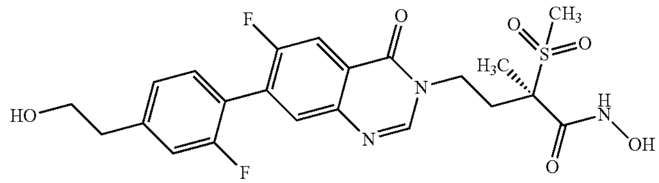 [SMILES: C[C@@](CCn1cnc2cc(-c3ccc(CCO)cc3F)c(F)cc2c1=O)(C(=O)NO)S(C)(=O)=O] |
| 28 | (2R)-4-{6-fluoro-7-[4-(2-hydroxyethyl)phenyl]-4-oxo-3,4-dihydroquinazolin-3-yl}-N-hydroxy-2-methanesulfonyl-2-methylbutanamide | 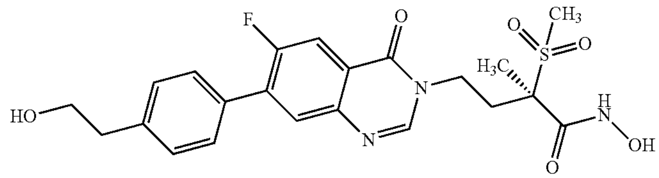 [SMILES: C[C@@](CCn1cnc2cc(-c3ccc(CCO)cc3)c(F)cc2c1=O)(C(=O)NO)S(C)(=O)=O] |
| 29 | (2R)-N-hydroxy-2-methanesulfonyl-2-methyl-4-(8-methyl-7-{4-[(morpholin-4-yl)methyl]phenyl}-4-oxo-3,4-dihydroquinazolin-3-yl)butanamide | 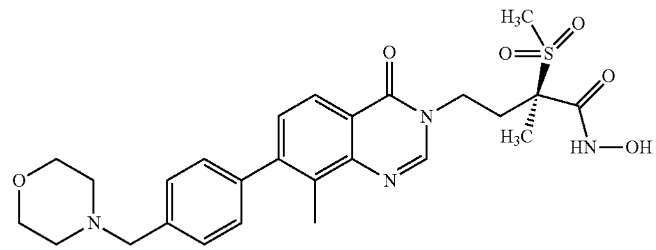 |
| 30 | (2R)-4-[6-fluoro-7-(6-methoxypyridin-3-yl)-4-oxo-3,4-dihydroquinazolin-3-yl]-N-hydroxy-2-methanesulfonyl-2-methylbutanamide | 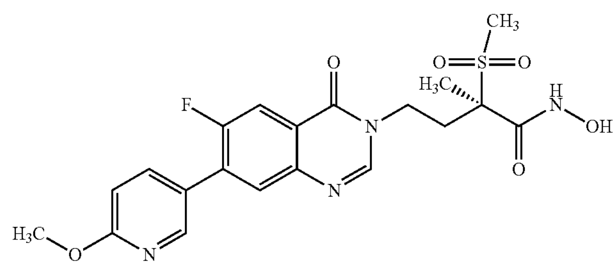 [SMILES: COc1ccc(-c2cc3ncn(CC[C@](C)(C(=O)NO)S(C)(=O)=O)c(=O)c3cc2F)cn1] |
| 31 | (2R)-4-(6-fluoro-4-oxo-7-phenyl-3,4-dihydroquinazolin-3-yl)-N-hydroxy-2-methanesulfonyl-2-methylbutanamide | 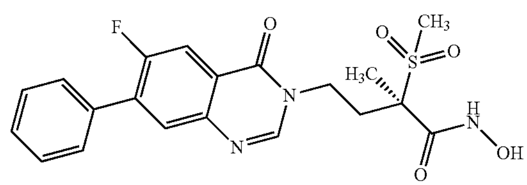 [SMILES: C[C@@](CCn1cnc2cc(-c3ccccc3)c(F)cc2c1=O)(C(=O)NO)S(C)(=O)=O] |
| 32 | (2R)-4-[7-(1,3-dihydro-2-benzofuran-5-yl)-6-fluoro-4-oxo-3,4-dihydroquinazolin-3-yl]-N-hydroxy-2-methanesulfonyl-2-methylbutanamide | 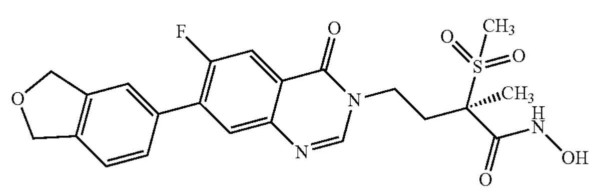 [SMILES: C[C@@](CCn1cnc2cc(-c3ccc4c(c3)COC4)c(F)cc2c1=O)(C(=O)NO)S(C)(=O)=O] |
| 33 | (2R)-4-{7-[6-(dimethylamino)pyridin-3-yl]-6-fluoro-4-oxo-3,4-dihydroquinazolin-3-yl}-N-hydroxy-2-methanesulfonyl-2-methylbutanamide GSK3339142A | 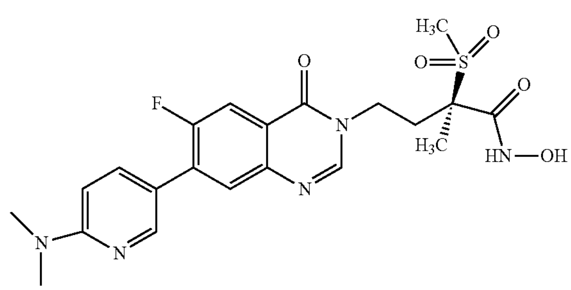 |

-continued

| Ex. | Compound Name | Chemical Structure |
|---|---|---|
| 34 | 2-(4-{6-fluoro-3-[(3R)-3-(hydroxycarbamoyl)-3-methanesulfonyl-3-methylpropyl]-4-oxo-3,4-dihydroquinazolin-7-yl}phenyl)ethyl acetate | 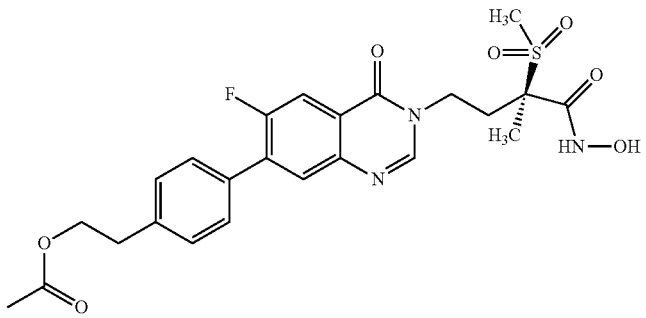 |
| 35 | (2R)-N-hydroxy-2-methanesulfonyl-2-methyl-4-(7-{4-[(morpholin-4-yl)methyl]phenyl}-4-oxo-3,4-dihydroquinazolin-3-yl)butanamide | 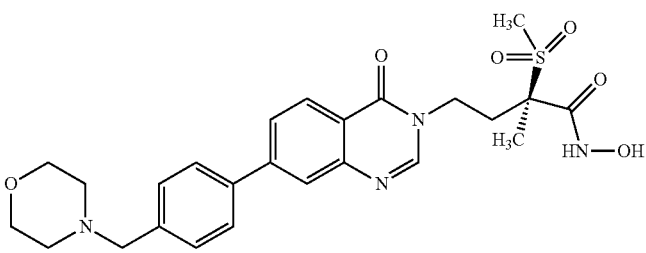 |
| 36 | (2R)-4-[7-(2-fluoro-4-{[(2-methoxyethyl)(methyl)amino]methyl}phenyl)-4-oxo-3,4-dihydroquinazolin-3-yl]-N-hydroxy-2-methanesulfonyl-2-methylbutanamide | 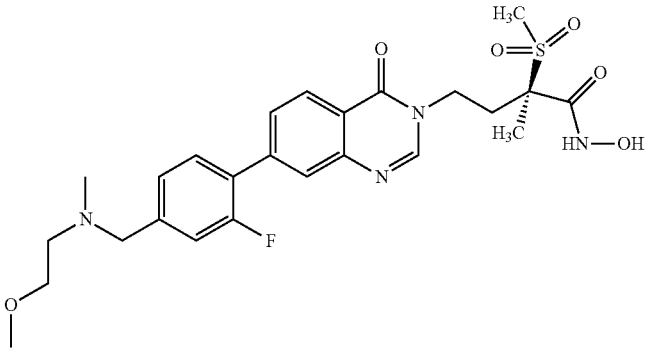 |
| 37 | (2R)-4-(7-{2-fluoro-4-[(morpholin-4-yl)methyl]phenyl}-4-oxo-3,4-dihydroquinazolin-3-yl)-N-hydroxy-2-methanesulfonyl-2-methylbutanamide | 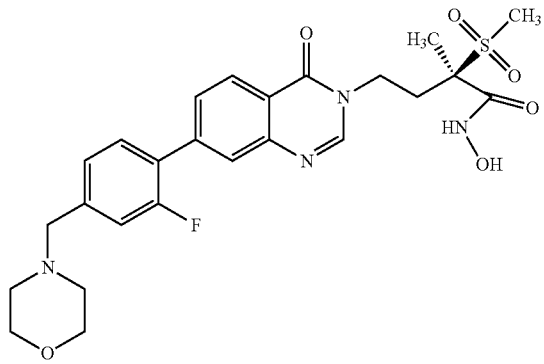 [SMILES: C[C@@](CCn1cnc2cc(-c3ccc(CN4CCOCC4)cc3F)ccc2c1=O)(C(=O)NO)S(C)(=O)=O] |

-continued

| Ex. | Compound Name | Chemical Structure |
|---|---|---|
| 38 | (2R)-4-[7-(2,3-difluoro-4-{[(2-methoxyethyl)(methyl)amino]methyl}phenyl)-4-oxo-3,4-dihydroquinazolin-3-yl]-N-hydroxy-2-methanesulfonyl-2-methylbutanamide | 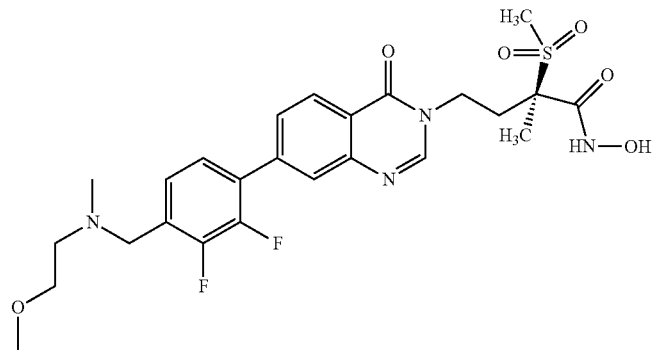 |
| 39 | (2R)-4-[7-(4-{[cyclopropyl(methyl)amino]methyl}-3-fluorophenyl)-4-oxo-3,4-dihydroquinazolin-3-yl]-N-hydroxy-2-methanesulfonyl-2-methylbutanamide | 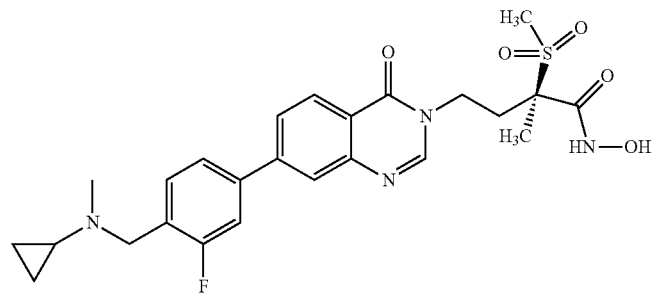 |
| 40 | (2R)-4-(7-{4-[(3,3-difluoroazetidin-1-yl)methyl]-2-fluorophenyl}-4-oxo-3,4-dihydroquinazolin-3-yl)-N-hydroxy-2-methanesulfonyl-2-methylbutanamide | 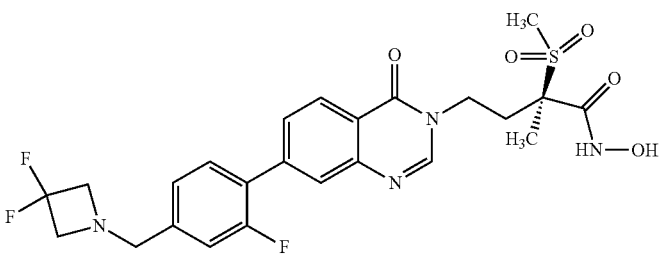 |
| 41 | (2R)-4-(7-{4-[(cyclopropylamino)methyl]-2-fluorophenyl}-4-oxo-3,4-dihydroquinazolin-3-yl)-N-hydroxy-2-methanesulfonyl-2-methylbutanamide | 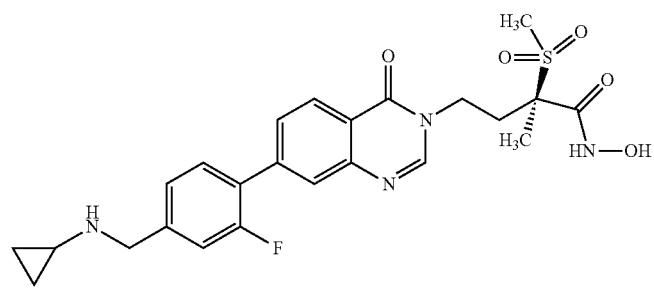 |
| 42 | (2R)-N-hydroxy-2-methanesulfonyl-2-methyl-4-(7-{4-[2-(morpholin-4-yl)ethyl]phenyl}-4-oxo-3,4-dihydroquinazolin-3-yl)butanamide | 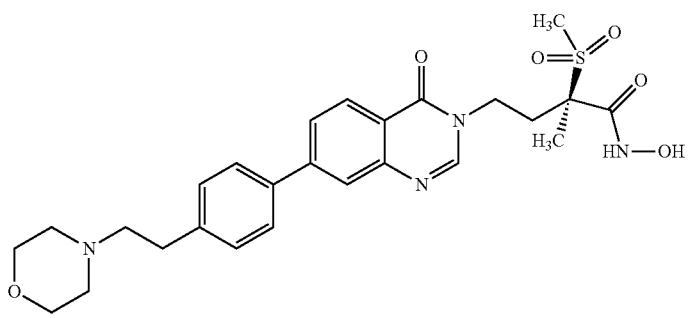 |

-continued

| Ex. | Compound Name | Chemical Structure |
|---|---|---|
| 43 | (2R)-4-(7-{2-fluoro-4-[2-(morpholin-4-yl)ethyl]phenyl}-4-oxo-3,4-dihydroquinazolin-3-yl)-N-hydroxy-2-methanesulfonyl-2-methylbutanamide | 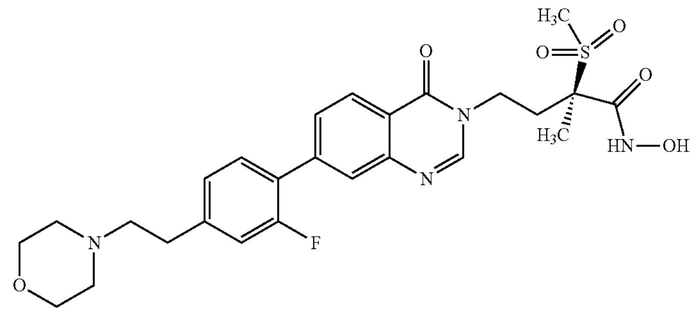 |
| 44 | (2R)-N-hydroxy-4-{7-[4-(2-hydroxyethyl)phenyl]-4-oxo-3,4-dihydroquinazolin-3-yl}-2-methanesulfonyl-2-methylbutanamide | 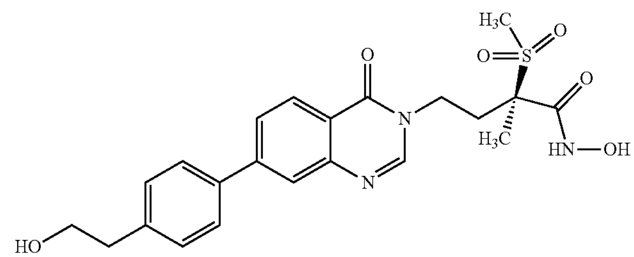 |
| 45 | (2R)-4-{7-[2-fluoro-4-(2-hydroxyethyl)phenyl]-4-oxo-3,4-dihydroquinazolin-3-yl}-N-hydroxy-2-methanesulfonyl-2-methylbutanamide | 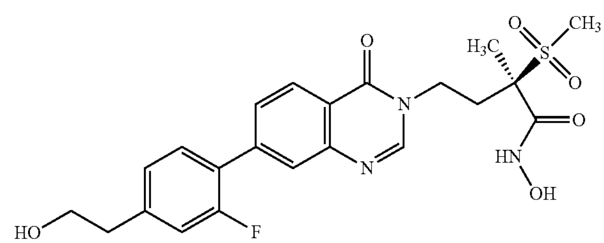 [SMILES: C[C@@](CCn1cnc2cc(-c3ccc(CCO)cc3F)ccc2c1=O)(C(=O)NO)S(C)(=O)=O] |
| 46 | (2R)-4-[7-(4-ethoxyphenyl)-4-oxo-3,4-dihydroquinazolin-3-yl]-N-hydroxy-2-methanesulfonyl-2-methylbutanamide | 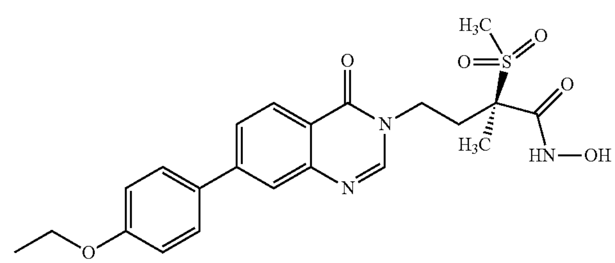 |
| 47 | (2R)-N-hydroxy-2-methanesulfonyl-4-{7-[4-(methoxymethyl)phenyl]-4-oxo-3,4-dihydroquinazolin-3-yl}-2-methylbutanamide | 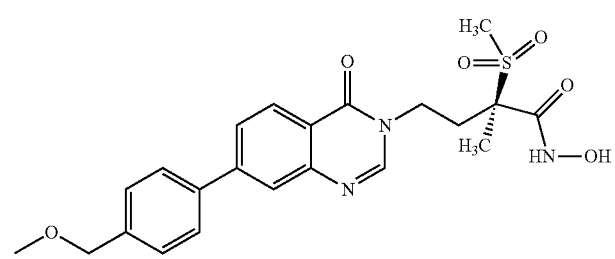 |
| 48 | (2R)-4-{7-[2-fluoro-4-(2-methoxyethyl)phenyl]-4-oxo-3,4-dihydroquinazolin-3-yl}-N-hydroxy-2-methanesulfonyl-2-methylbutanamide | 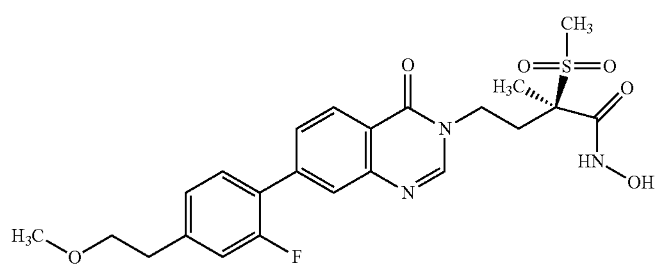 [SMILES: COCCc1ccc(-c2ccc3c(=O)n(CC[C@](C)(C(=O)NO)S(C)(=O)=O)cnc3c2)c(F)c1] |

| Ex. | Compound Name | Chemical Structure |
|---|---|---|
| 49 | (2R)-4-[7-(3-fluoro-4-{[methoxy(methyl)amino]methyl}phenyl)-4-oxo-3,4-dihydroquinazolin-3-yl]-N-hydroxy-2-methanesulfonyl-2-methylbutanamide | 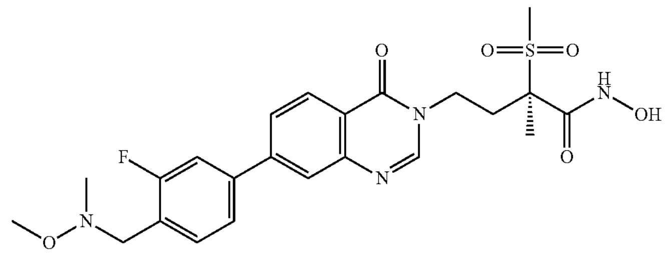 [SMILES: CON(C)Cc1ccc(-c2ccc3c(=O)n(CC[C@](C)(C(=O)NO)S(C)(=O)=O)cnc3c2)cc1F] |
| 50 | (2R)-4-(7-{2-fluoro-4-[(methoxyamino)methyl]phenyl}-4-oxo-3,4-dihydroquinazolin-3-yl)-N-hydroxy-2-methanesulfonyl-2-methylbutanamide | 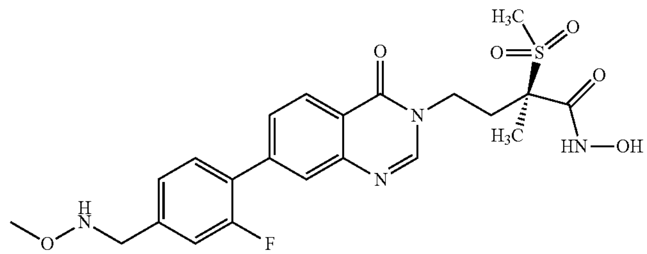 |
| 51 | (2R)-4-(7-{4-[(ethoxyamino)methyl]-2-fluorophenyl}-4-oxo-3,4-dihydroquinazolin-3-yl)-N-hydroxy-2-methanesulfonyl-2-methylbutanamide | 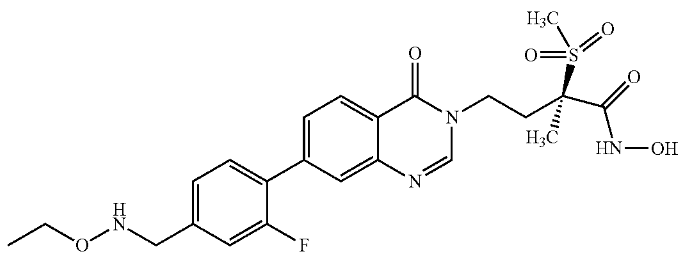 |
| 52 | (2R)-N-hydroxy-2-methanesulfonyl-4-[7-(4-{[methoxy(methyl)amino]methyl}phenyl)-4-oxo-3,4-dihydroquinazolin-3-yl]-2-methylbutanamide | | or a pharmaceutically acceptable salt thereof.

In one aspect, the present invention relates to a compound of Formula (III):

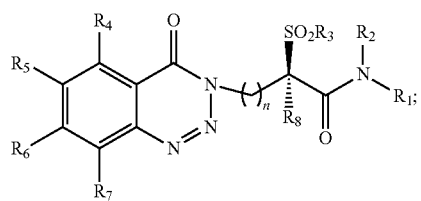

(III)

where:

each $R^1$ or $R^2$ independently is selected from hydrogen, hydroxy or straight or branched $C_1$-$C_6$ alkyl;

$R^3$ is —O$^-$, -hydroxy, -straight or branched $C_1$-$C_6$ alkyl or -straight or branched $C_1$-$C_6$ alkoxy;

each $R^4$, $R^5$, $R^7$, $R^8$ or $R^9$ independently is selected from hydrogen, halogen, —OH, —(CH$_2$)$_x$OH, —C≡N, —NR$_a$R$_b$, -straight or branched $C_1$-$C_6$ alkyl, -straight or branched-$C_1$-$C_6$ haloalkyl, -straight or branched $C_1$-$C_6$ alkoxy, -straight or branched $C_1$-$C_6$ haloalkoxy, —O-straight or branched-$C_1$-$C_6$ haloalkyl;

$R^{6'}$ is heterocyclyl, aryl, or heteroaryl;

where:

each $R^4$, $R^5$, $R^6$, $R^7$, $R^8$ or $R^9$ as defined above optionally is further substituted with one or more substituents selected from hydrogen, halogen, —OH, —(CH$_2$)$_x$OH, —C≡N, —NR$_c$R$_d$, —(CH$_2$)$_x$NR$_e$R$_f$, -straight or branched $C_1$-$C_6$ alkyl, -straight or branched-$C_1$-$C_6$ haloalkyl, -straight or branched $C_1$-$C_6$ alkoxy, —(CH$_2$)$_x$ straight or branched $C_1$-$C_6$ alkoxy, -straight or branched $C_1$-$C_6$ haloalkoxy, —O-straight or branched-$C_1$-$C_6$ haloalkyl, —$C_1$—C cycloalkyl, —(CH$_2$)$_x$— cycloalkyl, -heterocyclyl, —(CH$_2$)$_x$— heterocyclyl, —N-heterocyclyl, —(CH$_2$)$_x$N-heterocyclyl, aryl, -heteroaryl, —(CH$_2$)$_x$-heteroaryl, —O—(CH$_2$)$_x$CH(OH)CH$_2$(OH), —C(O)OR$_f$, —(CH$_2$)$_x$—C(O)OR$_f$, —NR$_g$—NR$_h$R$_i$, —(CH$_2$)$_x$—NR$_g$—NR$_h$R$_i$, —O—(CH$_2$)$_x$—N(R$_g$)—NR$_h$R$_i$;

each $R_a$, $R_b$, $R_c$, $R_d$, $R_e$, or $R_f$ as defined above independently is selected from hydrogen, -straight or branched $C_1$-$C_6$ alkyl, -straight or branched $C_1$-$C_6$ alkoxy, —$(CH_2)_x$ straight or branched $C_1$-$C_6$ alkoxy, —$(CH_2)_x$OH, -straight or branched-$C_1$-$C_6$ haloalkyl, —$C_1$-$C_6$-cycloalkyl, —$(CH_2)_x C_1$-$C_6$-cycloalkyl, heterocyclyl, —$(CH_2)_x$heterocyclyl, —N-heterocyclyl, —$(CH_2)_x$N-heterocyclyl, aryl, heteroaryl, or —$(CH_2)_x$heteroaryl, —$(CHR_g)_x$heteroaryl, —$NR_g R_h$, —$C(O)OR_i$, —$(CH_2)_x C(O)OR_j$;

where:
each $R_g$, $R_h$, $R_i$, or $R_j$ is hydrogen, -straight or branched $C_1$-$C_6$ alkyl or -straight or branched-$C_1$-$C_6$ haloalkyl;
n is an integer selected from 1 to 3;
x is 0 or an integer from 1 to 6; or
a pharmaceutically salt thereof.

In one aspect, the present invention relates to a compound which is:

-straight or branched $C_1$-$C_6$ alkyl, -straight or branched-$C_1$-$C_6$ haloalkyl, -straight or branched $C_1$-$C_6$ alkoxy, -straight or branched $C_1$-$C_6$ haloalkoxy, —O-straight or branched-$C_1$-$C_6$ haloalkyl;

$R^{6\prime}$ is heterocyclyl, aryl, or heteroaryl;

where:
each $R^4$, $R^5$, $R^6$, $R^7$, $R^8$ or $R^9$ as defined above optionally is further substituted with one or more substituents selected from hydrogen, halogen, —OH, —$(CH_2)_x$OH, —C≡N, —$NR_c R_d$, —$(CH_2)_x NR_e R_f$, -straight or branched $C_1$-$C_6$ alkyl, -straight or branched-$C_1$-$C_6$ haloalkyl, -straight or branched $C_1$-$C_6$ alkoxy, —$(CH_2)_x$ straight or branched $C_1$-$C_6$ alkoxy, -straight or branched $C_1$-$C_6$ haloalkoxy, —O-straight or branched-$C_1$-$C_6$ haloalkyl, —$C_1$-$C_6$ cycloalkyl, —$(CH_2)_x$— cycloalkyl, -heterocyclyl, —$(CH_2)_x$— heterocyclyl, —N-heterocyclyl, —$(CH_2)_x$N-heterocyclyl, aryl, -heteroaryl, —$(CH_2)_x$-heteroaryl, —O—$(CH_2)_x$CH(OH)

| Ex. | Compound Name | Chemical Structure |
|---|---|---|
| 18 | (2R)-N-hydroxy-2-methanesulfonyl-2-methyl-4-[7-(4-methylphenyl)-4-oxo-3,4-dihydro-1,2,3-benzotriazin-3-yl]butanamide | 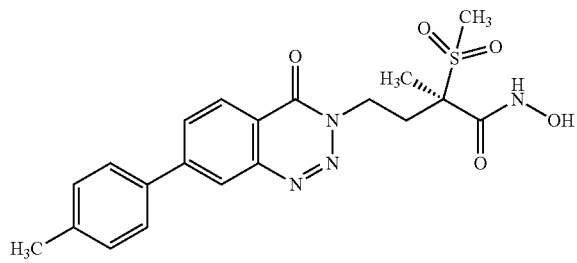 [SMILES: Cc1ccc(-c2ccc3c(=O)n(CC[C@](C)(C(=O)NO)S(C)(=O)=O)nnc3c2)cc1] |
| 19 | (2R)-4-[7-(2-fluoro-4-methylphenyl)-4-oxo-3,4-dihydro-1,2,3-benzotriazin-3-yl]-N-hydroxy-2-methanesulfonyl-2-methylbutanamide | 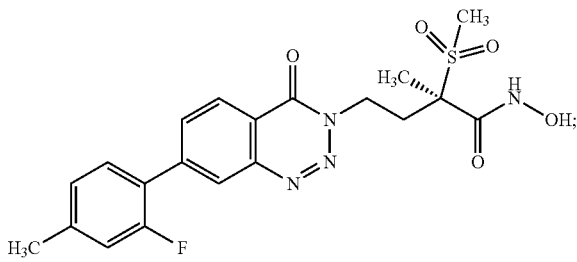 [SMILES: Cc1ccc(-c2ccc3c(=O)n(CC[C@](C)(C(=O)NO)S(C)(=O)=O)nnc3c2)c(F)c1] | or a pharmaceutically acceptable salt thereof.

In one aspect, the present invention relates to a compound of Formula (IV):

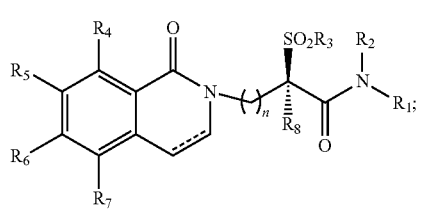

where:
═══ represents a double bond or is non-existent such that a single bond exists in position;

each $R^1$ or $R^2$ independently is selected from hydrogen, hydroxy or straight or branched $C_1$-$C_6$ alkyl;

$R^3$ is —$O^-$, -hydroxy, -straight or branched $C_1$-$C_6$ alkyl or -straight or branched $C_1$-$C_6$ alkoxy;

each $R^4$, $R^5$, $R^7$, $R^8$ or $R^9$ independently is selected from hydrogen, halogen, —OH, —$(CH_2)_x$OH, —C≡N, —$NR_a R_b$, $CH_2(OH)$, —$C(O)OR_f$, —$(CH_2)_x$— $C(O)OR_j$; —$NR_g$N-$R_h R_i$, —$(CH_2)_x$—$NR_g$—$NR_h R_i$, —O—$(CH_2)_x$—$N(R_g)$—$NR_h R_i$;

each $R_a$, $R_b$, $R_c$, $R_d$, $R_e$, or $R_f$ as defined above independently is selected from hydrogen, -straight or branched $C_1$-$C_6$ alkyl, -straight or branched $C_1$-$C_6$ alkoxy, —$(CH_2)_x$ straight or branched $C_1$-$C_6$ alkoxy, —$(CH_2)_x$OH, -straight or branched-$C_1$-$C_6$ haloalkyl, —$C_1$-$C_6$-cycloalkyl, —$(CH_2)_x C_1$-$C_6$-cycloalkyl, heterocyclyl, —$(CH_2)_x$heterocyclyl, —N-heterocyclyl, —$(CH_2)_x$N-heterocyclyl, aryl, heteroaryl, or —$(CH_2)_x$heteroaryl, —$(CHR_g)_x$heteroaryl, —$NR_g R_h$, —$C(O)OR_i$, —$(CH_2)_x C(O)OR_j$;

where:
each $R_g$, $R_h$, $R_i$, or $R_j$ is hydrogen, -straight or branched $C_1$-$C_6$ alkyl or -straight or branched-$C_1$-$C_6$ haloalkyl;

n is an integer selected from 1 to 3;
x is 0 or an integer from 1 to 6; or
a pharmaceutically salt thereof.

In one aspect, the present invention relates to a A compound of Formula (V):

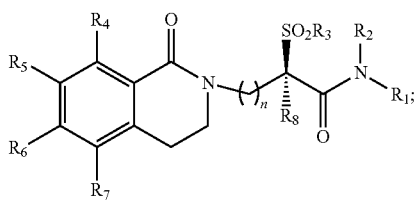

(V)

where:

each $R^1$ or $R^2$ independently is selected from hydrogen, hydroxy or straight or branched $C_1$-$C_6$ alkyl;

$R^3$ is —O—, -hydroxy, -straight or branched $C_1$-$C_6$ alkyl or -straight or branched $C_1$-$C_6$ alkoxy;

each $R^4$, $R^5$, $R^7$, $R^8$ or $R^9$ independently is selected from hydrogen, halogen, —OH, —(CH$_2$)$_x$OH, —C≡N, —NR$_a$R$_b$, -straight or branched $C_1$-$C_6$ alkyl, -straight or branched-$C_1$-$C_6$ haloalkyl, -straight or branched $C_1$-$C_6$ alkoxy, -straight or branched $C_1$-$C_6$ haloalkoxy, —O-straight or branched-$C_1$-$C_6$ haloalkyl;

$R^{6'}$ is heterocyclyl, aryl, or heteroaryl;

where:

each $R^4$, $R^5$, $R^6$, $R^7$, $R^8$ or $R^9$ as defined above optionally is further substituted with one or more substituents selected from hydrogen, halogen, —OH, —(CH$_2$)$_x$OH, —C≡N, —NR$_c$R$_d$, —(CH$_2$)$_x$NR$_e$R$_f$, -straight or branched $C_1$-$C_6$ alkyl, -straight or branched-$C_1$-$C_6$ haloalkyl, -straight or branched $C_1$-$C_6$ alkoxy, —(CH$_2$)$_x$ straight or branched $C_1$-$C_6$ alkoxy, -straight or branched $C_1$-$C_6$ haloalkoxy, —O-straight or branched-$C_1$-$C_6$ haloalkyl, —$C_1$-$C_6$ cycloalkyl, —(CH$_2$)$_x$— cycloalkyl, -heterocyclyl, —(CH$_2$)$_x$— heterocyclyl, —N-heterocyclyl, —(CH$_2$)$_x$N-heterocyclyl, aryl, -heteroaryl, —(CH$_2$)$_x$-heteroaryl, —O—(CH$_2$)$_x$CH(OH) CH$_2$(OH), —C(O)OR$_f$, —(CH$_2$)$_x$—C(O)OR$_f$; —NR$_g$— NR$_h$R$_i$, —(CH$_2$)$_x$—NR$_g$—NR$_h$R$_i$, —O—(CH$_2$)$_x$—N(R$_g$)— NR$_h$R$_i$;

each R$_a$, R$_b$, R$_c$, R$_d$, R$_e$, or R$_f$ as defined above independently is selected from hydrogen, -straight or branched $C_1$-$C_6$ alkyl, -straight or branched $C_1$-$C_6$ alkoxy, —(CH$_2$)$_x$ straight or branched $C_1$-$C_6$ alkoxy, —(CH$_2$)$_x$OH, -straight or branched-$C_1$-$C_6$ haloalkyl, —$C_1$-$C_6$-cycloalkyl, —(CH$_2$)$_x$C$_1$-$C_6$-cycloalkyl, heterocyclyl, —(CH$_2$)$_x$heterocyclyl, —N-heterocyclyl, —(CH$_2$)$_x$N-heterocyclyl, aryl, heteroaryl, or —(CH$_2$)$_x$heteroaryl, —(CHR$_g$)$_x$heteroaryl, —NR$_g$R$_h$, —C(O)OR$_i$, —(CH$_2$)$_x$C(O)OR$_j$;

where:

each R$_g$, R$_h$, R$_i$, or R$_j$ is hydrogen, -straight or branched $C_1$-$C_6$ alkyl or -straight or branched-$C_1$-$C_6$ haloalkyl;

n is an integer selected from 1 to 3;

x is 0 or an integer from 1 to 6; or a pharmaceutically salt thereof.

In one aspect, the present invention relates to a compound which is:

| Ex. | Compound Name | Chemical Structure |
|---|---|---|
| 91 | (2R)-4-[6-(2-fluorophenyl)-1-oxo-1,2,3,4-tetrahydroisoquinolin-2-yl]-N-hydroxy-2-methanesulfonyl-2-methylbutanamide | 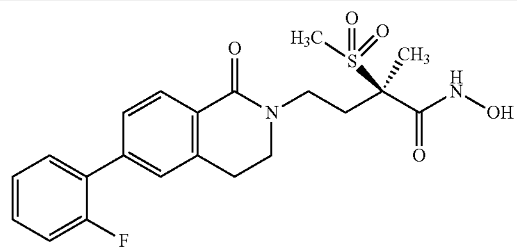 [SMILES: C[C@@](CCN1CCc2cc(-c3ccccc3F)ccc2C1=O)(C(=O)NO)S(C)(=O)=O] |
| 92 | (2R)-N-hydroxy-2-methanesulfonyl-2-methyl-4-(6-[4-[(morpholin-4-yl)methyl]phenyl}-1-oxo-1,2,3,4-tetrahydroisoquinolin-2-yl)butanamide | | or a pharmaceutically acceptable salt thereof.

In one aspect, the present invention relates to a compound of Formula (VI):

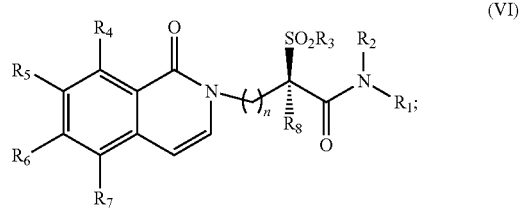

(VI)

wherein:

each $R^1$ or $R^2$ independently is selected from hydrogen, hydroxy or straight or branched $C_1$-$C_6$ alkyl;

$R^3$ is —O⁻, -hydroxy, -straight or branched $C_1$-$C_6$ alkyl or -straight or branched $C_1$-$C_6$ alkoxy;

each $R^4$, $R^5$, $R^7$, $R^8$ or $R^9$ independently is selected from hydrogen, halogen, —OH, —(CH$_2$)$_x$OH, —C≡N, —NR$_a$R$_b$, -straight or branched $C_1$-$C_6$ alkyl, -straight or branched-$C_1$-$C_6$ haloalkyl, -straight or branched $C_1$-$C_6$ alkoxy, -straight or branched $C_1$-$C_6$ haloalkoxy, —O-straight or branched-$C_1$-$C_6$ haloalkyl;

$R^{6'}$ is heterocyclyl, aryl, or heteroaryl;

where:

each $R^4$, $R^5$, $R^6$, $R^7$, $R^8$ or $R^9$ as defined above optionally is further substituted with one or more substituents selected from hydrogen, halogen, —OH, —(CH$_2$)$_x$OH, —C≡N, —NR$_c$R$_d$, —(CH$_2$)$_x$NR$_e$R$_f$, -straight or branched C$_1$-C$_6$ alkyl, -straight or branched-C$_1$-C$_6$ haloalkyl, -straight or branched C$_1$-C$_6$ alkoxy, —(CH$_2$)$_x$ straight or branched C$_1$-C$_6$ alkoxy, -straight or branched C$_1$-C$_6$ haloalkoxy, —O-straight or branched-C$_1$-C$_6$ haloalkyl, —C$_1$-C$_6$ cycloalkyl, —(CH$_2$)$_x$— cycloalkyl, -heterocyclyl, —(CH$_2$)$_x$— heterocyclyl, —N-heterocyclyl, —(CH$_2$)$_x$N-heterocyclyl, aryl, -heteroaryl, —(CH$_2$)$_x$-heteroaryl, —O—(CH$_2$)$_x$CH(OH)CH$_2$(OH), —C(O)OR$_f$, —(CH$_2$)$_x$—C(O)OR$_i$; —NR$_g$—NR$_h$R$_i$, —(CH$_2$)$_x$—NR$_g$—NR$_h$R$_i$, —O—(CH$_2$)$_x$—N(R$_g$)—NR$_h$R$_i$;

each R$_a$, R$_b$, R$_c$, R$_d$, R$_e$, or R$_f$ as defined above independently is selected from hydrogen, -straight or branched C$_1$-C$_6$ alkyl, -straight or branched C$_1$-C$_6$ alkoxy, —(CH$_2$)$_x$ straight or branched C$_1$-C$_6$ alkoxy, —(CH$_2$)$_x$OH, -straight or branched-C$_1$-C$_6$ haloalkyl, —C$_1$-C$_6$-cycloalkyl, —(CH$_2$)$_x$C$_1$-C$_6$-cycloalkyl, heterocyclyl, —(CH$_2$)$_x$heterocyclyl, —N-heterocyclyl, —(CH$_2$)$_x$N-heterocyclyl, aryl, heteroaryl, or —(CH$_2$)$_x$heteroaryl, —(CHR$_g$)$_x$heteroaryl, —NR$_g$R$_h$, —C(O)OR$_i$, —(CH$_2$)$_x$C(O)OR$_i$;

where:

each R$_g$, R$_h$, R$_i$, or R$_l$ is hydrogen, -straight or branched C$_1$-C$_6$ alkyl or -straight or branched-C$_1$-C$_6$ haloalkyl;

n is an integer selected from 1 to 3;

x is 0 or an integer from 1 to 6; or a pharmaceutically salt thereof.

In one aspect, the present invention relates to a compound which is:

| Ex. | Compound Name | Chemical Structure |
|---|---|---|
| 53 | (2R)-N-hydroxy-2-methanesulfonyl-4-[6-(4-methoxyphenyl)-1-oxo-1,2-dihydroisoquinolin-2-yl]-2-methylbutanamide | 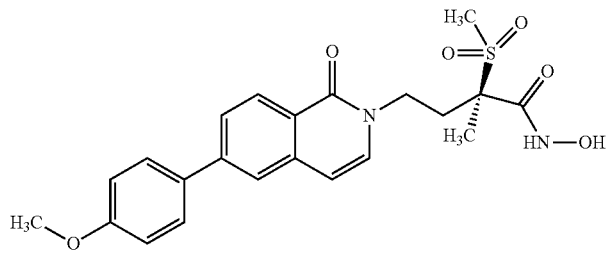 |
| 54 | (2R)-N-hydroxy-2-methanesulfonyl-2-methyl-4-[6-(4-methylphenyl)-1-oxo-1,2-dihydroisoquinolin-2-yl]butanamide | 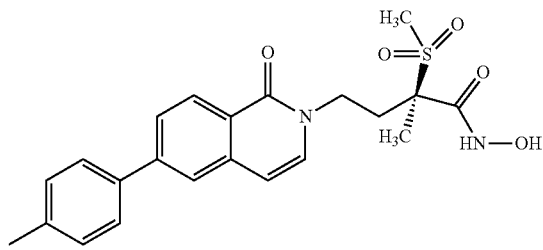 |
| 55 | (2R)-4-[6-(2-fluoro-4-methoxyphenyl)-1-oxo-1,2-dihydroisoquinolin-2-yl]-N-hydroxy-2-methanesulfonyl-2-methylbutanamide | 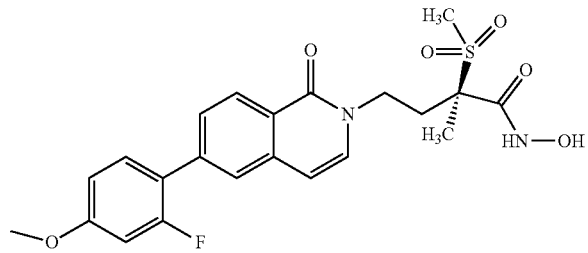 |
| 56 | (2R)-N-hydroxy-2-methanesulfonyl-2-methyl-4-(1-oxo-6-phenyl-1,2-dihydroisoquinolin-2-yl)butanamide | 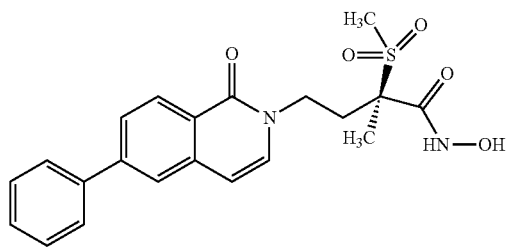 |

| Ex. | Compound Name | Chemical Structure |
|---|---|---|
| 57 | (2R)-4-[6-(1,3-dihydro-2-benzofuran-5-yl)-1-oxo-1,2-dihydroisoquinolin-2-yl]-N-hydroxy-2-methanesulfonyl-2-methylbutanamide | 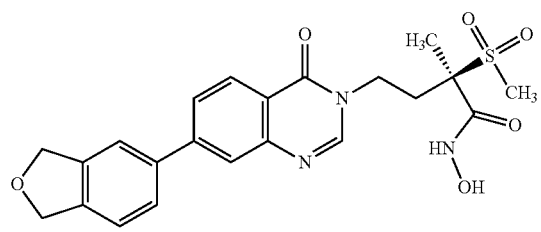 [SMILES: C[C@@](CCn1cnc2cc(-c3ccc4c(c3)COC4)ccc2c1=O)(C(=O)NO)S(C)(=O)=O] |
| 58 | (2R)-N-hydroxy-2-methanesulfonyl-2-methyl-4-[6-(5-methyl-1,3-thiazol-2-yl)-1-oxo-1,2-dihydroisoquinolin-2-yl]butanamide | 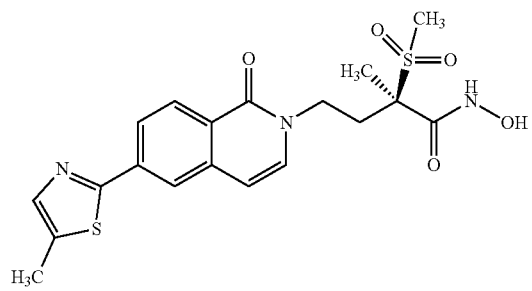 [SMILES: Cc1cnc(-c2ccc3c(=O)n(CC[C@](C)(C(=O)NO)S(C)(=O)=O)ccc3c2)s1] |
| 59 | (2R)-4-[6-(4-cyano-2-fluorophenyl)-1-oxo-1,2-dihydroisoquinolin-2-yl]-N-hydroxy-2-methanesulfonyl-2-methylbutanamide | 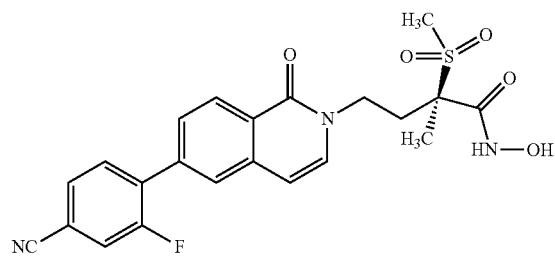 |
| 60 | (2R)-N-hydroxy-2-methanesulfonyl-4-[6-(6-methoxypyridin-3-yl)-1-oxo-1,2-dihydroisoquinolin-2-yl]-2-methylbutanamide | 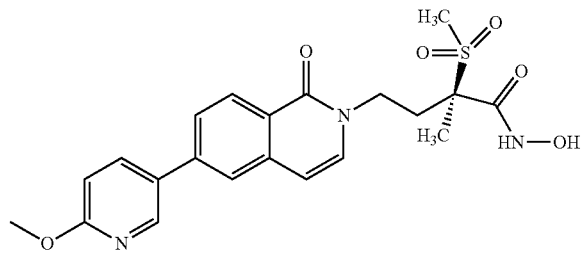 |
| 61 | (2R)-4-{6-[4-(dimethylamino)phenyl]-1-oxo-1,2-dihydroisoquinolin-2-yl}-N-hydroxy-2-methanesulfonyl-2-methylbutanamide | 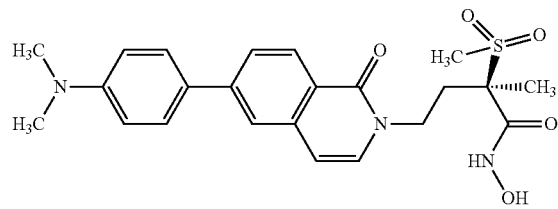 [SMILES: CN(C)c1ccc(-c2ccc3c(=O)n(CC[C@](C)(C(=O)NO)S(C)(=O)=O)ccc3c2)cc1] |
| 62 | (2R)-4-{6-[6-(dimethylamino)pyridin-3-yl]-1-oxo-1,2-dihydroisoquinolin-2-yl}-N-hydroxy-2-methanesulfonyl-2-methylbutanamide | 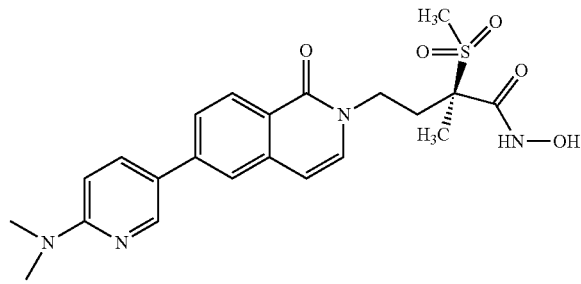 |

-continued

| Ex. | Compound Name | Chemical Structure |
|---|---|---|
| 63 | (2R)-4-{6-[2-(dimethylamino)pyrimidin-5-yl]-1-oxo-1,2-dihydroisoquinolin-2-yl}-N-hydroxy-2-methanesulfonyl-2-methylbutanamide | 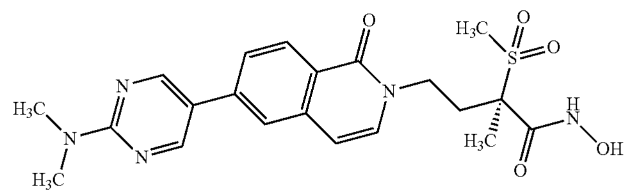 [SMILES: CN(C)c1ncc(-c2ccc3c(=O)n(CC[C@](C)(C(=O)NO)S(C)(=O)=O)ccc3c2)cn1] |
| 64 | (2R)-N-hydroxy-2-methanesulfonyl-2-methyl-4-(6-{4-[(morpholin-4-yl)methyl]phenyl}-1-oxo-1,2-dihydroisoquinolin-2-yl)butanamide | 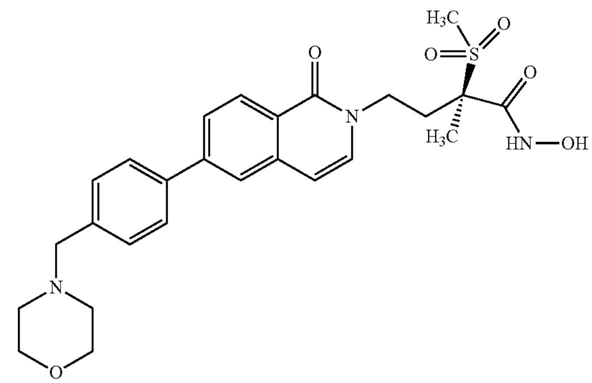 |
| 65 | (2R)-4-(6-{4-[(dimethylamino)methyl]-2-fluorophenyl}-1-oxo-1,2-dihydroisoquinolin-2-yl)-N-hydroxy-2-methanesulfonyl-2-methylbutanamide | 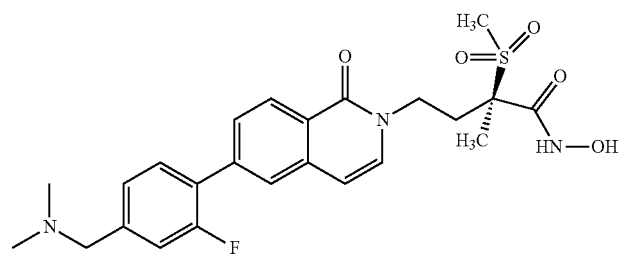 |
| 66 | (2R)-4-[6-(2-fluoro-4-{[(2-methoxyethyl)(methyl)amino]methyl}phenyl)-1-oxo-1,2-dihydroisoquinolin-2-yl]-N-hydroxy-2-methanesulfonyl-2-methylbutanamide (GSK3212160A) | 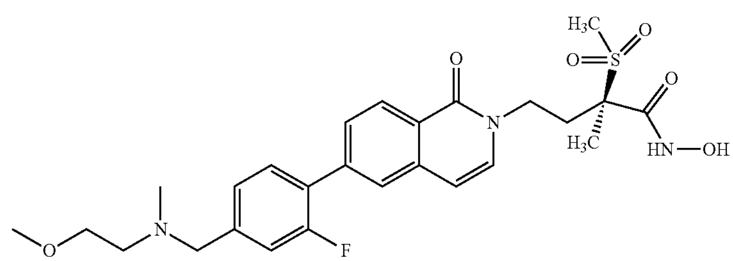 |
| 67 | (2R)-4-[6-(2-fluoro-4-{[(2-methoxyethyl)amino]methyl}phenyl)-1-oxo-1,2-dihydroisoquinolin-2-yl]-N-hydroxy-2-methanesulfonyl-2-methylbutanamide | 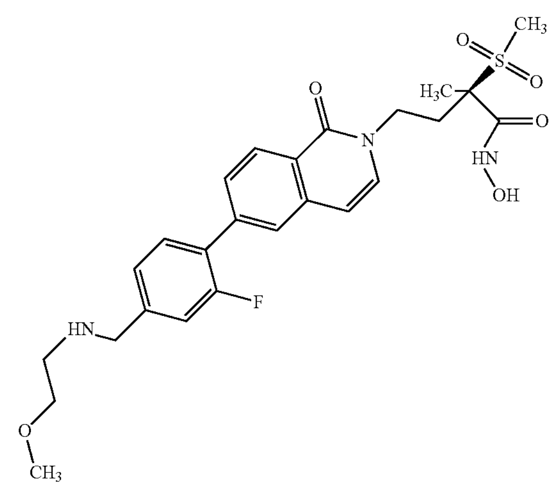 [SMILES: COCCNCc1ccc(-c2ccc3c(=O)n(CC[C@](C)(C(=O)NO)S(C)(=O)=O)ccc3c2)c(F)c1] |

-continued

| Ex. | Compound Name | Chemical Structure |
|---|---|---|
| 68 | (2R)-4-[6-(2-fluoro-4-{[(2-methoxy-2-methylpropyl)amino]methyl}phenyl)-1-oxo-1,2-dihydroisoquinolin-2-yl]-N-hydroxy-2-methanesulfonyl-2-methylbutanamide | 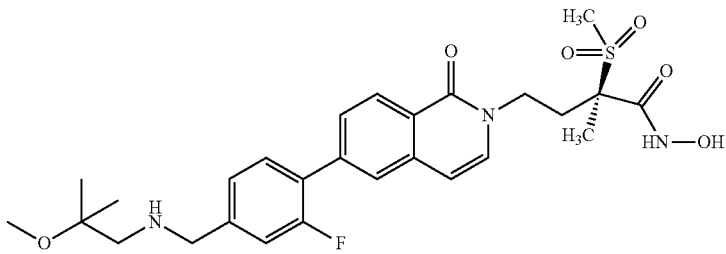 |
| 69 | (2R)-4-(6-{4-[(dimethylamino)methyl]-2,3-difluorophenyl}-1-oxo-1,2-dihydroisoquinolin-2-yl)-N-hydroxy-2-methanesulfonyl-2-methylbutanamide | 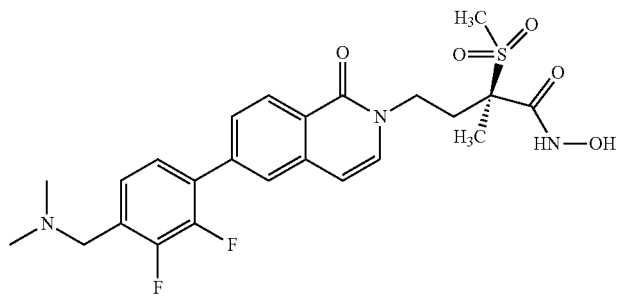 |
| 70 | (2R)-4-[6-(2-fluoro-4-{[(3-methoxypropyl)(methyl)amino]methyl}phenyl)-1-oxo-1,2-dihydroisoquinolin-2-yl]-N-hydroxy-2-methanesulfonyl-2-methylbutanamide | 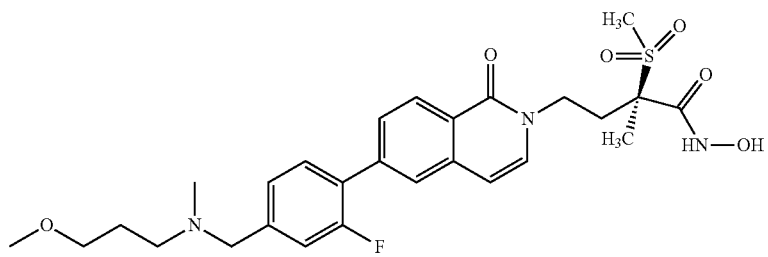 |
| 71 | (2R)-4-[6-(2,3-difluoro-4-{[(2-methoxyethyl)amino]methyl}phenyl)-1-oxo-1,2-dihydroisoquinolin-2-yl]-N-hydroxy-2-methanesulfonyl-2-methylbutanamide | 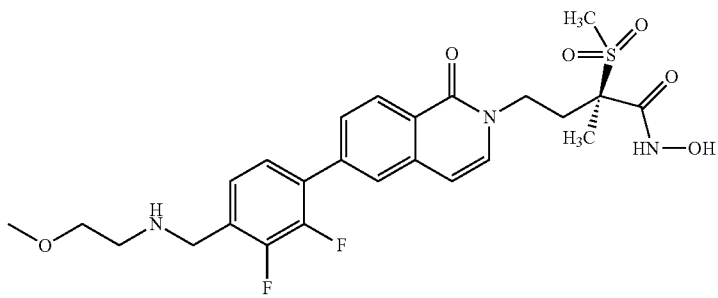 |
| 72 | (2R)-4-[6-(4-{[(2-ethoxyethyl)amino]methyl}-2-fluorophenyl)-1-oxo-1,2-dihydroisoquinolin-2-yl]-N-hydroxy-2-methanesulfonyl-2-methylbutanamide | 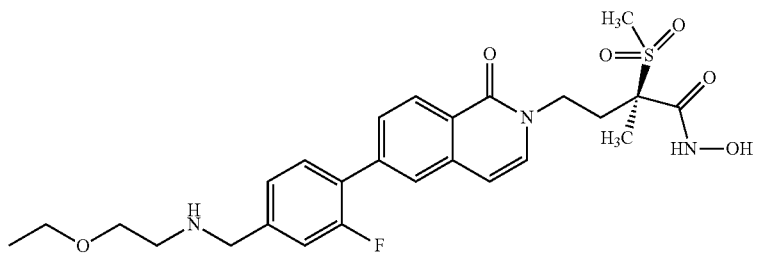 |

-continued

| Ex. | Compound Name | Chemical Structure |
|---|---|---|
| 73 | (2R)-4-{6-[2-fluoro-4-({[2-(propan-2-yloxy)ethyl]amino}methyl)phenyl]-1-oxo-1,2-dihydroisoquinolin-2-yl}-N-hydroxy-2-methanesulfonyl-2-methylbutanamide | 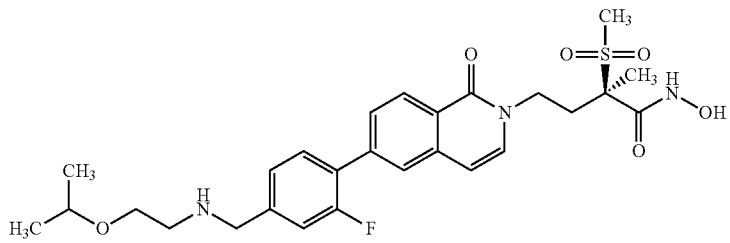 [SMILES: CC(C)OCCNCc1ccc(-c2ccc3c(=O)n(CC[C@](C)(C(=O)NO)S(C)(=O)=O)ccc3c2)c(F)c1] |
| 74 | (2R)-4-[6-(2-fluoro-4-{[(2-hydroxyethyl)(methyl)amino]methyl}phenyl)-1-oxo-1,2-dihydroisoquinolin-2-yl]-N-hydroxy-2-methanesulfonyl-2-methylbutanamide | 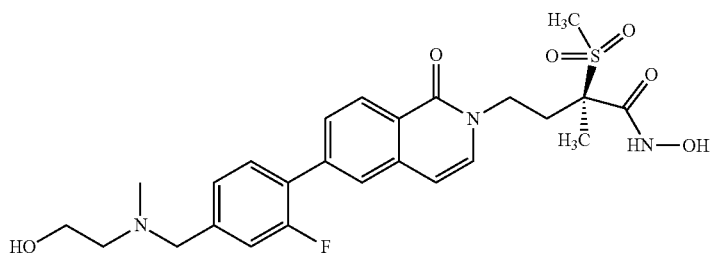 [SMILES: CN(CCO)Cc1ccc(-c2ccc3c(=O)n(CC[C@@](C)(C(=O)NO)S(C)(=O)=O)ccc3c2)c(F)c1] |
| 75 | (2R)-4-(6-{4-[(cyclopropylamino)methyl]phenyl}-1-oxo-1,2-dihydroisoquinolin-2-yl)-N-hydroxy-2-methanesulfonyl-2-methylbutanamide | 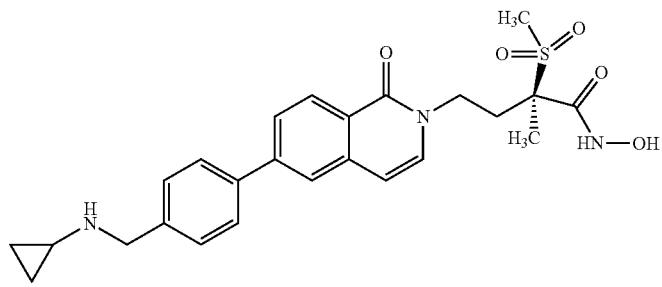 [SMILES: C[C@](CCn1ccc2cc(-c3ccc(CNC4CC4)cc3)ccc2c1=O)(C(=O)NO)S(C)(=O)=O] |
| 76 | (2R)-4-(6-{4-[(cyclopropylamino)methyl]-2-fluorophenyl}-1-oxo-1,2-dihydroisoquinolin-2-yl)-N-hydroxy-2-methanesulfonyl-2-methylbutanamide | 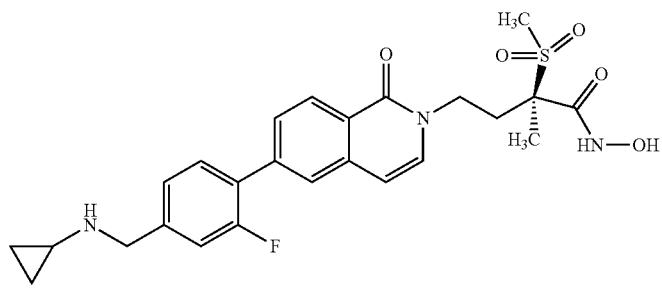 [SMILES: C[C@](CCn1ccc2cc(-c3ccc(CNC4CC4)cc3F)ccc2c1=O)(C(=O)NO)S(C)(=O)=O] |
| 77 | (2R)-N-hydroxy-2-methanesulfonyl-2-methyl-4-(1-oxo-6-{4-[(1,2,2-trimethylhydrazin-1-yl)methyl]phenyl}-1,2-dihydroisoquinolin-2-yl)butanamide | 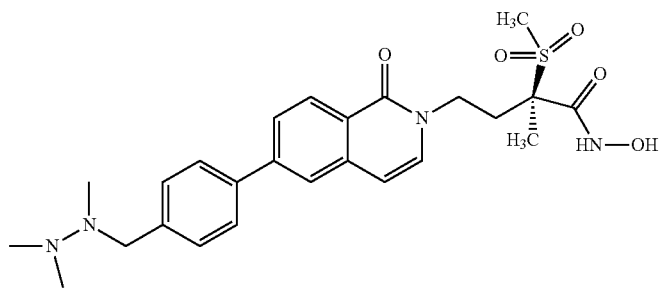 [SMILES: CN(C)N(C)Cc1ccc(-c2ccc3c(=O)n(CC[C@@](C)(C(=O)NO)S(C)(=O)=O)ccc3c2)cc1] |

| Ex. | Compound Name | Chemical Structure |
|---|---|---|
| 78 | (2R)-N-hydroxy-2-methanesulfonyl-4-(6-{4-[(methoxyamino)methyl]phenyl}-1-oxo-1,2-dihydroisoquinolin-2-yl)-2-methylbutanamide | 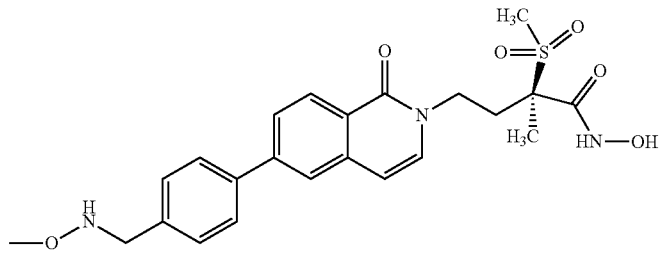 [SMILES: CONCc1ccc(-c2ccc3c(=O)n(CC[C@@](C)(C(=O)NO)S(C)(=O)=O)ccc3c2)cc1] |
| 79 | (2R)-4-(6-{4-[(2,2-dimethylhydrazin-1-yl)methyl]phenyl}-1-oxo-1,2-dihydroisoquinolin-2-yl)-N-hydroxy-2-methanesulfonyl-2-methylbutanamide | 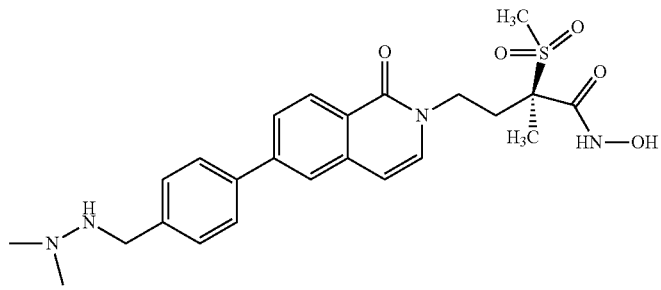 [SMILES: CN(C)NCc1ccc(-c2ccc3c(=O)n(CC[C@@](C)(C(=O)NO)S(C)(=O)=O)ccc3c2)cc1] |
| 80 | (2R)-N-hydroxy-2-methanesulfonyl-2-methyl-4-(6-{4-[2-(morpholin-4-yl)ethyl]phenyl}-1-oxo-1,2-dihydroisoquinolin-2-yl)butanamide | 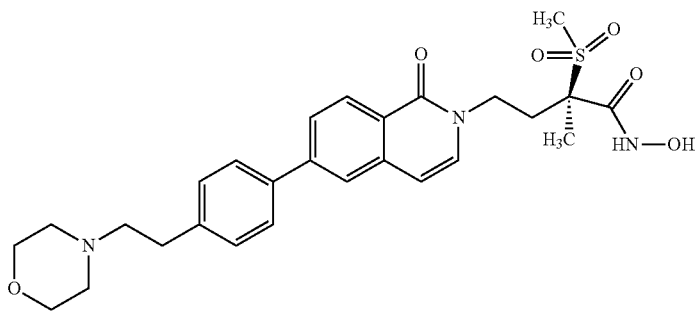 [SMILES: C[C@](CCn1ccc2cc(-c3ccc(CCN4CCOCC4)cc3)ccc2c1=O)(C(=O)NO)S(C)(=O)=O] |
| 81 | (2R)-N-hydroxy-2-methanesulfonyl-2-methyl-4-(1-oxo-6-{4-[(2-oxopyrrolidin-1-yl)methyl]phenyl}-1,2-dihydroisoquinolin-2-yl)butanamide | 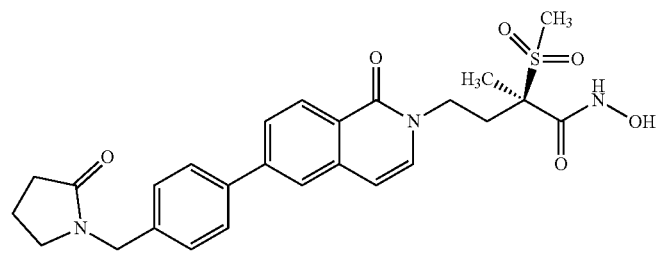 [SMILES: C[C@@](CCn1ccc2cc(-c3ccc(CN4CCCC4=O)cc3)ccc2c1=O)(C(=O)NO)S(C)(=O)=O] |
| 82 | (2R)-4-[6-(6-{2-[cyclopropyl(methyl)amino]ethoxy}pyridin-3-yl)-1-oxo-1,2-dihydroisoquinolin-2-yl]-N-hydroxy-2-methanesulfonyl-2-methylbutanamide | 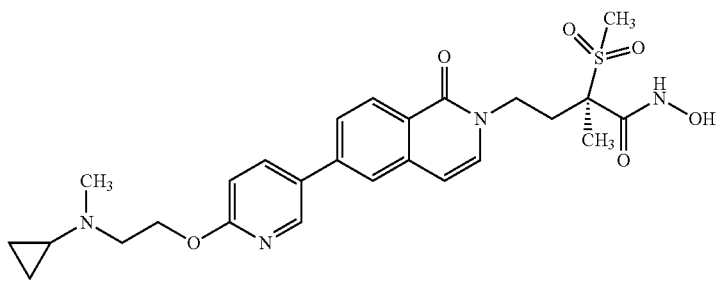 [SMILES: CN(CCOc1ccc(-c2ccc3c(=O)n(CC[C@](C)(C(=O)NO)S(C)(=O)=O)ccc3c2)cn1)C1CC1] |

| Ex. | Compound Name | Chemical Structure |
|---|---|---|
| 83 | (2R)-4-[4-fluoro-6-(4-methoxyphenyl)-1-oxo-1,2-dihydroisoquinolin-2-yl]-N-hydroxy-2-methanesulfonyl-2-methylbutanamide | 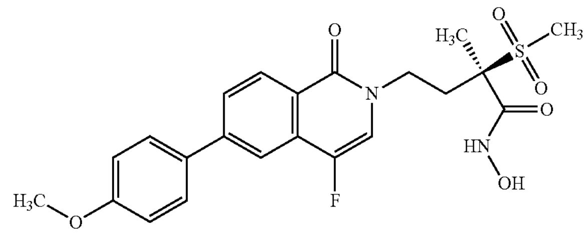 |
| 84 | (2R)-4-(4-fluoro-1-oxo-6-phenyl-1,2-dihydroisoquinolin-2-yl)-N-hydroxy-2-methanesulfonyl-2-methylbutanamide | 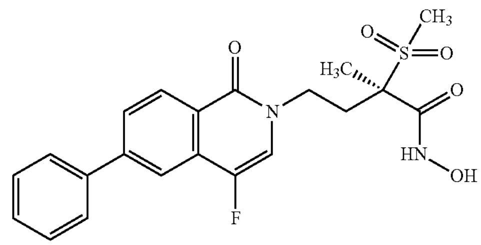 [SMILES: C[C@@](CCn1cc(F)c2cc(-c3ccccc3)ccc2c1=O)(C(=O)NO)S(C)(=O)=O] |
| 85 | (2R)-4-(6-{4-[(dimethylamino)methyl]phenyl}-4-fluoro-1-oxo-1,2-dihydroisoquinolin-2-yl)-N-hydroxy-2-methanesulfonyl-2-methylbutanamide | 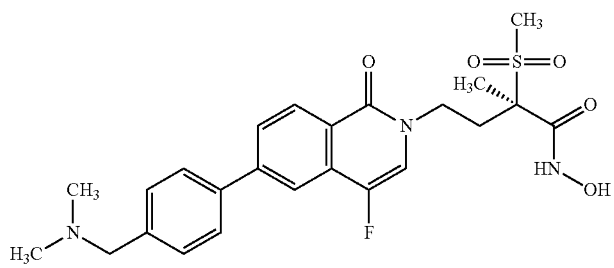 [SMILES: CN(C)Cc1ccc(-c2ccc3c(=O)n(CC[C@](C)(C(=O)NO)S(C)(=O)=O)cc(F)c3c2)cc1] |
| 86 | (2R)-4-[6-(6-ethoxypyridin-3-yl)-4-fluoro-1-oxo-1,2-dihydroisoquinolin-2-yl]-N-hydroxy-2-methanesulfonyl-2-methylbutanamide | 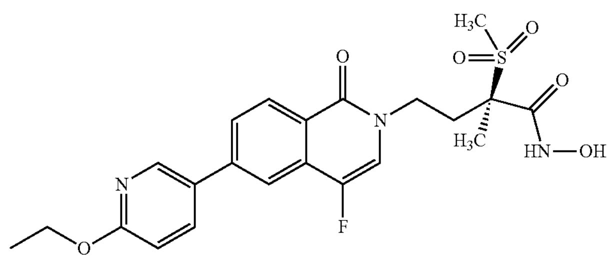 |
| 87 | (2R)-4-[4-fluoro-6-(6-methoxypyridin-3-yl)-1-oxo-1,2-dihydroisoquinolin-2-yl]-N-hydroxy-2-methanesulfonyl-2-methylbutanamide | 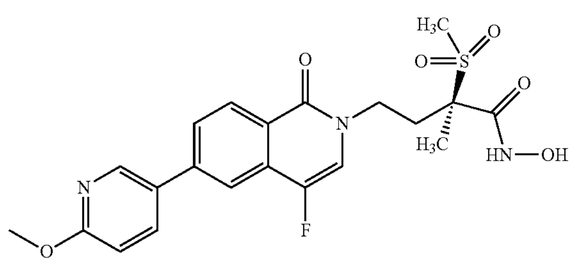 |
| 88 | (2R)-4-[4-fluoro-6-(2-fluoro-4-{[(2-methoxyethyl)amino]methyl}phenyl)-1-oxo-1,2-dihydroisoquinolin-2-yl]-N-hydroxy-2-methanesulfonyl-2-methylbutanamide | 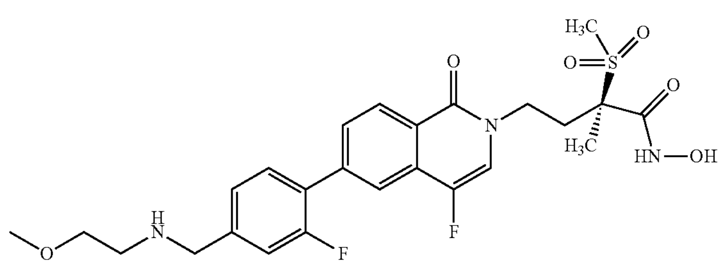 |

| Ex. | Compound Name | Chemical Structure |
|---|---|---|
| 89 | (2R)-4-(6-{4-[(dimethylamino)methyl]-2-fluorophenyl}-4-fluoro-1-oxo-1,2-dihydroisoquinolin-2-yl)-N-hydroxy-2-methanesulfonyl-2-methylbutanamide | 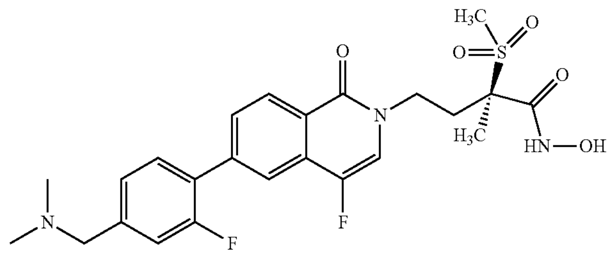 |
| 90 | (2R)-4-{6-[6-(dimethylamino)pyridin-3-yl]-4-fluoro-1-oxo-1,2-dihydroisoquinolin-2-yl}-N-hydroxy-2-methanesulfonyl-2-methylbutanamide | 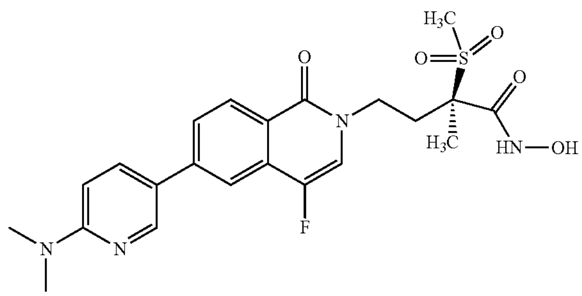 [SMILES: CN(C)c1ccc(-c2ccc3c(=O)n(CC[C@@](C)(C(=O)NO)S(C)(=O)=O)cc(F)c3c2)cn1] |
| 93 | (2R)-N-hydroxy-4-{6-[4-(2-hydroxyethyl)phenyl]-1-oxo-1,2-dihydroisoquinolin-2-yl}-2-methanesulfonyl-2-methylbutanamide | 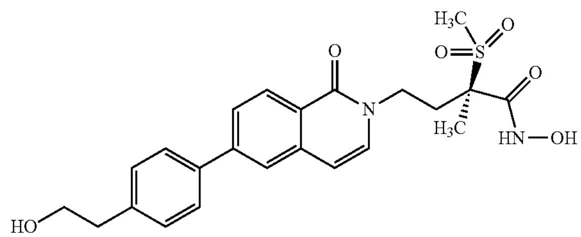 |
| 94 | 2-(4-{2-[(3R)-3-(hydroxycarbamoyl)-3-methanesulfonyl-3-methylpropyl]-1-oxo-1,2-dihydroisoquinolin-6-yl}phenyl)ethyl 2-(dimethylamino)acetate | | or a pharmaceutically acceptable salt thereof.

In one aspect, the present invention relates to a compound which is:

(R)—N-hydroxy-2-methyl-2-(methylsulfonyl)-4-(4-oxo-7-phenylquinazolin-3(4H)-yl)butanamide (Example 1

(R)—N-hydroxy-2-methyl-2-(methylsulfonyl)-4-(4-oxo-7-(p-tolyl)quinazolin-3(4H)-yl)butanamide (Example 2

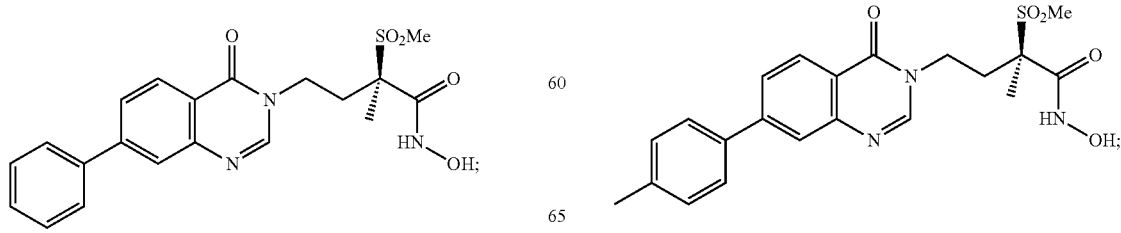

(R)—N-hydroxy-4-(7-(4-methoxyphenyl)-4-oxoquinazolin-3(4H)-yl)-2-methyl-2-(methylsulfonyl)butanamide (Example 3

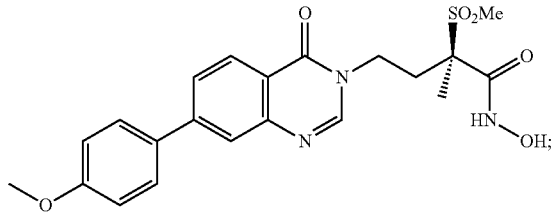 [SMILES: COc1ccc(-c2ccc3c(=O)n(CC[C@](C)(C(=O)NO)S(C)(=O)=O)cnc3c2)cc1]

(R)-4-(7-(4-(dimethylamino)phenyl)-4-oxoquinazolin-3(4H)-yl)-N-hydroxy-2-methyl-2-(methylsulfonyl)butanamide trifluoroacetic acid salt (Example 4

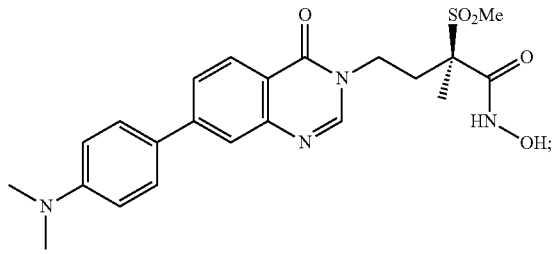 [SMILES: CN(C)c1ccc(-c2ccc3c(=O)n(CC[C@](C)(C(=O)NO)S(C)(=O)=O)cnc3c2)cc1]

(R)-4-(7-(4-(difluoromethoxy)phenyl)-4-oxoquinazolin-3(4H)-yl)-N-hydroxy-2-methyl-2-(methylsulfonyl)butanamide (Example 5)

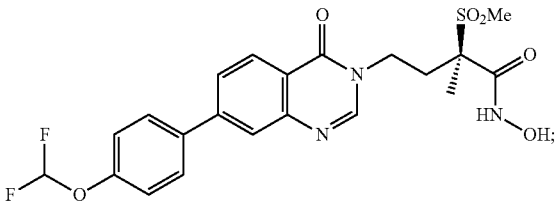 [SMILES: C[C@@](CCn1cnc2cc(-c3ccc(OC(F)F)cc3)ccc2c1=O)(C(=O)NO)S(C)(=O)=O]

(R)-4-(7-(2,3-difluorophenyl)-4-oxoquinazolin-3(4H)-yl)-N-hydroxy-2-methyl-2-(methylsulfonyl)butanamide (Example 6)

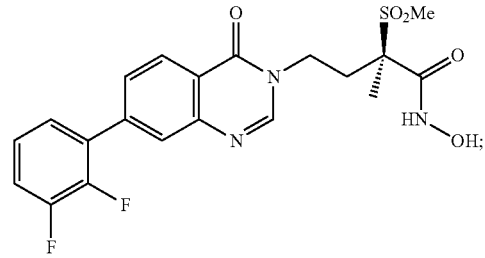 [SMILES: C[C@@](CCn1cnc2cc(-c3cccc(F)c3F)ccc2c1=O)(C(=O)NO)S(C)(=O)=O]

(R)-4-(7-(2,5-difluorophenyl)-4-oxoquinazolin-3(4H)-yl)-N-hydroxy-2-methyl-2-(methylsulfonyl)butanamide (Example 7)

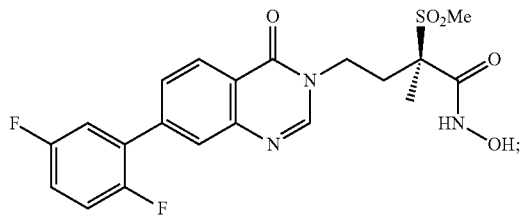 [SMILES: C[C@@](CCn1cnc2cc(-c3cc(F)ccc3F)ccc2c1=O)(C(=O)NO)S(C)(=O)=O]

(R)-4-(7-(2-fluorophenyl)-4-oxoquinazolin-3(4H)-yl)-N-hydroxy-2-methyl-2-(methylsulfonyl)butanamide (Example 8)

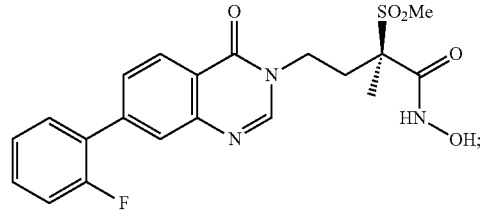 [SMILES: C[C@@](CCn1cnc2cc(-c3ccccc3F)ccc2c1=O)(C(=O)NO)S(C)(=O)=O]

(R)-4-(7-(3-fluoro-4-methylphenyl)-4-oxoquinazolin-3(4H)-yl)-N-hydroxy-2-methyl-2-(methylsulfonyl)butanamide (Example 9)

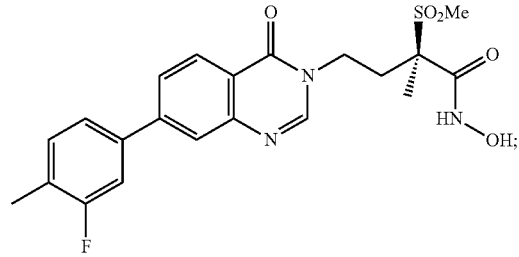 [SMILES: Cc1ccc(-c2ccc3c(=O)n(CC[C@](C)(C(=O)NO)S(C)(=O)=O)cnc3c2)cc1F]

(R)-4-(7-(4-(difluoromethyl)phenyl)-4-oxoquinazolin-3(4H)-yl)-N-hydroxy-2-methyl-2-(methylsulfonyl)butanamide (Example 10)

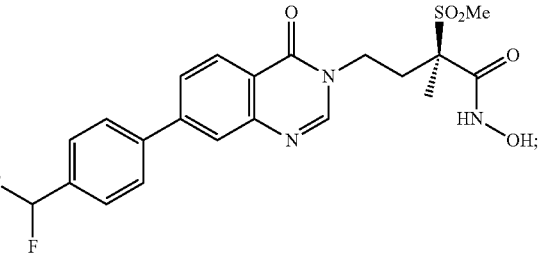

(2R)-4-[7-(2,6-difluorophenyl)-4-oxo-3,4-dihydro-
quinazolin-3-yl]-N-hydroxy-2-methanesulfonyl-2-
methylbutanamide (Example 11)

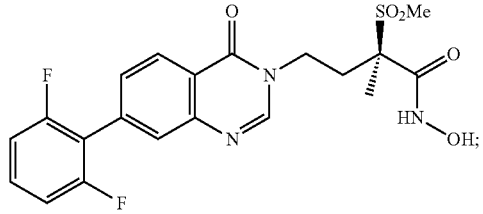 [SMILES: C[C@@](CCn1cnc2cc(-c3c(F)cccc3F)ccc2c1=O)(C(=O)NO)S(C)(=O)=O]

(2R)-4-[7-(1,3-dihydro-2-benzofuran-5-yl)-4-oxo-3,
4-dihydroquinazolin-3-yl]-N-hydroxy-2-methanesul-
fonyl-2-methylbutanamide (Example 12)

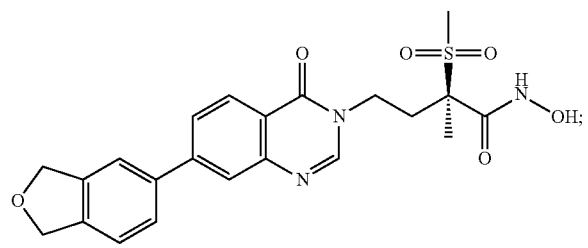

(2R)-4-[6-fluoro-7-(4-methoxyphenyl)-4-oxo-3,4-
dihydroquinazolin-3-yl]-N-hydroxy-2-methanesulfo-
nyl-2-methylbutanamide (Example 13)

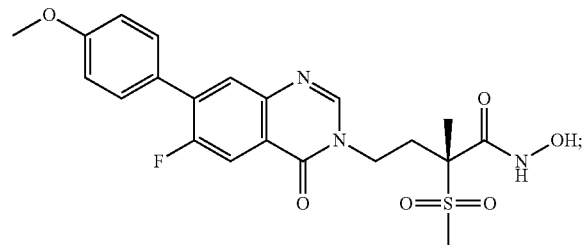 [SMILES: COc1ccc(-c2cc3ncn(CC[C@](C)(C(=O)NO)S(C)(=O)=O)c(=O)c3cc2F)cc1]

(2R)-4-[8-fluoro-7-(4-methoxyphenyl)-4-oxo-3,4-
dihydroquinazolin-3-yl]-N-hydroxy-2-methanesulfo-
nyl-2-methylbutanamide (Example 14)

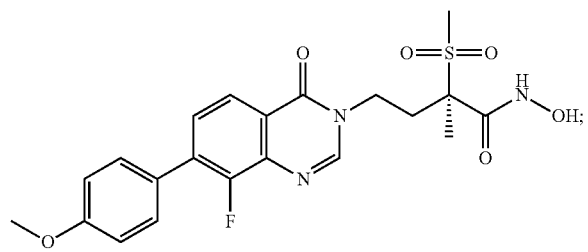 [SMILES: COc1ccc(-c2ccc3c(=O)n(CC[C@](C)(C(=O)NO)S(C)(=O)=O)cnc3c2F)cc1]

(2R)-4-[6-fluoro-7-(4-methoxyphenyl)-4-oxo-3,4-
dihydroquinazolin-3-yl]-N-hydroxy-2-methanesulfo-
nyl-2-methylbutanamide (Example 15)

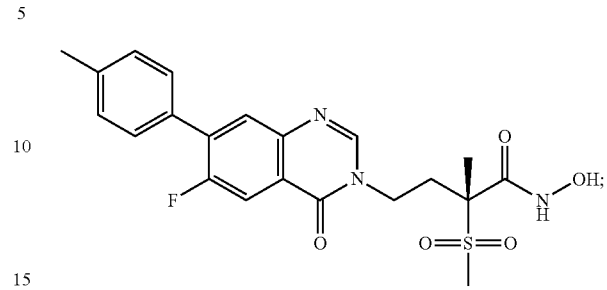

(2R)-4-[5-fluoro-7-(4-methoxyphenyl)-4-oxo-3,4-
dihydroquinazolin-3-yl]-N-hydroxy-2-methanesulfo-
nyl-2-methylbutanamide (Example 16)

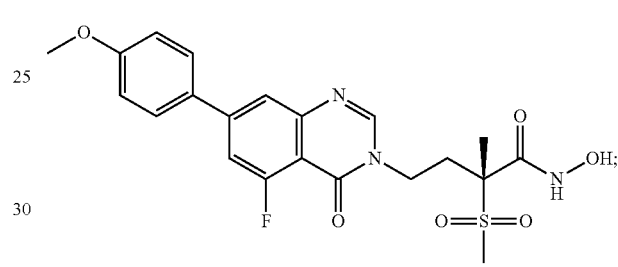

(2R)-4-[5-fluoro-7-(4-methoxyphenyl)-4-oxo-3,4-
dihydroquinazolin-3-yl]-N-hydroxy-2-methanesulfo-
nyl-2-methylbutanamide (Example 17)

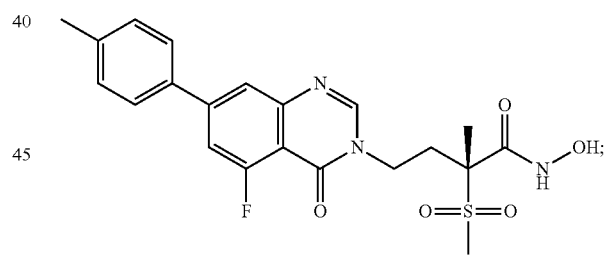

(2R)—N-hydroxy-2-methanesulfonyl-2-methy-4-[7-
(4-methylphenyl)-4-oxo-3,4-dihydro-1,2,3-benzotri-
azin-3-yl]butanamide (Example 18)

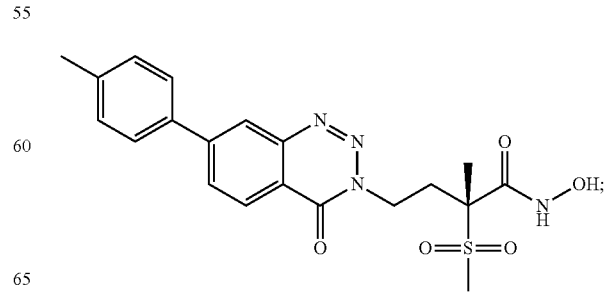

(2R)-4-[7-(2-fluoro-4-methylphenyl)-4-OXO-3,4-dihydro-1,2,3-benzotriazin-3-yl]-N-hydroxy-2-methanesulfonyl-2-methylbutanamide (Example 19)

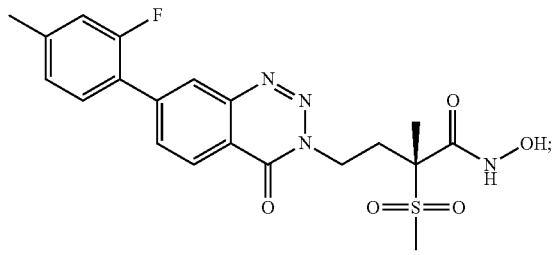 [SMILES: Cc1ccc(-c2ccc3c(=O)n(CC[C@](C)(C(=O)NO)S(C)(=O)=O)nnc3c2)c(F)c1]

(2R)-4-(6-fluoro-7-{4-[(morpholin-4-yl)methyl]phenyl}-4-oxo-3,4-dihydroquinazolin-3-yl)-N-hydroxy-2-methanesulfonyl-2-methylbutanamide) Example 20)

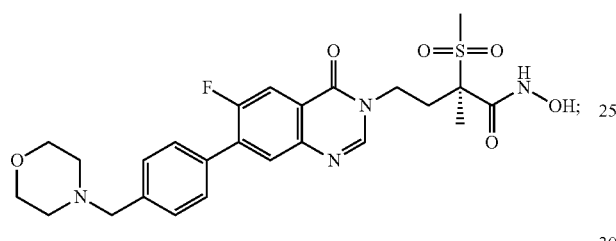

(2)-4(6-fluoro-7-{4-[2-(morpholin-4-yl)ethyl]phenyl}-4-oxo-3,4-dihydroquinazolin-3-yl)-N-hydroxy-2-methanesulfonyl-2-methylbutanamide (Example 21)

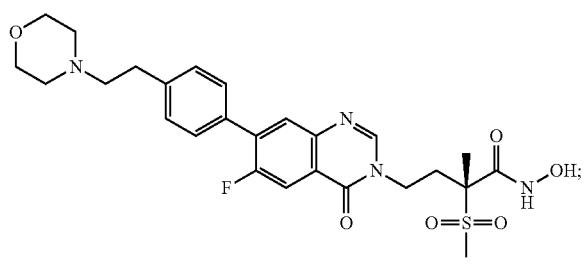 [SMILES: C[C@@](CCn1cnc2cc(-c3ccc(CCN4CCOCC4)cc3)c(F)cc2c1=O)(C(=O)NO)S(C)(=O)=O]

(2R)-4-[7-(4-{[cyclopropyl(methyl)amino]methyl}phenyl)-6-fluoro-4-oxo-3,4-dihydroquinazolin-3-yl]-N-hydroxy-2-methanesulfonyl-2-methylbutanamide (Example 22)

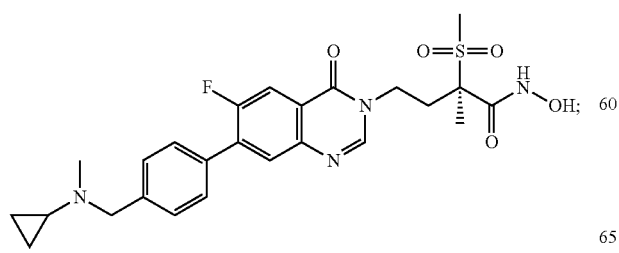

(2R)-4-[6-fluoro-7-(2-fluoro-4-{[(2-methoxyethyl)(methyl)amino]methyl}phenyl)-4-oxo-3,4-dihydroquinazolin-3-yl]-N-hydroxy-2-methanesulfonyl-2-methylbutanamide (Example 23)

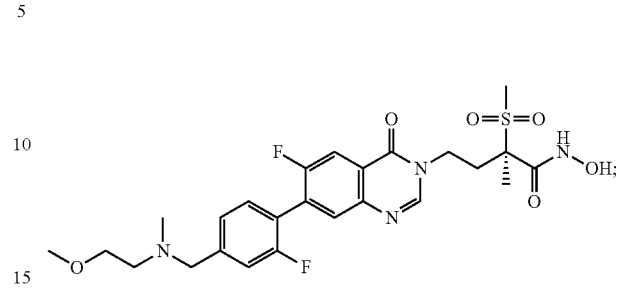

(2R)-4-(7-{2,3-difluoro-4-[2-(3-methoxyazetidin-1-yl)ethyl]phenyl}-6-fluoro-4-oxo-3,4-dihydroquinzolin-3-yl)-N-hydroxy-2-methanesulfonyl-2-methylbutanamide

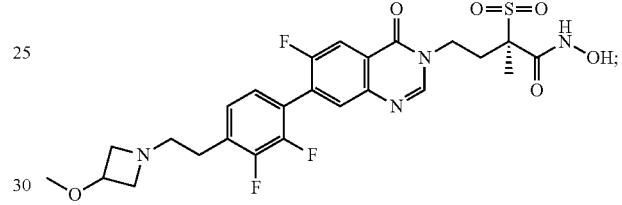

(2R)-4-(7-{4-[(cyclopropylamino)methyl]-2-fluorophenyl}-6-fluoro-4-oxo-3,4-dihydroquinazolin-3-yl)-N-hydroxy-2-methanesulfonyl-2-methylbutanamide (Example 25)

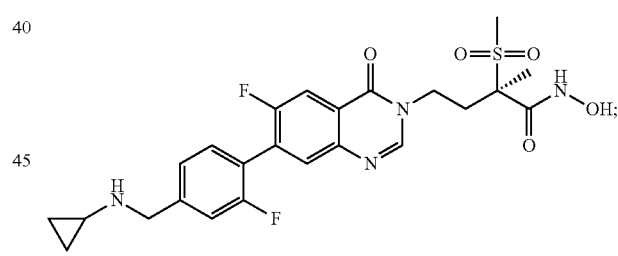

(2R)-4-(6-fluoro-7-{2-fluoro-4-[(morpholin-4-yl)methyl]phenyl}-4-oxo-3,4-dihydroquinazolin-3-yl)-N-hydroxy-2-methanesulfonyl-2-methylbutanamide (Example 26)

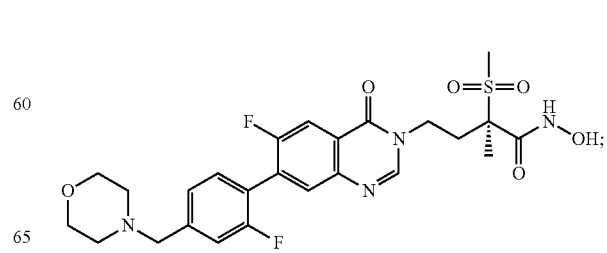

| 51 | 52 |

(2R)-4-{6-fluoro-7-[2-fluoro-4-(2-hydroxyethyl)phenyl]-4-oxo-3,4-dihydroquinazolin-3-yl}-N-hydroxy-2-methanesulfonyl-2-methylbutanamide (Example 27)

(2R)-4-(6-fluoro-4-oxo-7-phenyl-3,4-dihydroquinazolin-3-yl)-N-hydroxy-2-methanesulfonyl-2-methylbutanamide (Example 31)

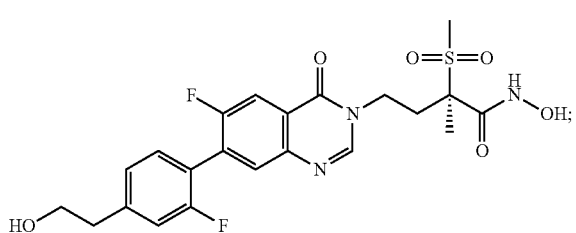 [SMILES: C[C@@](CCn1cnc2cc(-c3ccc(CCO)cc3F)c(F)cc2c1=O)(C(=O)NO)S(C)(=O)=O]

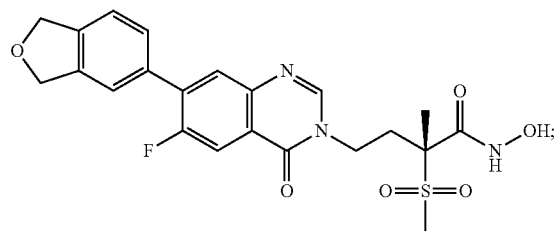 [SMILES: C[C@@](CCn1cnc2cc(-c3ccc4c(c3)COC4)c(F)cc2c1=O)(C(=O)NO)S(C)(=O)=O]

(2R)-4-{6-fluoro-7-[4-(2-hydroxyethyl)phenyl]-4-oxo-3,4-dihydroquinazolin-3-yl}-N-hydroxy-2-methanesulfonyl-2-methylbutanamide (Example 28)

(2R)-4-[7-(1,3-dihydro-2-benzofuran-5-yl)-6-fluoro-4-oxo-3,4-dihydroquinazolin-3-yl]-N-hydroxy-2-methanesulfonyl-2-methylbutanamide (Example 32)

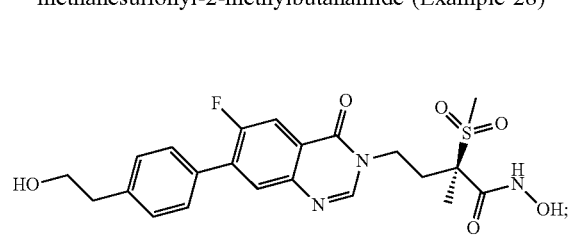

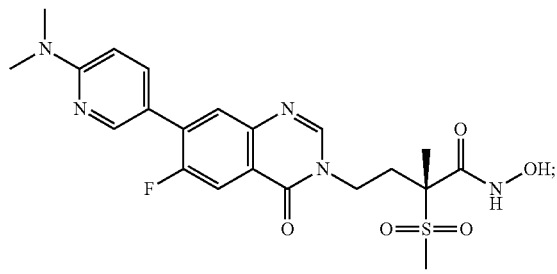 [SMILES: CN(C)c1ccc(-c2cc3ncn(CC[C@](C)(C(=O)NO)S(C)(=O)=O)c(=O)c3cc2F)cn1]

(2R)—N-hydroxy-2-methanesulfonyl-2-methyl-4-(8-methyl-7-{4-[(morpholin-4-yl)methyl]phenyl}-4-oxo-3,4-dihydroquinazolin-3-yl)butanamide (Example 29)

(2R)-4-{7-[6-(dimethylamino)pyridin-3-yl]-6-fluoro-4-oxo-3,4-dihydroquinazolin-3-yl}-N-hydroxy-2-methanesulfonyl-2-methylbutanamide (Example 33)

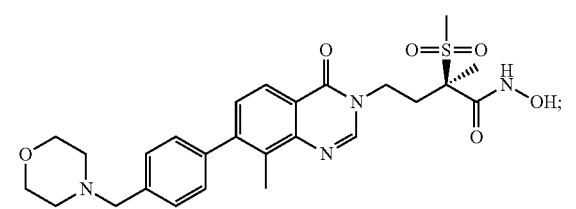

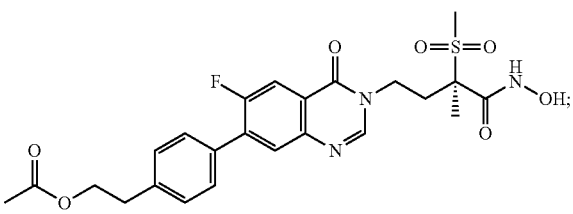 [SMILES: CC(=O)OCCc1ccc(-c2cc3ncn(CC[C@](C)(C(=O)NO)S(C)(=O)=O)c(=O)c3cc2F)cc1]

(2R)-4-[6-fluoro-7-(6-methoxypyridin-3-yl)-4-oxo-3,4-dihydroquinazolin-3-yl]-N-hydroxy-2-methanesulfonyl-2-methylbutanamide (Example 30)

2-(4-{6-fluoro-3-[(3R)-3-(hydroxycarbamoyl)-3-methanesulfonyl-3-methylpropyl]-4-oxo-3,4-dihydroquinazolin-7-yl}phenyl)ethyl acetate (Example 34)

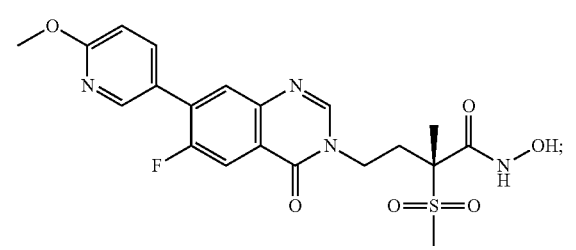

53

(2R)—N-hydroxy-2-methanesulfonyl-2-methyl-4-(7-
{4-[(morpholin-4-yl)methyl]phenyl}-4-oxo-3,4-di-
hydroquinazolin-3-yl)butanamide (Example 35)

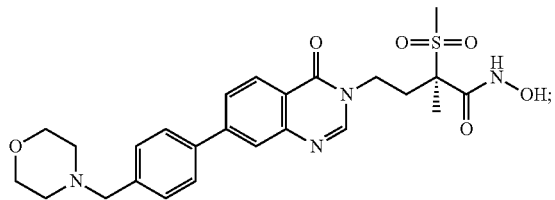 [SMILES: C[C@@](CCn1cnc2cc(-c3ccc(CN4CCOCC4)cc3)ccc2c1=O)(C(=O)NO)S(C)(=O)=O]

(2)-4-[7-(2-fluoro-4-{[(2-methyoxyethyl)(methyl)
amino]methyl}phenyl)-4-oxo-3,4-dihydroquinazo-
lin-3-yl]-N-hydroxy-2-methanesulfonyl-2-methylbu-
tanamide (Example 36)

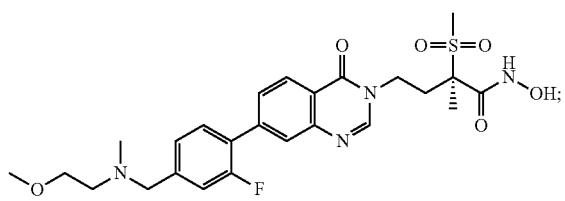 [SMILES: COCCN(C)Cc1ccc(-c2ccc3c(=O)n(CC[C@](C)(C(=O)NO)S(C)(=O)=O)cnc3c2)c(F)c1]

(2R)-4-(7-{2-fluoro-4-[(morpholin-4-yl)methyl]phe-
nyl}-4-oxo-3,4-dihydroquinazolin-3-yl)-N-hydroxy-
2-methanesulfonyl-2-methylbutanamide (Example
37)

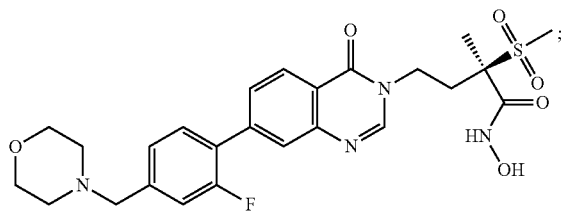 [SMILES: C[C@@](CCn1cnc2cc(-c3ccc(CN4CCOCC4)cc3F)ccc2c1=O)(C(=O)NO)S(C)(=O)=O]

(2R)-4-[7-(2,3-difluoro-4-{[(2-methoxyethyl)
(methyl)amino]methyl}phenyl)-4-oxo-3,4-dihydro-
quinazolin-3-yl]-N-hydroxy-2-methanesulfonyl-2-
methylbutanamide (Example 38)

54

(2R)-4-[7-(4-{[cyclopropyl(methyl)amino]methyl}-
3-fluorophenyl)-4-oxo-3,4-dihydroquinazolin-3-yl]-
N-hydroxy-2-methanesulfonyl-2-methylbutanamide
(Example 39)

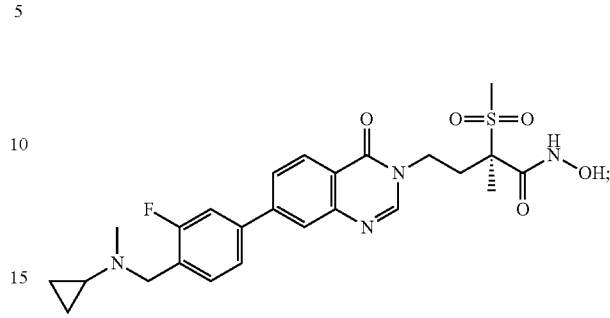

(2R)-4-(7-{4-[(3,3-difluoroazetidin-1-yl)methyl]-2-
fluorophenyl}-4-oxo-3,4-dihydroquinazolin-3-yl)-N-
hydroxy-2-methanesulfonyl-2-methylbutanamide
(Example 40)

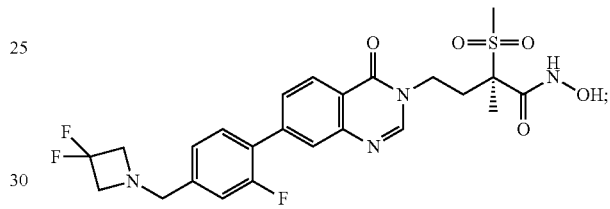

(2R)-4-(7-{4-[(cyclopropylamino)methy]-2-fluoro-
phenyl}-4-oxo-3,4-dihydroquinazolin-3-yl)-N-hy-
droxy-2-methanesulfonyl-2-methylbutanamide (Ex-
ample 41)

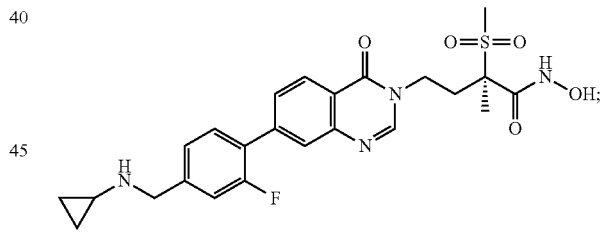

(2R)—N-hydroxy-2-methanesulfonyl-2-methyl-4-(7-
{4-[2-(morpholin-4-yl)ethyl]phenyl}-4-oxo-3,4-
dihydroquinazolin-3-yl)butanamide (Example 42)

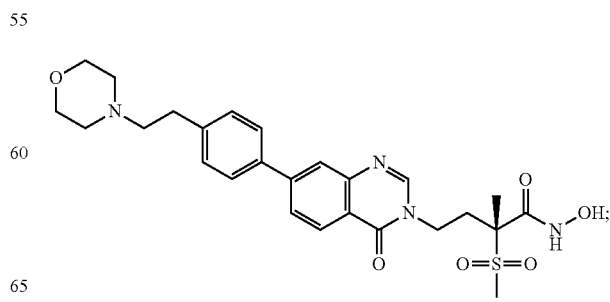

(2R)-4-(7-{2-fluoro-4-[2-(morpholin-4-yl)ethyl]
phenyl}-4-oxo-3,4-dihydroquinazolin-3-yl)-N-hy-
droxy-2-methanesulfonyl-2-methylbutanamide (Ex-
ample 43)

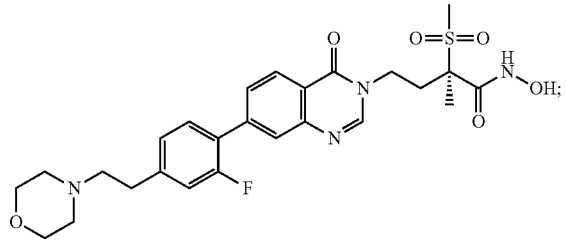 [SMILES: C[C@@](CCn1cnc2cc(-c3ccc(CCN4CCOCC4)cc3F)ccc2c1=O)(C(=O)NO)S(C)(=O)=O]

(2R)—N-hydroxy-4-{7-[4-(2-hydroxyethyl)phenyl]-
4-oxo-3,4-dihydroquinazolin-3-yl}-2-methanesulfo-
nyl-2-methylbutanamide (Example 44)

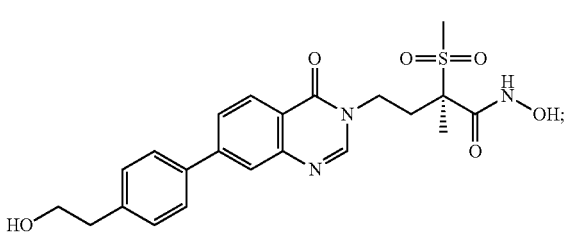 [SMILES: C[C@@](CCn1cnc2cc(-c3ccc(CCO)cc3)ccc2c1=O)(C(=O)NO)S(C)(=O)=O]

(2R)-4-{7-[2-fluoro-4-(2-hydroxyethyl)phenyl]-4-
oxo-3,4-dihydroquinazolin-3-yl}-N-hydroxy-2-
methanesulfonyl-2-methylbutanamide (Example 45)

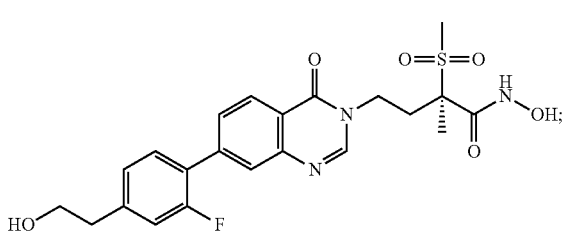 [SMILES: C[C@@](CCn1cnc2cc(-c3ccc(CCO)cc3F)ccc2c1=O)(C(=O)NO)S(C)(=O)=O]

(2R)-4-[7-(4-ethoxyphenyl)-4-oxo-3,4-dihydroqui-
nazolin-3-yl]-N-hydroxy-2-methanesulfonyl-2-meth-
ylbutanamide (Example 46)

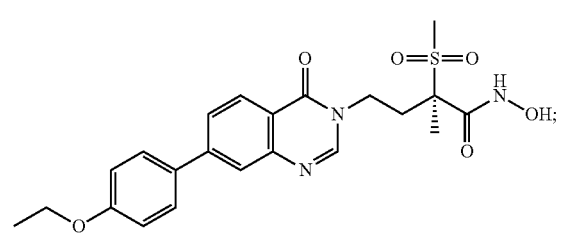 [SMILES: CCOc1ccc(-c2ccc3c(=O)n(CC[C@](C)(C(=O)NO)S(C)(=O)=O)cnc3c2)cc1]

(2R)—N-hydroxy-2-methanesulfonyl-4-{7-[4-
(methoxymethyl)phenyl]-4-oxo-3,4-dihydroquinazo-
lin-3-yl}-2-methylbutanamide (Example 47)

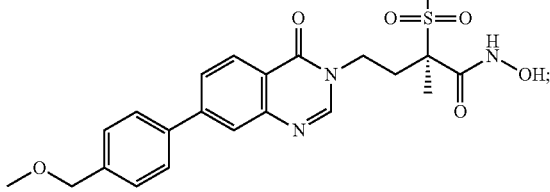

(2)-4-{7-[2-fluoro-4-(2-methoxyethyl)phenyl]-4-
oxo-3,4-dihydroquinazolin-3-yl}-N-hydroxy-2-
methanesulfonyl-2-methylbutanamide (Example 48)

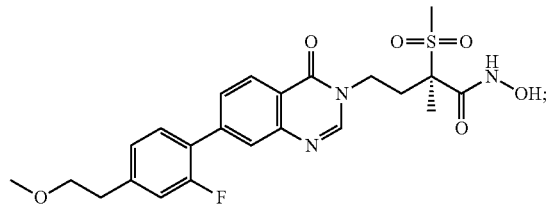 [SMILES: COCCc1ccc(-c2ccc3c(=O)n(CC[C@](C)(C(=O)NO)S(C)(=O)=O)cnc3c2)c(F)c1]

(2R)-4-[7-(3-fluoro-4-{[methoxy(methyl-amino]
methyl}phenyl)-4-oxo-3,4-dihydroquinazolin-3-yl]-
N-hydroxy-2-methanesulfonyl-2-methylbutanamide
(Example 49)

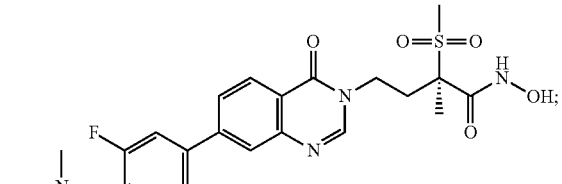

(2R)-4-(7-{2-fluoro-4-[(methoxyamino)methyl]phe-
nyl}-4-oxo-3,4-dihydroquinazolin-3-yl)-N-hydroxy-
2-methanesulfonyl-2-methylbutanamide (Example
50)

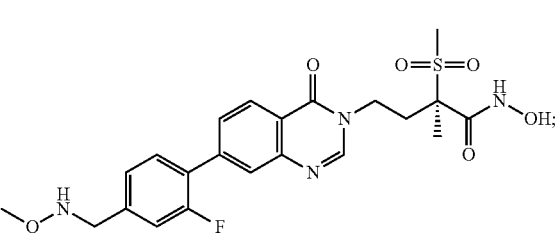 [SMILES: CONCc1ccc(-c2ccc3c(=O)n(CC[C@](C)(C(=O)NO)S(C)(=O)=O)cnc3c2)c(F)c1]

(2R)-4-(7-{4-[(ethoxyamino)methyl]-2-fluorophe-
nyl}-4-oxo-3,4-dihydroquinazolin-3-yl)-N-hydroxy-
2-methanesulfonyl-2-methylbutanamide (Example
51)

(2R)-4-[6-(2-fluoro-4-methoxyphenyl)-1-oxo-1,2-
dihydroisoquinolin-2-yl]-N-hydroxy-2-methanesul-
fonyl-2-methylbutanamide (Example 55)

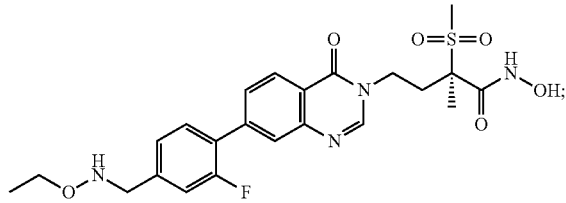 [SMILES: CCONCc1ccc(-c2ccc3c(=O)n(CC[C@](C)(C(=O)NO)S(C)(=O)=O)cnc3c2)c(F)c1]

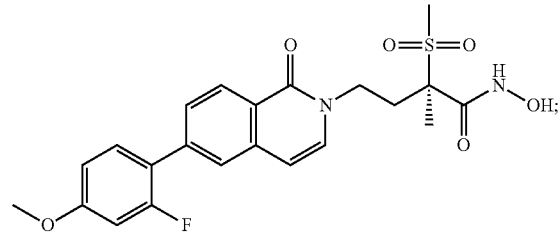

(2R)—N-hydroxy-2-methanesulfonyl-4-[7-(4-{
[methoxy(methyl)amino]methyl}phenyl)-4-oxo-3,4-
dihydroquinazolin-3-yl]-2-methylbutanamide (Ex-
ample 52)

(2R)—N-hydroxy-2-methanesulfonyl-2-methyl-4-(1-
oxo-6-phenyl-1,2-dihydroisoquinolin-2-yl)butana-
mide (Example 56)

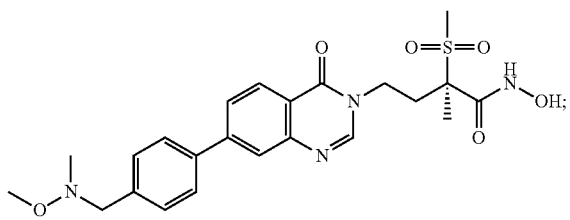 [SMILES: CON(C)Cc1ccc(-c2ccc3c(=O)n(CC[C@](C)(C(=O)NO)S(C)(=O)=O)cnc3c2)cc1]

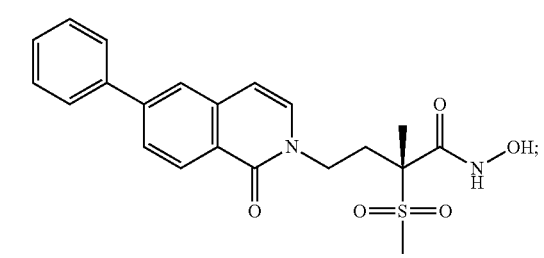

(2R)—N-hydroxy-2-methanesulfonyl-4-[6-(4-
methoxyphenyl)-1-oxo-1,2-dihydroisoquinolin-2-
yl]-2-methylbutanamide (Example 53)

(2R)-4-[6-(1,3-dihydro-2-benzofuran-5-yl)-1-oxo-1,
2-dihydroisoquinolin-2-yl]-N-hydroxy-2-methane-
sulfonyl-2-methylbutanamide (Example 57)

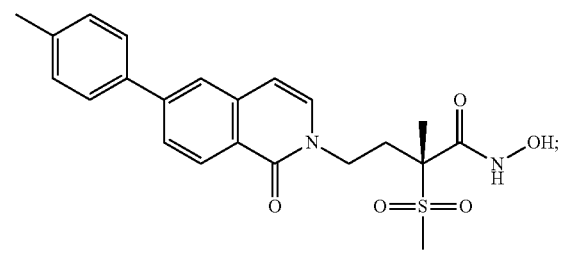 [SMILES: Cc1ccc(-c2ccc3c(=O)n(CC[C@](C)(C(=O)NO)S(C)(=O)=O)ccc3c2)cc1]

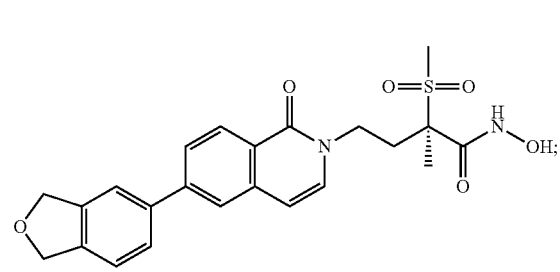

(2)-N-hydroxy-2-methanesulfonyl-2-methyl-4-[6-(4-
methylphenyl)-1-oxo-1,2-dihydroisoquinolin-2-yl]-
2-methylbutanamide (Example 54)

(2R)—N-hydroxy-2-methanesulfonyl-2-methyl-4-[6-
(5-methyl-1,3-thiazol-2-yl)-1-oxo-1,2-dihydroisoqui-
nolin-2-yl]butanamide (Example 58)

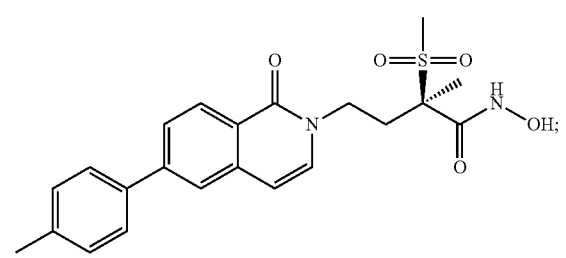 [SMILES: Cc1ccc(-c2ccc3c(=O)n(CC[C@](C)(C(=O)NO)S(C)(=O)=O)ccc3c2)cc1]

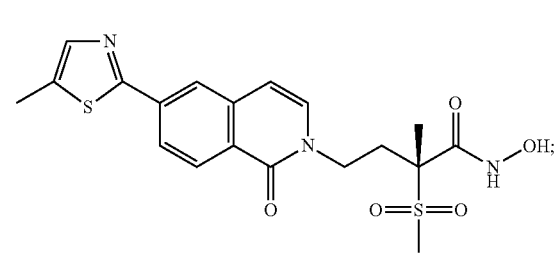 [SMILES: Cc1cnc(-c2ccc3c(=O)n(CC[C@](C)(C(=O)NO)S(C)(=O)=O)ccc3c2)s1]

(2R)-4-[6-(4-cyano-2-fluorophenyl)-1-oxo-1,2-dihydroisoquinolin-2-yl]-N-hydroxy-2-methanesulfonyl-2-methylbutanamide (Example 59)

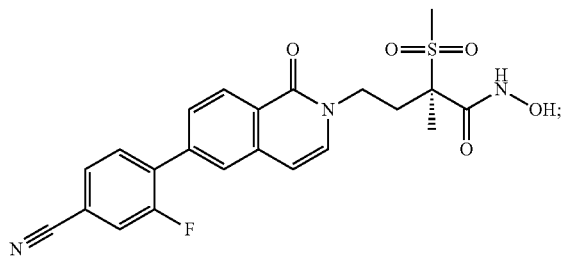 [SMILES: C[C@@](CCn1ccc2cc(-c3ccc(C#N)cc3F)ccc2c1=O)(C(=O)NO)S(C)(=O)=O]

(2R)—N-hydroxy-2-methanesulfonyl-4-[6-(6-methoxypyridin-3-yl)-1-oxo-1,2-dihydroisoquinolin-2-yl]-2-methylbutanamide (Example 60)

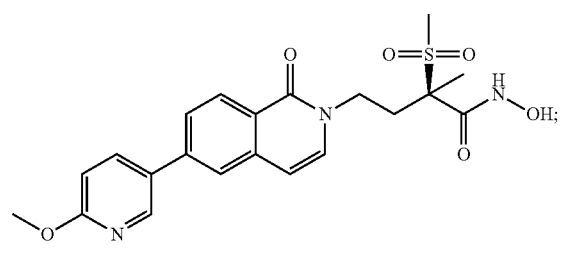 [SMILES: COc1ccc(-c2ccc3c(=O)n(CC[C@](C)(C(=O)NO)S(C)(=O)=O)ccc3c2)cn1]

(2R)-4-{6-[4-(dimethylamino)phenyl]-1-oxo-1,2-dihydroisoquinolin-2-yl}-N-hydroxy-2-methanesulfonyl-2-methylbutanamide (Example 61)

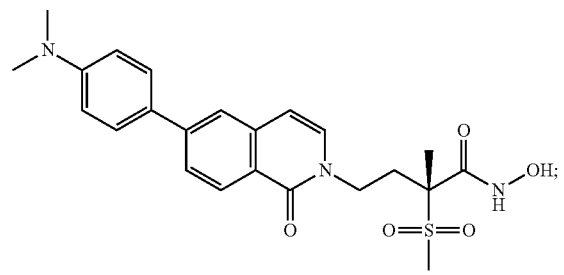 [SMILES: CN(C)c1ccc(-c2ccc3c(=O)n(CC[C@](C)(C(=O)NO)S(C)(=O)=O)ccc3c2)cc1]

(2R)-4-{6-[6-(dimethylamino)pyridin-3-yl]-1-oxo-1,2-dihydroisoquinolin-2-yl}-N-hydroxy-2-methanesulfonyl-2-methylbutanamide (Example 62)

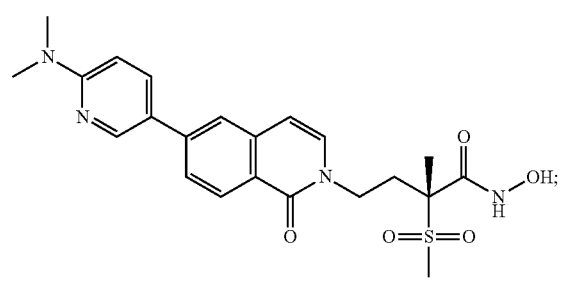 [SMILES: CN(C)c1ccc(-c2ccc3c(=O)n(CC[C@](C)(C(=O)NO)S(C)(=O)=O)ccc3c2)cn1]

(2R)-4-{6-[2-(dimethylamino)pyrimidin-5-yl]-1-oxo-1,2-dihydroisoquinolin-2-yl}-N-hydroxy-2-methanesulfonyl-2-methylbutanamide (Example 61)

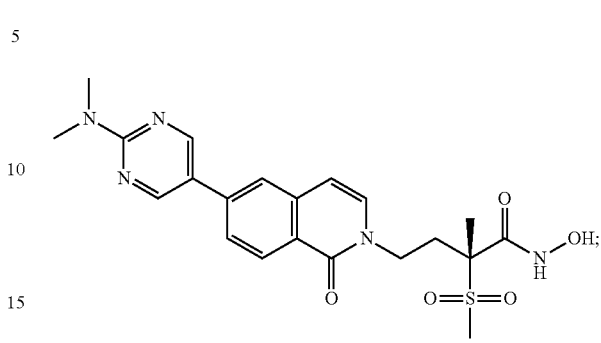

(2R)—N-hydroxy-2-methanesulfonyl-2-methyl-4-(6-{4-[(morpholin-4-yl)methyl]phenyl}-1-oxo-1,2-dihydroisoquinolin-2-yl)butanamide (Example 64)

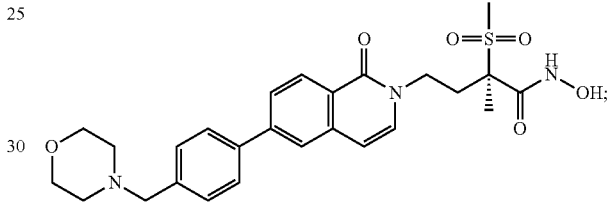

(2R)-4-(6-{4-[(dimethylamino)methyl]-2-fluorophenyl}-1-oxo-1,2-dihydroisoquinolin-2-yl)-N-hydroxy-2-methanesulfonyl-2-methylbutanamide (Example 65)

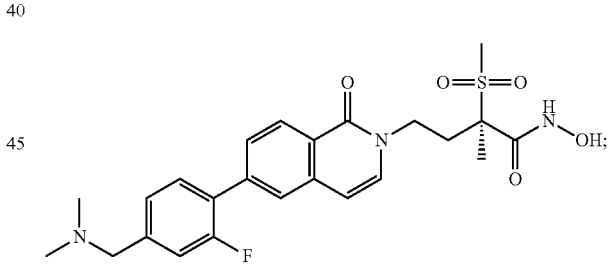

(2R)-4-[6-(2-fluoro-4-{[(2-methoxyethyl)(methyl)amino]methyl}phenyl)-1-oxo-1,2-dihydroisoquinolin-2-yl]-N-hydroxy-2-methanesulfonyl-2-methylbutanamide (Example 66)

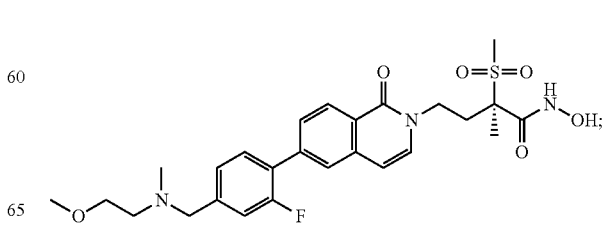

| 61 | 62 |
|---|---|
| (2R)-4-[6-(2-fluoro-4-{[(2-methoxyethyl)amino]methyl}phenyl)-1-oxo-1,2-dihydroisoquinolin-2-yl]-N-hydroxy-2-methanesulfonyl-2-methylbutanamide (Example 67) | (2R)-4-[6-(2-fluoro-4-{[(3-methoxypropyl)(methyl)amino]methyl}phenyl)-1-oxo-1,2-dihydroisoquinolin-2-yl]-N-hydroxy-2-methanesulfonyl-2-methylbutanamide (Example 70) |

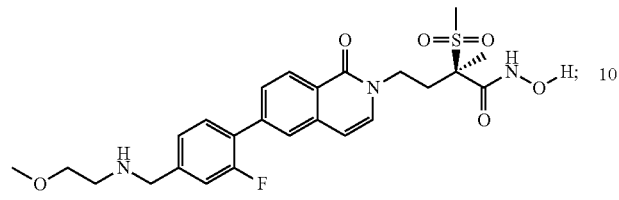

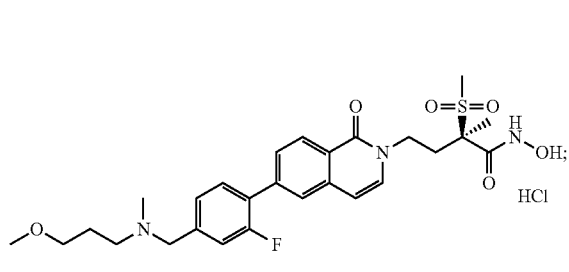

(2R)-4-[6-(2-fluoro-4-{[(2-methoxy-2-methylpropyl)amino]methyl}phenyl)-1-oxo-1,2-dihydroisoquinolin-2-yl]-N-hydroxy-2-methanesulfonyl-2-methylbutanamide (Example 68)

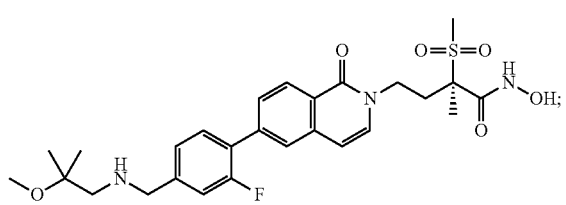 [SMILES: COC(C)(C)CNCc1ccc(-c2ccc3c(=O)n(CC[C@](C)(C(=O)NO)S(C)(=O)=O)ccc3c2)c(F)c1]

(2R)-4-[6-(2-fluoro-4-{[(3-methoxypropyl)(methyl)amino]methyl}phenyl)-1-oxo-1,2-dihydroisoquinolin-2-yl]-N-hydroxy-2-methanesulfonyl-2-methylbutanamide (Example 71)

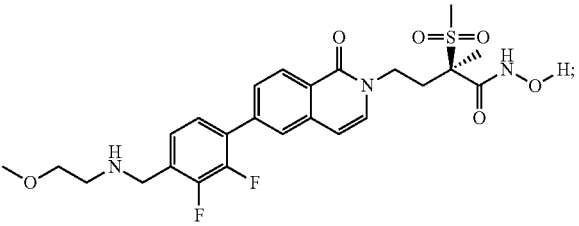

(2R)-4-(6-{4-[(dimethylamino)methyl]-2,3-difluorophenyl}-1-oxo-1,2-dihydroisoquinolin-2-yl)-N-hydroxy-2-methanesulfonyl-2-methylbutanamide (Example 69)

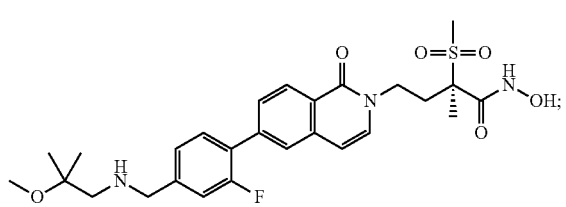 [SMILES: COC(C)(C)CNCc1ccc(-c2ccc3c(=O)n(CC[C@](C)(C(=O)NO)S(C)(=O)=O)ccc3c2)c(F)c1]

(2R)-4-[6-(4-{[(2-ethoxyethyl)amino]methyl}-2-fluorophenyl)-1-oxo-1,2-dihydroisoquinolin-2-yl]-N-hydroxy-2-methanesulfonyl-2-methylbutanamide (Example 72)

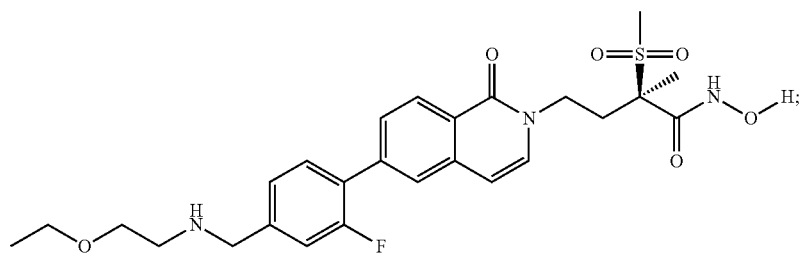

(2R)-4-{6-[2-fluoro-4-({[2-(propan-2-yloxy)ethyl]amino}methyl)phenyl]-1-oxo-1,2-dihydroisoquinolin-2-yl}-N-hydroxy-2-methanesulfonyl-2-methylbutanamide (Example 73)

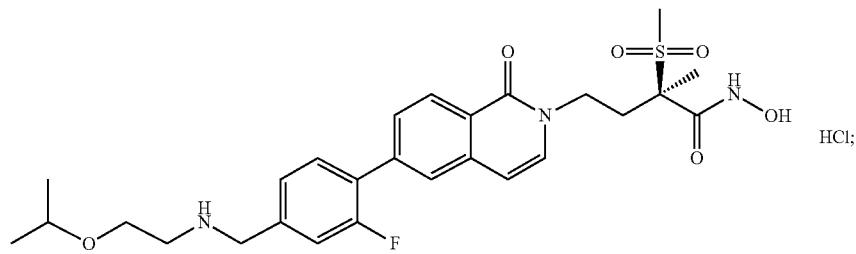

HCl;

(2R)-4-[6-(2-fluoro-4-{[2-hydroxyethyl)(methyl)amino]methyl}phenyl)-1-oxo-1,2-dihydroisoquinolin-2-yl]-N-hydroxy-2-methanesulfonyl-2-methylbutanamide (Example 74)

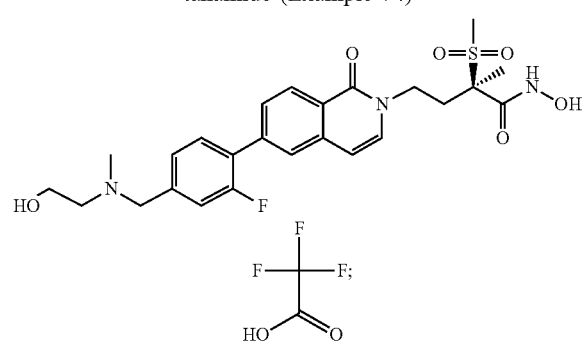

(2R)-4-(6-{4-[(cyclopropylamino)methyl]phenyl}-1-oxo-1,2-dihydroisoquinolin-2-yl)-N-hydroxy-2-methanesulfonyl-2-methylbutanamide (Example 75)

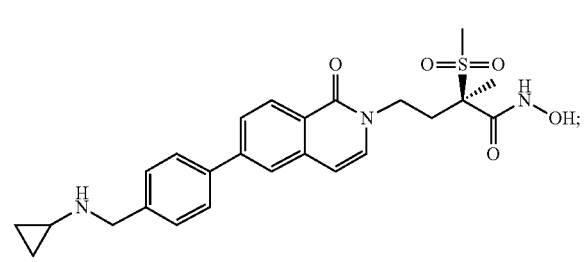 [SMILES: C[C@@](CCn1ccc2cc(-c3ccc(CNC4CC4)cc3)ccc2c1=O)(C(=O)NO)S(C)(=O)=O]

(2R)-4-(6-{4-[(cyclopropylamino)methyl]-2-fluorophenyl}-1-oxo-1,2-dihydroisoquinolin-2-yl)-N-hydroxy-2-methanesulfonyl-2-methylbutanamide (Example 76)

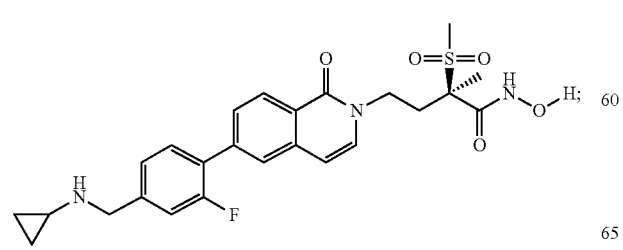

(2R)—N-hydroxy-2-methanesulfonyl-2-methyl-4-(1-oxo-6-{4-[(1,2,2-trimethylhydrazin-1-yl)methyl]phenyl}-1,2-dihydroisoquinolin-2-yl)butanamide (Example 77)

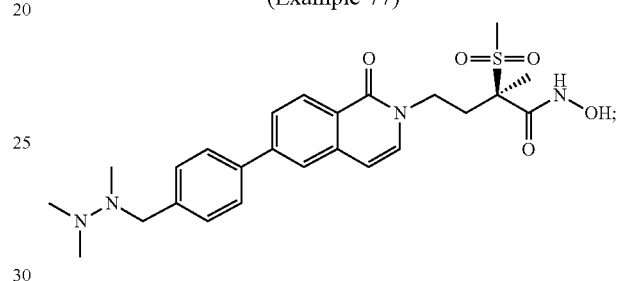

(2R)—N-hydroxy-2-methanesulfonyl-4-(6-{4-[(methoxyamino)methyl]phenyl}-1-oxo-1,2-dihydroisoquinolin-2-yl)-2-methylbutanamide (Example 78)

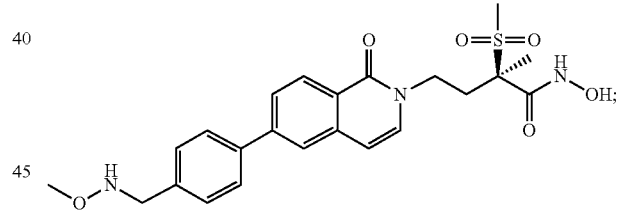

(2R)-4-(6-{4-[(2,2-dimethylhydrazin-1-yl)methyl]phenyl}-1-oxo-1,2-dihydroisoquinolin-2-yl)-N-hydroxy-2-methanesulfonyl-2-methylbutanamide (Example 79)

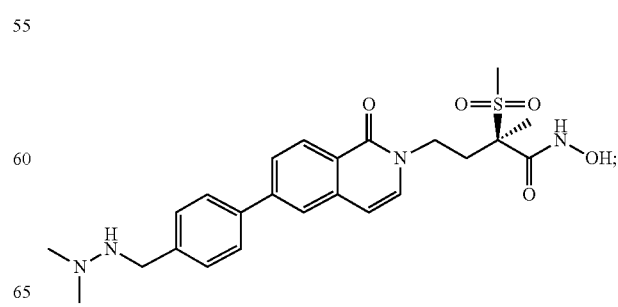

65

(2R)—N-hydroxy-2-methanesulfonyl-2-methyl-4-(6-{4-[2-(morpholin-4-yl)ethyl]phenyl}-1-oxo-1,2-dihydroisoquinolin-2-yl)butanamide (Example 80)

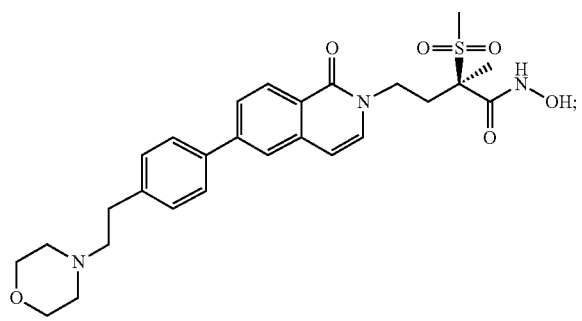 [SMILES: C[C@@](CCn1ccc2cc(-c3ccc(CCN4CCOCC4)cc3)ccc2c1=O)(C(=O)NO)S(C)(=O)=O]

(2R)—N-hydroxy-2-methanesulfonyl-2-methyl-4-(1-oxo-6-{4-[(2-oxopyrrolidin-1-yl)methyl]phenyl}-1,2-dihydroisoquinolin-2-yl)butanamide (Example 81)

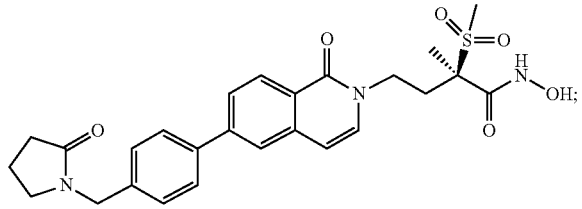 [SMILES: C[C@@](CCn1ccc2cc(-c3ccc(CN4CCCC4=O)cc3)ccc2c1=O)(C(=O)NO)S(C)(=O)=O]

(2R)-4-[6-(6-{2-[cyclopropyl(methyl)amino]ethoxy}pyridin-3-yl)-1-oxo-1,2-dihydroisoquinolin-2-yl]-N-hydroxy-2-methanesulfonyl-2-methylbutanamide (Example 82)

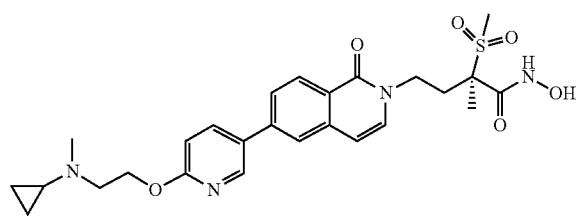

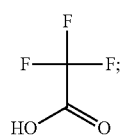

66

(2R)-4-[4-fluoro-6-(4-methoxyphenyl)-1-oxo-1,2-dihydroisoquinolin-2-yl]-N-hydroxy-2-methanesulfonyl-2-methylbutanamide (Example 83)

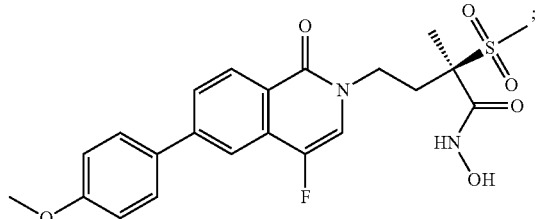

(2R)-4-(4-fluoro-1-oxo-6-phenyl-1,2-dihydroisoquinolin-2-yl)-N-hydroxy-2-methanesulfonyl-2-methylbutanamide (Example 84)

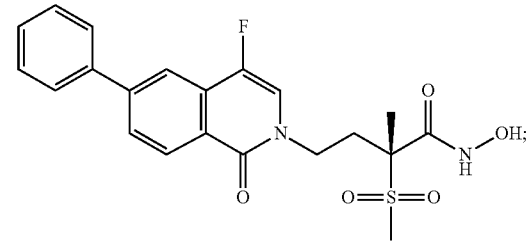 [SMILES: C[C@@](CCn1cc(F)c2cc(-c3ccccc3)ccc2c1=O)(C(=O)NO)S(C)(=O)=O]

(2R)-4-(6-{4-[(dimethylamino)methyl]phenyl}-4-fluoro-1-oxo-1,2-dihydroisoquinolin-2-yl)-N-hydroxy-2-methanesulfonyl-2-methylbutanamide (Example 85)

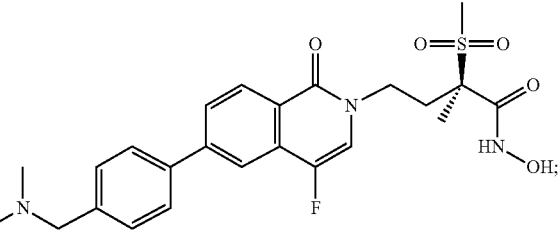

(2R)-4-[6-(6-ethoxypyridin-3-yl)-4-fluoro-1-oxo-1,2-dihydroisoquinolin-2-yl]-N-hydroxy-2-methanesulfonyl-2-methylbutanamide (Example 86)

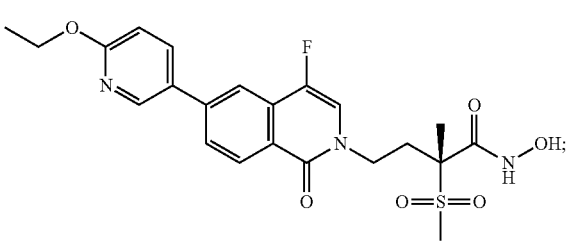 [SMILES: CCOc1ccc(-c2ccc3c(=O)n(CC[C@](C)(C(=O)NO)S(C)(=O)=O)cc(F)c3c2)cn1]

67

(2R)-4-[4-fluoro-6-(6-methoxypyridin-3-yl)-1-oxo-1,2-dihydroisoquinolin-2-yl]-N-hydroxy-2-methanesulfonyl-2-methylbutanamide (Example 87)

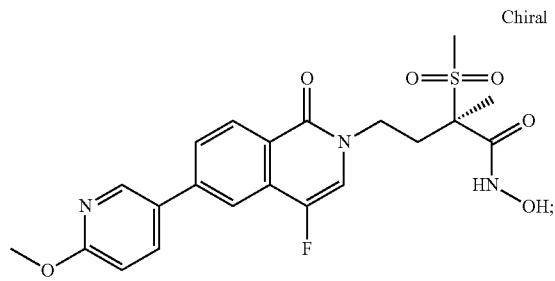 [SMILES: COc1ccc(-c2ccc3c(=O)n(CC[C@](C)(C(=O)NO)S(C)(=O)=O)cc(F)c3c2)cn1]

(2R)-4-[4-fluoro-6-(2-fluoro-4-{[(2-methoxyethyl)amino]methyl}phenyl)-1-oxo-1,2-dihydroisoquinolin-2-yl]-N-hydroxy-2-methanesulfonyl-2-methylbutanamide (Example 88)

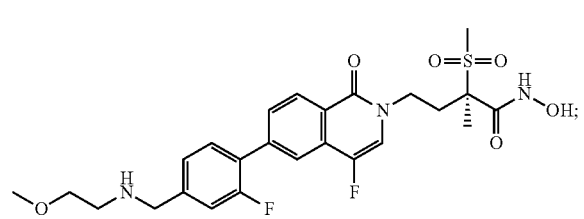 [SMILES: COCCNCc1ccc(-c2ccc3c(=O)n(CC[C@](C)(C(=O)NO)S(C)(=O)=O)cc(F)c3c2)c(F)c1]

(2R)-4-(6-{4-[(dimethylamino)methyl]-2-fluorophenyl}-4-fluoro-1-oxo-1,2-dihydroisoquinolin-2-yl)-N-hydroxy-2-methanesulfonyl-2-methylbutanamide (Example 89)

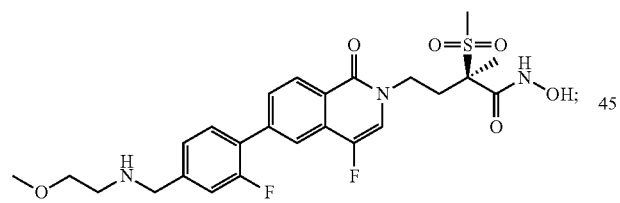

(2R)-4-{6-[6-(dimethylamino)pyridin-3-yl]-4-fluoro-1-oxo-1,2-dihydroisoquinolin-2-yl}-N-hydroxy-2-methanesulfonyl-2-methylbutanamide (Example 90)

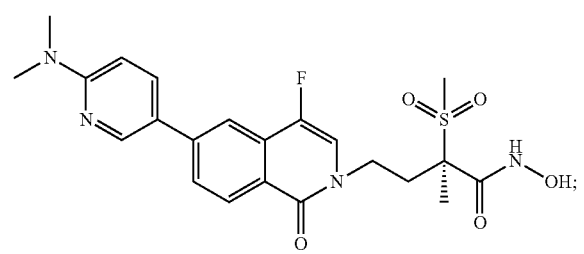 [SMILES: CN(C)c1ccc(-c2ccc3c(=O)n(CC[C@](C)(C(=O)NO)S(C)(=O)=O)cc(F)c3c2)cn1]

68

(2R)-4-[6-(2-fluorophenyl)-1-oxo-1,2,3,4-tetrahydroisoquinolin-2-yl]-N-hydroxy-2-methanesulfonyl-2-methylbutanamide (Example 91)

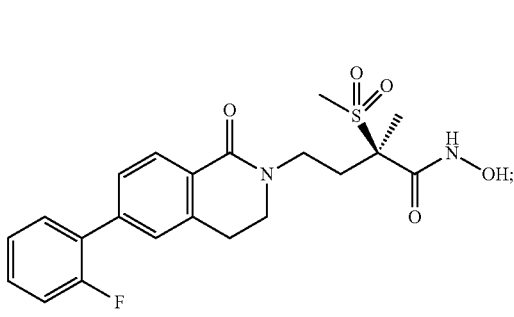 [SMILES: C[C@@](CCN1CCc2cc(-c3ccccc3F)ccc2C1=O)(C(=O)NO)S(C)(=O)=O]

(2R)-N-hydroxy-2-methanesulfonyl-2-methyl-4-(6-{4-[(morpholin-4-yl)methyl]phenyl}-1-oxo-1,2,3,4-tetrahydroisoquinolin-2-yl)butanamide (Example 92)

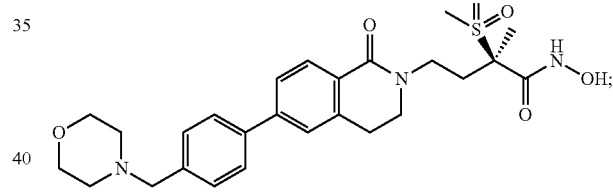

(2R)-N-hydroxy-4-{6-[4-(2-hydroxyethyl)phenyl]-1-oxo-1,2-dihydroisoquinolin-2-yl}-2-methanesulfonyl-2-methylbutanamide (Example 93)

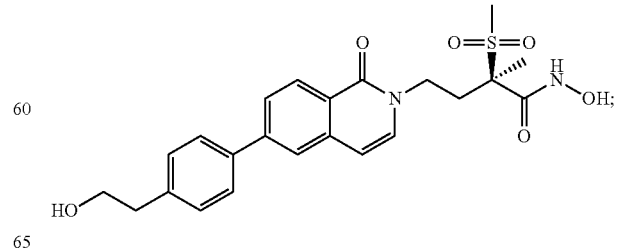

2-(4-{2-[(3R)-3-(hydroxycarbamoyl)-3-methanesulfonyl-3-methylpropyl]-1-oxo-1,2-dihydroisoquinolin-6-yl}phenyl)ethyl 2-(dimethylamino)acetate (Example 94)

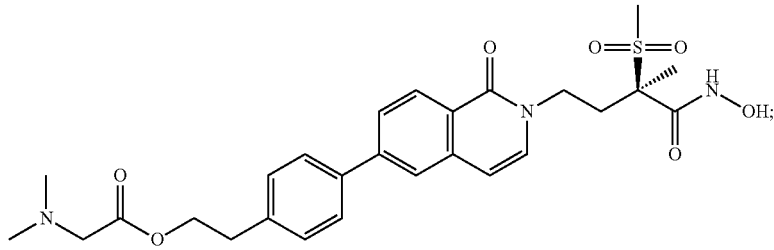 [SMILES: CN(C)CC(=O)OCCc1ccc(-c2ccc3c(=O)n(CC[C@](C)(C(=O)NO)S(C)(=O)=O)ccc3c2)cc1]

In another aspect, the present invention relates to a compound which is:

(R)—N-hydroxy-2-methyl-2-(methylsulfonyl)-4-(4-oxo-7-phenylquinazolin-3(4H)-yl)butanamide (Example 1)

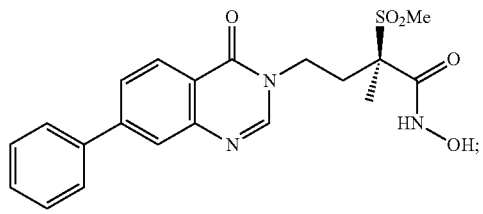 [SMILES: C[C@@](CCn1cnc2cc(-c3ccccc3)ccc2c1=O)(C(=O)NO)S(C)(=O)=O]

(R)—N-hydroxy-2-methyl-2-(methylsulfonyl)-4-(4-oxo-7-(p-tolyl)quinazolin-3(4H)-yl)butanamide (Example 2)

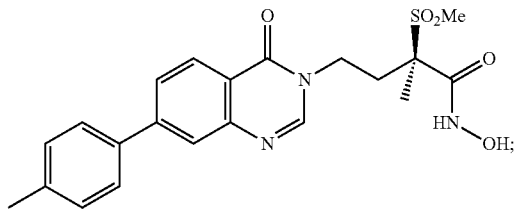 [SMILES: Cc1ccc(-c2ccc3c(=O)n(CC[C@](C)(C(=O)NO)S(C)(=O)=O)cnc3c2)cc1]

(R)—N-hydroxy-4-(7-(4-methoxyphenyl)-4-oxoquinazolin-3(4H)-yl)-2-methyl-2-(methylsulfonyl)butanamide (Example 3)

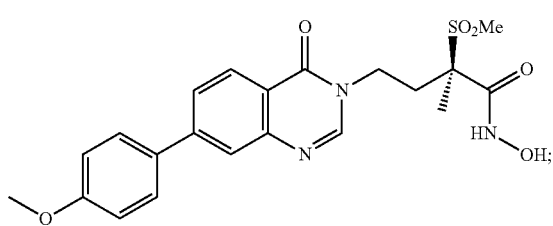 [SMILES: COc1ccc(-c2ccc3c(=O)n(CC[C@](C)(C(=O)NO)S(C)(=O)=O)cnc3c2)cc1]

(R)-4-(7-(4-(dimethylamino)phenyl)-4-oxoquinazolin-3(4H)-yl)-N-hydroxy-2-methyl-2-(methylsulfonyl)butanamide-trifluoroacetic-acid Salt (Example 4)

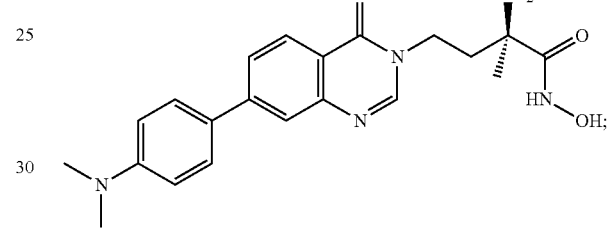

(R)-4-(7-(4-(difluoromethoxy)phenyl)-4-oxoquinazolin-3(4H)-yl)-N-hydroxy-2-methyl-2-(methylsulfonyl)butanamide (Example 5)

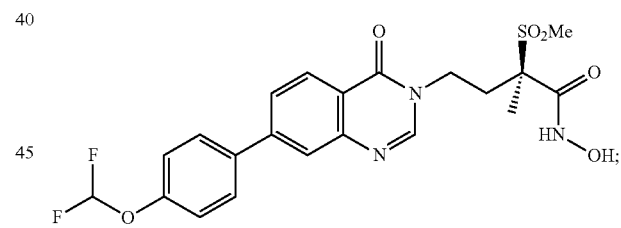

(R)-4-(7-(2,3-difluorophenyl)-4-oxoquinazolin-3(4H)-yl)-N-hydroxy-2-methyl-2-(methylsulfonyl)butanamide (Example 6)

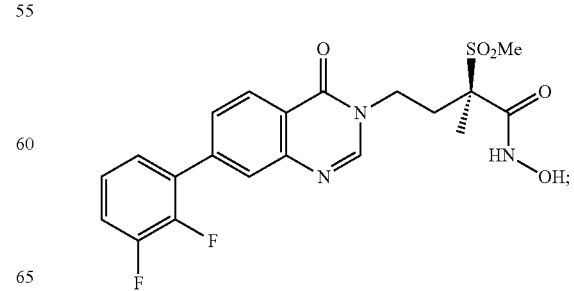

(R)-4-(7-(2,5-difluorophenyl)-4-oxoquinazolin-3 (4H)-yl)-N-hydroxy-2-methyl-2-(methylsulfonyl) butanamide (Example 7)

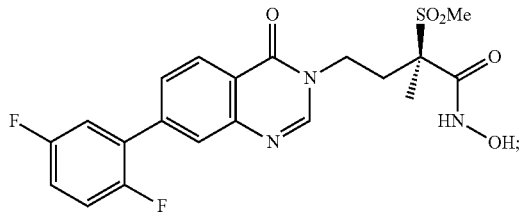 [SMILES: C[C@@](CCn1cnc2cc(-c3cc(F)ccc3F)ccc2c1=O)(C(=O)NO)S(C)(=O)=O]

(R)-4-(7(2-fluorophenyl)-4-oxoquinazolin-3(4H)-yl)-N-hydroxy-2-methyl-2-(methylsulfonyl)butanamide (Example 8)

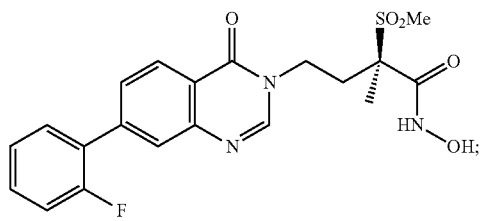 [SMILES: C[C@@](CCn1cnc2cc(-c3ccccc3F)ccc2c1=O)(C(=O)NO)S(C)(=O)=O]

(R)-4-(7-(3-fluoro-4-methylphenyl)-4-oxoquinazolin-3(4H)-yl)-N-hydroxy-2-methyl-2-(methylsulfonyl)butanamide (Example 9)

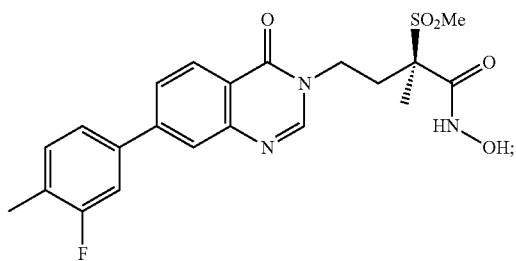 [SMILES: Cc1ccc(-c2ccc3c(=O)n(CC[C@](C)(C(=O)NO)S(C)(=O)=O)cnc3c2)cc1F]

(R)-4-(7-(4-(difluoromethyl)phenyl)-4-oxoquinazolin-3(4H)-yl)-N-hydroxy-2-methyl-2-(methylsulfonyl)butanamide (Example 10)

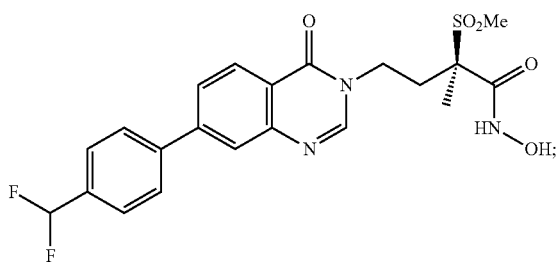 [SMILES: C[C@@](CCn1cnc2cc(-c3ccc(C(F)F)cc3)ccc2c1=O)(C(=O)NO)S(C)(=O)=O]

or
a pharmaceutically acceptable salt thereof,

In one aspect, the present invention relates to a compound (R)-4-(7-(4-(dimethylamino)phenyl)-4-oxoquinazolin-3 (4H)-yl)-N-hydroxy-2-methyl-2-(methylsulfonyl)butanamide

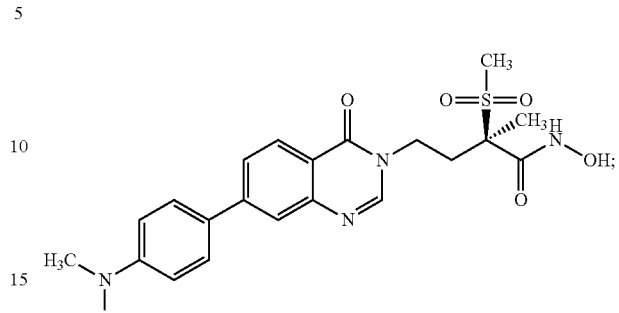

or
a pharmaceutically acceptable salt thereof.

In one aspect, the present invention relates to a compound which is (R)-4-(7-(2-fluorophenyl)-4-oxoquinazolin-3(4H)-yl)-N-hydroxy-2-methyl-2-(methylsulfonyl)butanamide

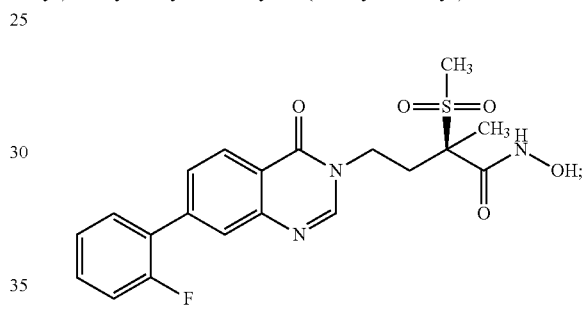

or
a pharmaceutically acceptable salt thereof

It is recognized that the compounds of Formulas (IA), (I) to (VI), respectively, or pharmaceutically acceptable salts thereof of the present invention as defined above may exist in forms as stereoisomers, regioisomers, or diastereiomers.

These compounds may contain one or more asymmetric carbon atoms and may exist in racemic and optically active forms. For example, compounds of the present invention may exist as a racemic mixture of R(+) and S(−) enantiomers, or in separate respectively optical forms, i.e., existing separately as either the R(+) enantiomer form or in the S(+) enantiomer form. All of these individual compounds, isomers, and mixtures thereof are included within the scope of the present invention.

Substituent Definitions

As used herein, the term alkali metal is intended to mean the Group I elements, which include, but are not limited to lithium (Li), sodium (Na), or potassium (K) and the like. The term alkali earth metal include, but are not limited to calcium (Ca) or magnesium (Mg) and the like.

As used herein, the term "alkyl" represents a saturated, straight or branched hydrocarbon moiety, which may be unsubstituted or substituted by one, or more of the substituents defined herein. Exemplary alkyls include, but are not limited to methyl (Me), ethyl (Et), propyl, isopropyl, butyl, isobutyl, t-butyl, pentyl and the like. The term "$C_1$-$C_6$" refers to an alkyl containing from 1 to 6 carbon atoms.

When the term "alkyl" is used in combination with other substituent groups, such as "haloalkyl" or "hydroxyalkyl", "arylalkyl", the term "alkyl" is intended to encompass a divalent straight or branched-chain hydrocarbon radical.

The terms "halogen" and "halo" represent chloro, fluoro, bromo or iodo substituents.

"Hydroxy" or "hydroxyl" is intended to mean the radical —OH.

For example, haloalkyl is intended to mean a saturated, straight or branched hydrocarbon moiety substituted with one or more halogen groups, where halogen is fluoro, chloro, bromo or iodo. Representative haloalkyls include, but are not limited to trifluoromethyl (—$CF_3$). tetrafluoroethyl (—$CF_2CHF_2$), pentafluoroethyl (—$CF_2CF_3$) and the like. For example, hydroxyalkyl is intended to mean a saturated, straight or branched hydrocarbon moiety substituted with one or more hydroxy groups. The term "$C_1$-$C_6$" refers to an haloalkyl containing from 1 to 6 carbon atoms.

As used herein, the term "alkenyl" refers to a straight or branched hydrocarbon moiety containing at least 1 and up to 3 carbon-carbon double bonds. Examples include ethenyl and propenyl.

As used herein, the term "alkynyl" refers to a straight or branched hydrocarbon moiety containing at least 1 and up to 3 carbon-carbon triple bonds. Examples include ethynyl and propynyl.

As used herein, the term "cycloalkyl" refers to a non-aromatic, saturated, cyclic hydrocarbon ring. The term "($C_3$-$C_5$)cycloalkyl" refers to a non-aromatic cyclic hydrocarbon ring having from three to eight ring carbon atoms. Exemplary "($C_3$-$C_8$)cycloalkyl" groups useful in the present invention include cyclopropyl, cyclobutyl, cyclopentyl, cyclohexyl, cycloheptyl, and cyclooctyl.

"Alkoxy" refers to a group containing an alkyl radical attached through an oxygen linking atom. The term "($C_1$-$C_6$)alkoxy" refers to a straight- or branched-chain hydrocarbon radical having at least 1 and up to 6 carbon atoms attached through an oxygen linking atom. Exemplary "($C_1$-$C_4$)-alkoxy" groups useful in the present invention include, but are not limited to, methoxy, ethoxy, n-propoxy, isopropoxy, n-butoxy, s-butoxy, and t-butoxy. Representative haloalkoxy include, but are not limited to difluoromethoxy (—$OCHCF_2$), trifluoromethoxy (—$OCF_3$), tetrafluoroethoxy (—$OCF_2CHF_2$) and the like.

"Alkylthio-" refers to a group containing an alkyl radical atoms attached through an sulfur linking atom. The term "($C_1$-$C_4$)alkylthio-" refers to a straight- or branched-chain hydrocarbon radical having at least 1 and up to 4 carbon atoms attached through a sulfur linking atom. Exemplary "($C_1$-$C_4$)alkylthio-" groups useful in the present invention include, but are not limited to, methylthio-, ethylthio-, n-propylthio-, isopropylthio-, n-butylthio-, s-butylthio-, t-butylthio- and the like.

Carbocyclic ring refers to a ring in which all ring atoms are carbon atoms, which may be aromatic or non-aromatic, fused or non-fused and the like. Examples of carbocyclic rings, may include, but are not limited to cycloalkyls, such as cyclopropyl, cyclobutyl, cyclopentyl, cyclohexyl and the like, aromatic or aryl rings, which include, but are not limited to rings such as benzyl, naphthyl and the like, which include, but are not limited to fused ring compounds, such as 1,2,3,4-tetrahydronaphthyl and the like.

"Cycloalkyloxy", "cycloalkylthio", "cycloalkylamino" refers to a group containing a saturated carbocyclic ring atoms attached through an oxygen, nitrogen or sulfur linking atom, respectively.

"Aryl" represents a group or moiety comprising an aromatic, monovalent monocyclic or bicyclic hydrocarbon radical containing from 6 to 10 carbon ring atoms, which may be unsubstituted or substituted by one or more of the substituents defined herein, and to which may be fused one or more cycloalkyl rings, which may be unsubstituted or substituted by one or more substituents defined herein. Representative aryl groups suitable for use in the present invention, may include, but are not limited to phenyl, naphthalenyl, fluorenyl, and the like.

Heteroatoms are defined as oxygen, nitrogen, sulfur and the like.

Heterocyclic groups may be heteroaryl or heterocycloalkyl groups.

Each monocyclic heterocyclic ring of the present invention has from 3 to 7 ring atoms and contains up to four heteroatoms. Monocyclic heterocyclic rings or fused heterocyclic rings include substituted aromatic and non-aromatics;

Each fused heterocyclic ring of the present invention optionally includes carbocyclic rings or heterocyclic rings;

"Heterocycloalkyl" represents a group or moiety comprising a monovalent monocyclic or bicyclic radical, which is saturated or partially unsaturated (non-aromatic), containing 3 to 10 ring atoms, which includes 1 to 4 heteroatoms independently selected from nitrogen, oxygen and sulfur, and which may be unsubstituted or substituted by one or more of the substituents defined herein.

Illustrative examples of heterocycloalkyls include, but are not limited to, Generally, in the compounds of this invention, heterocycloalkyl groups are 5-membered and/or 6-membered heterocycloalkyl groups, such as azetidinyl, pyrrolidyl (or pyrrolidinyl), tetrahydrofuryl (or tetrahydrofuranyl), tetrahydrothienyl, dihydrofuryl, oxazolinyl, thiazolinyl or pyrazolinyl, piperidyl (or piperidinyl), piperazinyl, morpholinyl, tetrahydropyranyl, dihydropyranyl, 1,3-dioxanyl, tetrahydro-2H-1,4-thiazinyl, 1,4-dioxanyl, 1,3-oxathianyl, and 1,3-dithianyl.

Additional examples of substituted heterocycloalkyl groups, which are partially saturated non-aromatic groups that are suitable in the present invention, may include, but are not limited to: 1,3-dihydroisobenzofuranyl, pyridin-4(1H)-one-yl, 3-hydroxy-1-methylpyridin-4(1H)-one-yl, 3,4-dihydroisoquinolin-1(2H)-one-yl, quinolin-4(1H)-one-yl, 3-hydroxyquinolin-4(1H)-one-yl, 3-hydroxy-1-methylquinolin-4(1H)-one-yl, 5-chloro-1-ethyl-6,7-dihydroxyquinolin-4(1H)-one-yl, 5-chloro-6,7-dihydroxy-1-methylquinolin-4(1H)-one-yl, 1-ethyl-8-fluoro-6,7-dihydroxyquinolin-4(1H)-one-yl, 5-chloro-1-ethyl-6,7-dihydroxyquinolin-4(1H)-one-yl, 1-ethyl-5-fluoro-6,7-dihydroxyquinolin-4(1H)-one-yl, 1-ethyl-6-fluoro-7,8-dihydroxyquinolin-4(1H)-one-yl, 1-ethyl-7,8-dihydroxyquinolin-4(1H)-one-yl, 6,7-dihydroxy-1-isopropylquinolin-4(1H)-one-yl, 1-ethyl-5,6-dihydroxyquinolin-4(1H)-one-yl, 5-chloro-1-cyclopropyl-6,7-dihydroxyquinolin-4(1H)-one-yl, 1-cyclopropyl-6,7-dihydroxyquinolin-4(1H)-one-yl, 1-(tert-butyl)-6,7-dihydroxyquinolin-4(1H)-one-yl, 6,7-dihydroxy-1-methylquinolin-4(1H)-one-yl, cinnolin-4(1H)-one-yl, 1-ethyl-6,7-dihydroxycinnolin-4(1H)-one-yl, 5-chloro-1-ethyl-6,7-dihydroxycinnolin-4(1H)-one-yl, 1-ethyl-5-fluoro-6,7-dihydroxycinnolin-4(1H)-one-yl, 1-ethyl-6,7-dihydroxycinnolin-4(1H)-one-yl and the like.

Additional examples of substituted heterocycloalkyl groups, which are non-aromatic that are suitable in the present invention, may include, but are not limited to:

"Heteroaryl" represents a group or moiety comprising an aromatic monovalent monocyclic or bicyclic radical, containing 5 to 10 ring atoms, including 1 to 4 heteroatoms independently selected from nitrogen, oxygen and sulfur, which may be unsubstituted or substituted by one or more of the substituents defined herein. This term also encompasses bicyclic heterocyclic-aryl compounds containing an aryl ring moiety fused to a heterocycloalkyl ring moiety, containing 5 to 10 ring atoms, including 1 to 4 heteroatoms independently selected from nitrogen, oxygen and sulfur, which may be unsubstituted or substituted by one or more of the substituents defined herein. Illustrative examples of heteroaryls include, but are not limited to, thienyl, pyrrolyl, imidazolyl, pyrazolyl, furyl (or furanyl), isothiazolyl, furazanyl, isoxazolyl, oxazolyl, oxadiazolyl, thiazolyl, pyridyl (or pyridinyl), pyrazinyl, pyrimidinyl, pyridazinyl, triazinyl, tetrazinyl, triazolyl, tetrazolyl, benzo[b]thienyl, isobenzofuryl, 2,3-dihydrobenzofuryl, chromenyl, chromanyl, indolizinyl, isoindolyl, indolyl, indazolyl, purinyl, isoquinolyl, quinolyl, phthalazinyl, naphthridinyl, quinzolinyl, benzothiazolyl, benzimidazolyl, tetrahydroquinolinyl, cinnolinyl, pteridinyl, isothiazolyl, carbazolyl, 1,2,3,4 tetrahydro isoquinolinyl and the like.

Generally, the heteroaryl groups present in the compounds of this invention are 5-membered and/or 6-membered monocyclic heteroaryl groups. Selected 5-membered heteroaryl groups contain one nitrogen, oxygen or sulfur ring heteroatom, and optionally contain 1, 2 or 3 additional nitrogen ring atoms. Selected 6-membered heteroaryl groups contain 1, 2, 3 or 4 nitrogen ring heteroatoms. Selected 5- or 6-membered heteroaryl groups include thienyl, pyrrolyl, imidazolyl, pyrazolyl, furyl, isothiazolyl, furazanyl, isoxazolyl, oxazolyl, oxadiazolyl, thiazolyl, triazolyl, and tetrazolyl or pyridyl, pyrazinyl, pyrimidinyl, pyridazinyl, and triazinyl.

"Oxo" represents a double-bonded oxygen moiety; for example, if attached directly to a carbon atom forms a carbonyl moiety (C=O), or attached to an N or S forms oxides, N-oxides, sulfones or sulfoxides.

As used herein, the term "compound(s) of the invention" means a compound of Formulas (I) to (VI), respectively (as defined above) in any form, i.e., any salt or non-salt form (e.g., as a free acid or base form, or as a pharmaceutically acceptable salt thereof) and any physical form thereof (e.g., including non-solid forms (e.g., liquid or semi-solid forms), and solid forms (e.g., amorphous or crystalline forms, specific polymorphic forms, solvates, including hydrates (e.g., mono-, di- and hemi-hydrates)), and mixtures of various forms.

As used herein, the term "optionally substituted" means that a group, such as, which may include, but is not limited to alkyl, aryl, heteroaryl, etc., may be unsubstituted, or the group may be substituted with one or more substituent(s) as defined. In the case where groups may be selected from a number of alternative groups the selected groups may be the same or different.

The term "independently" means that where more than one substituent is selected from a number of possible substituents, those substituents may be the same or different.

The present invention relates to a compound of Formulas (I) to (VI), which definition referred herein includes, but are not limited to the following related sub-generic Formulas (II) and (IX).

The alternative definitions for the various groups and substitutent groups of Formulas (IA), (I) to (VI), respectively, or a pharmaceutically acceptable salt thereof, provided throughout the specification are intended to particularly describe each compound species disclosed herein, individually, as well as groups of one or more compound species. The scope of this invention includes any combination of these group and substituent group definitions.

The alternative definitions for the various groups and substitutent groups of Formulas (IA), (I) to (VI), respectively, or a pharmaceutically acceptable salt thereof, provided throughout the specification are intended to particularly describe each compound species disclosed herein, individually, as well as groups of one or more compound species. The scope of this invention includes any combination of these group and substituent group definitions.

Enantiomers, Diastereomers and Polymorphs

The compounds according to Formulas (IA), (I) to (VI), respectively, or a pharmaceutically acceptable salt thereof of the present invention may contain one or more asymmetric center (also referred to as a chiral center) and may, therefore, exist as individual enantiomers, diastereomers, or other stereoisomeric forms, or as mixtures thereof. Chiral centers, such as chiral carbon atoms, may also be present in a substituent such as an alkyl group. Where the stereochemistry of a chiral center present in Formulas (IA), (I) to (VI), respectively, or a pharmaceutically acceptable salt thereof, or in any chemical structure illustrated herein, is not specified the structure is intended to encompass all individual stereoisomers and all mixtures thereof. Thus, compounds according to Formulas (IA), (I) to (VI), respectively, or a pharmaceutically acceptable salt thereof, containing one or more chiral center may be used as racemic mixtures, enantiomerically enriched mixtures, or as enantiomerically pure individual stereoisomers.

Individual stereoisomers of a compound according to Formulas (IA), (I) to (VI), respectively, or a pharmaceutically acceptable salt thereof, which contain one or more asymmetric center may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. The skilled artisan will appreciate that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation. When a disclosed compound or its salt is named or depicted by structure, it is to be understood that the compound or salt, including solvates (particularly, hydrates) thereof, may exist in crystalline forms, non-crystalline forms or a mixture thereof. The compound or salt, or solvates (particularly, hydrates) thereof, may also exhibit polymorphism (i.e. the capacity to occur in different crystalline forms). These different crystalline forms are typically known as "polymorphs." It is to be understood that when named or depicted by structure, the disclosed compound, or solvates (particularly, hydrates) thereof, also include all polymorphs thereof. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. One of ordinary skill in the art will appreciate that different polymorphs may be produced, for example, by changing or adjusting the conditions used in crystallizing/recrystallizing the compound.

Salts

Because of their potential use in medicine, the salts of the compounds of Formulas (I) to (VI), respectively, are preferably pharmaceutically acceptable salts. Suitable pharmaceutically acceptable salts include those described by Berge, Bighley and Monkhouse J. Pharm. Sci (1977) 66, pp 1-19.

When a compound of the invention is a base (contain a basic moiety), a desired salt form may be prepared by any suitable method known in the art, including treatment of the free base with an inorganic acid, such as hydrochloric acid, hydrobromic acid, sulfuric acid, nitric acid, phosphoric acid, and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, pyranosidyl acid, such as glucuronic acid or galacturonic acid, alpha-hydroxy acid, such as citric acid or tartaric acid, amino acid, such as aspartic acid or glutamic acid, aromatic acid, such as benzoic acid or cinnamic acid, sulfonic acid, such as p-toluenesulfonic acid, methanesulfonic acid, ethanesulfonic acid or the like. Examples of pharmaceutically acceptable salts include sulfates, pyrosulfates, bisulfates, sulfites, bisulfites, phosphates, chlorides, bromides, iodides, acetates, propionates, decanoates, caprylates, acrylates, formates, isobutyrates, caproates, heptanoates, propiolates, oxalates, malonates succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, phenylacetates, phenylpropionates, phenylbutrates, citrates, lactates, γ-hydroxybutyrates, glycollates, tartrates mandelates, and sulfonates, such as xylenesulfonates, methanesulfonates, propanesulfonates, naphthalene-1-sulfonates and naphthalene-2-sulfonates.

If an inventive basic compound is isolated as a salt, the corresponding free base form of that compound may be prepared by any suitable method known to the art, including treatment of the salt with an inorganic or organic base, suitably an inorganic or organic base having a higher $pK_a$ than the free base form of the compound.

When a compound of the invention is an acid (contains an acidic moiety), a desired salt may be prepared by any suitable method known in the art, including treatment of the free acid with an inorganic or organic base, such as an amine (primary, secondary, or tertiary), an alkali metal or alkaline earth metal hydroxide, or the like. Illustrative examples of suitable salts include organic salts derived from amino acids such as glycine and arginine, ammonia, primary, secondary, and tertiary amines, and cyclic amines, such as ethylene diamine, dicyclohexylamine, ethanolamine, piperidine, morpholine, and piperazine, as well as inorganic salts derived from sodium, calcium, potassium, magnesium, manganese, iron, copper, zinc, aluminum, and lithium.

Certain of the compounds of this invention may form salts with one or more equivalents of an acid (if the compound contains a basic moiety) or a base (if the compound contains an acidic moiety). The present invention includes within its scope all possible stoichiometric and non-stoichiometric salt forms.

Because the compounds of this invention may contain both acid and base moieties, pharmaceutically acceptable salts may be prepared by treating these compounds with an alkaline reagent or an acid reagent, respectively. Accordingly, this invention also provides for the conversion of one pharmaceutically acceptable salt of a compound of this invention, e.g., a hydrochloride salt, into another pharmaceutically acceptable salt of a compound of this invention, e.g., a sodium salt or a disodium salt.

Carboxylate functional groups of compounds of the present invention have coordinated mono or di-valent cations, where such cations may include, but are not limited to alkali metals, which may include, but are not limited to lithium (Li), sodium (Na), potassium, or mixtures thereof and the like.

Quarternary amine functional groups of compounds of the present invention, which are positively charged species, also may have coordinated anions, where such anions may include, but are not limited to halogens, which may include, but are not limited to chlorides, fluorides, bromides, iodides and the like.

Compounds of Formulas (I) to (VI) of the present invention, also may form a zwitterion(s) (formerly called a dipolar ion), which is a neutral molecule with a positive and a negative electrical charge (i.e., not dipoles) at different locations within that molecule. Zwitterions are sometimes also called inner salts.

Solvates

For solvates of the compounds of the invention, or salts thereof, that are in crystalline form, the skilled artisan will appreciate that pharmaceutically-acceptable solvates may be formed wherein solvent molecules are incorporated into the crystalline lattice during crystallization. Solvates may involve nonaqueous solvents such as ethanol, isopropanol, DMSO, acetic acid, ethanolamine, and ethyl acetate, or they may involve water as the solvent that is incorporated into the crystalline lattice. Solvates wherein water is the solvent that is incorporated into the crystalline lattice are typically referred to as "hydrates." Hydrates include stoichiometric hydrates as well as compositions containing variable amounts of water. The invention includes all such solvates.

Deuterated Compounds

The invention also includes various deuterated forms of the compounds of Formulas (IA), (I) to (VI), respectively, or a pharmaceutically acceptable salt thereof. Each available hydrogen atom attached to a carbon atom may be independently replaced with a deuterium atom. A person of ordinary skill in the art will know how to synthesize deuterated forms of the compounds of Formulas (IA), (I) to (VI), respectively, or a pharmaceutically acceptable salt thereof of the present invention. For example, deuterated materials, such as alkyl groups may be prepared by conventional techniques (see for example: methyl-$d_3$-amine available from Aldrich Chemical Co., Milwaukee, Wis., Cat. No. 489, 689-2).

Isotopes

The subject invention also includes isotopically-labeled compounds which are identical to those recited in Formulas (I) to (VI), respectively, or a pharmaceutically acceptable salt thereof but for the fact that one or more atoms are replaced by an atom having an atomic mass or mass number different from the atomic mass or mass number most commonly found in nature. Examples of isotopes that can be incorporated into compounds of the invention include isotopes of hydrogen, carbon, nitrogen, oxygen, fluorine, iodine and chlorine such as $^3H$, $^{11}C$, $^{14}C$, $^{18}F$, $^{123}I$ or $^{125}I$.

Compounds of the present invention and pharmaceutically acceptable salts of said compounds that contain the aforementioned isotopes and/or other isotopes of other atoms are within the scope of the present invention. Isotopically labeled compounds of the present invention, for example those into which radioactive isotopes such as $^3H$ or $^{14}C$ have been incorporated, are useful in drug and/or substrate tissue distribution assays. Tritiated, ie. $^3$H, and carbon-14, i.e. $^{14}$C, isotopes are particularly preferred for their ease of preparation and detectability. $^{11}$C and $^{18}$F isotopes are particularly useful in PET (positron emission tomography).

Purity

Because the compounds of the present invention are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

Synthetic Schemes and General Methods of Preparation

The compounds of Formulas (IA), (I) to (VI), respectively, or corresponding pharmaceutically acceptable salts thereof, may be obtained by using synthetic procedures illustrated in the Schemes below or by drawing on the knowledge of a skilled organic chemist.

The synthesis provided in these Schemes are applicable for producing compounds of the invention having a variety of different R$^1$ and R$^2$ groups employing appropriate precursors, which are suitably protected if needed, to achieve compatibility with the reactions outlined herein. Subsequent deprotection, where needed, affords compounds of the nature generally disclosed. While the Schemes are shown with compounds only of Formulas (IA), (I) to (VI), respectively, or a pharmaceutically acceptable salt thereof, they are illustrative of processes that may be used to make the compounds of the invention.

Intermediates (compounds used in the preparation of the compounds of the invention) may also be present as salts. Thus, in reference to intermediates, the phrase "compound(s) of formula (number)" means a compound having that structural formula or a pharmaceutically acceptable salt thereof.

The present invention also relates to processes for making compounds of Formulas (IA), (I) to (VI), respectively, or a pharmaceutically acceptable salt thereof.

The compounds of the present invention may be obtained by using synthetic procedures illustrated in Schemes below or by drawing on the knowledge of a skilled organic chemist.

The synthesis provided in these Schemes are applicable for producing compounds of the invention as defined by Formulas (IA), (I) to (VI), respectively, or a pharmaceutically acceptable salt thereof, respectively, having a variety of different functional groups as defined employing appropriate precursors, which are suitably protected if needed, to achieve compatibility with the reactions outlined herein. Subsequent deprotection, where needed, affords compounds of the nature generally disclosed. While the Schemes shown with compounds only as defined therein, they are illustrative of processes that may be used to make the compounds of the invention.

Intermediates (compounds used in the preparation of the compounds of the invention) also may be present as salts. Thus, in reference to intermediates, the phrase "compound(s) of formula (number)" means a compound having that structural formula or a pharmaceutically acceptable salt thereof.

The compounds according to Formulas (IA), (I) to (VI), respectively, or a pharmaceutically acceptable salt thereof, or pharmaceutically acceptable salts thereof, are prepared using conventional organic syntheses. Suitable synthetic routes are depicted below in the following general reaction schemes.

The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. Suitable protecting groups and the methods for protecting and de-protecting different substituents using such suitable protecting groups are well known to those skilled in the art; examples of which may be found in T. Greene and P. Wuts, *Protecting Groups in Chemical Synthesis* (3rd ed.), John Wiley & Sons, NY (1999). In some instances, a substituent may be specifically selected to be reactive under the reaction conditions used. Under these circumstances, the reaction conditions convert the selected substituent into another substituent that is either useful as an intermediate compound or is a desired substituent in a target compound.

Synthetic Schemes

The compounds of Formulas (IA), (I) to (VI), respectively, or corresponding pharmaceutically acceptable salts thereof, of the present invention are prepared using conventional organic syntheses. Suitable synthetic routes are depicted below in the following general reaction schemes.

The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. Suitable protecting groups and the methods for protecting and de-protecting different substituents using such suitable protecting groups are well known to those skilled in the art; examples of which may be found in T. Greene and P. Wuts, *Protecting Groups in Chemical Synthesis* (3rd ed.), John Wiley & Sons, NY (1999). In some instances, a substituent may be specifically selected to be reactive under the reaction conditions used. Under these circumstances, the reaction conditions convert the selected substituent into another substituent that is either useful as an intermediate compound or is a desired substituent in a target compound.

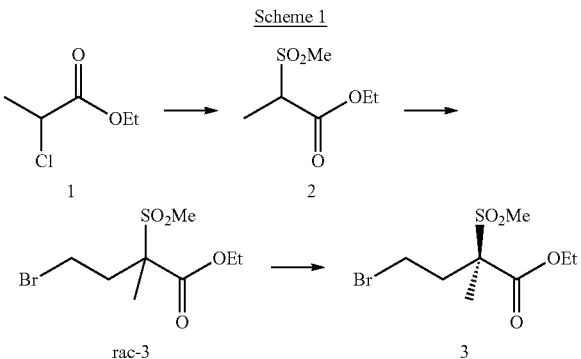

As shown in Scheme 1, 3 can be prepared by reacting the appropriate alkyl chloride 1 with a nucleophilic sulfinate, such as sodium methansulfinate, in an appropriate solvent, such as ethanol. The resulting sulfonyl compound 2 can be treated with an appropriate base, such as sodium hydride, and reacted with a suitable alkyl halogen, such as an alkyl bromide, can provide the analogous racemic compound, such as rac-3. This material can then be subject to chiral chromatography to resolve the enantiomers and can afford the appropriate chiral material, such as 3.

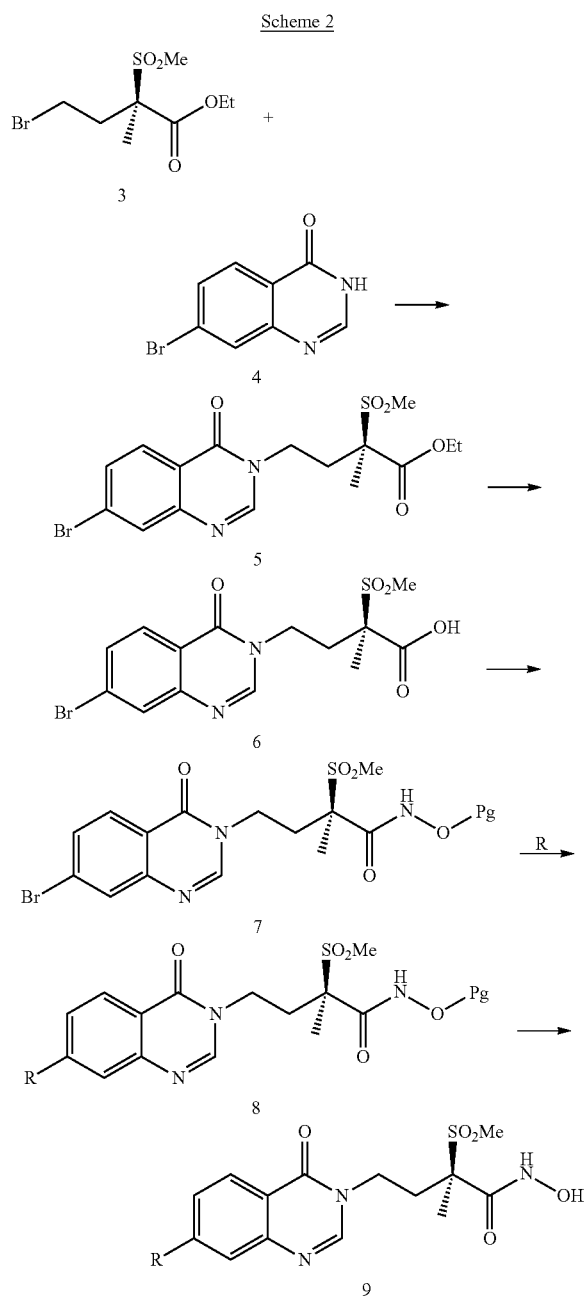

Scheme 2

As shown in Scheme 2, compound 3 can be condensed with compound 4 using a suitable base, such as cesium carbonate, in an appropriate polar solvent, such as dimethyl formamide or acetonitrile, affording compound 5. The ester can be converted to the acid using methods known in the literature and familiar to those skilled in the art using reagents, such as lithium hydroxide, in the appropriate solvents, such as water and/or tetrahydrofuran. The hydroxamic acid can be incorporated into the molecule using a suitably protected hydroxlamine (Pg=protecting group), such as O-tetrahydropyran-2-ylhydroxylamine, using standard amide coupling procedures, such as 2-chloro-4,6-dimethoxy-1,3,5-triazine, and an appropriate base, such a N-methylmorpholine, in a suitable solvent, such as tetrahydrofuran. The coupling reaction of 7 can be carried out may a variety of reactions or techniques. The carbon-carbon bond can be formed using a Suzuki-Miyaura coupling and such reagents R will be a boronic acid or boronic ester. These reactions can be carried out using suitable catalyst, such as palladium or nickel, in an appropriate solvent, such as dioxane and/or water. Depending upon the nature of the protecting group, the hydroxamic acid can be revealed using an appropriate deprotection reaction, such as HCl, in a suitable solvent such as 1,4-dioxane.

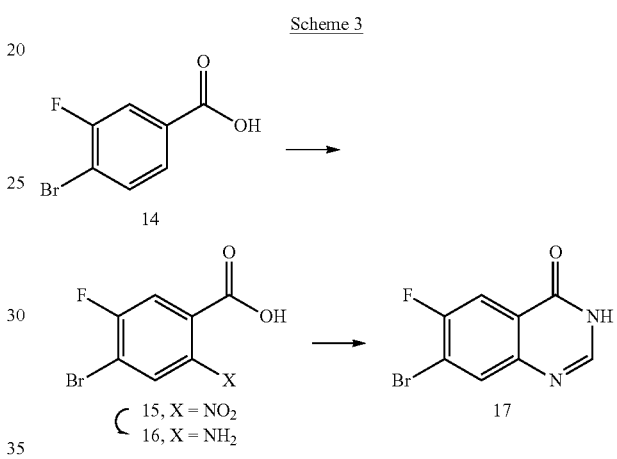

Scheme 3

As exemplified in scheme 3, acid 14 can be converted to compound 15 using a suitable nitration conditions such as sulfuric acid and potassium nitrate and this product can be reduced to the corresponding amine using a reduction systems, such as tin chloride in aqueous hydrochloric acid. The amine can be condensed with a suitable electrophile such as formamide at high temperatures to form the quinazolinone core. Compound 17 can be condensed as described in scheme 2.

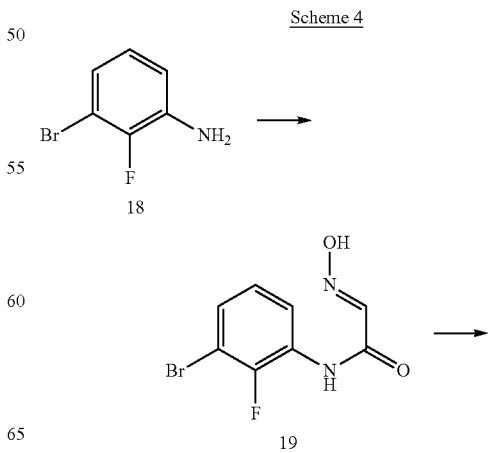

Scheme 4

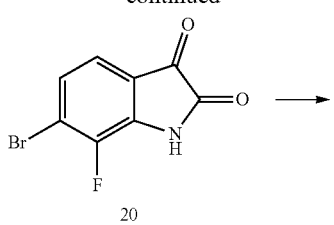

20

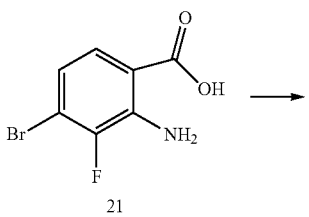

21

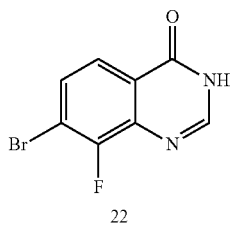

22

Scheme 4 describes the synthesis of the 8-fluoroquinazalinone core starting with the appropriate aniline. Compound 18 can be converted to 19 using an aldehyde equivalent such as 2,2,2-trichloroethane-1,1-diol, hydroxylamine hydrochloride and sodium sulfate in aqueous HCl. Compound 19 can be converted to 20 using a strong acid such as sulfuric acid. Ring opened compound 21 can be generated using a suitable system such as hydrogen peroxide in aqueous sodium hydroxide solution. The quinazalinone core can then be made as described in Scheme 3 and this can be condensed with compound 3 as described in scheme 2.

Scheme 5

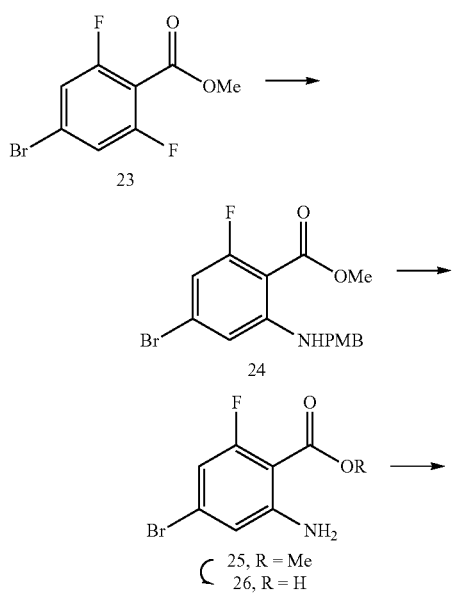

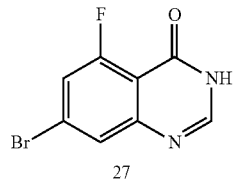

27

Compound 27 can be synthesized following the general procedure outlined in scheme 5. The appropriate di-fluoro aryl ester 23 can be reacted with an appropriate amine nucleophile, such as (2,4-dimethoxyphenyl)methanamine using the appropriate conditions, such as potassium carbonate as a base, heat and a polar solven such as DMF. The PMB group can be cleaved using acidic conditions such as HCl in a solvent such as DCM. The ester in compound 25 can be cleaved to acid 26 using appropriate conditions such as LiOH in water and the quinazalinone core can be synthesized as described previously. Compound 27 can be condensed with compound 3 as described in scheme 2.

Scheme 6

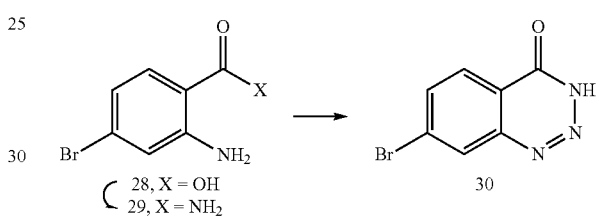

Triazinone compound 30 can be prepared starting from acid 28, which can be converted to primary amide 28 using the appropriate amide coupling conditions, such as HOBt/EDC in THF with ammonia. Compound 30 can be condensed with compound 3 as described in scheme 2.

Scheme 7

9 ⟶

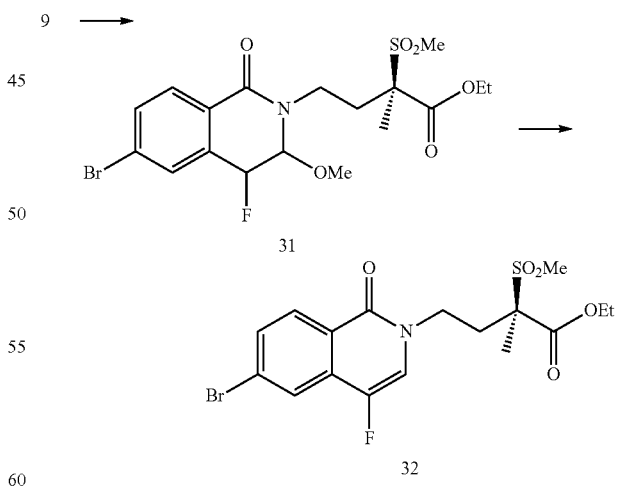

The 4-fluoroisoquinolinone derivative 32 can be can made as shown in scheme 7. Previously described compound 9 can be converted to compound 31 using the appropriate fluorinating reagent, such as Selectfluor in aqueous acetonitrile. The methanol can be eliminated using the appropriate condition such as HCl in DCM.

Scheme 8

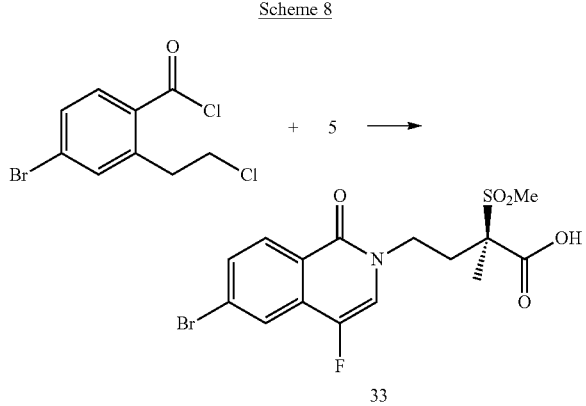

Compound 33 can be made by directly condensing compound 5 with commercially available 4-bromo-2-(2-chloroethyl)benzoyl chloride using the appropriate conditions, such as triethylamine in THF followed by treatment with potassium tert-butoxide in 1,4-dioxane.

Scheme 9

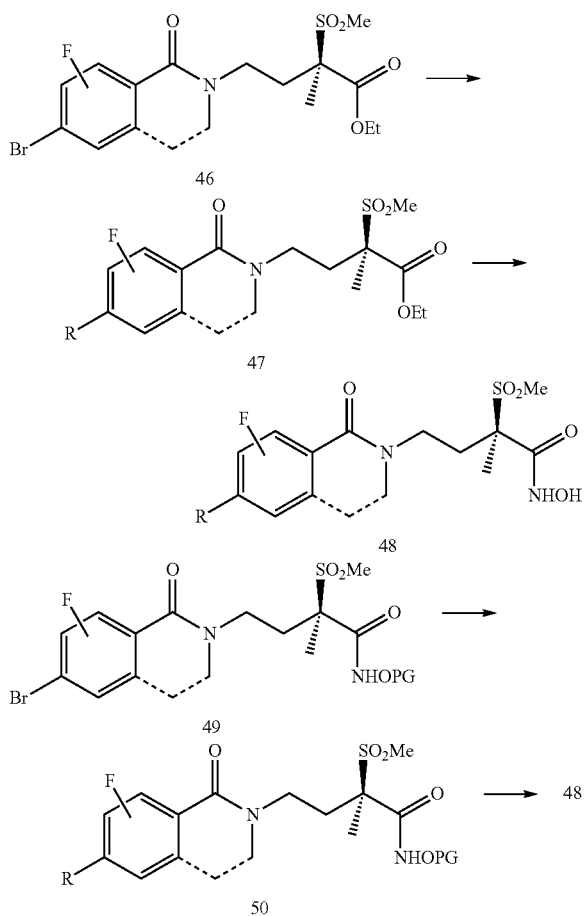

Compounds 46 and 49 can be transformed to 47 and 50, respectively, using typical Suzuki coupling conditions such as an appropriate aryl boronate or aryl boronic acid, PdCl$_2$(dppf), K$_2$CO$_3$ in acetonitrile and water. The suitably protected hydroxylamines, such as O-tetrahydropyran-2-ylhydroxylamine derivatives (50) can be deprotected using a suitable acid system, such as TFA or HCl. Alternatively, the ethyl esters, such as compound 47, can be directly converted to the hydroxylamine 48.

Scheme 10

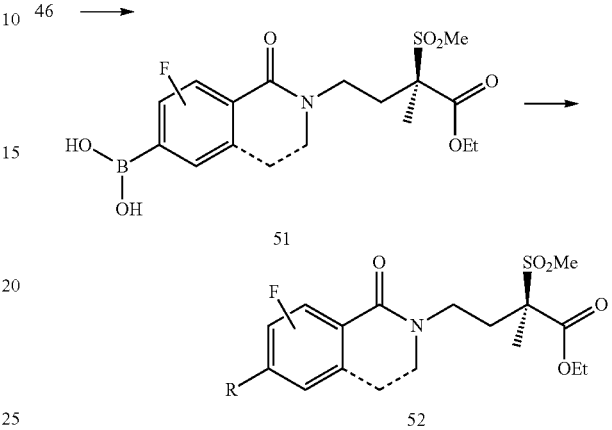

As shown in scheme 13, certain compounds can be made by converting the aryl bromide derivatives (46) to the aryl boronic acid using the appropriate conditions such as 4,4,4',4',5,5,5',5'-octamethyl-2,2'-bi(1,3,2-dioxaborolane), PdCl$_2$(dppf)-DCM adduct, KOAc in 1,4-dioxane to afford derivatives related to compound 51. Suzuki coupling the appropriate aryl halide can then be performed as described in scheme 12 to afford compounds related to 52. Conversion of 52 to the desired hydroxamates can be accomplished as described previously.

Pharmaceutical Compositions, Dosage Forms and Regimens

The present invention relates to pharmaceutical compositions comprised of novel compounds of Formulas (IA), (I) to (VI), respectively, or a pharmaceutically acceptable salt thereof and at least one pharmaceutically acceptable excipient(s).

The pharmaceutical composition of the present invention, further may comprise an additional active agent.

The compounds of the invention will normally, but not necessarily, be formulated into a pharmaceutical composition prior to administration to a patient.

Accordingly, the present invention is directed to pharmaceutical compositions or formulations, which comprise a compound or compound species of the present invention and pharmaceutically-acceptable excipient(s). In particular, the present invention also may relate to a pharmaceutical composition or formulation, which comprises a compound as defined by Formulas (IA), (I) to (VI), respectively, or a pharmaceutically acceptable salt thereof, and at least one pharmaceutically acceptable excipient(s), and optionally one or more other therapeutic ingredients.

The pharmaceutical compositions of the invention may be prepared and packaged in bulk form wherein an effective amount of a compound of the invention can be extracted and then given to the patient such as with powders, syrups, and solutions for injection. Alternatively, the pharmaceutical compositions of the invention may be prepared and packaged in unit dosage form. For oral application, for example, one or more tablets or capsules may be administered. A dose of the pharmaceutical composition contains at least a therapeutically effective amount of a compound of this invention (i.e., a compound of Formulas (IA), (I) to (VI), respectively, or a pharmaceutically acceptable salt thereof, particularly a pharmaceutically acceptable salt, thereof). When prepared in unit dosage form, the pharmaceutical compositions or formulations may contain from 1 mg to 1000 mg of a compound of this invention.

The pharmaceutical compositions or formulations as defined herein typically contain one compound of the present invention. However, in certain embodiments, the pharmaceutical compositions may contain more than one compound of the present invention. In addition, the pharmaceutical compositions of the present invention may optionally further comprise one or more additional pharmaceutically active compounds.

As used herein, "pharmaceutically-acceptable excipient" means a material, composition or vehicle involved in giving form or consistency to the composition. Each excipient must be compatible with the other ingredients of the pharmaceutical composition when commingled such that interactions which would substantially reduce the efficacy of the compound of the invention when administered to a patient and interactions which would result in pharmaceutical compositions that are not pharmaceutically-acceptable are avoided. In addition, each excipient must of course be of sufficiently high purity to render it pharmaceutically-acceptable.

Suitable pharmaceutically-acceptable excipients will vary depending upon the particular dosage form chosen. In addition, suitable pharmaceutically-acceptable excipients may be chosen for a particular function that they may serve in the composition.

For example, certain pharmaceutically-acceptable excipients may be chosen for their ability to facilitate the production of uniform dosage forms. Certain pharmaceutically-acceptable excipients may be chosen for their ability to facilitate the production of stable dosage forms. Certain pharmaceutically-acceptable excipients may be chosen for their ability to facilitate the carrying or transporting the compound or compounds of the invention once administered to the patient from one organ, or portion of the body, to another organ, or portion of the body. Certain pharmaceutically-acceptable excipients may be chosen for their ability to enhance patient compliance. Moreover, pharmaceutical compositions, formulations, dosage forms, and the like, etc. may conveniently be presented in unit dosage form and may be prepared by any of the methods well known in the art of pharmacy.

All methods include the step of bringing the active ingredient into association with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Suitable pharmaceutically-acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anti-caking agents, humectants, chelating agents, plasticizers, viscosity increasing agents, antioxidants, preservatives, stabilizers, surfactants, and buffering agents. The skilled artisan will appreciate that certain pharmaceutically-acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The compounds of the invention and the pharmaceutically-acceptable excipient or excipients will typically be formulated into a dosage form adapted for administration to the patient by the desired route of administration.

With regard to the present invention, conventional dosage forms include those adapted for (1) oral administration such as tablets, capsules, caplets, pills, troches, powders, syrups, elixirs, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols and solutions; and (6) topical administration such as creams, ointments, lotions, solutions, pastes, sprays, foams, and gels.

The pharmaceutical compositions or formulations of the invention are prepared using techniques and methods known to those skilled in the art. Some of the methods commonly used in the art are described in Remington's *Pharmaceutical Sciences* (Mack Publishing Company).

In general, pharmaceutical compositions of the present invention are prepared using conventional materials and techniques, such as mixing, blending and the like.

The term "active agent" is defined for purposes of the present invention as any chemical substance or composition of the present invention, which can be delivered from the device into an environment of use to obtain a desired result.

The percentage of the compound in compositions can, of course, be varied as the amount of active in such therapeutically useful compositions is such that a suitable dosage will be obtained.

In one aspect, the present invention is directed to a pharmaceutical composition comprising a compound of Formulas (I) to (VI), respectively, or a pharmaceutically acceptable salt thereof and one or more pharmaceutically acceptable excipients.

In another aspect, the present invention is directed to a pharmaceutical composition comprising a compound of Formulas (I) to (VI), respectively, or a pharmaceutically acceptable salt thereof and one or more pharmaceutically acceptable excipients.

In another aspect, the present invention is directed to a pharmaceutical composition comprising a compound or compound species or a pharmaceutically acceptable salt thereof of the present invention as defined herein and one or more pharmaceutically acceptable excipients.

It will be appreciated that the actual preferred dosages of the compounds being used in the compositions of this invention will vary according to the particular composition formulated, the mode of administration, the particular site of administration and the host being treated.

The active compounds of the present invention may be orally administered, for example, with an inert diluent, or with an assimilable edible carrier, or they can be enclosed in hard or soft shell capsules, or they can be compressed into tablets, or they can be incorporated directly with the food of the diet, etc.

In one aspect, the invention is directed to a solid oral dosage form such as a tablet or capsule comprising a safe and effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

Where appropriate, dosage unit formulations for oral administration can be microencapsulated. The composition can also be prepared to prolong or sustain the release as for example by coating or embedding particulate material in polymers, wax or the like.

The compounds of the invention may also be coupled with soluble polymers as targetable drug carriers. Such polymers can include polyvinylpyrrolidone, pyran copolymer, polyhydroxypropylmethacrylamide-phenol, polyhydroxyethyl aspartamide phenol, or polyethyleneoxide-polylysine substituted with palmitoyl residues. Furthermore, the compounds of the invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Methods of Treatment

The present invention also relates to methods for treating bacterial infections, which comprises administering to a subject in need thereof an effective amount of a compound of Formulas (IA), (I) to (VI), respectively, or a pharmaceutically acceptable salt thereof or a corresponding pharmaceutical composition.

As used herein, "patient" refers to a human subject or other mammal.

As used herein, "infectious disease" refers to any disease characterized by the presence of a microbial infection, such as a bacterial infection.

As used herein, "treat" in reference to a condition means: (1) to ameliorate or prevent the condition or one or more of the biological manifestations of the condition, (2) to interfere with (a) one or more points in the biological cascade that leads to or is responsible for the condition or (b) one or more of the biological manifestations of the condition, (3) to alleviate one or more of the symptoms or effects associated with the condition, or (4) to slow the progression of the condition or one or more of the biological manifestations of the condition.

As indicated above "treatment" of a condition includes prevention of the condition. The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof.

As used herein, "effective amount" in reference to a compound of the invention means an amount of the compound sufficient to treat the patient's condition, but low enough to avoid serious side effects (at a reasonable benefit/risk ratio) within the scope of sound medical judgment. An effective amount of a compound will vary with the particular compound chosen (e.g., consider the potency, efficacy, and half-life of the compound); the route of administration chosen; the condition being treated; the severity of the condition being treated; the age, size, weight, and physical condition of the patient being treated; the medical history of the patient being treated; the duration of the treatment; the nature of concurrent therapy; the desired therapeutic effect; and like factors, and can be routinely determined by the skilled artisan.

Therapeutics Applications

The invention provides methods of treating Gram-negative bacterial infections, the method comprising administering to a subject in need of such treatment an effective amount of one or more compounds of the invention. Particular Gram-negative bacteria are *Pseudomonas aeruginosa, Stenotrophomonas maltophilia, Burkholderia cepacia, Alcaligenes xylosoxidans, Acinetobacter, Enterobacteriaceae, Haemophilus, Neisseria* species, *Francisella tularensis, Yersinia pestis, Burkholderia pseudomallei, Burkholderia mallei, Rickettsia prowazekii, Coxiella burnetti, Campylobacter jejuni, Shigella, Moraxella catarrhalis*, and *Chlamydia trachomatis*. In one embodiment, the Gram-negative bacteria is *Neisseria gonorrhoeae*. In another embodiment, the Gram-negative bacteria is *Acinetobacter Baumannii*.

Specific enterobacteriaceae is selected from the group consisting of *Serratia, Proteus, Klebsiella, Enterobacter, Citrobacter, Salmonella, Providencia, Morganella, Cedecea, Edwardsiella, Escherichia coli, Enterobacter cloacae*, and *Enterobacter aerogenes*.

In a more specific embodiment, the Gram-negative bacteria are selected from the group consisting of *Acinetobacter baumanni, Acinetobacter* spp., *Citrobacter* spp., *Enterobacter aerogenes, Enterobacter cloacae, Escherichia coli, Klebsiella oxytoca, Klebsiella pneumonlae, Serratla marcescens, Stenotrophomonas maltophilla, Pseudomonas aeruginosa* and members of the Enterobacteriaceae and *Pseudomonas* that express ESBLs, KPCs, CTX-M, metallo-β-lactamases, and AmpC-type beta-lactamases that confer resistance to currently available cephalosporins, cephamycins, carbapenems, and beta-lactam/beta-lactamase inhibitor combinations.

Examples of infections that may be treated with the compounds of Formula I include nosocomial pneumonia, urinary tract infections, systemic infections (bacteremia and sepsis), skin and soft tissue infections, surgical infections, intraabdominal infections, lung infections in patients with cystic fibrosis, patients suffering from lung infections, endocarditis, diabetic foot infections, osteomyelitis, and central nervous system infections.

In addition, the compounds can be used to treat *Helicobacter pyori* infections in the GI tract of humans (and other mammals). Elimination of these bacteria is associated with improved health outcomes including fewer dyspeptic symptoms, reduced peptic ulcer recurrence and rebleeding, reduced risk of gastric cancer, etc. A more detailed discussion of eradicating *H. pylori* and its impact on gastrointestinal illness may be found at: www.informahealthcare.com, Expert Opin. Drug Saf. (2008) 7(3).

Thus, in a particular aspect, the invention provides methods for treating *Neisseria gonorrhoeae* bacterial infections, the methods comprising administering to a subject in need of such treatment an effective amount of one or more compounds of the invention. In another aspect, the invention provides methods for inhibiting a deacetylase enzyme in Gram-negative bacteria, the method comprising contacting the bacteria with an effective amount of one or more compounds of the invention. A specific deacetylase enzyme is LpxC.

Methods or Uses in Treatment of Diseases

In one aspect, a compound of Formulas (IA), (I) to (VI), respectively, or a pharmaceutically acceptable salt or corresponding pharmaceutical compositions of the present invention have a wide antimicrobial activity spectrum, and may be used for prevention or therapy against a variety of diseases caused by causative bacteria in a variety of mammals including humans, for example, may include, but are not limited to airway infectious diseases, urinary system infectious diseases, resipiratory system infectious diseases, sepsis, nephritis, cholecystitis, oral cavity infectious diseases, endocarditis, pneumonia, bone marrow membrane myelitis, otitis media, enteritis, empyema, wound infectious diseases, opportunistic infection and the like.

Compounds of Formulas (IA), (I) to (VI), respectively, or a pharmaceutically acceptable salt thereof and/or corresponding pharmaceutical compositions of the present invention exhibit high antimicrobial activity in particular against Gram negative bacteria, preferably, Gram negative bacteria of enterobacteria (*E. coli, Klebsiella, Serratia, Enterobacter, Citrobacter, Morganella, Providencia, Proteus* and the like), Gram negative bacteria colonized in respiratory system (*Haemophilus, Moraxella* and the like), and Gram negative bacteria of glucose non fermentation (*Pseudomonas aeruginosa, Pseudomonas* other than *P. aeruginosa, Stenotrophomonas, Burkholderia, Acinetobacter* and the like).

Suitable compounds of Formulas (IA), (I) to (VI), respectively, or a pharmaceutically acceptable salt thereof and/or corresponding pharmaceutical compositions of the present invention are useful in treatment of infections caused by causative bacteria in a variety of mammals including humans, which include, but are not limited to infectious diseases, urinary system infectious diseases, respiratory system infectious diseases, sepsis, nephritis, cholecystitis, oral cavity infectious diseases, endocarditis, pneumonia, bone marrow membrane myelitis, otitis media, enteritis, empyema, wound infectious diseases, opportunistic infection and the like Suitably the compounds of Formulas (IA), (I) to (VI), respectively, or a pharmaceutically acceptable salt thereof and/or corresponding pharmaceutical compositions of the present invention are useful in the treatment of bacterial infections, more particularly gram negative bacterial infections caussed by:

Gram negative bacteria of enterobacteria, which include, but are not limited to *E. coli, Klebsiella, Serratia, Enterobacter, Citrobacter, Morganella, Providencia, Proteus* and the like;

Gram negative bacteria colonized in respiratory system, which include, but are not limited to *Haemophilus, Moraxella* and the like; and Gram negative bacteria of glucose non fermentation, which include, but are not limited to *Pseudomonas aeruginosa, Pseudomonas* other than *P. aeruginosa, Stenotrophomonas, Burkholderia, Acinetobacter* and the like.

Still compounds of Formulas (IA), (I) to (VI), respectively, or a pharmaceutically acceptable salt thereof and/or corresponding pharmaceutical compositions of the present invention have features regarding kinetics in the body, such as blood concentration in which such is highly bioavailable, long duration of effects, and/or significant tissue migration. More preferable compounds are safe in terms of side effects.

Compounds of Formulas (IA), (I) to (VI), respectively, or a pharmaceutically acceptable salt thereof and/or pharmaceutical compositions of the present invention have high water solubility, and thus preferable as an injecting drug, in particular.

The present invention specifically relate to methods or uses for the treatment infectious diseases including bacterial infections, comprise administering an effective amount of a compound according to Formulas (IA), (I) to (VI), respectively, or a pharmaceutically acceptable salt thereof and/or corresponding pharmaceutical compositions to a patient in need thereof. Such uses may include or specifically relate to:

use(s) of compounds or corresponding pharmaceutical compositions of the present invention for the treatment infectious diseases including bacterial infections as defined herein;

use(s) of compounds or corresponding pharmaceutical compositions of the present invention for the therapy in treating of infectious diseases including bacterial infections as defined herein; or use(s) of compounds or corresponding pharmaceutical compositions of the present invention, respectively, in the manufacture of a medicament;

which comprise administering an effective amount of a compound according to Formulas (IA), (I) to (VI), respectively, or a pharmaceutically acceptable salt thereof and/or corresponding pharmaceutical compositions to a patient in need thereof.

Additional Embodiments or Aspects of the Present Invention

One embodiment of the present invention provides for a method or use for treating a bacterial infection, which comprises administering a compound of Formulas (IA), (I) to (VI), respectively, or a pharmaceutically acceptable salt thereof.

Another embodiment of the present invention provides for a method or use of treating a bacterial infection, which comprises administering a pharmaceutical composition comprising a compound of Formulas (IA), (I) to (VI), respectively, or a pharmaceutically acceptable salt thereof and at least one pharmaceutically acceptable adjuvant, carrier or excipient.

In another embodiment of the present invention provides for a method or use of treating a bacterial infection in humans comprising administration of a compound or compound species or a pharmaceutically acceptable salt thereof as defined herein.

In one aspect, the present invention relates to a method or use of treating a bacterial infection comprising administering a therapeutically effective amount of a compound of Formulas (IA), (I) to (VI), respectively, or a pharmaceutically acceptable salt thereof to a human in need thereof.

In another aspect, the present invention relates to a method or use of treating a bacterial infection, where the bacterial infection is caused by Gram negative bacteria.

In another aspect, the present invention relates to a method or use of treating a bacterial infection, where the Gram negative bacteria selected from Gram negative bacteria of enterobacteria, Gram negative bacteria colonized in respiratory, Gram negative bacteria of glucose non fermentation or β-lactam drug resistant Gram negative bacteria.

In another aspect, the present invention relates to a method or use of treating a bacterial infection, where the Gram negative bacteria selected from Gram negative bacteria of Enterobacteriaceae, Gram negative bacteria colonized in the respiratory tract, Gram negative bacteria of glucose non fermentation or drug resistant Gram negative bacteria.

In another aspect, the present invention relates to a method of treating a bacterial infection, where:

the Gram negative bacteria of Enterobacteriaceae selected from *Escherichia, Klebsiella, Serratia, Enterobacter, Citrobacter, Morganella, Salmonella, Shigella, Providencia* or *Proteus;* the Gram negative bacteria colonized in respiratory system selected from *Haemophilus* or *Moraxella;* the Gram negative bacteria of glucose non fermentation selected from *Pseudomonas aeruginosa, Pseudomonas* other than *P. aeruginosa, Stenotrophomonas, Burkholderia* or *Acinetobacter*; and the drug resistant Gram negative bacteria is selected from Carbapenem-Resistant Enterobacteriaceae producing bacteria.

In another aspect, the present invention relates to a method or use, where the bacterial infection is an airway infection, urinary system infection, respiratory system infection, intra-abdominal infection, sepsis infection, skin infection, nephritis, cholecystitis, oral cavity infection, endocarditis, pneumonia, bone marrow membrane myelitis, otitis media, enteritis, empyema, wound infection or an opportunistic infection.

In another aspect, the present invention relates to a method or use of treating a bacterial infection comprising administering a therapeutically effective amount of a compound of Formulas (IA), (I) to (VI), respectively, or a pharmaceutically acceptable salt thereof to a human in need thereof.

In another aspect, the present invention relates to a method or use for treating a gram-negative infection comprising administering a therapeutically effective amount of a compound of Formulas (IA), (I) to (VI), respectively, or a pharmaceutically acceptable salt thereof to a human in need thereof.

In another aspect, the present invention relates to a method or use for treating a gram-negative infection comprising administering a therapeutically effective amount of a compound of Formulas (IA), (I) to (VI), respectively, or a pharmaceutically acceptable salt thereof to a human in need thereof.

In another aspect, the present invention relates to a method or use for treating antimicrobial activity against Gram positive bacteria comprising administering a therapeutically effective amount of a compound of Formulas (IA), (I) to (VI), respectively, or a pharmaceutically acceptable salt thereof to a human in need thereof.

The present invention specifically relate to methods or uses for the treatment infectious diseases including bacterial infections, comprise administering an effective amount of a pharmaceutical composition comprising a compound according to Formulas (IA), (I) to (VI), respectively, or a pharmaceutically acceptable salt thereof, to a patient in need thereof.

One embodiment of the present invention provides for a method or use for treating a bacterial infection, which comprises administering a pharmaceutical composition comprising compound of Formulas (IA), (I) to (VI), respectively, or a pharmaceutically acceptable salt thereof.

Another embodiment of the present invention provides for a method or use of treating a bacterial infection, which comprises administering a pharmaceutical composition comprising a compound of Formulas (IA), (I) to (VI), respectively, or a pharmaceutically acceptable salt thereof and at least one pharmaceutically acceptable excipient.

In another embodiment of the present invention provides for a method or use of treating a bacterial infection in humans comprising administration of a pharmaceutical composition comprising a compound or compound species or a pharmaceutically acceptable salt thereof as defined herein.

In one aspect, the present invention relates to a method or use of treating a bacterial infection comprising administering a therapeutically effective amount of a pharmaceutical composition comprising a compound of Formulas (IA), (I) to (VI), respectively, or a pharmaceutically acceptable salt thereof to a human in need thereof.

In another aspect, the present invention relates to a method or use of treating a bacterial infection, where the bacterial infection is caused by Gram negative bacteria.

In another aspect, the present invention relates to a method of treating a bacterial infection, where the Gram negative bacteria selected from Gram negative bacteria of enterobacteria, Gram negative bacteria colonized in respiratory, Gram negative bacteria of glucose non fermentation or β-lactam drug resistant Gram negative bacteria.

In another aspect, the present invention relates to a method or use of treating a bacterial infection, where:

the Gram negative bacteria of enterobacteria selected from *E. coli, Klebsiella, Serratia, Enterobacter, Citrobacter, Morganella, Providencia* or *Proteus*; the Gram negative bacteria colonized in respiratory system selected from *Haemophilus* or *Moraxella;* the Gram negative bacteria of glucose non fermentation selected from *Pseudomonas aeruginosa, Pseudomonas* other than *P. aeruginosa, Stenotrophomonas* or *Burkholderia, Acinetobacter*; and the Carbapenum-Resistant Enterobacteriaceae producing bacteria resistant Gram negative bacteria is selected from ESBL producing bacteria.

In one aspect, the present invention relates to methods or uses for inhibiting activity of LpxC activity comprising administering a therapeutically effective amount of a compound of any one of Formulas (IA), (I) to (VI) or a pharmaceutically acceptable salt thereof of the present invention or a pharmaceutically acceptable salt thereof to a human in need thereof.

In one aspect, the present invention relates to methods or uses for treating multi-drug resistant pathogens, comprising administering a therapeutically effective amount of a compound of any one of the Formulas (IA), (I) to (VI) or a pharmaceutically acceptable salt thereof to a human in need thereof.

In one aspect, the present invention relates to methods or uses for treating drug-resistant Enterobacteriaceae, comprising administering a therapeutically effective amount of any one of the Formulas (IA), (I) to (VI) or a pharmaceutically acceptable salt thereof a pharmaceutically acceptable salt thereof to a human in need thereof.

In one aspect, the present invention relates to methods or uses for treating gram-negative bacterial sepsis, which comprises administering of any one of the Formulas (IA), (I) to (VI) or a pharmaceutically acceptable salt thereof or a corresponding pharmaceutical composition thereof to a subject in need thereof.

In one aspect, the present invention relates to a compound of any one of the Formulas (IA), (I) to (VI) or a pharmaceutically acceptable salt thereof for use in therapy in treating a subject suffering gram-negative bacterial sepsis in a subject.

In one aspect, the present invention relates to methods or uses of compound of any one of the Formulas (IA), (I) to (VI) or a pharmaceutically acceptable salt thereof as in the manufacture of a medicament for use in the treatment of gram-negative bacterial sepsis in a subject.

Administration

Treatment regimen for the administration of compounds of Formulas (IA), (I) to (VI), respectively, or pharmaceutically acceptable salts thereof or corresponding pharmaceutical compositions of the present invention also may be determined readily by those with ordinary skill in art.

Still more preferable compounds have features regarding kinetics in the body, such as blood concentration in which such is highly bioavailable, long duration of effects, and/or significant tissue migration. More preferable compounds are safe in terms of side effects. More preferable compounds have high water solubility, and thus preferable as an injecting drug, in particular.

Compounds of Formulas (IA), (I) to (VI), respectively, or a pharmaceutically acceptable salt thereof and/or corresponding pharmaceutical compositions may be administered parenterally or orally as an injecting agent, capsules, tablets, and granules, and preferably, administered as an injecting agent. Amounts to be administered may usually be, per 1 kg of body weight of a patient or animal, about 0.1 to 100 mg/day, preferably, about 0.5 to 50 mg/day, if desired, divided into 2-4 times per day. Carriers when used as an injecting agent is for example, distilled water, saline and the like, and base and the like may be used for pH adjustment.

When used as capsules, granules or tablets, carriers may be known excipients (e.g., starch, lactose, sucrose, calcium carbonate, calcium phosphate and the like), binders (e.g., starch, acacia gum, carboxymethyl cellulose, hydroxypropyl cellulose, crystalline cellulose, and the like), lubricants (e.g., magnesium stearate, talc and the like), and the like.

Still compounds of the present invention have features regarding kinetics in the body, such as blood concentration in which such is highly bioavailable, long duration of effects, and/or significant tissue migration. More preferable compounds are safe in terms of side effects. More preferable compounds have high water solubility, and thus preferable as an injecting drug, in particular.

The quantity of the compound, pharmaceutical composition, or dosage form of the present invention administered may vary over a wide range to provide in a unit dosage in an effective amount based upon the body weight of the patient per day to achieve the desired effect and as based upon the mode of administration.

The scope of the present invention includes all compounds, pharmaceutical compositions, or controlled-release formulations or dosage forms, which is contained in an amount effective to achieve its intended purpose. While individual needs vary, determination of optimal ranges of effective amounts of each component is within the skill of the art.

Compounds of Formulas (IA), (I) to (VI), respectively, or pharmaceutically acceptable salts thereof or corresponding pharmaceutical compositions of the present invention may be administered by any suitable route of administration, including both systemic administration and topical administration. Systemic administration includes oral administration, parenteral administration, transdermal administration, rectal administration, and administration by inhalation.

Parenteral administration refers to routes of administration other than enteral, transdermal, or by inhalation, and is typically by injection or infusion. Parenteral administration includes intravenous, intramuscular, and subcutaneous injection or infusion.

Inhalation refers to administration into the patient's lungs whether inhaled through the mouth or through the nasal passages. In one aspect, pharmaceutical compositions, formulations, dosages, dosage forms or dosing regimens of the present invention are adapted for administration by inhalation.

Topical administration includes application to the skin as well as intraocular, intravaginal, and intranasal administration.

Compounds of Formulas (IA), (I) to (VI), respectively, or pharmaceutically acceptable salts thereof or corresponding pharmaceutical compositions of the present invention may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect.

Suitable dosing regimens for compounds of Formulas (IA), (I) to (VI), respectively, or pharmaceutically acceptable salts thereof or corresponding pharmaceutical compositions of the present invention depend on the pharmacokinetic properties of that compound, such as absorption, distribution, and half-life, which can be determined by the skilled artisan. In addition, suitable dosing regimens, including the duration such regimens are administered, for a compound of the invention depend on the condition being treated, the severity of the condition being treated, the age and physical condition of the patient being treated, the medical history of the patient being treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

In another aspect, the invention is directed to a liquid oral dosage form. Oral liquids such as solution, syrups and elixirs can be prepared in dosage unit form so that a given quantity contains a predetermined amount of a compound of the invention. Syrups can be prepared by dissolving the compound of the invention in a suitably flavored aqueous solution, while elixirs are prepared through the use of a non-toxic alcoholic vehicle. Suspensions can be formulated by dispersing the compound of the invention in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

In another aspect, the invention is directed to parenteral administration. Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Typical daily dosages may vary depending upon the particular route of administration chosen. Typical daily dosages for oral administration, to a human weighing approximately 70 kg, would range from 7 mg to 7 g, suitably 3.5 mg to 3.5 g of a compound of the invention a day.

Compounds of Formulas (IA), (I) to (VI), respectively, or pharmaceutically acceptable salts thereof or corresponding pharmaceutical compositions of the present invention may be administered parenterally or orally as an injecting agent, capsules, tablets, and granules, and preferably, administered as an injecting agent. Amounts to be administered may usually be, per 1 kg of body weight of a patient or animal, about 0.1 to 100 mg/day, preferably, about 0.5 to 50 mg/day, if desired, divided into 2-4 times per day. Carriers when used as an injecting agent for example, distilled water, saline and the like, and base and the like may be used for pH adjustment. When used as capsules, granules or tablets, carriers may be known excipients (e.g., starch, lactose, sucrose, calcium carbonate, calcium phosphate and the like), binders (e.g., starch, acacia gum, carboxymethyl cellulose, hydroxypropyl cellulose, crystalline cellulose, and the like), lubricants (e.g., magnesium stearate, talc and the like), and the like.

For all methods of use disclosed herein for the compounds of Formulas (IA), (I) to (VI), the daily oral dosage regimen will preferably be from about 0.05 to about 80 mg/kg of total body weight, preferably from about 0.1 to 30 mg/kg, more preferably from about 0.5 mg to 15 mg/kg, administered in one or more daily doses. For example, the daily parenteral dosage regimen about 0.1 to about 80 mg/kg of total body weight, preferably from about 0.2 to about 30 mg/kg, and more preferably from about 0.5 mg to 15 mg/kg, administered in one or more daily doses. The daily topical dosage regimen will preferably be from 0.01 mg to 150 mg, administered one to four times daily. The daily inhalation dosage regimen will preferably be from about 0.05 microgram/kg to about 5 mg/kg per day, or from about 0.2 microgram/kg to about 20 microgram/kg, administered in one or more daily doses.

It will also be recognized by one of skill in the art that the optimal quantity and spacing of individual dosages of a compound of Formulas (IA), (I) to (VI), respectively, or a pharmaceutically acceptable salt thereof will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a compound of Formulas (IA), (I) to (VI), respectively, or a pharmaceutically acceptable salt thereof given per day for a defined number of days, can be ascertained by those skilled in the art using conventional course of treatment determination tests.

The amount of a compounds of Formulas (IA), (I) to (VI), respectively, or pharmaceutically acceptable salts thereof or corresponding pharmaceutical compositions of the present invention which is required to achieve a therapeutic effect will, of course, vary with the particular compound, the route of administration, the subject under treatment, and the particular disorder or disease being treated.

Suitable dosing regimens for a compound of the invention depend on the pharmacokinetic properties of that compound, such as absorption, distribution, and half-life, which can be determined by the skilled artisan. In addition, suitable dosing regimens, including the duration such regimens are administered, for a compound of the invention depend on the condition being treated, the severity of the condition being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

Additionally, the compounds of the present invention may be administered as prodrugs. As used herein, a "prodrug" of a compound of the invention is a functional derivative of the compound which, upon administration to a patient, eventually liberates the compound of the invention in vivo. Administration of a compound of the invention as a prodrug may enable the skilled artisan to do one or more of the following: (a) modify the onset of the compound in vivo; (b) modify the duration of action of the compound in vivo; (C) modify the transportation or distribution of the compound in vivo; (d) modify the solubility of the compound in vivo; and (e) overcome a side effect or other difficulty encountered with the compound. Typical functional derivatives used to prepare prodrugs include modifications of the compound that are chemically or enzymatically cleaved in vivo. Such modifications, which include the preparation of phosphates, amides, esters, thioesters, carbonates, and carbamates, are well known to those skilled in the art.

The invention also provides a compound of the invention for use in medical therapy, particularly in bacterial infections. Thus, in a further aspect, the invention is directed to the use of a compound according to Formulas (IA), (I) to (VI), respectively, or a pharmaceutically-acceptable salt thereof in the preparation of a medicament for the treatment of bacterial infections.

Combination Therapies

Active drug or therapeutic agents, when employed in combination with the compounds, or pharmaceutical compositions of the present invention, may be used or administered, for example, in dosage amounts indicated in the Physicians' Desk Reference (PDR) or as otherwise determined by one of ordinary skill in the art.

In the context of this specification, the term "simultaneously" when referring to simultaneous administration of the relevant drugs means at exactly the same time, as would be the case, for example in embodiments where the drugs are combined in a single preparation. In other embodiments, "simultaneously" can mean one drug taken a short duration after another, wherein "a short duration" means a duration which allows the drugs to have their intended synergistic effect.

In light of the foregoing, the present invention also relates to a combination therapy, which may be a comprised of a simultaneous or co-administration, or serial administration of a combination of compounds or pharmaceutical compositions of the present invention with other active drug or therapeutic agents, such as described above, and where such administration also is determined by one of ordinary skill in the art.

In addition, the present invention also relates to a combination therapy for the treatment or prevention of respiratory tract or respiratory diseases as described herein, which is comprised of a composition, dosage form or formulation formed from a synergistic combination or mixture of compounds, controlled release compositions, dosage forms or formulations of the present invention and another active drug or therapeutic agent or agents as those described above and optionally which comprises pharmaceutically acceptable carrier, diluent or adjuvent. In such an aforementioned combination composition, dosage form or formulation of the present invention, each of the active drug components are contained in therapeutically effective and synergistic dosage amounts.

The Examples set forth below are illustrative of the present invention and are not intended to limit, in any way, the scope of the present invention.

EXAMPLES

The following examples illustrate the invention. These examples are not intended to limit the scope of the present invention, but rather to provide guidance to the skilled artisan to prepare and use the compounds, compositions, and methods of the present invention.

While particular embodiments of the present invention are described, the skilled artisan will appreciate that various changes and modifications can be made without departing from the spirit and scope of the invention.

Biological Examples

Mechanism of Action

The outer membrane of Gram-negative bacteria serves as a barrier to small molecules, including drugs. This outer membrane consists of lipopolysaccharide (LPS) and is essential for bacterial viability. The hydrophobic anchor of LPS is Lipid A which is synthesized by nine enzymes of the Lpx pathway. LpxC (UDP-3-O—(R-3-hydroxymyristoyl)-N-acetylglucosamine) is the second step in the Lpx pathway and is the first committed step (Barb and Zhou Curr. Pharm. Biotechnol., 2008, 9-15). It is a Zn-dependent deacetylase that is highly conserved in Gram-negative bacteria with no known mammalian homologue. Inhibition of LpxC results in cell death of Gram-negative organisms and has not been shown to be present in Gram-positive bacteria and as such is an attractive target for the discovery of novel antibacterials targeted to Gram-negative pathogens (Barb, et al, Biochemistry, 2007, 46, 3793-3802).

The compounds described inhibit the enzyme activity of LpxC in in vitro assays of LpxC activity.

In addition, they show whole cell antibacterial activity against a variety of Gram-negative pathogens, including multi-drug resistant (MDR) pathogens as set forth in detail below and as defined throughout the present specification, including, but not limited to Carbapenem-Resistant Enterobacteriaceae (CRE) and MDR *P. aeruginosa*.

Therapeutic Targets

In one aspect, the present invention relates treatment of bacterial infections caused by Gram negative bacteria, where the Gram negative bacteria selected from Gram negative bacteria of enterobacteria, Gram negative bacteria colonized in respiratory, Gram negative bacteria of glucose non fermentation or β-lactam drug resistant Gram negative bacteria.

In another aspect, the present invention relates to treatment of bacterial infections, caused by Gram negative bacteria, where:

the Gram negative bacteria of enterobacteria selected from *E. coli, Klebsiella, Serratia, Enterobacter, Citrobacter, Morganella, Providencia* or *Proteus;* the Gram negative bacteria colonized in respiratory system selected from *Haemophilus* or *Moraxella;* the Gram negative bacteria of glucose non fermentation selected from *Pseudomonas aeruginosa, Pseudomonas* other than *P. aeruginosa, Stenotrophomonas* or *Burkholderia, Acinetobacter*; and the beta-lactam drug resistant Gram negative bacteria is selected from Carbapenum-Resistant Enterobacteriaceae producing bacteria In another aspect, Gram-negative bacterial infections including but not limited to: *Pseudomonas aeruginosa, Klebsiella pneumoniae, E. coli,* and *Enterobacter* spp.

In another aspect, the present invention relates to treatment method or uses for bacterial infections, where the bacterial infection is an airway infection, urinary system infection, resipiratory system infection, sepsis infection, nephritis, cholecystitis, oral cavity infection, endocarditis, pneumonia, bone marrow membrane myelitis, otitis media, enteritis, empyema, wound infection or an opportunistic infection.

In another aspect other Possible Therapeutic Target(s), include: Gram-negative bacterial sepsis.

Biological Assay(S)

*P. aeruginosa* Enzymatic Assay

Materials:

Untagged *Pseudomonas* LpxC was expressed in *E. coli* from *Psuedomonas aeruginosa* PAO1 and purified from Q-Sepharose 1 and Q-Sepharose 2 columns. UDP-3-O—(R-3-hydroxymyristoyl)-N-Acetylglucosamine Substrate was obtained through a custom synthesis from Alberta Innovates Technology Futures.

Method:

Untagged *Pseudomonas* LpxC is a deacetylase, which can remove an acetyl-group from UDP-3-O—(R-3-hydroxymyristoyl)-N-Acetylglucosamine to result in a product that is 42 Daltons less than the original acetylated substrate. Direct detection of the deactylated product and acetylated substrate is accomplished through an Agilent RapidFire v. 3.4/Sciex 4000 Q-Trap RF-MS instrument.

400 nL of 100× inhibitor sample in DMSO (or DMSO controls) were stamped into a 384-well Greiner PP V-shape plate (127.8/85/15 mm), followed by addition of 20 µL of 2× enzyme [7.680 mL buffer (0.05% CHAPS, 100 ug/mL BSA, 50 mM HEPES pH 7.5, 150 mM NaCl in water)+2 µL of 125 uM Untagged *Pseudomonas* LpxC] and 10 uL 1N HCl to the inactive control wells. Following a 30 minute incubation, 20 µL of 2× substrate [7.680 buffer+5 uL of UDP-3-O—(R-3-hydroxymyristoyl)-N-Acetylglucosamine (at 10 mM Stock)] was added and incubated for 25 minutes. 10 uL of 1N HCl was added to quench the reaction. The plate was loaded onto the Agilent RapidFire v. 3.4/Sciex 4000 Q-Trap RF-MS instrument for analysis, using a $C_4$ SPE cartridge and 2 mM ammonium acetate in 100 v/v water as the aqueous eluent and 5 mM ammonium acetate in 25% v/v/25% v/v acetonitrile/water as the organic eluent. For dose response experiments, % conversion were determined from the substrate and product analytes and normalized data were fit by ABASE/XC50 using the equation $y=a+(b-a)/(1+(10^x/10^c)^d)$, where a is the minimum % activity, b is the maximum % activity, c is the pIC50, and d is the Hill slope. [1]Langsdorf, Erik F. et al. Screening for Antibacterial Inhibitors of the UDP-3-O—(R-3-Hydroxymyristoyl)-N-Acetylglucosamine Deacetylase (LpxC) Using a High-Throughput Mass Spectroscopy Assay.
See, J. Biomol. Screen. 2010, 15, 52-61.

E. coli Enzyme Assay

Materials

Untagged E. Coli LpxC 1-300 was expressed in E. Coli and purified with NiNTA Agarose, Superdex 200 and Mono Q columns. UDP-3-O—(R-3-hydroxymyristoyl)-N-Acetylglucosamine Substrate was obtained through a custom synthesis from Alberta Innovates Technology Futures.

Method

Untagged E. coli LpxC is a deacetylase, which can remove an acetyl-group from UDP-3-O—(R-3-hydroxymyristoyl)-N-Acetylglucosamine (m/z 832.1-385) to result in a product (m/z 790.3→385) that is 42 Daltons less than the original acetylated substrate. Direct detection of the deacetylated product and acetylated substrate was accomplished through an Agilent RapidFire v. 3.4/Sciex 4000 Q-Trap RF-MS instrument.

400 nL of 100× inhibitor sample in DMSO (or DMSO controls) were stamped into a 384-well Greiner PP V-shape plate (Cat. #781280), followed by addition of 20 µL of 2× enzyme [6 nM final concentration; 39.999 mL buffer (0.05% CHAPS, 100 µg/mL BSA, 50 mM HEPES pH 7.5, 150 mM NaCl in water)+1.5 µL of 324 pM Untagged E. coli LpxC] and 10 µL 1N HCl to the inactive control wells. Following a 30 minute preincubation, 20 µL of 2× substrate [2 µM final concentration; 39.984 mL buffer+16 µL of UDP-3-O—(R-3-hydroxymyristoyl)-N-Acetylglucosamine (at 10 mM Stock)] was added and incubated for 25 minutes. The reaction was quenched by the addition of 10 µL of 1N HCl. The plate was loaded onto the Agilent RapidFire v. 3.4/Sciex 4000 Q-Trap RF-MS instrument for analysis [$C_4$ SPE cartridge, 2 mM ammonium acetate in 100 v/v water as the aqueous eluent and 5 mM ammonium acetate in 25% v/v/25% v/v/50% v/v acetonitrile/acetone/water as the organic eluent]. For dose response experiments % conversion were determined from the substrate and product extracted ion chromatogram (XIC) areas and normalized to the assay high and low controls. Normalized data were fit by ActivityBase XE using the equation $y=a+(b-a)/(1+(10^x/10^c)^d)$, where a is the minimum % activity, b is the maximum % activity, c is the pIC50, and d is the Hill slope.

[1]Langsdorf, Erik F. et al. Screening for Antibacterial Inhibitors of the UDP-3-O—(R-3-Hydroxymyristoyl)-N-Acetylglucosamine Deacetylase (LpxC) Using a High-Throughput Mass Spectroscopy Assay.
See, J. Biomol. Screen. 2010, 15, 52-61.

Minimum Inhibitory Concentration Assay

Methods for dilution Antimicrobial Susceptibility TestS for Bacteria that Grow Aerobically; Approved Standard-Ninth Edition; M7-A9, Vol. 32 No. 2, Clinical and Laboratory Standards Institute, Wayne, Pa.; January 2012.

Performance Standards for Antimicrobial Susceptibility Testing; Twenty-Second Informational Supplement; M100-S22 Vol. 32 No. 3; Clinical and Laboratory Standards Institute, Wayne, Pa., January 2012.

Broth microdilution was performed in accordance with the CLSI recommended procedures for aerobic bacteria [CLSI, 2012].

Comparator compound stock solutions were prepared as recommended by CLSI [CLSI, 2012]. The stock solutions of novel GSK compounds were prepared at 512 mcg/mL by dissolving the compounds in dimethyl sulfoxide (DMSO) and diluting 1:10 with sterile water. The 512 mcg/mL stock was further serially diluted in the recommended broth media for the organisms being tested. Final DMSO concentration in test wells was less than 1%.

Microtitre plates were prepared using the Microlab STAR™ (Hamilton Co., Reno, Nev.) to add media (50 µL) and the Microlab AT Plus system (Hamilton Co., Reno, Nev.) to serially dilute the compounds (final concentration range 0.125 to 128 mcg/mL) and to add inoculum. A positive growth control well containing medium and the test isolate was included on each microtitre plate. Ten microliters of the test medium from the positive growth control well was plated to determine the purity of each test isolate. A microtitre mirror reader (Cooke Instruments, Ltd., England) was used to assist in determining the microdilution MIC endpoints. The MIC was determined as the lowest concentration of compound that inhibited visible growth of the organism.

Biological Assay Data

| Ex | Compounds | E. coli pIC$_{50}$ | P. aeruginosa pIC$_{50}$ | P. aeruginosa PA01 MIC (ug/mL) | K. pneumoniae 1161486 MIC (ug/mL) | E. coli 7623 MIC (ug/mL) |
|---|---|---|---|---|---|---|
| 1 | [structure: 7-phenyl-quinazolin-4(3H)-one with N-substituted chain bearing methanesulfonyl, methyl, and N-hydroxyamide groups] | 9.1 | 9.4 | 1 | 0.25 | 0.5 |

-continued

Biological Assay Data

| Ex | Compounds | E. coli pIC$_{50}$ | P. aeruginosa pIC$_{50}$ | P. aeruginosa PA01 MIC (ug/mL) | K. pneumoniae 1161486 MIC (ug/mL) | E. coli 7623 MIC (ug/mL) |
|---|---|---|---|---|---|---|
| 2 | (4-methylphenyl quinazolinone compound) | 9.4 | 9.4 | 0.5 | 0.125 | 0.06 |
| 3 | (4-methoxyphenyl quinazolinone compound) | 9 | 9.4 | 2 | 0.5 | 0.06 |
| 4 | (4-dimethylaminophenyl quinazolinone compound) | 9.4 | 9.4 | 8 | 0.25 | ≤0.03 |
| 5 | (4-difluoromethoxyphenyl quinazolinone compound) | 9.4 | 9.4 | 2 | 0.06 | ≤0.03 |
| 6 | (2,3-difluorophenyl quinazolinone compound) | 9.3 | 9.4 | 0.5 | 0.125 | ≤0.032 |

-continued

Biological Assay Data

| Ex | Compounds | E. coli pIC$_{50}$ | P. aeruginosa pIC$_{50}$ | P. aeruginosa PA01 MIC (ug/mL) | K. pneumoniae 1161486 MIC (ug/mL) | E. coli 7623 MIC (ug/mL) |
|---|---|---|---|---|---|---|
| 7 | (structure) | 9.4 | 9.4 | 2 | 0.25 | 0.06 |
| 8 | (structure) | 9.3 | 9.4 | 0.5 | 0.125 | ≤0.03 |
| 9 | (structure) | 9.4 | 9.4 | 8 | 0.125 | ≤0.03 |
| 10 | (structure) | 9.1 | 9.4 | 1 | 0.25 | 0.06 |
| 15 | (structure) | 9.3 | 9.4 | 0.5 | 0.063 | <0.03 |

-continued

Biological Assay Data

| Ex | Compounds | E. coli pIC$_{50}$ | P. aeruginosa pIC$_{50}$ | P. aeruginosa PA01 MIC (ug/mL) | K. pneumoniae 1161486 MIC (ug/mL) | E. coli 7623 MIC (ug/mL) |
|---|---|---|---|---|---|---|
| 16 | (structure) | 9.2 | 8.8 | 8 | 1 | 0.25 |
| 17 | (structure) | 9.2 | 9 | 16 | 1 | 0.25 |
| 18 | (structure) | 8.5 | 8.7 | 16 | 1 | 0.5 |
| 19 | (structure) | 9.2 | 9.2 | 8 | 0.25 | 0.125 |
| 20 | (structure) | 9.3 | 9.4 | 4 | 0.25 | 0.125 |

-continued
Biological Assay Data
| Ex | Compounds | E. coli pIC$_{50}$ | P. aeruginosa pIC$_{50}$ | P. aeruginosa PA01 MIC (ug/mL) | K. pneumoniae 1161486 MIC (ug/mL) | E. coli 7623 MIC (ug/mL) |
|---|---|---|---|---|---|---|
| 21 | 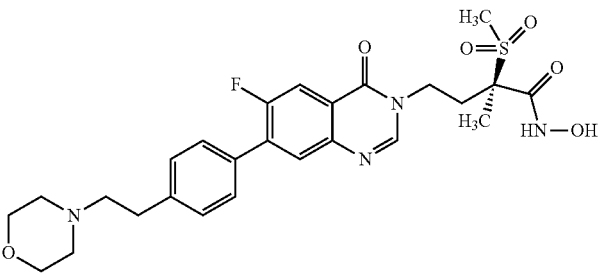 | 9.4 | 9.4 | 4 | 0.5 | 0.063 |
| 22 | 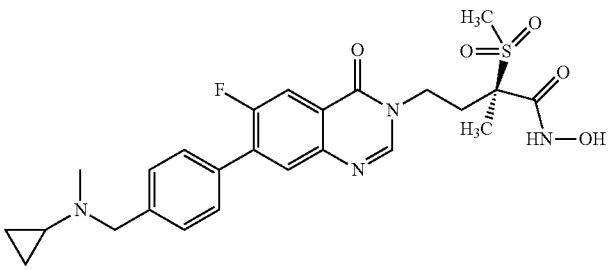 | 9.4 | 9.4 | 8 | 0.25 | <0.03 |
| 23 | 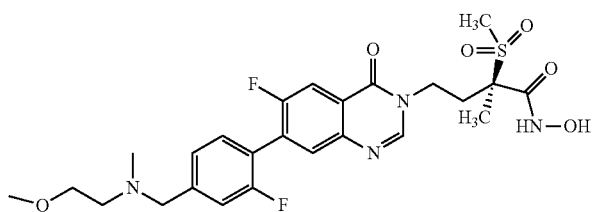 | 9.4 | 9.4 | 4 | 0.5 | 0.25 |
| 24 | 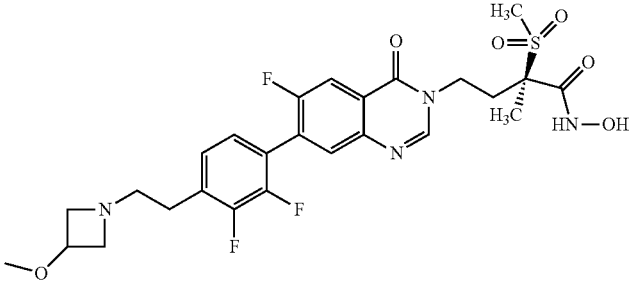 | 9.2 | 9.4 | 2 | 1 | 0.25 |
| 25 | 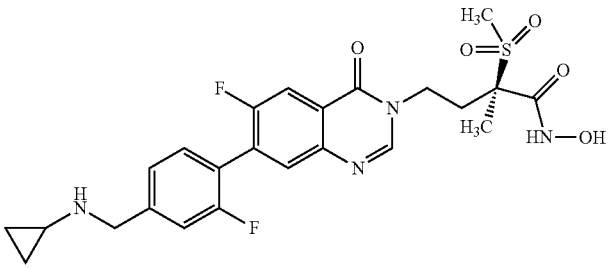 | 9.1 | 9.4 | 1 | 0.5 | 0.063 |

-continued
Biological Assay Data
| Ex | Compounds | E. coli pIC$_{50}$ | P. aeruginosa pIC$_{50}$ | P. aeruginosa PA01 MIC (ug/mL) | K. pneumoniae 1161486 MIC (ug/mL) | E. coli 7623 MIC (ug/mL) |
|---|---|---|---|---|---|---|
| 26 | 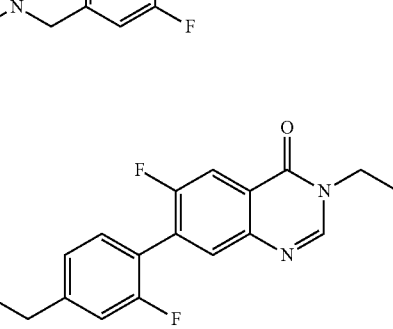 | 9.4 | 9.4 | 4 | 0.5 | 0.125 |
| 27 | 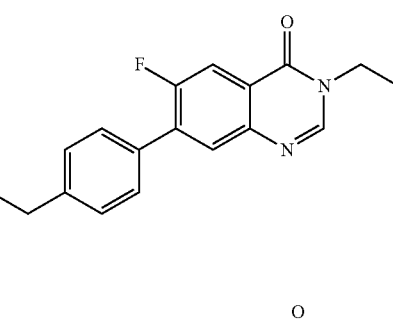 | 9.4 | 9.4 | 2 | 1 | <0.03 |
| 28 | 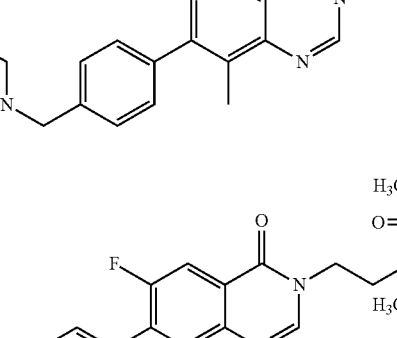 | 9.4 | 9.4 | 0.5 | 0.125 | <0.03 |
| 29 | 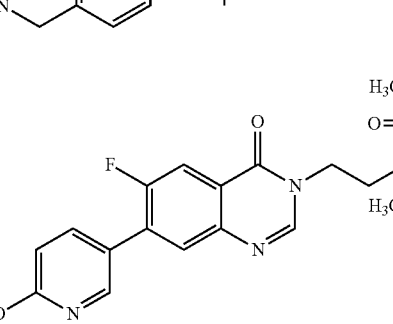 | 9.1 | 9.4 | 4 | 0.5 | 0.5 |
| 30 | 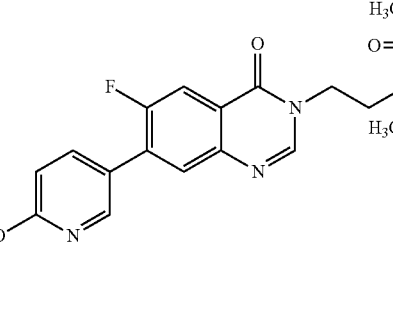 | 9.4 | 9.4 | 16 | 1 | 0.25 |

-continued

Biological Assay Data

| Ex | Compounds | E. coli pIC$_{50}$ | P. aeruginosa pIC$_{50}$ | P. aeruginosa PA01 MIC (ug/mL) | K. pneumoniae 1161486 MIC (ug/mL) | E. coli 7623 MIC (ug/mL) |
|---|---|---|---|---|---|---|
| 31 | [6-fluoro-7-phenyl-quinazolinone with methylsulfonyl hydroxamate sidechain] | 9.3 | 9.4 | 2 | 0.25 | 0.063 |
| 32 | [6-fluoro-7-(dihydroisobenzofuran)-quinazolinone derivative] | 9.4 | 9.4 | 4 | 0.5 | 0.125 |
| 33 | [6-fluoro-7-(6-dimethylamino-pyridin-3-yl)-quinazolinone derivative] | 9.2 | 9.2 | 8 | 0.5 | <0.03 |
| 34 | [6-fluoro-7-(4-(2-acetoxyethyl)phenyl)-quinazolinone derivative] | 9.4 | 9.4 | 4 | 0.25 | <0.03 |
| 35 | [7-(4-(morpholinomethyl)phenyl)-quinazolinone derivative] | 8.9 | 9.4 | 1 | 0.5 | 0.125 |

-continued

| | | | | P. aeruginosa PA01 | K. pneumoniae 1161486 | E. coli 7623 |
| | | E. coli | P. aeruginosa | MIC | MIC | MIC |
| Ex | Compounds | pIC$_{50}$ | pIC$_{50}$ | (ug/mL) | (ug/mL) | (ug/mL) |
| --- | --- | --- | --- | --- | --- | --- |
| 36 | | 9.2 | 9.4 | 1 | 1 | 0.125 |
| 37 | | 9.4 | 9.4 | 2 | 0.5 | 0.063 |
| 38 | | 9.3 | 9.4 | 4 | 0.5 | 0.125 |
| 39 | | 9.1 | 9.3 | 4 | 0.5 | <0.03 |

-continued

Biological Assay Data

| Ex | Compounds | E. coli pIC$_{50}$ | P. aeruginosa pIC$_{50}$ | P. aeruginosa PA01 MIC (ug/mL) | K. pneumoniae 1161486 MIC (ug/mL) | E. coli 7623 MIC (ug/mL) |
|---|---|---|---|---|---|---|
| 40 | | 9.1 | 9.4 | 4 | 0.5 | 0.5 |
| 41 | | 9.2 | 9.4 | 2 | 2 | 0.125 |
| 42 | | 9 | 9.4 | 2 | 0.5 | 0.25 |
| 43 | | 9.3 | 9.4 | 2 | 0.5 | 0.25 |
| 44 | | 9.4 | 9.4 | 1 | 1 | 0.125 |

-continued

Biological Assay Data

| Ex | Compounds | E. coli pIC$_{50}$ | P. aeruginosa pIC$_{50}$ | P. aeruginosa PA01 MIC (ug/mL) | K. pneumoniae 1161486 MIC (ug/mL) | E. coli 7623 MIC (ug/mL) |
|---|---|---|---|---|---|---|
| 45 | | 9.2 | 9.4 | 1 | 1 | 0.063 |
| 46 | | 9.4 | 9.4 | 1 | 0.125 | <0.03 |
| 47 | | 9.3 | 9.4 | 0.5 | 0.125 | 0.063 |
| 48 | | 9.1 | 9.4 | 1 | 0.125 | <0.03 |
| 50 | | 9.3 | 9.4 | 2 | 0.5 | 0.125 |

-continued

| | | Biological Assay Data | | | | |
|---|---|---|---|---|---|---|
| Ex | Compounds | E. coli pIC$_{50}$ | P. aeruginosa pIC$_{50}$ | P. aeruginosa PA01 MIC (ug/mL) | K. pneumoniae 1161486 MIC (ug/mL) | E. coli 7623 MIC (ug/mL) |
| 51 | | 9.3 | 9.4 | 2 | 0.5 | 0.125 |
| 52 | | 9.4 | 9.4 | 8 | 0.25 | 0.063 |
| 53 | | 9.2 | 9.4 | 0.5 | 0.25 | <0.03 |
| 54 | | 9.4 | 9.4 | 1 | 0.5 | <0.03 |
| 55 | | 9.4 | 9.4 | 1 | 0.063 | <0.03 |

-continued

Biological Assay Data

| Ex | Compounds | E. coli pIC$_{50}$ | P. aeruginosa pIC$_{50}$ | P. aeruginosa PA01 MIC (ug/mL) | K. pneumoniae 1161486 MIC (ug/mL) | E. coli 7623 MIC (ug/mL) |
|---|---|---|---|---|---|---|
| 56 | | 9.3 | 9.4 | 0.5 | 0.125 | 0.063 |
| 57 | | 9.1 | 9.4 | 2 | 0.25 | 0.063 |
| 58 | | 8.6 | 8.8 | 4 | 1 | 0.063 |
| 59 | | 9.2 | 9.4 | 0.5 | 0.125 | 0.063 |
| 60 | | 9.2 | 9.4 | 0.5 | 0.5 | <0.03 |

-continued

| | | Biological Assay Data | | | | |
|---|---|---|---|---|---|---|
| Ex | Compounds | E. coli pIC$_{50}$ | P. aeruginosa pIC$_{50}$ | P. aeruginosa PA01 MIC (ug/mL) | K. pneumoniae 1161486 MIC (ug/mL) | E. coli 7623 MIC (ug/mL) |
| 61 | | 9.1 | 9.4 | >32 | 1 | <0.03 |
| 62 | | 9.4 | 9.4 | 8 | 0.5 | 0.125 |
| 63 | | 9.4 | 9.4 | 4 | 1 | 0.125 |
| 64 | | 9 | 9.4 | 0.5 | 0.25 | <0.03 |

-continued

| | | Biological Assay Data | | | | |
|---|---|---|---|---|---|---|
| Ex | Compounds | E. coli pIC$_{50}$ | P. aeruginosa pIC$_{50}$ | P. aeruginosa PA01 MIC (ug/mL) | K. pneumoniae 1161486 MIC (ug/mL) | E. coli 7623 MIC (ug/mL) |
| 65 | | 9.4 | 9.4 | 4 | 0.5 | 0.25 |
| 66 | | 9.2 | 9.4 | 1 | 0.125 | 0.063 |
| 67 | | 8.7 | 9.4 | 1 | 1 | 0.125 |
| 68 | | 9 | 9.4 | 2 | 0.5 | 0.125 |
| 69 | | 9 | 9.4 | 1 | 1 | 0.125 |
| 70 | | 8.8 | 9.3 | 2 | 0.25 | 0.125 |

-continued
Biological Assay Data
| Ex | Compounds | E. coli pIC$_{50}$ | P. aeruginosa pIC$_{50}$ | P. aeruginosa PA01 MIC (ug/mL) | K. pneumoniae 1161486 MIC (ug/mL) | E. coli 7623 MIC (ug/mL) |
|---|---|---|---|---|---|---|
| 71 | 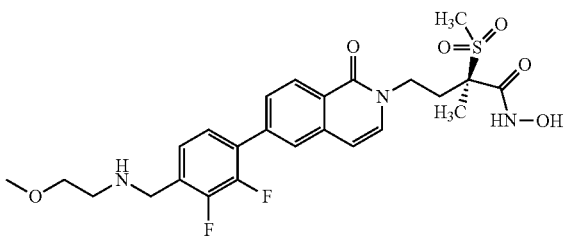 | 8.9 | 9.2 | 0.5 | 0.5 | 0.063 |
| 72 | 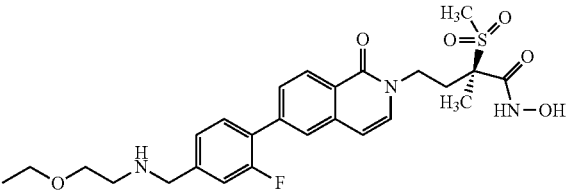 | 9 | 9.4 | 1 | 0.25 | 0.125 |
| 73 | 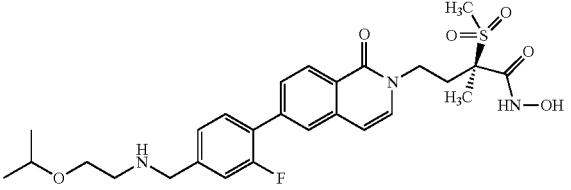 | 8.9 | 9.4 | 2 | 0.5 | 0.25 |
| 74 | 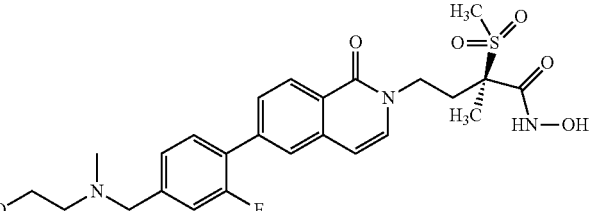 | 9.1 | 9.4 | 1 | 0.5 | 0.25 |
| 75 | 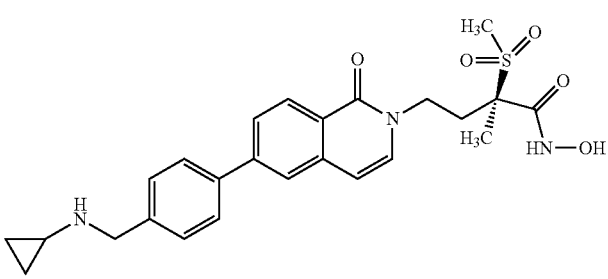 | 8.9 | 9 | 0.25 | 0.063 | 0.06 |
| 76 | 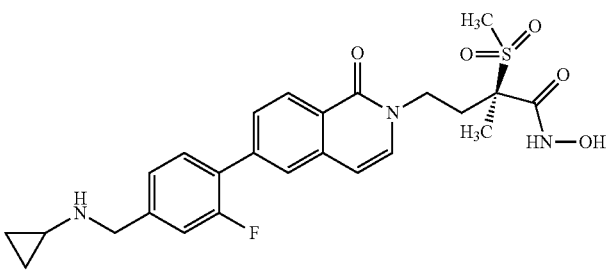 | 9.2 | 9.4 | 0.5 | 0.125 | <0.03 |

-continued
Biological Assay Data
| Ex | Compounds | E. coli pIC$_{50}$ | P. aeruginosa pIC$_{50}$ | P. aeruginosa PA01 MIC (ug/mL) | K. pneumoniae 1161486 MIC (ug/mL) | E. coli 7623 MIC (ug/mL) |
|---|---|---|---|---|---|---|
| 77 | 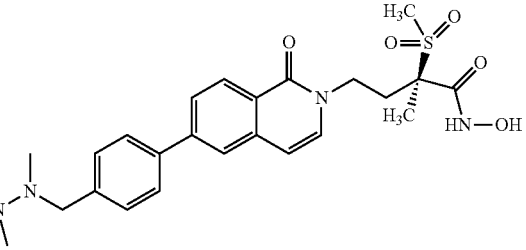 | N/T | N/T | 2 | 0.25 | 0.125 |
| 78 | 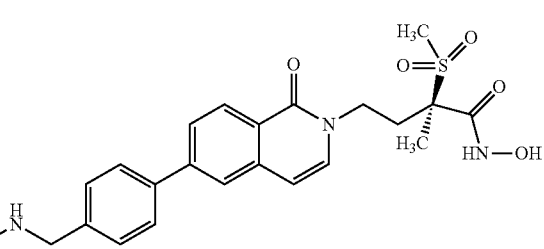 | 9.4 | 9.4 | 4 | 0.125 | 0.063 |
| 79 | 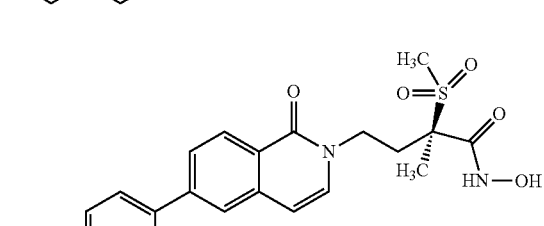 | 9.3 | 9.4 | 8 | 0.5 | 0.125 |
| 80 | 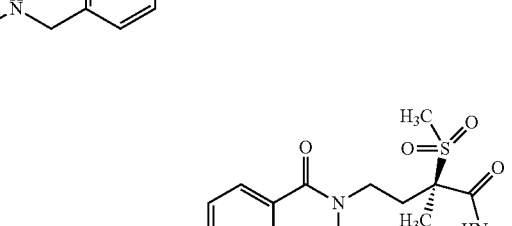 | 9.1 | 9.4 | 1 | 0.25 | 0.063 |
| 81 | 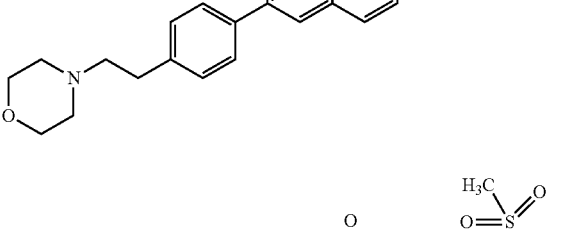 | 9.1 | 9.4 | 1 | 0.5 | 0.25 |

-continued

| | | | | P. aeruginosa PA01 MIC (ug/mL) | K. pneumoniae 1161486 MIC (ug/mL) | E. coli 7623 MIC (ug/mL) |
|---|---|---|---|---|---|---|
| Ex | Compounds | E. coli pIC$_{50}$ | P. aeruginosa pIC$_{50}$ | | | |
| 82 | | 9.4 | 9.4 | 4 | 0.25 | 0.25 |
| 83 | | 9.3 | 9.4 | 8 | 0.25 | <0.03 |
| 84 | | 9.2 | 9.4 | 4 | 0.25 | 0.5 |
| 85 | | 9.2 | 8.8 | 4 | 1 | 0.5 |
| 86 | | 9.3 | 9.3 | 16 | 0.25 | <0.03 |

-continued

Biological Assay Data

| Ex | Compounds | E. coli pIC$_{50}$ | P. aeruginosa pIC$_{50}$ | P. aeruginosa PA01 MIC (ug/mL) | K. pneumoniae 1161486 MIC (ug/mL) | E. coli 7623 MIC (ug/mL) |
|---|---|---|---|---|---|---|
| 87 | | 9.2 | 8.9 | 8 | 0.25 | 0.06 |
| 88 | | 9.3 | 9.4 | 2 | 0.25 | 0.125 |
| 89 | | 9.2 | 9.3 | 2 | 0.25 | 0.25 |
| 90 | | 9.4 | 9.3 | 32 | 1 | 0.063 |
| 91 | | 8.6 | 9 | 4 | 0.5 | 0.5 |

Biological Assay Data

| Ex | Compounds | E. coli pIC$_{50}$ | P. aeruginosa pIC$_{50}$ | P. aeruginosa PA01 MIC (ug/mL) | K. pneumoniae 1161486 MIC (ug/mL) | E. coli 7623 MIC (ug/mL) |
|---|---|---|---|---|---|---|
| 92 | (structure) | 9.4 | 8.9 | 4 | 0.5 | 0.5 |
| 93 | (structure) | 9.3 | 9.4 | 0.5 | 0.125 | 0.063 |
| 94 | (structure) | 9.4 | 9.4 | 2 | 0.25 | 0.125 |

Compound Examples

General Information

Unless otherwise noted, all starting materials were obtained from commercial suppliers and used without further purification. Unless otherwise indicated, all temperatures are expressed in ° C. (degrees Centigrade). Unless otherwise indicated, all reactions are conducted under an inert atmosphere at ambient temperature.

All temperatures are given in degrees Celsius, all solvents are highest available purity and all reactions run under anhydrous conditions in an argon (Ar) or nitrogen (N$_2$) atmosphere where necessary.

The following examples illustrate the invention. These examples are not intended to limit the scope of the present invention, but rather to provide guidance to the skilled artisan to prepare and use the compounds, compositions, and methods of the present invention.

While particular embodiments of the present invention are described, the skilled artisan will appreciate that various changes and modifications can be made without departing from the spirit and scope of the invention.

As used herein the symbols and conventions used in these processes, schemes and examples are consistent with those used in the contemporary scientific literature, for example, the *Journal of the American Chemical Society* or the *Journal of Biological Chemistry*. Unless otherwise noted, all starting materials were obtained from commercial suppliers and used without further purification.

All references to ether are to diethyl ether; brine refers to a saturated aqueous solution of NaCl. Unless otherwise indicated, all temperatures are expressed in ° C. (degrees Centigrade). All reactions are conducted under an inert atmosphere at room temperature unless otherwise noted, and all solvents are highest available purity unless otherwise indicated.

$^1$H NMR (hereinafter also "NMR") spectra were recorded on a Varian VXR-300, a Varian Unity-300, a Varian Unity-400 instrument, a Brucker AVANCE-400, a General Electric QE-300 or a Bruker AM 400 spectrometer. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), quint (quintet), m (multiplet), br (broad).

Mass spectra were run on an open access LC-MS system using electrospray ionization. LC conditions: 10% to 80% CH$_3$CN (0.018% TFA) in 3.0 min with a 1.25 min hold and 0.5 min re-equilibration; detection by MS, UV at 214 nm, and a light scattering detector (ELS). Column: 2.1×50 mm Zorbax SB-C$_8$.

For preparative (prep) HPLC; ca. 100 mg of the final products were injected in 1000 μL of MeOH, DMSO, or DMF onto a SunFire Prep C$_{18}$ OBD 5 um 30×75 mm column at 35 mL/min with a 10 min gradient from 5% CH$_3$CN to 95% CH$_3$CN in H$_2$O, followed by a 90% CH$_3$CN in H$_2$O hold for 1.9 min. Flash chromatography was run over Merck Silica gel 60 (230-400 mesh), or using a Teledyne Isco Combiflash Companion with normal phase, disposable Redi-Sep flash columns.

Intermediate Examples

Intermediate 1

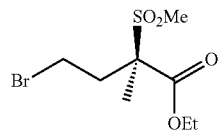

Part A

A solution of ethyl 2-chloropropanoate (1000 g, 7.35 mol) and sodium methanesulfinate (899 g, 8.82 mol) in ethanol (1350 mL) was stirred at 77° C. for 20 hrs. The reaction mixture was allowed to cool to r.t. The solids were removed by filtration through celite, and the filter pad was washed with ethanol. The filtrates were combined and concentrated in vacuo. The crude product was suspended in EtOAc and H$_2$O. The organic phase was washed by brine, dried over Na$_2$SO$_4$, filtered, concentrated to give ethyl 2-(methylsulfonyl)propanoate (1124 g, 84.9%) as a yellow oil.

$^1$H NMR: 400 MHz CDCl$_3$

δ: 4.25-4.28 (m, 2H), 3.84-3.90 (m, 1H), 3.04 (s, 3H), 1.63-1.65 (m, 3H), 1.29-1.33 (m, 3H).

Part B

Under N$_2$, to a solution of ethyl 2-(methylsulfonyl)propanoate (500 g, 2.78 mol) in N,N-dimethylformamide (DMF) (500 mL), sodium hydride (122 g, 3.06 mmol) was added at 0° C. in batches over 1 h. Then the reaction mixture was stirred at 0° C. for 1 h. Then 1,2-dibromoethane (1550 g, 8.33 mol) was added to the mixture and stirred at rt overnight. The mixture was quenched with H$_2$O at 0° C. and extracted with EtOAc (500 mL×3). The organic phase was washed with brine, dried over anhydrous sodium sulfate, filtered and concentrated in vacuo. The crude product was purified by column chromatography on silica gel, eluted with PE/EtOAc, EtOAc from 0 to 40% over 5 hrs. The desired fractions were collected and concentrated to afford ethyl-4-bromo-2-methyl-2-(methylsulfonyl)butanoate (283 g, yield: 35.5%).

$^1$H NMR: 400 MHz CDCl$_3$

δ: 4.25-4.31 (m, 2H), 3.48-3.49 (m, 1H), 3.45-3.47 (m, 1H), 3.04 (s, 3H), 2.55-2.57 (m, 3H), 2.52-2.54 (m, 3H), 1.63 (s, 3H), 1.31-1.3 (m, 3H).

HPLC: 95.52%.

Part C

Preparative Separation Method

Instrument: Thar200 preparative SFC
Column: ChiralPak AS-10 μm, 300×50 mm I.D.
Mobile phase: A for CO$_2$ and B for IPA:Heptane=1:1
Gradient: B 20%
Flow rate: 200 mL/min
Back pressure: 100 bar
Column temperature: 38° C.
Wavelength: 210 nm
Cycletime: ~3.5 min Sample preparation: Compound was dissolved in ethanol to ~130 mg/ml Injection: 3.5-5 ml per injection.

Work up: After separation, the fractions were dried off via rotary evaporator at bath temperature 40° C. affording the desired (R)-ethyl-4-bromo-2-methyl-2-(methylsulfonyl)butanoate.

Intermediate 2

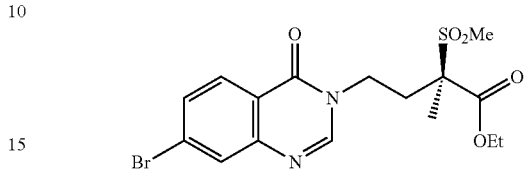

General Procedure

Part A

Under N$_2$, in a flask, was added 7-bromoquinazolin-4(3H)-one (1 g, 4.44 mmol), cesium carbonate (2.90 g, 8.89 mmol) and (R)-ethyl-4-bromo-2-methyl-2-(methylsulfonyl)butanoate (Intermediate 1) (1.340 g, 4.67 mmol) in N,N-dimethylformamide (DMF) (3 mL). The mixture was stirred at 50° C. for 1.5 hours. The mixture was poured into ice and extracted with AcOEt. The aqueous mixture was extracted with DCM, washed w/brine, dried w/Na$_2$SO$_4$ and concentrated.

Recrystallization with AcOEt and DCM afforded (R)-ethyl 4-(7-bromo-4-oxoquinazolin-3(4H)-yl)-2-methyl-2-(methylsulfonyl)butanoate (1.2 g, 2.78 mmol, 63% yield) as a white crystalline material.

LCMS: (M+1) 431.1, at 0.93 min $^1$H NMR (400 MHz, CHLOROFORM-d) δ: 1.34 (t, J=7.20 Hz, 3H) 1.80 (s, 3H) 2.47-2.65 (m, 2H) 3.13 (s, 3H) 4.10 (ddd, J=13.58, 10.04, 5.94 Hz, 1H) 4.20-4.38 (m, 3H) 7.63 (dd, J=8.46, 1.89 Hz, 1H) 7.91 (d, J=1.77 Hz, 1H) 8.08 (s, 1H) 8.15 (d, J=8.59 Hz, 1H).

Intermediate 3

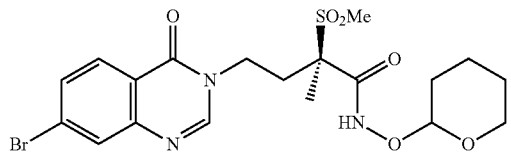 [SMILES: C[C@@](CCn1cnc2cc(Br)ccc2c1=O)(C(=O)NOC1CCCCO1)S(C)(=O)=O]

General Procedure

Part A

Two batches: To a solution of 7-bromoquinazolin-4(3H)-one (75 g, 333.0 mmol) and (R)-ethyl-4-bromo-2-methyl-2-(methylsulfonyl)butanoate (Intermediate 1) (100.5 g, 349.9 mmol) in acetonitrile (600 mL) was added Cs$_2$CO$_3$ (158 g, 486 mmol) in portions during 15 mins at 25° C. under N$_2$. The mixture was stirred at 25° C. for 15 mins, then heated to 80° C. and stirred at this temperature for 5 hrs. At this point the two batches were combined and the mixture was cooled to 25° C. The combined mixture was filtered and the filter pad was washed with ethyl acetate (200 mL×3). The combined organic layers were concentrated in vacuum to 200 mL and diluted with ethyl acetate (1 L) then water was added (300 mL). The organic layer was separated and the aqueous layer was extracted with ethyl acetate (100 mL×3). The combined organic layers were washed with water (200 mL) and brine (200 mL). The organic layers were dried over Na$_2$SO$_4$, filtered and the filtrate was concentrated to give the crude product. Then the crude product was triturated with (petroleum ether/ethyl acetate=200 mL/300 mL). The mixture was filtered to give crude (R)-ethyl 4-(7-bromo-4-oxoquinazolin-3(4H)-yl)-2-methyl-2-(methylsulfonyl)butanoate (142 g, yield 49%) as a yellow solid. The filtrate was purified by silica gel chromatography (100-200 mesh silica gel, weight 240 g, petroleum ether/ethyl acetate=50/1-1/1) to give (R)-ethyl 4-(7-bromo-4-oxoquinazolin-3(4H)-yl)-2-methyl-2-(methylsulfonyl)butanoate (96 g, yield 33%) as a yellow solid. Total yield was 82%.

$^1$H NMR: 400 MHz DMSO-$d_6$

δ 8.44 (s, 1H), 8.07 (d, J=8.8 Hz, 1H), 7.91 (d, J=1.6 Hz, 1H), 7.72 (dd, J=8.8, 1.6 Hz, 1H), 4.03-4.09 (m, 4H), 3.15 (s, 3H), 2.62-2.67 (m, 1H), 2.24-2.28 (m, 1H), 1.63 (s, 3H), 1.18 (t, J=6.8 Hz, 3H).

Part B

Two batches: To a solution of (R)-ethyl 4-(7-bromo-4-oxoquinazolin-3(4H)-yl)-2-methyl-2-(methylsulfonyl)butanoate (93 g, 215.6 mmol) in THF (648 mL) was added a solution of aqueous LiOH solution (2 mol/L, 646.8 mmol, 324 mL) at 10° C. The reaction mixture was stirred at 25° C. for 2 hrs. The mixture was adjusted to pH=3-4 with HCl (2 mol/L, 400 mL) at 10-12° C. A white precipitate was formed and the two batches were combined. The slurry was filtered and the filter cake was dried to give (R)-4-(7-bromo-4-oxoquinazolin-3(4H)-yl)-2-methyl-2-(methylsulfonyl)butanoic acid (160 g, yield 92%) as a white solid, which was used in next step without further purification.

$^1$H NMR: 400 MHz DMSO-$d_6$

δ 8.43 (s, 1H), 8.06 (d, J=8.8 Hz, 1H), 7.90 (s, 1H), 7.70-7.73 (m, 1H), 4.01-4.15 (m, 2H), 3.14 (s, 3H), 2.50-2.61 (m, 1H), 2.20-2.27 (m, 1H), 1.59 (s, 3H).

Part C

Two batches: To a solution of (R)-4-(7-bromo-4-oxoquinazolin-3(4H)-yl)-2-methyl-2-(methylsulfonyl)butanoic acid (95 g, 235.6 mmol) in THF (1400 mL) was added 4-methylmorpholine (42.9 g, 424.0 mmol) and 2-chloro-4,6-dimethoxy-1,3,5-triazine (62.0 g, 353.4 mmol) in portions during 20 mins at 20° C. After addition, this reaction mixture was mechanically stirred for 3 hrs at 25° C. Then O-tetrahydropyran-2-ylhydroxylamine (49.7 g, 424.1 mmol) was added to the reaction in portions during 5 mins at 25° C. and then the mixture was continued to mechanically stir for 1.5 hrs at 30° C. The two batches were combined and the mixture was filtered and filter cake was washed with dichloromethane (150 mL×3). The combined organic layers were concentrated in vacuum. The residue was dissolved in dichloromethane (1.2 L) and washed with water (400 mL), brine (100 mL) and dried over $Na_2SO_4$. The solution was filtered and the filtrate was concentrated to give the crude product, which was purified by washing with methyl terbutyl ether (200 mL), petroleum ether/ethyl acetate=2/1 (200 mL) and petroleum ether/ethyl acetate=1/1 (200 mL) to give pure (2R)-4-(7-bromo-4-oxoquinazolin-3(4H)-yl)-2-methyl-2-(methylsulfonyl)-N-((tetrahydro-2H-pyran-2-yl)oxy)butanamide (184 g, yield 78%) as a white solid.

$^1$H NMR: 400 MHz $CDCl_3$

δ 10.68 (d, J=9.2 Hz, 1H), 8.13-8.16 (m, 1H), 8.09 (s, 1H), 7.93 (s, 1H), 7.64 (d, J=8.0 Hz, 1H), 5.14 (s, 1H), 4.31-4.37 (m, 1H), 4.08-4.14 (m, 2H), 3.66-3.73 (m, 1H), 3.12 (d, J=4.8 Hz, 3H), 2.52-2.55 (m, 1H), 2.43-2.46 (m, 1H), 1.65-1.85 (m, 9H).

Intermediate 4

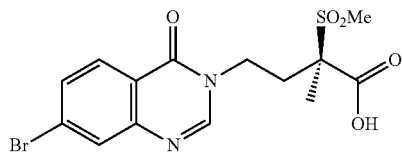 [SMILES: C[C@@](CCn1cnc2cc(Br)ccc2c1=O)(C(=O)O)S(C)(=O)=O]

General Procedure
Part A

To a solution of Intermediate 2 (12 g, 27.8 mmol) in tetrahydrofuran (THF) (100 mL) was added a solution of lithium hydroxide monohydrate (3.5 g, 83 mmol) at 0° C. The reaction mixture was warmed to rt and continued to stir at rt for 2 h. The reaction was then concentrated in vacuo to remove the THF and then washed with EtOAc (3×10 ml). The pH of aqueous layer was adjusted to 3 using 1 N aq. HCl to afford the solid, was filtered, washed with water (3×10 ml) and dried in air to afford the product (R)-4-(7-bromo-4-oxoquinazolin-3(4H)-yl)-2-methyl-2-(methylsulfonyl)butanoic acid (9.8 g, 24.30 mmol, 87% yield) as a white solid.

LCMS (M+1): 403.0, at 0.73 min

Intermediate 5

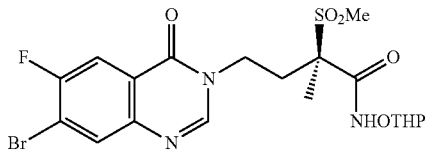

Part A

To a solution of 4-bromo-3-fluorobenzoic acid (20 g, 91 mmol) in concentrated $H_2SO_4$ (70 mL) at room temperature was added potassium nitrate (9.69 g, 96 mmol) portionwise and the reaction mixture was stirred at 20° C. for 3 hr. The reaction solution was combined with other batches and the mixture was poured onto ice. The solid was collected by filtration and dried to give 4-bromo-5-fluoro-2-nitrobenzoic acid (45 g, 153 mmol, 75% yield) as a white solid.

Part B

Tin(II) chloride (20.25 g, 107 mmol) was added to a solution of 4-bromo-5-fluoro-2-nitrobenzoic acid (9.4 g, 35.6 mmol) in water (70 mL) and hydrochloric acid (70 mL) at room temperature and the reaction mixture was stirred at 90° C. for 3 hr. After cooling to room temperature, the formed precipitate was filtered, washed with water and collected to give 2-amino-4-bromo-5-fluorobenzoic acid, hydrochloride (8.5 g, 31.4 mmol, 88% yield) as an off-white solid.

LCMS: [M+H] 234.1.

Part C

A mixture of 2-amino-4-bromo-5-fluorobenzoic acid hydrochloride (8.4 g, 31.1 mmol) in formamide (40 mL) was stirred at 160° C. for 6 hr under nitrogen. The reaction solution was cooled to room temperature and poured into ice. The resulting precipitate was collected by filtration and dried to afford 7-bromo-6-fluoroquinazolin-4(3H)-one (6.2 g, 24.24 mmol, 78% yield) as an off-white solid. The crude was used into next step without further purification.

LCMS: [M+H] 245.1.

Part D

To a mixture of 7-bromo-6-fluoroquinazolin-4(3H)-one (2.7 g, 11.11 mmol) and (R)-ethyl 4-bromo-2-methyl-2-(methylsulfonyl)butanoate (Intermediate 1) (3.35 g, 11.67 mmol) in N,N-dimethylformamide (30 mL) was added cesium carbonate (3.62 g, 11.11 mmol). The resulting mixture was stirred at 50° C. for 1 hr under a nitrogen atmosphere at which time the solution was cooled to room temperature. The mixture was poured into water (100 mL) and was washed with ethyl acetate (200 ml×2) and the combined organic layers were dried. The residue was purified by silica gel column chromatography (10%-50% ethyl acetate in petroleum ether) to afford (R)-ethyl 4-(7-bromo-6-fluoro-4-oxoquinazolin-3(4H)-yl)-2-methyl-2-(methylsulfonyl)butanoate (4.5 g, 8.62 mmol, 78% yield) as a white solid.

LCMS: [M+H] 449.0, 451.0.

Part E

Lithium hydroxide monohydrate (3.25 g, 77 mmol) was added to a solution of (R)-ethyl-4-(7-bromo-6-fluoro-4-oxoquinazolin-3(4H)-yl)-2-methyl-2-(methylsulfonyl)butanoate (11.6 g, 25.8 mmol) in tetrahydrofuran (40 mL) and water (20 mL) at room temperature and the reaction mixture was stirred at 20° C. for 1 hr. The solvent was removed by evaporation and the resulting aqueous layer was acidified to pH=3 using 1M HCl. The precipitate was collected by filtration and dried to give (R)-4-(7-bromo-6-fluoro-4-oxoquinazolin-3(4H)-yl)-2-methyl-2-(methylsulfonyl)butanoic acid (9.8 g, 20.94 mmol, 81% yield) as an off-white solid.

LCMS: [M+H] 421.0

Part F

To a solution of (R)-4-(7-bromo-6-fluoro-4-oxoquinazolin-3(4H)-yl)-2-methyl-2-(methylsulfonyl)butanoic acid (3 g, 7.12 mmol) and triethylamine (2.98 mL, 21.37 mmol) in tetrahydrofuran (THF) (5 mL) was added O-(tetrahydro-2H-pyran-2-yl)hydroxylamine (1.669 g, 14.24 mmol), HOBt (1.925 g, 14.24 mmol) and EDC.HCl (2.73 g, 14.24 mmol). The resulting mixture was stirred at 50° C. for 2 hr. The reaction was combined with another batch and the combined mixture was filtered and the filtrate was concentrated. The crude product was purified by silica gel chromatography (petroleum ether/EtOAc=1/2, then DCM/MeOH=30/1) to afford (2R)-4-(7-bromo-6-fluoro-4-oxoquinazolin-3(4H)-yl)-2-methyl-2-(methylsulfonyl)-N-((tetrahydro-2H-pyran-2-yl)oxy)butanamide (Intermediate 5) as a white solid (3.8 g, 93% yield based on the combined reactions).

LCMS: [M+H] 522.1.

1H NMR (400 MHz DMSO-$d_6$) δ: ppm 11.4 (s, 1H), 8.35 (d, 1H, J=8.8 Hz), 8.09 (d, 1H, J=5.6 Hz), 7.94 (d, 1H, J=8.0 Hz), 4.88 (d, 1H, J=18.4 Hz), 4.12-3.85 (m, 3H), 3.47 (d, 1H, J=10.4 Hz), 3.05 (d, 3H, J=9.2 Hz), 2.63-2.55 (m, 1H), 2.22-2.15 (m, 1H), 1.65-1.50 (m, 9H).

Intermediate 6

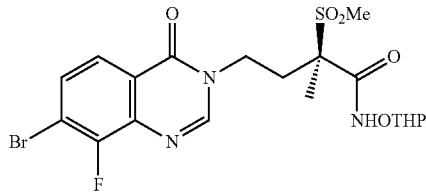

Part A

To a solution of 3-bromo-2-fluoroaniline (10 g, 52.6 mmol), 2,2,2-trichloroethane-1,1-diol (10.45 g, 63.2 mmol), hydroxylamine hydrochloride (11.70 g, 168 mmol) and sodium sulfate (44.9 g, 316 mmol) in water (300 mL) at room temperature was added hydrochloric acid (20 mL, 52.6 mmol) slowly. The reaction mixture was stirred at 90° C. for 1 hr. The reaction solution was combined with another batch and was cooled to room temperature and the precipitate was collected by filtration. The crude product was dried to afford (E)-N-(3-bromo-2-fluorophenyl)-2-(hydroxyimino)acetamide as an off-white solid (8 g, 52% yield based on the combined reactions).

LCMS: [M+H] 261.0.

Part B

To a stirred solution of $H_2SO_4$ (80 ml, 1501 mmol) at room temperature was added (E)-N-(3-bromo-2-fluorophenyl)-2-(hydroxyimino)acetamide (8 g, 30.6 mmol) portionwise and the reaction mixture was stirred at 90° C. for 2 hr. After cooling to room temperature, the mixture was poured onto ice-water (1500 g) and the resulting precipitate was filtered, washed with water (100 mL×2) and dried in vacuo to give 6-bromo-7-fluoroindoline-2,3-dione (6.4 g, 25.09 mmol, 82% yield) as a brown solid.

LCMS: [M+NH$_3$] 261.1.

$^1$H NMR (500 MHz, DMSO-d6) δ: ppm 11.74 (s, 1H), 7.38-7.35 (m, 1H), 7.29 (d, J=7.5 Hz, 1H).

Part C $H_2O_2$(10.0 mL, 98 mmol) was added to a solution of 6-bromo-7-fluoroindoline-2,3-dione (5.4 g, 22.13 mmol) and sodium hydroxide (27.7 mL, 55.3 mmol) in water (20 mL) at 0° C. and the reaction mixture was stirred at 0° C. for 2 hr. The reaction mixture was acidified by 2N HCl until the pH=6. The solid was collected by filtration and dried in vacuo to give 2-amino-4-bromo-3-fluorobenzoic acid (4.8 g, 20.51 mmol, 93% yield) as a yellow solid.

LCMS: [M+H] 234.1.

Part D

A mixture of 2-amino-4-bromo-3-fluorobenzoic acid (4.8 g, 20.51 mmol) in formamide (50 mL) was stirred at 160° C. for 6 hr under a nitrogen atmosphere. After cooling, the mixture was poured onto ice-water (500 g) and the resulting precipitate was filtered, washed with water (50 mL) and dried in vacuo to give 7-bromo-8-fluoroquinazolin-4(3H)-one (4.2 g, 16.94 mmol, 83% yield) as a yellow solid.

LCMS: [M+H] 242.4.

Part E

A mixture of 7-bromo-8-fluoroquinazolin-4(3H)-one (2.4 g, 9.88 mmol) and (R)-ethyl 4-bromo-2-methyl-2-(methylsulfonyl)butanoate (2.98 g, 10.37 mmol) and $Cs_2CO_3$ (6.44 g, 19.75 mmol) in N,N-dimethylformamide (DMF) (25 mL) was stirred at 50° C. under a nitrogen atmosphere. The reaction mixture was combined with another batch and this was poured into cooled water (300 mL). The resulting precipitate was filtered, dried in vacuo, and the crude product was purified by silica gel chromatography (1:3 EtOAc/petroleum ether) to give (R)-ethyl 4-(7-bromo-8-fluoro-4-oxoquinazolin-3(4H)-yl)-2-methyl-2-(methylsulfonyl)butanoate (4.0 g, 8.31 mmol, 84% yield) as a yellow solid.

LCMS: [M+H] 449.0.

Part F

A mixture of (R)-ethyl 4-(7-bromo-8-fluoro-4-oxoquinazolin-3(4H)-yl)-2-methyl-2-(methylsulfonyl)butanoate (2.0 g, 4.45 mmol), lithium hydroxide monohydrate (0.299 g, 7.12 mmol), tetrahydrofuran (THF) (20 mL) and water (10 mL) was stirred at 25° C. for 2 h. The organic layer was removed by evaporation and the resulting aqueous layer was acidified to pH=3 using 1M HCl (aq). The mixture was combined with another batch was filtered and the filter cake was dried in vacuo to give (R)-4-(7-bromo-8-fluoro-4-oxoquinazolin-3(4H)-yl)-2-methyl-2-(methylsulfonyl)butanoic acid (1.8 g, 3.62 mmol, 81% yield) as a yellow solid.

LCMS: [M+H] 420.7.

Part G

To a solution of (R)-4-(7-bromo-8-fluoro-4-oxoquinazolin-3(4H)-yl)-2-methyl-2-(methylsulfonyl)butanoic acid (1.8 g, 4.27 mmol) and triethylamine (1.787 mL, 12.82 mmol) in tetrahydrofuran (THF) (30 mL) was added O-(tetrahydro-2Hpyran-2-yl)hydroxylamine (1.001 g, 8.55 mmol), HOBt (1.155 g, 8.55 mmol) and EDC.HCl (1.638 g, 8.55 mmol). The resulting mixture was stirred at room temperature overnight. The mixture was concentrated under reduced pressure and the residue was purified by silica gel chromatography eluting with EtOAc to give (2R)-4-(7-bromo-8-fluoro-4-oxoquinazolin-3(4H)-yl)-2-methyl-2-(methylsulfonyl)-N-((tetrahydro-2H-pyran-2-yl)oxy)butanamide (Intermediate 6)(1.2 g, 2.306 mmol, 54% yield) as a yellow solid.

LCMS: [M+H] 521.7.

$^1$H NMR (400 MHz DMSO-$d_6$) δ: ppm 11.4 (s, 1H), 8.44 (d, 1H, J=9.6 Hz), 7.89 (d, 1H, J=8.4 Hz), 7.84-7.82 (m, 1H), 4.89 (d, 1H, J=16.8 Hz), 4.13-3.94 (m, 3H), 3.48-3.50 (m, 1H), 3.07 (d, 3H, J=9.6 Hz), 2.63-2.50 (m, 1H), 2.20 (m, 1H), 1.65-1.53 (m, 9H).

Intermediate 7

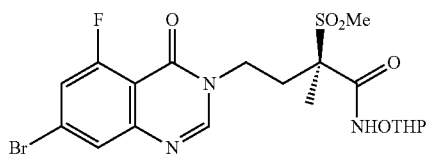

Part A

To a solution of methyl 4-bromo-2,6-difluorobenzoate (22.5 g, 90 mmol) in N,N-dimethylformamide (100 mL) was added (2,4-dimethoxyphenyl)methanamine (16.49 g, 99 mmol) and $K_2CO_3$ (18.58 g, 134 mmol) and the mixture was heated to 100° C. and stirred overnight. The mixture was added to 50 mL water, extracted with ethyl acetate (30 mL×3), dried over $Na_2SO_4$ and evaporated to afford a brown oil. The oil was purified by column chromatography on silica gel (ethyl acetate/petroleum ether=0-10%) affording methyl 4-bromo-2-((2,4-dimethoxybenzyl)amino)-6-fluorobenzoate (20 g, 45.2 mmol, 50% yield) as a yellow solid.

$^1$H NMR (400 Hz, DMSO-d6) δ: ppm 7.85 (t, 1H, J=4.4 Hz), 7.16 (d, 1H, J=6.4 Hz), 6.755 (s, 1H), 6.66 (d, 1H, J=8.8 Hz), 6.60 (m, 1H), 3.83 (s, 3H), 3.81 (s, 3H), 4.13-3.94 (m, 3H), 3.48-3.50 (m, 1H), 3.74 (s, 3H)

Part B

To a solution of methyl 4-bromo-2-((2,4-dimethoxybenzyl)amino)-6-fluorobenzoate (20 g, 50.2 mmol) in dichloromethane (200 mL) was added HCl (100 mL, 400 mmol) and the mixture was stirred at 25° C. for 2 hr. The mixture was evaporated in vacuo and a solution of $NaHCO_3$ was added. The aqueous layer extracted with ethyl acetate (100 mL×3), dried over $Na_2SO_4$ and evaporated to afford a yellow solid. The solid was purified by column chromatography on silica gel (ethyl acetate/petroleum ether 0-10%) affording methyl 2-amino-4-bromo-6-fluorobenzoate (13 g, 22.06 mmol, 44% yield) as a yellow solid.

LCMS: [M+H] 247.8.

Part C

To a solution of methyl 2-amino-4-bromo-6-fluorobenzoate (12.9 g, 21.89 mmol) in 1,4-dioxane (1 mL) was added a solution of lithium hydroxide hydrate (8.39 g, 200 mmol) in water (1 mL). The mixture was stirred at room temperature for 2 hr. The mixture was evaporated in vacuo and 1N HCl (200 mL) solution was added. The aqueous layer was extracted with ethyl acetate (300 mL×3), dried over $Na_2SO_4$ and evaporated to afford a yellow solid. The solid was purified by silica gel chromatography on silica gel (ethyl acetate/petroleum ether 10%-50%) affording 2-amino-4-bromo-6-fluorobenzoic acid (4 g, 14.90 mmol, 68% yield) as a yellow solid.

LCMS: [M+H] 236.0.

Part D

A mixture of 2-amino-4-bromo-6-fluorobenzoic acid (3.9 g, 16.67 mmol) in formamide (20 g, 444 mmol) was heated to 170° C. and stirred for 0.5 hr. The mixture was added to 100 mL water, extracted by ethyl acetate (50 mL×3), dried over $Na_2SO_4$ and evaporated to afford a yellow solid. The solid was purified by column chromatography on silica gel (ethyl acetate/petroleum ether=1/5-2/1) affording 7-bromo-5-fluoroquinazolin-4(3H)-one (1.5 g, 3.70 mmol, 22% yield) as a yellow solid.

LCMS: [M+H] 242.7.

Part E

A solution of 7-bromo-5-fluoroquinazolin-4(3H)-one (1.48 g, 6.09 mmol) in N,N-dimethylformamide (50 mL) was added (R)-ethyl 4-bromo-2-methyl-2-(methylsulfonyl)butanoate (Intermediate 1) (1.749 g, 6.09 mmol) and $Cs_2CO_3$ (1.984 g, 6.09 mmol). The mixture was heated to 50° C. and stirred for 2 hr. The mixture was added to 200 mL water, extracted with ethyl acetate times (200 mL×3), dried over $Na_2SO_4$ and evaporated to afford a yellow solid. The solid was purified by HPLC and afforded (R)-ethyl 4-(7-bromo-5-fluoro-4-oxoquinazolin-3(4H)-yl)-2-methyl-2-(methylsulfonyl)butanoate (700 mg, 1.558 mmol, 26% yield) as a yellow solid.

LCMS: [M+H] 449.0.

Part F

To a solution of (R)-ethyl 4-(7-bromo-5-fluoro-4-oxoquinazolin-3(4H)-yl)-2-methyl-2-(methylsulfonyl)butanoate (680 mg, 1.513 mmol) in 1,4-dioxane (10 mL) was added lithium hydroxide hydrate (168 mg, 4 mmol) in water (10.00 mL) and the mixture was stirred at 20° C. for 2 hr. To the mixture was added 6 mL of a 1N HCl solution and the aqueous layer was extracted by ethyl acetate (20 mL×3). The combined organic layers were dried over $Na_2SO_4$ and evaporated to afford a yellow solid. The solid was purified by column chromatography on silica gel (MeOH/DCM: 0-20%) and (R)-4-(7-bromo-5-fluoro-4-oxoquinazolin-3(4H)-yl)-2-methyl-2-(methylsulfonyl)butanoic acid (350 mg, 0.797 mmol, 53% yield) was obtained as a white solid.

LCMS: [M+H] 420.5.

Part G

To a solution of (R)-4-(7-bromo-5-fluoro-4-oxoquinazolin-3(4H)-yl)-2-methyl-2-(methylsulfonyl)butanoic acid (340 mg, 0.807 mmol) in tetrahydrofuran (20 mL) was added HATU (460 mg, 1.211 mmol), O-(tetrahydro-2H-pyran-2-yl)hydroxylamine (142 mg, 1.211 mmol) and $Et_3N$ (0.337 mL, 2.421 mmol). The mixture was stirred at room temperature for 2 hr. The mixture was evaporated in vacuo and 20 mL water was added. The aqueous layer was extracted with ethyl acetate (20 mL×3), dried over $Na_2SO_4$ and evaporated to afford a yellow solid. The solid was purified by column chromatography on silica gel (MeOH/DCM: 0-1/40) affording (2R)-4-(7-bromo-5-fluoro-4-oxoquinazolin-3(4H)-yl)-2-methyl-2-(methylsulfonyl)-N-((tetrahydro-2H-pyran-2-yl)oxy)butanamide (Intermediate 7)(500 mg, 0.551 mmol, 68% yield) as a white solid.

LCMS: [M+H] 521.3.

Intermediate 8

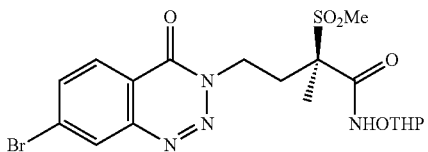

Part A

To a solution of 2-amino-4-bromobenzoic acid (10 g, 46.3 mmol) in tetrahydrofuran (THF) (10 mL) was added HOBT (16.30 g, 106 mmol) and EDC (20.41 g, 106 mmol). The mixture was stirred at 25° C. for 30 min when ammonia (30 mL, 1386 mmol) was added to the solution. The mixture was stirred at 25° C. for 18 hr. The solvent was removed in vacuo when EtOAc (200 mL) was added to the mixture. The organic phase was washed with NaHCO$_3$ (aq, 100 mL×3) and dried with NaS$_2$O$_4$. The solvent was removed to afford 2-amino-4-bromobenzamide (5.5 g, 24.55 mmol, 53% yield).

LCMS: [M+H]: 216.1.

Part B

To a solution of 2-amino-4-bromobenzamide (5.0 g, 23.25 mmol) in HCl (4.24 mL, 140 mmol) and water (50 mL) was added sodium nitrite (3.21 g, 46.5 mmol) at 0° C. The mixture was stirred at 0° C. for 30 min. The pH of the mixture was adjusted to 2 and the mixture was extracted with EtOAc (100 mL×3). The organic phase was dried with Na$_2$SO$_4$, filtered and removed in vacuo to afford 7-bromobenzo[d][1,2,3]triazin-4(3H)-one (5.0 g, 21.24 mmol, 91% yield) as white solid.

LCMS: [M+H] 228.1.

Part C

To a solution of 7-bromobenzo[d][1,2,3]triazin-4(3H)-one (5 g, 22.12 mmol) in N,N-dimethylformamide (DMF) (20 mL) was added (R)-ethyl 4-bromo-2-methyl-2-(methylsulfonyl)butanoate (Intermediate 1) (9.53 g, 33.2 mmol) and K$_2$CO$_3$ (6.11 g, 44.2 mmol) and the mixture was stirred at 80° C. for 18 hr. Water (20 mL) was added and the aqueous layer was extracted with EtOAc (100 mL×3). The combined organic layers were washed with aq. NaHCO$_3$ (40 mL), water (40 mL) and brine (40 mL) and the organic layer was dried (Na$_2$SO$_4$) and concentrated. The crude product was purified by a silica gel column chromatography (PE/EtOAc, EtOAc from 0 to 20%) to afford (R)-ethyl 4-(7-bromo-4-oxobenzo[d][1,2,3]triazin-3(4H)-yl)-2-methyl-2-(methylsulfonyl)butanoate (7.5 g, 17.35 mmol, 78% yield).

LCMS: [M+H] 432.0.

Part D

To a solution of (R)-ethyl 4-(7-bromo-4-oxobenzo[d][1,2,3]triazin-3(4H)-yl)-2-methyl-2-(methylsulfonyl)butanoate (2 g, 4.63 mmol) in dichloromethane (DCM) (30 mL) was added BBr$_3$ (1.750 mL, 18.51 mmol) at −78° C. The mixture was stirred at 0° C. for 1 hr. Methanol was added to the mixture at −78° C. and the solvent was removed in vacuo. Water (50 mL) was added to the mixture and the aqueous layer was extracted with EtOAc (100 mL×3). The organic phase was dried with Na$_2$SO$_4$, filtered and removed in vacuo to afford (R)-4-(7-bromo-4-oxobenzo[d][1,2,3]triazin-3(4H)-yl)-2-methyl-2-(methylsulfonyl)butanoic acid (1.8 g, 3.87 mmol, 84% yield) as a white solid.

LCMS: [M+H] 404.0.

Part E

To a solution of (R)-4-(7-bromo-4-oxobenzo[d][1,2,3]triazin-3(4H)-yl)-2-methyl-2-(methylsulfonyl)butanoic acid (2 g, 4.95 mmol) in tetrahydrofuran (THF) (5 mL) was added O-(tetrahydro-2H-pyran-2-yl)hydroxylamine (0.580 g, 4.95 mmol), HOBt (2.006 g, 14.84 mmol), EDC.HCl (2.85 g, 14.84 mmol) and triethylamine (3.45 mL, 24.74 mmol). The resulting mixture was stirred at 80° C. for 2 hr. To the mixture was added water (50 mL) and extracted with CH$_2$Cl$_2$ (100 mL×3) and the mixture was concentrated under vacuum. The crude product was purified by a silica gel column chromatography (PE/EtOAc: EtOAc from 0% to 50%) to afford (2R)-4-(7-bromo-4-oxobenzo[d][1,2,3]triazin-3(4H)-yl)-2-methyl-2-(methylsulfonyl)-N-((tetrahydro-2H-pyran-2-yl)oxy)butanamide (Intermediate 8) (1.8 g, 3.43 mmol, 69% yield) as a white solid.

LCMS: [M+Na] 525.0.

1H NMR (400 MHz DMSO-d$_6$) δ: ppm 11.4 (s, 1H), 8.46 (s, 1H), 8.16-8.14 (m, 1H), 8.10-8.08 (m, 1H), 4.86-4.77 (m, 1H), 4.50-4.49 (m, 1H), 4.40-4.39 (m, 1H), 4.03-4.0 (m, 1H), 3.43 (m, 1H), 3.07-3.04 (m, 3H), 2.51-2.50 (m, 1H), 2.26 (m, 1H), 1.65-1.50 (m, 9H).

Intermediate 9

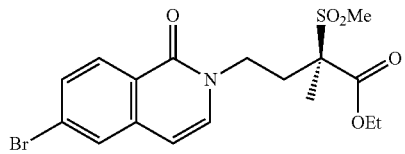 [SMILES: CCOC(=O)[C@@](C)(CCn1ccc2cc(Br)ccc2c1=O)S(C)(=O)=O]

To a mixture of 6-bromoisoquinolin-1(2H)-one (5 g, 22.32 mmol) and (R)-ethyl 4-bromo-2-methyl-2-(methylsulfonyl)butanoate (7.05 g, 24.55 mmol) in N,N-dimethylformamide (35 mL) was added Cs$_2$CO$_3$ (14.54 g, 44.6 mmol) at 30° C. The resulting mixture was stirred at 50° C. for 1 hr under a nitrogen atmosphere. To the mixture together with another batch was added EtOAc (150 mL) and water (250 mL). The layers were separated and the aqueous layer was extracted with EtOAc (100 mL). The combined organic layers were dried over Na$_2$SO$_4$, filtered and concentrated. The crude product was purified by silica gel chromatography (EtOAc/petroleum ether: 1/2) to give (R)-ethyl 4-(6-bromo-1-oxoisoquinolin-2(1H)-yl)-2-methyl-2-(methylsulfonyl)butanoate (Intermediate 9)(10 g, 21.45 mmol, 96% yield) as a yellow solid.

LCMS: [M+H] 430.1.

$^1$H NMR (400 MHz DMSO-d$_6$) δ: ppm 8.09 (d, J=8 Hz, 1H), 7.93 (s, 1H), 7.64 (d, J=4 Hz, 1H), 7.62 (d, J=4 Hz, 1H), 6.61 (d, J=8 Hz, 1H), 3.95-4.08 (m, 4H), 3.12 (s, 3H), 2.55-2.58 (m, 1H), 2.15-2.22 (m, 1H), 1.60 (s, 3H), 1.14 (t, J=8 Hz, 3H).

Intermediate 10

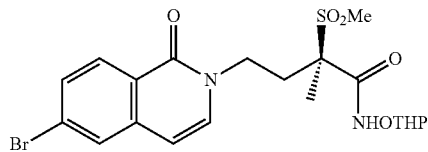

Part A

Ethyl 4-(6-bromo-1-oxoisoquinolin-2(1H)-yl)-2-methyl-2-(methylsulfonyl)butanoate (8 g, 18.59 mmol) in tetrahydrofuran (80 mL) at 0° C. was added a solution of lithium hydroxide (2.340 g, 55.8 mmol) in water (40 mL). The reaction mixture was stirred at room temperature for 2 hr. The mixture was cooled to 0° C. and adjusted to pH<3 with aq.HCl solution (2M) and the aqueous layer was extracted with EtOAc (150 mL×3). The combined organic layers were washed with water (100 ml) and brine (100 mL) and concentrated to afford (R)-4-(6-bromo-1-oxoisoquinolin-2 (1H)-yl)-2-methyl-2-(methylsulfonyl)butanoic acid (7.5 g, 18.64 mmol, 100% yield) as a white solid.

LCMS: [M+1] 402.1.

Part B

To a solution of (R)-4-(6-bromo-1-oxoisoquinolin-2(1H)-yl)-2-methyl-2-(methylsulfonyl)butanoic acid (7.5 g, 18.64 mmol) in tetrahydrofuran (100 mL) was added 4-methylmorpholine (3.39 g, 33.6 mmol) and 2-chloro-4,6-dimethoxy-1,3,5-triazine (4.91 g, 28.0 mmol) and this reaction was stirred for 1 hr. vO-(tetrahydro-2H-pyran-2-yl)hydroxylamine (3.93 g, 33.6 mmol) was added into above mixture stirred overnight. The reaction was filtered through celite and the filter pad was washed with DCM (10 mL×3). The combined filtrates were concentrated and the residue was purified via silica gel chromatography (EtOAc/hexanes: 20-85%) to afford (2R)-4-(6-bromo-1-oxoisoquinolin-2 (1H)-yl)-2-methyl-2-(methylsulfonyl)-N-((tetrahydro-2H-pyran-2-yl)oxy)butanamide (Intermediate 10) (8.7 g, 16.48 mmol, 88% yield) as a white solid.

LCMS: [M-THP] 417.1.

$^1$H NMR (METHANOL-d4) δ: ppm 8.20 (d, J=8.8 Hz, 1H), 7.86 (d, J=1.8 Hz, 1H), 7.65 (dd, J=8.7, 1.9 Hz, 1H), 7.41 (t, J=7.1 Hz, 1H), 6.66 (d, J=7.6 Hz, 1H), 4.98-5.08 (m, 1H), 3.88-4.40 (m, 3H), 3.53-3.69 (m, 1H), 3.12 (d, J=8.8 Hz, 3H), 2.53-2.72 (m, 1H), 2.28-2.46 (m, 1H), 1.50-1.94 (m, 9H).

Intermediate 11

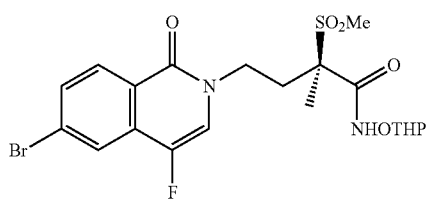

Part A

A mixture of (R)-ethyl 4-(6-bromo-1-oxoisoquinolin-2 (1H)-yl)-2-methyl-2-(methylsulfonyl)butanoate (Intermediate 9)(intermediate 10) (700 mg, 1.627 mmol), 1-chloromethyl-4-fluoro-1,4-diazoniabicyclo[2.2.2]octane bis (tetrafluoroborate) (576 mg, 1.627 mmol) and N,N-dimethylacetamide (3.5 mL) was heated in microwave at 150° C. for 15 min. The crude was combined with other batches. EtOAc (100 mL) and water (50 mL) were added. The aqueous layer was extracted with EtOAc (100 mL×2). The combined organic layers were washed with brine (50 mL), dried (Na$_2$SO$_4$), filtered and concentrated. The crude product was purified by reverse phase HPLC to afford (R)-ethyl 4-(6-bromo-4-fluoro-1-oxoisoquinolin-2(1H)-yl)-2-methyl-2-(methylsulfonyl)butanoate (1270 mg, 2.833 mmol, 31% yield) as a yellow oil.

LCMS [M+H] 448.0, 450.0.

Part B

A mixture of (R)-ethyl 4-(6-bromo-4-fluoro-1-oxoisoquinolin-2(1H)-yl)-2-methyl-2 (methylsulfonyl)butanoate (1.27 g, 2.83 mmol), lithium hydroxide monohydrate (0.357 g, 8.50 mmol), tetrahydrofuran (10 mL) and water (10 mL) was stirred at 30° C. for 3 hr. The organic layer was removed and water (20 mL) was added. The resulting aqueous layer was acidified to pH 3 with 1M aq. HCl (about 10 mL). The aqueous layer was extracted with 2-methyltetrahydrofuran (50 mL×3). The combined organic layers were dried (Na$_2$SO$_4$), filtered and concentrated. The crude product was purified by trituration with Et$_2$O (10 mL×2) to yield (R)-4-(6-bromo-4-fluoro-1-oxoisoquinolin-2(1H)-yl)-2-methyl-2-(methylsulfonyl)butanoic acid (1.07 g, 2.419 mmol, 85% yield) as a yellow solid.

LCMS: [M+H] 420.0, 422.0.

Part C

To a solution of (R)-4-(6-bromo-4-fluoro-1-oxoisoquinolin-2(1H)-yl)-2-methyl-2-(methylsulfonyl)butanoic acid (1010 mg, 2.403 mmol) and triethylamine (730 mg, 7.21 mmol) in N,N-dimethylformamide (10 mL) was added O-(tetrahydro-2H-pyran-2-yl)hydroxylamine (845 mg, 7.21 mmol), HOBt (974 mg, 7.21 mmol) and EDC.HCl (1382 mg, 7.21 mmol). The resulting mixture was stirred at 65° C. for 1 hr when water (50 mL) was added. The aqueous layer was extracted with EtOAc (100 mL×3) and the combined organic layers were washed with H$_2$O (50 mL) and brine (50 mL), dried (Na$_2$SO$_4$) and concentrated. The crude product was purified by silica gel chromatography (EtOAc/DCM: 0-33%) to give (2R)-4-(6-bromo-4-fluoro-1-oxoisoquinolin-2(1H)-yl)-2-methyl-2-(methylsulfonyl)-N-((tetrahydro-2H-pyran-2-yl)oxy)butanamide (Intermediate 11) (970 mg, 1.774 mmol, 74% yield) as a white solid.

LCMS: [M+Na] 541.2, 543.2.

Intermediate 12

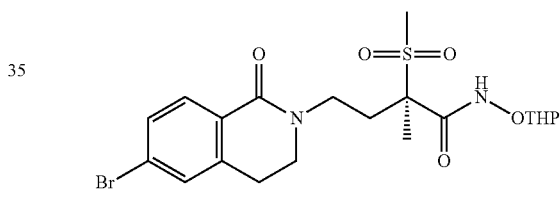

Part A 6-bromoisochroman-1-one (1 g, 4.40 mmol) and pentachlorophosphorane (1.192 g, 5.73 mmol) were dissolved in POCl$_3$ (20 ml, 215 mmol) and refluxed at 115° C. for 5 hours. The reaction mixture was cooled to room temperature and the POCl$_3$ was removed in vacuo. The residue was dried in vacuo for 2 hours. The crude solid was used for next step without any further purification.

Part B

To a solution of 4-bromo-2-(2-chloroethyl)benzoyl chloride (0.867 g, 3.07 mmol) and (R)-ethyl 4-amino-2-methyl-2-(methylsulfonyl)butanoate hydrochloride (1.038 g, 4.00 mmol) in tetrahydrofuran (30 mL) at 0° C. was added triethylamine (1.286 mL, 9.22 mmol) and the reaction was warmed to room temperature and stirred overnight. 1,4-Dioxane (30 mL) was added along with potassium 2-methylpropan-2-olate (1.380 g, 12.30 mmol) in small portions and the reaction was heated at 110° C. for 4 hr. The solvent was concentrated and 1N HCl was added and the organic phase was extracted with DCM (4×20 mL). The combined organic phases were washed with brine and dried over Na$_2$SO$_4$. The crude was purified by reverse phase chromatography (1% TFA, water/acetonitrile) to afford (R)-4-(6-brom(R(R)-4-(6-bromo-1-oxo-3,4-dihydroisoquinolin-2 (1H)-yl)-2-methyl-2-(methylsulfonyl)butanoic acid (0.426 g, 1.054 mmol, 34% yield) and (R)-ethyl 4-((R)-ethyl 4-(6- bromo-1-oxo-3,4-dihydroisoquinolin-2(1H)-yl)-2-methyl-2-(methylsulfonyl)butanoate (0.367 g, 0.849 mmol, 27% yield).

LCMS [M+H] for acid 404.0; for ester 432.1.

Part C (R)-ethyl 4-(6-bromo-1-oxo-3,4-dihydroisoquinolin-2(1H)-yl)-2-methyl-2-(methylsulfonyl)butanoate (0.420 mg, 0.971 mmol) was dissolved in a binary solvent mixture of tetrahydrofuran (2 ml) and water (7 ml) and lithium hydroxide hydrate (44.8 mg, 1.069 mmol) was added. The reaction mixture was allowed to stir overnight. 1N HCl was added and the product was extracted with ethyl acetate. The combined organic layers were dried with sodium sulfate and concentrated to yield (R)-4-(6-bromo-1-oxo-3,4-dihydroisoquinolin-2(1H)-yl)-2-methyl-2-(methylsulfonyl)butanoic acid (407 mg, 1.007 mmol, 104% yield).

LCMS: [M+H] 404.0.

Part D (R)-4-(6-Bromo-1-oxo-3,4-dihydroisoquinolin-2(1H)-yl)-2-methyl-2-(methylsulfonyl)butanoic acid (403 mg, 0.997 mmol), HATU (756 mg, 1.994 mmol) and 0-(tetrahydro-2H-pyran-2-yl)hydroxylamine (175 mg, 1.495 mmol) were dissolved in a binary solvent mixture of dry tetrahydrofuran (11 mL) and acetonitrile (4 mL) and N-ethyl-N-isopropylpropan-2-amine (258 mg, 1.994 mmol) was added at 0° C. The reaction mixture was stirred for 1.5 hr. The solvent was evaporated and the crude product was purified by silica gel chromatography (EtOAc/hexanes: 0-100%) to afford (2R)-4-(6-bromo-1-oxo-3,4-dihydroisoquinolin-2(1H)-yl)-2-methyl-2-(methylsulfonyl)-N-((tetrahydro-2H-pyran-2-yl)oxy)butanamide (Intermediate 12).

LCMS: [M+Na] 526.2.

Intermediate 13

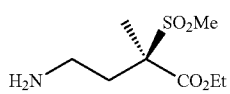

To a solution of (R)-ethyl 4-bromo-2-methyl-2-(methylsulfonyl)butanoate (2.3 g, 8.01 mmol) in N,N-dimethylformamide (10 mL) was added sodium azide (0.625 g, 9.61 mmol) and sodium iodide (0.240 g, 1.602 mmol). The reaction mixture was stirred at 80° C. for 4 hr. The mixture was extracted with EtOAc and washed with brine. The organic phase was dried with $Na_2SO_4$ and concentrated to afford (R)-ethyl 4-azido-2-methyl-2-(methylsulfonyl)butanoate (1.95 g, 7.82 mmol, 98% yield).

LCMS: [M+Na] 272.1.

Part B (R)-Ethyl 4-azido-2-methyl-2-(methylsulfonyl)butanoate (1.95 g, 7.82 mmol) was hydrogenated in the presence of a 4M solution of HCl in dioxane (7.82 mL, 31.3 mmol) and Pd/C (1.665 g, 1.564 mmol) for 5 hr. The reaction mixture was filtered and the filtrated was concentrated to afford the (R)-ethyl 4-amino-2-methyl-2-(methylsulfonyl)butanoate hydrochloride (2.4 g, 9.24 mmol, 118% yield).

LCMS: [M+H] 224.1.

Intermediate 14 and 15

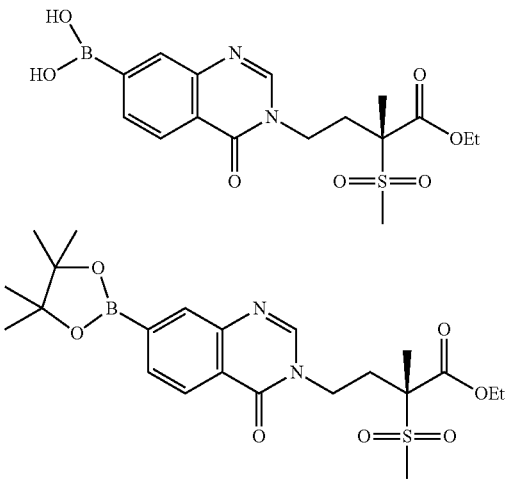

A mixture of (R)-ethyl 4-(7-bromo-4-oxoquinazolin-3(4H)-yl)-2-methyl-2-(methylsulfonyl)butanoate (Intermediate 2) (10 g, 23.19 mmol), 4,4,4',4',5,5,5',5'-octamethyl-2,2'-bi(1,3,2-dioxaborolane) (14.72 g, 58.0 mmol), $PdCl_2$(dppf)-$CH_2Cl_2$ adduct (1.893 g, 2.319 mmol), potassium acetate (6.83 g, 69.6 mmol) and 1,4-dioxane (150 ml) was stirred at 70° C. for 17 hr under a nitrogen atmosphere. The solvent was removed by evaporation and EtOAc (500 mL) and water (200 mL) were added and the mixture filtered. The filtrate was separated and the aqueous layer was extracted with EtOAc (50 mL). The combined organic layers were dried ($Na_2SO_4$) and concentrated. The residue was purified by silica gel (MeOH/DCM: 0-10%) to afford (R)-(3-(4-ethoxy-3-methyl-3-(methylsulfonyl)-4-oxobutyl)-4-oxo-3,4-dihydroquinazolin-7-yl)boronic acid (Intermediate 19) (3.0 g, 5.30 mmol, 23% yield) as a black solid and (R)-ethyl 2-methyl-2-(methylsulfonyl)-4-(4-oxo-7-(4,4,5,5-tetramethyl-1,3,2-dioxaborolan-2-yl)quinazolin-3(4H)-yl)butanoate (Intermediate 20) (6.2 g, 12.31 mmol, 53% yield) as a yellow oil LCMS: [M+H]: 478.9.

Compound Examples

Example 1. (R)—N-hydroxy-2-methyl-2-(methylsulfonyl)-4-(4-oxo-7-phenylquinazolin-3(4H)-yl)butanamide

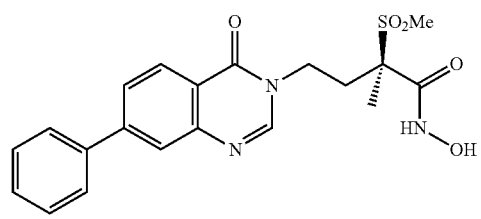 [SMILES: C[C@@](CCn1cnc2cc(-c3ccccc3)ccc2c1=O)(C(=O)NO)S(C)(=O)=O]

Part A

A mixture of (2R)-4-(7-bromo-4-oxoquinazolin-3(4H)-yl)-2-methyl-2-(methylsulfonyl)-N-((tetrahydro-2H-pyran-2-yl)oxy)butanamide (75 g, 149 mmol), potassium carbonate (30.9 g, 224 mmol), $PdCl_2$(dppf) (10.92 g, 14.93 mmol)

and phenylboronic acid (23.66 g, 194 mmol) in 1,4-dioxane (800 mL) and water (80 mL) was heated to 100° C. for 30 min. The mixture was cooled and filtered with celite. The filtrate was concentrated to 200 ml and then diluted with EtOAc (500 mL) and 10% citric acid solution (200 ml). The water phase was extracted with EtOAc (3×150 ml). The combined organic layers were washed with saturated brine 150 mL, dried over sodium sulphate and evaporated in vacuo. The residue was triturated with EtOAc (400 ml) to give a white solid and this was filtered off and collected. The filtrate was concentrated and purified with combiflash silical chromatography (eluted with hexane/EtOAc from 0-80% over 40 min). The solids were combined and the product (2R)-2-methyl-2-(methylsulfonyl)-4-(4-oxo-7-phenylquinazolin-3(4H)-yl)-N-((tetrahydro-2H-pyran-2-yl)oxy)butanamide (53 g, 101 mmol, 68% yield) was obtained as white solid.

LCMS: (M+1) 500.2 at 1.02 min.

Part B

To a solution of (2R)-2-methyl-2-(methylsulfonyl)-4-(4-oxo-7-phenylquinazolin-3(4H)-yl)-N-((tetrahydro-2H-pyran-2-yl)oxy)butanamide (53 g, 106 mmol) in dichloromethane (DCM) (1000 mL) and methanol (1000 mL) stirred under nitrogen at rt was added a solution of HCl 4M in dioxane (39.8 mL, 159 mmol). The reaction mixture was stirred at rt for 4 h. The reaction was filtered, washed with t-butyl methyl ether and concentrated in vacuo. The residue was triturated with ethyl acetate/methanol (10 ml/10 ml), filtered and washed with ethyl acetate. Water (800 ml×4, 4 batches) was added and the mixture was heated to reflux, cooled and filtered to give (R)—N-hydroxy-2-methyl-2-(methylsulfonyl)-4-(4-oxo-7-phenylquinazolin-3(4H)-yl) butanamide (41 g, 94 mmol, 88% yield) as white solid.

LCMS: (M+1) 416.2, at 0.84 min.

$^1$H NMR (METHANOL-$d_4$) δ: 9.46 (d, J=1.0 Hz, 1H), 8.46 (d, J=8.3 Hz, 1H), 7.91-8.07 (m, 2H), 7.67 (td, J=7.8, 1.8 Hz, 1H), 7.49-7.59 (m, 1H), 7.24-7.47 (m, 2H), 4.42 (td, J=9.2, 4.7 Hz, 1H), 4.19-4.35 (m, 1H), 3.11 (s, 3H), 2.88 (ddd, J=13.7, 9.2, 6.9 Hz, 1H), 2.48 (ddd, J=13.8, 9.1, 4.9 Hz, 1H), 1.79 (s, 3H)

Example 2. (R)—N-hydroxy-2-methyl-2-(methylsulfonyl)-4-(4-oxo-7-(p-tolyl)quinazolin-3(4H)-yl) butanamide

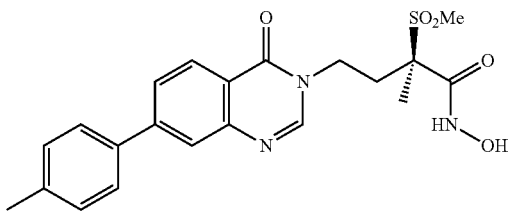 [SMILES: Cc1ccc(-c2ccc3c(=O)n(CC[C@](C)(C(=O)NO)S(C)(=O)=O)cnc3c2)cc1]

Part A

The reaction vessel was sealed with $K_2CO_3$ (77 mg, 0.556 mmol), $PdCl_2$(dppf) (20.36 mg, 0.028 mmol), 4,4,5,5-tetramethyl-2-(p-tolyl)-1,3,2-dioxaborolane (79 mg, 0.362 mmol) and (R)-ethyl 4-(7-bromo-4-oxoquinazolin-3(4H)-yl)-2-methyl-2-(methylsulfonyl)butanoate (Intermediate 2) (120 mg, 0.278 mmol) and heated in Emrys Optimiser to 110° C. for 30 min. The organic phase was diluted with DCM (20 mL) and washed with water 20 mL, saturated brine 30 mL, dried over sodium sulphate and evaporated in vacuo and the obtained residue was purified with combiflash silical chromatography (eluted with hexane/EtOAc from 0-80% over 20 min). The product (R)-ethyl 2-methyl-2-(methylsulfonyl)-4-(4-oxo-7-(ptolyl)quinazolin-3(4H)-yl) butanoate (120 mg, 0.209 mmol, 75% yield) were obtained as colorless oil.

LCMS: (M+1) 443.3 at 1.02 min.

Part B

To a solution of (R)-ethyl 2-methyl-2-(methylsulfonyl)-4-(4-oxo-7-(ptolyl) quinazolin-3(4H)-yl)butanoate (120 mg, 0.271 mmol) in 1,4-dioxane (2 mL) was added a solution of hydroxylamine (1 mL, 16.32 mmol) (50% in water) and LiOH (0.5 ml, 0.500 mmol) (1M in water) at rt. The reaction mixture was stirred at rt for overnight. Concentrated in vacuo and then purified by Gilson (Sunfire, 5-85% MeCN, H2O, 0.1% TFA, 18 min) to afford (R)—N-hydroxy-2-methyl-2-(methylsulfonyl)-4-(4-oxo-7-(p-tolyl)quinazolin-3(4H)-yl)butanamide (56 mg, 0.124 mmol, 45.7% yield) as light brown solid after freezed dried.

LCMS: (M+1) 430.3, at 0.93 min $^1$H NMR (METHANOL-d4) δ: 8.56 (br. s., 1H), 8.33 (d, J=8.3 Hz, 1H), 7.84-7.95 (m, 2H), 7.67 (d, J=8.1 Hz, 2H), 7.36 (d, J=7.8 Hz, 2H), 4.29-4.45 (m, 1H), 3.99-4.15 (m, 1H), 3.12 (s, 3H), 2.66-2.81 (m, 1H), 2.37-2.53 (m, 4H), 1.77 (s, 3H).

Example 3. (R)—N-hydroxy-4-(7-(4-methoxyphenyl)-4-oxoquinazolin-3(4H)-yl)-2-methyl-2-(methylsulfonyl)butanamide

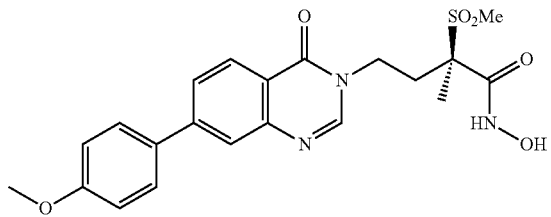 [SMILES: COc1ccc(-c2ccc3c(=O)n(CC[C@](C)(C(=O)NO)S(C)(=O)=O)cnc3c2)cc1]

Part A

The reaction vessel was sealed with $K_2CO_3$ (77 mg, 0.556 mmol), $PdCl_2$ (dppf) (20.36 mg, 0.028 mmol), (4-methoxyphenyl)boronic acid (55 mg, 0.362 mmol) and (R)-ethyl 4-(7-bromo-4-oxoquinazolin-3(4H)-yl)-2-methyl-2-(methylsulfonyl)butanoate (Intermediate 2) (120 mg, 0.278 mmol) and heated in Emrys Optimiser to 110° C. for 30 min. The organic phase was diluted with DCM (20 mL) and washed with water 20 mL, saturated brine 30 mL, dried over sodium sulphate and evaporated in vacuo and the residue was purified with combiflash silical chromatography (eluated with hexane/EtOAc from 0-80% over 20 min). The product (R)-ethyl 4-(7-(4-methoxyphenyl)-4-oxoquinazolin-3(4H)-yl)-2-methyl-2-(methylsulfonyl)butanoate (120 mg, 0.209 mmol, 75% yield) were obtained as colorless oil.

LCMS: (M+1) 459.4 at 0.97 min.

Part B

To a solution of (R)-ethyl 4-(7-(4-methoxyphenyl)-4-oxoquinazolin-3(4H)-yl)-2-methyl-2-(methylsulfonyl)butanoate (120 mg, 0.262 mmol) in 1,4-Dioxane (2 mL) was added a solution of hydroxylamine (1 mL, 16.32 mmol) (50% in water) and LiOH (0.5 ml, 0.500 mmol) (1M in water) at rt. The reaction mixture was stirred at rt overnight and concentrated in vacuo. The residue was purified by Gilson (Sunfire, 5-85% MeCN, $H_2O$, 0.1% TFA, 18 min) to afford (R)—N-hydroxy-4-(7-(4-methoxyphenyl)-4-oxoquinazolin-3(4H)-yl)-2-methyl-2-(methylsulfonyl)butanamide (42 mg, 0.090 mmol, 34% yield) as a light brown solid after freeze drying.

LCMS: (M+1) 446.3, at 0.84 min

¹H NMR (METHANOL-d4) δ: 8.60 (br. s., 1H), 8.33 (d, J=8.8 Hz, 1H), 7.85-7.97 (m, 2H), 7.74 (d, J=8.8 Hz, 2H), 7.10 (d, J=8.8 Hz, 2H), 4.29-4.46 (m, 1H), 4.01-4.16 (m, 1H), 3.89 (s, 3H), 3.12 (s, 3H), 2.69-2.87 (m, 1H), 2.34-2.52 (m, 1H), 1.77 (s, 3H).

Example 4. (R)-4-(7-(4-(dimethylamino)phenyl)-4-oxoquinazolin-3(4H)-yl)-N-hydroxy-2-methyl-2-(methylsulfonyl)butanamide Trifluoroacetic Acid Salt

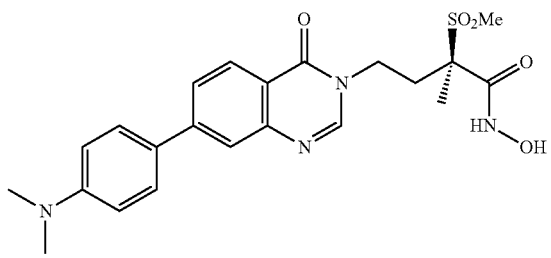 [SMILES: CN(C)c1ccc(-c2ccc3c(=O)n(CC[C@](C)(C(=O)NO)S(C)(=O)=O)cnc3c2)cc1]

Part A

The reaction vessel sealed with potassium carbonate (70.5 mg, 0.510 mmol), PdCl₂(dppf) (18.66 mg, 0.026 mmol), (R)-ethyl 4-(7-bromo-4-oxoquinazolin-3(4H)-yl)-2-methyl-2-(methylsulfonyl)butanoate (Intermediate 2) (110 mg, 0.255 mmol) and (4-(dimethylamino)phenyl)boronic acid (50.5 mg, 0.306 mmol was heated in an Emrys Optimiser to 110° C. for 30 min. The organic phase was diluted with DCM (20 mL) and washed with water 20 mL, saturated brine 30 mL, dried over sodium sulphate and evaporated in vacuo and the residue was purified with combiflash silical chromatography (eluted with DCM/MeOH from 0-20% over 20 min). The product (R)-ethyl 4-(7-(4-(dimethylamino)phenyl)-4-oxoquinazolin-3(4H)-yl)-2-methyl-2-(methylsulfonyl)butanoate (120 mg, 0.226 mmol, 89% yield) was obtained as a colorless oil.

LCMS: (M+1) 472.3 at 0.92 min.

Part B

To a solution of (R)-ethyl 4-(7-(4-(dimethylamino)phenyl)-4-oxoquinazolin-3(4H)-yl)-2-methyl-2-(methylsulfonyl)butanoate (120 mg, 0.254 mmol) in 1,4-dioxane (2 mL) was added a solution of hydroxylamine (1 mL, 16.32 mmol) (50% in water) and LiOH (0.5 ml, 0.500 mmol) (1M in water) at rt. The reaction mixture was stirred at rt overnight. The reaction was concentrated in vacuo and then purified by Gilson (Sunfire, 5-85% MeCN, H₂O, 0.1% TFA, 18 min) to afford (R)-4-(7-(4-(dimethylamino)phenyl)-4-oxoquinazolin-3(4H)-yl)-N-hydroxy-2-methyl-2-(methylsulfonyl)butanamide trifluoroacetic acid salt (40 mg, 0.066 mmol, 26% yield) as light brown solid after freezed drying.

LCMS: (M+1) 459.3, at 0.71 min

¹H NMR (METHANOL-d4) δ: 8.51 (s, 1H), 8.35 (d, J=8.3 Hz, 1H), 7.85-7.96 (m, 2H), 7.77 (d, J=7.3 Hz, 2H), 7.41-7.61 (m, 3H), 4.28-4.44 (m, 1H), 3.95-4.16 (m, 1H), 3.13 (s, 3H), 2.68-2.80 (m, 1H), 2.36-2.53 (m, 1H), 1.77 (s, 3H).

Example 5. (R)-4-(7-(4-(difluoromethoxy)phenyl)-4-oxoquinazolin-3(4H)-yl)-N-hydroxy-2-methyl-2-(methylsulfonyl)butanamide

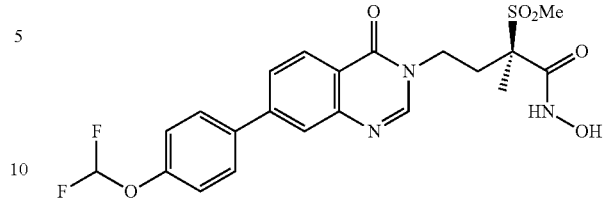

Part A

A reaction vessel was sealed with potassium carbonate (133 mg, 0.963 mmol), PdCl₂(dppf) (35.2 mg, 0.048 mmol), (2R)-4-(7-bromo-4-oxoquinazolin-3(4H)-yl)-2-methyl-2-(methylsulfonyl)-N-((tetrahydro-2H-pyran-2-yl)oxy)butanamide (Intermediate 3) (193 mg, 0.385 mmol) and 2-(4-(difluoromethoxy)phenyl)-4,4,5,5-tetramethyl-1,3,2-dioxaborolane (130 mg, 0.481 mmol) and heated in an Emrys to 110° C. for 30 min. The organic phase was diluted with DCM (20 mL) and washed with water 20 mL, saturated brine 30 mL, dried over sodium sulphate and evaporated in vacuo. The residue was purified with combiflash silical chromatography (eluted with hexane/EtOAc from 0-100% over 25 min). The product (2R)-4-(7-(4-(difluoromethoxy)phenyl)-4-oxoquinazolin-3(4H)-yl)-2-methyl-2-(methylsulfonyl)-N-((tetrahydro-2H-pyran-2-yl)oxy)butanamide (180 mg, 0.318 mmol, 66% yield) was obtained as colorless oil.

LCMS: (M+1) 566.3 at 1.07 min.

Part B

To a solution of (2R)-4-(7-(4-(difluoromethoxy)phenyl)-4-oxoquinazolin-3(4H)-yl)-2-methyl-2-(methylsulfonyl)-N-((tetrahydro-2H-pyran-2-yl)oxy)butanamide (180 mg, 0.318 mmol) in dichloromethane (DCM) (3 mL) and methanol (2 mL) stirred under nitrogen at rt was added a solution of HCl 4M in dioxane (0.796 mL, 3.18 mmol). The reaction mixture was stirred at rt for 4 h. The reaction was concentrated in vacuo and then triturated with ethyl acetate/methanol (10 ml/10 ml), filtered, and washed with ethyl acetate and ether to afford (R)-4-(7-(4-(difluoromethoxy)phenyl)-4-oxoquinazolin-3(4H)-yl)-N-hydroxy-2-methyl-2-(methylsulfonyl)butanamide (97 mg, 0.191 mmol, 60% yield) as white solid after high vacuum dried.

LCMS: (M+1) 482.2, at 0.91 min

¹H NMR (METHANOL-d4) δ: 9.40 (s, 1H), 8.44 (d, J=8.3 Hz, 1H), 8.06 (dd, J=8.5, 1.4 Hz, 1H), 7.94 (d, J=1.3 Hz, 1H), 7.86 (d, J=8.6 Hz, 2H), 7.35 (d, J=8.6 Hz, 2H), 6.75-7.18 (t, J=72.0 Hz, 1H), 4.42 (ddd, J=13.8, 9.3, 4.9 Hz, 1H), 4.20-4.34 (m, 1H), 3.11 (s, 3H), 2.76-2.93 (m, 1H), 2.47 (ddd, J=13.8, 9.2, 4.8 Hz, 1H), 1.78 (s, 3H).

Example 6. (R)-4-(7-(2,3-difluorophenyl)-4-oxoquinazolin-3(4H)-yl)-N-hydroxy-2-methyl-2-(methylsulfonyl)butanamide

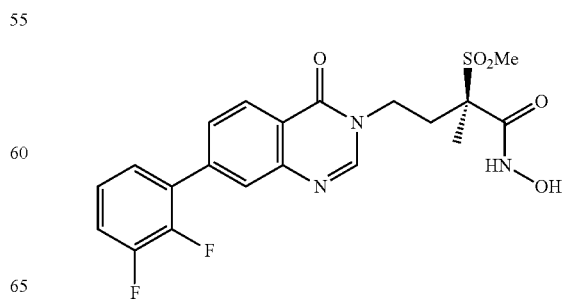

Part A

A reaction vessel was sealed with potassium carbonate (83 mg, 0.597 mmol), PdCl$_2$(dppf) (21.85 mg, 0.030 mmol), (2R)-4-(7-bromo-4-oxoquinazolin-3(4H)-yl)-2-methyl-2-(methylsulfonyl)-N-((tetrahydro-2H-pyran-2-yl)oxy)butanamide (Intermediate 3) (150 mg, 0.299 mmol) and (2,3-difluorophenyl)boronic acid (61.3 mg, 0.388 mmol and heated in Emrys Optimiser to 110° C. for 30 min. The organic phase was diluted with DCM (20 mL) and washed with water 20 mL, saturated brine 30 mL, dried over sodium sulphate and concentrated in vacuo. The residue was purified with combiflash silical chromatography (eluted with DCM/EtOAc from 0-80% over 25 min). The product (2R)-4-(7-(2,3-difluorophenyl)-4-oxoquinazolin-3(4H)-yl)-2-methyl-2-(methylsulfonyl)-N-((tetrahydro-2H-pyran-2-yl)oxy)butanamide (130 mg, 0.231 mmol, 77% yield) was obtained as a colorless oil.

LCMS: (M+1) 536.3 at 1.01 min.

Part B

To a solution of (2R)-4-(7-(2,3-difluorophenyl)-4-oxoquinazolin-3(4H)-yl)-2-methyl-2-(methylsulfonyl)-N-((tetrahydro-2H-pyran-2-yl)oxy)butanamide (130 mg, 0.243 mmol) in dichloromethane (DCM) (3 mL) and methanol (2 mL) stirred under nitrogen at rt was added a solution of HCl 4M in dioxane (0.607 mL, 2.427 mmol). The reaction mixture was stirred at rt for 4 h. The reaction was concentrated in vacuo and then triturated with ethyl acetate/methanol (10 ml/10 ml), filtered and washed with ethyl acetate and ether to afford (R)-4-(7-(2,3-difluorophenyl)-4-oxoquinazolin-3(4H)-yl)-N-hydroxy-2-methyl-2-(methylsulfonyl)butanamide (60 mg, 0.126 mmol, 52% yield) as white solid.

LCMS: (M+1) 452.2, at 0.88 min $^1$H NMR (METHANOL-d4) δ: 9.47 (s, 1H), 8.48 (d, J=8.3 Hz, 1H), 7.90-8.05 (m, 2H), 7.19-7.57 (m, 3H), 4.09-4.51 (m, 2H), 3.11 (s, 3H), 2.79-2.96 (m, 1H), 2.48 (ddd, J=13.6, 9.2, 4.5 Hz, 1H), 1.79 (s, 3H).

Example 7. (R)-4-(7-(2,5-difluorophenyl)-4-oxoquinazolin-3(4H)-yl)-N-hydroxy-2-methyl-2-(methylsulfonyl)butanamide

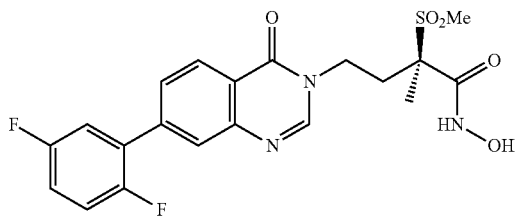 [SMILES: C[C@@](CCn1cnc2cc(-c3cc(F)ccc3F)ccc2c1=O)(C(=O)NO)S(C)(=O)=O]

Part A

A reaction vessel was sealed with potassium carbonate (83 mg, 0.597 mmol), PdCl$_2$(dppf) (21.85 mg, 0.030 mmol), (2R)-4-(7-bromo-4-oxoquinazolin-3(4H)-yl)-2-methyl-2-(methylsulfonyl)-N-((tetrahydro-2H-pyran-2-yl)oxy)butanamide (Intermediate 3) (150 mg, 0.299 mmol) and (2,5-difluorophenyl)boronic acid (61.3 mg, 0.388 mmol) and heated in Emrys Optimiser to 110° C. for 30 min. The organic phase was diluted with DCM (20 mL) and washed with water 20 mL, saturated brine 30 mL, dried over sodium sulphate and evaporated in vacuo. The residue was purified with combiflash silical chromatography (eluted with DCM/EtOAc from 0-80% over 25 min). The product (2R)-4-(7-(2,5-difluorophenyl)-4-oxoquinazolin-3(4H)-yl)-2-methyl-2-(methylsulfonyl)-N-((tetrahydro-2H-pyran-2-yl)oxy)butanamide (133 mg, 0.236 mmol, 79% yield) was obtained as a colorless oil.

LCMS: (M+1) 536.3 at 1.05 min.

Part B

To a solution of (2R)-4-(7-(2,5-difluorophenyl)-4-oxoquinazolin-3(4H)-yl)-2-methyl-2-(methylsulfonyl)-N-((tetrahydro-2H-pyran-2-yl)oxy)butanamide (130 mg, 0.243 mmol) in dichloromethane (DCM) (3 mL) and methanol (2 mL) stirred under nitrogen at rt was added a solution of HCl 4M in dioxane (0.607 mL, 2.427 mmol). The reaction mixture was stirred at rt for 4 h. The reaction was concentrated in vacuo and then triturated with ethyl acetate/methanol (10 ml/10 ml), filtered and washed with ethyl acetate and ether to afford (R)-4-(7-(2,5-difluorophenyl)-4-oxoquinazolin-3(4H)-yl)-N-hydroxy-2-methyl-2-(methylsulfonyl)butanamide (69 mg, 0.145 mmol, 60% yield) as white solid.

LCMS: (M+1) 452.2, at 0.87 min $^1$H NMR (METHANOL-d4) δ: 9.46 (s, 1H), 8.47 (d, J=8.3 Hz, 1H), 7.86-8.05 (m, 2H), 7.43-7.58 (m, 1H), 7.21-7.42 (m, 2H), 4.16-4.52 (m, 2H), 3.11 (s, 3H), 2.79-2.96 (m, 1H), 2.48 (ddd, J=13.5, 9.1, 4.7 Hz, 1H), 1.70-1.86 (m, 3H).

Example 8. (R)-4-(7-(2-fluorophenyl)-4-oxoquinazolin-3(4H)-yl)-N-hydroxy-2-methyl-2-(methylsulfonyl)butanamide

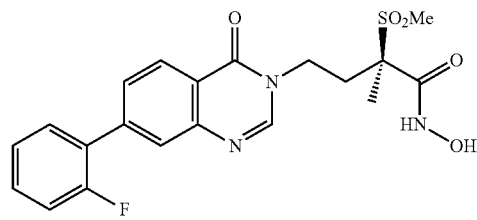 [SMILES: C[C@@](CCn1cnc2cc(-c3ccccc3F)ccc2c1=O)(C(=O)NO)S(C)(=O)=O]

Part A

Two reactions were carried out in parallel: To a solution of 7-bromoquinazolin-4(3H)-one (120 g, 533 mmol, 1.0 eq) and (R)-ethyl-4-bromo-2-methyl-2-(methylsulfonyl)butanoate (Intermediate 1) (161 g, 559 mmol, 1.05 eq) in acetonitrile (1.2 L) was added Cs$_2$CO$_3$ (254 g, 779 mmol, 1.5 eq) in portions for 20 min at 25° C. under N$_2$. The temperature of mixture solution changed very small, and the mixture solution was difficult to stir because of the addition of Cs$_2$CO$_3$. The mixture was stirred at 25° C. for 40 min, then heated to 80° C. for 20 hrs under N$_2$. The mixture was cooled to 25° C. Two reactions were combined for work up. The combined mixture was filtered and the filter cake was washed with ethyl acetate (500 mL). The combined organic layers were concentrated under vacuum to 300 mL and diluted with ethyl acetate (1000 mL) then water (1000 mL) was added. The organic layer was separated and the aqueous layer was extracted with ethyl acetate (400 mL×4). The combined organic layers were washed with water (300 mL) and brine (300 mL). The organic layers were dried over Na$_2$SO$_4$. The mixture was filtered and the filtrate was concentrated under reduced pressure to give the crude product as yellow oil. The crude product was washed with MTBE (400 mL) and a yellow solid precipitated. The mixture was filtered and the filter cake was washed with (petroleum ether/ethyl acetate=100 mL/200 mL). The mixture was filtered to give the desired product (330 g) as a light yellow solid. The filtrate was purified by silica gel column chromatography (petroleum ether/ethyl acetate=10:1, 5:1, 3:1, 1:1, 1:2) to give the crude product. The crude product was concentrated in vacuum at 45° C. and washed with (petroleum ether/ethyl acetate=100 mL/200 mL) and filtered. The filter cake was concentrated in vacuum affording (R)-ethyl 4-(7-bromo-4-oxoquinazolin-3(4H)-yl)-2-methyl-2-(methylsulfonyl)butanoate (395 g, 916 mmol, 86% yield) as a light yellow solid.

$^1$H NMR: 400 MHz DMSO-$d_6$

δ 8.42 (s, 1H), 8.06 (d, J=8.0 Hz, 1H), 7.90 (d, J=4.0 Hz, 1H), 7.70-7.72 (dd, J=8.0 Hz, 1H), 4.02-4.08 (m, 24H), 3.13 (s, 3H), 2.61-2.64 (m, 1H), 2.23-2.27 (m, 1H), 1.62 (s, 3H), 1.16 (t, J=12 Hz, 3H).

Part B

Two reactions were carried out in parallel: To a solution of (R)-ethyl 4-(7-bromo-4-oxoquinazolin-3(4H)-yl)-2-methyl-2-(methylsulfonyl)butanoate (230 g, 533 mmol, 1.0 eq) in THF (1.4 L) was added a solution of aqueous LiOH.H$_2$O (2 M, 800 mL, 3.0 eq) dropwise at 15° C. The reaction mixture was stirred at 23° C. for 2 hrs. Two reactions were combined for work up and the mixture was concentrated under vacuum at 45° C. The residue was adjusted to pH=3-4 with HCl (2 mol/L, 1300 mL) at 0-5° C. and a white precipitate slowly formed. The white solid was filtered and the filter cake was dried under vacuum at 40° C. for 72 h. (R)-4-(7-bromo-4-oxoquinazolin-3(4H)-yl)-2-methyl-2-(methylsulfonyl)butanoic acid (415 g, 1.0 mol, 96% yield) was obtained and the desired product was used in next step without further purification.

$^1$H NMR: 400 MHz DMSO-$d_6$

δ 8.42 (s, 1H), 8.04 (d, J=12 Hz, 1H), 7.88 (s, 1H), 7.68-7.71 (m, 1H), 4.03-4.12 (m, 2H), 3.13 (s, 3H), 2.53-2.56 (m, 1H), 2.21-2.22 (m, 1H), 1.57 (s, 3H).

Part C

Two reactions were carried out in parallel: To a solution of (R)-4-(7-bromo-4-oxoquinazolin-3(4H)-yl)-2-methyl-2-(methylsulfonyl)butanoic acid (182 g, 450 mmol, 1.0 eq) in dry THF (2.5 L) was added 4-methylmorpholine (81.9 g, 810 mmol, 1.8 eq) and 2-chloro-4,6-dimethoxy-1,3,5-triazine (118 g, 675 mmol, 1.5 eq) in portions for 40 min at 20° C. The resulting reaction mixture was mechanically stirred for 4 h at 20° C. A white solid precipitated and the reaction suspension became difficult to stir. O-tetrahydropyran-2-ylhydroxylamine (94.9 g, 810 mmol, 1.8 eq) was then added to the reaction mixture in portions for 40 min at 20° C. and the mixture was continually mechanically stirred for 6 h at 30° C. Two reactions were combined for work up and the combined mixture was filtered and the filter cake was washed with dichloromethane (500 mL×2). The combined organic layers were concentrated in vacuum at 45° C. The residue was dissolved in dichloromethane (2 L) and washed with water (500 mL×3), brine (300 mL×2) and dried over Na$_2$SO$_4$. The mixture was filtered and the filtrate was concentrated to give the crude product. The crude product was washed with ethyl acetate (2 L) and a white solid precipitated and was filtered. This procedure was repeated three times. (2R)-4-(7-bromo-4-oxoquinazolin-3(4H)-yl)-2-methyl-2-(methylsulfonyl)-N-((tetrahydro-2H-pyran-2-yl)oxy)butanamide (260 g, 517 mmol, 57% yield) was obtained as a white solid.

$^1$H NMR: 400 MHz CDCl$_3$

δ 10.7 (d, J=8.0 Hz, 1H), 8.13-8.16 (m, 1H), 8.08 (s, 1H), 7.93 (d, J=1.6 Hz, 1H), 7.63-7.66 (m, 1H), 5.14 (s, 1H), 4.33-4.34 (m, 1H), 4.10-4.15 (m, 2H), 3.97-4.09 (m, 1H), 3.13 (t, J=8.0 Hz, 3H), 2.52-2.55 (m, 1H), 2.43-2.54 (m, 2H), 1.63-1.85 (m, 10H).

Part D

Two reactions were carried out in parallel: To a mixture of (2R)-4-(7-bromo-4-oxoquinazolin-3(4H)-yl)-2-methyl-2-(methylsulfonyl)-N-((tetrahydro-2H-pyran-2-yl)oxy)butanamide (130 g, 259 mmol, 1.0 eq) and (2-fluorophenyl)boronic acid (43.5 g, 310 mmol, 1.2 eq) in H$_2$O (120 mL) was added K$_2$CO$_3$ (53.7 g, 388 mmol, 1.5 eq) in one portion at 15° C. The mixture was bubbled with N$_2$ for 5 min and pdCl$_2$(dppf) (12 g, 25.9 mmol, 0.1 eq) was added in one portion at 15° C. under N$_2$. The mixture was degassed under vacuum and purged with N$_2$ five times. The mixture was stirred at 15° C. for 25 min and then heated to 95° C. for 0.5 hour. The color of the mixture turned red after 10 min. and then brown after another 10 min. Two reactions were combined for work up and the mixture was cooled to 20° C. and filtered. The filtrate was concentrated under reduced pressure to give the crude product. The crude product was purified by silica gel chromatography (dichloromethane/methanol=50:1, 30:1, 20:1, 10:1, 1:1, 0:1) to give crude product and this progress was repeated two more times. 4-(7-(2-fluorophenyl)-4-oxoquinazolin-3(4H)-yl)-2-methyl-2-(methylsulfonyl)-N-((tetrahydro-2H-pyran-2-yl)oxy)butanamide (230 g, 444 mmol, 86% yield) was obtained as a brown solid.

$^1$H NMR: 400 MHz CDCl$_3$

δ 10.96 (d, J=20 Hz, 1H), 8.32-8.35 (m, 1H), 8.10 (s, 1H), 7.92 (s, 1H), 7.74 (s, 1H), 7.51 (m, 1H), 7.26-7.28 (m, 1H), 7.19-7.24 (m, 2H), 4.12-4.18 (m, 1H), 3.93 (s, 1H), 3.67-3.68 (m, 6H), 3.12-3.15 (m, 3H), 2.53-2.56 (m, 2H), 1.60-1.84 (m, 10H).

Part E

Two reactions were carried out in parallel: To a solution of 4-(7-(2-fluorophenyl)-4-oxoquinazolin-3(4H)-yl)-2-methyl-2-(methylsulfonyl)-N-((tetrahydro-2H-pyran-2-yl)oxy)butanamide (110 g, 212 mmol, 1.0 eq) in DCM (1000 mL) and MeOH (1000 mL) was added dropwise a solution of HCl(g)/dioxane (4 M, 250 mL, 4.7 eq) at 0° C. The reaction mixture was stirred at 20° C. for 2 hours. A brown solid precipitated and the resulting suspension became difficult to stir. Two reactions were combined for work up, the mixture was concentrated in vacuum and purified by prep-HPLC (Instrument: Shimadzu LC-20AP preparative HPLC, Column: Phenomenex Luna(2) C18 250*50 mm i.d. 10 u, Mobile phase: A for H$_2$O (0.04% HCl) and B for CH$_3$CN. Gradient: B from 15% to 45% in 20 min, Flow rate: 80 ml/min, Wavelength: 220 & 254 nm. Injection amount: 1 g per injection). The integral liquid was concentrated in vacuum at 45° C. to remove ACN and most of the H$_2$O. A light yellow solid precipitated after most of water was removed. The solid was filtered and combined with water (1200 mL, and stirred at 20° C. for 2 h. The solid was isolated by vacuum filtration and air-dried for 1 h. The solid was dried in a vacuum oven at 50° C. for 5 hours, 40° C. for 5 hours and 35° C. for 16 hours. (R)-4-(7-(2-fluorophenyl)-4-oxoquinazolin-3(4H)-yl)-N-hydroxy-2-methyl-2-(methylsulfonyl)butanamide (100 g, 231 mmol, 54% yield) was obtained as a light pink solid.

LCMS: (M+1) 434.3

$^1$H NMR: 400 MHz DMSO-$d_6$

δ 11.0 (s, 1H), 9.22 (s, 1H), 8.37 (s, 1H), 8.21 (d, J=8.0 Hz, 1H), 7.72 (d, J=8.0 Hz, 1H), 7.63 (d, J=32 Hz, 1H), 7.48 (d, J=8 Hz, 1H), 7.33-7.38 (m, 2H), 4.09-4.14 (m, 1H), 3.86-3.89 (m, 1H), 3.07 (s, 3H), 2.54 (s, 1H), 2.15-2.20 (m, 1H), 1.58 (s, 3H).

$^1$H NMR: 400 MHz MeOD

δ 8.33 (s, 1H), 8.21-8.23 (d, J=8.0 Hz, 1H), 7.77 (s, 1H), 7.66-7.68 (d, J=8.0 Hz, 1H), 7.49-7.50 (d, J=4.0 Hz, 1H), 7.24-7.26 (d, J=8.0 Hz, 1H), 7.16-7.20 (m, 2H), 4.21-4.27 (m, 1H), 3.95-3.97 (m, 1H), 3.03 (s, 3H), 2.61-2.66 (m, 1H), 2.34-2.39 (m, 1H), 1.67 (s, 3H).

$^1$H NMR: 400 MHz CDCl$_3$

δ 11.99 (s, 1H), 8.33 (d, J=8.0 Hz, 1H), 8.07 (s, 1H), 7.80 (d, J=28 Hz, 1H), 7.69 (s, 1H), 7.46 (d, J=4.0 Hz, 1H), 7.15-7.23 (m, 1H), 6.93-7.15 (m, 1H), 4.25-4.30 (m, 1H), 4.11-4.15 (m, 1H), 3.16 (s, 3H), 2.50-2.55 (m, 1H), 2.33-2.37 (m, 1H), 1.71 (s, 3H).

Example 9. (R)-4-(7-(3-fluoro-4-methylphenyl)-4-oxoquinazolin-3(4H)-yl)-N-hydroxy-2-methyl-2-(methylsulfonyl)butanamide

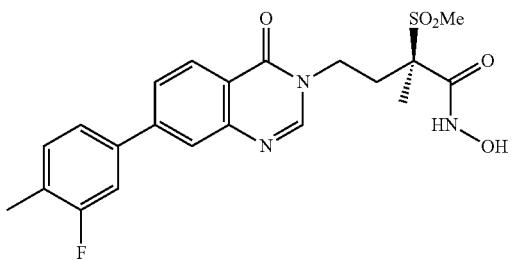 [SMILES: Cc1ccc(-c2ccc3c(=O)n(CC[C@](C)(C(=O)NO)S(C)(=O)=O)cnc3c2)cc1F]

Preparation

A reaction vessel was sealed with potassium carbonate (83 mg, 0.597 mmol), PdCl$_2$(dppf) (21.85 mg, 0.030 mmol), (2R)-4-(7-bromo-4-oxoquinazolin-3(4H)-yl)-2-methyl-2-(methylsulfonyl)-N-((tetrahydro-2H-pyran-2-yl)oxy)butanamide (Intermediate 3) (150 mg, 0.299 mmol) and (3-fluoro-4-methylphenyl)boronic acid (59.8 mg, 0.388 mmol) and heated in Emrys Optimiser to 110° C. for 30 min. The organic phase was diluted with DCM (20 mL) and extracted with DCM (3×10 ml) and then washed with water 20 mL, saturated brine 30 mL, dried over sodium sulphate and evaporated in vacuo. The residue was purified with combiflash silical chromatography (eluted with DCM/EtOAc from 10-100% over 20 min). The product (2R)-4-(7-(3-fluoro-4-methylphenyl)-4-oxoquinazolin-3(4H)-yl)-2-methyl-2-(methylsulfonyl)-N-((tetrahydro-2H-pyran-2-yl)oxy)butanamide (142 mg, 0.254 mmol, 85% yield) was obtained as a colorless oil.

LCMS: (M+1) 532.3 at 1.12 min.

Preparation

To a solution of (2R)-4-(7-(3-fluoro-4-methylphenyl)-4-oxoquinazolin-3(4H)-yl)-2-methyl-2-(methylsulfonyl)-N-((tetrahydro-2H-pyran-2-yl)oxy)butanamide (140 mg, 0.263 mmol) in dichloromethane (DCM) (3 mL) and methanol (2 mL) stirred under nitrogen at rt was added a solution of HCl 4M in dioxane (0.658 mL, 2.63 mmol). The reaction mixture was stirred at rt for 4 h. The reaction was concentrated in vacuo and then triturated with ethyl acetate/methanol (10 ml/10 ml), filtered and washed with ethyl acetate and ether to afford (R)-4-(7-(3-fluoro-4-methylphenyl)-4-oxoquinazolin-3(4H)-yl)-N-hydroxy-2-methyl-2-(methylsulfonyl)butanamide (76 mg, 0.161 mmol, 61% yield) as a white solid.

LCMS: (M+1) 448.2, at 0.95 min $^1$H NMR (DMSO-d6) δ: 11.03 (br. s., 1H), 8.43 (s, 1H), 8.21 (d, J=8.3 Hz, 1H), 7.98 (d, J=1.5 Hz, 1H), 7.90 (dd, J=8.3, 1.8 Hz, 1H), 7.54-7.73 (m, 2H), 7.44 (t, J=8.1 Hz, 1H), 4.91 (br. s., 1H), 4.06-4.24 (m, 1H), 3.72-3.99 (m, 1H), 3.11 (s, 3H), 2.54-2.66 (m, 1H), 2.30 (s, 3H), 2.13-2.26 (m, 1H), 1.62 (s, 3H)

Example 10. (R)-4-(7-(4-(difluoromethyl)phenyl)-4-oxoquinazolin-3(4H)-yl)-N-hydroxy-2-methyl-2-(methylsulfonyl)butanamide

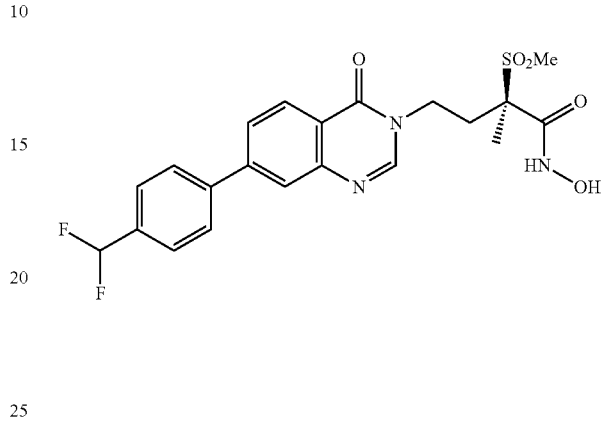

Part A

A reaction vessel was sealed with potassium carbonate (83 mg, 0.597 mmol), PdCl$_2$(dppf) (21.85 mg, 0.030 mmol), (2R)-4-(7-bromo-4-oxoquinazolin-3(4H)-yl)-2-methyl-2-(methylsulfonyl)-N-((tetrahydro-2H-pyran-2-yl)oxy)butanamide (Intermediate 3) (150 mg, 0.299 mmol) and (4-(difluoromethyl)phenyl)boronic acid (66.7 mg, 0.388 mmol) and heated in Emrys Optimiser to 110° C. for 30 min. The organic phase was diluted with DCM (20 mL) and washed with water 20 mL, saturated brine 30 mL, dried over sodium sulphate and evaporated in vacuo. The residue was purified with combiflash silical chromatography (eluted with DCM/EtOAc from 0-80% over 25 min) affording (2R)-4-(7-(4-(difluoromethyl)phenyl)-4-oxoquinazolin-3(4H)-yl)-2-methyl-2-(methylsulfonyl)-N-((tetrahydro-2H-pyran-2-yl)oxy)butanamide (140 mg, 0.252 mmol, 84% yield) as a colorless oil.

LCMS: (M+1) 550.1 at 1.05 min.

Part B

To a solution of (2R)-4-(7-(4-(difluoromethyl)phenyl)-4-oxoquinazolin-3(4H)-yl)-2-methyl-2-(methylsulfonyl)-N-((tetrahydro-2H-pyran-2-yl)oxy)butanamide (140 mg, 0.255 mmol) in dichloromethane (DCM) (3 mL) and methanol (2 mL) stirred under nitrogen at rt was added a solution of HCl 4M in dioxane (0.637 mL, 2.55 mmol). The reaction mixture was stirred at rt for 4 h. The reaction was concentrated in vacuo and then triturated with ethyl acetate/methanol (10 ml/10 ml), filtered and washed with ethyl acetate and to afford (R)-4-(7-(4-(difluoromethyl)phenyl)-4-oxoquinazolin-3(4H)-yl)-N-hydroxy-2-methyl-2-(methylsulfonyl)butanamide (72 mg, 0.147 mmol, 58% yield) as a white solid.

LCMS: (M+1) 466.2, at 0.89 min.

$^1$H NMR (METHANOL-d4) δ: 9.43 (s, 1H), 8.47 (d, J=8.3 Hz, 1H), 8.10 (dd, J=8.6, 1.5 Hz, 1H), 7.86-8.04 (m, 3H), 7.76 (d, J=8.1 Hz, 2H), 6.89 (t, J=56 Hz, 1H), 4.16-4.48 (m, 2H), 3.12 (s, 3H), 2.88 (ddd, J=13.6, 9.1, 6.8 Hz, 1H), 2.48 (ddd, J=13.8, 9.2, 4.8 Hz, 1H), 1.79 (s, 3H).

Example 11. (2R)-4-[7-(2,6-difluorophenyl)-4-oxo-3,4-dihydroquinazolin-3-yl]-N-hydroxy-2-methanesulfonyl-2-methylbutanamide

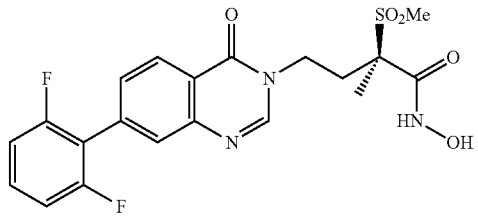 [SMILES: C[C@@](CCn1cnc2cc(-c3c(F)cccc3F)ccc2c1=O)(C(=O)NO)S(C)(=O)=O]

Part A

To a flask was placed cesium carbonate (2.59 g, 7.96 mmol), PdCl$_2$(dppf) (0.291 g, 0.398 mmol), (2R)-4-(7-bromo-4-oxoquinazolin-3(4H)-yl)-2-methyl-2-(methylsulfonyl)-N-((tetrahydro-2H-pyran-2-yl)oxy)butanamide (Intermediate 3) (2 g, 3.98 mmol) and (2,6-difluorophenyl) boronic acid (0.817 g, 5.18 mmol) and the mixture was stirred at 100° C. for 30 min. The organic phase was diluted with DCM (20 mL) and extracted with DCM (10 mL×3) and then washed with water (20 mL), brine (30 mL), dried over sodium sulphate and evaporated. The residue was purified with silical gel chromatography (MeOH/DCM: 0-10%) to effort (2R)-4-(7-(2,6-difluorophenyl)-4-oxoquinazolin-3(4H)-yl)-2-methyl-2-(methylsulfonyl)-N-((tetrahydro-2H-pyran-2-yl)oxy)butanamide (0.4 g, 0.747 mmol, 19% yield) as a colorless oil.

LCMS: [M+H] 536.2.

Part B

To a solution of (2R)-4-(7-(2,6-difluorophenyl)-4-oxoquinazolin-3(4H)-yl)-2-methyl-2-(methylsulfonyl)-N-((tetrahydro-2H-pyran-2-yl)oxy)butanamide (1.2 g, 2.241 mmol) in ethanol (3 mL) was added hydrogen chloride (1.680 ml, 6.72 mmol) solution in dioxane (4M). The resulting solution was stirred overnight. The reaction was concentrated and purified by reverse phase chromatograph (0.1% TFA, MeCN/H$_2$O, 5-70%) to afford (R)-4-(7-(2,6-difluorophenyl)-4-oxoquinazolin-3(4H)-yl)-N-hydroxy-2-methyl-2-(methylsulfonyl)butanamide (630 mg, 1.396 mmol, 62% yield) as a white powder.

LCMS: [M+H] 452.1.

$^1$H NMR (400 MHz, METHANOL-d$_4$) δ: ppm 1.77 (s, 3H) 2.45 (ddd, J=13.39, 10.61, 5.05 Hz, 1H) 2.65-2.78 (m, 1H) 3.13 (s, 3H) 3.98-4.10 (m, 1H) 4.28-4.41 (m, 1H) 7.15 (t, J=8.21 Hz, 2H) 7.43-7.54 (m, 1H) 7.65 (d, J=8.08 Hz, 1H) 7.79 (s, 1H) 8.34 (d, J=8.08 Hz, 1H) 8.39 (s, 1H).

Example 12. (2R)-4-[7-(1,3-dihydro-2-benzofuran-5-yl)-4-oxo-3,4-dihydroquinazolin-3-yl]-N-hydroxy-2-methanesulfonyl-2-methylbutanamide

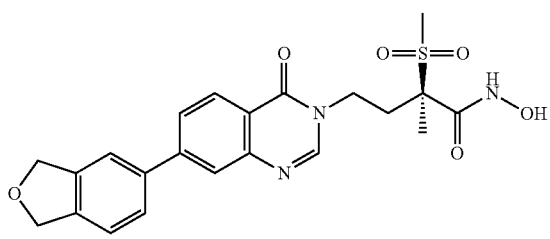

Part A

To a reaction vessel sealed with potassium carbonate (1.238 g, 8.96 mmol), PdCl$_2$(dppf) (0.437 g, 0.597 mmol), (2R)-4-(7-bromo-4-oxoquinazolin-3(4H)-yl)-2-methyl-2-(methylsulfonyl)-N-((tetrahydro-2H-pyran-2-yl)oxy)butanamide (Intermediate 3) (3 g, 5.97 mmol) and 2-(1,3-dihydroisobenzofuran-5-yl)-4,4,5,5-tetramethyl-1,3,2-dioxaborolane (1.911 g, 7.76 mmol) and heated to 100° C. for 60 min. The mixture was filtered and the filtrate was diluted with DCM (20 mL) and washed with water (20 mL), brine (30 mL), dried over sodium sulfate and evaporated in vacuo and the obtained residue was purified with combiflash silical chromatography (eluted with hexane/EtOAc from 0-80% over 25 min). The product (2R)-4-(7-(1,3-dihydroisobenzofuran-5-yl)-4-oxoquinazolin-3(4H)-yl)-2-methyl-2-(methylsulfonyl)-N-((tetrahydro-2H-pyran-2-yl)oxy)butanamide (1.1 g, 1.544 mmol, 26% yield) was obtained as light brown solid

LCMS: [M+H] 542.5.

Part B

To a solution of (2R)-4-(7-(1,3-dihydroisobenzofuran-5-yl)-4-oxoquinazolin-3(4H)-yl)-2-methyl-2-(methylsulfonyl)-N-((tetrahydro-2H-pyran-2-yl)oxy)butanamide (1.1 g, 2.031 mmol) in dichloromethane (50 mL) and methanol (50 mL) stirred under nitrogen at room temperature was added a solution of HCl in dioxane (1.523 mL, 6.09 mmol) in dioxane (4M). The reaction mixture was stirred at room temperature for 4 hr. The reaction was concentrated in vacuo and then triturated with ethyl acetate/methanol (100 ml/10 ml), was filtered and washed with ethyl acetate to afford (R)-4-(7-(1,3-dihydroisobenzofuran-5-yl)-4-oxoquinazolin-3(4H)-yl)-N-hydroxy-2-methyl-2-(methylsulfonyl)butanamide (720 mg, 1.495 mmol, 74% yield) as white solid.

LCMS: [M+H] 460.2.

$^1$H NMR (METHANOL-d4) δ: ppm 9.28 (br s, 1H), 8.42 (d, J=8.3 Hz, 1H), 8.05 (d, J=8.3 Hz, 1H), 7.94 (s, 1H), 7.66-7.79 (m, 2H), 7.49 (d, J=8.3 Hz, 1H), 5.18 (d, J=6.1 Hz, 4H), 4.14-4.51 (m, 2H), 3.12 (s, 3H), 2.71-2.91 (m, 1H), 2.47 (ddd, J=13.6, 9.3, 4.7 Hz, 1H), 1.78 (s, 3H)

Example 13. (2R)-4-[6-fluoro-7-(4-methoxyphenyl)-4-oxo-3,4-dihydroquinazolin-3-yl]-N-hydroxy-2-methanesulfonyl-2-methylbutanamide

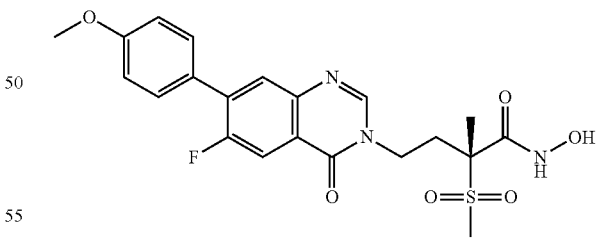

Part A

PdCl$_2$(dppf) (63.3 mg, 0.086 mmol) was added to a solution of (4-methoxyphenyl)boronic acid (96 mg, 0.634 mmol), (2R)-4-(7-bromo-6-fluoro-4-oxoquinazolin-3(4H)-yl)-2-methyl-2-(methylsulfonyl)-N-((tetrahydro-2H-pyran-2-yl)oxy)butanamide (Intermediate 5) (300 mg, 0.577 mmol) and K$_2$CO$_3$ (159 mg, 1.153 mmol) in acetonitrile (6 mL) and water (1 mL) at room temperature under an atmosphere of nitrogen. The mixture from combined batches was cooled to room temperature, diluted with ethyl acetate (50 mL) and dried over Na$_2$SO$_4$. The solvent was evaporated and the crude product was purified by silica gel chromatography (DCM/MeOH: 30/1) to afford (2R)-4-(6-fluoro-7-(4-methoxyphenyl)-4-oxoquinazolin-3(4H)-yl)-2-methyl-2-(methylsulfonyl)-N-((tetrahydro-2H-pyran-2-yl)oxy) butanamide as a brown solid (250 mg, 41% yield based on the combined reactions).

LCMS: [M+H] 548.1.

Part B

To a solution of (2R)-4-(6-fluoro-7-(4-methoxyphenyl)-4-oxoquinazolin-3(4H)-yl)-2-methyl-2-(methylsulfonyl)-N-((tetrahydro-2H-pyran-2-yl)oxy)butanamide (200 mg, 0.365 mmol) in dichloromethane (10 mL), HCl (10 mL, 40 mmol) in dioxane (4M) was added. The resulting solution was stirred at 20° C. for 1 hr when methanol (3 mL) was added and the reaction was stirred an additional 1 hr. The reaction solution was combined with another batch and was concentrated. The residue was purified by trituration with MeOH/diethyl ether to give (R)-4-(6-fluoro-7-(4-methoxyphenyl)-4-oxoquinazolin-3(4H)-yl)-N-hydroxy-2-methyl-2-(methylsulfonyl)butanamide (70 mg, 0.151 mmol, 41% yield) as a white solid.

LCMS: [M+H] 464.1.

$^1$H NMR (500 MHz, DMSO-d6) δ: ppm 11.01 (s, 1H), 8.34 (s, 1H), 7.90 (d, J=10.5 Hz, 1H), 7.80 (d, J=7.0 Hz, 1H), 7.63 (d, J=7.5 Hz, 2H), 7.10 (d, J=8.5 Hz, 2H), 4.14 (m, 1H), 3.91 (m, 1H), 3.83 (s, 3H), 3.10 (s, 3H), 2.59 (m, 1H), 2.21 (m, 1H), 1.61 (s, 3H).

Example 14. (2R)-4-[8-fluoro-7-(4-methoxyphenyl)-4-oxo-3,4-dihydroquinazolin-3-yl]-N-hydroxy-2-methanesulfonyl-2-methylbutanamide

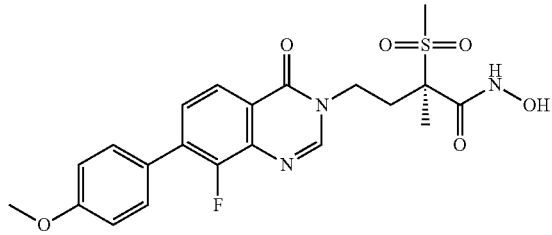 [SMILES: COc1ccc(-c2ccc3c(=O)n(CC[C@](C)(C(=O)NO)S(C)(=O)=O)cnc3c2F)cc1]

Part A

PdCl$_2$(dppf) (56.2 mg, 0.077 mmol) was added to a solution of (4-methoxyphenyl)boronic acid (175 mg, 1.153 mmol), (2R)-4-(7-bromo-8-fluoro-4-oxoquinazolin-3(4H)-yl)-2-methyl-2-(methylsulfonyl)-N-((tetrahydro-2H-pyran-2-yl)oxy)butanamide (Intermediate 6) (400 mg, 0.769 mmol) and potassium carbonate (212 mg, 1.537 mmol) in acetonitrile (10 mL) and water (2 mL) at room temperature under a nitrogen atmosphere and stirred at 80° C. for 1 hr. The mixture was concentrated under reduced pressure and the residue was purified by silica gel chromatography (1:50 EtOH/CH$_2$Cl$_2$) to give (2R)-4-(8-fluoro-7-(4-methoxyphenyl)-4-oxoquinazolin-3(4H)-yl)-2-methyl-2-(methylsulfonyl)-N-((tetrahydro-2Hpyran-2-yl)oxy)butanamide (340 mg, 0.515 mmol, 67% yield) as a brown solid.

LCMS: [M+H] 548.1

Part B

To a stirred solution of (2R)-4-(8-fluoro-7-(4-methoxyphenyl)-4-oxoquinazolin-3(4H)-yl)-2-methyl-2-(methylsulfonyl)-N-((tetrahydro-2H-pyran-2-yl)oxy)butanamide (320 mg, 0.584 mmol) in methanol (6.0 mL) and dichloromethane (6 mL) was added a solution of HCl (7.30 mL, 29.2 mmol) in 1,4-dioxane at room temperature and this mixture was then stirred for 1 hr. The mixture from combined batches was concentrated under reduced pressure. The residue was purified by reverse phase HPLC to give (R)-4-(8-fluoro-7-(4-methoxyphenyl)-4-oxoquinazolin-3(4H)-yl)-N-hydroxy-2-methyl-2-(methylsulfonyl)butanamide (56 mg, 0.118 mmol, 20% yield) as an off-white solid.

LCMS: [M+H] 464.2.

$^1$H NMR (500 MHz, DMSO-d6) δ: ppm 11.01 (s, 1H), 9.24 (s, 1H), 8.43 (s, 1H), 8.00 (d, J=8.5 Hz, 1H), 7.66 (t, J=8.0 Hz, 1H), 7.62 (d, J=8.5 Hz, 2H), 7.11 (d, J=9.0 Hz, 2H), 4.18-4.12 (m, 1H), 3.94-3.89 (m, 1H), 3.83 (s, 3H), 3.10 (s, 3H), 2.64-2.57 (m, 1H), 2.24-2.18 (m, 1H), 1.61 (s, 3H).

Example 15. (2R)-4-[6-fluoro-7-(4-methylphenyl)-4-oxo-3,4-dihydroquinazolin-3-yl]-N-hydroxy-2-methanesulfonyl-2-methylbutanamide

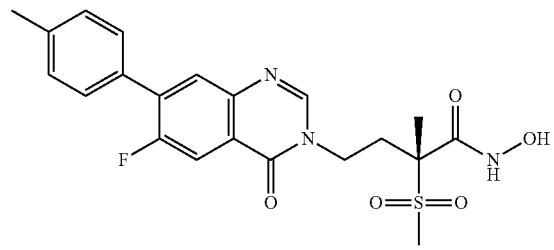 [SMILES: Cc1ccc(-c2cc3ncn(CC[C@](C)(C(=O)NO)S(C)(=O)=O)c(=O)c3cc2F)cc1]

Part A

PdCl$_2$(dppf) (63.3 mg, 0.086 mmol) was added to a solution of p-tolylboronic acid (86 mg, 0.634 mmol), (2R)-4-(7-bromo-6-fluoro-4-oxoquinazolin-3(4H)-yl)-2-methyl-2-(methylsulfonyl)-N-((tetrahydro-2H-pyran-2-yl)oxy)butanamide (Intermediate 5)(300 mg, 0.577 mmol) and K$_2$CO$_3$ (159 mg, 1.153 mmol) in acetonitrile (6 mL) and water (1 mL) at room temperature under an atmosphere of nitrogen. The resulting solution was stirred at 80° C. for 30 min. The mixture from combined batches was cooled to room temperature, diluted with ethyl acetate (100 mL) and dried over Na$_2$SO$_4$. The solvent was evaporated and the crude product was purified by flash column chromatography (DCM/MeOH: 30/1) to afford (2R)-4-(6-fluoro-4-oxo-7-(p-tolyl)quinazolin-3(4H)-yl)-2-methyl-2-(methylsulfonyl)-N-((tetrahydro-2H-pyran-2-yl)oxy)butanamide as a brown solid (230 mg, 53% yield based on the combined reactions).

LCMS: [M+H] 532.2.

Part B

To a solution of (2R)-4-(6-fluoro-4-oxo-7-(p-tolyl)quinazolin-3(4H)-yl)-2-methyl-2-(methylsulfonyl)-N-((tetrahydro-2H-pyran-2-yl)oxy)butanamide (200 mg, 0.376 mmol) in dichloromethane (20 mL), HCl (10 mL, 20 mmol) in dioxane (4M) was added. The resulting solution was stirred at 20° C. for 1 hr. Methanol (5 mL) was added and the reaction was stirred an additional 1 hr. The mixture from combined batches was concentrated and the residue was purified by trituration with MeOH/diethyl ether to give (R)-4-(6-fluoro-4-oxo-7-(p-tolyl)quinazolin-3(4H)-yl)-N-hydroxy-2-methyl-2-(methylsulfonyl)butanamide (75 mg, 0.168 mmol, 45% yield based on the combined reactions) as a white solid.

LCMS: [M+H] 448.2.

$^1$H NMR (500 MHz, DMSO-d6) δ: ppm 11.00 (s, 1H), 8.41 (s, 1H), 7.92 (d, J=10.5 Hz, 1H), 7.81 (d, J=7.0 Hz, 1H), 7.56 (d, J=7.0 Hz, 2H), 7.35 (d, J=8.0 Hz, 2H), 4.14 (m, 1H), 3.91 (m, 1H), 3.10 (s, 3H), 2.59 (m, 1H), 2.39 (s, 3H), 2.21 (m, 1H), 1.62 (s, 3H).

Example 16. (2R)-4-[5-fluoro-7-(4-methoxyphenyl)-4-oxo-3,4-dihydroquinazolin-3-yl]-N-hydroxy-2-methanesulfonyl-2-methylbutanamide

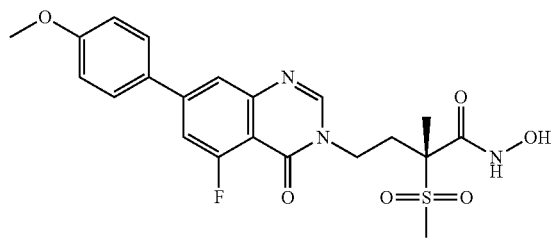 [SMILES: COc1ccc(-c2cc(F)c3c(=O)n(CC[C@](C)(C(=O)NO)S(C)(=O)=O)cnc3c2)cc1]

Part A

To a solution of (2R)-4-(7-bromo-5-fluoro-4-oxoquinazolin-3(4H)-yl)-2-methyl-2-(methylsulfonyl)-N-((tetrahydro-2H-pyran-2-yl)oxy)butanamide (Intermediate 7)(240 mg, 0.461 mmol) in water (1 mL) and acetonitrile (5 mL) was added potassium carbonate (127 mg, 0.922 mmol), (4-methoxyphenyl)boronic acid (105 mg, 0.692 mmol) and PdCl$_2$(dppf) (33.7 mg, 0.046 mmol). The mixture was heated to 80° C. under N$_2$ and stirred for 1 hr. The mixture was evaporated in vacuo and 20 mL water was added. The aqueous layer was extracted ethyl acetate (20 mL×3), dried over Na$_2$SO$_4$ and evaporated to afford a brown oil. The oil was purified by silica gel chromatography (EtOAc/petroleum ether: 1/1-3/1) affording (2R)-4-(5-fluoro-7-(4-methoxyphenyl)-4-oxoquinazolin-3(4H)-yl)-2-methyl-2-(methylsulfonyl)-N-((tetrahydro-2H-pyran-2-yl)oxy)butanamide (200 mg, 0.341 mmol, 74% yield) as a yellow solid.

Part B

To a solution of (2R)-4-(5-fluoro-7-(4-methoxyphenyl)-4-oxoquinazolin-3-(4H)-yl)-2-methyl-2-(methylsulfonyl)-N-((tetrahydro-2H-pyran-2-yl)oxy)butanamide (190 mg, 0.347 mmol) in dichloromethane (4 mL) and methanol (4 mL) was added HCl (1 mL, 4 mmol) and the mixture was stirred at room temperature for 1 hr. The mixture was evaporated in vacuo and the residue was purified by HPLC affording (R)-4-(5-fluoro-7-(4-methoxyphenyl)-4-oxoquinazolin-3(4H)-yl)-N-hydroxy-2-methyl-2-(methylsulfonyl)butanamide (45 mg, 0.087 mmol, 25% yield) as a yellow solid.

LCMS: [M+H] 464.2.

$^1$H NMR (500 MHz, DMSO-d$_6$) δ: ppm 11.00 (s, 1H), 8.48 (d, J=3.1 Hz, 1H), 7.81-7.72 (m, 3H), 7.67 (d, J=12.3 Hz, 1H), 7.34 (d, J=8.0 Hz, 2H), 4.16-4.06 (m, 1H), 3.87 (td, J=13.0, 5.3 Hz, 1H), 3.10 (s, 3H), 2.58 (td, J=13.2, 5.5 Hz, 1H), 2.38 (s, 3H), 2.25-2.16 (m, 1H), 1.61 (s, 3H).

Example 17. (2R)-4-[5-fluoro-7-(4-methylphenyl)-4-oxo-3,4-dihydroquinazolin-3-yl]-N-hydroxy-2-methanesulfonyl-2-methylbutanamide

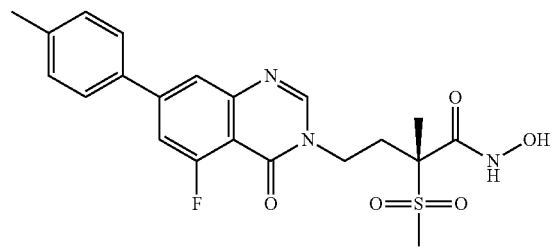 [SMILES: Cc1ccc(-c2cc(F)c3c(=O)n(CC[C@](C)(C(=O)NO)S(C)(=O)=O)cnc3c2)cc1]

Part A

To a solution of (2R)-4-(7-bromo-5-fluoro-4-oxoquinazolin-3(4H)-yl)-2-methyl-2-(methylsulfonyl)-N-((tetrahydro-2H-pyran-2-yl)oxy)butanamide (Intermediate 7) (240 mg, 0.461 mmol) in water (1 mL) and acetonitrile (6 mL) was added potassium carbonate (127 mg, 0.922 mmol), p-tolylboronic acid (94 mg, 0.692 mmol) and PdCl$_2$(dppf) (33.7 mg, 0.046 mmol). The mixture was heated to 80° C. under N$_2$ and stirred for 1 hr. The mixture was evaporated in vacuo, 20 mL water was added, the aqueous layer extracted with ethyl acetate (20 mL×3) and the combined organic layers were dried over Na$_2$SO$_4$ and evaporated to afford a brown oil. The oil was purified by silica gel chromatography (EtOAc/petroleum ether: 1/1-3/1) affording (2R)-4-(5-fluoro-4-oxo-7-(p-tolyl)quinazolin-3(4H)-yl)-2-methyl-2-(methylsulfonyl)-N-((tetrahydro-2H-pyran-2-yl)oxy)butanamide (200 mg, 0.334 mmol, 72% yield) as a yellow solid.

LCMS: [M+H] 532.2.

Part B

To a solution of (2R)-4-(5-fluoro-4-oxo-7-(p-tolyl)quinazolin-3(4H)-yl)-2-methyl-2-(methylsulfonyl)-N-((tetrahydro-2H-pyran-2-yl)oxy)butanamide (190 mg, 0.357 mmol) in dichloromethane (4 mL) and methanol (4 mL) was added HCl (1 mL, 4 mmol). The mixture was stirred at room temperature for 1 hr. The mixture was evaporated in vacuo and the residue was purified by HPLC affording (R)-4-(5-fluoro-4-oxo-7-(p-tolyl)quinazolin-3(4H)-yl)-N-hydroxy-2-methyl-2-(methylsulfonyl)butanamide (50 mg, 0.101 mmol, 28% yield) as a yellow solid.

LCMS: [M+H] 448.2.

$^1$H NMR (500 MHz, DMSO-d$_6$) δ: ppm 11.02 (s, 1H), 8.45 (s, 1H), 7.84 (d, J=8.8 Hz, 2H), 7.76 (d, J=1.4 Hz, 1H), 7.66 (J=12.6, 1.4 Hz, 1H), 7.07 (t, J=8.5 Hz, 2H), 4.16-4.05 (m, 1H), 3.94-3.85 (m, 1H), 3.83 (d, J=4.3 Hz, 3H), 3.10 (s, 3H), 2.62-2.54 (m, 1H), 2.27-2.14 (m, 1H), 1.61 (s, 3H).

Example 18. (2R)—N-hydroxy-2-methanesulfonyl-2-methyl-4-[7-(4-methylphenyl)-4-oxo-3,4-dihydro-1,2,3-benzotriazin-3-yl]butanamide

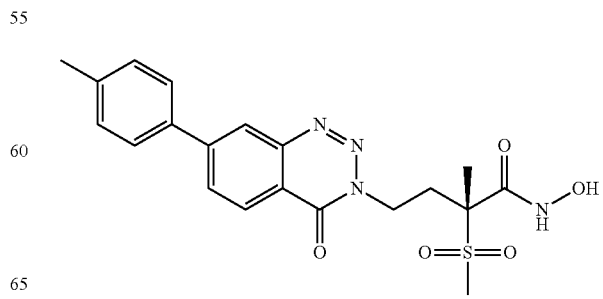

Part A

A mixture of p-tolylboronic acid (97 mg, 0.715 mmol), (2R)-4-(7-bromo-4-oxobenzo[d][1,2,3]triazin-3(4H)-yl)-2-methyl-2-(methylsulfonyl)-N-((tetrahydro-2H-pyran-2-yl)oxy)butanamide, $K_2CO_3$ (165 mg, 1.192 mmol), $PdCl_2$(dppf)-CH2Cl2 adduct (97 mg, 0.119 mmol), acetonitrile (9 mL) and water (1.5 mL) was stirred at 80° C. for 30 min under $N_2$. The acetonitrile was removed by evaporation and the aqueous layer was extracted with DCM (50 mL×2). The combined organic layers were dried ($Na_2SO_4$), filtered and concentrated. The crude product was purified by a silica gel column chromatography (Hex/EtOAc: EtOAc from 0% to 50% then DCM/MeOH: MeOH from 0 to 2%). affording (2R)-2-methyl-2-(methylsulfonyl)-4-(4-oxo-7-(p-tolyl)benzo[d][1,2,3]triazin-3(4H)-yl)-N-((tetrahydro-2H-pyran-2-yl)oxy)butanamide (270 mg, 0.477 mmol, 80% yield).

LCMS: [M-THP+H]: 431.1.

Part B

To a solution of (2R)-2-methyl-2-(methylsulfonyl)-4-(4-oxo-7-(p-tolyl)benzo[d][1,2,3]triazin-3(4H)-yl)-N-((tetrahydro-2H-pyran-2-yl)oxy)butanamide (220 mg, 0.428 mmol) in dichloromethane (5 mL) and methanol (5 mL) was added 4M HCl in 1,4-dioxane (0.428 mL, 1.710 mmol). The mixture was stirred at 25° C. for 30 min and the solvent was removed in vacuo. The residue was purified by preparative HPLC to afford (R)—N-hydroxy-2-methyl-2-(methylsulfonyl)-4-(4-oxo-7-(p-tolyl)benzo[d][1,2,3]triazin-3(4H)-yl)butanamide (119 mg, 0.263 mmol, 61% yield) as a white solid.

LCMS: [M+Na] 453.1.

$^1$H NMR (500 MHz, DMSO-$d_6$) δ: ppm 11.03 (s, 1H), 9.23 (s, 1H), 8.45 (s, 1H), 8.36-8.14 (m, 2H), 7.82 (d, J=6.1 Hz, 2H), 7.38 (d, J=7.3 Hz, 2H), 4.51 (J=15.8, 6.9 Hz, 1H), 4.34 (J=17.6, 11.6 Hz, 1H), 3.08 (s, 3H), 2.78 (J=17.5, 11.5 Hz, 1H), 2.39 (s, 3H), 2.31-2.22 (m, 1H), 1.63 (s, 3H).

Example 19. (2R)-4-[7-(2-fluoro-4-methylphenyl)-4-oxo-3,4-dihydro-1,2,3-benzotriazin-3-yl]-N-hydroxy-2-methanesulfonyl-2-methylbutanamide

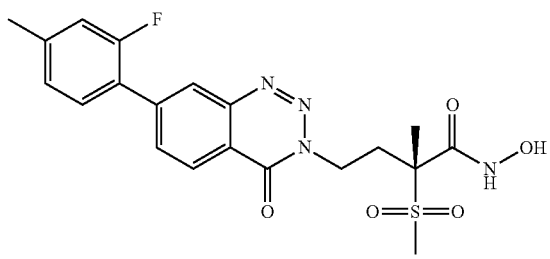 [SMILES: Cc1ccc(-c2ccc3c(=O)n(CC[C@](C)(C(=O)NO)S(C)(=O)=O)nnc3c2)c(F)c1]

Part A

A mixture of (2-fluoro-4-methylphenyl)boronic acid (110 mg, 0.715 mmol), (2R)-4-(7-bromo-4-oxobenzo[d][1,2,3]triazin-3(4H)-yl)-2-methyl-2-(methylsulfonyl)-N-((tetrahydro-2H-pyran-2-yl)oxy)butanamide, $K_2CO_3$ (165 mg, 1.192 mmol), $PdCl_2$(dppf)-$CH_2Cl_2$ adduct (97 mg, 0.119 mmol), acetonitrile (9 mL) and water (1.500 mL) was stirred at 80° C. for 30 min under $N_2$. The acetonitrile was removed by evaporation and the aqueous layer was extracted with DCM (50 mL×2). The combined organic layers were dried ($Na_2SO_4$), filtered and concentrated. The crude product was purified by silica gel column chromatography (EtOAc/hexanes: 0-50%) affording (2R)-4-(7-(2-fluoro-4-methylphenyl)-4-oxobenzo[d][1,2,3]triazin-3(4H)-yl)-2-methyl-2-(methylsulfonyl)-N-((tetrahydro-2H-pyran-2-yl)oxy)butanamide (280 mg, 0.489 mmol, 82% yield).

LCMS: [M-THP+H] 449.1.

Part B

To a solution of (2R)-4-(7-(2-fluoro-4-methylphenyl)-4-oxobenzo[d][1,2,3]triazin-3(4H)-yl)-2-methyl-2-(methylsulfonyl)-N-((tetrahydro-2H-pyran-2-yl)oxy)butanamide (230 mg, 0.432 mmol) in dichloromethane (5 mL) and methanol (5 mL) was added 4M HCl in 1,4-dioxane (0.432 mL, 1.727 mmol). The mixture was stirred at 25° C. for 30 min. The solvent was removed in vacuo and the residue was purified by preparative HPLC to afford (R)-4-(7-(2-fluoro-4-methylphenyl)-4-oxobenzo[d][1,2,3]triazin-3(4H)-yl)-N-hydroxy-2-methyl-2-(methylsulfonyl)butanamide (129 mg, 0.273 mmol, 63% yield) as a white solid.

LCMS: [M+H] 449.1.

$^1$H NMR (500 MHz, DMSO-$d_6$) δ: ppm 11.03 (s, 1H), 9.22 (s, 1H), 8.32 (d, J=8.4 Hz, 2H), 8.10 (d, J=8.3 Hz, 1H), 7.65 (t, J=8.2 Hz, 1H), 7.25 (J=20.7, 10.1 Hz, 2H), 4.52 (d, J=14.3, 9.8, 4.9 Hz, 1H), 4.35 (d, J=13.3, 9.8, 6.3 Hz, 1H), 3.08 (s, 3H), 2.79 (d, J=13.2, 9.8, 6.4 Hz, 1H), 2.41 (s, 3H), 2.28 (d, J=14.4, 9.8, 4.8 Hz, 1H), 1.63 (s, 3H).

Example 20. (2R)-4-(6-fluoro-7-{4-[(morpholin-4-yl)methyl]phenyl}-4-oxo-3,4-

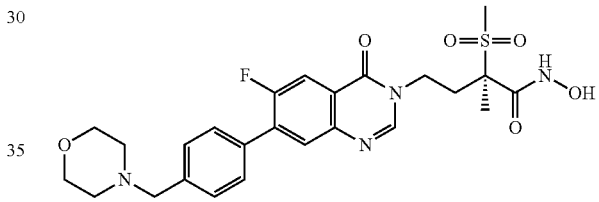

Part A

A mixture of (2R)-4-(7-bromo-6-fluoro-4-oxoquinazolin-3(4H)-yl)-2-methyl-2-(methylsulfonyl)-N-((tetrahydro-2H-pyran-2-yl)oxy)butanamide (Intermediate 5)(300 mg, 0.577 mmol), 4-(4-(4,4,5,5-tetramethyl-1,3,2-dioxaborolan-2-yl)benzyl)morpholine (350 mg, 1.153 mmol), $PdCl_2$(dppf)-$CH_2Cl_2$ adduct (94 mg, 0.115 mmol) and $K_2CO_3$ (159 mg, 1.153 mmol) in acetonitrile (12 mL) and water (2 mL) was stirred at 80° C. for 30 min. To the solution was added ethyl acetate (60 mL) and the organic layer was washed with water (2×60 mL) and brine (2×60 mL), dried ($Na_2SO_4$), filtered and concentrated. The residue was purified by silica gel chromatography column (60% ethyl acetate in petroleum ether then 10%-30% methanol in dichloromethane) to afford (2R)-4-(6-fluoro-7-(4-(morpholinomethyl)phenyl)-4-oxoquinazolin-3(4H)-yl)-2-methyl-2-(methylsulfonyl)-N-((tetrahydro-2H-pyran-2-yl)oxy)butanamide (250 mg, 0.397 mmol, 69% yield) as a yellow solid.

LCM: [M+H] 616.9.

Part B

To a solution of (2R)-4-(6-fluoro-7-(4-(morpholinomethyl)phenyl)-4-oxoquinazolin-3(4H)-yl)-2-methyl-2-(methylsulfonyl)-N-((tetrahydro-2H-pyran-2-yl)oxy)butanamide (220 mg, 0.357 mmol) in dichloromethane (2 mL) and methanol (2 mL) was added hydrogen chloride in 1,4-dioxane (1.784 mL, 7.13 mmol) at 0° C. The reaction mixture was stirred at 0° C. for 30 min. The solvent was removed and the residue was purified by trituration to give (R)-4-(6-fluoro-7-(4-(morpholinomethyl)phenyl)-4-oxoquinazolin-3(4H)-yl)-N-hydroxy-2-methyl-2-(methylsulfonyl) butanamide hydrochloride (81 mg, 0.131 mmol, 37% yield) as a pale yellow solid.

LCMS: [M+H] 532.9.

$^1$H NMR (400 MHz, DMSO-d$_6$) δ: ppm 11.03 (s, 2H), 9.26 (s, 1H), 8.41 (s, 1H), 7.96 (d, J=10.4 Hz, 1H), 7.87 (d, J=7.1 Hz, 1H), 7.78 (s, 4H), 4.42 (d, J=4.5 Hz, 2H), 4.19-4.10 (m, 1H), 3.92 (J=28.1, 9.1 Hz, 3H), 3.81 (d, J=11.1 Hz, 2H), 3.28 (d, J=12.5 Hz, 2H), 3.10-3.17 (m, 5H), 2.61 (J=15.6, 8.2 Hz, 1H), 2.28-2.11 (m, 1H), 1.62 (s, 3H).

Example 21. (2R)-4-(6-fluoro-7-{4-[2-(morpholin-4-yl)ethyl]phenyl}-4-oxo-3,4-dihydroquinazolin-3-yl)-N-hydroxy-2-methanesulfonyl-2-methylbutanamide

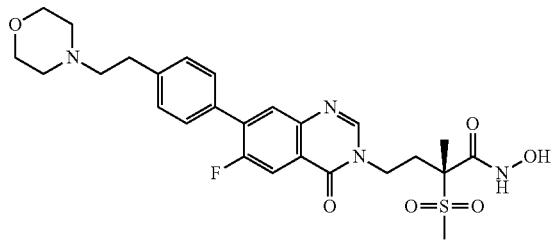 [SMILES: C[C@@](CCn1cnc2cc(-c3ccc(CCN4CCOCC4)cc3)c(F)cc2c1=O)(C(=O)NO)S(C)(=O)=O]

Part A

PdCl$_2$(dppf)-CH$_2$Cl$_2$ adduct (4.06 g, 4.97 mmol) was added to a solution of 2-(4-bromophenyl)ethanol (10.0 g, 49.7 mmol), 4,4,4',4',5,5,5',5'-octamethyl-2,2'-bi(1,3,2-dioxaborolane) (25.3 g, 99 mmol) and potassium acetate (14.64 g, 149 mmol) in 1,4-dioxane (200 mL) at room temperature under a nitrogen atmosphere and the reaction mixture was stirred at 80° C. overnight. The mixture was concentrated under reduced pressure and the residue was purified by silica gel chromatography (1:6 EtOAc/petroleum ether) to give 2-(4-(4,4,5,5-tetramethyl-1,3,2-dioxaborolan-2-yl)phenyl)ethanol (10.5 g, 39.2 mmol, 79% yield) as a yellow oil.

LCMS: [M+NH$_4$] 266.2.

Part B

A mixture of (2R)-4-(7-bromo-6-fluoro-4-oxoquinazolin-3(4H)-yl)-2-methyl-2-(methylsulfonyl)-N-((tetrahydro-2H-pyran-2-yl)oxy)butanamide (Intermediate 5)(100 mg, 0.192 mmol), 2-(4-(4,4,5,5-tetramethyl-1,3,2-dioxaborolan-2-yl)phenyl)ethanol (71.5 mg, 0.288 mmol), PdCl$_2$(dppf)-CH$_2$Cl$_2$ adduct (31.4 mg, 0.038 mmol) and K$_2$CO$_3$ (53.1 mg, 0.384 mmol) in acetonitrile (30 mL) and water (5 mL) was stirred at 80° C. for 30 min under nitrogen at which time the solution was cooled to room temperature. To the solution was added ethyl acetate (500 mL) and the organic layer was washed with brine (50 mL), dried over sodium sulfate and concentrated. The residue was purified by silica gel column chromatography (100% ethyl acetate then 10%-30% methanol in ethyl acetate then 30% methanol in 3% triethylamine/ethyl acetate) to give the (2R)-4-(6-fluoro-7-(4-(2-hydroxyethyl)phenyl)-4-oxoquinazolin-3(4H)-yl)-2-methyl-2-(methylsulfonyl)-N-((tetrahydro-2H-pyran-2-yl)oxy) butanamide (1.8 g, 2.75 mmol) as a black solid.

LC/MS: [M+H] 562.3.

Part C

To a mixture of (2R)-4-(6-fluoro-7-(4-(2-hydroxyethyl) phenyl)-4-oxoquinazolin-3(4H)-yl)-2-methyl-2-(methylsulfonyl)-N-((tetrahydro-2H-pyran-2-yl)oxy)butanamide (1.6 g, 2.85 mmol) in dichloromethane (40 mL) was added triphenylphosphine (2.99 g, 11.40 mmol) and 1-bromopyrrolidine-2,5-dione (1.521 g, 8.55 mmol) at 0° C. The resulting mixture was stirred at 0° C. for 45 min. The solution was quenched by MeOH (40 ml) at 0° C. and the reaction mixture was evaporated to dryness to afford (R)-4-(7-(4-(2-bromoethyl)phenyl)-6-fluoro-4-oxoquinazolin-3(4H)-yl)-N-hydroxy-2-methyl-2-(methylsulfonyl)butanamide as a yellow oil.

LCMS: [M+H] 540.0, 542.0.

Part D

A mixture of (R)-4-(7-(4-(2-bromoethyl)phenyl)-6-fluoro-4-oxoquinazolin-3(4H)-yl)-N-hydroxy-2-methyl-2-(methylsulfonyl)butanamide (192 mg, 0.356 mmol), morpholine (310 mg, 3.56 mmol), KI (5.91 mg, 0.036 mmol) and N,N-dimethylformamide (4.5 mL) was stirred at 70° C. for 20 min under microwave radiation. The reaction was concentrated and the residue was purified by preparative HPLC using 0.1% TFA in acetonitrile and water affording (R)-4-(6-fluoro-7-(4-(2-morpholinoethyl)phenyl)-4-oxoquinazolin-3(4H)-yl)-N-hydroxy-2-methyl-2-(methylsulfonyl) butanamide trifluoroacetic acid salt (78 mg, 0.112 mmol, 32% yield) as an off-white solid.

LCMS: [M+H] 547.2.

$^1$H NMR (500 MHz, DMSO-d$_6$) δ: ppm 11.02 (s, 1H), 9.96 (s, 1H), 9.25 (s, 1H), 8.39 (s, 1H), 7.94 (d, J=10.4 Hz, 1H), 7.84 (d, J=7.1 Hz, 1H), 7.68 (d, J=6.8 Hz, 2H), 7.46 (d, J=8.2 Hz, 2H), 4.15 (J=16.2, 7.6 Hz, 1H), 4.03 (d, J=11.5 Hz, 2H), 3.91 (s, 1H), 3.70 (d, J=12.5 Hz, 2H), 3.54 (d, J=11.9 Hz, 2H), 3.43 (s, 2H), 3.18-3.03 (m, 7H), 2.57 (dt, J=11.2, 8.2 Hz, 1H), 2.21 (J=17.2, 6.7 Hz, 1H), 1.61 (s, 3H).

Example 22. (2R)-4-[7-(4-{[cyclopropyl(methyl) amino]methyl}phenyl)-6-fluoro-4-oxo-3,4-dihydroquinazolin-3-yl]-N-hydroxy-2-methanesulfonyl-2-methylbutanamide

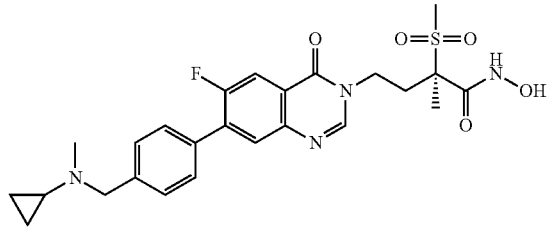 [SMILES: CN(Cc1ccc(-c2cc3ncn(CC[C@](C)(C(=O)NO)S(C)(=O)=O)c(=O)c3cc2F)cc1)C1CC1]

Part A

To a stirred solution of 2-(4-(bromomethyl)phenyl)-4,4,5,5-tetramethyl-1,3,2-dioxaborolane (4.5 g, 15.15 mmol) and N-methylcyclopropanamine hydrochloride (1.793 g, 16.67 mmol) in tetrahydrofuran (30 mL) was added N-methylcyclopropanamine hydrochloride (1.793 g, 16.67 mmol) and the reaction mixture was stirred at room temperature overnight. The mixture was concentrated under reduced pressure and purified by silica gel column chromatography affording N-methyl-N-(4-(4,4,5,5-tetramethyl-1,3,2-dioxaborolan-2-yl)benzyl)cyclopropanamine (3.5 g, 10.36 mmol, 64% yield) as a solid.

LCMS: [M+H] 288.0.

Part B

A mixture of (2R)-4-(7-bromo-6-fluoro-4-oxoquinazolin-3(4H)-yl)-2-methyl-2-(methylsulfonyl)-N-((tetrahydro-2H-pyran-2-yl)oxy)butanamide (Intermediate 5) (300 mg, 0.577 mmol), N-methyl-N-(4-(4,4,5,5-tetramethyl-1,3,2-dioxaborolan-2-yl)benzyl)cyclopropanamine (331 mg, 1.153 mmol), PdCl$_2$(dppf)-CH$_2$Cl$_2$ adduct (94 mg, 0.115 mmol) and K$_2$CO$_3$ (159 mg, 1.153 mmol) in acetonitrile (2 mL) and water (0.33 mL) was microwave at 80° C. for 30 min. To the mixture from combined batches was added ethyl acetate (100 mL) and the organic layer was dried over sodium sulfate and concentrated. The residue was purified by silica gel chromatography (60% ethyl acetate in petroleum ether then 10%-30% methanol in dichloromethane) to afford (2R)-4-(7-(4-((cyclopropyl(methyl)amino)methyl)phenyl)-6-fluoro-4-oxoquinazolin-3(4H)-yl)-2-methyl-2-(methylsulfonyl)-N-((tetrahydro-2H-pyran-2-yl)oxy)butanamide (220 mg, 0.37 mmol, 53.5% yield) as a brown solid.

LCMS: [M+H] 601.0.

Part C

To a solution (2R)-4-(7-(4-((cyclopropyl(methyl)amino)methyl)phenyl)-6-fluoro-4-oxoquinazolin-3(4H)-yl)-2-methyl-2-(methylsulfonyl)-N-((tetrahydro-2H-pyran-2-yl)oxy)butanamide (210 mg, 0.350 mmol), dichloromethane (1.5 mL) and methanol (1.5 mL) was added hydrogen chloride in 1,4-dioxane (3.50 mL, 13.98 mmol) and the reaction mixture was stirred at 20° C. for 30 min. The reaction mixture was evaporated to dryness under reduced pressure and the residue was purified by HPLC affording (R)-4-(7-(4-((cyclopropyl(methyl)amino)methyl)phenyl)-6-fluoro-4-oxoquinazolin-3(4H)-yl)-N-hydroxy-2-methyl-2-(methylsulfonyl)butanamide trifluoroacetic acid salt (46 mg, 0.069 mmol, 20% yield) as an off-white solid.

LCMS: [M+H] 517.2.

$^1$H NMR (500 MHz, DMSO-d$_6$) δ: ppm 11.02 (s, 1H), 9.46 (s, 1H), 9.26 (s, 1H), 8.40 (s, 1H), 7.97 (d, J=10.4 Hz, 1H), 7.89 (d, J=7.1 Hz, 1H), 7.79 (d, J=7.7 Hz, 2H), 7.68 (d, J=7.9 Hz, 2H), 4.52 (d, J=19.4 Hz, 2H), 4.18-4.08 (m, 1H), 3.97-3.88 (m, 1H), 3.10 (s, 3H), 2.87 (d, J=25.5 Hz, 4H), 2.66-2.56 (m, 1H), 2.26-2.16 (m, 1H), 1.62 (s, 3H), 0.85 (d, J=50.7 Hz, 4H).

Example 23. (2R)-4-[6-fluoro-7-(2-fluoro-4-{[(2-methoxyethyl)(methyl)amino]methyl}phenyl)-4-oxo-3,4-dihydroquinazolin-3-yl]-N-hydroxy-2-methanesulfonyl-2-methylbutanamide

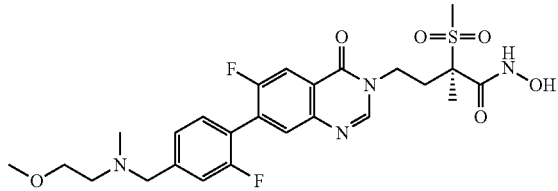 [SMILES: COCCN(C)Cc1ccc(-c2cc3ncn(CC[C@](C)(C(=O)NO)S(C)(=O)=O)c(=O)c3cc2F)c(F)c1]

Part A

A mixture of (2R)-4-(7-bromo-6-fluoro-4-oxoquinazolin-3(4H)-yl)-2-methyl-2-(methylsulfonyl)-N-((tetrahydro-2H-pyran-2-yl)oxy)butanamide (Intermediate 5) (3.34 g, 6.42 mmol), (2-fluoro-4-formylphenyl)boronic acid (1.293 g, 7.70 mmol), K$_2$CO$_3$ (1.331 g, 9.63 mmol), PdCl$_2$(dppf)-CH$_2$Cl$_2$ adduct (0.524 g, 0.642 mmol), 1,4-dioxane (50 mL) and water (5 mL) was stirred at 105° C. for 1 hr under a nitrogen atmosphere. 1,4-Dioxane was removed by evaporation and the aqueous layer was extracted with DCM (3×50 mL). The combined organic layers were dried (Na$_2$SO$_4$), filtered and concentrated under reduced pressure. The residue was purified by silica gel chromatography (EtOAc/DCM: 0-50%) affording (2R)-4-(6-fluoro-7-(2-fluoro-4-formylphenyl)-4-oxoquinazolin-3(4H)-yl)-2-methyl-2-(methylsulfonyl)-N-((tetrahydro-2H-pyran-2-yl)oxy)butanamide (2.44 g, 4.11 mmol, 64% yield) as a yellow solid.

LCMS: [M+H] 564.2.

Part B

To a solution of (2R)-4-(6-fluoro-7-(2-fluoro-4-formylphenyl)-4-oxoquinazolin-3(4H)-yl)-2-methyl-2-(methylsulfonyl)-N-((tetrahydro-2H-pyran-2-yl)oxy)butanamide (250 mg, 0.444 mmol), acetic acid (0.076 mL, 1.331 mmol) in 1,2-dichloroethane (5 mL) was added 2-methoxy-N-methylethanamine (198 mg, 2.218 mmol) and sodium triacetoxyborohydride (282 mg, 1.331 mmol). The mixture was stirred at 10° C. for 17 hr. The mixture from combined batches was diluted with DCM (15 mL), washed with aq. NaHCO$_3$ (5 mL), dried (Na$_2$SO$_4$) and evaporated in vacuo. The obtained residue was purified with silica gel chromatography (MeOH/DCM: 0-5%) affording (2R)-4-(6-fluoro-7-(2-fluoro-4-(((2-methoxyethyl)(methyl)amino)methyl)phenyl)-4-oxoquinazolin-3(4H)-yl)-2-methyl-2-(methylsulfonyl)-N-((tetrahydro-2H-pyran-2-yl)oxy)butanamide (280 mg, 78% yield) as a yellow solid.

LCMS: [M+H] 637.3.

Part C

To a solution of (2R)-4-(6-fluoro-7-(2-fluoro-4-(((2-methoxyethyl)(methyl)amino)methyl)phenyl)-4-oxoquinazolin-3(4H)-yl)-2-methyl-2-(methylsulfonyl)-N-((tetrahydro-2H-pyran-2-yl)oxy)butanamide (260 mg, 0.408 mmol), dichloromethane (3 mL) and methanol (3 mL) was added 4M HCl in dioxane (0.51 mL, 2.042 mmol) at 10° C. The reaction mixture was stirred at 10° C. for 15 min. The mixture was evaporated to dryness and the crude product was purified by preparative HPLC affording (R)-4-(6-fluoro-7-(2-fluoro-4-(((2-methoxyethyl)(methyl)amino)methyl)phenyl)-4-oxoquinazolin-3(4H)-yl)-N-hydroxy-2-methyl-2-(methylsulfonyl)butanamide trifluoroacetic acid salt (146 mg, 0.208 mmol, 51% yield) as an off-white solid.

LCMS: [M+H] 553.3.

$^1$H NMR (500 MHz, DMSO-d$_6$) δ: ppm 11.03 (s, 1H), 9.81 (s, 1H), 9.26 (s, 1H), 8.42 (s, 1H), 7.99 (d, J=9.6 Hz, 1H), 7.84 (d, J=6.6 Hz, 1H), 7.73 (t, J=7.4 Hz, 1H), 7.61 (d, J=10.3 Hz, 1H), 7.54 (d, J=7.9 Hz, 1H), 4.48 (s, 1H), 4.40 (s, 1H), 4.22-4.09 (m, 1H), 3.98-3.87 (m, 1H), 3.70 (s, 2H), 3.30 (d, J=27.5 Hz, 7H), 3.10 (s, 3H), 2.79 (s, 3H), 2.64-2.55 (m, 1H), 2.27-2.14 (m, 1H), 1.62 (s, 3H).

Example 24. (2R)-4-(7-{2,3-difluoro-4-[2-(3-methoxyazetidin-1-yl)ethyl]phenyl}-6-fluoro-4-oxo-3,4-dihydroquinazolin-3-yl)-N-hydroxy-2-methanesulfonyl-2-methylbutanamide

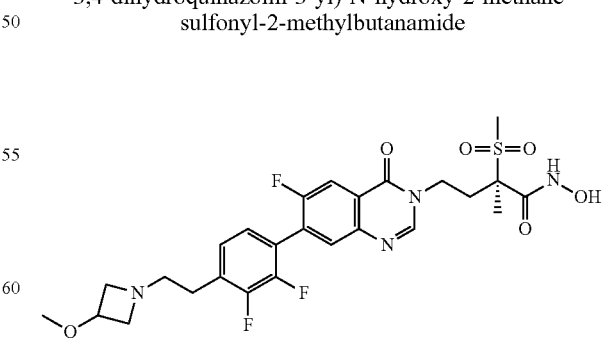

Part A

To a solution of 1-bromo-2,3-difluoro-4-(2-methoxyvinyl)benzene (20 g, 80 mmol) in acetone (1 L) was added a solution of 2 M HCl (300 ml, 600 mmol) in water. The mixture was heated to 60° C. and stirred for 2 hr. The mixture was evaporated in vacuo, the residue was extracted by DCM (300 mL×3) and the combined layers were dried over Na$_2$SO$_4$ affording 2-(4-bromo-2,3-difluorophenyl)acetaldehyde (16 g, 54.5 mmol, 68% yield) as a yellow solid without further purification.

Part B

A solution of 2-(4-bromo-2,3-difluorophenyl)acetaldehyde (16 g, 68.1 mmol) in methanol (200 mL) was added NaBH$_4$ (0.644 g, 17.02 mmol) and the mixture was stirred at room temperature for 2 hr. The mixture was evaporated in vacuo and to the residue was added 300 mL water. The aqueous layer was extracted by DCM (300 mL×2), dried over Na$_2$SO$_4$ and evaporated to afford a yellow oil. The oil was purified by silica gel column chromatography (EtOAc/petroleum ether: 1/30-1/5) to give 2-(4-bromo-2,3-difluorophenyl)ethanol (13 g, 49.4 mmol, 73% yield) as a yellow oil.

Part C

To a solution of 2-(4-bromo-2,3-difluorophenyl)ethanol (10 g, 42.2 mmol) in 1,4-dioxane (100 mL) was added 4,4,4',4',5,5,5',5'-octamethyl-2,2'-bi(1,3,2-dioxaborolane) (16.07 g, 63.3 mmol), PdCl$_2$(dppf) (3.09 g, 4.22 mmol) and potassium acetate (8.28 g, 84 mmol). The mixture was heated to reflux under N$_2$ and stirred overnight. The mixture was evaporated in vacuo and the residue was purified by silica gel chromatography (EtOAc/PE: 1/20-1/5) to give 2-(2,3-difluoro-4-(4,4,5,5-tetramethyl-1,3,2-dioxaborolan-2-yl)phenyl)ethanol (10 g, 31.7 mmol, 75% yield) as a yellow oil.

Part D

To a solution of (2R)-4-(7-bromo-6-fluoro-4-oxoquinazolin-3(4H)-yl)-2-methyl-2-(methylsulfonyl)-N-((tetrahydro-2H-pyran-2-yl)oxy)butanamide (Intermediate 5)(6 g, 11.53 mmol) in acetonitrile (100 mL) and water (16.67 mL) was added 2-(2,3-difluoro-4-(4,4,5,5-tetramethyl-1,3,2-dioxaborolan-2-yl)phenyl)ethanol (4.91 g, 17.30 mmol), PdCl$_2$(dppf) (0.844 g, 1.153 mmol) and K$_2$CO$_3$ (3.19 g, 23.06 mmol). The mixture was heated to 80° C. under N$_2$ for 2 hrs. The mixture was evaporated in vacuo and the residue was purified by column chromatography on silica gel (acetone/PE: 1/10-1/1) to give (2R)-4-(7-(2,3-difluoro-4-(2-hydroxyethyl)phenyl)-6-fluoro-4-oxoquinazolin-3(4H)-yl)-2-methyl-2-(methylsulfonyl)-N-((tetrahydro-2H-pyran-2-yl)oxy)butanamide (2.5 g, 3.81 mmol, 33% yield) as a yellow solid.

LCMS: [M+H] 598.0.

Part E

A solution of (2R)-4-(7-(2,3-difluoro-4-(2-hydroxyethyl)phenyl)-6-fluoro-4-oxoquinazolin-3(4H)-yl)-2-methyl-2-(methylsulfonyl)-N-((tetrahydro-2H-pyran-2-yl)oxy)butanamide (1 g, 1.673 mmol) in dichloromethane (20 mL) was cooled to 0° C. and Dess-Martin periodinane (0.852 g, 2.008 mmol) was added and the mixture was stirred at 0° C. for 3 hr. Then a mixture of NaHCO$_3$ and Na$_2$S$_2$O$_3$ in water was added and the mixture was stirred at 0° C. for 30 min. The aqueous layer was extracted with DCM (20 mL×2), dried over Na$_2$SO$_4$ and evaporated in vacuo at 0° C. to obtain (2R)-4-(7-(2,3-difluoro-4-(2-oxoethyl)phenyl)-6-fluoro-4-oxoquinazolin 3(4H)-yl)-2-methyl-2-(methylsulfonyl)-N-((tetrahydro-2H-pyran-2-yl)oxy)butanamide (800 mg, 0.537 mmol, 32% yield) as a yellow solid.

LCMS: [M+H] 596.0.

Part F

To a solution of (2R)-4-(7-(2,3-difluoro-4-(2-oxoethyl)phenyl)-6-fluoro-4-oxoquinazolin-3(4H)-yl)-2-methyl-2-(methylsulfonyl)-N-((tetrahydro-2H-pyran-2-yl)oxy)butanamide (250 mg, 0.420 mmol) in 1,2-dichloroethane (5 mL) was added 3-methoxyazetidine (73.1 mg, 0.840 mmol) and sodium triacetoxyborohydride (178 mg, 0.840 mmol). The mixture was stirred at 25° C. for 18 h. The pH was adjusted to 14 with 10 aq. NaOH and the mixture was extracted with EtOAc (50 mL×3). The organic phase was dried with Na$_2$SO$_4$, filtered and concentrated to afford (2R)-4-(7-(2,3-difluoro-4-(2-(3-methoxyazetidin-1-yl)ethyl)phenyl)-6-fluoro-4-oxoquinazolin-3(4H)-yl)-2-methyl-2-(methylsulfonyl)-N-((tetrahydro-2H-pyran-2-yl)oxy)butanamide (150 mg, 0.076 mmol, 18% yield) as oil liquid.

LCMS: [M+H] 583.0.

Part G

To a solution of (2R)-4-(7-(2,3-difluoro-4-(2-(3-methoxyazetidin-1-yl)ethyl)phenyl)-6-fluoro-4-oxoquinazolin-3(4H)-yl)-2-methyl-2-(methylsulfonyl)-N-((tetrahydro-2H-pyran-2-yl)oxy)butanamide (172 mg, 0.258 mmol) in dichloromethane (5 mL) was added HCl (0.322 mL, 1.29 mmol) in dioxane at room temperature. The resulting solution was stirred at 20° C. for 5 min. when methanol (5 mL) was added and the resulting mixture was stirred at 25° C. for 1 hr. The mixture from combined batches was concentrated and the residue was purified by reverse phase HPLC to give (R)-4-(7-(2,3-difluoro-4-(2-(3-methoxyazetidin-1-yl)ethyl)phenyl)-6-fluoro-4-oxoquinazolin-3(4H)-yl)-N-hydroxy-2-methyl-2-(methylsulfonyl) butanamide trifluoroacetic acid salt (13 mg, 0.017 mmol, 7% yield) as white solid.

LCMS: [M+H-THP] 583.0.

$^1$H NMR (500 MHz, DMSO-d$_6$) δ: ppm 11.04 (s, 1H), 8.42 (s, 1H), 8.00 (d, J=5.5 Hz, 1H), 7.84 (d, J=6.0 Hz, 1H), 7.36-7.45 (m, 2H), 4.43 (m, 1H), 3.90-4.92 (m, 6), 3.52 (m, 2H), 3.27 (d, J=7.5 Hz, 3H), 3.10 (s, 3H), 2.98 (m, 2H), 2.60 (m, 1H), 2.20 (m, 1H), 1.57 (s, 3H).

Example 25. (2R)-4-(7-{4-[(cyclopropylamino)methyl]-2-fluorophenyl}-6-fluoro-4-oxo-3,4-dihydroquinazolin-3-yl)-N-hydroxy-2-methanesulfonyl-2-methylbutanamide

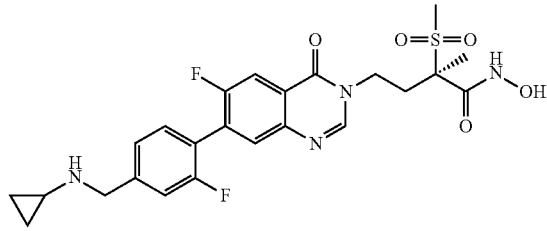 [SMILES: C[C@@](CCn1cnc2cc(-c3ccc(CNC4CC4)cc3F)c(F)cc2c1=O)(C(=O)NO)S(C)(=O)=O]

To a solution of 2-(4-(bromomethyl)-2-fluorophenyl)-4,4,5,5-tetramethyl-1,3,2-dioxaborolane (7 g, 22.22 mmol) in N,N-dimethylformamide (50 mL) was added DIPEA (9.70 mL, 55.6 mmol) and cyclopropanamine (2.54 g, 44.4 mmol). The reaction mixture was heated to 60° C. for 12 hr. The mixture was diluted with EtOAc (50 mL) and water (100 ml). The mixture was extracted with EtOAc (30 mL×3) and the combined organic layers were washed with brine (50 mL), dried over sodium sulphate and concentrated to give both N-(3-fluoro-4-(4,4,5,5-tetramethyl-1,3,2-dioxaborolan-2-yl)benzyl)cyclopropanamine (4.8 g, 8.57 mmol, 39% yield).

LCMS: [M+H] 292.1.

Part B

A mixture of potassium carbonate (3.19 g, 23.06 mmol), PdCl$_2$(dppf) (0.844 g, 1.153 mmol), (2R)-4-(7-bromo-6-fluoro-4-oxoquinazolin-3(4H)-yl)-2-methyl-2-(methylsulfonyl)-N-((tetrahydro-2H-pyran-2-yl)oxy)butanamide (Intermediate 5)(6 g, 11.53 mmol) and N-(3-fluoro-4-(4,4,5,5-tetramethyl-1,3,2-dioxaborolan-2-yl)benzyl)cyclopropanamine (4.36 g, 14.99 mmol) 1,4-dioxane (100 mL) and water (10 mL) was heated to 95° C. for 30 min. The mixture was filtered and filtrated was diluted with aq. ammonium chloride and extracted with DCM (60 mL×3). The combined organic layers were washed with water (50 ml), brine (50 ml), dried over sodium sulfate, concentrated in vacuo and the residue was purified by silical gel chromatography (MeOH/DCM: 0-20%) to give (2R)-4-(7-(4-((cyclopropylamino)methyl)-2,5-difluorophenyl)-4-oxoquinazolin-3(4H)-yl)-2-methyl-2-(methylsulfonyl)-N-((tetrahydro-2H-pyran-2-yl)oxy)butanamide (4.2 g, 5.83 mmol, 51% yield) as a white solid.

LCMS: [M+1] 605.3.

Part C

To a solution of (2R)-4-(7-(4-((cyclopropylamino)methyl)-2-fluorophenyl)-6-fluoro-4-oxoquinazolin-3(4H)-yl)-2-methyl-2-(methylsulfonyl)-N-((tetrahydro-2H-pyran-2-yl)oxy)butanamide (4 g, 6.62 mmol) in dichloromethane (10 mL) and methanol (20 mL) stirred under nitrogen was added a solution of HCl in dioxane (4.96 mL, 19.85 mmol). The reaction mixture was stirred at room temperature for 2 hr. The reaction was concentrated and purified by reverse phase column (water/acetonitrile, 0.1% TFA, 0-70%) to afford (R)-4-(7-(4-((cyclopropylamino)methyl)-2-fluorophenyl)-6-fluoro-4-oxoquinazolin-3(4H)-yl)-N-hydroxy-2-methyl-2-(methylsulfonyl)butanamide trifluoroacetic acid (1.77 g, 2.65 mmol, 40% yield) as white solid.

LCMS: [M+H] 521.3.

$^1$H NMR (400 MHz, METHANOL-d$_4$) ☐: ppm 0.80-1.10 (m, 4H) 1.77 (s, 3H) 2.32-2.52 (m, 1H) 2.74 (ddd, J=13.45, 10.29, 5.81 Hz, 1H) 2.82-2.94 (m, 1H) 3.12 (s, 3H) 4.06 (ddd, J=13.39, 10.36, 5.81 Hz, 1H) 4.27-4.38 (m, 1H) 4.45 (s, 2H) 7.40-7.56 (m, 2H) 7.61-7.70 (m, 1H) 7.78 (d, J=6.32 Hz, 1H) 8.01 (d, J=9.60 Hz, 1H) 8.36 (s, 1H).

Example 26. (2R)-4-(6-fluoro-7-{2-fluoro-4-[(morpholin-4-yl)methyl]phenyl}4-oxo-3,4-dihydroquinazolin-3-yl)-N-hydroxy-2-methanesulfonyl-2-methylbutanamide F

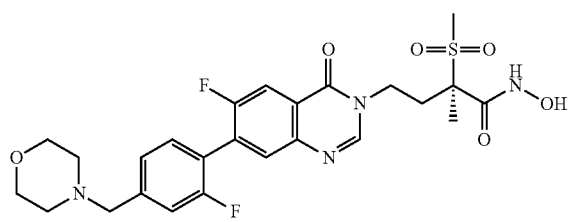 [SMILES: C[C@@](CCn1cnc2cc(-c3ccc(CN4CCOCC4)cc3F)c(F)cc2c1=O)(C(=O)NO)S(C)(=O)=O]

Part A

A mixture of (2R)-4-(7-bromo-6-fluoro-4-oxoquinazolin-3(4H)-yl)-2-methyl-2-(methylsulfonyl)-N-((tetrahydro-2H-pyran-2-yl)oxy)butanamide (Intermediate 5) (3.34 g, 6.42 mmol), (2-fluoro-4-formylphenyl)boronic acid (1.293 g, 7.70 mmol), K$_2$CO$_3$ (1.331 g, 9.63 mmol), PdCl$_2$(dppf)-CH$_2$Cl$_2$ adduct (0.524 g, 0.642 mmol), 1,4-dioxane (50 mL) and water (5 mL) was stirred at 105° C. for 1 hr under a nitrogen atmosphere. 1,4-Dioxane was removed by evaporation and the aqueous layer was extracted with DCM (3×50 mL). The combined organic layers were dried (Na$_2$SO$_4$), filtered and concentrated under reduced pressure. The residue was purified by silica gel chromatography (DCM/EtOAc, EtOAc from 0 to 50%) affording (2R)-4-(6-fluoro-7-(2-fluoro-4-formylphenyl)-4-oxoquinazolin-3(4H)-yl)-2-methyl-2-(methylsulfonyl)-N-((tetrahydro-2H-pyran-2-yl)oxy)butanamide (2.44 g, 4.11 mmol, 64% yield) as a yellow solid.

LCMS: [M+H] 564.2.

Part B

To a solution of (2R)-4-(6-fluoro-7-(2-fluoro-4-formylphenyl)-4-oxoquinazolin-3(4H)-yl)-2-methyl-2-(methylsulfonyl)-N-((tetrahydro-2H-pyran-2-yl)oxy)butanamide (250 mg, 0.444 mmol), acetic acid (0.076 mL, 1.331 mmol) in 1,2-dichloroethane (5 mL) was added morpholine (193 mg, 2.218 mmol) and sodium triacetoxyborohydride (282 mg, 1.331 mmol). The mixture was stirred at 10° C. for 17 hr. The mixture from combined batches was diluted with DCM (15 mL) and washed with aq. NaHCO$_3$ (5 mL), dried (Na$_2$SO$_4$) and evaporated in vacuo. The resulting residue was purified with silica gel chromatography (DCM/MeOH, MeOH from 0 to 5%) affording (2R)-4-(6-fluoro-7-(2-fluoro-4-(morpholinomethyl)phenyl)-4-oxoquinazolin-3(4H)-yl)-2-methyl-2-(methylsulfonyl)-N-((tetrahydro-2H-pyran-2-yl)oxy)butanamide (290 mg, 81% yield) as a yellow solid.

LCMS: [M+H] 634.9.

Part C

To a solution of (2R)-4-(6-fluoro-7(2-fluoro-4-(morpholinomethyl) phenyl)-4-oxoquinazolin-3(4H)-yl)-2-methyl-2-(methylsulfonyl)-N-((tetrahydro-2H-pyran-2-yl)oxy)butanamide (270 mg, 0.425 mmol), dichloromethane (4 mL) and methanol (4 mL) was added 4M HCl in dioxane (0.532 mL, 2.127 mmol) at 10° C. The reaction mixture was stirred at 10° C. for 15 min. when the reaction was evaporated to dryness. The crude product was purified by preparative HPLC affording (R)-4-(6-fluoro-7-(2-fluoro-4-(morpholinomethyl)phenyl)-4-oxoquinazolin-3(4H)-yl)-N-hydroxy-2-methyl-2-(methylsulfonyl)butanamide trifluoroacetic acid salt (71 mg, 0.101 mmol, 24% yield) as an off-white solid.

LCMS: [M+H] 551.2.

$^1$H NMR (500 MHz, DMSO-d$_6$) δ: ppm 11.03 (s, 1H), 10.05 (s, 1H), 9.26 (s, 1H), 8.41 (s, 1H), 7.99 (d, J=9.6 Hz, 1H), 7.82 (d, J=6.6 Hz, 1H), 7.74 (s, 1H), 7.55 (d, J=28.7 Hz, 2H), 4.46 (s, 2H), 4.14 (d, J=10.0 Hz, 1H), 3.99 (s, 2H), 3.92 (s, 1H), 3.66 (s, 2H), 3.34 (s, 2H), 3.18 (s, 2H), 3.10 (s, 3H), 2.59 (s, 1H), 2.21 (d, J=10.7 Hz, 1H), 1.62 (s, 3H).

Example 27. (2R)-4-{6-fluoro-7-[2-fluoro-4-(2-hydroxyethyl)phenyl]-4-oxo-3,4-dihydroquinazolin-3-yl}-N-hydroxy-2-methanesulfonyl-2-methylbutanamide

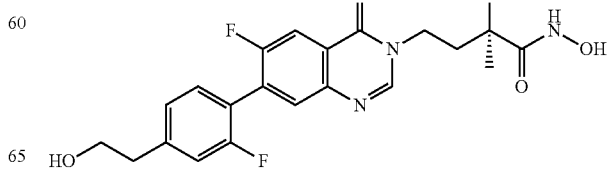

Part A 2-(4-bromo-3-fluorophenyl)acetic acid (9 g, 38.6 mmol) was dissolved in tetrahydrofuran (10 mL) and a solution of BH$_3$.THF (77 mL, 77 mmol) was added slowly under nitrogen at 0° C. The reaction was stirred for 1 hr. To the mixture from combined batches was added methanol slowly to quench and the mixture was concentrated at which time more methanol was added and the reaction was again concentrated. This was repeat two more times. The solution was passed through a short pad of silica gel eluting with 1:1 EtOAc/heptane and then concentrated to give 2-(4-bromo-3-fluorophenyl)ethanol as a colorless oil.

LCMS: [M−H$_2$O+H] 203.1.

Part B

A mixture of 2-(4-bromo-3-fluorophenyl)ethanol (7 g, 32.0 mmol), 4,4,4',4',5,5,5',5'-octamethyl-2,2'-bi(1,3,2-dioxaborolane) (9.74 g, 38.3 mmol), PdCl$_2$(dppf)-CH$_2$Cl$_2$ adduct (1.305 g, 1.598 mmol), potassium acetate (9.41 g, 96 mmol) and 1,4-dioxane (150 mL) was stirred at 100° C. for 17 hr under nitrogen atmosphere. The mixture from combined batches was filtered and the filtrate was concentrated. The crude product was purified by silica gel chromatography, eluting with PE/EtOAc: 3/1) to afford 2-(3-fluoro-4-(4,4,5,5-tetramethyl-1,3,2-dioxaborolan-2-yl)phenyl)ethanol as a yellow oil affording 2-(3-fluoro-4-(4,4,5,5-tetramethyl-1,3,2-dioxaborolan-2-yl)phenyl)ethanol (18 g, 64% yield) LCMS: [M+H] 267.1.

Part C

PdCl$_2$(dppf) (0.070 g, 0.096 mmol) was added to a solution of 2-(3-fluoro-4-(4,4,5,5-tetramethyl-1,3,2-dioxaborolan-2-yl)phenyl)ethanol (0.384 g, 1.441 mmol), (2R)-4-(7-bromo-6-fluoro-4-oxoquinazolin-3(4H)-yl)-2-methyl-2-(methylsulfonyl)-N-((tetrahydro-2H-pyran-2-yl)oxy)butanamide (Intermediate 5) (0.5 g, 0.961 mmol) and K$_2$CO$_3$ (0.266 g, 1.922 mmol) in acetonitrile (12 mL) and water (2 mL) at room temperature under an atmosphere of nitrogen. The resulting solution was stirred at 80° C. for 30 min. The reaction solution was cooled to room temperature, diluted with ethyl acetate (50 mL) and dried over Na$_2$SO$_4$. The solvent was evaporated to afford crude product which was purified by silica gel column chromatography (PE/acetone: 1/1) to afford (2R)-4-(6-fluoro-7-(2-fluoro-4-(2-hydroxyethyl)phenyl)-4-oxoquinazolin-3(4H)-yl)-2-methyl-2-(methylsulfonyl)-N-((tetrahydro-2H-pyran-2-yl)oxy)butanamide (200 mg, 0.328 mmol, 34% yield) as an off-white solid.

LCMS: [M+H] 579.9.

Part D

To a solution of (2R)-4-(6-fluoro-7-(2-fluoro-4-(2-hydroxyethyl)phenyl)-4-oxoquinazolin-3(4H)-yl)-2-methyl-2-(methylsulfonyl)-N-((tetrahydro-2H-pyran-2-yl)oxy)butanamide (150 mg, 0.259 mmol) in dichloromethane (10.00 mL) was added 4M HCl in 1,4-dioxane (4 mL, 16.00 mmol). The resulting solution was stirred at 20° C. for 5 min when methanol (10 mL) was added. The reaction was stirred additional 1 hr. The mixture from combined batches was concentrated and the residue was purified by prep-HPLC to give (R)-4-(6-fluoro-7-(2-fluoro-4-(2-hydroxyethyl)phenyl)-4-oxoquinazolin-3(4H)-yl)-N-hydroxy-2-methyl-2-(methylsulfonyl)butanamide (60 mg, 0.115 mmol, 45% yield) as a white solid.

LCMS: [M+H] 496.1.

$^1$H NMR (500 MHz, DMSO-d6) δ: ppm 11.03 (s, 1H), 9.26 (brs, 2H), 8.40 (s, 1H), 7.94 (d, J=6 10.0 Hz, 1H), 7.78 (d, J=6.5 Hz, 1H), 7.48 (m, 1H), 7.28-7.23 (m, 2H), 4.19-4.10 (m, 1H), 3.95-3.87 (m, 1H), 3.68 (t, J=7.0 Hz, 2H), 3.10 (s, 3H), 2.82 (t, J=7.0 Hz, 2H), 2.59 (m, 1H), 2.21 (m, 1H), 1.61 (s, 3H).

Example 28. (2R)-4-(6-fluoro-7-[4-(2-hydroxyethyl)phenyl]-4-oxo-3,4-dihydroquinazolin-3-yl)-N-hydroxy-2-methanesulfonyl-2-methylbutanamide

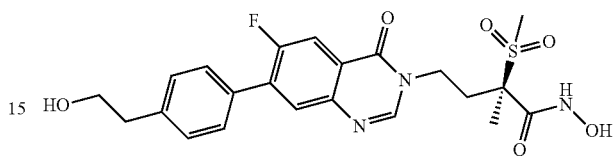

Part A

PdCl$_2$(dppf) (0.042 g, 0.058 mmol) was added to a solution of 2-(4-(4,4,5,5-tetramethyl-1,3,2-dioxaborolan-2-yl)phenyl)ethanol (0.215 g, 0.865 mmol), (2R)-4-(7-bromo-6-fluoro-4-oxoquinazolin-3(4H)-yl)-2-methyl-2-(methylsulfonyl)-N-((tetrahydro-2H-pyran-2-yl)oxy)butanamide (Intermediate 5) (0.3 g, 0.577 mmol) and K$_2$CO$_3$ (0.159 g, 1.153 mmol) in acetonitrile (6 mL) and water (1 mL) under an atmosphere of nitrogen. The resulting solution was stirred at 80° C. for 30 min. The reaction solution was cooled to room temperature, diluted with ethyl acetate (100 mL) and dried over Na$_2$SO$_4$. The solvent was removed and the crude material was purified by silica gel chromatography (petroleum ether/acetone: 1/1) to afford (2R)-4-(6-fluoro-7-(4-(2-hydroxyethyl)phenyl)-4-oxoquinazolin-3(4H)-yl)-2-methyl-2-(methylsulfonyl)-N-((tetrahydro-2H-pyran-2-yl)oxy)butanamide (150 mg, 0.246 mmol, 43% yield) as an off-white solid.

LCMS: [M+H] 561.9.

Part B

To a solution of (2R)-4-(6-fluoro-7-(4-(2-hydroxyethyl)phenyl)-4-oxoquinazolin-3(4H)-yl)-2-methyl-2-(methylsulfonyl)-N-((tetrahydro-2H-pyran-2-yl)oxy)butanamide (120 mg, 0.214 mmol) in dichloromethane (10 mL) was added a solution of HCl (4 mL, 16.00 mmol) in dioxane (4M). The resulting mixture was stirred at 20° C. for 5 min when methanol (10 mL) was added. The reaction was stirred additional 1 hr and the reaction solution was combined with another batch and the combined mixture was concentrated. The residue was purified by reverse phase HPLC to give (R)-4-(6-fluoro-7-(4-(2-hydroxyethyl)phenyl)-4-oxoquinazolin-3(4H)-yl)-N-hydroxy-2-methyl-2-(methylsulfonyl)butanamide (50 mg, 0.098 mmol, 46% yield) as an off-white solid.

LCMS: [M+H] 478.0.

$^1$H NMR (500 MHz, DMSO-d6) δ: ppm 11.03 (s, 1H), 9.27 (brs, 1H), 8.38 (s, 1H), 7.92 (d, J=11.0 Hz, 1H), 7.82 (d, J=6.5 Hz, 1H), 7.58 (d, J=7.0 Hz, 2H), 7.39 (d, J=8.0 Hz, 2H), 4.13 (m, 1H), 3.91 (m, 1H), 3.66 (t, J=7.0 Hz, 2H), 3.10 (s, 3H), 2.80 (t, J=7.0 Hz, 2H), 2.59 (m, 1H), 2.21 (m, 1H), 1.61 (s, 3H).

Example 29. (2R)—N-hydroxy-2-methanesulfonyl-2-methyl-4-(8-methyl-7-{4-[(morpholin-4-yl)methyl]phenyl}-4-oxo-3,4-dihydroquinazolin-3-yl)butanamide

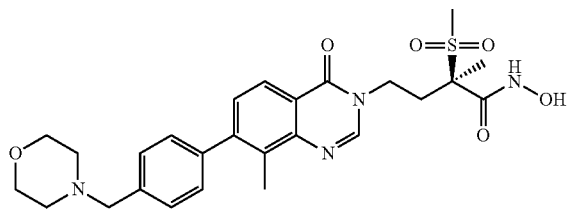 [SMILES: Cc1c(-c2ccc(CN3CCOCC3)cc2)ccc2c(=O)n(CC[C@](C)(C(=O)NO)S(C)(=O)=O)cnc12]

Part A

To a solution of sodium sulfate (61.1 g, 430 mmol), hydroxylamine hydrochloride (8.96 g, 129 mmol), 2,2,2-trichloro-1-ethoxyethanol (9.98 g, 51.6 mmol) and 3-bromo-2-methylaniline (8 g, 43 mmol) in water (300 mL) was added hydrochloric acid (3.92 mL, 129 mmol) slowly. This mixture was heated to 90° C. for 1 hr. The reaction was cooled, filtered and the solid was washed with water and dried to give 6-bromo-7-methylindoline-2,3-dione (8.6 g, 35.8 mmol, 83% yield) as a brown solid.

LCMS: [M+H] 239.9, 241.9.

Part B

To a solution of 6-bromo-7-methylindoline-2,3-dione (7.17 mL, 35.8 mmol) and NaOH (44.8 mL, 90 mmol) in water (300 mL) was added $H_2O_2$ (14.84 mL, 179 mmol) slowly at 0° C. This mixture was stirred for 2 hr at 0° C. The reaction mixture was acidified with 2N HCl (aq) until pH=6. The solid was collected by filtration and washed with water and dried to give 2-amino-4-bromo-3-methylbenzoic acid (6 g, 19.82 mmol, 55% yield) as a light brown solid.

LCMS: [M+H] 229.9, 231.9.

Part C

A mixture of 2-amino-4-bromo-3-methylbenzoic acid (5.00 mL, 26.1 mmol), ammonium acetate (20.10 g, 261 mmol), trimethyl orthoformate (57.7 mL, 522 mmol) in methanol (100 mL) was heated to 120° C. for 3 hr. The mixture was cooled to room temperature and poured onto ice water. The solid was collected and washed with water to afford 7-bromo-8-methylquinazolin-4(3H)-one (4.4 g, 13.62 mmol, 52% yield) as a light brown solid.

LCMS: [M+H] 238.9, 240.9.

Part D

To a solution of 7-bromo-8-methylquinazolin-4(3H)-one (1.8 g, 7.53 mmol) and (R) ethyl 4-bromo-2-methyl-2-(methylsulfonyl)butanoate (2.59 g, 9.04 mmol) in acetonitrile (20 ml) was added cesium carbonate (3.68 g, 11.29 mmol). The reaction mixture was heated to 80° C. for 4 hr. The reaction was filtered and the filter pad was washed with EtOAc (5 mL×3). The filtrate was concentrated and diluted with EtOAc (50 mL), washed with aq. ammonium chloride. The aqueous phase was extracted with EtOAc (20 mL×3) and the combined organic layers were dried with sodium sulfate, concentrated and the residue purified by silica gel chromatography (EtOAc/hexanes: 0-80%) to afford (R)-ethyl 4-(7-bromo-8-methyl-4-oxoquinazolin-3(4H)-yl)-2-methyl-2-(methylsulfonyl)butanoate (2.1 g, 4.48 mmol, 60% yield) as a white solid.

LCMS: [M+H] 445.1, 447.1.

$^1$H NMR (CHLOROFORM-d) δ: ppm 8.11 (s, 1H), 8.01 (d, J=8.6 Hz, 1H), 7.70 (d, J=8.6 Hz, 1H), 4.30-4.39 (m, 1H), 4.26 (q, J=7.2 Hz, 2H), 4.11 (ddd, J=13.5, 9.9, 5.9 Hz, 1H), 3.13 (s, 3H), 2.73 (s, 3H), 2.46-2.67 (m, 2H), 1.80 (s, 3H), 1.34 (t, J=7.2 Hz, 3H).

Part E

A mixture of potassium carbonate (69.8 mg, 0.505 mmol), PdCl$_2$(dppf) (24.65 mg, 0.034 mmol), (R)-ethyl 4-(7-bromo-8-methyl-4-oxoquinazolin-3(4H)-yl)-2-methyl-2-(methylsulfonyl)butanoate (150 mg, 0.337 mmol) and (4-(morpholinomethyl)phenyl)boronic acid (89 mg, 0.404 mmol) in 1,4-dioxane (20 mL) and water (3 mL) was heated to 110° C. for 0.5 hr. The mixture was diluted with saturated ammonium chloride solution (10 ml) and extracted with DCM (10 mL×3). The combined organic layers were dried over sodium sulphate, concentrated and the residue was purified silical gel chromatography (MeOH/DCM: 0-20%) to afford (R)-ethyl 2-methyl-4-(8-methyl-7-(4-(morpholinomethyl)phenyl)-4-oxoquinazolin-3(4H)-yl)-2-(methylsulfonyl)butanoate (150 mg, 0.277 mmol, 82% yield) as a white solid.

LCMS: [M+H] 542.2.

Part F

To a solution of (R)-ethyl 2-methyl-4-(8-methyl-7-(4-(morpholinomethyl)phenyl)-4-oxoquinazolin-3(4H)-yl)-2-(methylsulfonyl)butanoate (130 mg, 0.240 mmol) in 1,4-dioxane (2 mL) and methanol (2 ml) was added a solution of hydroxylamine (1 mL, 16.32 mmol) (50% in water) and LiOH (0.5 ml, 0.500 mmol) (1M in water). The reaction mixture was stirred for 2 hr. The mixture was concentrated and purified by reverse phase HPLC (5-75% MeCN/H$_2$O, 0.1% TFA) to afford (R)—N-hydroxy-2-methyl-4-(8-methyl-7-(4-(morpholinomethyl)phenyl)-4-oxoquinazolin-3(4H)-yl)-2-(methylsulfonyl)butanamide trifluoroacetic acid salt (111 mg, 0.164 mmol, 68.4% yield) as a white solid.

LCMS: [M+H] 529.

$^1$H NMR (METHANOL-d$_4$) δ: ppm 8.37 (br. s., 1H), 8.18 (d, J=8.3 Hz, 1H), 7.68 (d, J=7.8 Hz, 2H), 7.55 (d, J=7.8 Hz, 2H), 7.42 (d, J=8.3 Hz, 1H), 4.48 (s, 2H), 4.35 (t, J=9.3 Hz, 1H), 3.97-4.19 (m, 3H), 3.78 (t, J=11.7 Hz, 2H), 3.39-3.56 (m, 2H), 3.24-3.31 (m, 2H), 3.13 (s, 3H), 2.64-2.79 (m, 1H), 2.38-2.56 (m, 4H), 1.77 (s, 3H).

Example 30. (2R)-4-[6-fluoro-7-(6-methoxypyridin-3-yl)-4-oxo-3,4-dihydroquinazolin-3-yl]-N-hydroxy-2-methanesulfonyl-2-methylbutanamide

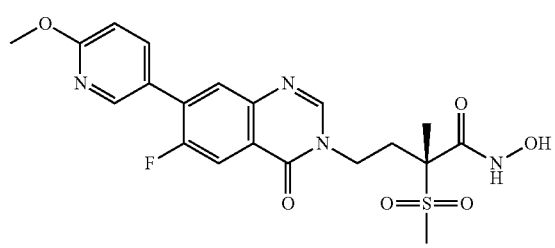 [SMILES: COc1ccc(-c2cc3ncn(CC[C@](C)(C(=O)NO)S(C)(=O)=O)c(=O)c3cc2F)cn1]

Part A

PdCl$_2$(dppf) (49.2 mg, 0.067 mmol) was added to a solution of (6-methoxypyridin-3-yl)boronic acid (154 mg, 1.009 mmol), (2R)-4-(7-bromo-6-fluoro-4-oxoquinazolin-3(4H)-yl)-2-methyl-2-(methylsulfonyl)-N-((tetrahydro-2H-pyran-2-yl)oxy)butanamide (Intermediate 5) (350 mg, 0.673 mmol) and K$_2$CO$_3$ (186 mg, 1.345 mmol) in acetonitrile (12 mL) and water (2 mL) at room temperature under an atmosphere of nitrogen. The resulting solution was stirred at 80° C. for 30 min. The reaction solution was cooled to room temperature, diluted with ethyl acetate (50 mL) and dried over Na$_2$SO$_4$. The solvent was evaporated to afford crude product which was purified by silica gel chromatography (PE/acetone: 1/1) to afford (2R)-4-(6-fluoro-7-(6-methoxypyridin-3-yl)-4-oxoquinazolin-3(4H)-yl)-2-methyl-2-(methylsulfonyl)-N-((tetrahydro-2H-pyran-2-yl)oxy)butanamide (362 mg, 0.581 mmol, 86% yield) as an off-white solid.

LCMS: [M+H] 549.0.

Part B

To a solution of (2R)-4-(6-fluoro-7-(6-methoxypyridin-3-yl)-4-oxoquinazolin-3(4H)-yl)-2-methyl-2-(methylsulfonyl)-N-((tetrahydro-2H-pyran-2-yl)oxy)butanamide (131 mg, 0.239 mmol) in dichloromethane (5 mL) was added 4M HCl in dioxane (0.298 mL, 1.194 mmol) at room temperature. The resulting solution was stirred at 20° C. for 5 min when methanol (5 mL) was added. The resulting mixture was stirred at 25° C. for 1 hr. The mixture from combined batches was concentrated and the residue was purified by reverse phase HPLC to give (R)-4-(6-fluoro-7-(6-methoxypyridin-3-yl)-4-oxoquinazolin-3(4H)-yl)-N-hydroxy-2-methyl-2-(methylsulfonyl)butanamide trifluoroacetic acid salt (35 mg, 0.057 mmol, 24% yield) as a white solid LCMS: [M+H-THP] 465.0.

$^1$H NMR (500 MHz, DMSO-d$_6$) δ: ppm 11.03 (s, 1H), 8.49 (s, 1H), 8.39 (s, 1H), 8.04 (d, J=8.7 Hz, 1H), 7.92 (J=17.9, 8.7 Hz, 2H), 6.99 (d, J=8.7 Hz, 1H), 4.14 (td, J=13.3, 4.8 Hz, 1H), 3.99-3.86 (m, 4H), 3.11 (s, 3H), 2.60 (td, J=13.1, 5.5 Hz, 1H), 2.21 (td, J=13.2, 4.8 Hz, 1H), 1.62 (s, 3H).

Example 31. (2R)-4-(6-fluoro-4-oxo-7-phenyl-3,4-dihydroquinazolin-3-yl)-N-hydroxy-2-methanesulfonyl-2-methylbutanamide

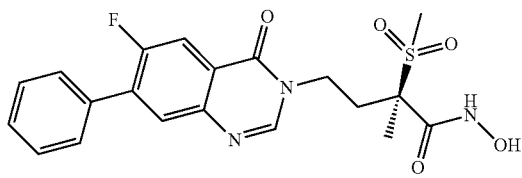

Part A

PdCl$_2$(dppf) (0.169 g, 0.231 mmol) was added to a solution of phenylboronic acid (0.422 g, 3.46 mmol), (2R)-4-(7 bromo-6-fluoro-4-oxoquinazolin-3(4H)-yl)-2-methyl-2-(methylsulfonyl)-N-((tetrahydro-2H-pyran-2-yl)oxy)butanamide (Intermediate 5) (1.2 g, 2.306 mmol) and K$_2$CO$_3$ (0.637 g, 4.61 mmol) in acetonitrile (24 mL) under an atmosphere of nitrogen. The resulting solution was stirred at 80° C. for 30 min. The reaction solution was combined with another batch and the combined mixture was cooled to room temperature, diluted with water (50 mL) and extracted with DCM (100 mL×2). The organic layers were combined, dried over Na$_2$SO$_4$ and concentrated. The crude product was purified by silica gel chromatography (petroleum ether/acetone: 1/1) to afford (2R)-4-(6-fluoro-4-oxo-7-phenylquinazolin-3(4H)-yl)-2-methyl-2-(methylsulfonyl)-N-((tetrahydro-2H-pyran-2-yl)oxy)butanamide (combined yield: 1 g, 67% yield) as yellow solid.

LCMS: [M+H] 518.0.

Part B

To a solution of (2R)-4-(6-fluoro-4-oxo-7-phenylquinazolin-3(4H)-yl)-2-methyl-2-(methylsulfonyl)-N-((tetrahydro-2H-pyran-2-yl)oxy)butanamide (900 mg, 1.739 mmol) in dichloromethane (30 mL) was added a solution of HCl (10 mL, 40 mmol) in dioxane (4M). The resulting solution was stirred at 20° C. for 5 min when methanol (30 mL) was added. The reaction was stirred additional 1 hr. The reaction solution was combined with another batch, the combined mixture was concentrated and the residue was purified by trituration with acetone to give (R)-4-(6-fluoro-4-oxo-7-phenylquinazolin-3(4H)-yl)-N-hydroxy-2-methyl-2-(methylsulfonyl)butanamide (670 mg, 1.468 mmol, 84% yield) as a white solid.

LCMS: [M+H] 434.2.

$^1$H NMR (500 MHz, DMSO-d6) δ: ppm 11.03 (brs, 1H), 8.46 (s, 1H), 7.95 (d, J=10.0 Hz, 1H), 7.85 (d, J=7.0 Hz, 1H), 7.67 (d, J=8.0 Hz, 2H), 7.57-7.49 (m, 3H), 4.20-4.10 (m, 1H), 3.98-3.86 (m, 1H), 3.11 (s, 3H), 2.66-2.56 (m, 1H), 2.27-2.11 (m, 1H), 1.62 (s, 3H).

Example 32. (2R)-4-[7-(1,3-dihydro-2-benzofuran-5-yl)-6-fluoro-4-oxo-3,4-dihydroquinazolin-3-yl]-N-hydroxy-2-methanesulfonyl-2-methylbutanamide

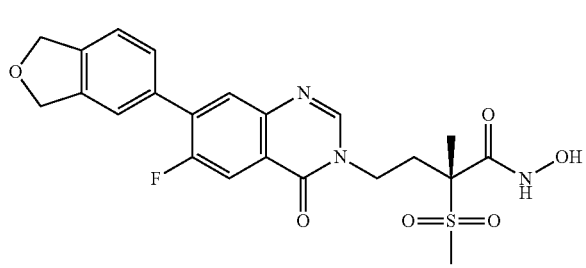 [SMILES: C[C@@](CCn1cnc2cc(-c3ccc4c(c3)COC4)c(F)cc2c1=O)(C(=O)NO)S(C)(=O)=O]

Part A

To 1,3-dihydroisobenzofuran-5-amine (3 g, 22.20 mmol) slurried in HBr (45 mL, 829 mmol) in ice was added sodium nitrite (1.531 g, 22.20 mmol) in water (15 mL) dropwise over 2 min and the mixture stirred at 0° C. for 30 min to give a brown-yellow solution. The reaction was then added to a solution of copper(I) bromide (4.78 g, 33.3 mmol) in HBr (15 mL, 276 mmol) at −10° C. The resulting dark brown mixture was stirred overnight. The mixture was diluted with water (200 mL) producing an orange precipitate. The solid was filtered off and retreated with sat. NaHCO$_3$ (100 mL) and extracted with ethyl acetate (200 mL). The extract was washed with brine, dried (Na$_2$SO$_4$) and concentrated. The residue was purified by silica gel chromatography (EtOAc/petroleum ether: 10%) to give 5-bromo-1,3-dihydroisobenzofuran (2.5 g, 12.56 mmol, 57% yield) as a white solid.

Part B

PdCl$_2$(dppf)-CH$_2$Cl$_2$ adduct (0.615 g, 0.754 mmol) was added to a solution of 4,4,4',4',5,5,5',5'-octamethyl-2,2'-bi(1,3,2-dioxaborolane) (2.87 g, 11.30 mmol), 5-bromo-1,3-dihydroisobenzofuran (1.5 g, 7.54 mmol) and potassium acetate (2.219 g, 22.61 mmol) in 1,4-dioxane (40 mL) at room temperature under an atmosphere of nitrogen. The resulting solution was stirred at 100° C. for 12 hr. The crude was filtered and the filtrate was concentrated to afford a residue that was purified by silica gel chromatography (EtOAc/petroleum ether: 10%) to afford 2-(1,3-dihydroisobenzofuran-5-yl)-4,4,5,5-tetramethyl-1,3,2-dioxaborolane (1.5 g, 5.49 mmol, 73% yield) as a white solid.

LCMS: [M+H] 247.

Part C

A solution of PdCl$_2$(dppf)-CH$_2$Cl$_2$ adduct (47.1 mg, 0.058 mmol), K$_2$CO$_3$ (239 mg, 1.730 mmol), 2-(1,3-dihydroisobenzofuran-5-yl)-4,4,5,5-tetramethyl-1,3,2-dioxaborolane (213 mg, 0.865 mmol) and (2R)-4-(7-bromo-6-fluoro-4-oxoquinazolin-3(4H)-yl)-2-methyl-2-(methylsulfonyl)-N-((tetrahydro-2H-pyran-2-yl)oxy)butanamide (Intermediate 5) (300 mg, 0.577 mmol) in acetonitrile (20 mL) and water (10 mL) was stirred at 80° C. under N$_2$ for 3 hr. The solid was filtered off and the solvent was removed. The residue was purified by silica gel chromatography (MeOH/DCM: 0-5%) to give (2R)-4-(7-(1,3-dihydroisobenzofuran-5-yl)-6-fluoro-4-oxoquinazolin-3(4H)-yl)-2-methyl-2-(methylsulfonyl)-N-((tetrahydro-2H-pyran-2-yl)oxy)butanamide (220 mg, 0.216 mmol, 38% yield) as a white solid.

LCMS: [M+H] 560.

Part D

To a solution of (2R)-4-(7-(1,3-dihydroisobenzofuran-5-yl)-6-fluoro-4-oxoquinazolin-3(4H)-yl)-2-methyl-2-(methylsulfonyl)-N-((tetrahydro-2H-pyran-2-yl)oxy)butanamide (200 mg, 0.357 mmol) in dichloromethane (20 mL) was added a solution of HCl (10 mL, 40 mmol) in dioxane (4M). The resulting solution was stirred at 20° C. for 2 hr. The mixture from combined batches was concentrated and the residue was purified by preparative HPLC to give (R)-4-(7-(1,3-dihydroisobenzofuran-5-yl)-6-fluoro-4-oxoquinazolin-3(4H)-yl)-N-hydroxy-2-methyl-2-(methylsulfonyl)butanamide (90 mg, 0.180 mmol, 50% yield) as a white solid.

LCMS: [M+H] 476.1

$^1$H NMR (500 MHz, DMSO-d$_6$) δ: ppm 11.03 (s, 1H), 9.27 (s, 1H), 8.39 (s, 1H), 7.93 (d, J=10.3 Hz, 1H), 7.83 (d, J=7.1 Hz, 1H), 7.61 (s, 1H), 7.57 (d, J=7.8 Hz, 1H), 7.48 (d, J=7.8 Hz, 1H), 5.08 (s, 4H), 4.20-4.07 (m, 1H), 3.91 (td, J=13.1, 5.4 Hz, 1H), 3.10 (s, 3H), 2.66-2.55 (m, 1H), 2.26-2.14 (m, 1H), 1.61 (s, 3H).

Example 33. (2R)-4-{7-[6-(dimethylamino)pyridin-3-yl]-6-fluoro-4-oxo-3,4-dihydroquinazolin-3-yl}-N-hydroxy-2-methanesulfonyl-2-methylbutanamide

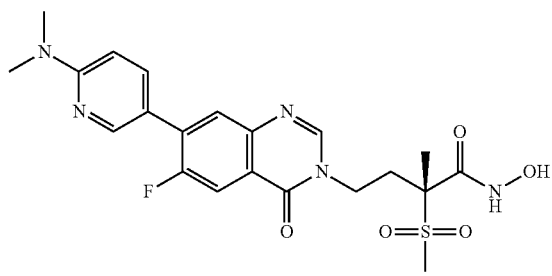 [SMILES: CN(C)c1ccc(-c2cc3ncn(CC[C@](C)(C(=O)NO)S(C)(=O)=O)c(=O)c3cc2F)cn1]

Part A

To a sealed tube was added 5-bromo-2-fluoropyridine (2.0 g, 11.36 mmol), dimethylamine (7.0 mL, 45.6 mmol) in water and tetrahydrofuran (3 mL) and the reaction was heated to 100° C. overnight. The reaction mixture was cooled to room temperature and extracted with EtOAc (15 mL×3), the organic layers were combined and washed with brine and dried over Na$_2$SO$_4$, filtered and concentrated under reduced pressure to give 5-bromo-N,N-dimethylpyridin-2-amine (1.7 g, 8.46 mmol, 75% yield) as a white solid.

LCMS: [M+H] 201.1.

Part B

To a solution of 5-bromo-N,N-dimethylpyridin-2-amine (400 mg, 1.989 mmol) in 1,4-dioxane (20 mL) was added 4,4,4',4',5,5,5',5'-octamethyl-2,2'-bi(1,3,2-dioxaborolane) (606 mg, 2.387 mmol), PdCl$_2$(dppf)-CH$_2$Cl$_2$ adduct (162 mg, 0.199 mmol) and potassium acetate (390 mg, 3.98 mmol). The reaction mixture was heated to 100° C. under N$_2$ and stirred overnight. The mixture was filtered and the filtrate evaporated in vacuo to give crude (6-(dimethylamino)pyridin-3-yl)boronic acid (420 mg, 0.496 mmol, 25% yield) as a brown oil.

LCMS: [M+H] 167.1.

Part C

To a solution of (2R)-4-(7-bromo-6-fluoro-4-oxoquinazolin-3(4H)-yl)-2-methyl-2-(methylsulfonyl)-N-((tetrahydro-2H-pyran-2-yl)oxy)butanamide (Intermediate 5) (280 mg, 0.538 mmol) in acetonitrile (20 mL) and water (3.33 mL) was added (6-(dimethylamino)pyridin-3-yl)boronic acid (134 mg, 0.807 mmol), PdCl$_2$(dppf) (39.4 mg, 0.054 mmol) and K$_2$CO$_3$ (149 mg, 1.076 mmol). The mixture was heated to 80° C. under N$_2$ and stirred for 2 hr. The mixture was evaporated in vacuo and the residue was purified by silica gel column chromatography (acetone/PE: 1/10-1/1) to give (2R)-4-(7-(6-(dimethylamino)pyridin-3-yl)-6-fluoro-4-oxoquinazolin-3(4H)-yl)-2-methyl-2-(methylsulfonyl)-N-((tetrahydro-2H-pyran-2-yl)oxy)butanamide (200 mg, 0.338 mmol, 63% yield) as a yellow solid.

LCMS: [M+H] 562.0.

Part D

To a solution of (2R)-4-(7-(6-(dimethylamino)pyridin-3-yl)-6-fluoro-4-oxoquinazolin-3(4H)-yl)-2-methyl-2-(methylsulfonyl)-N-((tetrahydro-2H-pyran-2-yl)oxy)butanamide (190 mg, 0.338 mmol) in dichloromethane (5 mL) and methanol (5 mL) was added a solution of HCl (4 mL, 16 mmol) in dioxane. The mixture was stirred at 20° C. for 2 hr. The mixture was evaporated in vacuo and the residue was purified by HPLC, to (R)-4-(7-(6-(dimethylamino)pyridin-3-yl)-6-fluoro-4-oxoquinazolin-3(4H)-yl)-N-hydroxy-2-methyl-2-(methylsulfonyl)butanamide trifluoroacetic acid salt (105 mg, 0.169 mmol, 50% yield) as a yellow solid.

LCMS: [M+H] 478.1.

$^1$H NMR (500 MHz, DMSO-d$_6$) δ: ppm 11.02 (s, 1H), 8.39 (d, J=10.4 Hz, 2H), 8.12 (d, J=9.2 Hz, 1H), 7.99-7.84 (m, 2H), 7.12 (d, J=9.1 Hz, 1H), 4.21-4.06 (m, 1H), 3.97-3.84 (m, 1H), 3.21 (s, 6H), 3.12 (d, J=14.1 Hz, 3H), 2.66-2.55 (m, 1H), 2.26-2.14 (m, 1H), 1.62 (s, 3H).

Example 34. 2-(4-{6-fluoro-3-[(3R)-3-(hydroxycarbamoyl)-3-methanesulfonyl-3-methylpropyl]-4-oxo-3,4-dihydroquinazolin-7-yl}phenyl)ethyl acetate

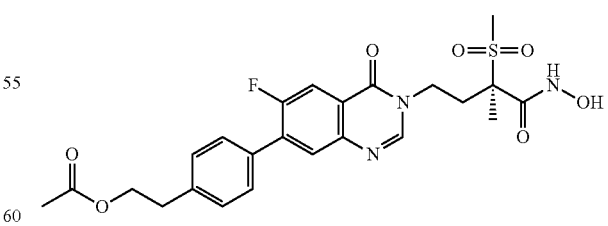

Part A

To a reaction vessel was added (2R)-4-(7-bromo-6-fluoro-4-oxoquinazolin-3(4H)-yl)-2-methyl-2-(methylsulfonyl)-N-((tetrahydro-2H-pyran-2-yl)oxy)butanamide (Intermediate 5) (400 mg, 0.769 mmol), (4-(2-hydroxyethyl)phenyl)boronic acid (134 mg, 0.807 mmol), potassium carbonate (212 mg, 1.537 mmol), PdCl₂(dppf) (56.2 mg, 0.077 mmol), 1,4-dioxane (2.4 mL) and water (0.8 mL). The reaction vessel was sealed and heated in Emrys Optimiser at 110° C. for 30 min. After cooling the reaction, the crude product was purified by normal phase silica gel chromatography (ethyl acetate/hexanes: 0-100%) to give (2R)-4-(6-fluoro-7-(4-(2-hydroxyethyl)phenyl)-4-oxoquinazolin-3(4H)-yl)-2-methyl-2-(methylsulfonyl)-N-((tetrahydro-2H-pyran-2-yl)oxy)butanamide (553 mg, 0.679 mmol, 88% yield).

LCMS: [M+H] 562.2.

Part B

To a solution of (2R)-4-(6-fluoro-7-(4-(2-hydroxyethyl)phenyl)-4-oxoquinazolin-3(4H)-yl)-2-methyl-2-(methylsulfonyl)-N-((tetrahydro-2H-pyran-2-yl)oxy)butanamide (300 mg, 0.534 mmol) in dichloromethane (5 mL) was then added acetic anhydride (60 mg, 0.588 mmol), triethylamine (81 mg, 0.801 mmol) and a catalytic amount of N,N-dimethylpyridin-4-amine (6.53 mg, 0.053 mmol). The mixture was allowed to stir for 2 hr at room temperature. The solvent was removed and the crude reside was purified by normal phase silica gel chromatography (ethyl acetate/hexanes 0-100%) to give 4-(6-fluoro-3-((3R)-3-methyl-3-(methylsulfonyl)-4-oxo-4-(((tetrahydro-2H-pyran-2-yl)oxy)amino)butyl)-4-oxo-3,4-dihydroquinazolin-7-yl)phenethyl acetate (221 mg, 0.366 mmol, 69% yield).

LCMS: [M+H] 604.2.

Part C

To a solution of 4-(6-fluoro-3-((3R)-3-methyl-3-(methylsulfonyl)-4-oxo-4-(((tetrahydro-2H-pyran-2-yl)oxy)amino)butyl)-4-oxo-3,4-dihydroquinazolin-7-yl)phenethyl acetate (221 mg, 0.366 mmol) in dichloromethane (5 mL) was added 2,2,2-trifluoroacetic acid (1.410 mL, 18.31 mmol). The resulting solution was stirred at room temperature for 4 hr and was concentrated. The residue was purified by preparative HPLC (Sunfire, 5-65% MeCN, H₂O, 0.1% TFA) to afford (R)-4-(6-fluoro-3-(4-(hydroxyamino)-3-methyl-3-(methylsulfonyl)-4-oxobutyl)-4-oxo-3,4-dihydroquinazolin-7-yl)phenethyl acetate (107 mg, 0.194 mmol, 53% yield) as a white powder.

LCMS: [M+H] 520.1.

¹H NMR (400 MHz, CHLOROFORM-d) δ: ppm 1.64-1.96 (m, 3H) 2.09 (s, 3H) 2.32-2.81 (m, 2H) 3.04 (t, J=6.82 Hz, 3H) 3.17 (br.s., 3H) 4.36 (t, J=6.95 Hz, 4H) 7.31-8.16 (m, 7H).

Example 35. (2R)—N-hydroxy-2-methanesulfonyl-2-methyl-4-(7-{4-[(morpholin-4-yl)methyl]phenyl}-4-oxo-3,4-dihydroquinazolin-3-yl)butanamide

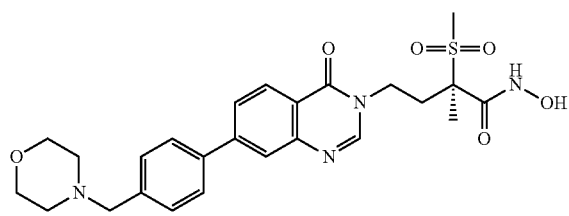 [SMILES: C[C@@](CCn1cnc2cc(-c3ccc(CN4CCOCC4)cc3)ccc2c1=O)(C(=O)NO)S(C)(=O)=O]

Part A

A reaction vessel was sealed with potassium carbonate (70.5 mg, 0.510 mmol), PdCl₂(dppf) (18.66 mg, 0.026 mmol), (R)-ethyl-4-(7-bromo-4-oxoquinazolin-3(4H)-yl)-2-methyl-2-(methylsulfonyl)butanoate (Intermediate 2) (110 mg, 0.255 mmol) and (4-(morpholinomethyl)phenyl)boronic acid (67.7 mg, 0.306 mmol) and heated a microwave at 110° C. for 30 min. After cooling, the organic phase was diluted with DCM (20 mL) and washed with water (20 mL), saturated brine (30 mL), dried over sodium sulphate and evaporated in vacuo. The resulting residue was purified with silica gel chromatography (MeOH/DCM: 0-20%) affording (R)-ethyl-2-methyl-2-(methylsulfonyl)-4-(7-(4-(morpholinomethyl)phenyl)-4-oxoquinazolin-3(4H)-yl)butanoate (125 mg, 0.220 mmol, 86% yield) as white solid.

LCMS: [M+H] 528.4.

Part B

To a solution of (R)-ethyl-2-methyl-2-(methylsulfonyl)-4-(7-(4-(morpholinomethyl)phenyl)-4-oxoquinazolin-3(4H)-yl)butanoate (125 mg, 0.237 mmol) in 1,4-dioxane (2 mL) was added a 50% solution of aq. hydroxylamine (1 mL, 16.32 mmol) and 1M aq. LiOH (0.5 ml, 0.5 mmol) at room temperature. The reaction mixture was stirred for 2 hr. The reaction was concentrated in vacuo and purified by preparative HPLC (Sunfire, 5-75% MeCN, H₂O, 0.1% TFA) to afford (R)—N-hydroxy-2-methyl-2-2(methylsulfonyl)-4-(7-(4-(morpholinomethyl)phenyl)-4-oxoquinazolin-3(4H)-yl)butanamide trifluoroacetic acid salt (85 mg, 0.128 mmol, 54% yield) as white solid.

LCMS: [M+H] 515.3.

¹H NMR (METHANOL-d) δ: ppm 8.40 (s, 1H), 8.35 (d, J=8.3 Hz, 1H), 7.86-8.02 (m, 4H), 7.70 (d, J=8.1 Hz, 2H), 4.48 (s, 2H), 4.26-4.38 (m, 1H), 3.97-4.16 (m, 3H), 3.77 (br.s., 2H), 3.44 (br.s., 2H), 3.29 (d, J=6.6 Hz, 2H), 3.13 (s, 3H), 2.66-2.80 (m, 1H), 2.37-2.51 (m, 1H), 1.77 (s, 3H).

Example 36. (2R)-4-[7-(2-fluoro-4-{[(2-methoxyethyl)(methyl)amino]methyl}phenyl)-4-oxo-3,4-dihydroquinazolin-3-yl]-N-hydroxy-2-methanesulfonyl-2-methylbutanamide

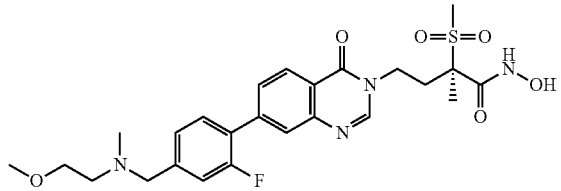 [SMILES: COCCN(C)Cc1ccc(-c2ccc3c(=O)n(CC[C@](C)(C(=O)NO)S(C)(=O)=O)cnc3c2)c(F)c1]

Part A

A reaction vessel was sealed with potassium carbonate (83 mg, 0.597 mmol), PdCl₂(dppf) (21.85 mg, 0.030 mmol), (2R)-4-(7-bromo-4-oxoquinazolin-3(4H)-yl)-2-methyl-2-(methylsulfonyl)-N-((tetrahydro-2H-pyran-2-yl)oxy)butanamide (Intermediate 3) (150 mg, 0.299 mmol) and (2-fluoro-4-formylphenyl) boronic acid (60.2 mg, 0.358 mmol) and heated in a microwave to 110° C. for 30 min. The organic phase was diluted with DCM (20 mL) and washed with water (20 mL), saturated brine (30 mL), dried over sodium sulphate and concentrated. The residue was purified with silica gel chromatography (EtOAc/hexanes: 0-100%) to afford (2R)-4-(7-(2-fluoro-4-formylphenyl)-4-oxoquinazolin-3(4H)-yl)-2-methyl-2-(methylsulfonyl)-N-((tetrahydro-2H-pyran-2-yl)oxy)butanamide (142 mg, 0.260 mmol, 87% yield) as colorless oil.

LCMS: [M+H] 546.3.

Part B

To a solution of (2R)-4-(7-(2-fluoro-4-formylphenyl)-4-oxoquinazolin-3(4H)-yl)-2-methyl-2-(methylsulfonyl)-N-

((tetrahydro-2H-pyran-2-yl)oxy)butanamide (142 mg, 0.260 mmol) in 1,2-dichloroethane (2 mL) at 0° C. was added 2-methoxy-N-methylethanamine (69.6 mg, 0.781 mmol), acetic acid (15.63 mg, 0.260 mmol) and sodium triacetoxyhydroborate (165 mg, 0.781 mmol). The reaction mixture was allowed to warm to room temperature and stirred overnight. The organic phase was diluted with DCM (20 mL) and saturated sodium bicarbonate solution (15 ml) was added. The mixture was extracted with DCM (10 ml×3) and the combined organic layers were washed with water (20 mL), brine (30 mL), dried over sodium sulphate and concentrated. The residue was purified with silica gel chromatography (methanol/DCM: 0-20%) to afford (2R)-4-(7-(2-fluoro-4-(((2-methoxyethyl)-(methyl)amino)methyl) phenyl)-4-oxoquinazolin-3(4H)-yl)-2-methyl-2-(methylsulfonyl)-N-((tetrahydro-2H-pyran-2-yl)oxy) butanamide (138 mg, 0.223 mmol, 86% yield) was obtained as colorless oil.

LCMS: [M+H] 535.3.

Part C

To a solution of (2R)-4-(7-(2-fluoro-4-(((2-methoxyethyl)(methyl)amino)methyl)phenyl)-4-oxoquinazolin-3(4H)-yl)-2-methyl-2-(methylsulfonyl)-N-((tetrahydro-2H-pyran-2-yl)oxy)butanamide (138 mg, 0.223 mmol) in dichloromethane (3 mL) and methanol (2 mL) stirred under nitrogen at room temperature was added a solution of 4M HCl in dioxane (0.558 mL, 2.230 mmol). The reaction mixture was stirred at room temperature for 4 hr. The reaction was concentrated and the residue triturated with ethyl acetate/methanol (10 ml/10 ml), filtered and washed with ethyl acetate to afford (R)-4-(7-(2-fluoro-4-(((2-methoxyethyl)(methyl)amino)methyl)phenyl)-4-oxoquinazolin-3(4H)-yl)-N-hydroxy-2-methyl-2-(methylsulfonyl) butanamide, hydrochloride (95 mg, 0.158 mmol, 71% yield) as a white solid.

LCMS: [M+H] 535.3.

$^1$H NMR (METHANOL-d) δ: ppm 9.33 (s, 1H), 8.47 (d, J=8.3 Hz, 1H), 7.93-8.03 (m, 2H), 7.82 (t, J=7.7 Hz, 1H), 7.58 (d, J=9.6 Hz, 2H), 4.59 (d, J=12.9 Hz, 1H), 4.37-4.50 (m, 2H), 4.21-4.34 (m, 1H), 3.80 (t, J=4.4 Hz, 2H), 3.43-3.57 (m, 4H), 3.35-3.42 (m, 1H), 3.12 (s, 3H), 2.95 (s, 3H), 2.78-2.91 (m, 1H), 2.39-2.53 (m, 1H), 1.79 (s, 3H).

Example 37. (2R)-4-(7-{2-fluoro-4-[(morpholin-4-yl)methyl]phenyl}-4-oxo-3,4-dihydroquinazolin-3-yl)-N-hydroxy-2-methanesulfonyl-2-methylbutanamide

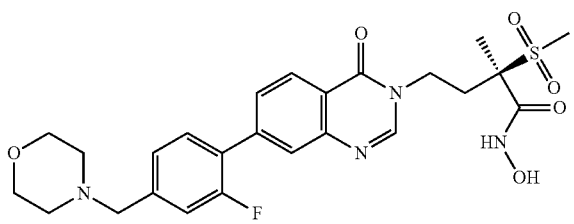 [SMILES: C[C@@](CCn1cnc2cc(-c3ccc(CN4CCOCC4)cc3F)ccc2c1=O)(C(=O)NO)S(C)(=O)=O]

Part A

A mixture of 1-bromo-4-(bromomethyl)-2-fluorobenzene (1 g, 3.73 mmol), morpholine (0.358 g, 4.11 mmol), potassium carbonate (0.516 g, 3.73 mmol) in acetonitrile (10 mL) was stirred at 25° C. for 17 hr. The reaction was filtered and the filtrate was evaporated to dryness. The residue was purified by silica gel chromatography (EtOAc/hexanes: 0-17%) to give 4-(4-bromo-3-fluorobenzyl)morpholine (930 mg, 3.22 mmol, 86% yield) as a yellow oil.

LCMS: [M+H] 274.1, 276.1.

N30116-4

Part B

A mixture of (R)-(3-(4-ethoxy-3-methyl-3-(methylsulfonyl)-4-oxobutyl)-4-oxo-3,4-dihydroquinazolin-7-yl)boronic acid (Intermediate 19) (320 mg, 0.646 mmol) lithium hydroxide monohydrate (81 mg, 1.938 mmol) in tetrahydrofuran (5 mL) and water (5.00 mL) was stirred at 25° C. for 2 hr under a nitrogen atmosphere. The reaction was concentrated and H$_2$O (20 mL) was added. The aqueous layer was extracted with DCM (20 mL) and 2-methyl tetrahydrofuran (20 mL). The resulting aqueous layer was acidified to pH 3 using 1M HCl (about 2 mL) and was extracted with 2-methyl tetrahydrofuran (20 mL×2). The organic layers were concentrated to afford (R)-4-(7-borono-4-oxoquinazolin-3(4H)-yl)-2-methyl-2-(methylsulfonyl)butanoic acid (250 mg, 0.611 mmol, 95% yield) as a yellow solid.

LCMS: [M+H] 369.1.

Part C

To a mixture of (R)-4-(7-borono-4-oxoquinazolin-3(4H)-yl)-2-methyl-2-(methylsulfonyl)butanoic acid (250 mg, 0.679 mmol), O-(tetrahydro-2H-pyran-2-yl)hydroxylamine (239 mg, 2.037 mmol), Et$_3$N (0.284 mL, 2.037 mmol) and N,N-dimethylformamide (2.5 mL) was added HOBT (312 mg, 2.037 mmol) and EDC (391 mg, 2.037 mmol). The resulting mixture was stirred at 65° C. for 3 hr under a nitrogen atmosphere. The reaction was filtered and the filtrate was evaporated to yield (3-((3R)-3-methyl-3-(methylsulfonyl)-4-oxo-4-(((tetrahydro-2H-pyran-2-yl)oxy) amino)butyl)-4-oxo-3,4-dihydroquinazolin-7-yl)boronic acid (531 mg, 0.679 mmol, 60% pure) as a yellow oil.

LCMS: [M+H] 468.1.

Part D

A mixture of (3-((3R)-3-methyl-3-(methylsulfonyl)-4-oxo-4-(((tetrahydro-2H-pyran-2-yl)oxy)amino)butyl)-4-oxo-3,4-dihydroquinazolin-7-yl)boronic acid (2 mL, 0.540 mmol), 4-(4-bromo-3-fluorobenzyl)morpholine (222 mg, 0.810 mmol), K$_2$CO$_3$ (149 mg, 1.080 mmol), PdCl$_2$(dppf) (88 mg, 0.108 mmol) in acetonitrile (3 mL) and water (0.5 mL) was heated in a microwave at 100° C. for 0.5 hr. The reaction was concentrated and the aqueous layer was extracted with DCM (50 mL×2). The combined organic layers were dried (Na$_2$SO$_4$), filtered and concentrated. The crude product was purified by silica gel chromatography (EtOAc/hexanes: 0-50%, then DCM/MeOH: 10:1) to yield (2R)-4-(7-(2-fluoro-4-(morpholinomethyl)phenyl)-4-oxoquinazolin-3(4H)-yl)-2-methyl-2-(methylsulfonyl)-N-((tetrahydro-2H-pyran-2-yl)oxy)butanamide (150 mg, 0.218 mmol, 40% yield) as a black solid.

LCMS: [M+H] 616.8.

Part E

To a solution of (2R)-4-(7-(2-fluoro-4-(morpholinomethyl)phenyl)-4-oxoquinazolin-3(4H)-yl)-2-methyl-2-(methylsulfonyl)-N-((tetrahydro-2H-pyran-2-yl)oxy)butanamide (150 mg, 0.243 mmol) in methanol (3 mL) was added HCl in dioxane (4M) (3 mL, 12 mmol) and the solution was stirred for one hr. The mixture was concentrated to give a crude product, which was purified by reverse phase HPLC (0.1% TFA, CH$_3$CN/H$_2$O) to give (R)-4-(7-(2-fluoro-4-(morpholinomethyl)phenyl)-4-oxoquinazolin-3 (4H)-yl)-N-hydroxy-2-methyl-2-(methylsulfonyl)butanamide trifluoroacetic acid (50 mg, 0.076 mmol, 31% yield).

LCMS: [M+H] 533.2.

¹H NMR (500 MHz, DMSO-de) δ: ppm 11.02 (s, 1H), 10.20 (s, 1H), 9.25 (s, 1H), 8.41 (s, 1H), 8.27 (d, J=8.3 Hz, 1H), 7.86 (s, 1H), 7.81 (s, 1H), 7.75 (d, J=8.1 Hz, 1H), 7.60-7.44 (m, 2H), 4.43 (s, 2H), 4.15 (d, J=9.9 Hz, 1H), 3.91 (s, 3H), 3.58-3.46 (m, 2H), 3.34 (s, 2H), 3.10 (s, 5H), 2.59 (s, 1H), 2.23 (d, J=8.9 Hz, 1H), 1.62 (s, 3H).

Example 38. (2R)-4-[7-(2,3-difluoro-4-{[(2-methoxyethyl)(methyl)amino]methyl}phenyl)-4-oxo-3,4-dihydroquinazolin-3-yl]-N-hydroxy-2-methanesulfonyl-2-methylbutanamide

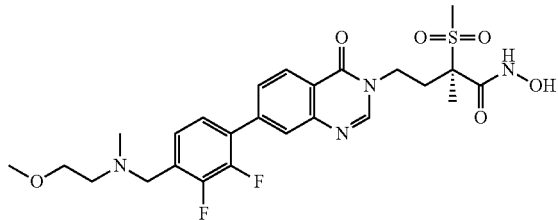 [SMILES: COCCN(C)Cc1ccc(-c2ccc3c(=O)n(CC[C@](C)(C(=O)NO)S(C)(=O)=O)cnc3c2)c(F)c1F]

Part A

A mixture of potassium carbonate (2.476 g, 17.91 mmol), PdCl₂(dppf) (0.874 g, 1.194 mmol), (2R)-4-(7-bromo-4-oxoquinazolin-3(4H)-yl)-2-methyl-2-(methylsulfonyl)-N-((tetrahydro-2H-pyran-2-yl)oxy)butanamide (Intermediate 3) (6 g, 11.94 mmol) and (2,3-difluoro-4-formylphenyl) boronic acid (2.66 g, 14.33 mmol) in 1,4-dioxane (80 mL) and water (8 mL), was heated to 105° C. for 1 hr. The mixture was filtered and the filtrate was concentrated. The residue was diluted with DCM (150 mL) and washed with water (50 mL), brine (50 mL), dried over sodium sulphate and concentrated. The residue was purified with silica gel chromatography (EtOAc/DCM: 0-80%). The product (2R)-4-(7-(2,3-difluoro-4-formylphenyl)-4-oxoquinazolin-3(4H)-yl)-2-methyl-2-(methylsulfonyl)-N-((tetrahydro-2H-pyran-2-yl)oxy)butanamide (4.8 g, 8.01 mmol, 67% yield) was obtained as white solid.

LCMS: [M+H] 564.3.

Part B

To a solution of (2R)-4-(7-(2,3-difluoro-4-formylphenyl)-4-oxoquinazolin-3(4H)-yl)-2-methyl-2-(methylsulfonyl)-N-((tetrahydro-2H-pyran-2-yl)oxy)butanamide (2.4 g, 4.26 mmol) in 1,2-dichloroethane (20 mL) at 0° C. was added 2-methoxy-N-methylethanamine (1.139 g, 12.78 mmol), acetic acid (0.256 g, 4.26 mmol) and sodium triacetoxyhydroborate (2.71 g, 12.78 mmol). The reaction mixture was allowed to warm to room temperature and stirred overnight. The mixture was diluted with DCM (20 mL) and saturated NaHCO₃ solution and extracted with DCM (20 ml×3) The combined organic layers were washed with brine (30 mL), dried over sodium sulphate and concentrated. The residue was purified with silica gel chromatography (MeOH/DCM: 0-20%) to afford (2R)-4-(7-(2,3-difluoro-4-(((2-methoxyethyl)(methyl)amino)methyl)phenyl)-4-oxoquinazolin-3(4H)-yl)-2-methyl-2-(methylsulfonyl)-N-((tetrahydro-2H-pyran-2-yl)oxy)butanamide (2.39 g, 3.57 mmol, 84% yield) as a white solid.

LCMS: [M+H] 637.4.

Part C

A solution of (2R)-4-(7-(2,3-difluoro-4-(((2-methoxyethyl)(methyl)amino)methyl)phenyl)-4-oxoquinazolin-3(4H)-yl)-2-methyl-2-(methylsulfonyl)-N-((tetrahydro-2H-pyran-2-yl)oxy)butanamide (2.3 g, 3.61 mmol) in dichloromethane (50 mL) and methanol (50 mL) was stirred under nitrogen at room temperature followed by the addition of a 4M solution of HCl in dioxane (2.71 mL, 10.84 mmol). The reaction mixture was stirred at room temperature for 4 hr. The reaction was concentrated and the residue was triturated with ethyl acetate/methanol (100 ml/10 ml), filtered, washed with ethyl acetate and concentrated to afford (R)-4-(7-(2,3-difluoro-4-(((2-methoxyethyl)(methyl)amino)methyl)phenyl)-4-oxoquinazolin-3(4H)-yl)-N-hydroxy-2-methyl-2-(methylsulfonyl)butanamide hydrochloride (2.2 g, 3.55 mmol, 98% yield) as white solid.

LCMS: [M+H] 553.3.

¹H NMR (METHANOL-d) δ: ppm 9.33 (s, 1H), 8.49 (d, J=8.3 Hz, 1H), 7.90-8.07 (m, 2H), 7.52-7.77 (m, 2H), 4.74 (d, J=13.4 Hz, 1H), 4.36-4.57 (m, 2H), 4.17-4.35 (m, 1H), 3.75-3.92 (m, 2H), 3.41-3.65 (m, 5H), 3.12 (s, 3H), 2.97 (s, 3H), 2.81-2.92 (m, 1H), 2.48 (ddd, J=13.8, 9.2, 4.8 Hz, 1H), 1.79 (s, 3H).

Example 39. (2R)-4-[7-(4-{[cyclopropyl(methyl)amino]methyl}-3-fluorophenyl)-4-oxo-3,4-dihydroquinazolin-3-yl]-N-hydroxy-2-methanesulfonyl-2-methylbutanamide

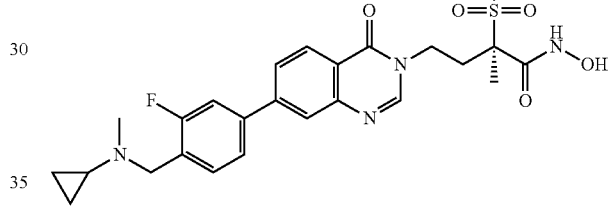

Part A

A reaction vessel was sealed with potassium carbonate (1.651 g, 11.94 mmol), PdCl₂(dppf) (0.437 g, 0.597 mmol), (2R)-4-(7-bromo-4-oxoquinazolin-3(4H)-yl)-2-methyl-2-(methylsulfonyl)-N-((tetrahydro-2H-pyran-2-yl)oxy)butanamide (Intermediate 3) (3 g, 5.97 mmol) and (3-fluoro-4-formylphenyl) boronic acid (1.203 g, 7.17 mmol) and the mixture was heated to 105° C. for 1 hr. The mixture was filtered and the filtrate was concentrated and then diluted with DCM (100 mL). The organic layer was washed with water (50 mL), brine (50 mL), dried over sodium sulphate and concentrated. The residue was purified with silica gel chromatography (EtOAc: 0-100%) to afford (2R)-4-(7-(3-fluoro-4-formylphenyl)-4-oxoquinazolin-3(4H)-yl)-2-methyl-2-(methylsulfonyl)-N-((tetrahydro-2H-pyran-2-yl)oxy)butanamide (2.4 g, 4.27 mmol, 72% yield) as white solid.

LCMS: [M+H] 546.3

Part B

To a solution of (2R)-4-(7-(3-fluoro-4-formylphenyl)-4-oxoquinazolin-3(4H)-yl)-2-methyl-2-(methylsulfonyl)-N-((tetrahydro-2H-pyran-2-yl)oxy) butanamide (160 mg, 0.293 mmol) in 1,2-dichloroethane (2 mL) and methanol (2 mL) at 0° C. was added N-methylcyclopropanamine hydrochloride (63.1 mg, 0.587 mmol), acetic acid (70.4 mg, 1.173 mmol) and sodium triacetoxyhydroborate (249 mg, 1.173 mmol). The reaction mixture was allowed to warm to room temperature and stirred overnight. The mixture was diluted with DCM (20 mL) and saturated NaHCO₃ and the organic layer was washed with water (20 mL), brine (30 mL), dried over sodium sulphate and concentrated. The residue was purified with silica gel chromatography (MeOH/DCM: 0-20%) to arrow (2R)-4-(7-(4-((cyclopropyl(methyl)amino)methyl)-3-fluorophenyl)-4-oxoquinazolin-3(4H)-yl)-2-methyl-2-(methylsulfonyl)-N-((tetrahydro-2H-pyran-2-yl)oxy)butanamide (60 mg, 0.076 mmol, 26% yield) as colorless oil.

LCMS: [M+H] 601.4.

Part C

To a solution of (2R)-4-(7-(4-((cyclopropyl(methyl)amino)methyl)-3-fluorophenyl)-4-oxoquinazolin-3(4H)-yl)-2-methyl-2-(methylsulfonyl)-N-((tetrahydro-2H-pyran-2-yl)oxy)butanamide (60 mg, 0.1 mmol) in dichloromethane (2 mL) and methanol (1 mL) stirred under nitrogen at room temperature was added a 4M solution of HCl in dioxane (0.075 mL, 0.300 mmol). The reaction mixture was stirred at room temperature for 2 hr. The reaction was concentrated and the residue purified by preparative HPLC (5-75% MeCN, H$_2$O, 0.1% TFA) to afford (2R)-4-(7-(4-((cyclopropyl(methyl)amino)methyl)-3-fluorophenyl)-4-oxoquinazolin-3(4H)-yl)-N-hydroxy-2-methyl-2-(methylsulfonyl)butanamide trifluoroacetic acid salt (10 mg, 0.015 mmol, 15% yield) as white solid.

LCMS: [M+H] 517.2.

$^1$H NMR (METHANOL-d) δ: ppm 8.30-8.53 (m, 2H), 8.01 (d, J=1.5, 4 Hz, 1H), 7.93 (dd, J=8.3, 1.8 Hz, 1H), 7.67-7.82 (m, 3H), 4.67 (br.s., 2H), 4.29-4.43 (m, 1H), 4.05 (ddd, J=134, 10.6, 5.6 Hz, 1H), 2.96-3.17 (m, 7H), 2.73 (ddd, J=13.4, 10.4, 5.8 Hz, 1H), 2.35-2.51 (m, 1H), 1.77 (s, 3H), 0.78-1.11 (m, 4H).

Example 40. (2R)-4-(7-{4-[(3,3-difluoroazetidin-1-yl)methyl]-2-fluorophenyl}-4-oxo-3,4-dihydroquinazolin-3-yl)-N-hydroxy-2-methanesulfonyl-2-methylbutanamide

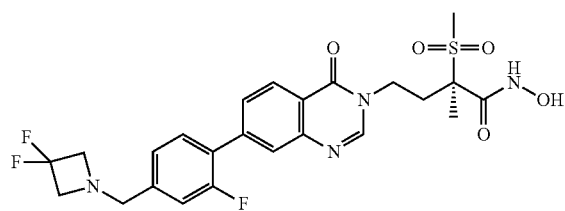 [SMILES: C[C@@](CCn1cnc2cc(-c3ccc(CN4CC(F)(F)C4)cc3F)ccc2c1=O)(C(=O)NO)S(C)(=O)=O]

Part A

To a solution of 2-(4-(bromomethyl)-2-fluorophenyl)-4,4,5,5-tetramethyl-1,3,2-dioxaborolane (200 mg, 0.635 mmol) in acetonitrile (10 mL) was added 3,3-difluoroazetidine hydrochloride (107 mg, 0.825 mmol) and DIPEA (0.244 mL, 1.397 mmol). The reaction mixture was heated to 60° C. overnight. The mixture was diluted with DCM (20 mL) and water (10 ml) and the mixture was extracted with DCM (10 ml×3). The combined organic layers were washed with brine (30 mL), dried over sodium sulphate and evaporated in vacuo to give crude 3,3-difluoro-1-(3-fluoro-4-(4,4,5,5-tetramethyl-1,3,2-dioxaborolan-2-yl)benzyl)azetidine (210 mg, 0.321 mmol, 51% yield) as colorless oil.

LCMS: [M+H] 328.1.

Part B

A reaction vessel was sealed with potassium carbonate (83 mg, 0.597 mmol), PdCl$_2$(dppf) (29.1 mg, 0.040 mmol), (2R)-4-(7-bromo-4-oxoquinazolin-3(4H)-yl)-2-methyl-2-(methylsulfonyl)-N-((tetrahydro-2H-pyran-2-yl)oxy)butanamide (Intermediate 3) (200 mg, 0.398 mmol) and 3,3-difluoro-1-(3-fluoro-4-(4,4,5,5-tetramethyl-1,3,2-dioxaborolan-2-yl)benzyl)azetidine (195 mg, 0.597 mmol) and heated in a microwave to 105° C. for 30 min. The organic phase was diluted with DCM (20 mL) and washed with water (20 mL), brine (30 mL), dried over sodium sulphate and evaporated in vacuo. The residue was purified with silica gel chromatography (MeOH/DCM: 0-20%) affording (2R)-4-(7-(4-((3,3-difluoroazetidin-1-yl)methyl)-2-fluorophenyl)-4-oxoquinazolin-3(4H)-yl)-2-methyl-2-(methylsulfonyl)-N-((tetrahydro-2Hpyran-2-yl)oxy)butanamide (250 mg, 0.353 mmol, 89% yield) as a colorless oil.

LCMS: [M+H] 623.3.

N30349-89

Part C

To a solution of (2R)-4-(7-(4-((3,3-difluoroazetidin-1-yl)methyl)-2-fluorophenyl)-4-oxoquinazolin-3(4H)-yl)-2-methyl-2-(methylsulfonyl)-N-((tetrahydro-2H-pyran-2-yl)oxy)butanamide (100 mg, 0.161 mmol) in dichloromethane (3 mL) and methanol (3 mL) stirred under nitrogen at room temperature was added a solution of hydrogen chloride in dioxane (0.120 mL, 0.482 mmol). The reaction mixture was stirred at room temperature for 2 hr. The reaction was concentrated and then purified by preparative HPLC (5-75% MeCN, H$_2$O, 0.1% TFA) to afford (R)-4-(7-(4-((3,3-difluoroazetidin-1-yl)methyl)-2-fluorophenyl)-4-oxoquinazolin-3(4H)-yl)-N-hydroxy-2-methyl-2-(methylsulfonyl)butanamide trifluoroacetic acid salt (80 mg, 0.116 mmol, 73% yield) as a white solid.

LCMS: [M+H] 539.2.

$^1$H NMR (METHANOL-d4) δ: ppm 8.29-8.50 (m, 1H), 7.90 (s, 1H), 7.69-7.84 (m, 2H), 7.40-7.58 (m, 2H), 4.76 (t, J=11.0 Hz, 4H), 4.58 (s, 2H), 4.28-4.42 (m, 1H), 3.97-4.14 (m, 1H), 3.13 (s, 3H), 2.73 (ddd, J=13.3, 10.4, 5.6 Hz, 1H), 2.44 (ddd, J=13.4, 10.5, 4.9 Hz, 1H), 1.77 (s, 3H).

Example 41. (2R)-4-(7-{4-[(cyclopropylamino)methyl]-2-fluorophenyl}-4-oxo-3,4-dihydroquinazolin-3-yl)-N-hydroxy-2-methanesulfonyl-2-methylbutanamide

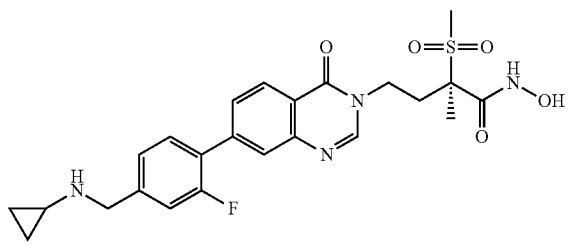 [SMILES: C[C@@](CCn1cnc2cc(-c3ccc(CNC4CC4)cc3F)ccc2c1=O)(C(=O)NO)S(C)(=O)=O]

Part A

A mixture of potassium carbonate (1.376 g, 9.95 mmol), PdCl$_2$(dppf) (0.364 g, 0.498 mmol), (2R)-4-(7-bromo-4-oxoquinazolin-3(4H)-yl)-2-methyl-2-(methylsulfonyl)-N-((tetrahydro-2H-pyran-2-yl)oxy)butanamide (Intermediate 3) (2.5 g, 4.98 mmol) and N-(3-fluoro-4-(4,4,5,5-tetramethyl-1,3,2-dioxaborolan-2-yl)benzyl)cyclopropanamine (1.884 g, 6.47 mmol) in 1,4-dioxane (30 mL) and water (3 mL) was heated to 95° C. for 30 min. The mixture was filtered and the filtrated was diluted with DCM (50 mL) and water (50 ml). The aqueous layer was extracted with DCM (50 ml×3) and the combined organic layers were washed with brine (50 mL), dried over sodium sulphate and evaporated in vacuo and the residue was purified with silica gel chromatography (MeOH/DCM 0-20%) to afford (2R)-4-(7-(4-((cyclopropylamino)methyl)-2-fluorophenyl)-4-oxoquinazolin-3(4H)-yl)-2-methyl-2-(methylsulfonyl)-N-((tetrahydro-2H-pyran-2-yl)oxy)butanamide (1 g, 1.705 mmol, 34% yield) was obtained as colorless gum.

LCMS: [M+H] 587.2.

Part B

To a solution of (2R)-4-(7-(4-((cyclopropylamino)methyl)-2-fluorophenyl)-4-oxoquinazolin-3(4H)-yl)-2-methyl-2-(methylsulfonyl)-N-((tetrahydro-2H-pyran-2-yl)oxy)butanamide (1 g, 1.705 mmol) in dichloromethane (10 mL) and methanol (15 mL) stirred under nitrogen at room temperature was added a solution of HCl in dioxane (0.426 mL, 1.705 mmol). The reaction mixture was stirred at room temperature for 2 hr. The reaction was concentrated in vacuo and the residue triturated with methanol/ethyl acetate/diethyl ether and filtered. The solid was dissolved in water (10 ml) and lyophilized to give (R)-4-(7-(4-((cyclopropylamino)methyl)-2-fluorophenyl)-4-oxoquinazolin-3(4H)-yl)-N-hydroxy-2-methyl-2-(methylsulfonyl)butanamide hydrochloride (817 mg, 1.440 mmol, 84% yield) as a white solid.

LCMS: [M+H] 503.2.

$^1$H NMR (400 MHz, METHANOL-d4) δ: ppm 0.74-1.14 (m, 4H), 1.79 (s, 3H), 2.36-2.59 (m, 1H), 2.73-2.95 (m, 2H), 3.12 (s, 3H), 4.16-4.34 (m, 1H), 4.35-4.58 (m, 3H), 7.42-7.66 (m, 2H), 7.79 (t, J=7.96 Hz, 1H), 7.90-8.10 (m, 2H), 8.46 (d, J=8.34 Hz, 1H), 9.36 (br.s., 1H).

Example 42. (2R)—N-hydroxy-2-methanesulfonyl-2-methyl-4-(7-{4-[2-(morpholin-4-yl)ethyl]phenyl}-4-oxo-3,4-dihydroquinazolin-3-yl)butanamide

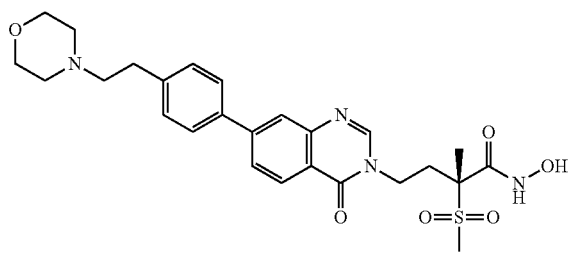 [SMILES: C[C@@](CCn1cnc2cc(-c3ccc(CCN4CCOCC4)cc3)ccc2c1=O)(C(=O)NO)S(C)(=O)=O]

Part A

A reaction vessel sealed with potassium carbonate (70.5 mg, 0.510 mmol), PdCl$_2$(dppf) (18.66 mg, 0.026 mmol), (R)-ethyl 4-(7-bromo-4-oxoquinazolin-3(4H)-yl)-2-methyl-2-(methylsulfonyl)butanoate (Intermediate 2) (110 mg, 0.255 mmol) and (4-(2-morpholinoethyl)phenyl)boronic acid (71.9 mg, 0.306 mmol) was heated in a microwave to 110° C. for 30 min. The organic phase was diluted with DCM (20 mL) and washed with water (20 mL), saturated brine (30 mL), dried over sodium sulphate and concentrated. The residue was purified with silica gel chromatography (MeOH/DCM: 0-20%) affording (R)-ethyl 2-methyl-2-(methylsulfonyl)-4-(7-(4-(2-morpholinoethyl)phenyl)-4-oxoquinazolin-3(4H)-yl)butanoate (123 mg, 0.198 mmol, 77% yield) as a white solid.

LCMS: [M+H] 542.4.

Part B

To a solution of (R)-ethyl 2-methyl-2-(methylsulfonyl)-4-(7-(4-(2-morpholinoethyl)phenyl)-4-oxoquinazolin-3(4H)-yl)butanoate (123 mg, 0.227 mmol) in 1,4-dioxane (2 mL) was added a 50% solution of hydroxylamine in water (1 mL, 16.32 mmol) and 1M LiOH in water (0.5 ml, 0.500 mmol) at room temperature and the reaction stirred overnight. The reaction was concentrated and purified by preparative HPLC (5-70% MeCN, H$_2$O, 0.1% TFA) to afford (R)—N-hydroxy-2-methyl-2-(methylsulfonyl)-4-(7-(4-(2-morpholinoethyl)phenyl)-4-oxoquinazolin-3(4H)-yl)butanamide trifluoroacetic acid salt (76 mg, 0.112 mmol, 50% yield) as white solid.

LCMS: [M+H] 529.4.

$^1$H NMR (METHANOL-d4) δ: ppm 8.39 (s, 1H), 8.30 (d, J=8.3 Hz, 1H), 7.90 (s, 1H), 7.85 (d, J=8.3 Hz, 1H), 7.76 (d, J=7.8 Hz, 2H), 7.48 (d, J=7.8 Hz, 2H), 4.24-4.40 (m, 1H), 3.95-4.21 (m, 3H), 3.82 (t, J=12.0 Hz, 2H), 3.63 (d, J=11.6 Hz, 2H), 3.41-3.54 (m, 2H), 3.05-3.31 (m, 7H), 2.62-2.77 (m, 1H), 2.33-2.50 (m, 1H), 1.77 (s, 3H).

Example 43. (2R)-4-(7-{2-fluoro-4-[2-(morpholin-4-yl)ethyl]phenyl}-4-oxo-3,4-dihydroquinazolin-3-yl)-N-hydroxy-2-methanesulfonyl-2-methylbutanamide

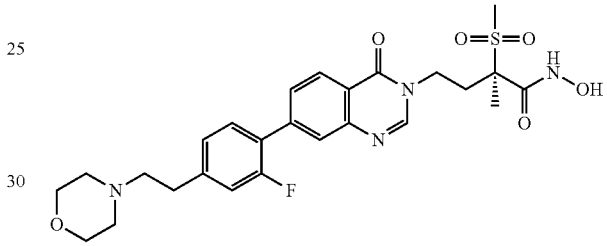

Part A

To a solution of 1-bromo-4-(bromomethyl)-2-fluorobenzene (9 g, 33.6 mmol) in ethanol (180 mL) was added NaCN (1.811 g, 37.0 mmol) and the reaction was refluxed for 20 hr. The mixture was concentrated under vacuum and the resulting residue was dissolved in water and extracted with ethyl acetate. The organic phase was washed with brine, dried over sodium sulfate and concentrated. The residue was purified by silica gel column chromatography (EtOAc/PE: 0-15%) to give 2-(4-bromo-3-fluorophenyl)acetonitrile (5.8 g, 25.9 mmol, 77% yield) as a yellow solid.

Part B

A suspension of 2-(4-bromo-3-fluorophenyl)acetonitrile (4.5 g, 21.02 mmol) in HCl (25 ml, 823 mmol) was stirred at 80° C. overnight. The reaction mixture was treated with saturated NaHCO$_3$ (aq.) and then extracted with ethyl acetate. The aqueous layer was acidified with conc. HCl and filtered to provide 2-(4-bromo-3-fluorophenyl)acetic acid (4.3 g, 18.45 mmol, 88% yield) as a white solid.

LCMS: [M+H] 232.8.

Part C 2-(4-bromo-3-fluorophenyl)acetic acid (5.44 g, 23.34 mmol) was dissolved in tetrahydrofuran (5 mL) and a solution of BH$_3$.THF (46.7 mL, 46.7 mmol) was added slowly under nitrogen at 0° C. The reaction was stirred for about 1 hr. when methanol was slowly added to quench the reaction. The mixture was concentrated and methanol was added. This was repeat two more times. The solution was passed through a short pad of silica gel eluting with 1:1 EtOAc/heptane and concentrated to give 2-(3-methoxy-4-methylphenyl)ethanol as a colorless oil.

LCMS: [M+Na] 240.

Part D

A mixture of (R)-(3-(4-ethoxy-3-methyl-3-(methylsulfonyl)-4-oxobutyl)-4-oxo-3,4-dihydroquinazolin-7-yl)boronic acid (Intermediate 19) (6.3 g, 7.95 mmol), 2-(4-bromo-3-fluorophenyl)ethanol (2.090 g, 9.54 mmol), K$_2$CO$_3$ (2.197 g, 15.90 mmol), PdCl$_2$(dppf)-CH$_2$Cl$_2$ adduct (1.298 g, 1.59 mmol) in acetonitrile (150 mL) and water (25.00 mL) was stirred overnight at 80° C. under N$_2$. The reaction mixture was concentrated and the residue was extracted with EtOAc (300 ml). The organic phase was washed with brine, dried over sodium sulphate and concentrated. The residue was purified by silica gel column chromatography (EtOAc/PE: 25-100%) to give (R)-ethyl 4-(7-(2-fluoro-4-(2-hydroxyethyl)phenyl)-4-oxoquinazolin-3(4H)-yl)-2-methyl-2-(methylsulfonyl)butanoate (2.2 g, 3.36 mmol, 42% yield) as a yellow solid.

LCMS: [M+H] 491.2.

Part E

A mixture of (R)-ethyl 4-(7-(2-fluoro-4-(2-hydroxyethyl)phenyl)-4-oxoquinazolin-3(4H)-yl)-2-methyl-2-(methylsulfonyl)butanoate (2.2 g, 4.48 mmol), lithium hydroxide monohydrate (0.565 g, 13.45 mmol) in tetrahydrofuran (15 mL) and water (15 mL) was stirred at 25° C. for 2 hr under a nitrogen atmosphere. The solvent was removed and water (80 mL) was added. The aqueous layer was extracted with 2-methyl tetrahydrofuran (100 mL) and the resulting aqueous layer was acidified to pH 3 using 1M HCl (about 10 mL). The solvent was extracted 2-methyl tetrahydrofuran (200 mL) and dried with Na$_2$SO$_4$, filtered and concentrated to give (R)-4-(7-(2-fluoro-4-(2-hydroxyethyl)phenyl)-4-oxoquinazolin-3(4H)-yl)-2-methyl-2-(methylsulfonyl)butanoic acid (2.05 g, 4.43 mmol, 99% yield) as a yellow solid.

LCMS: [M+H] 462.8.

Part F

To a solution of (R)-4-(7-(2-fluoro-4-(2-hydroxyethyl)phenyl)-4-oxoquinazolin-3(4H)-yl)-2-methyl-2-(methylsulfonyl)butanoic acid (2.0 g, 4.32 mmol) in dichloromethane (100 mL) was added O-(tetrahydro-2H-pyran-2-yl)hydroxylamine (1.013 g, 8.65 mmol), HATU (3.29 g, 8.65 mmol) and triethylamine (3.01 mL, 21.62 mmol). The resulting mixture was stirred at 25° C. for 2 hr. The reaction mixture was diluted with DCM (100 ml) and the organic phase was washed with saturated sodium carbonate, brine, dried over sodium sulphate and concentrated. The residue was purified by silica gel column chromatography (MeOH/DCM: 0-10%) to give (2R)-4-(7-(2-fluoro-4-(2-hydroxyethyl)phenyl)-4-oxoquinazolin-3(4H)-yl)-2-methyl-2-(methylsulfonyl)-N-((tetrahydro-2H-pyran-2-yl)oxy)butanamide (3 g, 4 mmol, 93% yield) as a yellow foam.

Part G

To a mixture of (2R)-4-(7-(2-fluoro-4-(2-hydroxyethyl)phenyl)-4-oxoquinazolin-3(4H)-yl)-2-methyl-2-(methylsulfonyl)-N-((tetrahydro-2H-pyran-2-yl)oxy)butanamide (300 mg, 0.534 mmol) in dichloromethane (7.5 mL) was added triphenylphosphine (560 mg, 2.137 mmol) and 1-bromopyrrolidine-2,5-dione (285 mg, 1.603 mmol) at 0° C. The resulting mixture was stirred at 0° C. for 45 min. MeOH (7.5 mL) was added at 0° C. and the reaction mixture was evaporated to dryness affording (2R)-4-(7-(4-(2-bromoethyl)-2-fluorophenyl)-4-oxoquinazolin-3(4H)-yl)-2-methyl-2-(methylsulfonyl)-N-((tetrahydro-2H-pyran-2-yl)oxy)butanamide (1.1 g, 0.440 mmol, 82% yield) as a yellow oil.

LCMS: [M+H] 540.0.

Part H

A mixture of (R)-4-(7-(4-(2-bromoethyl)-2-fluorophenyl)-4-oxoquinazolin-3(4H)-yl)-N-hydroxy-2-methyl-2-(methylsulfonyl)butanamide (1 g, 0.463 mmol), morpholine (0.806 g, 9.25 mmol), KI (0.038 g, 0.231 mmol) and N,N-dimethylformamide (5.5 mL) was stirred at 70° C. for 30 min under microwave radiation. The crude was evaporated and the residue was purified by preparative HPLC affording (R)-4-(7-(2-fluoro-4-(2-morpholinoethyl)phenyl)-4-oxoquinazolin-3(4H)-yl)-N-hydroxy-2-methyl-2-(methylsulfonyl)butanamide trifluoroacetic acid salt (97 mg, 0.138 mmol, 30% yield) as a white solid.

LCMS: [M+H] 547.2.

$^1$H NMR (500 MHz, DMSO-d$_6$) δ: ppm 11.02 (s, 1H), 10.20 (s, 1H), 9.25 (s, 1H), 8.41 (s, 1H), 8.25 (d, J=8.3 Hz, 1H), 7.83 (s, 1H), 7.73 (d, J=8.3 Hz, 1H), 7.68 (t, J=8.1 Hz, 1H), 7.37 (d, J=12.0 Hz, 1H), 7.30 (d, J=8.0 Hz, 1H), 4.20-4.11 (m, 1H), 4.03 (d, J=11.1 Hz, 2H), 3.96-3.87 (m, 1H), 3.70 (s, 2H), 3.52 (s, 2H), 3.48-3.41 (m, 2H), 3.20-3.04 (m, 7H), 2.58 (d, J=14.4, 12.0, 5.4 Hz, 1H), 2.27-2.16 (m, 1H), 1.62 (s, 3H).

Example 44. (2R)—N-hydroxy-4-{7-[4-(2-hydroxyethyl)phenyl]-4-oxo-3,4-dihydroquinazolin-3-yl}-2-methanesulfonyl-2-methylbutanamide

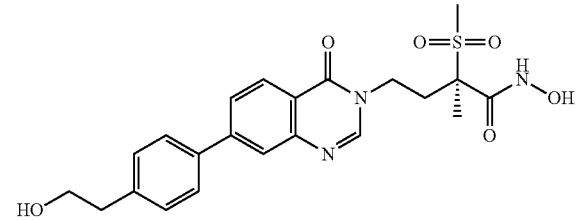 [SMILES: C[C@@](CCn1cnc2cc(-c3ccc(CCO)cc3)ccc2c1=O)(C(=O)NO)S(C)(=O)=O]

Part A

A reaction vessel was sealed with potassium carbonate (83 mg, 0.597 mmol), PdCl$_2$(dppf) (21.85 mg, 0.030 mmol), (2R)-4-(7-bromo-4-oxoquinazolin-3(4H)-yl)-2-methyl-2-(methylsulfonyl)-N-((tetrahydro-2H-pyran-2-yl)oxy)butanamide (Intermediate 3) (150 mg, 0.299 mmol) and (4-(2-hydroxyethyl)phenyl)boronic acid (64.4 mg, 0.388 mmol) and heated in a microwave to 110° C. for 30 min. The organic phase was diluted with DCM (20 mL) and washed with water (20 mL), brine (30 mL), dried over sodium sulphate and evaporated in vacuo and the residue was purified with silica gel chromatography (EtOAc/hexanes: 0-20%) to afford (2R)-4-(7-(4-(2-hydroxyethyl)phenyl)-4-oxoquinazolin-3(4H)-yl)-2-methyl-2-(methylsulfonyl)-N-((tetrahydro-2H-pyran-2-yl)oxy)butanamide (130 mg, 0.237 mmol, 79% yield) as a colorless oil.

LCMS: [M+H] 544.4.

Part B

To a solution of (2R)-4-(7-(4-(2-hydroxyethyl)phenyl)-4-oxoquinazolin-3(4H)-yl)-2-methyl-2-(methylsulfonyl)-N-((tetrahydro-2H-pyran-2-yl)oxy)butanamide (128 mg, 0.235 mmol) in dichloromethane (3 mL) and methanol (2 mL) stirred under nitrogen at room temperature was added a solution of 4M HCl in dioxane (0.589 mL, 2.355 mmol). The reaction mixture was stirred at room temperature for 4 hr. The reaction was concentrated in vacuo and then triturated with ethyl acetate/methanol (10 ml/10 ml), filtered and the residue washed with ethyl acetate to afford (R)—N-hydroxy-4-(7-(4-(2-hydroxyethyl)phenyl)-4-oxoquinazolin-3(4H)-yl)-2-methyl-2-(methylsulfonyl)butanamide (105 mg, 0.217 mmol, 92% yield) as white solid.

LCMS: [M+H] 460.3.

¹H NMR (METHANOL-d4) δ: ppm 9.44 (s, 1H), 8.42 (d, J=8.3 Hz, 1H), 8.07 (dd, J=8.5, 1.1 Hz, 1H), 7.94 (s, 1H), 7.74 (d, J=8.1 Hz, 2H), 7.46 (d, J=8.1 Hz, 2H), 4.19-4.49 (m, 2H), 3.84 (t, J=6.8 Hz, 2H), 3.11 (s, 3H), 2.76-2.97 (m, 3H), 2.47 (ddd, J=13.6, 9.1, 4.5 Hz, 1H), 1.78 (s, 3H).

Example 45. (2R)-4-{7-[2-fluoro-4-(2-hydroxyethyl)phenyl]-4-oxo-3,4-dihydroquinazolin-3-yl}-N-hydroxy-2-methanesulfonyl-2-methylbutanamide

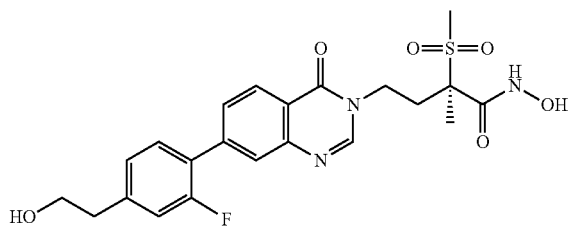 [SMILES: C[C@@](CCn1cnc2cc(-c3ccc(CCO)cc3F)ccc2c1=O)(C(=O)NO)S(C)(=O)=O]

Part A

A mixture of (R)-(3-(4-ethoxy-3-methyl-3-(methylsulfonyl)-4-oxobutyl)-4-oxo-3,4-dihydroquinazolin-7-yl)boronic acid (Intermediate 19) (6.3 g, 7.95 mmol), 2-(4-bromo-3-fluorophenyl)ethanol (2.09 g, 9.54 mmol), K₂CO₃ (2.197 g, 15.90 mmol), PdCl₂(dppf)-CH₂Cl₂ adduct (1.298 g, 1.590 mmol) in acetonitrile (150 mL) and water (25 mL) was stirred overnight at 80° C. under N₂. The reaction mixture was concentrated and the residue was extracted with EtOAc (300 ml). The organic phase was washed with brine, dried over sodium sulphate and evaporated in vacuo. The residue was purified by silica gel column chromatography (EtOAc/PE: 25-100%) to give (R)-ethyl 4-(7-(2-fluoro-4-(2-hydroxyethyl)phenyl)-4-oxoquinazolin-3(4H)-yl)-2-methyl-2-(methylsulfonyl)butanoate (2.2 g, 3.36 mmol, 42% yield) as a yellow solid.

LCMS: [M+H] 491.2.

Part B

A mixture of (R)-ethyl 4-(7-(2-fluoro-4-(2-hydroxyethyl)phenyl)-4-oxoquinazolin-3(4H)-yl)-2-methyl-2-(methylsulfonyl)butanoate (2.2 g, 4.48 mmol), lithium hydroxide monohydrate (0.565 g, 13.45 mmol) in tetrahydrofuran (15 mL) and water (15 mL) was stirred at 25° C. for 2 hr under a nitrogen atmosphere. The solvent was removed and water (80 mL) was added. The aqueous layer was extracted with 2-methyl tetrahydrofuran (100 mL) and the resulting aqueous layer was acidified to pH 3 using 1M HCl (about 10 mL). The solvent was extracted 2-methyl tetrahydrofuran (200 mL) and dried with Na₂SO₄, filtered and concentrated to give (R)-4-(7-(2-fluoro-4-(2-hydroxyethyl)phenyl)-4-oxoquinazolin-3(4H)-yl)-2-methyl-2-(methylsulfonyl)butanoic acid (2.05 g, 4.43 mmol, 99% yield) as a yellow solid.

LCMS: [M+H] 462.8.

Part C

To a solution of (R)-4-(7-(2-fluoro-4-(2-hydroxyethyl)phenyl)-4-oxoquinazolin-3(4H)-yl)-2-methyl-2-(methylsulfonyl)butanoic acid (2.0 g, 4.32 mmol) in dichloromethane (100 mL) was added O-(tetrahydro-2H-pyran-2-yl)hydroxylamine (1.013 g, 8.65 mmol), HATU (3.29 g, 8.65 mmol) and triethylamine (3.01 mL, 21.62 mmol). The resulting mixture was stirred at 25° C. for 2 hr. The reaction mixture was diluted with DCM (100 ml) and the organic phase was washed with saturated sodium carbonate, brine, dried over sodium sulphate and evaporated in vacuo. The residue was purified by silica gel column chromatography (MeOH/DCM 0-10%) to give (2R)-4-(7-(2-fluoro-4-(2-hydroxyethyl)phenyl)-4-oxoquinazolin-3(4H)-yl)-2-methyl-2-(methylsulfonyl)-N-((tetrahydro-2H-pyran-2-yl)oxy)butanamide (3 g, 4.00 mmol, 93% yield) as a yellow foam.

LCMS: [M+H] 562.2.

Part D

To a stirred solution of (2R)-4-(7-(2-fluoro-4-(2-hydroxyethyl)phenyl)-4-oxoquinazolin-3(4H)-yl)-2-methyl-2-(methylsulfonyl)-N-((tetrahydro-2H-pyran-2-yl)oxy)butanamide (150 mg, 0.267 mmol) in dichloromethane (5 mL) and methanol (5.00 mL) was added HCl (0.668 mL, 2.67 mmol) at 30° C. and this mixture was stirred at this temperature for an hour. The solvent was removed in vacuo and the residue was purified by preparative HPLC to afford (R)-4-(7-(2-fluoro-4-(2-hydroxyethyl)phenyl)-4-oxoquinazolin-3(4H)-yl)-N-hydroxy-2-methyl-2-(methylsulfonyl)butanamide (60 mg, 0.126 mmol, 47% yield) as a white solid.

LCMS: [M+H] 477.9.

¹H NMR (500 MHz, DMSO-d₆) δ: ppm 11.02 (s, 1H), 8.40 (s, 1H), 8.23 (d, J=8.3 Hz, 1H), 7.81 (s, 1H), 7.73 (d, J=8.3 Hz, 1H), 7.57 (t, J=8.2 Hz, 1H), 7.24 (J=15.0, 10.2 Hz, 2H), 4.20-4.10 (m, 1H), 3.92-3.86 (m, 1H), 3.67 (t, J=6.7 Hz, 2H), 3.10 (s, 3H), 2.80 (t, J=6.7 Hz, 2H), 2.62-2.55 (m, 1H), 2.21 (td, J=13.1, 4.9 Hz, 1H), 1.61 (s, 3H).

N29830-62

Example 46. (2R)-4-[7-(4-ethoxyphenyl)-4-oxo-3,4-dihydroquinazolin-3-yl]-N-hydroxy-2-methanesulfonyl-2-methylbutanamide

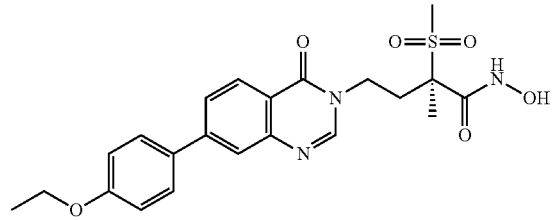 [SMILES: CCOc1ccc(-c2ccc3c(=O)n(CC[C@](C)(C(=O)NO)S(C)(=O)=O)cnc3c2)cc1]

Part A

A reaction vessel was sealed with potassium carbonate (83 mg, 0.597 mmol), PdCl₂(dppf) (21.85 mg, 0.030 mmol), (2R)-4-(7-bromo-4-oxoquinazolin-3(4H)-yl)-2-methyl-2-(methylsulfonyl)-N-((tetrahydro-2H-pyran-2-yl)oxy)butanamide (Intermediate 3) (150 mg, 0.299 mmol) and (4-ethoxyphenyl)boronic acid (64.4 mg, 0.388 mmol) and heated in a microwave to 110° C. for 30 min. The organic phase was diluted with DCM (20 mL) and washed with water (20 mL), brine (30 mL), dried over sodium sulphate and evaporated in vacuo. The residue was purified by silica gel chromatography (EtOAc/DCM: 0-80%) to afford (2R)-4-(7-(4-ethoxyphenyl)-4-oxoquinazolin-3(4H)-yl)-2-methyl-2-(methylsulfonyl)-N-((tetrahydro-2H-pyran-2-yl)oxy)butanamide (130 mg, 0.237 mmol, 79% yield) as a colorless oil.

LCMS: [M+H] 544.3.

Part B

To a solution of (2R)-4-(7-(4-ethoxyphenyl)-4-oxoquinazolin-3(4H)-yl)-2-methyl-2-(methylsulfonyl)-N-((tetrahydro-2H-pyran-2-yl)oxy)butanamide (130 mg, 0.239 mmol) in dichloromethane (3 mL) and methanol (2 mL) stirred under nitrogen at room temperature was added a solution of 4M HCl in dioxane (0.598 mL, 2.391 mmol). The reaction mixture was stirred at room temperature for 4 hr. The reaction was concentrated and triturated with ethyl acetate/methanol (10 ml/10 ml), filtered, and washed with ethyl acetate to afford (R)-4-(7-(4-ethoxyphenyl)-4-oxoquinazolin-3(4H)-yl)-N-hydroxy-2-methyl-2-(methylsulfonyl) butanamide (103 mg, 0.213 mmol, 89% yield) as a white solid.

LCMS: [M+H] 460.2.

$^1$H NMR (METHANOL-d4) δ: ppm 9.38 (s, 1H), 8.40 (d, J=8.6 Hz, 1H), 8.04 (dd, J=8.5, 1.6 Hz, 1H), 7.89 (d, J=1.5 Hz, 1H), 7.76 (d, J=8.8 Hz, 2H), 7.11 (d, J=8.8 Hz, 2H), 4.40 (ddd, J=13.8, 9.2, 4.8 Hz, 1H), 4.21-4.32 (m, 1H), 4.14 (q, J=7.0 Hz, 2H), 3.11 (s, 3H), 2.86 (ddd, J=13.6, 9.2, 6.7 Hz, 1H), 2.47 (td, J=9.2, 4.7 Hz, 1H), 1.78 (s, 3H), 1.45 (t, J=6.9 Hz, 3H).

Example 47. (2R)—N-hydroxy-2-methanesulfonyl-4-{7-[4-(methoxymethyl)phenyl]-4-oxo-3,4-dihydroquinazolin-3-yl}-2-methylbutanamide

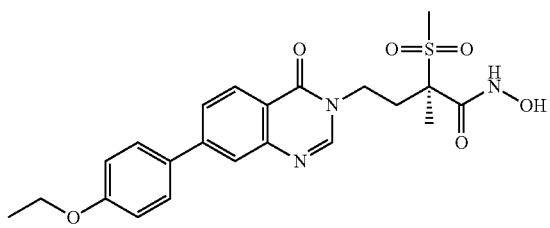 [SMILES: CCOc1ccc(-c2ccc3c(=O)n(CC[C@](C)(C(=O)NO)S(C)(=O)=O)cnc3c2)cc1]

Part A

A mixture of potassium carbonate (1.238 g, 8.96 mmol), PdCl$_2$(dppf) (0.437 g, 0.597 mmol), (2R)-4-(7-bromo-4-oxoquinazolin-3(4H)-yl)-2-methyl-2-(methyl)-N-((tetrahydro-2H-pyran-2-yl)oxy)butanamide (Intermediate 3) (3 g, 5.97 mmol) and (4-(methoxymethyl)phenyl)boronic acid (1.189 g, 7.17 mmol) in 1,4-dioxane (80 mL) and water (8 mL) was heated to 105° C. for 30 min. The mixture was filtered and the organic phase was concentrated. The residue was diluted with DCM (200 mL) and washed with water (50 mL), brine (50 mL), dried over sodium sulphate and concentrated. The residue was purified with silica gel chromatography (EtOAc/DCM: 0-80%) to give (2R)-4-(7-(4-(methoxymethyl)phenyl)-4-oxoquinazolin-3(4H)-yl)-2-methyl-2-(methylsulfonyl)-N-((tetrahydro-2H-pyran-2-yl)oxy)butanamide (3 g, 5.46 mmol, 91% yield) as a white solid.

LCMS: [M+H] 544.3.

Part B

To a solution of (2R)-4-(7-(4-(methoxymethyl)phenyl)-4-oxoquinazolin-3(4H)-yl)-2-methyl-2-(methylsulfonyl)-N-((tetrahydro-2H-pyran-2-yl)oxy)butanamide (3 g, 5.52 mmol) in dichloromethane (50 mL) and methanol (50 mL) stirred under nitrogen at room temperature was added a solution of 4M HCl in dioxane (4.14 mL, 16.56 mmol) and the reaction mixture was stirred at room temperature for 2 hr. The reaction was concentrated and the residue triturated with ethyl acetate/methanol (10 ml/10 ml), filtered and was washed with ethyl acetate and to afford (R)—N-hydroxy-4-(7-(4-(methoxymethyl)phenyl)-4-oxoquinazolin-3(4H)-yl)-2-methyl-2-(methylsulfonyl)butanamide (2 g, 4.13 mmol, 75% yield) as white solid.

LCMS: [M+H] 460.2.

$^1$H NMR (METHANOL-d4) δ: ppm 9.46 (d, J=1.0 Hz, 1H), 8.46 (d, J=8.3 Hz, 1H), 7.91-8.07 (m, 2H), 7.67 (td, J=7.8, 1.8 Hz, 1H), 7.49-7.59 (m, 1H), 7.24-7.47 (m, 2H), 4.42 (td, J=9.2, 4.7 Hz, 1H), 4.19-4.35 (m, 1H), 3.11 (s, 3H), 2.88 (ddd, J=13.7, 9.2, 6.9 Hz, 1H), 2.48 (ddd, J=13.8, 9.1, 4.9 Hz, 1H), 1.79 (s, 3H).

Example 48. (2R)-4-{7-[2-fluoro-4-(2-methoxyethyl)phenyl]-4-oxo-3,4-dihydroquinazolin-3-yl}-N-hydroxy-2-methanesulfonyl-2-methylbutanamide

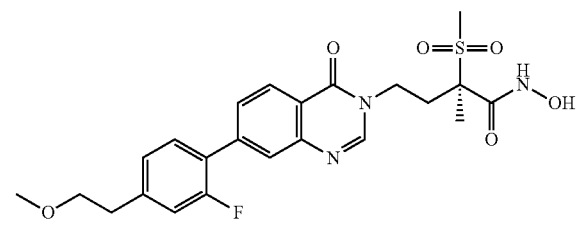 [SMILES: COCCc1ccc(-c2ccc3c(=O)n(CC[C@](C)(C(=O)NO)S(C)(=O)=O)cnc3c2)c(F)c1]

Part A

Under N$_2$, to a solution of 2-(4-bromo-3-fluorophenyl) ethanol (1 g, 4.57 mmol) in tetrahydrofuran (THF) (10 mL) was added sodium hydride (0.219 g, 5.48 mmol) at 0° C. and the reaction was stirred at 30° C. for 30 min. Iodomethane (6.48 g, 45.7 mmol) was added to the reaction mixture at 0° C. and the reaction was stirred at 30° C. for 17 hr. To this was added aq. NH$_4$OH (5 mL) and the reaction was stirred at 30° C. for 1 hr and the solvent was removed. EtOAc (100 mL) and water (100 mL) was added and the aqueous layer was extracted with EtOAc (100 mL×2). The combined organic layers were washed with brine (200 mL), dried (Na$_2$SO$_4$) and concentrated. The crude product was purified by silica gel chromatography (EtOAc/hexanes: 0-10%) to give 1-bromo-2-fluoro-4-(2-methoxyethyl)benzene (800 mg, 3.26 mmol, 65% yield) as an oil.

LCMS: [M-MeOH] 201.0.

Part B

A mixture of 1-bromo-2-fluoro-4-(2-methoxyethyl)benzene (439 mg, 1.881 mmol), (R)-ethyl-2-methyl-2-(methylsulfonyl)-4-(4-oxo-7-(4,4,5,5-tetramethyl-1,3,2-dioxaborolan-2-yl)quinazolin-3(4H)-yl)butanoate (Intermediate 20) (750 mg, 1.568 mmol), PdCl$_2$(dppf)-CH$_2$Cl$_2$ adduct (256 mg, 0.314 mmol) and K$_2$CO$_3$ (433 mg, 3.14 mmol) in acetonitrile (24 mL) and water (4 mL) was stirred at 80° C. under a nitrogen atmosphere overnight. The solvent was removed under vacuum when EtOAc (50 mL) and water (50 mL) was added. The aqueous layer was extracted with EtOAc (50 mL×2). The combined organic layers were washed with brine (100 mL), dried (Na$_2$SO$_4$) and concentrated. The crude product was purified by silica gel chromatography (MeOH/DCM: 0-5%) to give (R)-ethyl 4-(7-(2-fluoro-4-(2-methoxyethyl)phenyl)-4-oxoquinazolin-3(4H)-yl)-2-methyl-2-(methylsulfonyl)butanoate (350 mg, 0.659 mmol, 39% yield) as a solid.

LC/MS: [M+H] 505.0.

Part C

A mixture of (R)-ethyl 4-(7-(2-fluoro-4-(2-methoxyethyl) phenyl)-4-oxoquinazolin-3(4H)-yl)-2-methyl-2-(methylsulfonyl)butanoate (320 mg, 0.634 mmol), lithium hydroxide monohydrate (80 mg, 1.903 mmol), tetrahydrofuran (5 mL) and water (5 mL) was stirred at 25° C. for 3 hr. The THF was removed by evaporation and water (50 mL) was added and acidified to pH=4 with an aqueous solution of 1N HCl. 2-Methyltetrahydrofuran (50 mL) was added and the aqueous layer was extracted with 2-methyltetrahydrofuran (50 mL×2). The combined organic layers were washed with brine (100 mL), dried ($Na_2SO_4$) and concentrated. The crude residue was triturated with diethyl ether affording (R)-4-(7-(2-fluoro-4-(2-methoxyethyl)phenyl)-4-oxoquinazolin-3 (4H)-yl)-2-methyl-2-(methylsulfonyl)butanoic acid (300 mg, 0.567 mmol, 84% yield) as a white solid.

LCMS: [M+H] 477.2.

Part D

To a solution of (R)-4-(7-(2-fluoro-4-(2-methoxyethyl)phenyl)-4-oxoquinazolin-3(4H)-yl)-2-methyl-2-(methylsulfonyl)butanoic acid (270 mg, 0.567 mmol) in tetrahydrofuran (5 mL) was added O-(tetrahydro-2H-pyran-2-yl)hydroxylamine (133 mg, 1.133 mmol), N-ethyl-N-isopropylpropan-2-amine (0.504 mL, 2.83 mmol) and EDC (217 mg, 1.133 mmol) at 60° C. The reaction mixture was stirred at 60° C. for 2 hr under a nitrogen atmosphere. The reaction mixture was concentrated under reduced pressure and the crude product was purified by a silica gel chromatography (MeOH/DCM: 0-10%) to afford (2R)-4-(7-(2-fluoro-4-(2-methoxyethyl)phenyl)-4-oxoquinazolin-3(4H)-yl)-2-methyl-2-(methylsulfonyl)-N-((tetrahydro-2H-pyran-2-yl)oxy)butanamide (250 mg, 0.413 mmol, 68% yield) as a white solid.

LCMS: [M+H] 576.2.

Part E

To a stirred solution of (2R)-4-(7-(2-fluoro-4-(2-methoxyethyl)phenyl)-4-oxoquinazolin-3(4H)-yl)-2-methyl-2-(methylsulfonyl)-N-((tetrahydro-2H-pyran-2-yl)oxy)butanamide (220 mg, 0.382 mmol) in dichloromethane (5 mL) and methanol (5 mL) was added HCl (0.955 mL, 3.82 mmol) at 25° C. and this mixture was then stirred for an hour. The solvent was removed in vacuo to and the residue was purified by preparative HPLC to give (R)-4-(7-(2-fluoro-4-(2-methoxyethyl)phenyl)-4-oxoquinazolin-3 (4H)-yl)-N-hydroxy-2-methyl-2-(methylsulfonyl)butanamide (127 mg, 0.258 mmol, 68% yield) as a white solid.

LCMS: [M+H] 492.2.

$^1$H NMR (500 MHz, DMSO-$d_6$) δ: ppm 11.02 (s, 1H), 9.40-9.10 (br, 1H), 8.40 (s, 1H), 8.23 (d, J=8.3 Hz, 1H), 7.82 (s, 1H), 7.73 (d, J=8.3 Hz, 1H), 7.58 (t, J=8.2 Hz, 1H), 7.25 (J=17.4, 10.1 Hz, 2H), 4.34-4.02 (m, 1H), 3.98-3.76 (m, 1H), 3.60 (t, J=6.6 Hz, 2H), 3.27 (s, 3H), 3.10 (s, 3H), 2.90 (t, J=6.6 Hz, 2H), 2.70-2.54 (m, 1H), 2.31-2.15 (m, 1H), 1.61 (s, 3H).

Example 49. (2R)-4-[7-(3-fluoro-4-{[methoxy(methyl)amino]methyl}phenyl)-4-oxo-3,4-dihydroquinazolin-3-yl]-N-hydroxy-2-methanesulfonyl-2-methylbutanamide

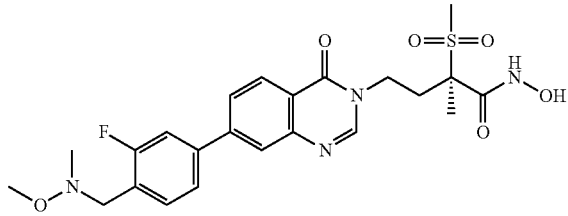 [SMILES: CON(C)Cc1ccc(-c2ccc3c(=O)n(CC[C@](C)(C(=O)NO)S(C)(=O)=O)cnc3c2)cc1F]

Part A

A reaction vessel was sealed with potassium carbonate (1.651 g, 11.94 mmol), $PdCl_2$(dppf) (0.437 g, 0.597 mmol), (2R)-4-(7-bromo-4-oxoquinazolin-3(4H)-yl)-2-methyl-2-(methylsulfonyl)-N-((tetrahydro-2H-pyran-2-yl)oxy)butanamide (Intermediate 3) (3 g, 5.97 mmol) and (3-fluoro-4-formylphenyl)boronic acid (1.203 g, 7.17 mmol) and the mixture was heated to 105° C. for 1 hr. The mixture was filtered and the filtrate was concentrated and then diluted with DCM (100 mL). The solution was washed with water (50 mL), brine (50 mL), dried over sodium sulphate and concentrated. The residue was purified silica gel chromatography (EtOAc/hexanes: 0-100%) to give (2R)-4-(7-(3-fluoro-4-formylphenyl)-4-oxoquinazolin-3(4H)-yl)-2-methyl-2-(methylsulfonyl)-N-((tetrahydro-2H-pyran-2-yl)oxy)butanamide (2.4 g, 4.27 mmol, 72% yield) was obtained as white solid.

LCMS: [M+H] 546.3.

Part B

To a solution of (2R)-4-(7-(3-fluoro-4-formylphenyl)-4-oxoquinazolin-3(4H)-yl)-2-methyl-2-(methylsulfonyl)-N-((tetrahydro-2H-pyran-2-yl)oxy)butanamide (200 mg, 0.367 mmol) in 1,2-dichloroethane (2 mL) at 0° C. was added N,O-dimethylhydroxylamine hydrochloride (107 mg, 1.1 mmol), acetic acid (22.01 mg, 0.367 mmol) and sodium triacetoxyhydroborate (233 mg, 1.100 mmol). The reaction mixture was allowed to warm to room temperature and stirred overnight. The organic phase was diluted with DCM (20 mL) and saturated $NaHCO_3$ and the organic layer was washed with water (20 mL), brine (30 mL), dried over sodium sulphate and concentrated. The residue was purified silica gel chromatography (MeOH/DCM: 0-20%) to afford (2R)-4-(7-(3-fluoro-4-((methoxy(methyl)amino)methyl)phenyl)-4-oxoquinazolin-3(4H)-yl)-2-methyl-2-(methylsulfonyl)-N-((tetrahydro-2H-pyran-2-yl)oxy)butanamide (100 mg, 0.154 mmol, 42% yield) as colorless oils.

LCMS: [M+H] 591.2.

Part C

To a solution of (2R)-4-(7-(3-fluoro-4-((methoxy(methyl)amino)methyl)phenyl)-4-oxoquinazolin-3(4H)-yl)-2-methyl-2-(methylsulfonyl)-N-((tetrahydro-2H-pyran-2-yl)oxy)butanamide (20 mg, 0.034 mmol) in dichloromethane (2 mL) and methanol (2 mL) stirred under nitrogen at room temperature was added a solution of 4M HCl in dioxane (0.025 mL, 0.102 mmol). The reaction mixture was stirred at room temperature for 2 hr. The reaction was concentrated and the residue was purified by preparative HPLC (5-75% MeCN in water, 0.1% TFA) to afford (R)-4-(7-(3-fluoro-4-((methoxy(methyl)amino)methyl)phenyl)-4-oxoquinazolin-3(4H)-yl)-N-hydroxy-2-methyl-2-(methylsulfonyl)butanamide trifluoroacetic acid salt (10 mg, 0.015 mmol, 45% yield) as a white solid.

LCMS: [M+H] 507.3.

$^1$H NMR (METHANOL-d4) δ: ppm 8.50 (s, 1H), 8.36 (d, J=8.3 Hz, 1H), 7.85-8.03 (m, 2H), 7.48-7.69 (m, 3H), 4.35 (t, J=9.7 Hz, 1H), 3.91-4.14 (m, 3H), 3.44 (s, 3H), 3.13 (s, 3H), 2.72 (s, 4H), 2.36-2.51 (m, 1H), 1.77 (s, 3H).

Example 50. (2R)-4-(7-{2-fluoro-4-[(methoxyamino)methyl]phenyl}-4-oxo-3,4-dihydroquinazolin-3-yl)-N-hydroxy-2-methanesulfonyl-2-methylbutanamide

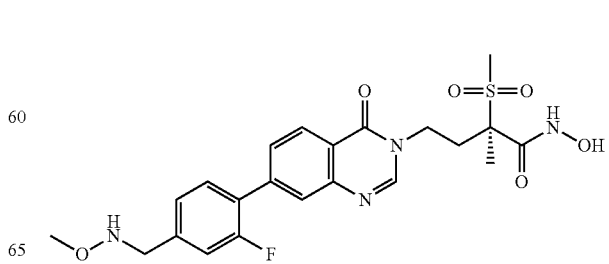

Part A

A mixture of 2-(2-fluoro-4-methylphenyl)-4,4,5,5-tetramethyl-1,3,2-dioxaborolane (25 g, 106 mmol) and NBS (19.79 g, 111 mmol) in acetonitrile (250 ml) was stirred for 5 min followed by addition of AIBN (0.869 g, 5.29 mmol). The mixture was heated to 90° C. overnight. The mixture was filtered and the filtrate was concentrated and the residue was filtered through a plug of silica eluting with hexane. The filtrate was concentrated in vacuo and the residue was recrystallized with hexanes at 0° C. The solid was collected and dried in vacuo to give 2-(4-(bromomethyl)-2-fluorophenyl)-4,4,5,5-tetramethyl-1,3,2-dioxaborolane (15 g, 16.19 mmol, 15% yield) as colorless crystals.

LCMS: [M+H] 315.0.

Part B

To a solution of 2-(4-(bromomethyl)-2-fluorophenyl)-4,4,5,5-tetramethyl-1,3,2-dioxaborolane (15 g, 47.6 mmol) in N,N-dimethylformamide (50 mL) was added DIPEA (24.95 mL, 143 mmol), O-methylhydroxylamine hydrochloride (7.95 g, 95 mmol). The reaction mixture was heated to 60° C. for 12 hr. The mixture was diluted with EtOAc (50 mL) and water (100 ml) and the mixture was extracted with EtOAc (30 mL×3) and the combined organic layers were washed with brine (100 mL×2), dried over sodium sulphate and concentrated to afford N-(3-fluoro-4-(4,4,5,5-tetramethyl-1,3,2-dioxaborolan-2-yl)benzyl)-O-methylhydroxylamine (8 g, 11.10 mmol, 23% yield) which was directly used in next step.

LCMS: [M+H] 282.1.

Part C

A mixture of potassium carbonate (5.50 g, 39.8 mmol), PdCl₂(dppf) (1.456 g, 1.991 mmol), (2R)-4-(7-bromo-4-oxoquinazolin-3(4H)-yl)-2-methyl-2-(methylsulfonyl)-N-((tetrahydro-2H-pyran-2-yl)oxy)butanamide (Intermediate 3) (10 g, 19.91 mmol) and N-(3-fluoro-4-(4,4,5,5-tetramethyl-1,3,2-dioxaborolan-2-yl)benzyl)-O-methylhydroxylamine (6.72 g, 23.89 mmol) in 1,4-dioxane (100 mL) and water (10 mL) was heated to 100° C. for 30 min. The mixture was filtered and the filtrate was diluted with aq. ammonium chloride. The mixture was extracted with DCM (50 mL×3) and the combined organic layers were washed with water (50 ml), brine (50 ml), dried over sodium sulfate, and concentrated in vacuo. The residue was purified by silica gel chromatography (methanol/DCM: 0-20%) to give (2R)-4-(7-(2-fluoro-4-((methoxyamino)methyl)phenyl)-4-oxoquinazolin-3(4H)-yl)-2-methyl-2-(methylsulfonyl)-N-((tetrahydro-2H-pyran-2-yl)oxy)butanamide (8 g, 12.49 mmol, 63% yield) as a colorless gum.

LCMS: [M+H] 577.4.

Part D

To a solution of (2R)-4-(7-(2-fluoro-4-((methoxyamino)methyl)phenyl)-4-oxoquinazolin-3(4H)-yl)-2-methyl-2-(methylsulfonyl)-N-((tetrahydro-2H-pyran-2-yl)oxy)butanamide (8 g, 13.87 mmol) in dichloromethane (10 mL) and methanol (20 mL) stirred under nitrogen at room temperature was added a solution of HCl in dioxane (10.41 mL, 41.6 mmol). The reaction mixture was stirred at room temperature for 2 hr. The reaction was concentrated and the residue was purified by reverse phase column chromatography (acetonitrile/water, 0.1% TFA: 0-70%) to afford (R)-4-(7-(2-fluoro-4-((methoxyamino)methyl)phenyl)-4-oxoquinazolin-3(4H)-yl)-N-hydroxy-2-methyl-2-(methylsulfonyl) butanamide trifluoroacetic acid salt (5.3 g, 8.30 mmol, 60% yield) as a white solid.

LCMS: [M+H] 493.2.

¹H NMR (400 MHz, METHANOL-d4) δ: ppm 1.77 (s, 3H), 2.33-2.52 (m, 1H), 2.68-2.82 (m, 1H), 3.13 (s, 3H), 3.89 (s, 3H), 3.99-4.13 (m, 1H), 4.23-4.41 (m, 1H), 4.50 (s, 2H), 7.36-7.52 (m, 2H), 7.63-7.74 (m, 1H), 7.77 (d, J=8.34 Hz, 1H), 7.88 (s, 1H), 8.34 (d, J=8.34 Hz, 1H), 8.43 (s, 1H).

Example 51. (2R)-4-(7-{4-[(ethoxyamino)methyl]-2-fluorophenyl}-4-oxo-3,4-dihydroquinazolin-3-yl)-N-hydroxy-2-methanesulfonyl-2-methylbutanamide

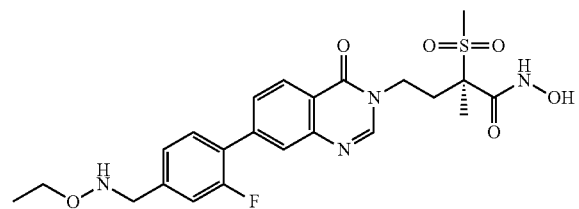 [SMILES: CCONCc1ccc(-c2ccc3c(=O)n(CC[C@](C)(C(=O)NO)S(C)(=O)=O)cnc3c2)c(F)c1]

Part A

To a solution of 2-(4-(bromomethyl)-2-fluorophenyl)-4,4,5,5-tetramethyl-1,3,2-dioxaborolane (2.5 g, 7.94 mmol) in N,N-dimethylformamide (12.41 ml) was added DIPEA (3.47 ml, 19.84 mmol), O-ethylhydroxylamine hydrochloride (1.548 g, 15.87 mmol) and the reaction mixture was heated to 60° C. for 12 hr. The mixture was diluted with EtOAc (50 mL) and water (100 ml) and the mixture was extracted with EtOAc (30 ml×3) and the combined organic layers were washed with brine (30 mL), dried over sodium sulphate and concentrated to give O-ethyl-N-(3-fluoro-4-(4,4,5,5-tetramethyl-1,3,2-dioxaborolan-2-yl)benzyl)hydroxylamine (2.4 g, 3.58 mmol, 45% yield).

LCMS: [M+H] 295.1.

Part B

A mixture of potassium carbonate (1.376 g, 9.95 mmol), PdCl₂(dppf) (0.364 g, 0.498 mmol), (2R)-4-(7-bromo-4-oxoquinazolin-3(4H)-yl)-2-methyl-2-(methyl)-N-((tetrahydro-2H-pyran-2-yl)oxy)butanamide (Intermediate 3) (2.5 g, 4.98 mmol) and O-ethyl-N-(3-fluoro-4-(4,4,5,5-tetramethyl-1,3,2-dioxaborolan-2-yl)benzyl)hydroxylamine (1.909 g, 6.47 mmol) in water (3 mL) and 1,4-dioxane (30 mL) and heated to 95° C. for 30 min. The mixture was filtered and filtrated was diluted with DCM (50 mL) and water (50 ml), extracted with DCM (50 ml×3), washed with brine (30 mL), dried over sodium sulphate and concentrated. The residue was purified with silica gel chromatography (methanol/DCM: 0-20%) to give (2R)-4-(7-(4-((ethoxyamino)methyl)-2-fluorophenyl)-4-oxoquinazolin-3(4H)-yl)-2-methyl-2-(methylsulfonyl)-N-((tetrahydro-2H-pyran-2-yl)oxy)butanamide (1.9 g, 3.18 mmol, 64% yield) as a colorless gum.

LCMS: [M+H] 591.2.

Part C

To a solution of (2R)-4-(7-(4-((ethoxyamino)methyl)-2-fluorophenyl)-4-oxoquinazolin-3(4H)-yl)-2-methyl-2-(methylsulfonyl)-N-((tetrahydro-2H-pyran-2-yl)oxy)butanamide (1.9 g, 3.22 mmol) in dichloromethane (10 mL) and methanol (10 mL) stirred under nitrogen at room temperature was added a solution of 4M HCl in dioxane (0.804 mL, 3.22 mmol). The reaction mixture was stirred at room temperature for 2 hr. The reaction was concentrated and the residue was triturated with methanol/ethyl acetate/diethyl ether and filtered. The solid was redissolved in water (15 ml) and concentrated to afford (R)-4-(7-(4-((ethoxyamino)methyl)-2-fluorophenyl)-4-oxoquinazolin-3

(4H)-yl)-N-hydroxy-2-methyl-2-(methylsulfonyl)butanamide hydrochloride (1.32 g, 2.309 mmol, 72% yield) as white solid.

LCMS: [M+H] 507.1.

$^1$H NMR (400 MHz, METHANOL-d4) δ: ppm 1.36 (t, J=6.95 Hz, 3H), 1.79 (s, 3H), 2.47 (ddd, J=13.83, 9.28, 4.93 Hz, 1H), 2.72-2.92 (m, 1H), 3.12 (s, 3H), 4.13-4.32 (m, 3H), 4.41 (ddd, J=13.71, 9.28, 4.80 Hz, 1H), 4.64 (s, 2H), 7.47-7.62 (m, 2H), 7.79 (t, J=7.96 Hz, 1H), 7.89-8.04 (m, 2H), 8.47 (d, J=9.09 Hz, 1H), 9.27 (d, J=5.81 Hz, 1H).

Example 52. (2R)—N-hydroxy-2-methanesulfonyl-4-[7-(4-{[methoxy(methyl)amino]methyl}phenyl)-4-oxo-3,4-dihydroquinazolin-3-yl]-2-methylbutanamide

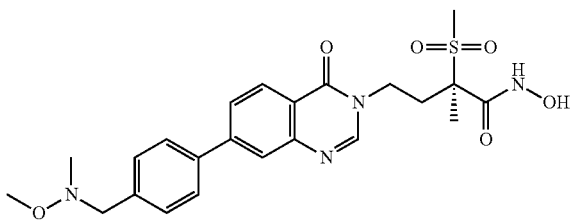 [SMILES: CON(C)Cc1ccc(-c2ccc3c(=O)n(CC[C@](C)(C(=O)NO)S(C)(=O)=O)cnc3c2)cc1]

Part A

To a solution of 2-(4-(bromomethyl)phenyl)-4,4,5,5-tetramethyl-1,3,2-dioxaborolane (500 mg, 1.684 mmol) in N,N-dimethylformamide (5 ml) was added DIPEA (0.735 ml, 4.21 mmol) and N,O-dimethylhydroxylamine hydrochloride (328 mg, 3.37 mmol). The reaction mixture was heated to 60° C. for 12 hr. when the mixture was diluted with EtOAc (50 mL) and water (50 ml). The mixture was extracted with EtOAc (20 ml×3) and the combined organic layers were washed with brine (30 mL), dried over sodium sulphate and concentrated to give N,O-dimethyl-N-(4-(4,4,5,5-tetramethyl-1,3,2-dioxaborolan-2-yl)benzyl)hydroxylamine (470 mg, 1.255 mmol, 75% yield) as colorless oil.

LCMS: [M+H] 278.1.

Part B

A reaction vessel was sealed with potassium carbonate (138 mg, 0.995 mmol), PdCl$_2$(dppf) (36 mg, 0.05 mmol), (2R)-4-(7-bromo-4-oxoquinazolin-3(4H)-yl)-2-methyl-2-(methylsulfonyl)-N-((tetrahydro-2H-pyran-2-yl)oxy)butanamide (Intermediate 3) (250 mg, 0.498 mmol) and N,O-dimethyl-N-(4-(4,4,5,5-tetramethyl-1,3,2-dioxaborolan-2-yl)benzyl)hydroxylamine (166 mg, 0.597 mmol) and heated in a microwave to 95° C. for 30 min. The organic phase was diluted with DCM (20 mL) and water (10 ml), extracted with DCM (10 ml×3), washed with brine (30 mL), dried over sodium sulphate and concentrated. The residue was purified with silica gel chromatography (methanol/DCM: 0-20%) to afford (2R)-4-(7-(4-((methoxy(methyl)amino)methyl)phenyl)-4-oxoquinazolin-3(4H)-yl)-2-methyl-2-(methylsulfonyl)-N-((tetrahydro-2H-pyran-2-yl)oxy)butanamide (280 mg, 0.479 mmol, 96% yield) as a colorless oil.

LCMS: [M+H] 573.2.

Part C

To a solution of (2R)-4-(7-(4-((methoxy(methyl)amino)methyl)phenyl)-4-oxoquinazolin-3(4H)-yl)-2-methyl-2-(methylsulfonyl)-N-((tetrahydro-2H-pyran-2-yl)oxy)butanamide (280 mg, 0.489 mmol) in dichloromethane (5 mL) and methanol (5 mL) stirred under nitrogen at room temperature was added a solution of HCl in dioxane (0.367 mL, 1.467 mmol). The reaction mixture was stirred at room temperature for 2 hr. The reaction was concentrated and the residue triturated with methanol/ethyl acetate/diethyl ether, filtered, and dried in vacuo to afford (R)—N-hydroxy-4-(7-(4-((methoxy(methyl)amino)methyl)phenyl)-4-oxoquinazolin-3(4H)-yl)-2-methyl-2-(methylsulfonyl)butanamide hydrochloride (214 mg, 0.387 mmol, 79% yield) as a white solid.

LCMS: [M+H] 489.2.

$^1$H NMR (400 MHz, METHANOL-d4) δ: ppm 1.79 (s, 3H), 2.48 (ddd, J=13.77, 9.22, 4.80 Hz, 1H), 2.77-2.94 (m, 1H), 3.12 (s, 3H), 3.21 (s, 3H), 3.90 (s, 3H), 4.21-4.32 (m, 1H), 4.42 (ddd, J=13.71, 9.28, 4.80 Hz, 1H), 4.69 (s, 2H), 7.77 (d, J=8.34 Hz, 2H), 7.93 (d, J=8.34 Hz, 2H), 8.02 (d, J=1.01 Hz, 1H), 8.09 (dd, J=8.34, 1.52 Hz, 1H), 8.46 (d, J=8.34 Hz, 1H), 9.36 (s, 1H).

Example 53. (2R)—N-hydroxy-2-methanesulfonyl-4-[6-(4-methoxyphenyl)-1-oxo-1,2-dihydroisoquinolin-2-yl]-2-methylbutanamide

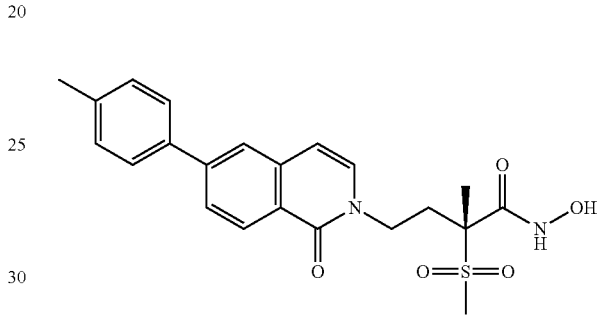

Part A

A reaction vessel was sealed with (R)-ethyl 4-(6-bromo-1-oxoisoquinolin-2(1H)-yl)-2-methyl-2-(methylsulfonyl)butanoate (Intermediate 9) (100 mg, 0.232 mmol), K$_2$CO$_3$ (64 mg, 0.465 mmol), PdCl$_2$(dppf) (17.00 mg, 0.023 mmol) and 2-(4-methoxyphenyl)-4,4,5,5-tetramethyl-1,3,2-dioxaborolane (70.7 mg, 0.302 mmol) and heated in a microwave to 110° C. for 30 min. The organic phase was diluted with DCM (20 mL) and washed with water (20 mL), brine (30 mL), dried over sodium sulphate and concentrated. The residue was purified with silica gel chromatography (EtOAc/hexanes: 0-80%) to afford (R)-ethyl 4-(6-(4-methoxyphenyl)-1-oxoisoquinolin-2(1H)-yl)-2-methyl-2-(methylsulfonyl)butanoate (110 mg, 0.202 mmol, 87% yield) as a colorless oil.

LCMS: [M+H] 458.3.

Part B

To a solution of (R)-ethyl 4-(6-(4-methoxyphenyl)-1-oxoisoquinolin-2(1H)-yl)-2-methyl-2-(methylsulfonyl)butanoate (110 mg, 0.240 mmol) in 1,4-dioxane (2 mL) was added a solution of hydroxylamine (2 mL, 32.6 mmol) (50% in water) and 1M LiOH (1 ml, 1 mmol). The reaction mixture was stirred overnight and then concentrated. The residue was purified by reverse phase HPLC (10-90% MeCN/H$_2$O, 0.1% TFA) to afford (R)—N-hydroxy-4-(6-(4-methoxyphenyl)-1-oxoisoquinolin-2(1H)-yl)-2-methyl-2-(methylsulfonyl)butanamide (28.2 mg, 0.060 mmol, 25% yield) as a light brown solid.

LCMS: [M+H] 445.2.

$^1$H NMR (METHANOL-d$_4$) δ: ppm 8.36 (d, J=8.3 Hz, 1H), 7.84 (s, 1H), 7.80 (d, J=8.3 Hz, 1H), 7.71 (d, J=8.3 Hz, 2H), 7.39 (d, J=7.1 Hz, 1H), 7.07 (d, J=8.3 Hz, 2H), 6.80 (d, J=6.8 Hz, 1H), 4.36 (t, J=9.2 Hz, 1H), 3.70-4.03 (m, 4H), 3.13 (s, 3H), 2.57-2.73 (m, 1H), 2.29-2.50 (m, 1H), 1.75 (s, 3H).

Example 54. (2R)—N-hydroxy-2-methanesulfonyl-2-methyl-4-[6-(4-methylphenyl)-1-oxo-1,2-dihydroisoquinolin-2-yl]butanamide

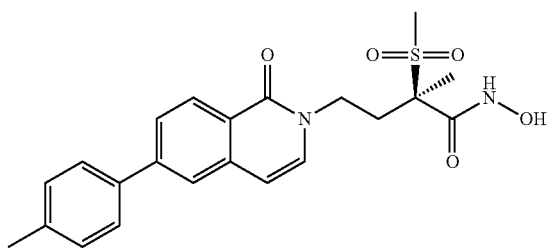 [SMILES: Cc1ccc(-c2ccc3c(=O)n(CC[C@](C)(C(=O)NO)S(C)(=O)=O)ccc3c2)cc1]

Part A

A reaction vessel charged with (R)-ethyl 4-(6-bromo-1-oxoisoquinolin-2(1H)-yl)-2-methyl-2-(methylsulfonyl)butanoate (Intermediate 9) (100 mg, 0.232 mmol), $K_2CO_3$ (64.2 mg, 0.465 mmol), $PdCl_2$(dppf) (17 mg, 0.023 mmol) and 4,4,5,5-tetramethyl-2-(p-tolyl)-1,3,2-dioxaborolane (65.9 mg, 0.302 mmol) was heated in a microwave to 110° C. for 30 min. The organic phase was diluted with DCM (20 mL) and washed with water (20 mL), brine (30 mL), dried over sodium sulphate and evaporated in vacuo. The residue was purified with silica gel chromatography (EtOAc/hexanes: 0-80%) to afford (R)-ethyl 2-methyl-2-(methylsulfonyl)-4-(1-oxo-6-(p-tolyl)isoquinolin-2(1H)-yl)butanoate (109 mg, 0.212 mmol, 91% yield) as a colorless oil.

LCMS: [M+H] 442.3.

Part B

To a solution of (R)-ethyl 2-methyl-2-(methylsulfonyl)-4-(1-oxo-6-(p-tolyl)isoquinolin-2(1H)-yl)butanoate (103 mg, 0.233 mmol) in 1,4-dioxane (2 mL) was added a solution of hydroxylamine (2 mL, 32.6 mmol) (50% in water) and LiOH (1 ml, 1 mmol) (1M in water) at room temperature and stirred for 2 hr. The reaction was concentrated in vacuo and purified by preparative HPLC (8-85% MeCN/H$_2$O, 0.1% TFA) to afford (R)—N-hydroxy-2-methyl-2 (methylsulfonyl)-4-(1-oxo-6-(p-tolyl)isoquinolin-2(1H)-yl)butanamide (16.6 mg, 0.037 mmol, 16% yield) as light brown solid.

LCMS: [M+H] 429.3.

$^1$H NMR (METHANOL-d4) δ: ppm 8.39 (d, J=8.6 Hz, 1H), 7.88 (s, 1H), 7.82 (d, J=8.3 Hz, 1H), 7.66 (d, J=8.1 Hz, 2H), 7.41 (d, J=7.3 Hz, 1H), 7.34 (d, J=7.8 Hz, 2H), 6.82 (d, J=7.1 Hz, 1H), 4.29-4.44 (m, 1H), 3.87-4.04 (m, 1H), 3.13 (s, 3H), 2.59-2.73 (m, 1H), 2.31-2.49 (m, 4H), 1.75 (s, 3H).

Example 55. (2R)-4-[6-(2-fluoro-4-methoxyphenyl)-1-oxo-1,2-dihydroisoquinolin-2-yl]-N-hydroxy-2-methanesulfonyl-2-methylbutanamide

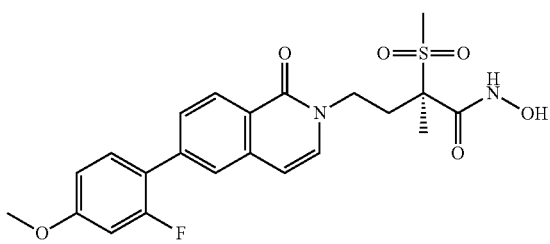 [SMILES: COc1ccc(-c2ccc3c(=O)n(CC[C@](C)(C(=O)NO)S(C)(=O)=O)ccc3c2)c(F)c1]

Part A

A reaction vessel was sealed with $K_2CO_3$ (110 mg, 0.798 mmol), $PdCl_2$(dppf) (29.2 mg, 0.040 mmol), (2R)-4-(6-bromo-1-oxoisoquinolin-2(1H)-yl)-2-methyl-2-(methylsulfonyl)-N-((tetrahydro-2H-pyran-2-yl)oxy)butanamide (Intermediate 10) (200 mg, 0.399 mmol) and (2-fluoro-4-methoxyphenyl)boronic acid (88 mg, 0.519 mmol) and was heated in a microwave to 110° C. for 30 min. The organic phase was diluted with DCM (20 mL), washed with water (20 mL), brine (30 mL), dried over sodium sulphate and concentrated. The residue was purified with silica gel chromatography (MeOH/DCM: 0-20%) to give (2R)-4-(6-(2-fluoro-4-methoxyphenyl)-1-oxoisoquinolin-2(1H)-yl)-2-methyl-2-(methylsulfonyl)-N-((tetrahydro-2H-pyran-2-yl)oxy)butanamide (200 mg, 0.348 mmol, 87% yield) as a colorless oil.

LCMS: [M-THP] 463.3.

Part B

To a solution of (2R)-4-(6-(2-fluoro-4-methoxyphenyl)-1-oxoisoquinolin-2(1H)-yl)-2-methyl-2-(methylsulfonyl)-N-((tetrahydro-2H-pyran-2-yl)oxy)butanamide (200 mg, 0.366 mmol) in dichloromethane stirred under nitrogen at room temperature was added a solution of 4M HCl in dioxane (0.5 mL, 2.000 mmol). The reaction mixture was stirred at room temperature for 2 hr. The reaction was concentrated and the residue was purified by preparative HPLC (5-85% MeCN/H$_2$O, 0.1% TFA) and then purified by silica gel chromatography (methanol/DCM: 0-20%) to afford (R)-4-(6-(2-fluoro-4-methoxyphenyl)-1-oxoisoquinolin-2(1H)-yl)-N-hydroxy-2-methyl-2-(methylsulfonyl)butanamide (26 mg, 0.053 mmol, 15% yield) as a white solid.

LCMS: [M+H] 463.3.

$^1$H NMR (METHANOL-d4) δ: ppm 8.32 (d, J=8.6 Hz, 1H), 7.72 (s, 1H), 7.65 (d, J=8.6 Hz, 1H), 7.47 (t, J=8.8 Hz, 1H), 7.36 (d, J=7.6 Hz, 1H), 6.77-6.92 (m, 2H), 6.73 (d, J=7.3 Hz, 1H), 4.34 (ddd, J=12.9, 11.1, 5.3 Hz, 1H), 3.76-4.00 (m, 4H), 3.13 (s, 3H), 2.57-2.71 (m, 1H), 2.40 (ddd, J=13.3, 11.2, 5.3 Hz, 1H), 1.74 (s, 3H).

Example 56. (2R)—N-hydroxy-2-methanesulfonyl-2-methyl-4-(1-oxo-6-phenyl-1,2-dihydroisoquinolin-2-yl)butanamide

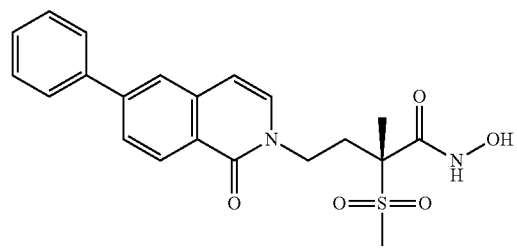 [SMILES: C[C@@](CCn1ccc2cc(-c3ccccc3)ccc2c1=O)(C(=O)NO)S(C)(=O)=O]

Part A

A mixture of $K_2CO_3$ (4.80 g, 34.7 mmol), $PdCl_2$(dppf) (1.270 g, 1.735 mmol), (2R)-4-(6-bromo-1-oxoisoquinolin-2(1H)-yl)-2-methyl-2-(methylsulfonyl)-N-((tetrahydro-2H-pyran-2-yl)oxy)butanamide (Intermediate 10) (8.7 g, 17.35 mmol) and 4,4,5,5-tetramethyl-2-phenyl-1,3,2-dioxaborolane (4.25 g, 20.82 mmol) in 1,4-dioxane (50 mL) and water (5 mL) was heated to 105° C. for 2 hr. The organic phase was diluted with DCM (100 mL) and washed with water (100 mL), brine (100 mL), dried over sodium sulphate and concentrated. The residue was purified by silica gel chromatography (EtOAc/hexanes: 20-90%) to afford (2R)-2-methyl-2-(methylsulfonyl)-4-(1-oxo-6-phenylisoquinolin-2(1H)-yl)-N-((tetrahydro-2H-pyran-2-yl)oxy)butanamide (7.2 g, 14.15 mmol, 82% yield) as a white solid.

LCMS: [M+H] 415.2.

Part B

To a solution of (2R)-2-methyl-2-(methylsulfonyl)-4-(1-oxo-6-phenylisoquinolin-2(1H)-yl)-N-((tetrahydro-2H-pyran-2-yl)oxy)butanamide (7.2 g, 14.44 mmol) in dichloromethane (50 mL) and methanol (10 mL) stirred under nitrogen at room temperature was added a solution of 4M HCl in dioxane (18.05 mL, 72.2 mmol). The reaction mixture was stirred at room temperature for 4 hr. and concentrated. The residue was treated with DCM/hexane (20 ml/100 ml) to give white solid which was washed with hexane (20 ml×3) to afford (R)—N-hydroxy-2-methyl-2-(methylsulfonyl)-4-(1-oxo-6-phenylisoquinolin-2(1H)-yl)butanamide (5.4 g, 12.38 mmol, 86% yield) as a white solid.

LCMS: [M+H] 415.2.

$^1$H NMR (METHANOL-d4) δ: ppm 8.40 (d, J=8.3 Hz, 1H), 7.90 (d, J=1.5 Hz, 1H), 7.83 (dd, J=8.5, 1.6 Hz, 1H), 7.72-7.79 (m, 2H), 7.47-7.57 (m, 2H), 7.36-7.47 (m, 2H), 6.83 (d, J=7.6 Hz, 1H), 4.37 (ddd, J=13.0, 11.0, 5.3 Hz, 1H), 3.94 (ddd, J=13.0, 11.2, 5.1 Hz, 1H), 3.13 (s, 3H), 2.65 (ddd, J=13.3, 11.0, 5.1 Hz, 1H), 2.41 (ddd, J=13.4, 11.1, 5.3 Hz, 1H), 1.75 (s, 3H).

Example 57. (2R)-4-[6-(1,3-dihydro-2-benzofuran-5-yl)-1-oxo-1,2-dihydroisoquinolin-2-yl]-N-hydroxy-2-methanesulfonyl-2-methylbutanamide

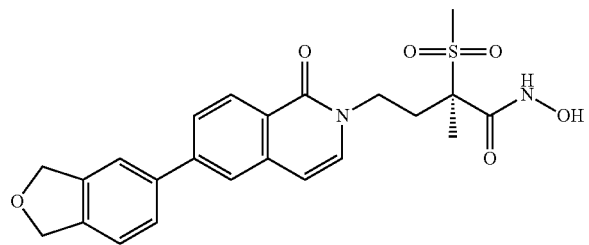 [SMILES: C[C@@](CCn1ccc2cc(-c3ccc4c(c3)COC4)ccc2c1=O)(C(=O)NO)S(C)(=O)=O]

Part A 1,3-Dihydroisobenzofuran-5-amine (3 g, 22.20 mmol) slurried in HBr (45 mL, 829 mmol) was cooled on ice and sodium nitrite (1.531 g, 22.20 mmol) in water (15 mL) was added dropwise over 2 min and stirred at 0° C. for 30 min to give a yellow-brown solution. This mixture was added to a solution of copper(I) bromide (4.78 g, 33.3 mmol) in HBr (15 mL, 276 mmol) at −10° C. The resulting dark brown mixture was stirred overnight. The reaction was combined another batch and was diluted with water (100 mL) producing an orange precipitate. This was filtered off and treated with sat. NaHCO$_3$ (100 mL) and extracted with ethyl acetate (200 mL). The extract was washed with brine, dried (Na$_2$SO$_4$) and concentrated to an orange oil, which was purified by silica gel chromatography (EtOAc/petroleum ether: 10%) to give 5-bromo-1,3-dihydroisobenzofuran (4.5 g, 22.61 mmol, 76% yield).

Part B

A solution of 4,4,4',4',5,5,5',5'-octamethyl-2,2'-bi(1,3,2-dioxaborolane) (2.296 g, 9.04 mmol), potassium acetate (1.331 g, 13.56 mmol), 5-bromo-1,3-dihydroisobenzofuran (0.9 g, 4.52 mmol) and PdCl$_2$(dppf)-CH$_2$Cl$_2$ adduct (0.739 g, 0.904 mmol) in 1,4-dioxane (50 mL) was stirred at 80° C. under nitrogen overnight. The solution was cooled to room temperature when ethyl acetate (100 mL) was added. The organic layer was washed with brine (30 mL×3), dried over sodium sulfate and concentrated. The residue by silica gel chromatography (EtOAc/petroleum ether: 0-10%) to give 2-(1,3-dihydroisobenzofuran-5-yl)-4,4,5,5-tetramethyl-1,3,2-dioxaborolane (900 mg, 3.47 mmol, 77% yield).

Part C

A mixture of (2R)-4-(6-bromo-1-oxoisoquinolin-2(1H)-yl)-2-methyl-2-(methylsulfonyl)-N-((tetrahydro-2H-pyran-2-yl)oxy)butanamide (Intermediate 10) (300 mg, 0.598 mmol), 2-(1,3-dihydroisobenzofuran-5-yl)-4,4,5,5-tetramethyl-1,3,2-dioxaborolane (295 mg, 1.197 mmol), PdCl$_2$(dppf)-CH$_2$Cl$_2$ adduct (98 mg, 0.120 mmol) and K$_2$CO$_3$ (165 mg, 1.197 mmol) in acetonitrile (1.2 mL) and water (0.200 mL) was stirred at 80° C. for 30 min. The reaction was cooled to room temperature. To this mixture was added ethyl acetate (50 mL) and the solution was washed with brine (20 mL×3), dried over sodium sulfate and concentrated. The residue was purified by silica gel chromatography (EtOAc/hexanes: 20%-50%) to give (2R)-4-(6-(1,3-dihydroisobenzofuran-5-yl)-1-oxoisoquinolin-2(1H)-yl)-2-methyl-2-(methylsulfonyl)-N-((tetrahydro-2H-pyran-2-yl)oxy)butanamide (300 mg, 0.534 mmol, 89% yield) LCMS: [M+Na]: 457.2.

Part D

To a solution of (2R)-4-(6-(1,3-dihydroisobenzofuran-5-yl)-1-oxoisoquinolin-2(1H)-yl)-2-methyl-2-(methylsulfonyl)-N-((tetrahydro-2H-pyran-2-yl)oxy)butanamide (300 mg, 0.555 mmol) in methanol (5 mL) was added 4M HCl in dioxane (5 mL, 20.00 mmol) stirred 1 hr at room temperature. The mixture was concentrated and the residue was purified by preparative HPLC to give (R)-4-(6-(1,3-dihydroisobenzofuran-5-yl)-1-oxoisoquinolin-2(1H)-yl)-N-hydroxy-2-methyl-2-(methylsulfonyl)butanamide (120 mg, 0.248 mmol, 45% yield)

LCMS: [M+H] 456.8.

$^1$H NMR (500 MHz, DMSO-d$_6$) δ: ppm 11.07 (s, 1H), 9.26 (s, 1H), 8.29 (d, J=8.4 Hz, 1H), 7.97 (s, 1H), 7.82 (J=8.4, 1.4 Hz, 1H), 7.77-7.66 (m, 2H), 7.47 (t, J=7.8 Hz, 2H), 6.74 (d, J=7.4 Hz, 1H), 5.08 (d, J=7.9 Hz, 4H), 4.19 (td, J=12.5, 5.0 Hz, 1H), 3.79 (td, J=12.2, 4.8 Hz, 1H), 3.11 (s, 3H), 2.56 (td, J=12.9, 5.1 Hz, 1H), 2.18 (td, J=12.9, 5.1 Hz, 1H), 1.60 (s, 3H).

Example 58. (2R)—N-hydroxy-2-methanesulfonyl-2-methyl-4-[6-(5-methyl-1,3-thiazol-2-yl)-1-oxo-1,2-dihydroisoquinolin-2-yl]butanamide

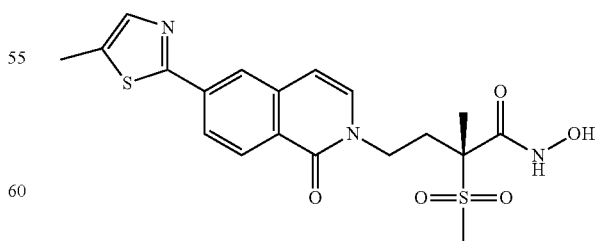

Part A

PdCl$_2$(dppf) (92 mg, 0.126 mmol) was added to a solution of (R)-ethyl 2-methyl-2-(methylsulfonyl)-4-(1-oxo-6-(4,4,5,5-tetramethyl-1,3,2-dioxaborolan-2-yl)isoquinolin-2(1H)- yl)butanoate (Intermediate 20) (400 mg, 0.838 mmol), 2-bromo-5-methylthiazole (373 mg, 2.095 mmol) and potassium carbonate (232 mg, 1.676 mmol) in acetonitrile (15 mL) and water (3 mL) at room temperature under a nitrogen atmosphere. The reaction mixture was stirred at 80° C. overnight and was combined with another batch and the solution was concentrated and the residue was purified by silica gel chromatography (EtOAc/petroleum ether: 1/1) to give (R)-ethyl 2-methyl-2-(methylsulfonyl)-4-(6-(5-methylthiazol-2-yl)-1-oxoisoquinolin-2(1H)-yl)butanoate (222 mg, 0.495 mmol, 59% yield) as a yellow oil.

LCMS: [M+H] 449.0.

Part C

A mixture of (R)-ethyl 2-methyl-2-(methylsulfonyl)-4-(6-(5-methylthiazol-2-yl)-1-oxoisoquinolin-2(1H)-yl)butanoate (222 mg, 0.495 mmol) and lithium hydroxide monohydrate (33.2 mg, 0.792 mmol) in tetrahydrofuran (10 mL) and water (5 mL) was stirred at 25° C. for 2 hr. The mixture was concentrated and the resulting aqueous layer was acidified to pH 3 using 1M HCl. The precipitate was collected by filtration and dried in vacuo to give (R)-2-methyl-2-(methylsulfonyl)-4-(6-(5-methylthiazol-2-yl)-1-oxoisoquinolin-2(1H)-yl)butanoic acid (180 mg, 0.355 mmol, 72% yield) as a white solid.

LCMS: [M+H] 421.0.

Part D

To a solution of (R)-2-methyl-2-(methylsulfonyl)-4-(6-(5-methylthiazol-2-yl)-1-oxoisoquinolin-2(1H)-yl)butanoic acid (180 mg, 0.428 mmol) and triethylamine (0.179 mL, 1.284 mmol) in tetrahydrofuran (15 mL) was added O-(tetrahydro-2H-pyran-2-yl)hydroxylamine (100 mg, 0.856 mmol), HOBt (116 mg, 0.856 mmol) and EDC.HCl (164 mg, 0.856 mmol). The resulting mixture was stirred at room temperature overnight. The mixture was concentrated under reduced pressure and the residue was purified by silica gel chromatography to give (2R)-2-methyl-2-(methylsulfonyl)-4-(6-(5-methylthiazol-2-yl)-1-oxoisoquinolin-2(1H)-yl)-N-((tetrahydro-2H-pyran-2-yl)oxy)butanamide (210 mg, 0.284 mmol, 66% yield) as a yellow oil.

LCMS: [M+H-THP] 436.0.

Part E

To a stirred solution of (2R)-2-methyl-2-(methylsulfonyl)-4-(6-(5-methylthiazol-2-yl)-1-oxoisoquinolin-2(1H)-yl)-N-((tetrahydro-2H-pyran-2-yl)oxy)butanamide (180 mg, 0.346 mmol) in methanol (6 mL) and dichloromethane (6 mL) was added a solution of HCl (4.33 mL, 17.32 mmol) in 1,4-dioxane at room temperature and this mixture was then stirred at this temperature for 2 hr. The mixture from combined batches was purified with preparative HPLC to give (R)—N-hydroxy-2-methyl-2-(methylsulfonyl)-4-(6-(5-methylthiazol-2-yl)-1-oxoisoquinolin-2(1H)-yl)butanamide (68 mg, 0.156 mmol, 45% yield) as a white solid.

LCMS: [M+H] 436.2.

$^1$H NMR (500 MHz, DMSO-d6) δ: ppm 11.05 (s, 1H), 9.25 (s, 1H), 8.30 (d, J=8.5 Hz, 1H), 8.17 (d, J=1.0 Hz, 1H), 8.00 (dd, J1=8.0 Hz, J2=1.0 Hz, 1H), 7.71 (d, J=1.0 Hz, 1H), 7.50 (d, J=7.5 Hz, 1H), 6.80 (d, J=7.5 Hz, 1H), 4.20-4.14 (m, 1H), 3.83-3.77 (m, 1H), 3.10 (s, 3H), 2.54 (d, J=1.0 Hz, 3H), 2.50-2.48 (m, 1H), 2.20-2.14 (m, 1H), 1.60 (s, 3H).

Example 59. (2R)-4-[6-(4-cyano-2-fluorophenyl)-1-oxo-1,2-dihydroisoquinolin-2-yl]-N-hydroxy-2-methanesulfonyl-2-methylbutanamide

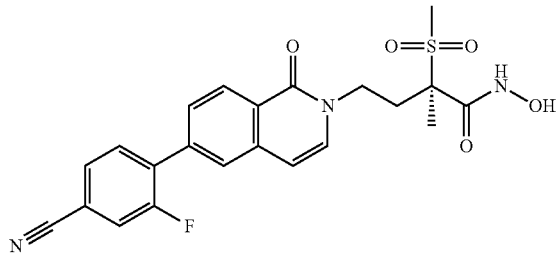 [SMILES: C[C@@](CCn1ccc2cc(-c3ccc(C#N)cc3F)ccc2c1=O)(C(=O)NO)S(C)(=O)=O]

Part A

A reaction vessel was sealed with potassium carbonate (110 mg, 0.798 mmol), PdCl$_2$(dppf) (29.2 mg, 0.04 mmol), (2R)-4-(6-bromo-1-oxoisoquinolin-2(1H)-yl)-2-methyl-2-(methylsulfonyl)-N-((tetrahydro-2H-pyran-2-yl)oxy)butanamide (Intermediate 10) (200 mg, 0.399 mmol) and (4-cyano-2-fluorophenyl)boronic acid (86 mg, 0.519 mmol) and heated in a microwave to 110° C. for 30 min. The organic phase was diluted with DCM (20 mL) and extracted with DCM (10 ml×3) and the combined organic layers were washed with water (20 mL), brine (30 mL), dried over sodium sulphate and concentrated. The residue was purified by silica gel chromatography (EtOAc/DCM: 10-100%) to give (2R)-4-(6-(4-cyano-2-fluorophenyl)-1-oxoisoquinolin-2(1H)-yl)-2-methyl-2-(methylsulfonyl)-N-((tetrahydro-2H-pyran-2-yl)oxy)butanamide (159 mg, 0.294 mmol, 74% yield) as colorless oil.

LCMS: [M+Na] 564.3.

Part B

To a solution of (2R)-4-(6-(4-cyano-2-fluorophenyl)-1-oxoisoquinolin-2(1H)-yl)-2-methyl-2-(methylsulfonyl)-N-((tetrahydro-2H-pyran-2-yl)oxy)butanamide (159 mg, 0.294 mmol) in ethanol (3 mL) was added 4M HCl in dioxane (0.220 mL, 0.881 mmol). The resulting solution was stirred at room temperature for 2 hr. and concentrated. The reaction was diluted with DMSO and purified by preparative HPLC (5-70% MeCN/H$_2$O, 0.1% TFA) to afford (R)-4-(6-(4-cyano-2-fluorophenyl)-1-oxoisoquinolin-2(1H)-yl)-N-hydroxy-2-methyl-2-(methylsulfonyl)butanamide (87 mg, 0.181 mmol, 62% yield) as a white powder.

LCMS: [M+H] 458.1.

$^1$H NMR (DMSO-d6) δ: ppm 11.07 (s, 1H), 9.28 (s, 1H), 8.33 (d, J=8.3 Hz, 1H), 8.05 (d, J=10.4 Hz, 1H), 7.80-7.97 (m, 3H), 7.72 (d, J=8.1 Hz, 1H), 7.52 (d, J=7.3 Hz, 1H), 6.76 (d, J=7.1 Hz, 1H), 4.11-4.26 (m, 1H), 3.81 (td, J=11.7, 4.5 Hz, 1H), 3.44 (d, J=6.3 Hz, 1H), 3.11 (s, 3H), 2.10-2.28 (m, 1H), 1.61 (s, 3H).

Example 60. (2R)—N-hydroxy-2-methanesulfonyl-4-[6-(6-methoxypyridin-3-yl)-1-oxo-1,2-dihydroisoquinolin-2-yl]-2-methylbutanamide

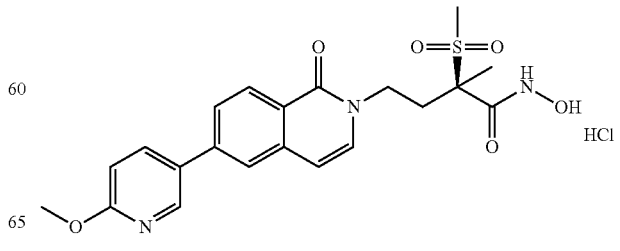

Part A

A reaction vessel was sealed with potassium carbonate (110 mg, 0.798 mmol), PdCl$_2$(dppf) (29.2 mg, 0.040 mmol), (2R)-4-(6-bromo-1-oxoisoquinolin-2(1H)-yl)-2-methyl-2-(methylsulfonyl)-N-((tetrahydro-2H-pyran-2-yl)oxy)butanamide (Intermediate 10) (200 mg, 0.399 mmol) and (6-methoxypyridin-3-yl)boronic acid (79 mg, 0.519 mmol) in water (0.5 mL) and 1,4-dioxane (3 mL). The mixture was heated in microwave at 100° C. for 30 min. The organic phase was diluted with DCM (20 mL) washed with water 20 mL, brine 30 mL, dried over sodium sulphate and concentrated. The residue was purified by silica gel chromatography (EtOAc/DCM: 10-100%) to afford (2R)-4-(6-(6-methoxypyridin-3-yl)-1-oxoisoquinolin-2(1H)-yl)-2-methyl-2-(methylsulfonyl)-N-((tetrahydro-2H-pyran-2-yl)oxy)butanamide (140 mg, 0.264 mmol, 66% yield) as a colorless oil.

LCMS: [M+H] 530.2.

Part B

To a solution of (2R)-4-(6-(6-methoxypyridin-3-yl)-1-oxoisoquinolin-2(1H)-yl)-2-methyl-2-(methylsulfonyl)-N-((tetrahydro-2H-pyran-2-yl)oxy)butanamide (140 mg, 0.264 mmol) in ethanol (3 mL) was added a 4M hydrogen chloride solution (0.198 ml, 0.793 mmol). The resulting solution was stirred at room temperature overnight and was concentrated. The residue was taken up in DMSO and purified by preparative HPLC (5-70% MeCN/H$_2$O, 0.1% TFA) to afford (R)—N-hydroxy-4-(6-(6-methoxypyridin-3-yl)-1-oxoisoquinolin-2(1H)-yl)-2-methyl-2-(methylsulfonyl)butanamide hydrochloride (93.2 mg, 0.193 mmol, 73% yield).

LCMS: [M+1] 446.2.

$^1$H NMR (METHANOL-d4) δ: ppm 8.74 (d, J=2.0 Hz, 1H), 8.68 (dd, J=9.1, 2.5 Hz, 1H), 8.47 (d, J=8.6 Hz, 1H), 8.01 (d, J=1.5 Hz, 1H), 7.87 (dd, J=8.3, 1.8 Hz, 1H), 7.45-7.55 (m, 2H), 6.84 (d, J=7.3 Hz, 1H), 4.38 (ddd, J=13.1, 10.8, 5.2 Hz, 1H), 4.24 (s, 3H), 3.88-4.02 (m, 1H), 3.13 (s, 3H), 2.59-2.73 (m, 1H), 2.41 (ddd, J=13.4, 11.1, 5.3 Hz, 1H), 1.75 (s, 1H).

Example 61. (2R)-4-{6-[4-(dimethylamino)phenyl]-1-oxo-1,2-dihydroisoquinolin-2-yl}-N-hydroxy-2-methanesulfonyl-2-methylbutanamide

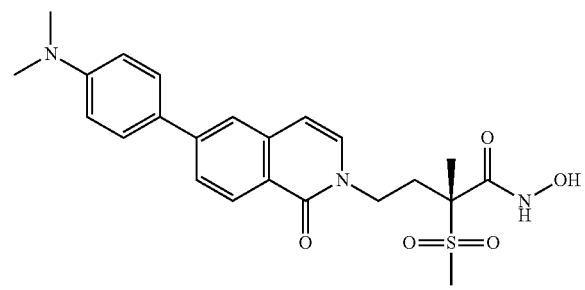 [SMILES: CN(C)c1ccc(-c2ccc3c(=O)n(CC[C@](C)(C(=O)NO)S(C)(=O)=O)ccc3c2)cc1]

Part A

To a mixture of (2R)-4-(6-bromo-1-oxoisoquinolin-2(1H)-yl)-2-methyl-2-(methylsulfonyl)-N-((tetrahydro-2H-pyran-2-yl)oxy)butanamide (Intermediate 10) (300 mg, 0.598 mmol) and (4-(dimethylamino)phenyl)boronic acid (148 mg, 0.898 mmol) in acetonitrile (2 mL) and water (0.2 mL) was added PdCl$_2$(dppf) (88 mg, 0.120 mmol) and K$_2$CO$_3$ (165 mg, 1.197 mmol) at 80° C. and was stirred for 1 hr. The reaction was cooled, filtered and diluted with ethyl acetate (50 mL). The organic layer was washed with water (20 mL) and brine (20 mL), dried over Na$_2$SO$_4$, filtered and concentrated. The residue was purified by silica gel chromatography (petroleum ether/EtOAc: 1/1 then 0/1) to afford (2R)-4-(6-(4-(dimethylamino)phenyl)-1-oxoisoquinolin-2(1H)-yl)-2-methyl-2-(methylsulfonyl)-N-((tetrahydro-2H-pyran-2-yl)oxy)butanamide (182 mg, 0.272 mmol, 46% yield).

Part B

To a mixture of (2R)-4-(6-(4-(dimethylamino)phenyl)-1-oxoisoquinolin-2(1H)-yl)-2-methyl-2-(methylsulfonyl)-N-((tetrahydro-2H-pyran-2-yl)oxy)butanamide (182 mg, 0.336 mmol) in dichloromethane (5 mL) was added HCl (0.420 mL, 1.680 mmol) in dioxane at room temperature. The resulting solution was stirred at 20° C. for 5 min when methanol (5 mL) was added. The reaction was stirred additional 1 hr. and warmed to room temperature for an additional 1 hr. The solution was concentrated and the residue was purified by preparative HPLC to give (R)-4-(6-(4-(dimethylamino)phenyl)-1-oxoisoquinolin-2(1H)-yl)-N-hydroxy-2-methyl-2-(methylsulfonyl)butanamide trifluoroacetic acid salt (70 mg, 0.122 mmol, 36% yield) as a white solid.

LCMS: [M+H] 458.3.

$^1$H NMR (500 MHz, DMSO-d6) δ: ppm 11.07 (s, 1H), 8.22 (d, J=8.5 Hz, 1H), 7.87 (d, J=1.5 Hz, 1H), 7.79-7.77 (m, 1H), 7.70 (d, J=8.5 Hz, 2H), 7.44 (d, J=7.5 Hz, 1H), 6.88 (s, 2H), 6.71 (d, J=7.0 Hz, 1H), 4.20-4.14 (m, 1H), 3.80-3.74 (m, 1H), 3.11 (s, 3H), 2.98 (s, 6H), 2.50-2.46 (m, 1H), 2.20-2.14 (m, 1H), 1.60 (s, 3H).

Example 62. (2R)-4-{6-[6-(dimethylamino)pyridin-3-yl]-1-oxo-1,2-dihydroisoquinolin-2-yl}-N-hydroxy-2-methanesulfonyl-2-methylbutanamide

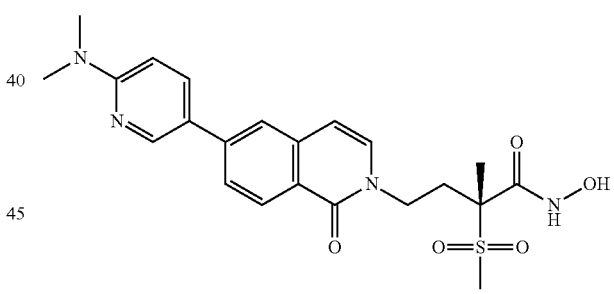

Part A

A reaction vessel was sealed with potassium carbonate (138 mg, 0.997 mmol), PdCl$_2$(dppf) (36.5 mg, 0.050 mmol), (2R)-4-(6-bromo-1-oxoisoquinolin-2(1H)-yl)-2-methyl-2-(methylsulfonyl)-N-((tetrahydro-2H-pyran-2-yl)oxy)butanamide (Intermediate 10) (250 mg, 0.499 mmol) and (6-(dimethylamino)pyridin-3-yl)boronic acid (83 mg, 0.499 mmol) and heated in a microwave to 110° C. for 30 min. The organic phase was diluted with DCM (20 mL), extracted with DCM (10 ml×3) and washed with water (20 mL), brine (30 mL), dried over sodium sulphate and concentrated and the residue was purified by silica gel chromatography (MeOH/DCM: 0-20%) to give (2R)-4-(6-(6-(dimethylamino)pyridine-3-yl)-1-oxoisoquinolin-2(1H)-yl)-2-methyl-2-(methylsulfonyl)-N-((tetrahydro-2H-pyran-2-yl)oxy)butanamide (230 mg, 0.424 mmol, 85% yield) as a colorless oil.

LCMS: [M+H] 543.2.

Part B

To a solution of (2R)-4-(6-(6-(dimethylamino)pyridin-3-yl)-1-oxoisoquinolin-2(1H)-yl)-2-methyl-2-(methylsulfonyl)-N-((tetrahydro-2H-pyran-2-yl)oxy)butanamide hydrochloride (230 mg, 0.397 mmol) in ethanol (3 mL) was added a 4M hydrogen chloride solution (0.298 ml, 1.191 mmol). The resulting solution was stirred at room temperature overnight. The reaction was concentrated, taken up in DMSO and purified by preparative HPLC (5-60% MeCN/$H_2O$, 0.1% TFA) to afford (R)-4-(6-(6-(dimethylamino)pyridin-3-yl)-1-oxoisoquinolin-2(1H)-yl)-N-hydroxy-2-methyl-2-(methylsulfonyl)butanamide trifluoroacetic acid salt (141 mg, 0.246 mmol, 62% yield) as a white powder.

LCMS: [M+H] 459.1.

$^1$H NMR (METHANOL-d4) δ: ppm 8.44 (dd, J=8.7, 2.7 Hz, 2H), 8.29 (d, J=1.8 Hz, 1H), 7.95 (br. s., 1H), 7.82 (d, J=8.3 Hz, 1H), 7.36-7.50 (m, 2H), 6.82 (d, J=7.3 Hz, 1H), 4.28-4.42 (m, 1H), 3.95 (td, J=11.6, 4.9 Hz, 1H), 3.38 (s, 6H), 3.12 (s, 3H), 2.57-2.73 (m, 1H), 2.33-2.47 (m, 1H), 1.75 (s, 3H).

Example 63. (2R)-4-{6-[2-(dimethylamino)pyrimidin-5-yl]-1-oxo-1,2-dihydroisoquinolin-2-yl}-N-hydroxy-2-methanesulfonyl-2-methylbutanamide

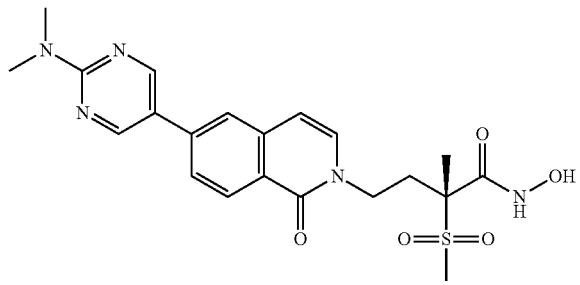 [SMILES: CN(C)c1ncc(-c2ccc3c(=O)n(CC[C@](C)(C(=O)NO)S(C)(=O)=O)ccc3c2)cn1]

Part A

To a solution of 5-bromo-2-chloropyrimidine (2 g, 10.34 mmol) and dimethylamine (5 ml, 10.00 mmol) in tetrahydrofuran (2 mL) was stirred at room temperature overnight. The solvent was removed and the residue was purified by silica gel chromatography 5% EtOAc/PE) to give 5-bromo-N,N-dimethylpyrimidin-2-amine (1.9 g, 8.93 mmol, 86% yield) as a white solid.

LCMS: [M+H] 202.

Part B $PdCl_2$(dppf)-$CH_2Cl_2$ adduct (323 mg, 0.396 mmol) was added to a solution of 4,4,4',4',5,5,5',5'-octamethyl-2,2'-bi(1,3,2-dioxaborolane) (1207 mg, 4.75 mmol), 5-bromo-N,N-dimethylpyrimidin-2-amine (800 mg, 3.96 mmol) and potassium acetate (1166 mg, 11.88 mmol) in 1,4-dioxane (10 mL) at room temperature under an atmosphere of nitrogen. The resulting solution was stirred at 100° C. for 12 hr. The reaction was filtered and the filtrate was concentrated to afford crude product.

LCMS: [M+H] 250.

Part C

A solution of $PdCl_2$(dppf)-$CH_2Cl_2$ adduct (65.1 mg, 0.080 mmol), $K_2CO_3$ (221 mg, 1.596 mmol), (2R)-4-(6-bromo-1-oxoisoquinolin-2(1H)-yl)-2-methyl-2-(methylsulfonyl)-N-((tetrahydro-2H-pyran-2-yl)oxy)butanamide (Intermediate 10) (400 mg, 0.798 mmol) and N,N-dimethyl-5-(4,4,5,5-tetramethyl-1,3,2-dioxaborolan-2-yl)pyrimidin-2-amine (298 mg, 1.197 mmol) in acetonitrile (40 mL) and water (10 mL) was stirred at 80° C. under $N_2$ for 3 hr. The reaction was filtered, the solvent removed and the residue purified by silica gel chromatography to give (2R)-4-(6-(2-(dimethylamino)pyrimidin-5-yl)-1-oxoisoquinolin-2(1H)-yl)-2-methyl-2-(methylsulfonyl)-N-((tetrahydro-2H-pyran-2-yl)oxy)butanamide (300 mg, 0.453 mmol, 57% yield)

LCMS: [M+H] 544.

Part D

A solution of (2R)-4-(6-(2-(dimethylamino)pyrimidin-5-yl)-1-oxoisoquinolin-2(1H)-yl)-2-methyl-2-(methylsulfonyl)-N-((tetrahydro-2H-pyran-2-yl)oxy)butanamide (270 mg, 0.497 mmol) and hydrogen chloride (10 ml, 40 mmol) in dichloromethane (5 mL) and methanol (5 ml) was stirred at room temperature for 2 hr. The solvent was removed and the residue was purified by preparative HPLC to give (R)-4-(6-(2-(dimethylamino)pyrimidin-5-yl)-1-oxoisoquinolin-2(1H)-yl)-N-hydroxy-2-methyl-2-(methylsulfonyl)butanamide trifluoroacetate (70 mg, 0.115 mmol, 23% yield) as a solid.

LCMS: [M+H] 460.

$^1$H NMR (400 MHz, DMSO-$d_6$) δ: ppm 11.08 (s, 1H), 8.84 (s, 2H), 8.25 (d, J=8.3 Hz, 1H), 7.95 (s, 1H), 7.82 (d, J=8.3 Hz, 1H), 7.47 (d, J=7.2 Hz, 1H), 6.68 (d, J=7.3 Hz, 1H), 4.28-4.05 (m, 1H), 3.88-3.65 (m, 1H), 3.20 (s, 6H), 3.07 (s, 3H), 2.25-2.06 (m, 2H), 1.60 (s, 3H).

Example 64. (2R)—N-hydroxy-2-methanesulfonyl-2-methyl-4-(6-{4-[(morpholin-4-yl)methyl]phenyl}-1-oxo-1,2-dihydroisoquinolin-2-yl)butanamide

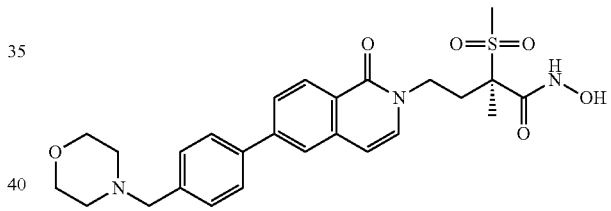

Part A

To a reaction vessel was added (2R)-4-(6-bromo-1-oxoisoquinolin-2(1H)-yl)-2-methyl-2-(methylsulfonyl)-N-((tetrahydro-2H-pyran-2-yl)oxy)butanamide (Intermediate 10) (2.5 g, 4.99 mmol), (4-(morpholinomethyl)phenyl)boronic acid (1.323 g, 5.98 mmol), potassium carbonate (1.378 g, 9.97 mmol), $PdCl_2$(dppf) (0.365 g, 0.499 mmol), 1,4-dioxane (15 mL) and water (5 mL). The reaction vessel was sealed and heated in a microwave to 120° C. for 30 min. The reaction was cooled and concentrated and the residue was purified by silica gel chromatography (EtOAc/hexanes: 0-100%) to give (2R)-2-methyl-2-(methylsulfonyl)-4-(6-(4-(morpholinomethyl)phenyl)-1-oxoisoquinolin-2(1H)-yl)-N-((tetrahydro-2H-pyran-2-yl)oxy)butanamide (3.12 g, 4.80 mmol, 96% yield).

LCMS: [M+H] 598.3.

Part B

To a solution of (2R)-2-methyl-2-(methylsulfonyl)-4-(6-(4-(morpholinomethyl)phenyl)-1-oxoisoquinolin-2(1H)-yl)-N-((tetrahydro-2H-pyran-2-yl)oxy)butanamide (3.12 g, 5.22 mmol) in ethanol (35 mL), was added a 4M hydrogen chloride in dioxane solution (3.91 mL, 15.66 mmol). The resulting solution was stirred at room temperature overnight. The reaction was concentrated and ether was added. The mixture was filtered and the solid was dissolved in water and lyophilized to afford (R)—N-hydroxy-2-methyl-2-(methylsulfonyl)-4-(6-(4-(morpholinomethyl)phenyl)-1-oxoisoquinolin-2(1H)-yl)butanamide hydrochloride (1.2 g, 2.072 mmol, 40% yield).

LCMS [M+H] 514.4.

$^1$H NMR (METHANOL-d4) δ: ppm 8.44 (d, J=8.6 Hz, 1H), 7.82-8.04 (m, 4H), 7.69 (d, J=7.8 Hz, 2H), 7.45 (d, J=7.6 Hz, 1H), 6.84 (d, J=7.3 Hz, 1H), 4.30-4.52 (m, 3H), 3.35-4.23 (m, 7H), 3.13 (s, 5H), 2.56-2.74 (m, 1H), 2.32-2.48 (m, 1H), 1.75 (s, 3H).

Example 65. (2R)-4-(6-{4-[(dimethylamino)methyl]-2-fluorophenyl}-1-oxo-1,2-dihydroisoquinolin-2-yl)-N-hydroxy-2-methanesulfonyl-2-methylbutanamide

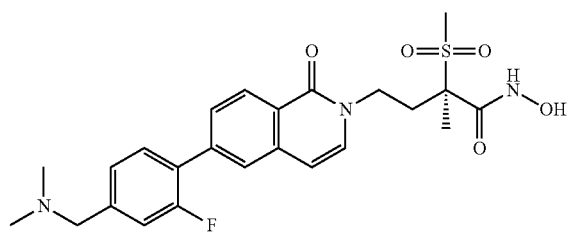 [SMILES: CN(C)Cc1ccc(-c2ccc3c(=O)n(CC[C@](C)(C(=O)NO)S(C)(=O)=O)ccc3c2)c(F)c1]

Part A

To a solution of (2R)-4-(6-(2-fluoro-4-formylphenyl)-1-oxoisoquinolin-2(1H)-yl)-2-methyl-2-(methylsulfonyl)-N-((tetrahydro-2H-pyran-2-yl)oxy)butanamide (2.0 g, 3.67 mmol) in 1,2-dichloroethane (25 mL) at 0° C. was added dimethylamine (27.5 mL, 55.1 mmol), acetic acid (0.21 mL, 3.67 mmol) and sodium triacetoxyhydroborate (2.335 g, 11.02 mmol). The reaction mixture was allowed to warm to room temperature and was stirred overnight. The organic phase was diluted with DCM (20 mL) and water (20 mL) was added. The mixture was extracted with DCM (3×20 ml) and the combined organic layers were washed with brine (30 mL), dried over sodium sulphate and concentrated to afford (2R)-4-(6-(4-((dimethylamino)methyl)-2-fluorophenyl)-1-oxoisoquinolin-2(1H)-yl)-2-methyl-2-(methylsulfonyl)-N-((tetrahydro-2H-pyran-2-yl)oxy)butanamide (2.37 g, 4.13 mmol, 112% yield).

LCMS: [M+H] 574.3.

Part B

To a solution of (2R)-4-(6-(4-((dimethylamino)methyl)-2-fluorophenyl)-1-oxoisoquinolin-2(1H)-yl)-2-methyl-2-(methylsulfonyl)-N-((tetrahydro-2H-pyran-2-yl)oxy)butanamide (2.4 g, 4.18 mmol) in ethanol (30 mL) was added a 4M solution of hydrogen chloride in dioxane (3.14 mL, 12.55 mmol). The resulting solution was stirred at room temperature overnight. The reaction was concentrated and ether was added. The mixture was filtered, the solid was dissolved in water and lyophilized to afford (R)-4-(6-(4-((dimethylamino)methyl)-2-fluorophenyl)-1-oxoisoquinolin-2(1H)-yl)-hydroxy-2-methyl-2-(methylsulfonyl)butanamide, Hydrochloride (1.61 g, 2.91 mmol, 70% yield).

LCMS: [M+H] 490.2.

$^1$H NMR (METHANOL-d4) δ: ppm 8.44 (d, J=8.6 Hz, 1H), 7.89 (s, 1H), 7.71-7.82 (m, 2H), 7.40-7.54 (m, 3H), 6.83 (d, J=7.3 Hz, 1H), 4.26-4.48 (m, 3H), 3.89-4.04 (m, 1H), 3.13 (s, 3H), 2.83-3.00 (m, 6H), 2.61-2.73 (m, 1H), 2.42 (ddd, J=13.3, 11.0, 5.3 Hz, 1H), 1.76 (s, 3H).

Example 66. (2R)-4-[6-(2-fluoro-4-{[(2-methoxyethyl)(methyl)amino]methyl}phenyl)-1-oxo-1,2-dihydroisoquinolin-2-yl]-N-hydroxy-2-methanesulfonyl-2-methylbutanamide

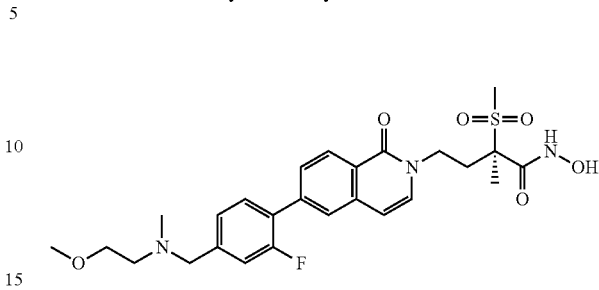

Part A (R)-ethyl 4-(6-bromo-1-oxoisoquinolin-2(1H)-yl)-2-methyl-2-(methylsulfonyl)butanoate (Intermediate 9) (1.5 g, 3.49 mmol), (2-fluoro-4-formylphenyl)boronic acid (0.702 g, 4.18 mmol), PdCl$_2$(dppf) (0.510 g, 0.697 mmol) and potassium carbonate (0.964 g, 6.97 mmol) was added to acetonitrile (2.4 mL) and water (0.4 mL). The resulting solution was stirred at 80° C. for 3 hr. The reaction was concentrated to afford crude product, which was purified by silica gel chromatography (EtOAc/hexanes: 0-100%) to afford (R)-ethyl 4-(6-(2-fluoro-4-formylphenyl)-1-oxoisoquinolin-2(1H)-yl)-2-methyl-2-(methylsulfonyl)butanoate (1.56 g, 3.29 mmol, 95% yield).

LCMS: [M+Na] 474.3.

$^1$H NMR (CHLOROFORM-d) δ: ppm 10.07 (d, J=1.5 Hz, 1H), 8.40-8.66 (m, 1H), 7.65-7.87 (m, 5H), 7.11-7.21 (m, 1H), 6.47-6.69 (m, 1H), 4.31-4.43 (m, 1H), 4.26 (q, J=7.1 Hz, 2H), 4.03-4.11 (m, 1H), 3.07-3.22 (m, 3H), 2.43-2.75 (m, 2H), 1.75-1.92 (m, 3H), 1.56-1.69 (m, 2H), 1.34 (t, J=7.1 Hz, 3H).

Part B

To a solution of (R)-ethyl 4-(6-(2-fluoro-4-formylphenyl)-1-oxoisoquinolin-2(1H)-yl)-2-methyl-2-(methylsulfonyl)butanoate (200 mg, 0.422 mmol), acetic acid (25.4 mg, 0.422 mmol) and sodium triacetoxyhydroborate (269 mg, 1.267 mmol) in 1,2-dichloroethane (2 mL) was added 2-methoxy-N-methylethanamine (113 mg, 1.267 mmol). The reaction mixture was stirred at room temperature for 3 hr. The solvent was removed and the crude product was purified by silica gel chromatography (MeOH/DCM: 0-20%) to afford (R)-ethyl 4-(6-(2-fluoro-4-(((2methoxyethyl)(methyl)amino)methyl)phenyl)-1-oxoisoquinolin-2(1H)-yl)-2-methyl-2-(methylsulfonyl)butanoate (239 mg, 0.415 mmol, 98% yield).

LCMS: [M+Na] 547.4.

$^1$H NMR (METHANOL-d4) δ: ppm 8.40 (d, J=8.6 Hz, 1H), 7.86 (s, 1H), 7.75 (d, J=8.6 Hz, 1H), 7.59-7.69 (m, 1H), 7.30-7.52 (m, 3H), 6.73-6.85 (m, 1H), 4.03-4.42 (m, 4H), 3.91 (s, 2H), 3.57-3.72 (m, 2H), 3.40 (s, 3H), 3.17 (s, 3H), 2.90 (t, J=5.4 Hz, 2H), 2.68-2.82 (m, 1H), 2.47-2.56 (m, 3H), 2.42 (ddd, J=13.8, 9.0, 5.1 Hz, 1H), 1.73-1.83 (m, 3H), 1.28 (t, J=7.2 Hz, 3H).

Part C

To a slurry of (R)-ethyl 4-(6-(2-fluoro-4-(((2-methoxyethyl)(methyl)amino)methyl)phenyl)-1-oxoisoquinolin-2 (1H)-yl)-2-methyl-2-(methylsulfonyl)butanoate (235 mg, 0.430 mmol), hydroxylamine (14.20 mg, 0.430 mmol) in 1,4-dioxane (3 mL) was added lithium hydroxide (10.30 mg, 0.430 mmol) under nitrogen. The reaction was stirred at room temp for 3 hr, was concentrated, diluted with DMSO and purified by reverse phase HPLC (5-70% MeCN/H$_2$O, 0.1% TFA) to afford (R)-4-(6-(2-fluoro-4-(((2-methoxy-ethyl)(methyl)amino)methyl)phenyl)-1-oxoisoquinolin-2(1H)-yl)-N-hydroxy-2-methyl-2-(methylsulfonyl)butanamide, trifluoroacetic acid salt (91 mg, 0.133 mmol, 31% yield) as a white powder.

LCMS: [M+H] 534.3.

$^1$H NMR (METHANOL-d4) δ: ppm 8.44 (d, J=8.3 Hz, 1H), 7.88 (s, 1H), 7.70-7.82 (m, 2H), 7.33-7.59 (m, 3H), 6.82 (d, J=7.3 Hz, 1H), 4.54 (br. s., 1H), 4.31-4.47 (m, 2H), 3.88-4.05 (m, 1H), 3.79 (br. s., 2H), 3.46 (s, 5H), 3.13 (s, 3H), 2.81-3.02 (m, 3H), 2.58-2.74 (m, 1H), 2.33-2.51 (m, 1H), 1.63-1.87 (m, 3H).

Example 67. (2R)-4-[6-(2-fluoro-4-{[(2-methoxy-ethyl)amino]methyl}phenyl)-1-oxo-1,2-dihydroiso-quinolin-2-yl]-N-hydroxy-2-methanesulfonyl-2-methylbutanamide

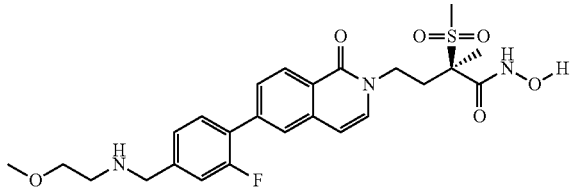 [SMILES: COCCNCc1ccc(-c2ccc3c(=O)n(CC[C@](C)(C(=O)NO)S(C)(=O)=O)ccc3c2)c(F)c1]

Part A

To a solution of (2R)-4-(6-(2-fluoro-4-formylphenyl)-1-oxoisoquinolin-2(1H)-yl)-2-methyl-2-(methylsulfonyl)-N-((tetrahydro-2H-pyran-2-yl)oxy)butanamide (3.5 g, 6.43 mmol) in 1,2-dichloroethane (40 mL) was added 2-methoxyethanamine (1.448 g, 19.28 mmol). The reaction mixture was stirred overnight when sodium triacetoxyhydroborate (4.09 g, 19.28 mmol) was added and the mixture was stirred and additional 3 hr. The organic phase was diluted with DCM (20 mL) and water (20 mL). The mixture was extracted with DCM (20 mL×3) and the combined organic layers were washed by brine (30 mL), dried over sodium sulphate and concentrated. The residue was purified by silical gel chromatography (MeOH/DCM: 0-20%) to afford (2R)-4-(6-(2-fluoro-4-(((2-methoxyethyl)amino)methyl) phenyl)-1-oxoisoquinolin-2(1H)-yl)-2-methyl-2-(methylsulfonyl)-N-((tetrahydro-2H-pyran-2-yl)oxy)butanamide (3.1 g, 5.13 mmol, 80% yield) as a colorless oil.

LCMS: [M+H] 604.4.

Part B

To a solution of (2R)-4-(6-(2-fluoro-4-(((2-methoxyethyl)amino)methyl)phenyl)-1-oxoisoquinolin-2(1H)-yl) 2-methyl-2-(methylsulfonyl)-N-((tetrahydro-2H-pyran-2-yl)oxy)butanamide (3.1 g, 5.13 mmol) in ethanol (3 mL) was added a hydrogen chloride (2.57 ml, 10.27 mmol) solution in dioxane (4M) and the resulting solution was stirred overnight. The reaction was concentrated, diluted with ethanol (10 mL), tert-butyl methyl ether (50 mL), and the mixture was stirred for 1 hr. The solid was filtered and dried to give (R)-4-(6-(2-fluoro-4-(((2-methoxyethyl)amino)methyl)phenyl)-1-oxoisoquinolin-2(1H)-yl)-N-hydroxy-2-methyl-2-(methylsulfonyl)butanamide hydrochloride (1.6 g, 2.88 mmol, 56% yield) as a light yellow solid.

LCMS: [M+H] 520.2.

$^1$H NMR (METHANOL-d$_4$) δ: ppm 8.39 (d, J=8.6 Hz, 1H), 7.84 (s, 1H), 7.67-7.75 (m, 2H), 7.46-7.53 (m, 2H), 7.43 (d, J=7.3 Hz, 1H), 6.79 (d, J=7.3 Hz, 1H), 4.28-4.42 (m, 3H), 3.89-4.02 (m, 1H), 3.66-3.77 (m, 2H), 3.45 (s, 3H), 3.29-3.32 (m, 2H), 3.13 (s, 3H), 2.57-2.72 (m, 1H), 2.41 (ddd, J=13.2, 11.2, 5.2 Hz, 1H), 1.75 (s, 3H).

Example 68. (2R)-4-[6-(2-fluoro-4-{[(2-methoxy-2-methylpropyl)amino]methyl}phenyl)-1-oxo-1,2-dihydroisoquinolin-2-yl]-N-hydroxy-2-methanesulfonyl-2-methylbutanamide

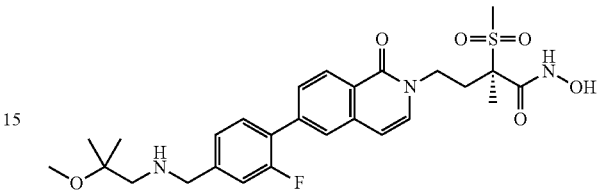

Part A

A flask was charged with potassium carbonate (5.51 g, 39.9 mmol), PdCl$_2$(dppf) (1.459 g, 1.994 mmol), (2R)-4-(6-bromo-1-oxoisoquinolin-2(1H)-yl)-2-methyl 2-(methylsulfonyl)-N-((tetrahydro-2H-pyran-2-yl)oxy)butanamide (10 g, 19.94 mmol) and (2-fluoro-4-formylphenyl)boronic acid (4.35 g, 25.9 mmol) and heated to 100° C. for 30 min. The organic phase was diluted with DCM (20 mL) and extracted with DCM (10 ml×3) and the combined organic layers were washed with water (20 mL), brine (30 mL), dried with sodium sulphate and concentrated. The residue was purified by silica gel chromatography (EtOAc/DCM: 10-100%) to afford (2R)-4-(6-(2-fluoro-4-formylphenyl)-1-oxoisoquinolin-2(1H)-yl)-2-methyl-2-(methylsulfonyl)-N-((tetrahydro-2H-pyran-2-yl)oxy)butanamide (9.8 g, 18.00 mmol, 90% yield) as a colorless oil.

LCMS: [M+H] 545.2.

Part B

To a solution of (2R)-4-(6-(2-fluoro-4-formylphenyl)-1-oxoisoquinolin-2(1H)-yl)-2-methyl-2-(methylsulfonyl)-N-((tetrahydro-2H-pyran-2-yl)oxy)butanamide (2.2 g, 4.04 mmol) in 1,2-dichloroethane (30 mL) at 0° C. was added 2-methoxy-2-methylpropan-1-amine (1.250 g, 12.12 mmol). The reaction mixture was stirred at room temperature overnight and sodium triacetoxyhydroborate (2.57 g, 12.12 mmol) was added at 0° C. The reaction was allowed to warm to room temperature and was stirred for 1 hr. The reaction was diluted with DCM (20 mL) and water (20 mL) and the aqueous phase was extracted with DCM (20 ml×3). The combined organic layers were washed with brine (30 mL), dried over sodium sulphate and concentrated. The residue was purified by silical gel chromatography (MeOH/DCM: 0-20%) to afford (2R)-4-(6-(2-fluoro-4-(((2-methoxy-2-methylpropyl)amino)methyl)phenyl)-1-oxoisoquinolin-2(1H)-yl)-2-methyl-2-(methylsulfonyl)-N-((tetrahydro-2H-pyran-2-yl)oxy)butanamide (2.32 g, 3.67 mmol, 91% yield) as a colorless oil.

LCMS: [M+H] 632.4.

Part C

To a solution of (2R)-4-(6-(2-fluoro-4-(((2-methoxy-2-methylpropyl)amino)methyl)phenyl)-1-oxoisoquinolin-2(1H)-yl)-2-methyl-2-(methylsulfonyl)-N-((tetrahydro-2H-pyran-2-yl)oxy)butanamide (2.32 g, 3.67 mmol) in ethanol (3 mL) was added a 4M solution of hydrogen chloride in dioxane (2.75 ml, 11.02 mmol). The reaction was stirred at room temperature overnight, was concentrated and diluted with ethanol (10 mL) and tert butyl methyl ether (50 mL). The mixture was stirred at room temperature for 1 hr. A precipitate formed and the solid was filtered to give (R)-4-(6-(2-fluoro-4-(((2-methoxy-2-methylpropyl)amino)methyl)phenyl)-1-oxoisoquinolin-2(1H)-yl)-N-hydroxy-2-methyl-2-(methylsulfonyl)butanamide hydrochloride (2.1 g, 3.60 mmol, 98% yield) as light yellow solid.

LCMS: [M+H] 548.3.

$^1$H NMR (METHANOL-d4) δ: ppm 8.37 (d, J=8.3 Hz, 1H), 7.83 (s, 1H), 7.66-7.74 (m, 2H), 7.53 (d, J=9.6 Hz, 2H), 7.42 (d, J=7.3 Hz, 1H), 6.78 (d, J=7.3 Hz, 1H), 4.28-4.43 (m, 3H), 3.94 (td, J=12.0, 4.8 Hz, 1H), 3.26 (s, 3H), 3.13 (s, 3H), 3.09 (s, 2H), 2.59-2.71 (m, 1H), 2.34-2.46 (m, 1H), 1.75 (s, 3H), 1.30 (s, 6H).

Example 69. (2R)-4-(6-{4-[(dimethylamino)methyl]-2,3-difluorophenyl}-1-oxo-1,2-dihydroisoquinolin-2-yl)-N-hydroxy-2-methanesulfonyl-2-methylbutanamide

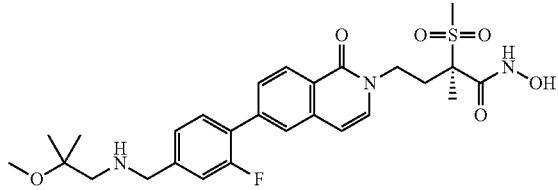 [SMILES: COC(C)(C)CNCc1ccc(-c2ccc3c(=O)n(CC[C@](C)(C(=O)NO)S(C)(=O)=O)ccc3c2)c(F)c1]

Part A

A reaction vessel sealed with potassium carbonate (2.76 g, 19.94 mmol), PdCl$_2$(dppf) (0.730 g, 0.997 mmol), (2R)-4-(6-bromo-1-oxoisoquinolin-2(1H)-yl)-2-methyl-2-(methylsulfonyl)-N-((tetrahydro-2H-pyran-2-yl)oxy)butanamide (Intermediate 10) (5 g, 9.97 mmol) and (2,3-difluoro-4-formylphenyl)boronic acid (2.410 g, 12.96 mmol) was heated in a microwave to 100° C. for 30 min. The organic phase was diluted with DCM (20 mL) and extracted with DCM (10 ml×3) and then washed with water (20 mL), brine (30 mL), dried over sodium sulphate and concentrated. The residue was purified with silica gel chromatography (MeOH/DCM: 0-20%) to afford (2R)-4-(6-(2,3-difluoro-4-formylphenyl)-1-oxoisoquinolin-2(1H)-yl)-2-methyl-2-(methylsulfonyl)-N-((tetrahydro-2H-pyran-2-yl)oxy)butanamide (3.9 g, 6.93 mmol, 70% yield) as a colorless oil.

LCMS: [M+Na] 585.3.

Part B

To a solution of (2R)-4-(6-(2,3-difluoro-4-formylphenyl)-1-oxoisoquinolin-2(1H)-yl)-2-methyl-2-(methylsulfonyl)-N-((tetrahydro-2H-pyran-2-yl)oxy)butanamide (2 g, 3.56 mmol) in 1,2-dichloroethane (30 mL) at 0° C. was added dimethylamine (2M, solution in THF) (26.7 mL, 53.3 mmol). The reaction mixture was stirred at room temperature overnight. Sodium triacetoxyhydroborate (2.260 g, 10.67 mmol) was added at 0° C. and the mixture was allowed to warm to room temperature and stirred for 2 hr. The organic phase was diluted with DCM (20 mL) and water (20 mL). The mixture was extracted with DCM (20 ml×3) and the combined organic layers were washed with brine (30 mL), dried over sodium sulphate and concentrated. The residue was purified by silica gel chromatography (MeOH/DCM: 0-20%) to afford (2R)-4-(6-(4-((dimethylamino)methyl)-2,3-difluorophenyl)-1-oxoisoquinolin-2(1H)-yl)-2-methyl-2-(methylsulfonyl)-N-((tetrahydro-2H-pyran-2-yl)oxy)butanamide (1.93 g, 3.26 mmol, 92% yield) as a colorless oil.

LCMS: [M+H] 592.3.

Part C

To a solution of (2R)-4-(6-(4-((dimethylamino)methyl)-2,3-difluorophenyl)-1-oxoisoquinolin-2(1H)-yl)-2-methyl-2-(methylsulfonyl)-N-((tetrahydro-2H-pyran-2-yl)oxy)butanamide (1.93 g, 3.26 mmol) in ethanol (3 mL) was added 4M hydrogen chloride solution in dioxane (2.45 ml, 9.79 mmol). The resulting solution was stirred at room temperature overnight. The reaction was concentrated and the residue taken up with ethanol (10 mL) and tert-butyl methyl ether (50 mL). The mixture was stirred at room temperature for 1 hr. The solid was filtered to give (R)-4-(6-(4-((dimethylamino)methyl)-2,3-difluorophenyl)-1-oxoisoquinolin-2(1H)-yl)-N-hydroxy-2-methyl-2-(methylsulfonyl)butanamide hydrochloride (1.36 g, 2.500 mmol, 77% yield) as a light yellow solid.

LCMS: [M+H] 508.2.

$^1$H NMR (METHANOL-d4) δ: ppm 8.42 (d, J=8.3 Hz, 1H), 7.88 (s, 1H), 7.74 (d, J=8.3 Hz, 1H), 7.55 (br. s 2H), 7.46 (d, J=7.3 Hz, 1H), 6.81 (d, J=7.1 Hz, 1H), 4.56 (s, 2H), 4.31-4.42 (m, 1H), 3.91-4.03 (m, 1H), 3.14 (s, 3H), 3.00 (s, 6H), 2.59-2.71 (m, 1H), 2.34-2.49 (m, 1H), 1.76 (s, 3H).

Example 70. (2R)-4-[6-(2-fluoro-4-{[(3-methoxypropyl)(methyl)amino]methyl}phenyl)-1-oxo-1,2-dihydroisoquinolin-2-yl]-N-hydroxy-2-methanesulfonyl-2-methylbutanamide

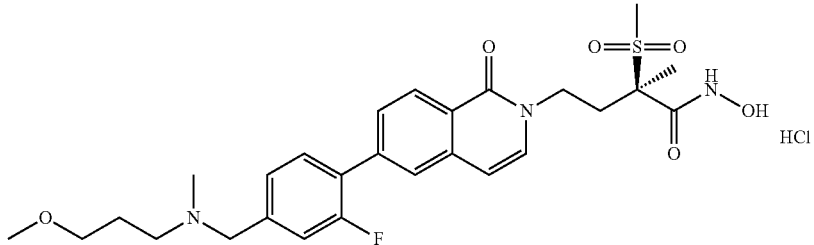 [SMILES: COCCCN(C)Cc1ccc(-c2ccc3c(=O)n(CC[C@](C)(C(=O)NO)S(C)(=O)=O)ccc3c2)c(F)c1 ; Cl]

Part A

To a solution of (2R)-4-(6-(2-fluoro-4-formylphenyl)-1-oxoisoquinolin-2(1H)-yl)-2-methyl-2-(methylsulfonyl)-N-((tetrahydro-2H-pyran-2-yl)oxy)butanamide (2.2 g, 4.04 mmol) in 1,2-dichloroethane (30 mL) at 0° C. was added 3-methoxy-N-methylpropan-1-amine (1.250 g, 12.12 mmol) and the reaction mixture was stirred at room temperature overnight. Sodium triacetoxyhydroborate (2.57 g, 12.12 mmol) was added at 0° C. and the mixture was allowed to warm to room temperature and stirred for 2 hr. The organic phase was diluted with DCM (20 mL) and water (20 mL) was added. The mixture was extracted with DCM (20 ml×3) and the combined organic layers were washed with brine (30 mL), dried over sodium sulphate and evaporated in vacuo and the residue was purified by silica gel chromatography (MeOH/DCM: 0-20%) to afford (2R)-4-(6-(2-fluoro-4-(((3-methoxypropyl)(methyl)amino)methyl)phenyl)-1-oxoisoquinolin-2(1H)-yl)-2-methyl-2-(methylsulfonyl)-N-((tetrahydro-2H-pyran-2-yl)oxy)butanamide (2.1 g, 3.32 mmol, 82% yield) as a colorless oil.

LCMS: [M+H] 632.4.

Part B

To a solution of (2R)-4-(6-(2-fluoro-4-(((3-methoxypropyl)(methyl)amino)methyl)phenyl)-1-oxoisoquinolin-2(1H)-yl)-2-methyl-2-(methylsulfonyl)-N-((tetrahydro-2H-pyran-2-yl)oxy)butanamide (2.1 g, 3.32 mmol) in ethanol (3 mL) was added a 4M solution of hydrogen chloride in dioxane (2.493 ml, 9.97 mmol). The resulting solution was stirred at room temperature overnight. The reaction was concentrated and diluted with ethanol (10 mL) and tert-butyl methyl ether (50 mL) and the mixture was stirred at room temperature for 1 hr. The solid was filtered to afford (R)-4-(6-(2-fluoro-4-(((3-methoxypropyl)(methyl)amino)methyl)phenyl)-1-oxoisoquinolin-2(1H)-yl)-N-hydroxy-2-methyl-2-(methylsulfonyl)butanamide hydrochloride (1.78 g, 3.05 mmol, 92% yield) as a light yellow solid.

LCMS: [M+H] 548.3.

$^1$H NMR (DEUTERIUM OXIDE) δ: ppm 7.62 (d, J=8.1 Hz, 1H), 6.96-7.30 (m, 5H), 6.80 (d, J=6.3 Hz, 1H), 6.14 (d, J=6.3 Hz, 1H), 4.21 (br. s., 2H), 3.73 (br. s., 1H), 3.33-3.53 (m, 3H), 3.06-3.25 (m, 5H), 3.00 (s, 3H), 2.72 (s, 3H), 2.25 (br. s., 1H), 1.92 (br. s., 3H), 1.52 (s, 3H).

Example 71. (2R)-4-[6-(2-fluoro-4-{[(3-methoxypropyl)(methyl)amino]methyl}phenyl)-1-oxo-1,2-dihydroisoquinolin-2-yl]-N-hydroxy-2-methanesulfonyl-2-methylbutanamide

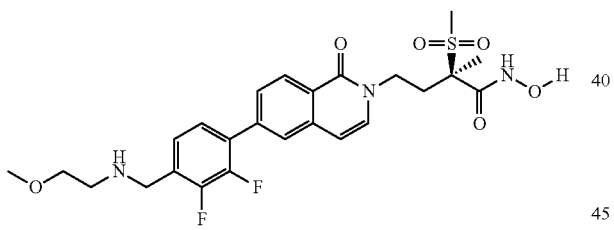

Part A

To a solution of (2R)-4-(6-(2,3-difluoro-4-formylphenyl)-1-oxoisoquinolin-2(1H)-yl)-2-methyl-2-(methylsulfonyl)-N-((tetrahydro-2H-pyran-2-yl)oxy)butanamide (1.9 g, 3.38 mmol) in 1,2-dichloroethane (30 mL) at 0° C. was added 2-methoxyethanamine (3.80 g, 50.7 mmol). The reaction mixture was stirred at room temperature overnight. Sodium cyanoborohydride (0.637 g, 10.13 mmol) was added at 0° C. and the mixture was allowed to warm to room temperature and stirred for 1 hr. The organic phase was diluted with DCM (20 mL) and water (20 mL) was added. The mixture was extracted with DCM (20 ml×3) and the combined organic layers were washed with brine (30 mL), dried over sodium sulphate and evaporated in vacuo and the residue was purified silica gel chromatography (MeOH/DCM: 0-20%) to afford (2R)-4-(6-(2,3-difluoro-4-(((2-methoxyethyl)amino)methyl)phenyl)-1-oxoisoquinolin-2(1H)-yl)-2-methyl-2-(methylsulfonyl)-N-((tetrahydro-2H-pyran-2-yl)oxy)butanamide (1.7 g, 2.73 mmol, 81% yield) as a colorless oil.

LCMS: [M+H] 622.3

Part B

To a solution of (2R)-4-(6-(2,3-difluoro-4-(((2-methoxyethyl)amino)methyl)phenyl)-1-oxoisoquinolin-2(1H)-yl)-2-methyl-2-(methylsulfonyl)-N-((tetrahydro-2H-pyran-2-yl)oxy)butanamide (1.7 g, 2.73 mmol) in ethanol (3 mL), was added a 4M solution of hydrogen chloride in dioxane (2.051 ml, 8.20 mmol). The resulting solution was stirred at room temperature overnight. The reaction was concentrated and diluted with ethanol (10 mL) and tert-butyl methyl ether (50 mL), and then the mixture was stirred at room temperature for 1 hr. The residue was filtered to give the product (R)-4-(6-(2,3-difluoro-4-(((2-methoxyethyl)amino)methyl)phenyl)-1-oxoisoquinolin-2(1H)-yl)-N-hydroxy-2-methyl-2-(methylsulfonyl)butanamide, trifluoroacetic acid salt (1.03 g, 1.581 mmol, 58% yield) as a light yellow solid.

LCMS: [M+H] 538.2.

$^1$H NMR (METHANOL-d4) δ: ppm 8.40 (d, J=8.3 Hz, 1H), 7.86 (s, 1H), 7.71 (d, J=8.6 Hz, 1H), 7.47-7.55 (m, 2H), 7.45 (d, J=7.3 Hz, 1H), 6.80 (d, J=7.3 Hz, 1H), 4.45 (s, 2H), 4.36 (ddd, J=12.9, 11.0, 5.2 Hz, 1H), 3.96 (ddd, J=12.9, 11.2, 4.9 Hz, 1H), 3.71-3.76 (m, 2H), 3.46 (s, 3H), 3.35-3.40 (m, 2H), 3.13 (s, 3H), 2.59-2.72 (m, 1H), 2.41 (ddd, J=13.3, 11.1, 5.2 Hz, 1H), 1.75 (s, 3H).

Example 72. (2R)-4-[6-(4-{[(2-ethoxyethyl)amino]methyl}-2-fluorophenyl)-1-oxo-1,2-dihydroisoquinolin-2-yl]-N-hydroxy-2-methanesulfonyl-2-methylbutanamide

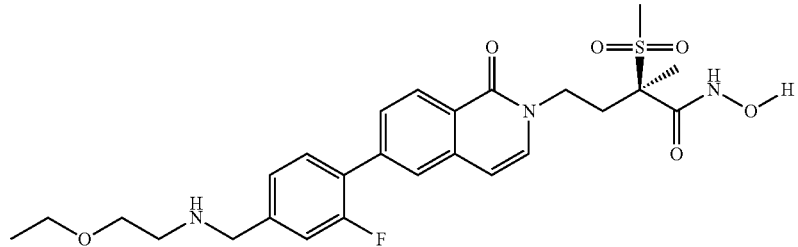 [SMILES: CCOCCNCc1ccc(-c2ccc3c(=O)n(CC[C@](C)(C(=O)NO)S(C)(=O)=O)ccc3c2)c(F)c1]

Part A

A reaction vessel was sealed with potassium carbonate (5.51 g, 39.9 mmol), PdCl$_2$(dppf) (1.459 g, 1.994 mmol), (2R)-4-(6-bromo-1-oxoisoquinolin-2(1H)-yl)-2-methyl-2-(methylsulfonyl)-N-((tetrahydro-2H-pyran-2-yl)oxy)butanamide (Intermediate 10) (10 g, 19.94 mmol) and (2-fluoro-4-formylphenyl)boronic acid (4.35 g, 25.9 mmol)

and heated to 100° C. for 30 min. The organic phase was diluted with DCM (20 mL) and extracted with DCM (10 ml×3) and then washed with water (20 mL), brine (30 mL), dried over sodium sulphate and evaporated in vacuo and the obtained residue was purified silica gel chromatography (EtOAc/Hexanes: 0-100%) to afford (2R)-4-(6-(2-fluoro-4-formylphenyl)-1-oxoisoquinolin-2(1H)-yl)-2-methyl-2-(methylsulfonyl)-N-((tetrahydro-2H-pyran-2-yl)oxy)butanamide (8.9 g, 16.34 mmol, 82% yield) as a colorless oil.

LCMS: [M+23] 567.2.

Part B

To a solution of (2R)-4-(6-(2-fluoro-4-formylphenyl)-1-oxoisoquinolin-2(1H)-yl)-2-methyl-2-(methylsulfonyl)-N-((tetrahydro-2H-pyran-2-yl)oxy)butanamide (2.3 g, 4.22 mmol) in 1,2-dichloroethane (30 mL) at 0° C. was added 2-ethoxyethanamine (1.129 g, 12.67 mmol). The reaction mixture was stirred at room temperature overnight. Sodium triacetoxyhydroborate (2.69 g, 12.67 mmol) was added at 0° C. and the mixture was allowed to warm to room temperature and stirred for 1 h. The organic phase was diluted with DCM (20 mL) and water (20 mL) was added. The mixture was extracted with DCM (20 ml×3) and the combined organic layers were washed with brine (30 mL), dried over sodium sulphate and evaporated in vacuo and the residue was purified by silica gel chromatography (MeOH/DCM: 0-20%) to afford (2R)-4-(6-(4-(((2-ethoxyethyl)amino)methyl)-2-fluorophenyl)-1-oxoisoquinolin-2(1H)-yl)-2-methyl-2-(methylsulfonyl)-N-((tetrahydro-2H-pyran-2-yl)oxy)butanamide (2.2 g, 3.56 mmol, 84% yield) as a colorless oil.

LCMS: [M+H] 618.3.

Part C

To a solution of (2R)-4-(6-(4-(((2-ethoxyethyl)amino)methyl)-2-fluorophenyl)-1-oxoisoquinolin-2(1H)-yl)-2-methyl-2-(methylsulfonyl)-N-((tetrahydro-2H-pyran-2-yl)oxy)butanamide (2.2 g, 3.56 mmol) in ethanol (3 mL) was added a 4M solution of hydrogen chloride in dioxane (2.67 ml, 10.68 mmol). The resulting solution was stirred at room temperature overnight. The reaction was concentrated and diluted with ethanol (10 mL) and tert-butyl methyl ether (50 mL) and the mixture was stirred at room temperature for 1 hr. The solid was filtered to afford (R)-4-(6-(4-(((2-ethoxyethyl)amino)methyl)-2-fluorophenyl)-1-oxoisoquinolin-2(1H)-yl)-N-hydroxy-2-methyl-2-(methylsulfonyl)butanamide, hydrochloride (1.49 g, 2.61 mmol, 73% yield) as a light yellow solid.

LCMS: [M+H] 534.2.

$^1$H NMR (METHANOL-d4) δ: ppm 8.38 (d, J=8.3 Hz, 1H), 7.83 (s, 1H), 7.65-7.75 (m, 2H), 7.45-7.53 (m, 2H), 7.42 (d, J=7.3 Hz, 1H), 6.78 (d, J=7.3 Hz, 1H), 4.30-4.40 (m, 3H), 3.90-4.00 (m, 1H), 3.77 (t, J=4.8 Hz, 2H), 3.62 (q, J=6.9 Hz, 2H), 3.13 (s, 3H), 2.58-2.71 (m, 1H), 2.34-2.46 (m, 1H), 1.75 (s, 3H), 1.27 (t, J=7.1 Hz, 3H).

Example 73. (2R)-4-{6-[2-fluoro-4-({[2-(propan-2-yloxy)ethyl]amino}methyl)phenyl]-1-oxo-1,2-dihydroisoquinolin-2-yl}-N-hydroxy-2-methanesulfonyl-2-methylbutanamide

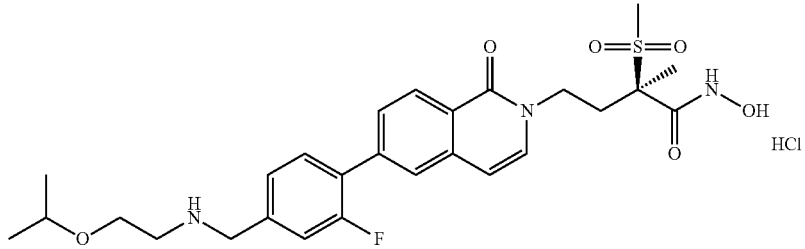 [SMILES: CC(C)OCCNCc1ccc(-c2ccc3c(=O)n(CC[C@](C)(C(=O)NO)S(C)(=O)=O)ccc3c2)c(F)c1 ; Cl]

Part A

To a solution of (2R)-4-(6-(2-fluoro-4-formylphenyl)-1-oxoisoquinolin-2(1H)-yl)-2-methyl-2-(methylsulfonyl)-N-((tetrahydro-2H-pyran-2-yl)oxy)butanamide (0.5 g, 0.918 mmol) in 1,2-dichloroethane (30 mL) at 0° C. was added 2-isopropoxyethanamine (0.284 g, 2.75 mmol). The reaction mixture was stirred at room temperature overnight. Sodium triacetoxyhydroborate (0.584 g, 2.75 mmol) was added at 0° C. and the mixture was allowed to warm to room temperature and stirred for 5 hr. The organic phase was diluted with DCM (20 mL) and water (20 mL) and the mixture was extracted with DCM (20 ml×3). The combined organic layers were washed with brine (30 mL), dried over sodium sulphate and evaporated in vacuo and the residue was purified by silica gel chromatography (MeOH/DCM: 0-20%) to afford (2R)-4-(6-(2-fluoro-4-(((2-isopropoxyethyl)amino)methyl)phenyl)-1-oxoisoquinolin-2(1H)-yl)-2-methyl-2-(methylsulfonyl)-N-((tetrahydro-2H-pyran-2-yl)oxy)butanamide (0.52 g, 0.823 mmol, 90% yield) as a colorless oil.

LCMS: [M+H] 632.4.

Part B

To a solution of (2R)-4-(6-(2-fluoro-4-(((2-isopropoxyethyl)amino)methyl)phenyl)-1-oxoisoquinolin-2(1H)-yl)-2-methyl-2-(methylsulfonyl)-N-((tetrahydro-2H-pyran-2-yl)oxy)butanamide (0.52 g, 0.823 mmol) in ethanol (3 mL) was added a 4M solution of hydrogen chloride in dioxane (0.617 ml, 2.469 mmol) and the solution was stirred at room temperature overnight. The reaction was concentrated, diluted with DMSO and purified by reverse phase HPLC (5-70%, MeCN/H$_2$O, 0.1% TFA) to afford (R)-4-(6-(2-fluoro-4-(((2-isopropoxyethyl)amino)methyl)phenyl)-1-oxoisoquinolin-2(1H)-yl)-N-hydroxy-2-methyl-2-(methylsulfonyl)butanamide hydrochloride (0.2 g, 0.342 mmol, 41.6% yield) as a white powder.

LCMS: [M+H] 548.2.

$^1$H NMR (DEUTERIUM OXIDE) δ: ppm 7.76 (br. s., 1H), 7.10-7.39 (m, 5H), 6.89 (br. s., 1H), 6.30 (br. s., 1H), 4.20 (br. s., 2H), 3.80 (br. s., 1H), 3.44-3.72 (m, 4H), 3.16 (br. s., 2H), 3.02 (br. s., 3H), 2.33 (br. s., 1H), 2.02 (br. s., 1H), 1.55 (br. s., 3H), 1.06 (d, J=5.8 Hz, 6H).

Example 74. (2R)-4-[6-(2-fluoro-4-{[(2-hydroxyethyl)(methyl)amino]methyl}phenyl)-1-oxo-1,2-dihydroisoquinolin-2-yl]-N-hydroxy-2-methanesulfonyl-2-methylbutanamide

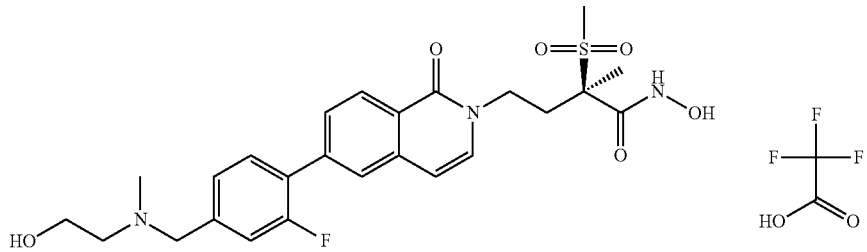 [SMILES: CN(CCO)Cc1ccc(-c2ccc3c(=O)n(CC[C@](C)(C(=O)NO)S(C)(=O)=O)ccc3c2)c(F)c1 ; O=C(O)C(F)(F)F]

Part A

To a solution of (2R)-4-(6-(2-fluoro-4-formylphenyl)-1-oxoisoquinolin-2(1H)-yl)-2-methyl-2-(methylsulfonyl)-N-((tetrahydro-2H-pyran-2-yl)oxy)butanamide (2.3 g, 4.22 mmol) in 1,2-dichloroethane (30 mL) at 0° C. was added 2-(methylamino)ethanol (0.952 g, 12.67 mmol) and the reaction mixture was stirred at room temperature overnight. Sodium triacetoxyhydroborate (2.69 g, 12.67 mmol) was added at 0° C. and the mixture was allowed to warm to room temperature and stirred for 1 hr. The organic phase was diluted with DCM (20 mL) and water (20 mL) and the mixture was extracted with DCM (20 mL×3). The combined organic layers were washed with brine (30 mL), dried over sodium sulphate and evaporated in vacuo and the residue was purified by silica gel chromatography (MeOH/DCM: 0-20%) to afford (2R)-4-(6-(2-fluoro-4-(((2-hydroxyethyl)(methyl)amino)methyl)phenyl)-1-oxoisoquinolin-2(1H)-yl)-2-methyl-2-(methylsulfonyl)-N-((tetrahydro-2H-pyran-2-yl)oxy)butanamide (2.3 g, 3.81 mmol, 90% yield) as a colorless oil.

LCMS: [M+H] 604.3.

Part B

To a solution of (2R)-4-(6-(2-fluoro-4-(((2-hydroxyethyl)(methyl)amino)methyl)phenyl)-1-oxoisoquinolin-2(1H)-yl)-2-methyl-2-(methylsulfonyl)-N-((tetrahydro-2H-pyran-2-yl)oxy)butanamide (2.23 g, 3.69 mmol) in ethanol (3 mL) was added a 4M solution of hydrogen chloride in dioxane (2.77 mL, 11.08 mmol) and the solution was stirred at room temperature for overnight. The reaction was concentrated, diluted with ethanol (10 mL) and tert-butyl methyl ether (50 mL) and the mixture was stirred at room temperature for 1 hr. The solid was filtered to afford (R)-4-(6-(2-fluoro-4-(((2-hydroxyethyl)(methyl)amino)methyl)phenyl)-1-oxoisoquinolin-2(1H)-yl)-N-hydroxy-2-methyl-2-(methylsulfonyl)butanamide trifluoroacetic acid salt (1.63 g, 2.57 mmol, 70% yield) as a light yellow solid.

LCMS: [M+H] 520.0.

$^1$H NMR (DEUTERIUM OXIDE) δ: ppm 7.55 (d, J=8.3 Hz, 1H), 7.10-7.19 (m, 3H), 7.03 (d, J=8.3 Hz, 1H), 6.98 (s, 1H), 6.70 (d, J=7.3 Hz, 1H), 6.04 (d, J=7.3 Hz, 1H), 4.24-4.37 (m, 1H), 4.07-4.21 (m, 1H), 3.77-3.85 (m, 2H), 3.57-3.72 (m, 1H), 3.32-3.44 (m, 1H), 3.24 (br. s., 1H), 3.14 (br. s., 1H), 2.98 (s, 3H), 2.74 (s, 3H), 2.12-2.25 (m, 1H), 1.84-1.98 (m, 1H), 1.48 (s, 3H).

Example 75. (2R)-4-(6-{4-[(cyclopropylamino)methyl]phenyl}-1-oxo-1,2-dihydroisoquinolin-2-yl)-N-hydroxy-2-methanesulfonyl-2-methylbutanamide

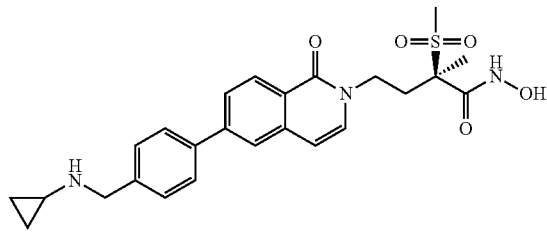 [SMILES: C[C@@](CCn1ccc2cc(-c3ccc(CNC4CC4)cc3)ccc2c1=O)(C(=O)NO)S(C)(=O)=O]

Part A

To a reaction vessel sealed with potassium carbonate (165 mg, 1.197 mmol), PdCl$_2$(dppf) (43.8 mg, 0.060 mmol), (2R)-4-(6-bromo-1-oxoisoquinolin-2(1H)-yl)-2-methyl-2-(methylsulfonyl)-N-((tetrahydro-2H-pyran-2-yl)oxy)butanamide (Intermediate 10)(300 mg, 0.598 mmol) was added (4-formylphenyl)boronic acid (117 mg, 0.778 mmol) and the reaction heated in a microwave to 110° C. for 30 min. The organic phase was diluted with DCM (20 mL) and extracted with DCM (10 mL×3) and washed with water (20 mL), brine (30 mL), dried over sodium sulphate and evaporated in vacuo. The residue was purified by silica gel chromatography (MeOH/DCM: 0-20%) to afford (2R)-4-(6-(4-formylphenyl)-1-oxoisoquinolin-2(1H)-yl)-2-methyl-2-(methylsulfonyl)-N-((tetrahydro-2H-pyran-2-yl)oxy)butanamide (190 mg, 0.361 mmol, 60% yield) as a colorless oil.

LCMS: [M+Na] 549.2.

Part B

To a solution of (2R)-4-(6-(4-formylphenyl)-1-oxoisoquinolin-2(1H)-yl)-2-methyl-2-(methylsulfonyl)-N-(tetrahydro-2H-pyran-2-yl)oxy)butanamide (2.5 g, 4.75 mmol) in 1,2-dichloroethane (30 mL) was added cyclopropanamine (0.813 g, 14.24 mmol), The reaction mixture was stirred at room temperature overnight. Sodium cyanoborohydride (0.895 g, 14.24 mmol) was added and the mixture was stirred for 1 hr. The organic phase was diluted with DCM (20 mL) and water (20 mL) was added. The mixture was extracted with DCM (20 mL×3) and the combined organic layers were washed with brine (30 mL), dried over sodium sulphate and concentrated. The residue was purified by silica gel chromatography (MeOH/DCM: 0-20%) to afford (2R)-4-(6-(4-((cyclopropylamino)methyl)phenyl)-1-oxoisoquinolin-2(1H)-yl)-2-methyl-2-(methylsulfonyl)-N-(tetrahydro-2H-pyran-2-yl)oxy)butanamide (1.9 g, 3.35 mmol, 71% yield) as a colorless oil.

LCMS: [M+H] 568.

Part C

To a solution of (2R)-4-(6-(4-(cyclopropylamino)methyl)phenyl)-1-oxoisoquinolin-2(1H)-yl)-2-methyl-2-(methylsulfonyl)-N-(tetrahydro-2H-pyran-2-yl)oxy)butanamide (1.9 g, 3.35 mmol) in ethanol (3 mL) was added a 4M solution of hydrogen chloride in dioxane (2.51 mL, 10.04 mmol). The resulting solution was stirred at room temperature overnight. The reaction was concentrated and diluted with ethanol (10 mL) and tert-butyl methyl ether (50 mL) and the mixture was stirred for 1 hr. The solid was filtered to give the product (R)-4-(6-(4-(cyclopropylamino)methyl)phenyl)-1-oxoisoquinolin-2(1H)-yl)-N-hydroxy-2-methyl-2-(methylsulfonyl)butanamide hydrochloride (1.63 g, 3.13 mmol, 94% yield) as a light yellow solid.

LCMS: [M+H] 484.2, $^1$H NMR (400 MHz, METHANOL-d4) δ: ppm 0.88-1.02 (m, 4H), 1.75 (s, 3H), 2.40 (ddd, J=13.26, 11.12, 5.18 Hz, 1H), 2.57-2.70 (m, 1H), 2.79-2.91 (m, 1H), 3.13 (s, 3H), 3.85-3.99 (m, 1H), 4.26-4.48 (m, 3H), 6.82 (d, J=7.33 Hz, 1H), 7.42 (d, J=7.33 Hz, 1H), 7.68 (d, J=8.34 Hz, 2H), 7.80-7.96 (m, 4H), 8.40 (d, J=8.34 Hz, 1H).

Example 76. (2R)-4-(6-{4-[(cyclopropylamino)methyl]-2-fluorophenyl}-1-oxo-1,2-dihydroisoquinolin-2-yl)-N-hydroxy-2-methanesulfonyl-2-methylbutanamide

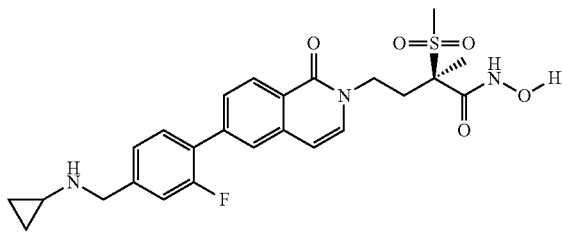 [SMILES: C[C@@](CCn1ccc2cc(-c3ccc(CNC4CC4)cc3F)ccc2c1=O)(C(=O)NO)S(C)(=O)=O]

Part A

A reaction vessel was sealed with potassium carbonate (5.51 g, 39.9 mmol), PdCl$_2$(dppf) (1.459 g, 1.994 mmol), (2R)-4-(6-bromo-1-oxoisoquinolin-2(1H)-yl)-2-methyl-2-(methylsulfonyl)-N-(tetrahydro-2H-pyran-2-yl)oxy)butanamide (10 g, 19.94 mmol) and (2-fluoro-4-formylphenyl)boronic acid (4.35 g, 25.9 mmol) and heated to 100° C. for 30 min. The organic phase was diluted with DCM (20 mL) and extracted with DCM (10 mL×3). The solution was washed with water (20 mL), brine (30 mL), dried over sodium sulphate and evaporated. The residue was purified by silica gel chromatography (EtOAc/hexanes: 0-100%) to afford (2R)-4-(6-(2-fluoro-4-formylphenyl)-1-oxoisoquinolin-2(1H)-yl)-2-methyl-2-(methylsulfonyl)-N-(tetrahydro-2H-pyran-2-yl)oxy)butanamide (8.9 g, 16.34 mmol, 82% yield) as a colorless oil.

LCMS: [M+H] 567.2.

Part B

To a solution of (2R)-4-(6-(2-fluoro-4-formylphenyl)-1-oxoisoquinolin-2(1H)-yl)-2-methyl-2-(methylsulfonyl)-N-(tetrahydro-2H-pyran-2-yl)oxy)butanamide (0.4 g, 0.734 mmol) in 1,2-dichloroethane (30 mL) at 0° C. was added cyclopropanamine (0.126 g, 2.203 mmol) and the reaction mixture was stirred at room temperature overnight. Sodium cyanoborohydride (0.138 g, 2.203 mmol) was added at 0° C. and the mixture was allowed to warm to room temperature and stirred for 1 hr. The organic phase was diluted with DCM (20 mL) and water (20 mL) was added. The mixture was extracted with DCM (20 mL×3) and the combined organic layers were washed with brine (30 mL), dried over sodium sulphate and evaporated and the residue was purified by silica gel chromatography (MeOH/DCM: 0-20%) to afford (2R)-4-(6-(4-(cyclopropylamino)methyl)-2-fluorophenyl)-1-oxoisoquinolin-2(1H)-yl)-2-methyl-2-(methylsulfonyl)-N-(tetrahydro-2H-pyran-2-yl)oxy)butanamide (0.36 g, 0.615 mmol, 84% yield) as a colorless oil.

LCMS: [M+H] 586.3.

Part C

To a solution of (2R)-4-(6-(4-(cyclopropylamino)methyl)-2-fluorophenyl)-1-oxoisoquinolin-2(1H)-yl)-2-methyl-2-(methylsulfonyl)-N-(tetrahydro-2H-pyran-2-yl)oxy)butanamide (0.36 g, 0.615 mmol) in ethanol (3 mL) was added a 4M solution of hydrogen chloride in dioxane (0.461 mL, 1.844 mmol) and was stirred at room temperature overnight. The reaction was concentrated and diluted with ethanol (10 mL) and tert-butyl methyl ether (50 mL) and stirred at room temperature for 1 hr. The solid was filtered to give the product (R)-4-(6-(4-(cyclopropylamino)methyl)-2-fluorophenyl)-1-oxoisoquinolin-2(1H)-yl)-N-hydroxy-2-methyl-2-(methylsulfonyl)butanamide hydrochloride (79 mg, 0.147 mmol, 24% yield) as a light yellow solid.

LCMS: [M+H] 502.2.

$^1$H NMR (METHANOL-d4) δ: ppm 8.42 (d, J=8.6 Hz, 1H), 7.86 (s, 1H), 7.69-7.77 (m, 2H), 7.40-7.54 (m, 3H), 6.81 (d, J=7.3 Hz, 1H), 4.43 (s, 2H), 4.33-4.41 (m, 1H), 3.95 (td, J=12.0, 5.1 Hz, 1H), 3.13 (s, 3H), 2.79-2.91 (m, 1H), 2.59-2.72 (m, 1H), 2.34-2.48 (m, 1H), 1.75 (s, 3H), 0.94-1.01 (m, 4H).

Example 77. (2R)—N-hydroxy-2-methanesulfonyl-2-methyl-4-(1-oxo-6-{4-[(1,2,2-trimethylhydrazin-1-yl)methyl]phenyl}-1,2-dihydroisoquinolin-2-yl)butanamide

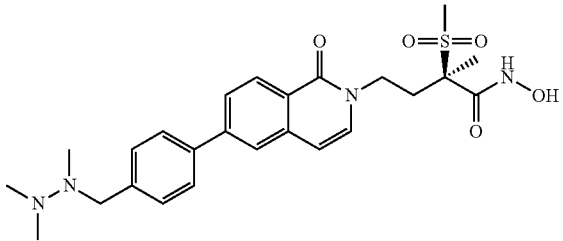 [SMILES: CN(C)N(C)Cc1ccc(-c2ccc3c(=O)n(CC[C@](C)(C(=O)NO)S(C)(=O)=O)ccc3c2)cc1]

Part A

To a solution of 2-(4-(bromomethyl)phenyl)-4,4,5,5-tetramethyl-1,3,2-dioxaborolane (500 mg, 1.684 mmol) in N,N-dimethylformamide (10 mL) was added DIPEA (0.735 mL, 4.21 mmol) and 1,1,2-trimethylhydrazine (374 mg, 5.05 mmol). The reaction mixture was heated to 60° C. for 24 hr. The reaction was diluted with DCM (20 mL) and water (10 mL) and extracted with DCM (20 mL×3) and the combined organic layers were washed with brine (30 mL), dried over sodium sulphate and evaporated to afford 1,1,2-trimethyl-2-(4-(4,4,5,5-tetramethyl-1,3,2-dioxaborolan-2-yl)benzyl)hydrazine (321 mg, 1.106 mmol, 66% yield) which were used in next step without further purification.

LCMS: [M+H] 291.2.

Part B

A reaction vessel was sealed with potassium carbonate (110 mg, 0.798 mmol), PdCl₂(dppf) (29.2 mg, 0.040 mmol), (2R)-4-(6-bromo-1-oxoisoquinolin-2(1H)-yl)-2-methyl-2-(methylsulfonyl)-N-(tetrahydro-2H-pyran-2-yl)oxy)butanamide (200 mg, 0.399 mmol) and 1,1,2-trimethyl-2-(4-(4,4,5,5-tetramethyl-1,3,2-dioxaborolan-2-yl)benzyl)hydrazine (116 mg, 0.399 mmol) and was heated in a microwave to 110° C. for 30 min. The organic phase was diluted with DCM (20 mL), extracted with DCM (10 mL×3) and washed with water (20 mL), brine 30 (mL), dried over sodium sulphate and concentrated. The resulting residue was purified with silica gel chromatography (MeOH/DCM: 0-20%) to afford (2R)-2-methyl-2-(methylsulfonyl)-4-(1-oxo-6-(4-(1,2,2-trimethylhydrazinyl)methyl)phenyl)isoquinolin-2(1H)-yl)-N-(tetrahydro-2H-pyran-2-yl)oxy)butanamide (120 mg, 0.127 mmol, 32% yield) as a colorless oil.

LCMS: [M+H] 585.2.

N31162-42

Part C

To a solution of (2R)-2-methyl-2-(methylsulfonyl)-4-(1-oxo-6-(4-(1,2,2-trimethylhydrazinyl)methyl)phenyl)isoquinolin-2(1H)-yl)-N-(tetrahydro-2H-pyran-2-yl)oxy)butanamide (0.12 g, 0.205 mmol) in ethanol (3 mL) was added a 4M solution of hydrogen chloride in dioxane (0.154 mL, 0.616 mmol) and the resulting solution was stirred at room temperature overnight. The reaction was concentrated, diluted with DMSO and purified by preparative HPLC (5-70% MeCN/H₂O, 0.1% TFA) to afford (R)—N hydroxy-2-methyl-2-(methylsulfonyl)-4-(1-oxo-6-(4-(1,2,2 trimethylhydrazinyl)methyl)phenyl)isoquinolin-2(1H)-yl)butanamide trifluoroacetic acid salt (5.3 mg, 8.62 μmol, 4.20% yield) as a white powder.

LCMS: [M+H] 501.2.

¹H NMR (METHANOL-d4) δ: ppm 8.43 (d, J=8.3 Hz, 1H), 7.94 (s, 1H), 7.80-7.89 (m, 3H), 7.59 (d, J=8.1 Hz, 2H), 7.44 (d, J=7.6 Hz, 1H), 6.84 (d, J=7.3 Hz, 1H), 4.30-4.46 (m, 1H), 4.18 (br. s., 2H), 3.84-3.99 (m, 1H), 3.00-3.21 (m, 9H), 2.55-2.78 (m, 4H), 2.32-2.53 (m, 1H), 1.75 (s, 3H).

Example 78. (2R)—N-hydroxy-2-methanesulfonyl-4-(6-{4-[(methoxyamino)methyl]phenyl}-1-oxo-1,2-dihydroisoquinolin-2-yl)-2-methylbutanamide

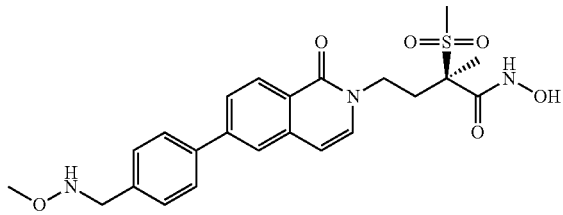 [SMILES: CONCc1ccc(-c2ccc3c(=O)n(CC[C@](C)(C(=O)NO)S(C)(=O)=O)ccc3c2)cc1]

Part A

A reaction vessel was sealed with potassium carbonate (110 mg, 0.798 mmol), PdCl₂(dppf) (29.2 mg, 0.040 mmol), (2R)-4-(6-bromo-1-oxoisoquinolin-2(1H)-yl)-2-methyl-2-(methylsulfonyl)-N-(tetrahydro-2H-pyran-2-yl)oxy)butanamide (200 mg, 0.399 mmol) and O-methyl-N-(4-(4,4,5,5-tetramethyl-1,3,2-dioxaborolan-2-yl)benzyl)hydroxylamine (105 mg, 0.399 mmol) and heated in a microwave to 110° C. for 30 min. The organic phase was diluted with DCM (20 mL), extracted with DCM (10 mL×3) and then washed with water (20 mL), brine (30 mL), dried over sodium sulphate and concentrated. The residue was purified silica gel chromatography (MeOH/DCM: 0-20%) to afford (2R)-4-(6-(4-(methoxyamino)methyl)phenyl)-1-oxoisoquinolin-2(1H)-yl)-2-methyl-2-(methylsulfonyl)-N-(tetrahydro-2H-pyran-2-yl)oxy)butanamide (230 mg, 0.322 mmol, 81% yield) as a colorless oil.

LCMS: [M+H] 558.2.

Part B

To a solution of (2R)-4-(6-(4-(methoxyamino)methyl)phenyl)-1-oxoisoquinolin-2(1H)-yl)-2-methyl-2-(methylsulfonyl)-N-(tetrahydro-2H-pyran-2-yl)oxy)butanamide hydrochloride (260 mg, 0.438 mmol) in ethanol (3 mL) was added a 4M solution of hydrogen chloride in dioxane (0.328 mL, 1.313 mmol) and was stirred at room temperature overnight. The reaction was concentrated, diluted with DMSO and purified by preparative HPLC (5-70%, MeCN/H₂O, 0.1% TFA) to afford (R)—N-hydroxy-4-(6-(4-(methoxyamino)methyl)phenyl)-1-oxoisoquinolin-2(1H)-yl)-2-methyl-2-(methylsulfonyl)butanamide hydrochloride (134 mg, 0.263 mmol, 60% yield) as a white solid.

LCMS: [M+H] 474.1.

¹H NMR (METHANOL-d4) δ: ppm 8.37 (d, J=8.3 Hz, 1H), 7.76-7.94 (m, 4H), 7.68 (d, J=7.3 Hz, 2H), 7.39 (d, J=7.1 Hz, 1H), 6.79 (d, J=7.1 Hz, 1H), 4.60 (s, 2H), 4.23-4.40 (m, 1H), 3.94-4.08 (m, 3H), 3.79-3.95 (m, 1H), 3.12 (s, 3H), 2.56-2.68 (m, 1H), 2.30-2.45 (m, 1H), 1.74 (s, 3H).

Example 79. (2R)-4-(6-{4-[(2,2-dimethylhydrazin-1-yl)methyl]phenyl}-1-oxo-1,2-dihydroisoquinolin-2-yl)-N-hydroxy-2-methanesulfonyl-2-methylbutanamide

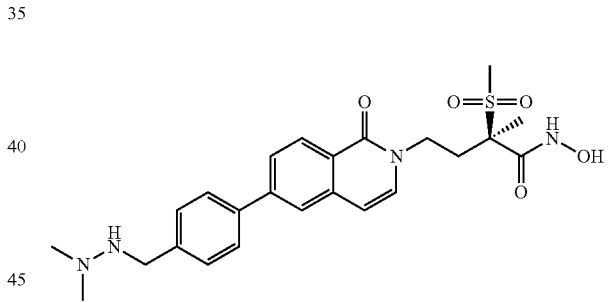

Part A

To a solution of (2R)-4-(6-(4-formylphenyl)-1-oxoisoquinolin-2(1H)-yl)-2-methyl-2-(methylsulfonyl)-N-(tetrahydro-2H-pyran-2-yl)oxy)butanamide (0.4 g, 0.760 mmol) in 1,2-dichloroethane (15 mL) at 0° C. was added 1,1-dimethylhydrazine (0.137 g, 2.279 mmol) and the reaction mixture was stirred at room temperature overnight. Sodium cyanoborohydride (0.143 g, 2.279 mmol) was added at 0° C., the mixture was allowed to warm to room temperature and was stirred for 1 hr. The organic phase was diluted with DCM (20 mL) and water (20 mL) was added. The mixture was extracted with DCM (20 mL×3) and the combined organic layers were washed with brine (30 mL), dried over sodium sulphate and evaporated in vacuo. The residue was purified silica gel chromatography (MeOH/DCM: 0-20%) to afford (2R)-4-(6-(4-(2,2-dimethylhydrazinyl)methyl)phenyl)-1-oxoisoquinolin-2(1H)-yl)-2-methyl-2-(methylsulfonyl)-N-(tetrahydro-2H-pyran-2-yl)oxy)butanamide (260 mg, 0.456 mmol, 60% yield) as a colorless oil.

LCMS: [M+H] 571.3.

Part B

To a solution of (2R)-4-(6-(4-(2,2-dimethylhydrazinyl)methyl)phenyl)-1-oxoisoquinolin-2(1H)-yl)-2-methyl-2-(methylsulfonyl)-N-(tetrahydro-2H-pyran-2-yl)oxy)butanamide (260 mg, 0.456 mmol) in ethanol (3 mL) was added a 4M solution of hydrogen chloride (0.342 mL, 1.367 mmol). The resulting solution was stirred at room temperature overnight. The reaction was concentrated, then diluted with DMSO and purified by preparative HPLC (5-70% MeCN/H$_2$O, 0.1% TFA) to afford (R)-4-(6-(4-(2,2-dimethylhydrazinyl)methyl)phenyl)-1-oxoisoquinolin-2(1H)-yl)-N hydroxyl-2-methyl-2-(methylsulfonyl)butanamide hydrochloride (123 mg, 0.235 mmol, 52% yield) as a white powder.

LCMS: [M+H] 487.2.

$^1$H NMR (METHANOL-d4) δ: ppm 8.42 (d, J=8.3 Hz, 1H), 7.93 (s, 1H), 7.80-7.88 (m, 3H), 7.61 (d, J=7.8 Hz, 2H), 7.43 (d, J=7.3 Hz, 1H), 6.83 (d, J=7.3 Hz, 1H), 4.19-4.49 (m, 3H), 3.87-4.03 (m, 1H), 2.93-3.21 (m, 9H), 2.62-2.71 (m, 1H), 2.36-2.48 (m, 1H), 1.75 (s, 3H).

Example 80. (2R)—N-hydroxy-2-methanesulfonyl-2-methyl-4-(6-{4-[2-(morpholin-4-yl)ethyl]phenyl}-1-oxo-1,2-dihdroisoquinolin-2-yl)butanamide

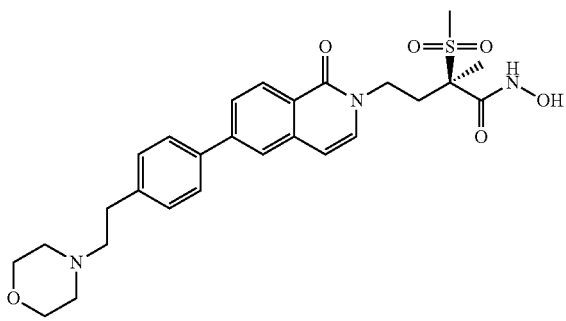 [SMILES: C[C@@](CCn1ccc2cc(-c3ccc(CCN4CCOCC4)cc3)ccc2c1=O)(C(=O)NO)S(C)(=O)=O]

Part A

A reaction vessel was sealed with K$_2$CO$_3$ (110 mg, 0.798 mmol), PdCl$_2$(dppf) (29.2 mg, 0.040 mmol), (2R)-4-(6-bromo-1-oxoisoquinolin-2(1H)-yl)-2-methyl-2-(methylsulfonyl)-N-(tetrahydro-2H-pyran-2-yl)oxy)butanamide (200 mg, 0.399 mmol) and (4-(2-morpholinoethyl)phenyl)boronic acid (122 mg, 0.519 mmol) and was heated in a microwave to 110° C. for 30 min. The organic phase was diluted with DCM (20 mL), washed with water (20 mL), brine (30 mL), dried over sodium sulphate and evaporated in vacuo. The residue was purified silica gel chromatography (MeOH/DCM: 0-20%) to afford (2R)-2-methyl-2-(methylsulfonyl)-4-(6-(4-(2-morpholinoethyl)phenyl)-1-oxoisoquinolin-2(1H)-yl)-N-(tetrahydro-2H-pyran-2-yl)oxy)butanamide (220 mg, 0.342 mmol, 86% yield) as a colorless oil.

LCMS: [M+H] 612.6.

Part B

To a solution of (2R)-2-methyl-2-(methylsulfonyl)-4-(6-(4-(2-morpholinoethyl)phenyl)-1-oxoisoquinolin-2(1H)-yl)-N-(tetrahydro-2H-pyran-2-yl)oxy)butanamide (220 mg, 0.36 mmol) in 3 mL of DCM stirred under nitrogen at room temperature was added a 4M solution of HCl in dioxane (0.5 mL, 2.0 mmol). The reaction mixture was stirred at room temperature for 2 hr. and concentrated. Methanol (5 mL) and EtOAc (20 mL) were added and the solid was collected, washed with EtOAc (5 mL×3), DCM (5 mL×3) and dried in vacuo to afforded (R)—N-hydroxy-2-methyl-2-(methylsulfonyl)-4-(6-(4-(2-morpholinoethyl)phenyl)-1-oxoisoquinolin-2(1H)-yl)butanamide hydrochloride (59 mg, 0.099 mmol, 28% yield) as a brown solid.

LCMS: [M+H] 528.4.

$^1$H NMR (DMSO-d6) δ: ppm 11.09 (br. s., 2H), 9.28 (br. s., 1H), 8.29 (d, J=8.1 Hz, 1H), 7.73-8.11 (m, 4H), 7.34-7.59 (m, 3H), 6.75 (d, J=7.1 Hz, 1H), 4.12-4.30 (m, 1H), 4.00 (d, J=10.6 Hz, 2H), 3.82 (br. s., 3H), 3.52 (d, J=8.3 Hz, 4H), 3.11 (br. s., 8H), 2.09-2.28 (m, 1H), 1.60 (s, 3H).

Example 81. (2R)—N-hydroxy-2-methanesulfonyl-2-methyl-4-(1-oxo-6-{4-[(2-oxopyrrolidin-1-yl)methyl]phenyl}-1,2-dihydroisoquinolin-2-yl)butanamide

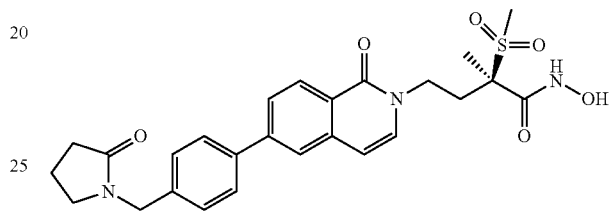

Part A

NaH (0.384 g, 9.60 mmol) was added to pyrrolidin-2-one (1.188 mL, 12.00 mmol) in tetrahydrofuran (30 mL) at 0° C. The reaction mixture was stirred at 20° C. for 0.5 hr when the mixture was cooled to 0° C. and 1-bromo-4-(bromomethyl)benzene (2.0 g, 8.00 mmol) was added. The reaction was stirred at 20° C. for 2 hr. and to the mixture was added EtOAc (80 mL). The mixture was filtered through celite, the filtrate was concentrated under reduced pressure, and the residue was purified by silica gel chromatography (EtOAc/petroleum ether: 1/3) to give 1-(4-bromobenzyl)pyrrolidin-2-one (1.8 g, 7.08 mmol, 89% yield) as a yellow oil.

LCMS: [M+H] 254.0.

Part B

PdCl$_2$(dppf)-CH$_2$Cl$_2$ adduct (0.578 g, 0.708 mmol) was added to a solution of 1-(4-bromobenzyl)pyrrolidin-2-one (1.8 g, 7.08 mmol), 4,4,4',4',5,5,5',5'-octamethyl-2,2'-bi(1,3,2-dioxaborolane) (3.60 g, 14.17 mmol) and potassium acetate (2.085 g, 21.25 mmol) in 1,4-dioxane (20 mL) at room temperature under a nitrogen atmosphere. The reaction mixture was stirred at 80° C. for 3 hr. The mixture was concentrated under reduced pressure, and the residue was purified by silica gel chromatography (EtOAc/petroleum ether: 1/3) to give 1-(4-(4,4,5,5-tetramethyl-1,3,2-dioxaborolan-2-yl)benzyl)pyrrolidin-2-one (1.2 g, 2.80 mmol, 40% yield) as a yellow solid.

LCMS: [M+H] 302.3.

Part C

A mixture of 1-(4-(4,4,5,5-tetramethyl-1,3,2-dioxaborolan-2-yl)benzyl)pyrrolidin-2-one (270 mg, 0.898 mmol), (2R)-4-(6-bromo-1-oxoisoquinolin-2(1H)-yl)-2-methyl-2-(methylsulfonyl)-N-(tetrahydro-2H-pyran-2-yl)oxy)butanamide (250 mg, 0.499 mmol), K$_2$CO$_3$ (138 mg, 0.997 mmol) and PdCl$_2$(dppf) (36.5 mg, 0.050 mmol) in acetonitrile (6 mL) and water (1 mL) under a nitrogen atmosphere was heated to 80° C. for 30 min. The was combined with another batch and was concentrated under reduced pressure, and the residue was purified by silica gel chromatography (EtOH/DCM: 1/80) to give (2R)-2-methyl-2-(methylsulfonyl)-4-(1- oxo-6-(4-(2-oxopyrrolidin-1-yl)methyl)phenyl)isoquinolin-2(1H)-yl)-N-(tetrahydro-2H-pyran-2-yl)oxy)butanamide (320 mg, 0.497 mmol, 100% yield) as a brown solid.

LCMS: [M+H-THP] 512.1.

Part D

To a stirred solution of (2R)-2-methyl-2-(methylsulfonyl)-4-(1-oxo-6-(4-(2-oxopyrrolidin-1-yl)methyl)phenyl)isoquinolin-2(1H)-yl)-N-(tetrahydro-2H-pyran-2-yl)oxy)butanamide (290 mg, 0.487 mmol) in methanol (6 mL) and dichloromethane (6 mL) was added a 4M solution of HCl (6.09 mL, 24.34 mmol) in 1,4-dioxane at room temperature and this mixture was stirred for 2 hr. The mixture was combined with another batch and was concentrated under reduced pressure and the residue was purified by reverse phase HPLC to give (R)—N-hydroxy-2-methyl-2-(methylsulfonyl)-4-(1-oxo-6-(4-(2-oxopyrrolidin-1-yl)methyl)phenyl)isoquinolin-2(1H)-yl)butanamide (70 mg, 0.135 mmol, 28% yield) as a white solid.

LCMS: [M+H] 512.2.

$^1$H NMR (500 MHz, DMSO-d6) δ: ppm 11.07 (s 1H), 8.29 (d, J=8.5 Hz, 1H), 7.97 (d, J=1.5 Hz, 1H), 7.83 (dd, J1=8.5 Hz, J2=1.5 Hz, 1H), 7.79 (d, J=8.0 Hz, 2H), 7.48 (d, J=8.0 Hz, 1H), 7.38 (d, J=8.0 Hz, 2H), 6.74 (d, J=7.5 Hz, 1H), 4.44 (s, 2H), 4.22-4.17 (m, 1H), 3.83-3.77 (m, 1H), 3.28 (t, J=7.0 Hz, 2H), 3.11 (s, 3H), 2.54-2.51 (m, 1H), 2.32 (t, J=8.0 Hz, 2H), 2.22-2.16 (m, 1H), 1.98-1.92 (m, 2H), 1.61 (s, 3H).

Example 82. (2R)-4-[6-(6-{2-[cyclopropyl(methyl)amino]ethoxy}pyridin-3-yl)-1-oxo-1,2-dihydroisoquinolin-2-yl]-N-hydroxy-2-methanesulfonyl-2-methylbutanamide

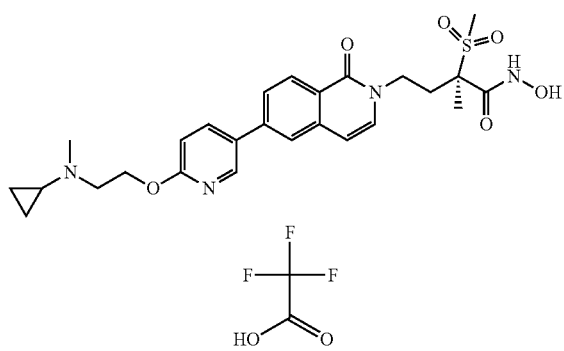

Part A

A solution of ethane-1,2-diol (17.63 g, 284 mmol) in tetrahydrofuran (100 mL) was added NaH (2.273 g, 56.8 mmol) and the mixture was stirred at 0° C. for 30 min. 5-Bromo-2-fluoropyridine (10 g, 56.8 mmol) was added and the mixture was stirred at room temperature for 1 hr. To the mixture was added water (100 mL) followed by extraction with ethyl acetate (100 mL×3). The combined organic layers were dried over Na$_2$SO$_4$ and concentrated. The residue was purified by silica gel chromatography (EtOAc/petroleum ether: 1/5-1/1) to give 2-((5 bromopyridin-2-yl)oxy)ethanol (8 g, 34.6 mmol, 61% yield) as a yellow solid.

LCMS: [M+H] 220.1.

Part B

A solution of 2-((5-bromopyridin-2-yl)oxy)ethanol (2 g, 9.17 mmol) in 1,4-dioxane (200 mL) was added 4,4,4',4',5,5,5',5'-octamethyl-2,2'-bi(1,3,2-dioxaborolane) (2.80 g, 11.01 mmol), PdCl$_2$(dppf)-CH$_2$Cl$_2$ adduct (0.749 g, 0.917 mmol) and potassium acetate (1.800 g, 18.34 mmol). The reaction mixture was heated to 100° C. under N$_2$ and stirred overnight. The mixture was filtered and the filtrate was concentrated to afford (6-(2-hydroxyethoxy)pyridin-3-yl) boronic acid (2 g, 5.47 mmol, 60% yield) LCMS: [M+H] 184.2.

Part C

A solution of (2R)-4-(6-bromo-1-oxoisoquinolin-2(1H)-yl)-2-methyl-2-(methylsulfonyl)-N-(tetrahydro-2H-pyran-2-yl)oxy)butanamide (3 g, 5.98 mmol) in water (10 mL) and acetonitrile (60 mL) was added potassium carbonate (1.654 g, 11.97 mmol), 2-(5-(4,4,5,5-tetramethyl-1,3,2-dioxaborolan-2-yl)pyridin-2-yl)oxy)ethanol (2.379 g, 8.98 mmol) and PdCl$_2$(dppf) (0.438 g, 0.598 mmol). The mixture was heated to 80° C. under N$_2$ and stirred for 1 hr. The mixture was evaporated in vacuo and the residue was purified by silica gel chromatography (acetone/petroleum ether 1/5-1/1) to give (2R)-4-(6-(6-(2-hydroxyethoxy)pyridin-3-yl)-1-oxoisoquinolin-2(1H)-yl)-2-methyl-2-(methylsulfonyl)-N-(tetrahydro-2H-pyran-2-yl)oxy)butanamide (1.5 g, 2.112 mmol, 35% yield) as a yellow solid.

LCMS: [M+H] 560.2.

Part D

A solution of (2R)-4-(6-(6-(2-hydroxyethoxy)pyridin-3-yl)-1-oxoisoquinolin-2(1H)-yl)-2-methyl-2-(methylsulfonyl)-N-(tetrahydro-2H-pyran-2-yl)oxy)butanamide (700 mg, 1.251 mmol) in dichloromethane (20 mL) was cooled to 0° C., Dess-Martin periodinane (1061 mg, 2.502 mmol) was added and the mixture was stirred at 0° C. for 3 hr. The mixture was filtered and the filtrate was evaporated in vacuo to give (2R)-2-methyl-2-(methylsulfonyl)-4-(1-oxo-6-(6-(2-oxoethoxy)pyridin-3-yl)isoquinolin-2(1H)-yl)-N-(tetrahydro-2H-pyran-2-yl)oxy)butanamide (500 mg, 0.475 mmol, 38% yield) as a yellow solid.

LCMS: [M+H] 558.2.

Part E

A solution of (2R)-2-methyl-2-(methylsulfonyl)-4-(1-oxo-6-(6-(2-oxoethoxy)pyridin-3-yl)isoquinolin-2(1H)-yl)-N-(tetrahydro-2H-pyran-2-yl)oxy)butanamide (550 mg, 0.986 mmol) in dichloromethane (20 mL) was added N-methylcyclopropanamine (140 mg, 1.973 mmol). The mixture was stirred at room temperature for 30 min when sodium triacetoxyborohydride (418 mg, 1.973 mmol) was added. The mixture was stirred at room temperature overnight. Water (10 mL) was added and the aqueous layer was extracted with DCM (20 mL×3). The combined organic layers were dried over Na$_2$SO$_4$ and concentrated to afford (2R)-4-(6-(6-(2-(cyclopropyl(methyl)amino)ethoxy)pyridin-3-yl)-1-oxoisoquinolin-2(1H)-yl)-2-methyl-2-(methylsulfonyl)-N-((tetrahydro-2H-pyran-2-yl)oxy)butanamide (500 mg, 0.219 mmol, 22% yield) as a yellow oil.

LCMS: [M+H] 613.3.

Part F

To a solution of (2R)-4-(6-(6-(2-(cyclopropyl(methyl)amino)ethoxy)pyridin-3-yl)-1-oxoisoquinolin-2(1H)-yl)-2-methyl-2-(methylsulfonyl)-N-(tetrahydro-2H-pyran-2-yl)oxy)butanamide (450 mg, 0.734 mmol) in dichloromethane (4 mL) and methanol (4 mL) was added HCl (1 mL, 4 mmol) and the reaction mixture was stirred at 20° C. for 2 hr. The mixture was evaporated in vacuo and the residue was purified by reversed phase HPLC to give (R)-4-(6-(6-(2-(cyclopropyl(methyl)amino)ethoxy)pyridin-3-yl)-1-oxoisoquinolin-2(1H)-yl)-N-hydroxy-2-methyl-2-(methylsulfonyl)butanamide, Trifluoroacetic acid (60 mg, 0.089 mmol, 12.08% yield) as a yellow solid.

LCMS: [M+H] 529.3.

$^1$H NMR (400 MHz, DMSO-d$_6$) δ: ppm 11.02 (d, J=77.1 Hz, 1H), 9.86 (s, 1H), 8.67 (d, J=2.3 Hz, 1H), 8.38-8.12 (m, 2H), 8.01 (s, 1H), 7.85 (J=8.4, 1.4 Hz, 1H), 7.50 (d, J=7.4 Hz, 1H), 7.03 (d, J=8.6 Hz, 1H), 6.73 (d, J=7.4 Hz, 1H), 4.72 (t, J=4.7 Hz, 2H), 4.20 (td, J=12.1, 4.8 Hz, 1H), 3.90-3.62 (m, 3H), 3.11 (d, J=10.3 Hz, 3H), 2.99 (s, 4H), 2.56 (s, 1H), 2.18 (tt, J=30.2, 15.2 Hz, 2H), 1.61 (s, 3H), 0.92 (d, J=41.8 Hz, 4H).

Example 83. (2R)-4-[4-fluoro-6-(4-methoxyphenyl)-1-oxo-1,2-dihydroisoquinolin-2-yl]-N-hydroxy-2-methanesulfonyl-2-methylbutanamide

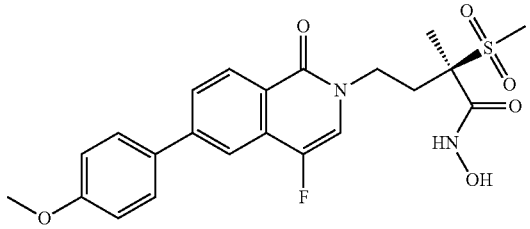

Part A

A mixture of (2R)-4-(6-bromo-4-fluoro-1-oxoisoquinolin-2(1H)-yl)-2-methyl-2-(methylsulfonyl)-N-(tetrahydro-2H-pyran-2-yl)oxy)butanamide (250 mg, 0.481 mmol), (4-methoxyphenyl)boronic acid (146 mg, 0.963 mmol), K$_2$CO$_3$ (133 mg, 0.963 mmol), PdCl$_2$(dppf)-CH$_2$Cl$_2$ adduct (79 mg, 0.096 mmol), acetonitrile (7.5 mL) and water (1.25 mL) was stirred at 80° C. for 0.5 hr under a nitrogen atmosphere. The acetonitrile was removed and the aqueous layer was extracted with DCM (50 mL×2). The combined organic layers were dried over Na$_2$SO$_4$, filtered and concentrated. The crude product was purified by silica gel column chromatography (EtOAc/hexanes: 0-50%) to afford (2R)-4-(4-fluoro-6-(4-methoxyphenyl)-1-oxoisoquinolin-2(1H)-yl)-2-methyl-2-(methylsulfonyl)-N-(tetrahydro-2H-pyran-2-yl)oxy)butanamide (200 mg, 0.329 mmol, 68% yield) as a yellow solid.

LCMS: [M+Na] 568.8.

Part B

To a solution of (2R)-4-(4-fluoro-6-(4-methoxyphenyl)-1-oxoisoquinolin-2(1H)-yl)-2-methyl-2-(methylsulfonyl)-N-(tetrahydro-2H-pyran-2-yl)oxy)butanamide (180 mg, 0.329 mmol) in dichloromethane (4 mL) and methanol (2 mL) was added 4M HCl in dioxane (0.412 mL, 1.647 mmol) at 30° C. and the reaction stirred for 15 min. The mixture was evaporated to dryness and the crude product was purified by preparative HPLC to afford (R)-4-(4-fluoro-6-(4-methoxyphenyl)-1-oxoisoquinolin-2(1H)-yl)-N-hydroxy-2-methyl-2-(methylsulfonyl)butanamide (70 mg, 0.151 mmol, 46% yield) as a yellow solid.

LCMS: [M+H] 463.2.

$^1$H NMR (500 MHz, DMSO-d$_6$) δ: ppm 11.03 (s, 1H), 9.23 (s, 1H), 8.30 (d, J=7.2 Hz, 1H), 8.01-7.87 (m, 2H), 7.79 (J=20.0, 7.7 Hz, 3H), 7.09 (d, J=8.7 Hz, 2H), 4.12 (td, J=12.7, 5.0 Hz, 1H), 3.88-3.72 (m, 4H), 3.11 (s, 3H), 2.59-2.52 (m, 1H), 2.18 (td, J=13.0, 5.0 Hz, 1H), 1.60 (s, 3H).

Example 84. (2R)-4-(4-fluoro-1-oxo-6-phenyl-1,2-dihydroisoquinolin-2-yl)-N-hydroxy-2-methanesulfonyl-2-methylbutanamide

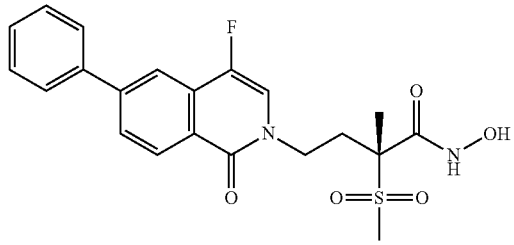 [SMILES: C[C@@](CCn1cc(F)c2cc(-c3ccccc3)ccc2c1=O)(C(=O)NO)S(C)(=O)=O]

Part A

A mixture of (2R)-4-(6-bromo-4-fluoro-1-oxoisoquinolin-2(1H)-yl)-2-methyl-2-(methylsulfonyl)-N-(tetrahydro-2H-pyran-2-yl)oxy)butanamide (1 g, 1.925 mmol), phenylboronic acid (0.470 g, 3.85 mmol), K$_2$CO$_3$ (0.532 g, 3.85 mmol) and PdCl$_2$(dppf)-CH$_2$Cl$_2$ adduct (0.314 g, 0.385 mmol) in acetonitrile (30 mL) and water (5.00 mL) was stirred at 80° C. for 0.5 hr under a nitrogen atmosphere. The acetonitrile was removed by evaporation and the aqueous layer was extracted with DCM (50 mL×2). The combined organic layers were dried over Na$_2$SO$_4$, filtered and concentrated. The crude product was purified by silica gel column chromatography (EtOAc/DCM: 0-33%) to afford (2R)-4-(4-fluoro-1-oxo-6 phenylisoquinolin-2(1H)-yl)-2-methyl-2-(methylsulfonyl)-N-(tetrahydro-2H-pyran-2-yl)oxy)butanamide (750 mg, 1.379 mmol, 72% yield) as a yellow solid.

LCMS: [M+Na] 539.2.

N30872-82

Part B

To a solution of (2R)-4-(4-fluoro-1-oxo-6-phenylisoquinolin-2(1H)-yl)-2-methyl-2-(methylsulfonyl)-N-(tetrahydro-2H-pyran-2-yl)oxy)butanamide (700 mg, 1.355 mmol) in dichloromethane (10 mL) and methanol (10.00 mL) was added 4M HCl in dioxane (1.694 mL, 6.78 mmol) at 10° C. and stirred 15 min. The reaction was concentrated and the crude product was purified by preparative HPLC to afford (R)-4-(4-fluoro-1-oxo-6-phenylisoquinolin-2(1H)-yl)-N-hydroxy-2-methyl-2-(methylsulfonyl)butanamide (380 mg, 0.835 mmol, 62% yield) as an off-white solid.

LCMS: [M+H] 433.2.

$^1$H NMR (500 MHz, DMSO-d$_6$) δ: ppm 11.05 (s, 1H), 9.26 (s, 1H), 8.35 (d, J=8.8 Hz, 1H), 7.98 (d, J=5.6 Hz, 2H), 7.83 (J=21.9, 7.1 Hz, 3H), 7.53 (J=21.2, 13.5 Hz, 2H), 7.48 (t, J=7.3 Hz, 1H), 4.20-4.08 (m, 1H), 3.88-3.77 (m, 1H), 3.11 (s, 3H), 2.55 (d, J=11.4 Hz, 1H), 2.23-2.16 (m, 1H), 1.60 (s, 3H).

Example 85. (2R)-4-(6-{4-[(dimethylamino)methyl]phenyl}-4-fluoro-1-oxo-1,2-dihydroisoquinolin-2-yl)-N-hydroxy-2-methanesulfonyl-2-methylbutanamide

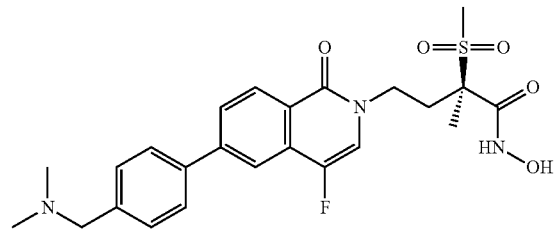 [SMILES: CN(C)Cc1ccc(-c2ccc3c(=O)n(CC[C@@](C)(C(=O)NO)S(C)(=O)=O)cc(F)c3c2)cc1]

Part A

A mixture of N, N-dimethyl-1-(4-(4,4,5,5-tetramethyl-1,3,2-dioxaborolan-2-yl)phenyl)methanamine (189 mg, 0.722 mmol), (2R)-4-(6-bromo-4-fluoro-1-oxoisoquinolin-2(1H)-yl)-2-methyl-2-(methylsulfonyl)-N-(tetrahydro-2H-pyran-2-yl)oxy)butanamide (250 mg, 0.481 mmol), PdCl$_2$(dppf)-CH$_2$Cl$_2$ adduct (59.0 mg, 0.072 mmol) and K$_2$CO$_3$ (133 mg, 0.963 mmol) in acetonitrile (6 mL) and water (1 mL) was stirred at room temperature under nitrogen atmosphere. The reaction mixture was stirred at 80° C. for 1 hr when acetonitrile was removed by evaporation. The aqueous layer was extracted with DCM (50 mL×2) and the combined organic layers were dried over Na$_2$SO$_4$, filtered and concentrated. The crude product was purified by silica gel column chromatography (MeOH/DCM: 0-2.5%) to afford (2R)-4-(6-(4-(dimethylamino)methyl)phenyl)-4-fluoro-1-oxoisoquinolin-2(1H)-yl)-2-methyl-2-(methylsulfonyl)-N-(tetrahydro-2H-pyran-2-yl)oxy)butanamide (339 mg, 0.425 mmol, 88% yield) as a brown solid.

LCMS: [M+H] 574.0.

Part B

To a solution of (2R)-4-(6-(4-(dimethylamino)methyl)phenyl)-4-fluoro-1-oxoisoquinolin-2(1H)-yl)-2-methyl-2-(methylsulfonyl)-N-(tetrahydro-2H-pyran-2-yl)oxy)butanamide (171 mg, 0.298 mmol) in dichloromethane (5 mL) was added HCl in dioxane (0.373 mL, 1.490 mmol) at room temperature and stirred for 5 min. Methanol (5 mL) was added and the resulting mixture was stirred at 25° C. for 1 hr. The mixture was combined with another batch and was concentrated and the residue was purified by reverse phase HPLC to give (R)-4-(6-(4-(dimethylamino)methyl)phenyl)-4-fluoro-1-oxoisoquinolin-2(1H)-yl)-N-hydroxy-2-methyl-2-(methylsulfonyl)butanamide trifluoroacetic acid salt (130 mg, 0.205 mmol, 69% yield) as brown solid.

LCMS: [M+H-THP] 489.9.

$^1$H NMR (500 MHz, DMSO-d$_6$) δ: ppm 11.05 (s, 1H), 9.87 (s, 1H), 9.26 (s, 1H), 8.36 (d, J=8.3 Hz, 1H), 8.09-7.98 (m, 4H), 7.82 (d, J=6.8 Hz, 1H), 7.66 (d, J=8.2 Hz, 2H), 4.37 (d, J=4.5 Hz, 2H), 4.17-4.04 (m, 1H), 3.90-3.79 (m, 1H), 3.11 (s, 3H), 2.78 (d, J=3.8 Hz, 6H), 2.60-2.55 (m, 1H), 2.18 (td, J=13.0, 4.8 Hz, 1H), 1.60 (s, 3H).

Example 86. (2R)-4-[6-(6-ethoxypyridin-3-yl)-4-fluoro-1-oxo-1,2-dihydroisoquinolin-2-yl]-N-hydroxy-2-methanesulfonyl-2-methylbutanamide

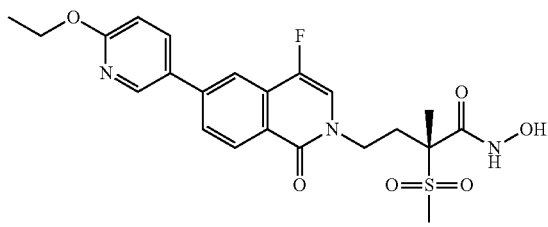 [SMILES: CCOc1ccc(-c2ccc3c(=O)n(CC[C@](C)(C(=O)NO)S(C)(=O)=O)cc(F)c3c2)cn1]

Part A

A mixture of (6-ethoxypyridin-3-yl)boronic acid (121 mg, 0.722 mmol), (2R)-4-(6-bromo-4-fluoro-1-oxoisoquinolin-2(1H)-yl)-2-methyl-2-(methylsulfonyl)-N-(tetrahydro-2H-pyran-2-yl)oxy)butanamide (250 mg, 0.481 mmol), PdCl$_2$(dppf)-CH$_2$C$_2$ adduct (59.0 mg, 0.072 mmol) and K$_2$CO$_3$ (133 mg, 0.963 mmol) in acetonitrile (6 mL) and water (1 mL) was stirred at room temperature under a nitrogen atmosphere. The reaction mixture was heated to 80° C. for 1 hr. when the acetonitrile was removed by evaporation. The aqueous layer was extracted with DCM (50 mL×2) and the combined organic layers were dried over Na$_2$SO$_4$, filtered and concentrated. The crude product was purified by silica gel column chromatography (MeOH/DCM: 0-5%) to afford (2R)-4-(6-(6-ethoxypyridin-3-yl)-4-fluoro-1-oxoisoquinolin-2(1H)-yl)-2-methyl-2-(methylsulfonyl)-N-(tetrahydro-2H-pyran-2-yl)oxy)butanamide (250 mg, 0.401 mmol, 69% yield) as an off-white solid.

LCMS: [M+H] 562.2.

Part B

To a stirred solution of (2R)-4-(6-(6-ethoxypyridin-3-yl)-4-fluoro-1-oxoisoquinolin-2(1H)-yl)-2-methyl-2-(methylsulfonyl)-N-(tetrahydro-2H-pyran-2-yl)oxy)butanamide (225 mg, 0.401 mmol) in dichloromethane (5 mL) and methanol (5 mL) was added HCl (0.100 mL, 0.401 mmol) at 20° C. and this mixture was stirred for an hour. The solvent was removed in vacuo and the residue was purified by preparative HPLC to afford (R)-4-(6-(6-ethoxypyridin-3-yl)-4-fluoro-1-oxoisoquinolin-2(1H)-yl)-N-hydroxy-2-methyl-2-(methylsulfonyl)butanamide (70 mg, 0.139 mmol, 35% yield) as white solid.

LCMS: [M+H] 478.2.

$^1$H NMR (400 MHz, DMSO-d$_6$) δ: ppm 11.04 (d, J=1.6 Hz, 1H), 9.25 (t, J=2.5 Hz, 1H), 8.66 (d, J=2.5 Hz, 1H), 8.38-8.29 (m, 1H), 8.21 (J=8.7, 2.6 Hz, 1H), 8.03-7.92 (m, 2H), 7.80 (d, J=6.8 Hz, 1H), 6.94 (d, J=8.7 Hz, 1H), 4.38 (q, J=7.0 Hz, 2H), 4.19-4.05 (m, 1H), 3.93-3.71 (m, 1H), 3.34 (s, 3H), 2.57-2.53 (m, 1H), 2.18 (td, J=13.1, 5.0 Hz, 1H), 1.60 (s, 3H), 1.36 (t, J=7.0 Hz, 3H).

Example 87. (2R)-4-[4-fluoro-6-(6-methoxypyridin-3-yl)-1-oxo-1,2-dihydroisoquinolin-2-yl]-N-hydroxy-2-methanesulfonyl-2-methylbutanamide

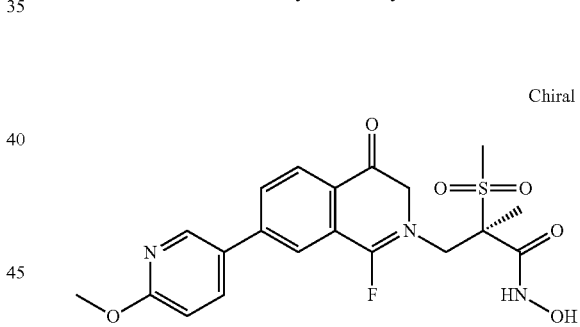

Part A

A mixture of (6-methoxypyridin-3-yl)boronic acid (110 mg, 0.722 mmol), (2R)-4-(6-bromo-4-fluoro-1-oxoisoquinolin-2(1H)-yl)-2-methyl-2-(methylsulfonyl)-N-(tetrahydro-2H-pyran-2-yl)oxy)butanamide (250 mg, 0.481 mmol), PdCl$_2$(dppf)-CH$_2$Cl$_2$ adduct (59.0 mg, 0.072 mmol) and K$_2$CO$_3$ (133 mg, 0.963 mmol) in acetonitrile (6 mL) and water (1 mL) at room temperature under a nitrogen atmosphere was stirred at 80° C. for 1 hr. The acetonitrile was removed by evaporation and water (50 mL) was added. The aqueous layer was extracted with DCM (50 mL×2) and the combined organic layers were dried over Na$_2$SO$_4$, filtered and concentrated. The crude product was purified by silica gel column chromatography (MeOH/DCM: 0-2.5%) to afford (2R)-4-(4-fluoro-6-(6-methoxypyridin-3-yl)-1-oxoisoquinolin-2-(1H)-yl)-2-methyl-2-(methylsulfonyl)-N-(tetrahydro-2H-pyran-2-yl)oxy)butanamide (195 mg, 0.320 mmol, 56% yield) as an off white solid.

LCMS: [M+H] 548.0.

Part B

To a stirred solution of (2R)-4-(4-fluoro-6-(6-methoxy-pyridin-3-yl)-1-oxoisoquinolin-2(1H)-yl)-2-methyl-2-(methylsulfonyl)-N-(tetrahydro-2H-pyran-2-yl)oxy)butanamide (175 mg, 0.32 mmol) in dichloromethane (5 mL) and methanol (5.00 mL) was added 4M HCl (0.080 mL, 0.320 mmol) at 20° C. and this mixture was stirred an hour. The solvent was removed in vacuo and the residue was purified by preparative HPLC to afford (R)-4-(4-fluoro-6-(6-methoxypyridin-3-yl)-1-oxoisoquinolin-2(1H)-yl)-N-hydroxy-2-methyl-2-(methylsulfonyl)butanamide (55 mg, 0.107 mmol, 33% yield) as white solid.

LCMS: [M+H] 464.1.

$^1$H NMR (400 MHz, DMSO-d$_6$) δ: ppm 11.04 (s, 1H), 9.27 (s, 1H), 8.68 (d, J=2.5 Hz, 1H), 8.33 (d, J=5.0 Hz, 1H), 8.24-8.18 (m, 1H), 8.05-7.91 (m, 2H), 7.80 (d, J=6.8 Hz, 1H), 6.98 (d, J=8.6 Hz, 1H), 4.23-4.07 (m, 1H), 3.93 (s, 3H), 3.84-3.77 (m, 1H), 3.11 (s, 3H), 2.61-2.54 (m, 1H), 2.22-2.13 (m, 1H), 1.60 (s, 3H).

Example 88. (2R)-4-[4-fluoro-6-(2-fluoro-4-{[(2-methoxyethyl)amino]methyl}phenyl)-1-oxo-1,2-dihydroisoquinolin-2-yl]-N-hydroxy-2-methanesulfonyl-2-methylbutanamide

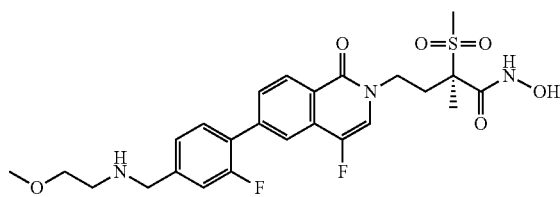 [SMILES: COCCNCc1ccc(-c2ccc3c(=O)n(CC[C@](C)(C(=O)NO)S(C)(=O)=O)cc(F)c3c2)c(F)c1]

Part A

To a reaction vessel was added (2R)-4-(6-bromo-4-fluoro-1-oxoisoquinolin-2(1H)-yl)-2-methyl-2-(methylsulfonyl)-N-(tetrahydro-2H-pyran-2-yl)oxy)butanamide (Intermediate 11) (3 g, 5.78 mmol), (2-fluoro-4 formylphenyl) boronic acid (1.164 g, 6.93 mmol), potassium carbonate (1.597 g, 11.55 mmol), PdCl$_2$(dppf) (0.423 g, 0.578 mmol), 1,4-dioxane (15 mL), water (5 mL) and the reaction was heated in a microwave to 100° C. for 15 min. After cooling, the reaction was concentrated and the crude product was purified with silica gel chromatography (EtOAc/hexanes: 0-100%) to give (2R)-4-(4-fluoro-6-(2-fluoro-4-formylphenyl)-1-oxoisoquinolin-2(1H)-yl)-2-methyl-2-(methylsulfonyl)-N-((tetrahydro-2H-pyran-2-yl)oxy)butanamide (2.3 g, 4.09 mmol, 71% yield).

LCMS: [M+Na] 585.2.

Part B

To a solution of (2R)-4-(4-fluoro-6-(2-fluoro-4-formyl-phenyl)-1-oxoisoquinolin-2(1H)-yl)-2-methyl-2-(methyl-sulfonyl)-N-(tetrahydro-2H-pyran-2-yl)oxy)butanamide (2.9 g, 5.15 mmol) in 1,2-dichloroethane (20 mL) at 0° C. was added 2-methoxyethanamine (1.162 g, 15.46 mmol), acetic acid (0.295 mL, 5.15 mmol) and sodium triacetoxy-hydroborate (3.28 g, 15.46 mmol). The reaction mixture was allowed to warm to room temperature and stirred overnight. The solvent was removed to afford the crude product which was purified by silica gel chromatography (EtOAc/hexanes, 1% TEA: 0-100%) to give (2R)-4-(4-fluoro-6-(2-fluoro-4-((2-methoxyethyl)amino)methyl)phenyl)-1-oxoisoquinolin-2(1H)-yl)-2-methyl-2-(methylsulfonyl)-N-(tetrahydro-2H-pyran-2-yl)oxy)butanamide (1.73 g, 2.78 mmol, 54% yield).

LCMS: [M+H] 622.3.

Part C

To a solution of (2R)-4-(4-fluoro-6-(2-fluoro-4-((2-methoxyethyl)amino)methyl)phenyl)-1-oxoisoquinolin-2(1H)-yl)-2-methyl-2-(methylsulfonyl)-N-(tetrahydro-2H-pyran-2-yl)oxy)butanamide (1.05 g, 1.689 mmol) in ethanol (10 mL) was added a 4M solution of HCl in dioxane (1.267 mL, 5.07 mmol) and was stirred at room temperature overnight. The reaction was concentrated and purified by reverse phase chromotography to give (R)-4-(4-fluoro-6-(2-fluoro-4-((2-methoxyethyl)amino)methyl)phenyl)-1-oxoisoquinolin-2(1H)-yl)-N-hydroxy-2-methyl-2-(methylsulfonyl)butanamide hydrochloride (904 mg, 1.496 mmol, 89% yield).

LCMS: [M+H] 538.2.

$^1$H NMR (400 MHz, METHANOL-d4) δ: ppm 1.75 (s, 3H), 2.40 (ddd, J=13.45, 10.67, 5.18 Hz, 1H), 2.62-2.76 (m, 1H), 3.13 (s, 3H), 3.24-3.31 (m, 2H), 3.39-3.50 (m, 3H), 3.65-3.74 (m, 2H), 3.96 (ddd, J=13.14, 10.74, 5.43 Hz, 1H), 4.28-4.39 (m, 3H), 7.45-7.53 (m, 2H), 7.62 (d, J=6.32 Hz, 1H), 7.73-7.81 (m, 1H), 7.87 (d, J=8.34 Hz, 1H), 8.01 (s, 1H), 8.48 (dd, J=8.46, 1.64 Hz, 1H).

Example 89. (2R)-4-(6-{4-[(dimethylamino)methyl]-2-fluorophenyl}-4-fluoro-1-oxo-1,2-dihydroisoquinolin-2-yl)-N-hydroxy-2-methanesulfonyl-2-methylbutanamide

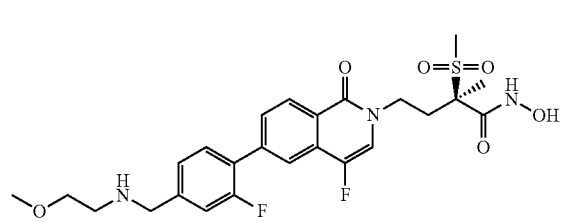 [SMILES: COCCNCc1ccc(-c2ccc3c(=O)n(CC[C@](C)(C(=O)NO)S(C)(=O)=O)cc(F)c3c2)c(F)c1]

Part A

To a reaction vessel was added (2R)-4-(6-bromo-4-fluoro-1-oxoisoquinolin-2(1H)-yl)-2-methyl-2-(methylsulfonyl)-N-(tetrahydro-2H-pyran-2-yl)oxy)butanamide (6 g, 11.55 mmol), (2-fluoro-4-formylphenyl)boronic acid (2.328 g, 13.86 mmol), potassium carbonate (3.19 g, 23.10 mmol), PdCl$_2$(dppf) (0.845 g, 1.155 mmol), 1,4-dioxane (30 mL) and water (10 mL) was heated in a microwave to 110° C. for 30 min. After cooling, the reaction was concentrated and the crude product was purified by silica gel chromatography (EtOAc/hexanes: 0-100%) to give (2R)-4-(4-fluoro-6-(2-fluoro-4-formylphenyl)-1-oxoisoquinolin-2(1H)-yl)-2-methyl-2-(methylsulfonyl)-N-((tetrahydro-2H-pyran-2-yl)oxy)butanamide (5.93 g, 10.54 mmol, 91% yield).

LCMS: [M+Na] 585.1.

Part B

To a solution of (2R)-4-(4-fluoro-6-(2-fluoro-4-formyl-phenyl)-1-oxoisoquinolin-2(1H)-yl)-2-methyl-2-(methyl-sulfonyl)-N-((tetrahydro-2H-pyran-2-yl)oxy)butanamide (2.9 g, 5.15 mmol) in 1,2-dichloroethane (20 mL) at 0° C. was added 2-methoxyethanamine (1.162 g, 15.46 mmol), acetic acid (0.295 mL, 5.15 mmol) and sodium triacetoxy-hydroborate (3.28 g, 15.46 mmol). The reaction mixture was allowed to warm to room temperature and stirred overnight. The reaction was concentrated and the residue by silica gel chromatography (EtOAc/hexanes with 1% TEA, 0-100%) to give (2R)-4-(4-fluoro-6-(2-fluoro-4-(((2-methoxyethyl)amino)methyl)phenyl)-1-oxoisoquinolin-2(1H)-yl)-2- methyl-2-(methylsulfonyl)-N-((tetrahydro-2H-pyran-2-yl)oxy)butanamide (1.73 g, 2.78 mmol, 54% yield).

LCMS: [M+H] 622.3.

Part C

To a solution of (2R)-4-(4-fluoro-6-(2-fluoro-4-(((2-methoxyethyl)amino)methyl)phenyl)-1-oxoisoquinolin-2-(1H)-yl)-2-methyl-2-(methylsulfonyl)-N-((tetrahydro-2H-pyran-2-yl)oxy)butanamide (1.05 g, 1.689 mmol) in ethanol (10 mL) was added HCl (1.267 mL, 5.07 mmol) solution in dioxane (4M). The resulting solution was stirred at room temperature overnight. The reaction was concentrated and purified by reverse phase chromatography (MeCN/water, 0-25%) to afford (R)-4-(4-fluoro-6-(2-fluoro-4-(((2-methoxyethyl)amino)methyl)phenyl)-1-oxoisoquinolin-2(1H)-yl)-N-hydroxy-2-methyl-2-(methylsulfonyl)butanamide hydrochloride (904 mg, 1.496 mmol, 89% yield).

LCMS: [M+H] 538.2.

$^1$H NMR (400 MHz, METHANOL-d$_4$) 85: ppm 1.75 (s, 3H) 2.40 (ddd, J=13.45, 10.67, 5.18 Hz, 1H) 2.62-2.76 (m, 1H) 3.13 (s, 3H) 3.24-3.31 (m, 2H) 3.39-3.50 (m, 3H) 3.65-3.74 (m, 2H) 3.96 (ddd, J=13.14, 10.74, 5.43 Hz, 1H) 4.28-4.39 (m, 3H) 7.45-7.53 (m, 2H) 7.62 (d, J=6.32 Hz, 1H) 7.73-7.81 (m, 1H) 7.87 (d, J=8.34 Hz, 1H) 8.01 (s, 1H) 8.48 (dd, J=8.46, 1.64 Hz, 1H).

$^1$H NMR (400 MHz, METHANOL-d$_4$) δ: ppm 1.76 (s, 3H), 2.05 (s, 3H), 2.34-2.50 (m, 1H), 2.73 (ddd, J=13.33, 10.42, 5.81 Hz, 1H), 3.06 (t, J=6.69 Hz, 2H), 3.12 (s, 3H), 4.05 (ddd, J=13.45, 10.42, 5.68 Hz, 1H), 4.23-4.44 (m, 3H), 7.11-7.32 (m, 2H), 7.46 (t, J=7.71 Hz, 1H), 7.77 (d, J=6.32 Hz, 1H), 8.00 (d, J=9.60 Hz, 1H), 8.34 (s, 1H).

Example 90. (2R)-4-{6-[6-(dimethylamino)pyridin-3-yl]-4-fluoro-1-oxo-1,2-dihydroisoquinolin-2-yl}-N-hydroxy-2-methanesulfonyl-2-methylbutanamide

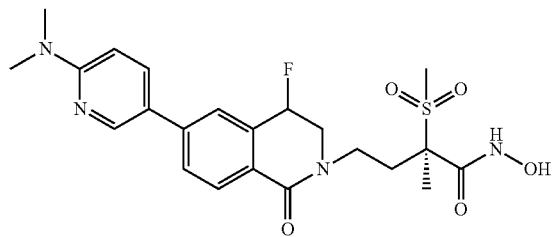 [SMILES: CN(C)c1ccc(-c2ccc3c(c2)C(F)CN(CC[C@](C)(C(=O)NO)S(C)(=O)=O)C3=O)cn1]

Part A

PdCl$_2$(dppf)-CH$_2$Cl$_2$ adduct (81 mg, 0.099 mmol) was added to a solution of 4,4,4',4',5,5,5',5'-octamethyl-2,2'-bi(1,3,2-dioxaborolane) (379 mg, 1.492 mmol), 5-bromo-N,N-dimethylpyridin-2-amine (200 mg, 0.995 mmol) and potassium acetate (293 mg, 2.98 mmol) in 1,4-dioxane (40 mL) at room temperature under an atmosphere of nitrogen. The resulting solution was stirred at 100° C. for 12 hr. The system was filtered and the filtrate was concentrated to afford crude product which was used for the next step.

LCMS: [M+H] 249.1.

Part B

A solution of PdCl$_2$(dppf)-CH$_2$Cl$_2$ adduct (55.3 mg, 0.068 mmol), K$_2$CO$_3$ (468 mg, 3.39 mmol), N,N-dimethyl-5-(4,4,5,5-tetramethyl-1,3,2-dioxaborolan-2-yl)pyridin-2-amine (200 mg, 0.806 mmol) and 3-(6-bromo-4-fluoro-1-oxoisoquinolin-2(1H)-yl)-N-(tetrahydro-2H-pyran-2-yl)oxy)propanamide (280 mg, 0.678 mmol) in acetonitrile (40 mL) and water (10 mL) was stirred at 80° C. under N$_2$ for 3 hr. The solid was filtered, the solvent removed and the residue purified by silica gel chromatography (MeOH/DCM: 0-5%) to give 3-(6-(6-(dimethylamino)pyridin-3-yl)-4-fluoro-1-oxoisoquinolin-2(1H)-yl)-N-(tetrahydro-2H-pyran-2-yl)oxy)propanamide (220 mg, 0.484 mmol, 71% yield) as a white solid.

LCMS: [M+H] 560.9.

Part C

A solution of (2R)-4-(6-(6-(dimethylamino)pyridin-3-yl)-4-fluoro-1-oxoisoquinolin-2(1H)-yl)-2-methyl-2-(methylsulfonyl)-N-(tetrahydro-2H-pyran-2-yl)oxy)butanamide (200 mg, 0.357 mmol) and hydrogen chloride (3 mL, 12.00 mmol) in dichloromethane (2 mL) was stirred at room temperature for 3 hr. The solvent was removed and the residue was purified with HPLC to give (R)-4-(6-(6-(dimethylamino)pyridin-3-yl)-4-fluoro-1-oxoisoquinolin-2(1H)-yl)-N-hydroxy-2-methyl-2-(methylsulfonyl)butanamide (150 mg, 0.299 mmol, 84% yield) as a yellow solid.

LCMS: [M+H] 477.2.

Example 91. (2R)-4-[6-(2-fluorophenyl)-1-oxo-1,2,3,4-tetrahydroisoquinolin-2-yl]-N-hydroxy-2-methanesulfonyl-2-methylbutanamide

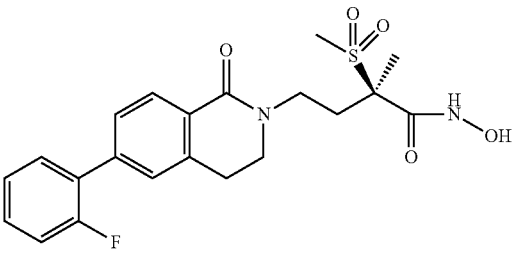 [SMILES: C[C@@](CCN1CCc2cc(-c3ccccc3F)ccc2C1=O)(C(=O)NO)S(C)(=O)=O]

Part A

To a flask charged with (2R)-4-(6-bromo-1-oxo-3,4-dihydroisoquinolin-2(1H)-yl)-2-methyl-2-(methylsulfonyl)-N-(tetrahydro-2H-pyran-2-yl)oxy)butanamide (Intermediate 12) (0.186 g, 0.369 mmol), (2-fluorophenyl)boronic acid (0.067 g, 0.480 mmol), PdCl$_2$(dppf) (0.027 g, 0.037 mmol) and potassium carbonate (0.102 g, 0.739 mmol) was added 1,4-dioxane (3 mL) and water (0.5 mL). The reaction in a microwave to 110° C. for 30 mins. After completion, the solvent was removed, which was purified by silica gel (EtOAc/hexanes: 0-100%) afford (2R)-4-(6-(2-fluorophenyl)-1-oxo-3,4-dihydroisoquinolin-2(1H)-yl)-2-methyl-2-(methylsulfonyl)-N-(tetrahydro-2H-pyran-2-yl)oxy)butanamide (0.12 g). This material was dissolved in dichloromethane (3 mL) and methanol (3 mL) and a 4M solution of HCl (0.583 mL, 19.19 mmol) in dioxane was added and stirred at room temperature for 2 hr. The mixture was concentrated and the residue was washed with acetonitrile/ether (1/2) to give (R)-4-(6-(2-fluorophenyl)-1-oxo-3,4-dihydroisoquinolin-2(1H)-yl)-N-hydroxy-2-methyl-2-(methylsulfonyl)butanamide (90 mg, 0.207 mmol, 56% yield) as a white solid.

LCMS: [M+H] 435.2.

247

Example 92. (2R)—N-hydroxy-2-methanesulfonyl-2-methyl-4-(6-{4-[(morpholin-4-yl)methyl]phenyl}-1-oxo-1,2,3,4-tetrahydroisoquinolin-2-yl)butanamide

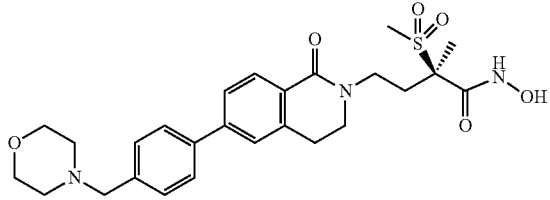 [SMILES: C[C@@](CCN1CCc2cc(-c3ccc(CN4CCOCC4)cc3)ccc2C1=O)(C(=O)NO)S(C)(=O)=O]

Part A (2R)-4-(6-bromo-1-oxo-3,4-dihydroisoquinolin-2(1H)-yl)-2-methyl-2-(methylsulfonyl)-N-(tetrahydro-2H-pyran-2-yl)oxy)butanamide (Intermediate 12) (0.186 g, 0.369 mmol), (4-(morpholinomethyl)phenyl)boronic acid (0.106 g, 0.480 mmol), PdCl$_2$(dppf) (0.027 g, 0.037 mmol) and potassium carbonate (0.102 g, 0.739 mmol) was dissolved in 1,4-dioxane (3 mL) and water (0.50 mL). The reaction vessel was heated in a microwave to 110° C. for 30 min. The solvent was removed and the residue was purified with silica gel chromatography (EtOAc/hexanes) to afford (2R)-2-methyl-2-(methylsulfonyl)-4-(6-(4-(morpholinomethyl)phenyl)-1-oxo-3,4-dihydroisoquinolin-2(1H)-yl)-N-(tetrahydro-2H-pyran-2-yl)oxy)butanamide (0.114 g). The reside was dissolved in dichloromethane (3 mL) and methanol (3 mL) and a 4M solution of hydrogen chloride in dioxane (0.277 mL, 1.108 mmol) was added and stirred at room temperature for 2 hr. The reaction was concentrated and the residue was dried to give (R)—N-hydroxy-2-methyl-2-(methylsulfonyl)-4-(6-(4-(morpholinomethyl)phenyl)-1-oxo-3,4-dihydroisoquinolin-2(1H)-yl)butanamide, hydrochloride (50 mg, 0.091 mmol, 25% yield) as an off white solid.

LCMS: [M+H] 516.3.

Example 93. (2R)—N-hydroxy-4-{6-[4-(2-hydroxyethyl)phenyl]-1-oxo-1,2-dihydroisoquinolin-2-yl}-2-methanesulfonyl-2-methylbutanamide

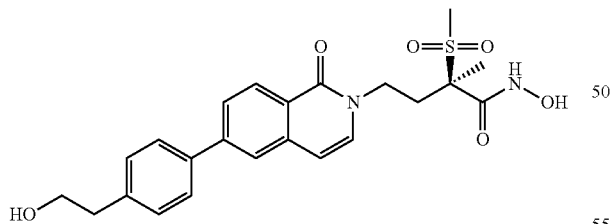

Part A

A reaction vessel was sealed with potassium carbonate (110 mg, 0.798 mmol), PdCl$_2$(dppf) (29 mg, 0.040 mmol), (2R)-4-(6-bromo-1-oxoisoquinolin-2(1H)-yl)-2-methyl-2-(methylsulfonyl)-N-(tetrahydro-2H-pyran-2-yl)oxy)butanamide (Intermediate 10) (200 mg, 0.399 mmol) and (4-(2 hydroxyethyl)phenyl)boronic acid (86 mg, 0.519 mmol) and was heated in microwave at 110° C. for 30 min. The organic phase was diluted with DCM (20 mL), extracted with DCM (10 mL×3) and washed with water (20 mL), brine (30 mL), dried over sodium sulphate and evaporated in vacuo. The residue was purified by silica gel chromatography (EtOAc/DCM: 10-100%) to afford (2R)-4-(6-(4-(2-hydroxyethyl)phenyl)-1-oxoisoquinolin-2(1H)-yl)-2-methyl-2-(methylsulfonyl)-N-(tetrahydro-2H-pyran-2-yl)oxy)butanamide (213 mg, 0.393 mmol, 98% yield) as colorless oil.

LCMS: [M+H] 543.3.

Part B

To a reaction vessel was added (2R)-4-(6-bromo-1-oxoisoquinolin-2(1H)-yl)-2-methyl-2-(methylsulfonyl)-N-(tetrahydro-2H-pyran-2-yl)oxy)butanamide (6 g, 11.97 mmol), (4-(2-hydroxyethyl)phenyl)boronic acid (2.384 g, 14.36 mmol), potassium carbonate (3.31 g, 23.93 mmol), PdCl$_2$(dppf) (0.876 g, 1.197 mmol), 1,4-dioxane (30 mL) and water (10 mL). The reaction vessel was sealed and heated in microwave at 110° C. for 30 min. After cooling, the crude product was purified by silica gel chromatography (EtOAc/hexanes: 0-100%) to give (2R)-4-(6-(4-(2-hydroxyethyl)phenyl)-1-oxoisoquinolin-2(1H)-yl)-2-methyl-2 (methylsulfonyl)-N-(tetrahydro-2H-pyran-2-yl)oxy)butanamide (3.16 g, 5.82 mmol, 49% yield).

LCMS: [M+H] 543.2.

Part C

To a solution of (2R)-4-(6-(4-(2-hydroxyethyl)phenyl)-1-oxoisoquinolin-2(1H)-yl)-2-methyl-2-(methylsulfonyl)-N-(tetrahydro-2H-pyran-2-yl)oxy)butanamide (213 mg, 0.393 mmol) in ethanol (3 mL) was added a 4M solution of hydrogen chloride in dioxane (0.294 mL, 1.178 mmol) and the solution was stirred at room temperature overnight. The reaction was concentrated and the residue was purified by reverse phase HPLC (5-70% MeCN/H$_2$O, 0.1% TFA) to afford (R)—N-hydroxy-4-(6-(4-(2-hydroxyethyl)phenyl)-1-oxoisoquinolin-2(1H)-yl)-2-methyl-2 (methylsulfonyl)butanamide (83 mg, 0.181 mmol, 46% yield) as a white powder.

LCMS: [M+H] 459.2.

$^1$H NMR (METHANOL-d4) δ: ppm 8.38 (d, J=8.6 Hz, 1H), 7.87 (s, 1H), 7.81 (dd, J=8.5, 1.4 Hz, 1H), 7.69 (d, J=8.1 Hz, 2H), 7.39 (d, J=7.8 Hz, 3H), 6.81 (d, J=7.1 Hz, 1H), 4.31-4.41 (m, 1H), 3.93 (td, J=12.1, 4.9 Hz, 1H), 3.82 (t, J=6.9 Hz, 2H), 3.13 (s, 3H), 2.91 (t, J=6.9 Hz, 2H), 2.59-2.69 (m, 1H), 2.35-2.47 (m, 1H), 1.74 (s, 3H).

Example 94. 2-(4-{2-[(3R)-3-(hydroxycarbamoyl)-3-methanesulfonyl-3-methylpropyl]-1-oxo-1,2-dihydroisoquinolin-6-yl}phenyl)ethyl 2-(dimethylamino)acetate

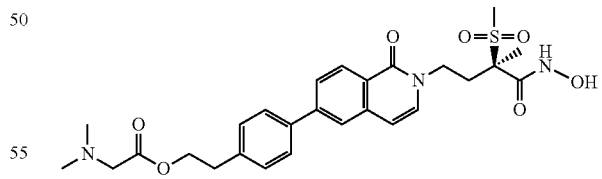

Part A

To a reaction vessel was added (2R)-4-(6-bromo-1-oxoisoquinolin-2(1H)-yl)-2-methyl-2-(methylsulfonyl)-N-((tetrahydro-2H-pyran-2-yl)oxy)butanamide (Intermediate 10) (6 g, 11.97 mmol), (4-(2-hydroxyethyl)phenyl)boronic acid (2.384 g, 14.36 mmol), potassium carbonate (3.31 g, 23.93 mmol), PdCl$_2$(dppf) (0.876 g, 1.197 mmol) in 1,4-dioxane (30 mL) and water (10 mL) and was heated in a microwave to 110° C. for 30 mins. After cooling, the crude product was purified by silica gel chromatography (EtOAc/ hexanes: 0-100%) to give (2R)-4-(6-(4-(2-hydroxyethyl) phenyl)-1-oxoisoquinolin-2(1H)-yl)-2-methyl-2-(methylsulfonyl)-N-((tetrahydro-2H-pyran-2-yl)oxy)butanamide (3.16 g, 5.82 mmol, 49% yield).

LCMS: [M+H] 543.2.

Part B

To a solution of (2R)-4-(6-(4-(2-hydroxyethyl)phenyl)-1-oxoisoquinolin-2(1H)-yl)-2-methyl-2-(methylsulfonyl)-N-(tetrahydro-2H-pyran-2-yl)oxy)butanamide (1.58 g, 2.91 mmol) in tetrahydrofuran (20 mL) was added N,N'-methanediylidenedicyclohexanamine (0.721 g, 3.49 mmol), N,N-dimethylpyridin-4-amine (0.427 g, 3.49 mmol) and 2-(dimethylamino)acetic acid (0.360 g, 3.49 mmol). The mixture was stirred at room temperature for 12 hr. The solvent was removed and the crude product was purified by silica gel chromatography (EtOAc/hexanes: 0-100%, 1% TEA) to afford 4-(2-(3R)-3-methyl-3-(methylsulfonyl)-4-oxo-4-((tetrahydro-2H-pyran-2-yl)oxy)amino)butyl)-1-oxo-1,2-dihydroisoquinolin-6-yl)phenethyl-2-(dimethylamino)acetate (2.36 g, 2.180 mmol, 75% yield).

LCMS: [M+H] 628.4.

Part C

To a solution of 4-(2-(3R)-3-methyl-3-(methylsulfonyl)-4-oxo-4-((tetrahydro-2H-pyran-2-yl)oxy)amino)butyl)-1-oxo-1,2-dihydroisoquinolin-6-yl)phenethyl-2-(dimethylamino)acetate (2.36 g, 3.76 mmol) in dichloromethane (20 mL) was added TFA (8.69 mL, 113 mmol). The resulting solution was stirred at 0° C. for 4 hr. The reaction was concentrated and purified by reverse phase chromatography (0-50% MeCN/$H_2O$) to give (R)-4-(2-(4-(hydroxyamino)-3-methyl-3-(methylsulfonyl)-4-oxobutyl)-1-oxo-1,2-dihydroisoquinolin-6-yl)phenethyl 2-(dimethylamino)acetate trifluoroacetic acid salt (610 mg, 0.881 mmol, 23% yield).

LCMS: [M+H] 544.2.

$^1$H NMR (400 MHz, METHANOL-d4) δ: ppm 1.68-1.81 (m, 3H) 2.40 (ddd, J=13.26, 11.24, 5.31 Hz, 1H), 2.56-2.71 (m, 1H), 2.88-2.98 (m, 6H), 3.01-3.19 (m, 5H), 3.85-4.01 (m, 1H), 4.10-4.20 (m, 2H), 4.27-4.43 (m, 1H), 4.57 (t, J=6.69 Hz, 2H), 6.81 (d, J=7.33 Hz, 1H), 7.30-7.52 (m, 3H), 7.62-7.94 (m, 4H), 8.38 (d, J=8.34 Hz, 1H).

Example 95. (2R)—N-hydroxy-2-methanesulfonyl-4-[5-(4-methoxyphenyl)-1-oxo-2,3-dihydro-1H-isoindol-2-yl]-2-methylbutanamide

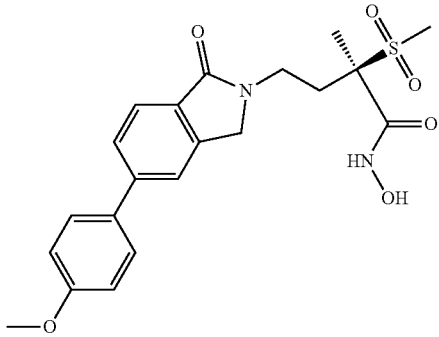 [SMILES: COc1ccc(-c2ccc3c(c2)CN(CC[C@](C)(C(=O)NO)S(C)(=O)=O)C3=O)cc1]

A mixture of 1-iodo-4-methoxybenzene (2 g, 8.55 mmol), 1,1,1,2,2,2-hexamethyldistannane (3.36 g, 10.25 mmol), Pd(Ph$_3$P)$_4$ (0.494 g, 0.427 mmol) and toluene (120 mL) was stirred at 110° C. for 17 hr under nitrogen. The reaction was filtered, washed with EtOAc (250 mL) and the organic layer was washed with water (100 mL), brine (100 mL) and concentrated to afford (4-methoxyphenyl)trimethylstannane (2.5 g, 7.38 mmol, 86% yield) as a yellow oil.

Part B

A mixture of (2R)-4-(5-bromo-1-oxoisoindolin-2-yl)-2-methyl-2-(methylsulfonyl)-N-(tetrahydro-2H-pyran-2-yl)oxy)butanamide (Intermediate 13) (400 mg, 0.817 mmol), (4-methoxyphenyl)trimethylstannane (443 mg, 1.635 mmol), Pd(PPh$_3$)$_2$Cl$_2$ (172 mg, 0.245 mmol) and 1,4-dioxane (10 mL) was stirred at 100° C. for 2 hr under a nitrogen atmosphere. A solution of KF was added to the reaction mixture. The mixture was extracted with CH$_2$Cl$_2$ (50 mL×3). The combined organic layers were washed with H$_2$O (20 mL) and brine (20 mL), dried over Na$_2$SO$_4$ and concentrated. The residue was purified by silica gel chromatography (EtOAc/petroleum ether: 0-67%) to afford (2R)-4-(5-(4-methoxyphenyl)-1-oxoisoindolin-2-yl)-2-methyl-2-(methylsulfonyl)-N-(tetrahydro-2H-pyran-2-yl)oxy)butanamide (180 mg, 0.209 mmol, 26% yield) as a yellow oil.

LCMS: [M-THP+H]: 432.9.

Part C

To a solution of (2R)-4-(5-(4-methoxyphenyl)-1-oxoisoindolin-2-yl)-2-methyl-2-(methylsulfonyl)-N-(tetrahydro-2H-pyran-2-yl)oxy)butanamide (180 mg, 0.209 mmol) in dichloromethane (2 mL) and methanol (2 mL) was added 4M HCl in dioxane (0.261 mL, 1.045 mmol) at 20° C. The reaction mixture was stirred at 20° C. for 1 hr. The reaction was concentrated and purified by reverse phase HPLC to afford (R)—N-hydroxy-4-(5-(4-methoxyphenyl)-1-oxoisoindolin-2-yl)-2-methyl-2-(methylsulfonyl)butanamide (24 mg, 0.050 mmol, 24% yield) as a yellow oil.

LCMS: [M+H] 432.9.

$^1$H NMR (500 MHz, METHANOL-d4) δ: ppm 7.79 (s, 2H), 7.73 (s, 1H), 7.65 (d, J=8.0 Hz, 2H), 7.06 (d, J=8.0 Hz, 2H), 4.60 (d, J=9.1 Hz, 2H), 3.87 (s, 3H), 3.77 (s, 2H), 3.10 (s, 3H), 2.78 (s, 1H), 2.21 (s, 1H), 1.73 (s, 3H), 1.32 (s, 1H).

Example 96. (2R)—N-hydroxy-2-methanesulfonyl-2-methyl-4-[5-(4-methylphenyl)-1-oxo-2,3-dihydro-1H-isoindol-2-yl]butanamide

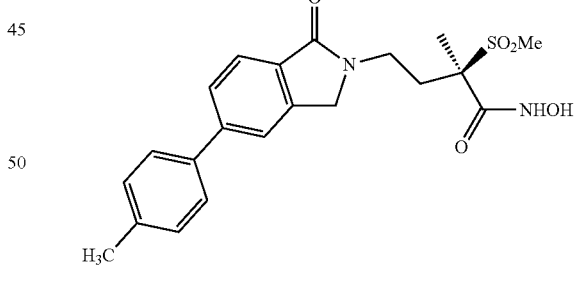

Part A

Potassium carbonate (78 mg, 0.564 mmol) in water (0.25 mL) was added to (R)-ethyl 4-(5-bromo-1-oxoisoindolin-2-yl)-2-methyl-2-(methylsulfonyl)butanoate (Intermediate 15) (118 mg, 0.282 mmol), p-tolylboronic acid (38.4 mg, 0.282 mmol) and PdCl$_2$(dppf) (41.3 mg, 0.056 mmol) in degassed acetonitrile (1.5 mL) at room temperature under an atmosphere of nitrogen. The resulting solution was stirred at 80° C. for 30 min. After completion, the reaction mixture was combined with the reaction mixture of N29228-60 and filtered. The filtrate was diluted with ethyl acetate and washed with water. The aqueous was further extracted with ethyl acetate and the combined organic layers were dried over sodium sulfate, filtered and evaporated to afford crude product which was purified by silica gel chromatography (ethyl acetate/hexane: 0-60%) to afford (R)-ethyl 2-methyl-2-(methylsulfonyl)-4-(1-oxo-5-(p-tolyl)isoindolin-2-yl)butanoate (188.5 mg, 0.439 mmol, 156% yield).

LCMS: [M+H] 430.3.

$^1$H NMR (CHLOROFORM-d) δ: ppm 7.88 (d, J=7.8 Hz, 1H), 7.61-7.75 (m, 2H), 7.54 (d, J=8.1 Hz, 2H), 7.31 (d, J=7.8 Hz, 2H), 4.27-4.65 (m, 2H), 3.90-4.18 (m, 3H), 3.69 (br. s., 1H), 3.01-3.16 (m, 3H), 2.65-2.83 (m, 1H), 2.37-2.53 (m, 3H), 2.28 (br. s., 1H), 1.83 (s, 3H), 1.23 (t, J=6.9 Hz, 3H).

Part B (R)-ethyl 2-methyl-2-(methylsulfonyl)-4-(1-oxo-5-(p-tolyl)isoindolin-2-yl)butanoate (51 mg, 0.119 mmol) was dissolved in dichloromethane (0.5 mL) and methanol (1 mL). The resulting solution was cooled to 0° C. and hydroxylamine (0.108 mL, 3.56 mmol) was added, followed by sodium hydroxide (47.5 mg, 1.187 mmol). The reaction was allowed to warm to room temperature and stirred for 1 hr. The solvent was then removed under reduced pressure and the residue was diluted purified by reverse phase HPLC (5-85% MeCN/H$_2$O, 0.1% TFA) to afford (R)—N-hydroxy-2-methyl-2-(methylsulfonyl)-4-(1-oxo-5-(p-tolyl)isoindolin-2-yl)butanamide (8 mg, 0.018 mmol, 15% yield) as a white powder.

LCMS: [M+H] 417.3.

$^1$H NMR (METHANOL-d4) δ: ppm 7.68-7.88 (m, 3H), 7.60 (d, J=8.1 Hz, 2H), 7.32 (d, J=8.1 Hz, 2H), 4.53-4.69 (m, 2H), 3.78 (t, J=7.3 Hz, 2H), 3.05-3.15 (m, 3H), 2.70-2.89 (m, 1H), 2.36-2.49 (m, 3H), 2.07-2.30 (m, 1H), 1.67-1.79 (m, 3H).

Example 97. (2R)-4-[5-(4-ethoxyphenyl)-1-oxo-2,3-dihydro-1H-isoindol-2-yl]-N-hydroxy-2-methanesulfonyl-2-methylbutanamide

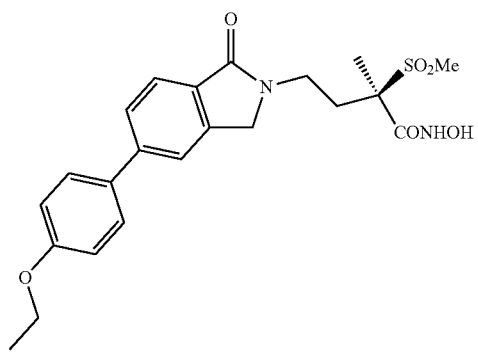

Part A

Potassium carbonate (66.1 mg, 0.478 mmol) in water (0.25 mL) was added to (R)-ethyl 4-(5-bromo-1-oxoisoindolin-2-yl)-2-methyl-2-(methylsulfonyl)butanoate (Intermediate 15) (100 mg, 0.239 mmol), (4-ethoxyphenyl)boronic acid (39.7 mg, 0.239 mmol) and PdCl$_2$(dppf) (35.0 mg, 0.048 mmol) in degassed acetonitrile (1.5 mL) at room temperature under an atmosphere of nitrogen. The resulting solution was stirred at 80° C. for 30 min. After completion, the solvent was removed and the residue was purified by silica gel chromatography (EtOAc/hexanes: 0-100%) to afford (R)-ethyl 4-(5-(4-ethoxyphenyl)-1-oxoisoindolin-2-yl)-2-methyl-2-(methylsulfonyl)butanoate (77.4 mg, 0.168 mmol, 71% yield).

LCMS: [M+H] 460.3.

Part B

To a solution of (R)-ethyl 4-(5-(4-ethoxyphenyl)-1-oxoisoindolin-2-yl)-2-methyl-2-(methylsulfonyl)butanoate (77.4 mg, 0.168 mmol) in tetrahydrofuran (2 mL) and water (1 mL) was added LiOH (16.13 mg, 0.674 mmol). The reaction mixture was stirred at room temperature for 2 hr. After completion, 2N HCl was added to reach pH=3 and the mixture was filtered and the solid was washed with water to obtain (R)-4-(5-(4-ethoxyphenyl)-1-oxoisoindolin-2-yl)-2-methyl-2-(methylsulfonyl)butanoic acid (46 mg, 0.107 mmol, 63% yield).

LCMS: [M+H] 432.2.

Part C

To a solution of (R)-4-(5-(4-ethoxyphenyl)-1-oxoisoindolin-2-yl)-2-methyl-2-(methylsulfonyl)butanoic acid (46 mg, 0.107 mmol) in DMF (1 mL) was added N1-(ethylimino)methylene)-N3,N3-dimethylpropane-1,3-diamine hydrochloride (61.3 mg, 0.320 mmol), O-(tetrahydro-2H-pyran-2-yl)hydroxylamine (24.98 mg, 0.213 mmol) followed by triethylamine (0.059 mL, 0.426 mmol). The reaction was stirred at 50° C. overnight when water was added to the reaction. The mixture was extracted with EtOAc, washed with brine, dried over Na$_2$SO$_4$ and concentrated. The crude product was purified by silica gel chromatography (EtOAc/hexanes: 0-100%) to give (2R)-4-(5-(4-ethoxyphenyl)-1-oxoisoindolin-2-yl)-2 methyl-2-(methylsulfonyl)-N-(tetrahydro-2H-pyran-2-yl)oxy)butanamide (51 mg, 0.096 mmol, 90% yield).

LCMS: [M+Na] 553.4.

Part D

To a solution of (2R)-4-(5-(4-ethoxyphenyl)-1-oxoisoindolin-2-yl)-2-methyl-2-(methylsulfonyl)-N-(tetrahydro-2H-pyran-2-yl)oxy)butanamide (51 mg, 0.096 mmol) in dichloromethane (1 mL) and methanol (1 mL) was added a 4M solution of HCl in dioxane (0.096 mL, 0.384 mmol). The resulting solution was stirred at room temperature for 1 hr and was concentrated, diluted w/DMSO and purified by reverse phase HPLC (5-85% MeCN/H$_2$O, 0.1% TFA) to afford (R)-4-(5-(4-ethoxyphenyl)-1-oxoisoindolin-2-yl)-N-hydroxy-2-methyl-2-(methylsulfonyl)butanamide (28 mg, 0.060 mmol, 62% yield) as a white solid.

LCMS: [M+H] 447.3.

$^1$H NMR (METHANOL-d4) δ: ppm 7.68-7.84 (m, 3H), 7.63 (d, J=8.8 Hz, 2H), 7.03 (d, J=8.8 Hz, 2H), 4.53-4.66 (m, 2H), 4.11 (q, J=7.0 Hz, 2H), 3.63-3.89 (m, 2H), 3.03-3.17 (m, 3H), 2.69-2.90 (m, 1H), 2.10-2.31 (m, 1H), 1.73 (s, 3H), 1.44 (t, J=7.1 Hz, 3H).

Example 98. (2R)-4-[5-(4-ethylphenyl)-1-oxo-2,3-dihydro-1H-isoindol-2-yl]-N-hydroxy-2-methanesulfonyl-2-methylbutanamide

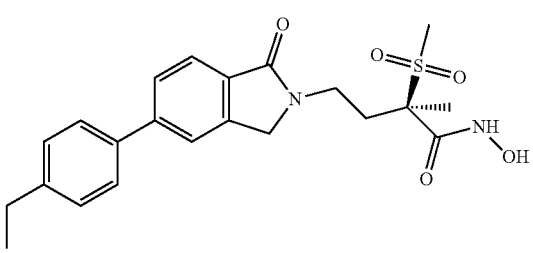 [SMILES: CCc1ccc(-c2ccc3c(c2)CN(CC[C@](C)(C(=O)NO)S(C)(=O)=O)C3=O)cc1]

A vessel was charged with (4-ethylphenyl)boronic acid (59.8 mg, 0.398 mmol), K₂CO₃ (85 mg, 0.613 mmol), (2R)-4-(5-bromo-1-oxoisoindolin-2-yl)-2-methyl-2-(methylsulfonyl)-N (tetrahydro-2H-pyran-2-yl)oxy)butanamide (Intermediate 13) (150 mg, 0.307 mmol) and PdCl₂(dppf) (22.43 mg, 0.031 mmol) and was heated in a microwave at 90° C. for 30 min. The organic phase was diluted with DCM (20 mL) and washed with water (20 mL), brine (30 mL), dried over sodium sulphate and evaporated in vacuo. The residue was purified by silical gel chromatography (EtOAc/hexanes: 0-80%) to afford (2R)-4-(5-(4-ethylphenyl)-1-oxoisoindolin-2-yl)-2-methyl-2-(methylsulfonyl)-N-(tetrahydro-2H-pyran-2-yl)oxy)butanamide (100 mg, 0.173 mmol, 56% yield) as a colorless oil.

LCMS: [M+H] 413.3.

Part B

To a solution of (2R)-4-(5-(4-ethylphenyl)-1-oxoisoindolin-2-yl)-2-methyl-2-(methylsulfonyl)-N-(tetrahydro-2H-pyran-2-yl)oxy)butanamide (100 mg, 0.194 mmol) in dichloromethane (2 mL) stirred under nitrogen at room temperature was added a solution of HCl in dioxane (0.5 mL, 2 mmol) in dioxane (4M). The reaction mixture was stirred at room temperature for 2 hr, was concentrated and then purified by reverse phase HPLC (5-85% MeCN/H₂O, 0.1% TFA) to afford (R)-4-(5 (4-ethylphenyl)-1-oxoisoindolin-2-yl)-N-hydroxy-2-methyl-2-(methylsulfonyl)butanamide (62.1 mg, 0.137 mmol, 71% yield) as a white solid.

LCMS: [M+H] 431.3.

¹H NMR (METHANOL-d4) δ: ppm 7.78-7.85 (m, 2H), 7.71-7.77 (m, 1H), 7.62 (d, J=8.1 Hz, 2H), 7.34 (d, J=8.1 Hz, 2H), 4.52-4.69 (m, 2H), 3.77 (t, J=7.2 Hz, 2H), 3.10 (s, 3H), 2.64-2.88 (m, 3H), 2.20 (dt, J=13.5, 6.8 Hz, 1H), 1.73 (s, 3H), 1.29 (t, J=7.6 Hz, 3H).

Example 99. (2R)-4-[5-(2-fluoro-4-methoxyphenyl)-1-oxo-2,3-dihydro-1H-isoindol-2-yl]-N-hydroxy-2-methanesulfonyl-2-methylbutanamide

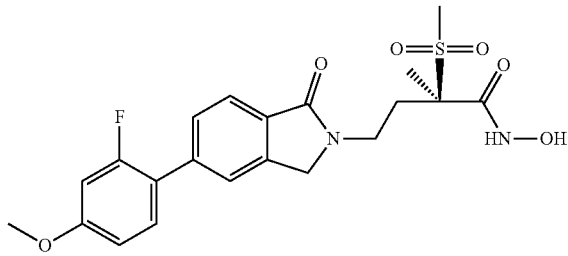 [SMILES: COc1ccc(-c2ccc3c(c2)CN(CC[C@](C)(C(=O)NO)S(C)(=O)=O)C3=O)c(F)c1]

To a solution of (2R)-4-(5-bromo-1-oxoisoindolin-2-yl)-2-methyl-2-(methylsulfonyl)-N-(tetrahydro 2H-pyran-2-yl) butanamide (Intermediate 13) (400 mg, 0.845 mmol), (2-fluoro-4-methoxyphenyl)boronic acid (200 mg, 1.177 mmol) in a solution of acetonitrile (12 mL) and water (2 mL) was added, PdCl₂(dppf) CH₂Cl₂ adduct (138 mg, 0.169 mmol) and K₂CO₃ (234 mg, 1.690 mmol). The mixture was stirred at 80° C. for 30 min under an atmosphere of nitrogen. DCM (50 mL) and water (50 mL) was added and the aqueous layer was extracted with CH₂Cl₂ (50 mL×2). The combined organic layers were dried over Na₂SO₄ and concentrated. The crude product was purified by silica gel chromatography (EtOAc/ether: 0-70%) to yield (2R)-4-(5-(2-fluoro-4-methoxyphenyl)-1-oxoisoindolin-2-yl)-2-methyl-2-(methylsulfonyl)-N-(tetrahydro-2H-pyran-2-yl)oxy)butanamide (300 mg, 0.477 mmol, 57% yield) as a solid.

LCMS: [M-THP+H] 450.9.

Part B

To a stirred solution of (2R)-4-(5-(2-fluoro-4-methoxyphenyl)-1-oxoisoindolin-2-yl)-2-methyl-2 (methylsulfonyl)-N-(tetrahydro-2H-pyran-2-yl)oxy)butanamide (270 mg, 0.505 mmol) in dichloromethane (5 mL) and methanol (5.00 mL) was added HCl (1.263 mL, 5.05 mmol) at 10° C. and this mixture was then stirred at this temperature for an hour. The solvent was removed and the crude was purified by reverse phase HPLC to yield (R)-4-(5-(2-fluoro-4-methoxyphenyl)-1-oxoisoindolin-2-yl)-N-hydroxy-2-methyl-2-(methylsulfonyl)butanamide (106 mg, 0.235 mmol, 47% yield) as a white solid.

LCMS: [M+H] 450.9.

¹H NMR (500 MHz, DMSO-d₆) δ: ppm 10.96 (s, 1H), 7.72 (d, J=7.8 Hz, 2H), 7.60 (d, J=8.0 Hz, 1H), 7.51 (t, J=9.0 Hz, 1H), 7.01-6.89 (m, 2H), 4.55 (d, J=4.1 Hz, 2H), 3.83 (s, 3H), 3.69-3.62 (m, 1H), 3.45 (d, J=6.1 Hz, 1H), 3.08 (s, 3H), 2.60 (d, J=13.2, 10.0, 6.2 Hz, 1H), 2.04-1.93 (m, 1H), 1.57 (s, 3H).

Example 100. (2R)—N-hydroxy-2-methanesulfonyl-2-methyl-4-{1-oxo-5-[4-(propan-2-yloxy)phenyl]-2,3-dihydro-1H-isoindol-2-yl}butanamide

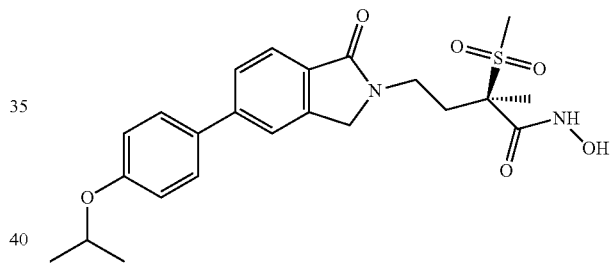

Part A

A vessel was charged with (4-isopropoxyphenyl)boronic acid (55.2 mg, 0.307 mmol), K₂CO₃ (85 mg, 0.613 mmol), (2R)-4-(5-bromo-1-oxoisoindolin-2-yl)-2-methyl-2-(methylsulfonyl)-N-(tetrahydro-2H-pyran-2-yl)oxy)butanamide (Intermediate 13) (150 mg, 0.307 mmol) and PdCl₂(dppf) (22.43 mg, 0.031 mmol) and heated in microwave at 90° C. for 30 min. The organic phase was diluted with DCM, (20 mL) and washed with water (20 mL), brine (30 mL), dried over sodium sulphate and concentrated. The residue was purified by silical gel chromatography (EtOAc/hexanes: 0-80%) to afford (2R)-4-(5-(4-isopropoxyphenyl)-1-oxoisoindolin-2-yl)-2-methyl-2-(methylsulfonyl)-N-(tetrahydro-2H-pyran-2-yl)oxy)butanamide (110 mg, 0.172 mmol, 56% yield) as a colorless oil.

LCMS: [M+Na] 567.3.

Part B

To a solution of (2R)-4-(5-(4-isopropoxyphenyl)-1-oxoisoindolin-2-yl)-2-methyl-2-(methylsulfonyl)-N-(tetrahydro-2H-pyran-2-yl)oxy)butanamide (100 mg, 0.184 mmol) in dichloromethane (5 mL) stirred under nitrogen at room temperature was added a solution of HCl (0.5 mL, 2.000 mmol) in dioxane (4M). The reaction mixture was stirred at room temperature for 2 hr and concentrated. The residue was purified by silica gel chromatography (MeOH/

DCM: 0-20%) to afford (R)—N-hydroxy-4-(5-(4-isopropoxyphenyl)-1-oxoisoindolin-2-yl)-2-methyl-2-(methylsulfonyl)butanamide (14 mg, 0.029 mmol, 16% yield) as a white solid.

LCMS: [M+H] 461.3.

$^1$H NMR (METHANOL-d$_4$) 65: ppm 7.74-7.82 (m, 2H), 7.67-7.74 (m, 1H), 7.62 (d, J=8.6 Hz, 2H), 7.02 (d, J=8.6 Hz, 2H), 4.62-4.74 (m, 1H), 4.58 (d, J=6.6 Hz, 2H), 3.67-3.84 (m, 2H), 3.10 (s, 3H), 2.79 (dt, J=13.5, 7.9 Hz, 1H), 2.20 (ddd, J=13.3, 7.8, 5.9 Hz, 1H), 1.73 (s, 3H), 1.36 (d, J=6.1 Hz, 6H).

Example 101. (2R)-4-[5-(2-fluoro-4-methylphenyl)-1-oxo-2,3-dihydro-1H-isoindol-2-yl]-N-hydroxy-2-methanesulfonyl-2-methylbutanamide

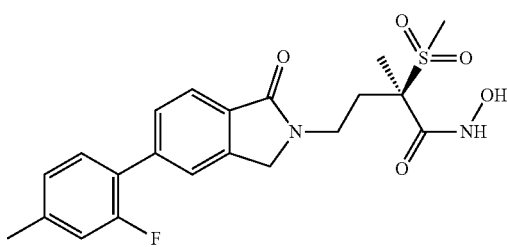 [SMILES: Cc1ccc(-c2ccc3c(c2)CN(CC[C@](C)(C(=O)NO)S(C)(=O)=O)C3=O)c(F)c1]

To a solution of (2R)-4-(5-bromo-1-oxoisoindolin-2-yl)-2-methyl-2-(methylsulfonyl)-N-(tetrahydro-2H-pyran-2-yl) butanamide (Intermediate 13) (420 mg, 0.887 mmol) in acetonitrile (12 mL) was added water (2 mL), (2-fluoro-4-methylphenyl)boronic acid (150 mg, 0.976 mmol), K$_2$CO$_3$ (245 mg, 1.774 mmol) and PdCl$_2$(dppf)-CH$_2$Cl$_2$ adduct (145 mg, 0.177 mmol). The mixture was stirred at 80° C. for 30 min under nitrogen. The solvent was removed, water (50 mL) was added to the mixture and the aqueous layer was extracted with EtOAc (100 mL×3). The combined organic layers were concentrated and the crude product was purified by silica gel chromatography (EtOAc/petroleum ether: 10-70%) to afford (2R)-4-(5-(2-fluoro-4-methylphenyl)-1-oxoisoindolin-2-yl)-2-methyl-2-(methylsulfonyl)-N-(tetrahydro-2H-pyran-2-yl)butanamide (360 mg, 0.645 mmol, 73% yield).

LCMS: [M+Na] 540.8.

Part B

To a solution of (2R)-4-(5-(2-fluoro-4-methylphenyl)-1-oxoisoindolin-2-yl)-2-methyl-2 (methylsulfonyl)-N-(tetrahydro-2H-pyran-2-yl)oxy)butanamide (360 mg, 0.694 mmol) in methanol (10 mL) and dichloromethane (10 mL) was added 4M HCl in 1,4-dioxane (0.694 mL, 2.78 mmol) at 25° C. The reaction mixture was stirred at 25° C. for 1 hr and the solvent was removed and the residue was purified by reversed phase HPLC to yield (R)-4-(5-(2-fluoro-4-methylphenyl)-1-oxoisoindolin-2-yl)-N-hydroxy-2-methyl-2 (methylsulfonyl)butanamide (100 mg, 0.230 mmol, 33% yield) LCMS: [M+H] 432.9.

$^1$H NMR (500 MHz METHANOL-d4) δ: ppm 7.83 (d, J=8.0 Hz, 1H), 7.75 (s, 1H), 7.67 (d, J=8.1 Hz, 1H), 7.44 (t, J=8.1 Hz, 1H), 7.14 (d, J=8.1 Hz, 1H), 7.08 (d, J=11.9 Hz, 1H), 4.62 (q, J=17.4 Hz, 2H), 3.78 (t, J=7.7 Hz, 2H), 3.10 (s, 3H), 2.84-2.75 (m, 1H), 2.43 (s, 3H), 2.25-2.17 (m, 1H), 1.74 (s, 3H).

Example 102. (2R)-4-[5-(2-fluorophenyl)-1-oxo-2,3-dihydro-1H-isoindol-2-yl]-N-hydroxy-2-methanesulfonyl-2-methylbutanamide

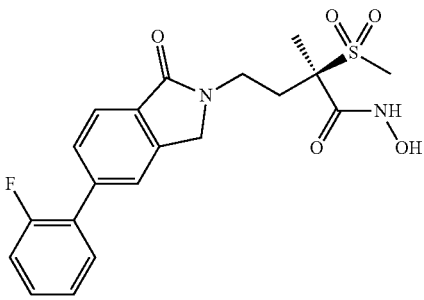 [SMILES: C[C@@](CCN1Cc2cc(-c3ccccc3F)ccc2C1=O)(C(=O)NO)S(C)(=O)=O]

Part A

A mixture of (2R)-4-(5-bromo-1-oxoisoindolin-2-yl)-2-methyl-2-(methylsulfonyl)-N-((tetrahydro 2H-pyran-2-yl)oxy)butanamide (Intermediate 13) (400 mg, 0.817 mmol), (2-fluorophenyl)boronic acid (229 mg, 1.635 mmol), PdCl$_2$(dppf)-CH$_2$Cl$_2$ adduct (133 mg, 0.163 mmol) and K$_2$CO$_3$ (226 mg, 1.635 mmol) in acetonitrile (1.2 mL) and water (0.200 mL) was stirred at 80° C. for 30 min. After cooling, ethyl acetate (100 mL) was added and the mixture was washed with brine (30 mL×2), dried over sodium sulfate and concentrated to give the (2R)-4-(5-(2-fluorophenyl)-1-oxoisoindolin-2-yl)-2-methyl-2-(methylsulfonyl)-N-((tetrahydro-2H-pyran-2-yl)oxy)butanamide (200 mg, 0.396 mmol, 49% yield)

LCMS: [M+H-THP] 420.8.

Part B

To a solution of (2R)-4-(5-(2-fluorophenyl)-1-oxoisoindolin-2-yl)-2-methyl-2-(methylsulfonyl)-N-(tetrahydro-2H-pyran-2-yl)oxy)butanamide (200 mg, 0.396 mmol) in methanol (5 mL) was added HCl in dioxane (4M) (5 mL, 20 mmol). The solution was stirred 1 hr at room temperature. The mixture was concentrated, the residue was triturated with ether (30 mL) twice and the residue was dissolved in DCM (5 mL) and MeOH (0.5 mL). Petroleum ether (30 mL) was added slowly and the solid was filtered and dried under reduce pressure to give (R)-4-(5-(2-fluorophenyl)-1-oxoisoindolin-2-yl)-N-hydroxy-2-methyl-2-(methylsulfonyl) butanamide (100 mg, 0.238 mmol, 60% yield) LCMS: [M+H] 420.8.

$^1$H NMR (500 MHz, DMSO-d$_6$) δ: ppm 10.96 (s, 1H), 9.17 (s, 1H), 7.81-7.71 (m, 2H), 7.64 (d, J=7.8 Hz, 1H), 7.58 (J=8.7, 7.0 Hz, 1H), 7.48 (J=13.6, 5.5 Hz, 1H), 7.35 (J=15.3, 8.1 Hz, 2H), 4.62-4.50 (m, 2H), 3.69-3.61 (m, 1H), 3.53-3.44 (m, 1H), 3.08 (s, 3H), 2.65-2.56 (m, 1H), 2.00 (d, J=14.7, 10.0, 5.1 Hz, 1H), 1.57 (s, 3H).

Example 103. (2R)-4-[5-(2H-1,3-benzodioxol-5-yl)-1-oxo-2,3-dihydro-1H-isoindol-2-yl]-N-hydroxy-2-methanesulfonyl-2-methylbutanamide

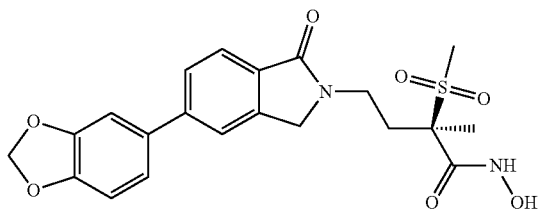 [SMILES: C[C@@](CCN1Cc2cc(-c3ccc4c(c3)OCO4)ccc2C1=O)(C(=O)NO)S(C)(=O)=O]

To a solution of (2R)-4-(5-bromo-1-oxoisoindolin-2-yl)-2-methyl-2-(methylsulfonyl)-N-(tetrahydro-2H-pyran-2-yl) butanamide (Intermediate 13) (400 mg, 0.845 mmol), (2-fluoro-4-methoxyphenyl)boronic acid (200 mg, 1.177 mmol) in a solution of acetonitrile (12 mL) and water (2 mL) was added PdCl$_2$(dppf)-CH$_2$Cl$_2$ adduct (138 mg, 0.169 mmol) and K$_2$CO$_3$ (234 mg, 1.690 mmol). The mixture was stirred at 80° C. for 30 min under an atmosphere of nitrogen. DCM (50 mL) and water (50 mL) was added and the aqueous layer was extracted with CH$_2$Cl$_2$ (50 mL×2). The combined organic layers were dried (Na$_2$SO$_4$) and concentrated. The crude product was purified by silica gel chromatography (EtOAc/petroleum ether: 0-70%) to yield (2R)-4-(5-(benzo[d][1,3]dioxol-5-yl)-1-oxoisoindolin-2-yl)-2-methyl-2-(methylsulfonyl)-N-(tetrahydro-2H-pyran-2-yl) oxy)butanamide (300 mg, 0.509 mmol, 60% yield) as a solid.

LCMS: [M+H] 552.8.

Part B

To a stirred solution of (2R)-4-(5-(benzo[d][1,3]dioxol-5-yl)-1-oxoisoindolin-2-yl)-2-methyl-2-(methylsulfonyl)-N-(tetrahydro-2H-pyran-2-yl)oxy)butanamide (270 mg, 0.509 mmol) in dichloromethane (5 mL) and methanol (5 mL) was added HCl (1.272 mL, 5.09 mmol) at room temperature and stirred for one hour. The solvent was removed and the crude material was purified by reverse phase HPLC to afford (R)-4-(5-(benzo[d][1,3]dioxol-5-yl)-1-oxoisoindolin-2-yl)-N hydroxy-2-methyl-2-(methylsulfonyl)butanamide (64 mg, 0.129 mmol, 25% yield).

LCMS: [M+H] 447.1.

$^1$H NMR (500 MHz, DMSO-de) δ: ppm 10.96 (s, 1H), 9.17 (s, 1H), 7.82 (s, 1H), 7.69 (q, J=8.0 Hz, 2H), 7.32 (s, 1H), 7.23 (d, J=8.1 Hz, 1H), 7.04 (d, J=8.1 Hz, 1H), 6.09 (s, 2H), 4.53 (d, J=3.2 Hz, 2H), 3.68-3.59 (m, 1H), 3.52-3.43 (m, 1H), 3.08 (s, 3H), 2.60 (d, J=15.8, 9.8, 6.2 Hz, 1H), 2.04-1.95 (m, 1H), 1.57 (s, 3H).

Example 104. (2R)-4-[5-(2-fluoro-3-methoxyphenyl)-1-oxo-2,3-dihydro-1H-isoindol-2-yl]-N-hydroxy-2-methanesulfonyl-2-methylbutanamide

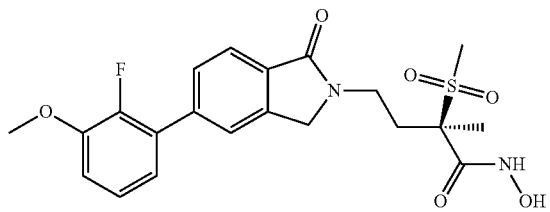 [SMILES: COc1cccc(-c2ccc3c(c2)CN(CC[C@](C)(C(=O)NO)S(C)(=O)=O)C3=O)c1F]

Part A

A mixture of (2R)-4-(5-bromo-1-oxoisoindolin-2-yl)-2-methyl-2-(methylsulfonyl)-N-(tetrahydro-2H-pyran-2-yl) oxy)butanamide (Intermediate 13) (360 mg, 0.736 mmol), (2-fluoro-3-methoxyphenyl)boronic acid (188 mg, 1.103 mmol), PdCl$_2$(dppf)-CH$_2$Cl$_2$ adduct (120 mg, 0.147 mmol) and K$_2$CO$_3$ (203 mg, 1.471 mmol) in acetonitrile (12 mL) and water (2 mL) was stirred at 80° C. for 30 min. DCM (50 mL) and water (50 mL) was added and the aqueous layer was extracted with CH$_2$Cl$_2$ (50 mL×2). The combined organic layers were dried over Na$_2$SO$_4$ and concentrated and residue was purified by silica gel (EtOAc/petroleum ether: 0-70%) to yield (2R)-4-(5-(2-fluoro-3-methoxyphenyl)-1-oxoisoindolin-2-yl)-2-methyl-2-(methylsulfonyl)-N-(tetrahydro-2H-pyran-2-yl)oxy)butanamide (300 mg, 0.505 mmol, 62% yield) as a solid.

LCMS: [M+Na] 556.8.

Part B

To a stirred solution of (2R)-4-(5-(2-fluoro-3-methoxyphenyl)-1-oxoisoindolin-2-yl)-2-methyl-2-(methylsulfonyl)-N-(tetrahydro-2H-pyran-2-yl)oxy)butanamide (250 mg, 0.468 mmol) in dichloromethane (5 mL) and methanol (5 mL) was added HCl (1.169 mL, 4.68 mmol) at 30° C. This mixture was stirred at this temperature for an hour. The solvent was removed to afford crude material which was purified by reverse phase HPLC to yield (R)-4-(5-(2-fluoro-3-methoxyphenyl)-1-oxoisoindolin-2-yl)-N-hydroxy-2-methyl-2-(methylsulfonyl)butanamide (130 mg, 0.289 mmol, 62% yield) as a white solid.

LCMS: [M+H] 451.0.

$^1$H NMR (500 MHz, DMSO-d$_6$) δ: ppm 10.95 (s, 1H), 9.16 (d, J=1.7 Hz, 1H), 7.78-7.70 (m, 2H), 7.62 (d, J=7.9 Hz, 1H), 7.30-7.18 (m, 2H), 7.09 (td, J=6.8, 2.2 Hz, 1H), 4.63-4.47 (m, 2H), 3.89 (s, 3H), 3.71-3.60 (m, 1H), 3.50-3.44 (m, 1H), 3.08 (s, 3H), 2.66-2.56 (m, 1H), 2.05-1.94 (m, 1H), 1.57 (s, 3H).

Example 105. (2R)—N-hydroxy-2-methanesulfonyl-2-methyl-4-[5-(5-methylthiophen-2-yl)-1-oxo-2,3-dihydro-1H-isoindol-2-yl]butanamide

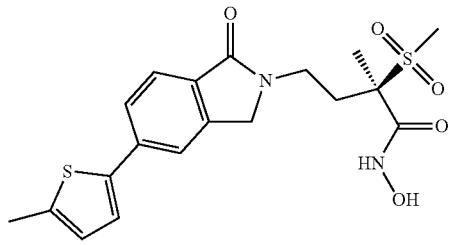 [SMILES: Cc1ccc(-c2ccc3c(c2)CN(CC[C@](C)(C(=O)NO)S(C)(=O)=O)C3=O)s1]

Part A (R)-ethyl 4-(5-bromo-1-oxoisoindolin-2-yl)-2-methyl-2-(methylsulfonyl)butanoate (Intermediate 15) (200 mg, 0.478 mmol), 4,4,4',4',5,5,5',5'-octamethyl-2,2'-bi(1,3,2-dioxaborolane) (182 mg, 0.717 mmol), PdCl$_2$(dppf) (35 mg, 0.048 mmol) and potassium acetate (141 mg, 1.434 mmol) was added to 1,2-dimethoxyethane (3 mL). The resulting solution was stirred at 80° C. for 3 hr and filtered through a pad of celite. The solvent was removed, the residue was dissolved in acetonitrile (2.4 mL) and water (0.4 mL) and 2-bromo-5-methylthiophene (102 mg, 0.574 mmol), PdCl$_2$(dppf) (70 mg, 0.096 mmol) and potassium carbonate (132 mg, 0.956 mmol) were added. The resulting solution was stirred at 80° C. for 1 hr. After completion, the solvent was removed and the crude product was purified by silica gel chromatography (EtOAc/hexanes: 0-100%) to afford (R)-ethyl 2-methyl-2-(methylsulfonyl)-4-(5-(5-methylthiophen-2-yl)-1-oxoisoindolin-2-yl)butanoate (153 mg, 0.351 mmol, 74% yield).

LCMS: [M+H] 436.2.

$^1$H NMR (CHLOROFORM-d) δ: ppm 7.75-7.84 (m, 1H), 7.58-7.70 (m, 2H), 7.24 (d, J=3.5 Hz, 1H), 6.79 (dd, J=3.5, 1.0 Hz, 1H), 4.26-4.54 (m, 2H), 3.81-4.22 (m, 2H), 3.55-3.76 (m, 1H), 2.97-3.15 (m, 3H), 2.72 (dt, J=13.5, 8.0 Hz, 1H), 2.47-2.63 (m, 3H), 2.18-2.36 (m, 1H), 1.76-1.89 (m, 3H), 1.62 (br. s., 1H), 1.21 (t, J=7.1 Hz, 3H).

Part B

To a slurry of (R)-ethyl 2-methyl-2-(methylsulfonyl)-4-(5-(5-methylthiophen-2-yl)-1-oxoisoindolin-2-yl)butanoate (149 mg, 0.342 mmol) and hydroxylamine (3.80 mL, 57.5 mmol) in 1,4-dioxane (2 mL) under nitrogen was added lithium hydroxide (1.895 mL, 1.895 mmol). The reaction was stirred at room temperature for 3 hr was concentrated and purified by reverse phase HPLC (5-75% MeCN/H$_2$O, 0.1% TFA) to afford (R)—N-hydroxy-2-methyl-2-(methylsulfonyl)-4-(5-(5-methylthiophen-2-yl)-1-oxoisoindolin-2-yl)butanamide (25 mg, 0.056 mmol, 16% yield) as a white powder.

LCMS: [M+H] 423.2.

$^1$H NMR (METHANOL-d4) δ: ppm 7.64-7.85 (m, 3H), 7.28-7.40 (m, 1H), 6.83 (dd, J=3.5, 1.0 Hz, 1H), 4.49-4.66 (m, 2H), 3.70-3.81 (m, 2H), 3.10 (s, 3H), 2.73-2.84 (m, 1H), 2.51-2.57 (m, 3H), 2.19 (dt, J=13.5, 6.6 Hz, 1H), 1.73 (s, 3H).

Example 106. (2R)-4-[5-(2,5-difluorophenyl)-1-oxo-2,3-dihydro-1H-isoindol-2-yl]-N-hydroxy-2-methanesulfonyl-2-methylbutanamide

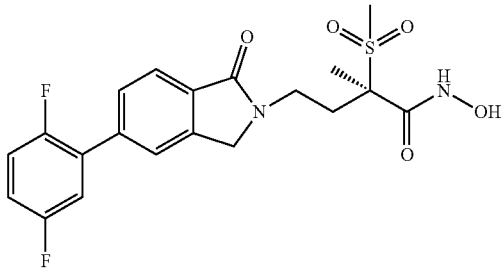 [SMILES: C[C@@](CCN1Cc2cc(-c3cc(F)ccc3F)ccc2C1=O)(C(=O)NO)S(C)(=O)=O]

Part A

A mixture of (2R)-4-(5-bromo-1-oxoisoindolin-2-yl)-2-methyl-2-(methylsulfonyl)-N-(tetrahydro-2H-pyran-2-yl)oxy)butanamide (Intermediate 13) (400 mg, 0.817 mmol), (2,5-difluorophenyl)boronic acid (258 mg, 1.635 mmol), K$_2$CO$_3$ (226 mg, 1.635 mmol), PdCl$_2$(dppf)-CH$_2$Cl$_2$ adduct (133 mg, 0.163 mmol) in acetonitrile (12 mL) and water (2 mL) was stirred at 80° C. for 0.5 hr under a nitrogen atmosphere. The reaction was concentrated and the aqueous layer was extracted with DCM (50 mL×2). The combined organic layers were dried over Na$_2$SO$_4$, filtered and concentrated. The residue was purified by silica gel chromatography (EtOAc/hexanes: 50-60%) to yield (2R)-4-(5-(2,5-difluorophenyl)-1-oxoisoindolin-2-yl)-2-methyl-2-(methylsulfonyl)-N-(tetrahydro-2H-pyran-2-yl)oxy)butanamide (330 mg, 0.600 mmol, 73% yield) as a yellow solid.

LCMS: [M+Na] 545.1.

Part B

To a solution of (2R)-4-(5-(2,5-difluorophenyl)-1-oxoisoindolin-2-yl)-2-methyl-2-(methylsulfonyl)-N-(tetrahydro-2H-pyran-2-yl)oxy)butanamide (310 mg, 0.593 mmol) in dichloromethane (5 mL) and methanol (2 mL) was added 4M HCl in dioxane (0.742 mL, 2.97 mmol) at 20° C. The reaction mixture was stirred at 20° C. for 15 min and concentrated. The crude was purified by reverse phase HPLC to afford (R)-4-(5-(2,5-difluorophenyl)-1-oxoisoindolin-2-yl)-N-hydroxy-2-methyl-2-(methylsulfonyl)butanamide (101 mg, 0.230 mmol, 39% yield) as an off white solid.

LCMS: [M+H]: 439.1.

$^1$H NMR (500 MHz, DMSO-d$_6$) δ: ppm 10.96 (s, 1H), 9.17 (s, 1H), 7.81 (s, 1H), 7.76 (d, J=7.9 Hz, 1H), 7.67 (d, J=7.9 Hz, 1H), 7.52-7.38 (m, 2H), 7.33 (dt, J=12.6, 6.1 Hz, 1H), 4.62-4.48 (m, 2H), 3.70-3.59 (m, 1H), 3.53-3.43 (m, 1H), 3.08 (s, 3H), 2.67-2.55 (m, 1H), 2.05-1.93 (m, 1H), 1.57 (s, 3H).

Example 107. 2R)-4-[5-(4-chloro-2-fluorophenyl)-1-oxo-2,3-dihydro-1H-isoindol-2-yl]-N-hydroxy-2-methanesulfonyl-2-methylbutanamide

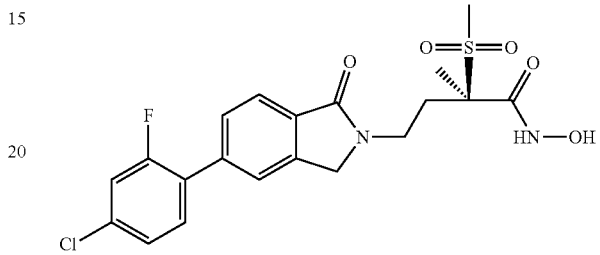

Part A

To a solution of (2R)-4-(5-bromo-1-oxoisoindolin-2-yl)-2-methyl-2-(methylsulfonyl)-N-(tetrahydro-2H-pyran-2-yl)butanamide (Intermediate 13) (350 mg, 0.739 mmol) in acetonitrile (6 mL) was added water (1 mL), (4-chloro-2-fluorophenyl)boronic acid (258 mg, 1.479 mmol), K$_2$CO$_3$ (204 mg, 1.479 mmol) and PdCl$_2$(dppf)-CH$_2$Cl$_2$ adduct (121 mg, 0.148 mmol). The mixture was stirred at 80° C. for 30 min under an atmosphere of nitrogen. AcOEt (10 mL) and water (10 mL) was added and the aqueous layer was extracted with AcOEt (8 mL×2). The combined organic layers were washed with H$_2$O (15 mL) and brine (10 mL), dried (Na$_2$SO$_4$) and concentrated. The crude product was purified by silica gel chromatography (EtOAc/hexanes: 20-100%) to yield (2R)-4-(5-(4-chloro-2-fluorophenyl)-1-oxoisoindolin-2-yl)-2-methyl-2-(methylsulfonyl)-N-(tetrahydro-2H-pyran-2-yl)oxy)butanamide (270 mg, 0.451 mmol, 61% yield) as a reddish-brown solid.

LCMS: [M+H] 455.1.

Part B

To a solution (2R)-4-(5-(4-chloro-2-fluorophenyl)-1-oxoisoindolin-2-yl)-2-methyl-2-(methylsulfonyl)-N-(tetrahydro-2H-pyran-2-yl)oxy)butanamide (250 mg, 0.464 mmol) in dichloromethane (2 mL) and methanol (2 mL) was added hydrogen chloride (4M) in 1,4-dioxane (4.64 mL, 18.55 mmol). The reaction mixture was stirred at 10° C. for 1 hr and concentrate. The residue was purified by reverse phase HPLC to yield (R)-4-(5-(4-chloro-2-fluorophenyl)-1-oxoisoindolin-2-yl)-N-hydroxy-2-methyl-2-(methylsulfonyl)butanamide (26 mg, 0.051 mmol, 11% yield) as a white solid.

LCMS: [M+H] 455.0.

$^1$H NMR (400 MHz, DMSO-d$_6$) □: ppm 8.98 (s, 1H), 7.79-7.36 (m, 6H), 4.65-4.46 (m, 2H), 3.64 (d, J=9.5 Hz, 2H), 3.08 (s, 3H), 2.61-2.59 (m, 1H), 1.98 (d, J=19.9 Hz, 1H), 1.57 (s, 3H).

Example 108. (2R)—N-hydroxy-2-methanesulfonyl-2-methyl-4-{5-[4-(morpholin-4-yl)phenyl]-1-oxo-2,3-dihydro-1H-isoindol-2-yl})butanamide

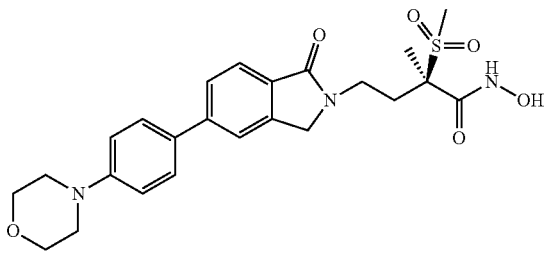 [SMILES: C[C@@](CCN1Cc2cc(-c3ccc(N4CCOCC4)cc3)ccc2C1=O)(C(=O)NO)S(C)(=O)=O]

Part A

Potassium carbonate (89 mg, 0.642 mmol) in water (0.25 mL) was added to (2R)-4-(5-bromo-1-oxoisoindolin-2-yl)-2-methyl-2-(methylsulfonyl)-N-(tetrahydro-2H-pyran-2-yl)oxy)butanamide (Intermediate 13) (157 mg, 0.321 mmol), (4-morpholinophenyl)boronic acid (66.4 mg, 0.321 mmol) and PdCl$_2$(dppf) (46.9 mg, 0.064 mmol) in degassed acetonitrile (1.5 mL) under an atmosphere of nitrogen. The resulting solution was stirred at 80° C. for 30 min. The solvent was removed and the residue was purified by silica gel chromatography (EtOAc/hexanes: 100%) to afford (2R)-2-methyl-2-(methylsulfonyl)-4-(5-(4-morpholinophenyl)-1-oxoisoindolin-2-yl)-N-(tetrahydro-2H-pyran-2-yl)oxy)butanamide (58.8 mg, 0.103 mmol, 32% yield).

LCMS: [M+H] 572.4.

Part B

To a solution of (2R)-2-methyl-2-(methylsulfonyl)-4-(5-(4-morpholinophenyl)-1-oxoisoindolin-2-yl)-N-(tetrahydro-2H-pyran-2-yl)oxy)butanamide (58.8 mg, 0.103 mmol) in dichloromethane (1 mL) and methanol (1 mL) was added a 4M solution of hydrogen chloride in dioxane (15 mg, 0.411 mmol). The resulting solution was stirred at room temperature for 1 hr. The solvent was removed and the residue was washed with ether to afford (R)—N-hydroxy-2-methyl-2-(methylsulfonyl)-4-(5-(4-morpholinophenyl)-1-oxoisoindolin-2-yl)butanamide hydrochloride (51 mg, 0.088 mmol, 85% yield).

LCMS: [M+H] 488.3.

$^1$H NMR (METHANOL-d4) δ: ppm 7.97 (d, J=8.6 Hz, 2H), 7.78-7.93 (m, 5H), 4.48-4.76 (m, 2H), 4.11-4.22 (m, 4H), 3.74-3.86 (m, 6H), 3.65-3.70 (m, 1H), 3.10 (s, 3H), 2.72-2.92 (m, 1H), 2.10-2.29 (m, 1H), 1.69-1.77 (m, 3H).

Example 109. (2R)-4-{5-[4-(dimethylamino)phenyl]-1-oxo-2,3-dihydro-1H-isoindol-2-yl}-N-hydroxy-2-methanesulfonyl-2-methylbutanamide

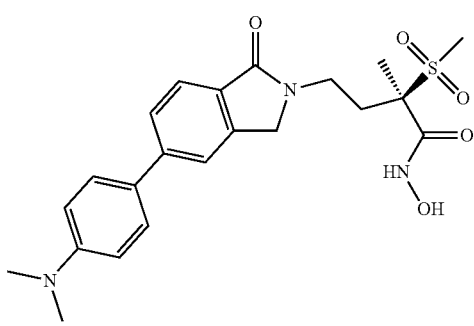 [SMILES: CN(C)c1ccc(-c2ccc3c(c2)CN(CC[C@](C)(C(=O)NO)S(C)(=O)=O)C3=O)cc1]

Part A

Potassium carbonate (90 mg, 0.650 mmol) in water (0.25 mL) was added into a mixture of (2R)-4-(5-bromo-1-oxoisoindolin-2-yl)-2-methyl-2-(methylsulfonyl)-N-(tetrahydro-2H-pyran-2 yl)oxy)butanamide (Intermediate 13) (159 mg, 0.325 mmol), (4-(dimethylamino)phenyl)boronic acid (64.3 mg, 0.390 mmol) and PdCl$_2$(dppf) (47.5 mg, 0.065 mmol) in degassed acetonitrile (1.5 mL) under an atmosphere of nitrogen. The resulting solution was stirred at 80° C. for 30 min. The solvent was removed and the residue was purified by silica gel chromatography (EtOAc/hexanes: 0-100%) to afford (2R)-4-(5-(4-(dimethylamino)phenyl)-1-oxoisoindolin-2-yl)-2-methyl-2-(methylsulfonyl)-N-(tetrahydro-2H-pyran-2-yl)oxy)butanamide (118 mg, 0.223 mmol, 69% yield).

LCMS: [M+H] 530.4.

Part B

To a solution of (2R)-4-(5-(4-(dimethylamino)phenyl)-1-oxoisoindolin-2-yl)-2-methyl-2-(methylsulfonyl)-N-(tetrahydro-2H-pyran-2-yl)oxy)butanamide (118 mg, 0.223 mmol) in dichloromethane (1 mL) and methanol (1 mL) was added a hydrogen chloride (0.223 mL, 0.891 mmol) solution in dioxane (4M). The resulting solution was stirred at room temperature for 1 hr. The solvent was removed and the residue was purified by reverse phase HPLC (5-80% MeCN/H$_2$O, 0.1% TFA) to give (R)-4-(5-(4-(dimethylamino)phenyl)-1-oxoisoindolin-2-yl)-N-hydroxy-2-methyl-2-(methylsulfonyl)butanamide trifluoroacetic acid salt (66 mg, 0.112 mmol, 50% yield).

LCMS: [M+H] 446.3.

$^1$H NMR (DMSO-d$_6$) δ: ppm 10.99 (br. s., 1H), 7.81 (br. s., 1H), 7.55-7.76 (m, 4H), 6.88 (d, J=8.3 Hz, 2H), 4.52 (br. s., 2H), 3.90-4.03 (m, 1H), 3.63 (br. s., 1H), 3.47 (br. s., 1H), 3.09 (br. s., 3H), 2.98 (s, 6H), 2.58-2.70 (m, 1H), 1.98 (br. s., 1H), 1.56 (br. s., 3H).

Example 110. (2R)-4-[5-(2-fluoro-4-{[methoxy(methyl)amino]methyl}phenyl)-1-oxo-2,3-dihydro-1H-isoindol-2-yl]-N-hydroxy-2-methanesulfonyl-2-methylbutanamide

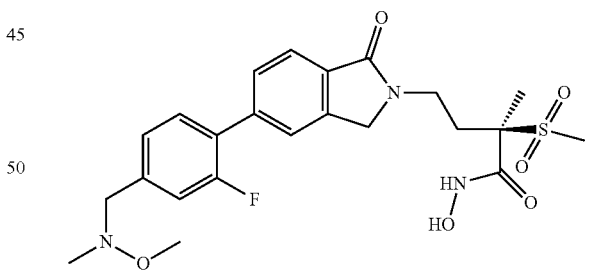

Part A (R)-ethyl 4-(5-bromo-1-oxoisoindolin-2-yl)-2-methyl-2-(methylsulfonyl)butanoate (Intermediate 15) (200 mg, 0.478 mmol), 4,4,4',4',5,5,5',5'-octamethyl-2,2'-bi(1,3,2-dioxaborolane) (182 mg, 0.717 mmol), PdCl$_2$(dppf) (35 mg, 0.048 mmol) and potassium acetate (141 mg, 1.434 mmol) was added to 1,2-dimethoxyethane (3 mL) and the resulting solution was stirred at 80° C. for 3 hr. The reaction was filter through a pad of celite and the solvent was removed. The residue was dissolved in acetonitrile (1.5 mL) and water (0.25 mL) and N-(4-bromo-3-fluorobenzyl)-N,O-dimethylhydroxylamine (178 mg, 0.717 mmol), PdCl$_2$(dppf) (70 mg, 0.096 mmol) and potassium carbonate (132 mg, 0.956 mmol) were added. The resulting solution was stirred at 80° C. for 1 hr. The solvent was removed and the residue was purified by silica gel chromatography (EtOAc/hexanes: 0-100%) to afford (R)-ethyl 4-(5-(2-fluoro-4-(methoxy (methyl)amino)methyl)phenyl)-1-oxoisoindolin-2-yl)-2-methyl-2-(methylsulfonyl)butanoate (231 mg, 0.456 mmol, 95% yield).

LCMS: [M+Na] 507.3.

¹H NMR (METHANOL-d₄) δ: ppm 7.76-7.88 (m, 2H), 7.70 (d, J=7.8 Hz, 1H), 7.47-7.57 (m, 1H), 7.23-7.36 (m, 2H), 4.44-4.68 (m, 2H), 3.80-4.08 (m, 5H), 3.62-3.73 (m, 1H), 3.37-3.44 (m, 3H), 3.06-3.18 (m, 3H), 2.76-2.90 (m, 1H), 2.59-2.70 (m, 3H), 2.16-2.29 (m, 1H), 1.71-1.81 (m, 3H), 1.13-1.21 (m, 3H).

Part B

To a slurry of (R)-ethyl 4-(5-(2-fluoro-4-(methoxy (methyl)amino)methyl)phenyl)-1-oxoisoindolin-2-yl)-2-methyl-2-(methylsulfonyl)butanoate trifluoroacetic acid salt (226 mg, 0.446 mmol), hydroxylamine (4.95 mL, 74.9 mmol) in 1,4-dioxane (3 mL) under nitrogen was added lithium hydroxide (2.472 mL, 2.472 mmol). The reaction mixture was stirred at room temperature for 3 hr. The mixture was concentrated and the residue was purified by reverse phase HPLC (5-70% MeCN/H₂O, 0.1% TFA) to afford (R)-4-(5-(2-fluoro-4-(methoxy(methyl)amino) methyl)phenyl)-1-oxoisoindolin-2-yl)-N-hydroxy-2-methyl-2-(methylsulfonyl)butanamide trifluoroacetic acid salt (129 mg, 0.202 mmol, 45% yield) as a white powder.

LCMS: [M+H] 494.3.

¹H NMR (METHANOL-d₄) δ: ppm 7.85 (d, J=7.8 Hz, 1H), 7.77 (s, 1H), 7.69 (d, J=8.1 Hz, 1H), 7.54 (t, J=8.0 Hz, 1H), 7.23-7.39 (m, 2H), 4.48-4.74 (m, 2H), 3.91-4.01 (m, 2H), 3.78 (t, J=7.3 Hz, 2H), 3.39-3.53 (m, 3H), 3.01-3.18 (m, 3H), 2.77-2.86 (m, 1H), 2.69-2.76 (m, 3H), 2.21 (dt, J=13.6, 6.7 Hz, 1H), 1.65-1.81 (m, 3H).

Example 111. (2R)-4-[4-fluoro-5-(4-methoxyphenyl)-1-oxo-2,3-dihydro-1H-isoindol-2-yl]-N-hydroxy-2-methanesulfonyl-2-methylbutanamide

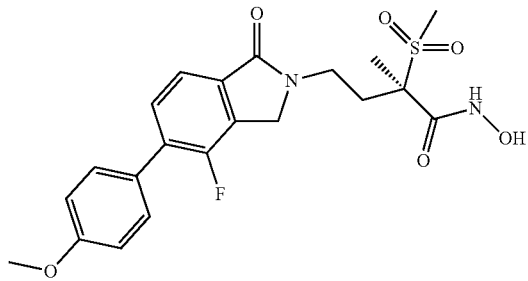 [SMILES: COc1ccc(-c2ccc3c(c2F)CN(CC[C@](C)(C(=O)NO)S(C)(=O)=O)C3=O)cc1]

Part A

PdCl₂(dppf) (54.1 mg, 0.074 mmol) was added to a solution of (4-methoxyphenyl)boronic acid (82 mg, 0.542 mmol), (2R)-4-(5-bromo-4-fluoro-1-oxoisoindolin-2-yl)-2-methyl-2-(methylsulfonyl)-N-(tetrahydro-2H-pyran-2-yl) oxy)butanamide (Intermediate 16) (250 mg, 0.493 mmol) and K₂CO₃ (136 mg, 0.985 mmol) in acetonitrile (6.00 mL) and water (1 mL) at room temperature under nitrogen. The resulting solution was stirred at 80° C. for 30 min. The reaction was combined with another batch and was diluted with ethyl acetate (50 mL) and dried over Na₂SO₄. The solvent was evaporated and the residue was purified by silica gel chromatography (EtOAc/petroleum ether: 25-100%) to afford (2R)-4-(4-fluoro-5-(4-methoxyphenyl)-1-oxoisoindolin-2-yl)-2-methyl-2-(methylsulfonyl)-N-(tetrahydro-2H-pyran-2-yl)oxy)butanamide (210 mg, 66%) as a brown oil.

LCMS: [M-83] 451.0.

Part B

To a solution of (2R)-4-(4-fluoro-5-(4-methoxyphenyl)-1-oxoisoindolin-2-yl)-2-methyl-2-(methylsulfonyl)-N-(tetrahydro-2H-pyran-2-yl)oxy)butanamide (210 mg, 0.393 mmol) in dichloromethane (4 mL) was added a 4M solution of HCl in dioxane (2 mL, 8.00 mmol). The resulting solution was stirred at 20° C. for 1 hr when methanol (2 mL) was added. The reaction was stirred additional 1 hr. The solution was combined with another batch and was concentrated and the residue was purified by reverse phase HPLC to give (R)-4-(4-fluoro-5-(4-methoxyphenyl)-1-oxoisoindolin-2-yl)-N-hydroxy-2-methyl-2-(methylsulfonyl)butanamide (60 mg, 0.128 mmol, 33% yield) as a white solid.

LCMS [M+H] 451.1.

¹H NMR (500 MHz, DMSO-d6): δ ppm 10.95 (s, 1H), 9.15 (s, 1H), 7.62 (m, 1H), 7.57-7.55 (m, 3H), 7.08 (d, J=8.5 Hz, 2H), 4.63 (m, 2H), 3.82 (s, 3H), 3.61 (m, 1H), 3.53 (m, 1H), 3.08 (s, 3H), 2.64 (m, 1H), 2.01 (m, 1H), 1.57 (s, 3H).

Example 112. (2R)-4-[4-fluoro-5-(4-methylphenyl)-1-oxo-2,3-dihydro-1H-isoindol-2-yl]-N-hydroxy-2-methanesulfonyl-2-methylbutanamide

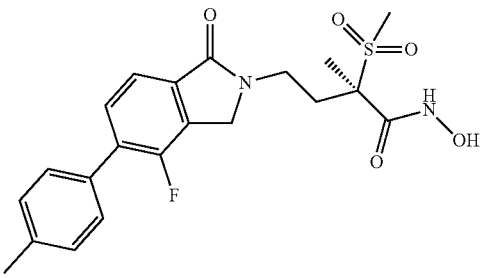 [SMILES: Cc1ccc(-c2ccc3c(c2F)CN(CC[C@](C)(C(=O)NO)S(C)(=O)=O)C3=O)cc1]

Part A

PdCl₂(dppf) (54.1 mg, 0.074 mmol) was added to a solution of p-tolylboronic acid (73.7 mg, 0.542 mmol), (2R)-4-(5-bromo-4-fluoro-1-oxoisoindolin-2-yl)-2-methyl-2-(methylsulfonyl)-N-(tetrahydro-2H-pyran-2-yl)oxy)butanamide (Intermediate 16) (250 mg, 0.493 mmol) and K₂CO₃ (136 mg, 0.985 mmol) in acetonitrile (6 mL) and water (1 mL) under an atmosphere of nitrogen. The resulting solution was stirred at 80° C. for 30 min. The reaction mixture was combined with another batch and was diluted with ethyl acetate (50 mL) and dried over Na₂SO₄. The solvent was evaporated and the residue was purified by silica gel chromatography (EtOAc/petroleum ether: 25-100%) to afford (2R)-4-(4-fluoro-1-oxo-5-(p-tolyl)isoindolin-2-yl)-2-methyl-2-(methylsulfonyl)-N-(tetrahydro-2H-pyran-2-yl) oxy)butanamide (200 mg, 54%) as a brown oil.

LCMS: [M+H] 435.0.

Part B

To a solution of (2R)-4-(4-fluoro-1-oxo-5-(p-tolyl)isoindolin-2-yl)-2-methyl-2-(methylsulfonyl)-N-(tetrahydro-2H-pyran-2-yl)oxy)butanamide (200 mg, 0.386 mmol) in dichloromethane (4 mL), was added a 4M solution of HCl in dioxane (2 mL, 8 mmol). The resulting solution was stirred at 20° C. for 1 hr when methanol (2 mL) was added and stirred an additional 1 hr. The solution was concentrated and the residue was purified by reverse phase HPLC to give (R)-4-(4-fluoro-1-oxo-5-(p-tolyl)isoindolin-2-yl)-N-hydroxy-2-methyl-2-(methylsulfonyl)butanamide (60 mg, 0.138 mmol, 36% yield) as an off-white solid.

LCMS: [M+H] 435.2.

$^1$H NMR (500 MHz, DMSO-$d_6$): δ ppm 10.95 (s, 1H), 7.64-7.575 (m, 2H), 7.50 (d, J=7.0 Hz, 2H), 7.33 (d, J=8.0 Hz, 2H), 4.63 (m, 2H), 3.62 (m, 1H), 3.53 (m, 1H), 3.08 (s, 3H), 2.64 (m, 1H), 2.37 (s, 3H), 2.00 (m, 1H), 1.57 (s, 3H).

Example 113. (2R)-4-[6-fluoro-5-(4-methylphenyl)-1-oxo-2,3-dihydro-1H-isoindol-2-yl]-N-hydroxy-2-methanesulfonyl-2-methylbutanamide

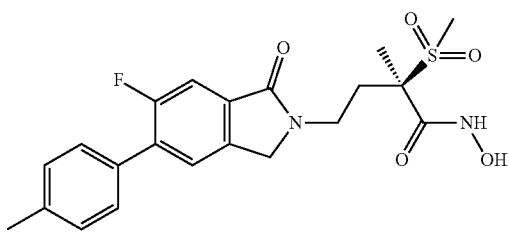 [SMILES: Cc1ccc(-c2cc3c(cc2F)C(=O)N(CC[C@](C)(C(=O)NO)S(C)(=O)=O)C3)cc1]

Part A

A solution of (2R)-4-(5-bromo-6-fluoro-1-oxoisoindolin-2-yl)-2-methyl-2-(methylsulfonyl)-N-(tetrahydro-2H-pyran-2-yl)oxy)butanamide (Intermediate 17) (350 mg, 0.690 mmol) in acetonitrile (12 mL) and water (2.000 mL) was added p-tolylboronic acid (113 mg, 0.828 mmol), PdCl$_2$(dppf)-CH$_2$Cl$_2$ adduct (56.3 mg, 0.069 mmol) and K$_2$CO$_3$ (191 mg, 1.380 mmol). The mixture was heated to 80° C. under nitrogen and stirred for 2 hr. The mixture was concentrated and water (30 mL) was added. The aqueous layer was extracted with AcOEt (30 mL×3), dried over Na$_2$SO$_4$ abd concentrated. The residue was purified by silica gel chromatography (ethyl acetate/petroleum ether: 1/5-2/1) to afford (2R)-4-(6-fluoro-1-oxo-5-(p-tolyl)isoindolin-2-yl)-2-methyl-2-(methylsulfonyl)-N-((tetrahydro-2H-pyran-2-yl)oxy)butanamide (220 mg, 0.402 mmol, 58% yield) as a yellow solid.

LCMS: [M+H] 435.

Part B

A solution of (2R)-4-(6-fluoro-1-oxo-5-(p-tolyl)isoindolin-2-yl)-2-methyl-2-(methylsulfonyl)-N-((tetrahydro-2H-pyran-2-yl)oxy)butanamide (200 mg, 0.386 mmol) in dichloromethane (5 mL) and methanol (5 mL) was added HCl (1 mL, 4 mmol) and the mixture was stirred at for 2 hr. The reaction was concentrated and the residue was washed with acetonitrile/ether (1/2) to afford (R)-4-(6-fluoro-1-oxo-5-(p-tolyl)isoindolin-2-yl)-N-hydroxy-2-methyl-2-(methylsulfonyl)butanamide (114 mg, 0.260 mmol, 67% yield) as a white solid.

LCMS: [M+H] 435.

$^1$H NMR (500 MHz, DMSO-$d_6$) δ: ppm 10.76 (s, 1H), 9.16 (s, 1H), 7.73 (d, J=6.5 Hz, 1H), 7.53 (d, J=9.5 Hz, 1H), 7.48 (d, J=6.5 Hz, 2H), 7.33 (d, J=8.0 Hz, 2H), 4.52 (s, 2H), 3.62 (m, 1H), 3.51 (m, 1H), 3.07 (s, 3H), 2.61 (m, 1H), 2.37 (s, 3H), 1.98 (m, 1H), 1.57 (s, 3H).

Example 114. (2R)-4-[6-fluoro-5-(4-methoxyphenyl)-1-oxo-2,3-dihydro-1H-isoindol-2-yl]-N-hydroxy-2-methanesulfonyl-2-methylbutanamide

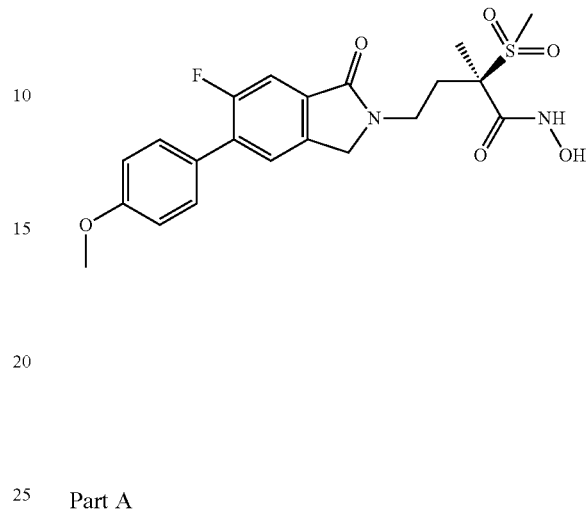

Part A

A solution of (2R)-4-(5-bromo-6-fluoro-1-oxoisoindolin-2-yl)-2-methyl-2-(methylsulfonyl)-N-(tetrahydro-2H-pyran-2-yl)oxy)butanamide (Intermediate 17) (350 mg, 0.690 mmol) in acetonitrile (12 mL) and water (2 mL) was added (4-methoxyphenyl)boronic acid (126 mg, 0.828 mmol), PdCl$_2$(dppf)-CH$_2$Cl$_2$ adduct (56.3 mg, 0.069 mmol) and K$_2$CO$_3$ (191 mg, 1.380 mmol). The mixture was heated to 80° C. under N$_2$ and stirred for 2 hr. The mixture was concentrated and water (30 mL) was added, extracted with ethyl acetate (30 mL×3), dried over Na$_2$SO$_4$ and concentrated. The residue was purified by silica gel chromatography (ethyl acetate/petroleum ether: 1/5-2/1) to afford (2R)-4-(6-fluoro-5-(4-methoxyphenyl)-1-oxoisoindolin-2-yl)-2-methyl-2-(methylsulfonyl)-N-(tetrahydro-2H-pyran-2-yl)oxy)butanamide (220 mg, 0.385 mmol, 56% yield) as a yellow solid.

LCMS: [M-THP] 451.

Part B

A solution of (2R)-4-(6-fluoro-5-(4-methoxyphenyl)-1-oxoisoindolin-2-yl)-2-methyl-2-(methylsulfonyl)-N-(tetrahydro-2H-pyran-2-yl)oxy)butanamide (200 mg, 0.374 mmol) in dichloromethane (5 mL) and methanol (5 mL) was added HCl (1 mL, 4.00 mmol) and the mixture was stirred for 2 hr. The mixture was concentrated and the residue was washed with acetonitrile/ether (1/2) to afford (R)-4-(6-fluoro-5-(4-methoxyphenyl)-1-oxoisoindolin-2-yl)-N-hydroxy-2-methyl-2-(methylsulfonyl)butanamide (125 mg, 0.277 mmol, 74% yield) as a white solid.

LCMS: [M+H] 451.

$^1$H NMR (500 MHz, DMSO-$d_6$) δ: ppm 10.96 (s, 1H), 9.16 (s, 1H), 7.72 (d, J=6.5 Hz, 1H), 7.50-7.55 (m, 3H), 7.08 (d, J=9.0 Hz, 2H), 4.52 (s, 2H), 3.82 (s, 3H), 3.62 (m, 1H), 3.49 (m, 1H), 3.08 (s, 3H), 2.61 (m, 1H), 1.99 (m, 1H), 1.57 (s, 3H).

Example 115. (2R)-4-(4-fluoro-5-{4-[2-(morpholin-4-yl)ethyl]phenyl}-1-oxo-2,3-dihydro-1H-isoindol-2-yl)-N-hydroxy-2-methanesulfonyl-2-methylbutanamide

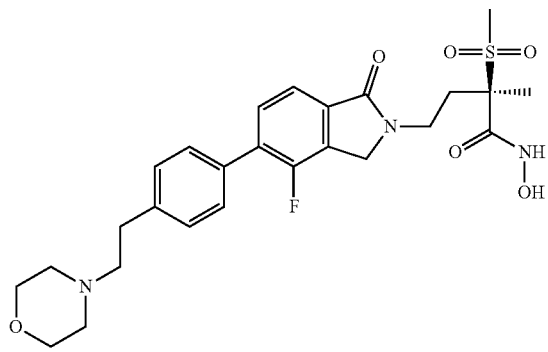 [SMILES: C[C@@](CCN1Cc2c(ccc(-c3ccc(CCN4CCOCC4)cc3)c2F)C1=O)(C(=O)NO)S(C)(=O)=O]

Part A

PdCl$_2$(dppf)-CH$_2$Cl$_2$ adduct (0.406 g, 0.497 mmol) was added to a solution of 2-(4-bromophenyl)ethanol (1 g, 4.97 mmol), potassium acetate (0.976 g, 9.95 mmol) and 4,4,4',4',5,5,5',5'-octamethyl-2,2'-bi(1,3,2-dioxaborolane) (1.263 g, 4.97 mmol) in DMSO (10 mL) under a nitrogen atmosphere and was stirred at 120° C. for 3 hr. The mixture was concentrated under reduced pressure and the residue was purified by silica gel chromatography (AcOEt/petroleum ether: 1/3) to give 2-(4-(4,4,5,5-tetramethyl-1,3,2-dioxaborolan-2-yl)phenyl)ethanol (740 mg, 2.446 mmol, 49% yield) as a yellow oil.

LCMS: [M+H] 249.2.

Part B

PdCl$_2$(dppf) (0.288 g, 0.394 mmol) was added to a solution of 2-(4-(4,4,5,5-tetramethyl-1,3,2-dioxaborolan-2-yl)phenyl)ethanol (1.467 g, 5.91 mmol), (2R)-4-(5-bromo-4-fluoro-1-oxoisoindolin-2-yl)-2-methyl-2-(methylsulfonyl)-N-(tetrahydro-2H-pyran-2-yl)oxy)butanamide (Intermediate 16) (2.0 g, 3.94 mmol) and K$_2$CO$_3$ (1.09 g, 7.88 mmol) in acetonitrile (5 mL) and water (1 mL) under a nitrogen atmosphere and stirred at 80° C. for 30 min. The reaction was combined with another batch and was washed with water (20 mL), brine (20 mL), dried over Na$_2$SO$_4$, filtered and concentrated. The crude was purified by silica gel chromatography (petroleum ether/AcOEt: 1/1-0/1) to give (2R)-4-(4-fluoro-5-(4-(2-hydroxyethyl)phenyl)-1-oxoisoindolin-2-yl)-2-methyl-2-(methylsulfonyl)-N-(tetrahydro-2H-pyran-2-yl)oxy)butanamide (2.11 g, 3.41 mmol, 87% yield).

LCMS: [M+H] 503.3.

Part C

To a mixture of (2R)-4-(4-fluoro-5-(4-(2-hydroxyethyl)phenyl)-1-oxoisoindolin-2-yl)-2-methyl-2-(methylsulfonyl)-N-(tetrahydro-2H-pyran-2-yl)oxy)butanamide (300 mg, 0.547 mmol) in dichloromethane (7.5 mL) was added triphenylphosphine (574 mg, 2.187 mmol) and 1-bromopyrrolidine-2,5-dione (292 mg, 1.640 mmol) at 0° C. The resulting mixture was stirred at 0° C. for 45 min. Methanol (7.5 mL) was added at 0° C. and the reaction mixture was concentrated to afford (R)-4-(5-(4-(2-bromoethyl)phenyl)-4-fluoro-1-oxoisoindolin-2-yl)-N-hydroxy-2-methyl-2-(methylsulfonyl)butanamide (653 mg, 0.547 mmol, 100% yield) as a yellow oil.

LCMS: [M+H] 527.0.

Part D

A mixture of (R)-4-(5-(4-(2-bromoethyl)phenyl)-4-fluoro-1-oxoisoindolin-2-yl)-N-hydroxy-2-methyl-2-(methylsulfonyl)butanamide (656 mg, 0.547 mmol), morpholine (477 mg, 5.47 mmol), KI (9.08 mg, 0.055 mmol) and N,N-dimethylformamide (5.5 mL) was heated in microwave at 70° C. for 10 min. The mixture was concentrated and the residue was purified by reverse phase HPLC (CH$_3$CN/H$_2$O, 0.1% TFA) to yield (R)-4-(4-fluoro-5-(4-(2-morpholinoethyl)phenyl)-1-oxoisoindolin-2-yl)-N-hydroxy-2-methyl-2-(methylsulfonyl)butanamide trifluoroacetic acid salt (75 mg, 0.114 mmol, 21% yield) as an off-white solid.

LCMS: [M+H] 534.2.

$^1$H NMR (500 MHz, METHANOL-d4) δ: ppm 7.62-7.68 (m, 4H), 7.47 (d, J=8.0 Hz, 2H), 4.67 (dd, J=45.0, 17.5 Hz, 2H), 4.02-4.15 (m, 2H), 3.72-3.89 (m, 4H), 3.38-3.65 (m, 5H), 3.25 (m, 1H), 3.17 (m, 2H), 3.10 (s, 3H), 2.84 (m, 1H), 2.20 (m, 1H), 1.75 (s, 3H).

Example 116. (2R)-4-[4-fluoro-5-(3-fluoro-4-methylphenyl)-1-oxo-2,3-dihydro-1H-isoindol-2-yl]-N-hydroxy-2-methanesulfonyl-2-methylbutanamide

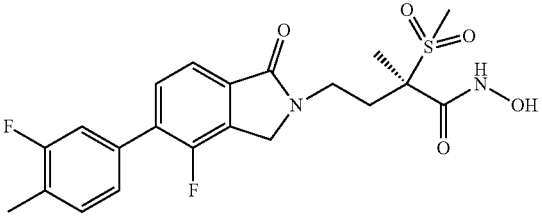 [SMILES: Cc1ccc(-c2ccc3c(c2F)CN(CC[C@](C)(C(=O)NO)S(C)(=O)=O)C3=O)cc1F]

Part A

PdCl$_2$(dppf) (0.361 g, 0.493 mmol) was added to a solution of (3-fluoro-4-methylphenyl)boronic acid (0.910 g, 5.91 mmol), (2R)-4-(5-bromo-4-fluoro-1-oxoisoindolin-2-yl)-2-methyl-2-(methylsulfonyl)-N-(tetrahydro-2H-pyran-2-yl)oxy)butanamide (Intermediate 16) (2.5 g, 4.93 mmol) and K$_2$CO$_3$ (1.362 g, 9.85 mmol) in acetonitrile (15 mL) and water (2 mL) under a nitrogen atmosphere. The resulting solution was stirred at 80° C. for 30 min. The reaction mixture was concentrated and the residue was purified by silica gel chromatography (EtOH/DCM: 1:50) to give (2R)-4-(4-fluoro-5-(3-fluoro-4-methylphenyl)-1-oxoisoindolin-2-yl)-2-methyl-2-(methylsulfonyl)-N-(tetrahydro-2H-pyran-2-yl)oxy)butanamide (2.2 g, 3.61 mmol, 73% yield) as a brown solid.

LCMS: [M+H] 559.2.

Part B

To a solution of (2R)-4-(4-fluoro-5-(3-fluoro-4-methylphenyl)-1-oxoisoindolin-2-yl)-2-methyl-2-(methylsulfonyl)-N-(tetrahydro-2H-pyran-2-yl)oxy)butanamide (1.8 g, 3.35 mmol) in dichloromethane (20 mL) was added HCl (4.19 mL, 16.77 mmol) in dioxane. The resulting solution was stirred at 20° C. for 5 min when methanol (20 mL) was added. The resulting mixture was stirred at 25° C. for 1 hr and concentrated. The crude was purified by triturating with acetone to give (R)-4-(4-fluoro-5-(3-fluoro-4-methylphenyl)-1-oxoisoindolin-2-yl)-N-hydroxy-2-methyl-2-(methylsulfonyl)butanamide (700 mg, 1.547 mmol, 46% yield) as a white solid.

LCMS: [M+H] 453.2.

$^1$H NMR (500 MHz, DMSO-d$_6$) δ: ppm 10.96 (s, 1H), 9.16 (brs, 1H), 7.67 (m, 1H), 7.59 (d, J=7.5 Hz, 1H), 7.35-7.45 (m, 3H), 4.64 (s, 2H), 3.62 (m, 1H), 3.53 (m, 1H), 3.08 (s, 3H), 2.63 (m, 1H), 2.30 (s, 3H), 2.00 (m, 1H), 1.56 (s, 3H).

Example 117. (2R)-4-[4-fluoro-5-(2-fluorophenyl)-1-oxo-2,3-dihydro-1H-isoindol-2-yl]-N-hydroxy-2-methanesulfonyl-2-methylbutanamide

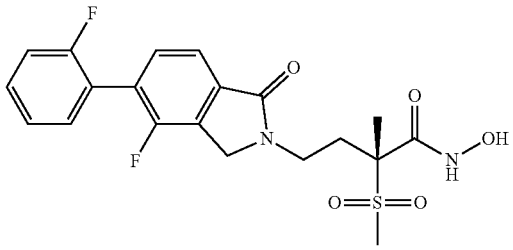 [SMILES: C[C@@](CCN1Cc2c(ccc(-c3ccccc3F)c2F)C1=O)(C(=O)NO)S(C)(=O)=O]

PdCl$_2$(dppf) (36.1 mg, 0.049 mmol) was added to a solution of (2-fluorophenyl)boronic acid (83 mg, 0.591 mmol), (2R)-4-(5-bromo-4-fluoro-1-oxoisoindolin-2-yl)-2-methyl-2-(methylsulfonyl)-N-(tetrahydro-2H-pyran-2-yl)oxy)butanamide (Intermediate 16) (250 mg, 0.493 mmol) and K$_2$CO$_3$ (136 mg, 0.985 mmol) in acetonitrile (12.0 mL) and water (2.0 mL) under a nitrogen atmosphere. The resulting solution was stirred at 80° C. for 30 min. The reaction mixture combined with another batch and was concentrated under reduced pressure. The residue was purified by silica gel chromatography (EtOH/DCM: 1:50) to give (2R)-4-(4-fluoro-5-(2-fluorophenyl)-1-oxoisoindolin-2-yl)-2-methyl-2-(methylsulfonyl)-N-(tetrahydro-2H-pyran-2-yl)oxy)butanamide (200 mg, 0.383 mmol, 78% yield) as a brown oil.

LCMS: [M+Na] 545.1.

Part B

To a stirred solution of (2R)-4-(4-fluoro-5-(2-fluorophenyl)-1-oxoisoindolin-2-yl)-2-methyl-2-(methylsulfonyl)-N-(tetrahydro-2H-pyran-2-yl)oxy)butanamide (180 mg, 0.344 mmol) in methanol (6 mL) and dichloromethane (6 mL) was added a solution of HCl (4.31 mL, 17.22 mmol) in 1,4-dioxane and was stirred for 1 hr. The mixture was combined with another batch and was concentrated under reduced pressure. The residue was purified by reverse phase HPLC to give (R)-4-(4-fluoro-5-(2-fluorophenyl)-1-oxoisoindolin-2-yl)-N-hydroxy-2-methyl-2-(methylsulfonyl)butanamide (90 mg, 0.205 mmol, 60% yield) as a white solid.

LCMS: [M+H] 439.1.

$^1$H NMR (500 MHz, DMSO-d$_6$): δ: ppm 10.95 (d, J=2.0 Hz, 1H), 9.15 (d, J=1.5 Hz, 1H), 7.62 (d, J=8.0 Hz, 1H), 7.66-7.50 (m, 3H), 7.40-7.35 (m, 2H), 4.70-4.62 (m, 2H), 3.66-3.61 (m, 1H), 3.55-3.49 (m, 1H), 3.08 (s, 3H), 2.67-2.61 (m, 1H), 2.04-1.98 (m, 1H), 1.57 (s, 3H).

Example 118. (2R)-4-[5-(2H-1,3-benzodioxol-5-yl)-4-fluoro-1-oxo-2,3-dihydro-1H-isoindol-2-yl]-N-hydroxy-2-methanesulfonyl-2-methylbutanamide

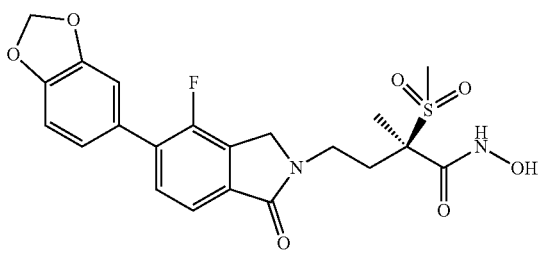 [SMILES: C[C@@](CCN1Cc2c(ccc(-c3ccc4c(c3)OCO4)c2F)C1=O)(C(=O)NO)S(C)(=O)=O]

Part A

PdCl$_2$(dppf) (36.1 mg, 0.049 mmol) was added to a solution of benzo[d][1,3]dioxol-5-ylboronic acid (106 mg, 0.641 mmol), (2R)-4-(5-bromo-4-fluoro-1-oxoisoindolin-2-yl)-2-methyl-2-(methylsulfonyl)-N-(tetrahydro-2H-pyran-2-yl)oxy)butanamide (Intermediate 16) (250 mg, 0.493 mmol) and K$_2$CO3 (136 mg, 0.985 mmol) in acetonitrile (6 mL) and water (1 mL) under a nitrogen atmosphere. The resulting mixture was stirred at 80° C. for 30 min. The reaction mixture was combined with another batch and was filtered and diluted with ethyl acetate (50 mL). The organic layer was washed with water (20 mL), brine (20 mL), dried over Na$_2$SO$_4$ and evaporated. The crude product was purified by silica gel chromatography (petroleum ether/AcOEt: 1/1-0/1) to afford (2R)-4-(5-(benzo[d][1,3]dioxol-5-yl)-4-fluoro-1-oxoisoindolin-2-yl)-2-methyl-2-(methylsulfonyl)-N-(tetrahydro-2H-pyran-2-yl)oxy)butanamide (200 mg, 0.365 mmol, 74% yield).

LCMS: [M+Na] 572.2.

Part B

To a solution of (2R)-4-(5-(benzo[d][1,3]dioxol-5-yl)-4-fluoro-1-oxoisoindolin-2-yl)-2-methyl-2-(methylsulfonyl)-N-(tetrahydro-2H-pyran-2-yl)oxy)butanamide (150 mg, 0.273 mmol) in dichloromethane (5 mL) was added HCl (0.342 mL, 1.367 mmol) in dioxane. The resulting solution was stirred at 20° C. for 5 min and methanol (5 mL) was added, The resulting mixture was stirred at 25° C. for 1 hr. The mixture was combined with another batch, was concentrated and the residue was purified by reverse phase HPLC to give (R)-4-(5-(benzo[d][1,3]dioxol-5-yl)-4-fluoro-1-oxoisoindolin-2-yl)-N-hydroxy-2-methyl-2-(methylsulfonyl)butanamide (20 mg, 0.043 mmol, 16% yield) as a white solid LCMS: [M+H] 465.2.

$^1$H NMR (500 MHz, DMSO-d$_6$) δ: ppm 10.95 (s, 1H), 9.15 (s, 1H), 7.61 (m, 1H), 7.55 (d, J=7.5 Hz, 1H), 7.17 (s, 1H), 7.05-7.10 (m, 2H), 6.10 (s, 2H), 4.62 (s, 2H), 3.61 (m, 1H), 3.52 (m, 1H), 3.07 (s, 3H), 2.62 (m, 1H), 1.99 (m, 1H), 1.56 (s, 3H).

Example 119. (2R)-4-{4-fluoro-5-[4-(methoxymethyl)phenyl]-1-oxo-2,3-dihydro-1H-isoindol-2-yl}-N-hydroxy-2-methanesulfonyl-2-methylbutanamide

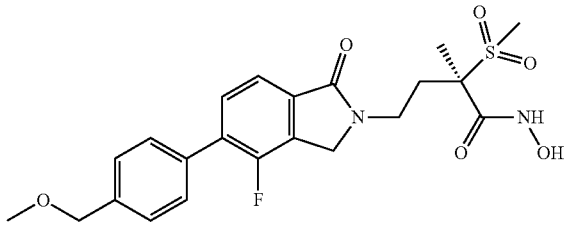 [SMILES: COCc1ccc(-c2ccc3c(c2F)CN(CC[C@](C)(C(=O)NO)S(C)(=O)=O)C3=O)cc1]

Part A

To a solution of 1-bromo-4-(methoxymethyl)benzene (500 mg, 2.487 mmol) in 1,4-dioxane (50 mL) was added 4,4,4',4',5,5,5',5'-octamethyl-2,2'-bi(1,3,2-dioxaborolane) (947 mg, 3.73 mmol), PdCl$_2$(dppf)-CH$_2$Cl$_2$ adduct (203 mg, 0.249 mmol) and potassium acetate (488 mg, 4.97 mmol). The reaction mixture was heated to 100° C. under N$_2$ and stirred overnight. The mixture was evaporated, water (50 mL) was added, and the aqueous layer was extracted with ethyl acetate (3×50 mL). The combined organic layers were dried over Na$_2$SO$_4$ and concentrated. The residue was purified with silica gel chromatography (ethyl acetate/petroleum ether: 0-1/40) to afford 2-(4-(methoxymethyl)phenyl)-4,4,5,5-tetramethyl-1,3,2-dioxaborolane (420 mg, 1.523 mmol, 61% yield) as a colourless oil.

Part B

To a solution of (2R)-4-(5-bromo-4-fluoro-1-oxoisoindolin-2-yl)-2-methyl-2-(methylsulfonyl)-N-(tetrahydro-2H-pyran-2-yl)oxy)butanamide (Intermediate 16) (654 mg, 1.29 mmol) in acetonitrile (6 mL) and water (1 mL) was added 2-(4-(methoxymethyl)phenyl)-4,4,5,5-tetramethyl-1,3,2-dioxaborolane (400 mg, 1.612 mmol), $PdCl_2(dppf)-CH_2Cl_2$ adduct (132 mg, 0.161 mmol) and $K_2CO_3$ (446 mg, 3.22 mmol) under nitrogen. The mixture was heated to 80° C. for 2 hr. The mixture was concentrated, water (20 mL) was added and the aqueous layer was extracted with ethyl acetate (20 mL×3), stirred over $Na_2SO_4$, and evaporated. The residue was purified by silica gel chromatography (ethyl acetate/petroleum ether: 1/2-2/1) to afford (2R)-4-(4-fluoro-5-(4-(methoxymethyl)phenyl)-1-oxoisoindolin-2-yl)-2-methyl-2-(methylsulfonyl)-N-(tetrahydro-2H-pyran-2-yl)oxy)butanamide (500 mg, 0.880 mmol, 55% yield) as a yellow solid.

LCMS: [M+H] 572.3.

Part C

A solution of (2R)-4-(4-fluoro-5-(4-(methoxymethyl)phenyl)-1-oxoisoindolin-2-yl)-2-methyl-2-(methylsulfonyl)-N-(tetrahydro-2H-pyran-2-yl)oxy)butanamide (2.27 g, 4.14 mmol) in dichloromethane (30 mL) and methanol (30.0 mL) was added HCl (10 mL, 40.0 mmol) and the mixture was stirred for 2 hr. The reaction was concentrated and to the residue was added acetone (20 mL). The mixture was filtered and washed with acetone (5 mL×2) and dried to afford (R)-4-(4-fluoro-5-(4-(methoxymethyl)phenyl)-1-oxoisoindolin-2-yl)-N-hydroxy-2-methyl-2-(methylsulfonyl) butanamide (920 mg, 1.943 mmol, 47% yield) as a white solid.

LCMS: [M+H] 465.2.

$^1$H NMR (500 MHz, DMSO-$d_6$) δ: ppm 10.96 (s, 1H), 9.17 (s, 1H), 7.65 (m, 1H), 7.59-7.60 (m, 3H), 7.46 (d, J=8.5 Hz, 2H), 4.64 (s, 2H), 4.49 (s, 2H), 3.64 (m, 1H), 3.52 (m, 1H), 3.33 (s, 3H), 3.08 (s, 3H), 2.64 (m, 1H), 2.00 (m, 1H), 1.57 (s, 3H).

Example 120. (2R)-4-[4-fluoro-5-(3-fluoro-4-methoxyphenyl)-1-oxo-2,3-dihydro-1H-isoindol-2-yl]-N-hydroxy-2-methanesulfonyl-2-methylbutanamide

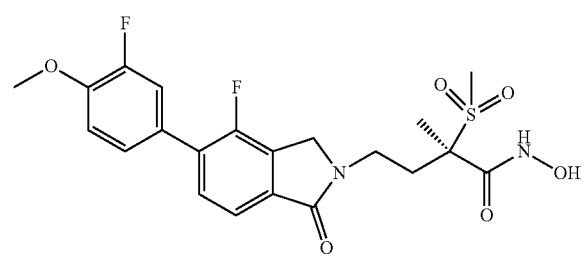 [SMILES: COc1ccc(-c2ccc3c(c2F)CN(CC[C@](C)(C(=O)NO)S(C)(=O)=O)C3=O)cc1F]

Part A $PdCl_2(dppf)$ (36.1 mg, 0.049 mmol) was added to a solution of (3-fluoro-4-methoxyphenyl)boronic acid (100 mg, 0.591 mmol), (2R)-4-(5-bromo-4-fluoro-1-oxoisoindolin-2-yl)-2-methyl-2-(methylsulfonyl)-N-(tetrahydro-2H-pyran-2-yl)oxy)butanamide (Intermediate 16) (250 mg, 0.493 mmol) and $K_2CO_3$ (136 mg, 0.985 mmol) in acetonitrile (8 mL) and water (1 mL) under a nitrogen atmosphere. The resulting solution was stirred at 80° C. for 30 min. The reaction mixture was concentrated and the residue was purified by silica gel chromatography (EtOH/DCM: 1/50) to give (2R)-4-(4-fluoro-5-(3-fluoro-4-methoxyphenyl)-1-oxoisoindolin-2-yl)-2-methyl-2-(methylsulfonyl)-N-((tetrahydro-2H-pyran-2-yl)oxy)butanamide (222 mg, 0.277 mmol, 56% yield) as a brown solid.

LCMS: [M+H-THP] 469.2.

Part B

To a solution of (2R)-4-(4-fluoro-5-(3-fluoro-4-methoxyphenyl)-1-oxoisoindolin-2-yl)-2-methyl-2-(methylsulfonyl)-N-(tetrahydro-2H-pyran-2-yl)oxy)butanamide (200 mg, 0.362 mmol) in dichloromethane (5 mL) was added HCl (0.452 mL, 1.810 mmol) in dioxane and the solution was stirred at 20° C. for 5 min. Methanol (5 mL) was added and the resulting mixture was stirred at 25° C. for 1 hr. The mixture was combined with another batch and was concentrated. The residue was purified by reverse phase HPLC to give (R)-4-(4-fluoro-5-(3-fluoro-4-methoxyphenyl)-1-oxoisoindolin-2-yl)-N-hydroxy-2-methyl-2-(methylsulfonyl) butanamide (44 mg, 0.094 mmol, 26% yield) as white solid

LCMS: [M+H-THP] 469.2.

$^1$H NMR (500 MHz, DMSO-$d_6$) δ: ppm 10.96 (s, 1H), 9.16 (s, 1H), 7.66 (m, 1H), 7.58 (d, J=8.0 Hz, 1H), 7.51 (m, 1H), 7.43 (m, 1H), 7.32 (m, 1H), 4.64 (s, 2H), 3.91 (s, 3H), 3.63 (m, 1H), 3.54 (m, 1H), 3.08 (s, 3H), 2.64 (m, 1H), 2.00 (m, 1H), 1.57 (s, 3H).

Example 121. (2R)-4-[4-fluoro-5-(2-fluoro-4-methoxyphenyl)-1-oxo-2,3-dihydro-1H-isoindol-2-yl]-N-hydroxy-2-methanesulfonyl-2-methylbutanamide

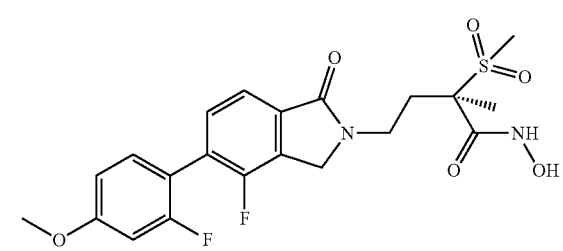 [SMILES: COc1ccc(-c2ccc3c(c2F)CN(CC[C@](C)(C(=O)NO)S(C)(=O)=O)C3=O)c(F)c1]

Part A $PdCl_2(dppf)$ (0.505 g, 0.690 mmol) was added to a solution of (2-fluoro-4-methoxyphenyl)boronic acid (1.524 g, 8.97 mmol), (2R)-4-(5-bromo-4-fluoro-1-oxoisoindolin-2-yl)-2-methyl-2-(methylsulfonyl)-N-(tetrahydro-2H-pyran-2-yl)oxy)butanamide (Intermediate 16) (3.5 g, 6.90 mmol) and $K_2CO_3$ (1.907 g, 13.80 mmol) in acetonitrile (15 mL) and water (3 mL) under a nitrogen atmosphere. The resulting solution was stirred at 80° C. for 30 min and the reaction mixture was concentrated. The residue was purified by silica gel chromatography (acetone/petroleum ether: 1/1) to give (2R)-4-(4-fluoro-5-(2-fluoro-4-methoxyphenyl)-1-oxoisoindolin-2-yl)-2-methyl-2-(methylsulfonyl)-N-(tetrahydro-2H-pyran-2-yl)oxy)butanamide (3.2 g, 5.62 mmol, 81% yield) as a yellow solid.

LCMS: [M+H-THP] 468.9

Part B

A solution of (2R)-4-(4-fluoro-5-(2-fluoro-4-methoxyphenyl)-1-oxoisoindolin-2-yl)-2-methyl-2-(methylsulfonyl)-N-(tetrahydro-2H-pyran-2-yl)oxy)butanamide (3.18 g, 5.75 mmol) in dichloromethane (30 mL) and methanol (30 mL) was added HCl (10 mL, 40 mmol) and the mixture was stirred for 2 hr. The mixture was concentrated and acetone (20 mL) was added and the mixture was filtered. The solid was washed with acetone (5 mL×2) and dried to afford (R)-4-(4-fluoro-5-(2-fluoro-4-methoxyphenyl)-1-oxoisoindolin-2-yl)-N-hydroxy-2-methyl-2-(methylsulfonyl)butanamide (1586 mg, 3.22 mmol, 56% yield) as a white solid.

LCMS: [M+H] 469.2.

$^1$H NMR (500 MHz, DMSO-d$_6$) δ: ppm 10.96 (s, 1H), 9.17 (brs, 1H), 7.60 (d, J=8.0 Hz, 1H), 7.54 (m, 1H), 7.42 (m, 1H), 7.01 (dd, J=12.5, 2.5 Hz, 1H), 6.94 (dd, J=8.0, 2.5 Hz, 1H), 4.64 (s, 2H), 3.84 (s, 3H), 3.62 (m, 1H), 3.52 (m, 1H), 3.08 (s, 3H), 2.63 (m, 1H), 2.00 (m, 1H), 1.57 (s, 3H).

Example 122. (2R)-4-[4-fluoro-1-oxo-5-(4-{2-[(2,2,2-trifluoroethyl)amino]ethyl}phenyl)-2,3-dihydro-1H-isoindol-2-yl]-N-hydroxy-2-methanesulfonyl-2-methylbutanamide

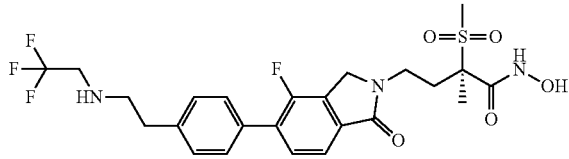 [SMILES: C[C@@](CCN1Cc2c(ccc(-c3ccc(CCNCC(F)(F)F)cc3)c2F)C1=O)(C(=O)NO)S(C)(=O)=O]

Part A

PdCl$_2$(dppf)-CH$_2$Cl$_2$ adduct (4.06 g, 4.97 mmol) was added to a solution of 2-(4-bromophenyl)ethanol (10.0 g, 49.7 mmol), 4,4,4',4',5,5,5',5'-octamethyl-2,2'-bi(1,3,2-dioxaborolane) (25.3 g, 99 mmol) and potassium acetate (14.64 g, 149 mmol) in 1,4-dioxane (200 mL) under a nitrogen atmosphere. The reaction mixture was stirred at 80° C. overnight and the mixture was concentrated. The residue was purified by silica gel chromatography (AcOEt/petroleum ether: 1/6) to give 2-(4-(4,4,5,5-tetramethyl-1,3,2-dioxaborolan-2-yl)phenyl)ethanol (10.5 g, 39.2 mmol, 79% yield) as a yellow oil.

LCMS: [M+NH$_4$] 266.2.

Part B

A mixture of 2-(4-(4,4,5,5-tetramethyl-1,3,2-dioxaborolan-2-yl)phenyl)ethanol (1.467 g, 5.91 mmol), (2R)-4-(5-bromo-4-fluoro-1-oxoisoindolin-2-yl)-2-methyl-2-(methylsulfonyl)-N-(tetrahydro-2H-pyran-2-yl)oxy)butanamide (Intermediate 16) (2.0 g, 3.94 mmol), PdCl$_2$(dppf)-CH$_2$Cl$_2$ adduct (0.322 g, 0.394 mmol) and K$_2$CO$_3$ (1.090 g, 7.88 mmol) in acetonitrile (30 mL) and water (5.00 mL) under a nitrogen atmosphere. The reaction mixture was stirred at 80° C. for 1 hr and the acetonitrile was removed by evaporation. The aqueous layer was extracted with DCM (50 mL×2) and the combined organic layers were dried over Na$_2$SO$_4$, filtered and concentrated. The crude product was purified by silica gel chromatography (MeOH/DCM: 0-2.5%) to (2R)-4-(4-fluoro-5-(4-(2-hydroxyethyl)phenyl)-1-oxoisoindolin-2-yl)-2-methyl-2-(methylsulfonyl)-N-((tetrahydro-2H-pyran-2-yl)oxy)butanamide (1.8 g, 3.12 mmol, 79% yield) as a yellow solid.

LCMS: [M+Na] 571.2.

Part C

To a mixture of (2R)-4-(4-fluoro-5-(4-(2-hydroxyethyl)phenyl)-1-oxoisoindolin-2-yl)-2-methyl-2-(methylsulfonyl)-N-(tetrahydro-2H-pyran-2-yl)oxy)butanamide (900 mg, 1.640 mmol) in dichloromethane (22.5 mL) was added triphenylphosphine (1721 mg, 6.56 mmol) and 1-bromopyrrolidine-2,5-dione (876 mg, 4.92 mmol) at 0° C. The resulting mixture was stirred for 45 min when MeOH (22.5 mL) was added at 0° C. The mixture was evaporated to dryness to yield the crude (R)-4-(5-(4-(2-bromoethyl)phenyl)-4-fluoro-1-oxoisoindolin-2-yl)-N-hydroxy-2-methyl-2-(methylsulfonyl)butanamide (1507 mg, 1.64 mmol, 100% yield).

LCMS: [M+H] 527.1, 529.1.

Part D

A mixture of (R)-4-(5-(4-(2-bromoethyl)phenyl)-4-fluoro-1-oxoisoindolin-2-yl)-N-hydroxy-2-methyl-2-(methylsulfonyl)butanamide (460 mg, 0.5 mmol), 2,2,2-trifluoroethanamine (495 mg, 5 mmol), KI (8.30 mg, 0.05 mmol) and N,N-dimethylformamide (5 mL) was heated in a microwave at 70° C. for 20 min. The mixture was concentrated and the residue was purified by preparative HPLC to yield (R)-4-(4-fluoro-1-oxo-5-(4-(2-(2,2,2-trifluoroethyl)amino)ethyl)phenyl)isoindolin-2-yl)-N-hydroxy-2-methyl-2-(methylsulfonyl)butanamide trifluoroacetic acid salt (82 mg, 0.118 mmol, 24% yield).

LCMS: [M+H] 546.2.

$^1$H NMR (500 MHz, METHANOL-d4) δ: ppm 7.62-7.68 (m, 4H), 7.45 (d, J=8.0 Hz, 2H), 4.67 (dd, J=46.5, 17.5 Hz, 2H), 4.07 (dd, J=18.0, 9.0 Hz, 2H), 3.86 (m, 1H), 3.76 (m, 1H), 3.42 (m, 2H), 3.12 (m, 2H), 3.10 (s, 3H), 2.85 (m, 1H), 2.19 (m, 1H), 1.74 (s, 3H).

Example 123. (2R)-4-[4-fluoro-5-(4-{2-[methoxy(methyl)amino]ethyl}phenyl)-1-oxo-2,3-dihydro-1H-isoindol-2-yl]-N-hydroxy-2-methanesulfonyl-2-methylbutanamide

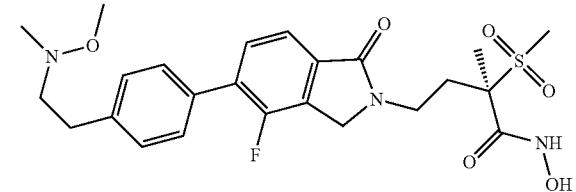 [SMILES: CON(C)CCc1ccc(-c2ccc3c(c2F)CN(CC[C@](C)(C(=O)NO)S(C)(=O)=O)C3=O)cc1]

Part A

A mixture of 2-(4-(4,4,5,5-tetramethyl-1,3,2-dioxaborolan-2-yl)phenyl)ethanol (0.734 g, 2.96 mmol), (2R)-4-(5-bromo-4-fluoro-1-oxoisoindolin-2-yl)-2-methyl-2-(methylsulfonyl)-N-(tetrahydro-2H-pyran-2-yl)oxy)butanamide (Intermediate 16) (1 g, 1.971 mmol), PdCl$_2$(dppf)-CH$_2$Cl$_2$ adduct (0.161 g, 0.197 mmol) and K$_2$CO$_3$ (0.545 g, 3.94 mmol) in acetonitrile (12 mL) and water (2 mL) under nitrogen atmosphere was stirred at 80° C. The reaction was concentrated and the aqueous layer was extracted with DCM (50 mL×2). The combined organic layers were dried over Na$_2$SO$_4$, filtered and concentrated. The crude product was purified by silica gel chromatography (MeOH/DCM: 0-2.5%) to (2R)-4-(4-fluoro-5-(4-(2-hydroxyethyl)phenyl)-1-oxoisoindolin-2-yl)-2-methyl-2-(methylsulfonyl)-N-((tetrahydro-2H-pyran-2-yl)oxy)butanamide (800 mg, 1.312 mmol, 67% yield) as a yellow solid.

LCM: [M-THP] 465.1.

Part B

To a mixture of (2R)-4-(4-fluoro-5-(4-(2-hydroxyethyl)phenyl)-1-oxoisoindolin-2-yl)-2-methyl-2-(methylsulfonyl)-N-(tetrahydro-2H-pyran-2-yl)oxy)butanamide (500 mg, 0.911 mmol) in dichloromethane (10 mL) was added triphenylphosphine (956 mg, 3.65 mmol) and 1-bromopyrrolidine-2,5-dione (487 mg, 2.73 mmol) at 0° C. and the resulting mixture was stirred for 45 min. Methanol (10 mL) was added at 0° C. and the reaction mixture was evaporated to dryness to yield (R)-4-(5-(4-(2-bromoethyl)phenyl)-4-fluoro-1-oxoisoindolin-2-yl)-N-hydroxy-2-methyl-2-(methylsulfonyl)butanamide (1.7 g, 0.806 mmol, 88% yield) as a yellow oil.

LCMS: [M+H] 527.7.

Part C

A mixture of (R)-4-(5-(4-(2-bromoethyl)phenyl)-4-fluoro-1-oxoisoindolin-2-yl)-N-hydroxy-2-methyl-2-(methylsulfonyl)butanamide (1.7 g, 0.806 mmol), N,O-dimethylhydroxylamine hydrochloride (1.179 g, 12.09 mmol), KI (0.134 g, 0.806 mmol), $K_2CO_3$ (2.227 g, 16.12 mmol) and N,N-dimethylformamide (5.5 mL) was heated in a microwave to 70° C. for 20 min. DCM (20 mL) was added and the mixture was filtered and the filtrate was acidified to pH=4 with HCl (2.5M in 1,4-dioxane). Water (20 mL) was added and the organic layers were extracted with water (20 mL×2). The aqueous layer was concentrated and purified by preparative HPLC to yield (R)-4-(4-fluoro-5-(4-(2-(methoxy(methyl)amino)ethyl)phenyl)-1-oxoisoindolin-2-yl)-N-hydroxy-2-methyl-2-(methylsulfonyl)butanamide trifluoroacetic acid (27 mg, 0.039 mmol, 5% yield) as yellow solid.

LCMS: [M+H] 508.2.

$^1$H NMR (500 MHz, METHANOL-d4) δ: ppm 7.64-7.67 (m, 2H), 7.57-7.58 (m, 2H), 7.41-7.42 (m, 2H), 4.67 (dd, J=43.5, 17.5 Hz, 2H), 3.76-3.86 (m, 2H), 3.69 (s, 3H), 3.17 (m, 2H), 3.11 (s, 3H), 3.03 (m, 2H), 2.82-2.85 (m, 4H), 2.20 (m, 1H), 1.74 (s, 3H).

It is to be understood that the invention is not limited to the embodiments illustrated hereinabove and the right is reserved to the illustrated embodiments and all modifications coming within the scope of the following claims.

The various references to journals, patents, and other publications which are cited herein comprise the state of the art and are incorporated herein by reference as though fully set forth.

What is claimed is:

1. A compound which is:

| EX. | Chemical Name | Chemical Structures |
|---|---|---|
| 2 | (2R)-N-hydroxy-2-methanesulfonyl-2-methyl-4-[7-(4-methylphenyl)-4-oxo-3,4-dihydroquinazolin-3-yl]butanamide | 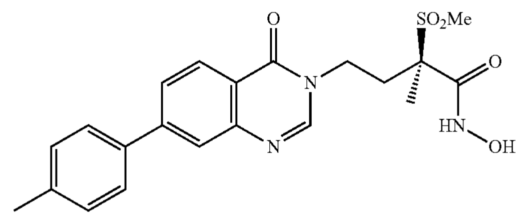 [SMILES: Cc1ccc(-c2ccc3c(=O)n(CC[C@](C)(C(=O)NO)S(C)(=O)=O)cnc3c2)cc1] |
| 3 | (2R)-N-hydroxy-2-methanesulfonyl-4-[7-(4-methoxyphenyl)-4-oxo-3,4-dihydroquinazolin-3-yl]-2-methylbutanamide | 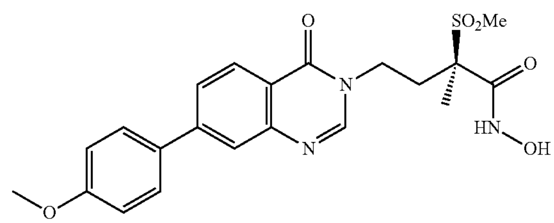 [SMILES: COc1ccc(-c2ccc3c(=O)n(CC[C@](C)(C(=O)NO)S(C)(=O)=O)cnc3c2)cc1] |
| 5 | (2R)-4-{7-[4-(difluoromethoxy)phenyl]-4-oxo-3,4-dihydroquinazolin-3-yl}-N-hydroxy-2-methanesulfonyl-2-methylbutanamide | 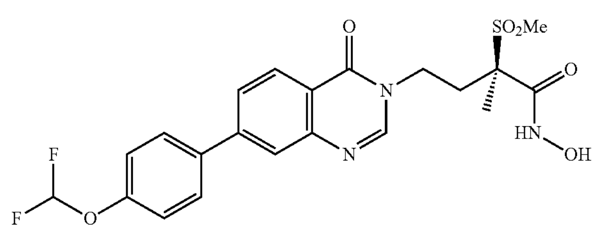 [SMILES: C[C@@](CCn1cnc2cc(-c3ccc(OC(F)F)cc3)ccc2c1=O)(C(=O)NO)S(C)(=O)=O] |
| 6 | (2R)-4-[7-(2,3-difluorophenyl)-4-oxo-3,4-dihydroquinazolin-3-yl]-N-hydroxy-2-methanesulfonyl-2-methylbutanamide | 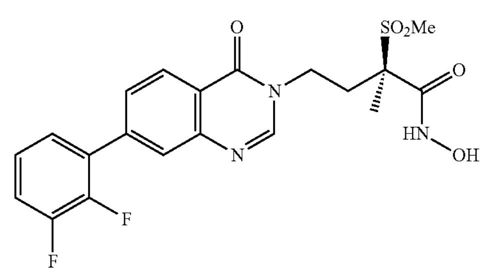 [SMILES: C[C@@](CCn1cnc2cc(-c3cccc(F)c3F)ccc2c1=O)(C(=O)NO)S(C)(=O)=O] |

| EX. | Chemical Name | Chemical Structures |
|---|---|---|
| 7 | (2R)-4-[7-(2,5-difluorophenyl)-4-oxo-3,4-dihydroquinazolin-3-yl]-N-hydroxy-2-methanesulfonyl-2-methylbutanamide | 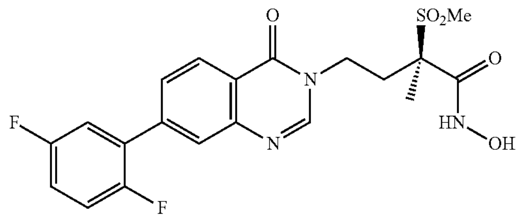 [SMILES: C[C@@](CCn1cnc2cc(-c3cc(F)ccc3F)ccc2c1=O)(C(=O)NO)S(C)(=O)=O] |
| 8 | (2R)-4-[7-(2-fluorophenyl)-4-oxo-3,4-dihydroquinazolin-3-yl]-N-hydroxy-2-methanesulfonyl-2-methylbutanamide | 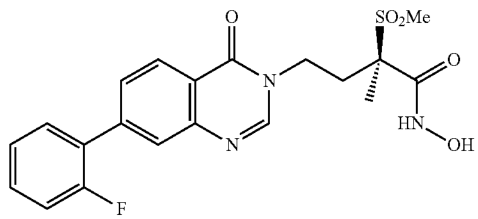 [SMILES: C[C@@](CCn1cnc2cc(-c3ccccc3F)ccc2c1=O)(C(=O)NO)S(C)(=O)=O] |
| 9 | (2R)-4-[7-(3-fluoro-4-methylphenyl)-4-oxo-3,4-dihydroquinazolin-3-yl]-N-hydroxy-2-methanesulfonyl-2-methylbutanamide | 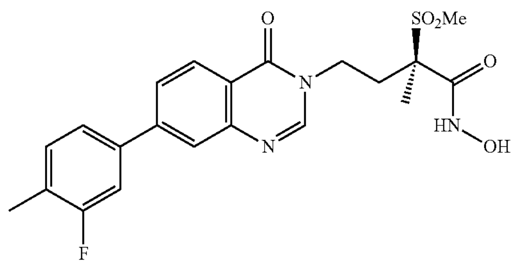 [SMILES: Cc1ccc(-c2ccc3c(=O)n(CC[C@](C)(C(=O)NO)S(C)(=O)=O)cnc3c2)cc1F] |
| 10 | (2R)-4-{7-[4-(difluoromethyl)phenyl]-4-oxo-3,4-dihydroquinazolin-3-yl}-N-hydroxy-2-methanesulfonyl-2-methylbutanamide | | or
a pharmaceutically acceptable salt thereof.

2. A compound which is:

| Ex. | Compound Name | Chemical Structure |
|---|---|---|
| 11 | (2R)-4-[7-(2,6-difluorophenyl)-4-oxo-3,4-dihydroquinazolin-3-yl]-N-hydroxy-2-methanesulfonyl-2-methylbutanamide | 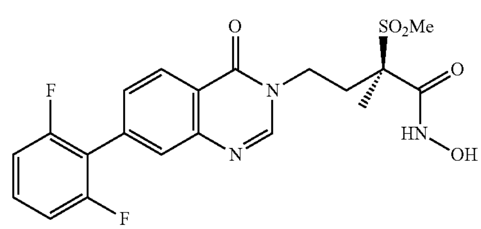 [SMILES: C[C@@](CCn1cnc2cc(-c3c(F)cccc3F)ccc2c1=O)(C(=O)NO)S(C)(=O)=O] |

-continued

| Ex. | Compound Name | Chemical Structure |
|---|---|---|
| 12 | (2R)-4-[7-(1,3-dihydro-2-benzofuran-5-yl)-4-oxo-3,4-dihydroquinazolin-3-yl]-N-hydroxy-2-methanesulfonyl-2-methylbutanamide | 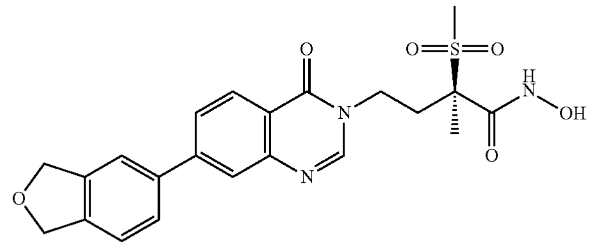 |
| 13 | (2R)-4-[6-fluoro-7-(4-methoxyphenyl)-4-oxo-3,4-dihydroquinazolin-3-yl]-N-hydroxy-2-methanesulfonyl-2-methylbutanamide | 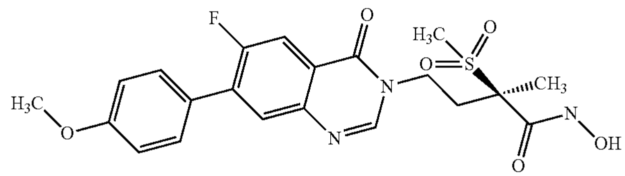 [SMILES: COc1ccc(-c2cc3ncn(CC[C@](C)(C(=O)NO)S(C)(=O)=O)c(=O)c3cc2F)cc1] |
| 14 | (2R)-4-[8-fluoro-7-(4-methoxyphenyl)-4-oxo-3,4-dihydroquinazolin-3-yl]-N-hydroxy-2-methanesulfonyl-2-methylbutanamide | 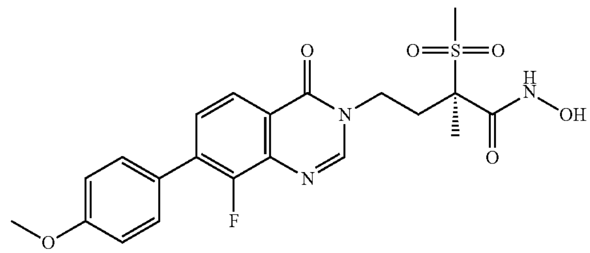 [SMILES: COc1ccc(-c2ccc3c(=O)n(CC[C@](C)(C(=O)NO)S(C)(=O)=O)cnc3c2F)cc1] |
| 15 | (2R)-4-[6-fluoro-7-(4-methylphenyl)-4-oxo-3,4-dihydroquinazolin-3-yl]-N-hydroxy-2-methanesulfonyl-2-methylbutanamide | 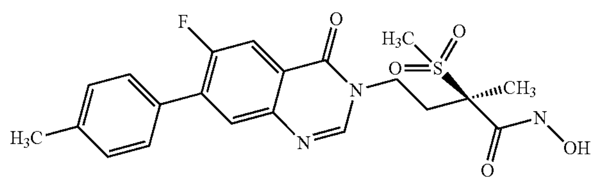 [SMILES: Cc1ccc(-c2cc3ncn(CC[C@](C)(C(=O)NO)S(C)(=O)=O)c(=O)c3cc2F)cc1] |
| 16 | (2R)-4-[5-fluoro-7-(4-methoxyphenyl)-4-oxo-3,4-dihydroquinazolin-3-yl]-N-hydroxy-2-methanesulfonyl-2-methylbutanamide | 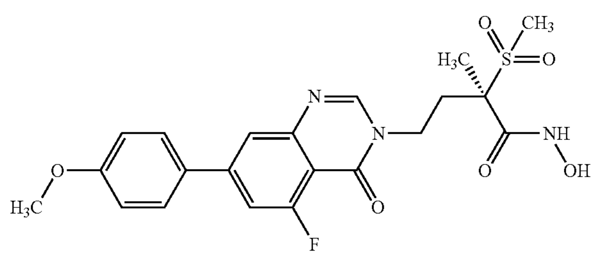 [SMILES: COc1ccc(-c2cc(F)c3c(=O)n(CC[C@](C)(C(=O)NO)S(C)(=O)=O)cnc3c2)cc1] |
| 17 | (2R)-4-[5-fluoro-7-(4-methylphenyl)-4-oxo-3,4-dihydroquinazolin-3-yl]-N-hydroxy-2-methanesulfonyl-2-methylbutanamide | 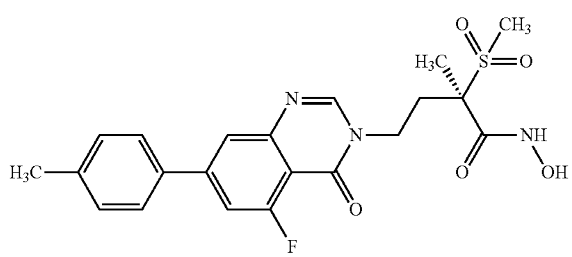 [SMILES: Cc1ccc(-c2cc(F)c3c(=O)n(CC[C@](C)(C(=O)NO)S(C)(=O)=O)cnc3c2)cc1] |
| 20 | (2R)-4-(6-fluoro-7-{4-[(morpholin-4-yl)methyl]phenyl}-4-oxo-3,4-dihydroquinazolin-3-yl)-N-hydroxy-2-methanesulfonyl-2-methylbutanamide | 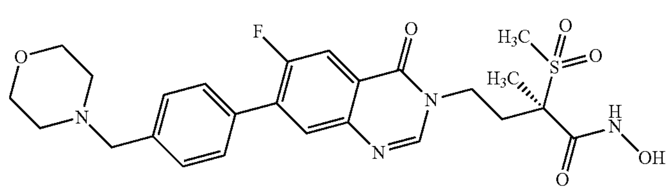 [SMILES: C[C@@](CCn1cnc2cc(-c3ccc(CN4CCOCC4)cc3)c(F)cc2c1=O)(C(=O)NO)S(C)(=O)=O] |

-continued

| Ex. | Compound Name | Chemical Structure |
|---|---|---|
| 21 | (2R)-4-(6-fluoro-7-{4-[2-(morpholin-4-yl)ethyl]phenyl}-4-oxo-3,4-dihydroquinazolin-3-yl)-N-hydroxy-2-methanesulfonyl-2-methylbutanamide | 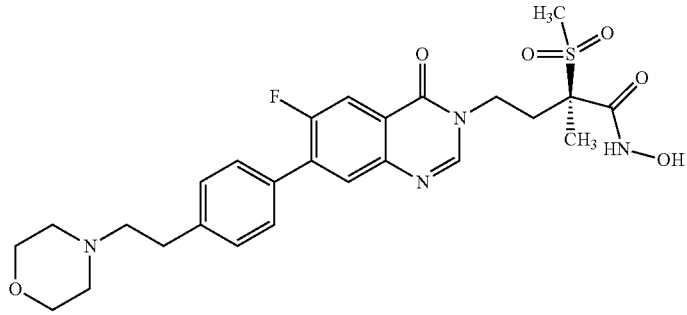 |
| 22 | (2R)-4-[7-(4-{[cyclopropyl(methyl)amino]methyl}phenyl)-6-fluoro-4-oxo-3,4-dihydroquinazolin-3-yl]-N-hydroxy-2-methanesulfonyl-2-methylbutanamide | 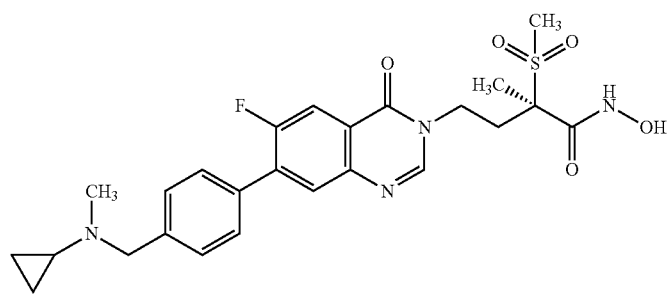 [SMILES: CN(Cc1ccc(-c2cc3ncn(CC[C@](C)(C(=O)NO)S(C)(=O)=O)c(=O)c3cc2F)cc1)C1CC1] |
| 23 | (2R)-4-[6-fluoro-7-(2-fluoro-4-{[(2-methoxethyl)(methyl)amino]methyl}phenyl)-4-oxo-3,4-dihydroquinazolin-3-yl]-N-hydroxy-2-methanesulfonyl-2-methylbutanamide | 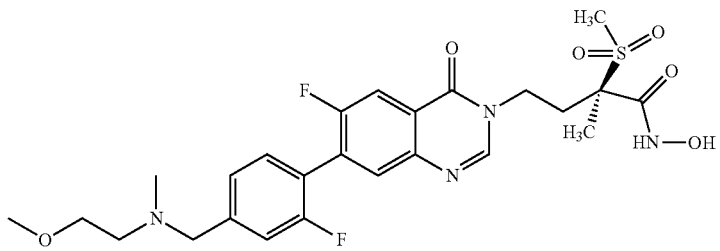 [SMILES: COCCN(C)Cc1ccc(-c2cc3ncn(CC[C@](C)(C(=O)NO)S(C)(=O)=O)c(=O)c3cc2F)c(F)c1] |
| 24 | (2R)-4-(7-{2,3-difluoro-4-[2-(3-methoxyazetidin-1-yl)ethyl]phenyl}-6-fluoro-4-oxo-3,4-dihydroquinazolin-3-yl)-N-hydroxy-2-methanesulfonyl-2-methylbutanamide | 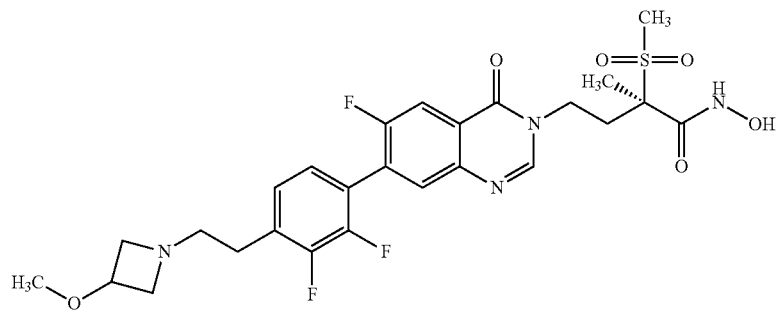 [SMILES: COC1CN(CCc2ccc(-c3cc4ncn(CC[C@](C)(C(=O)NO)S(C)(=O)=O)c(=O)c4cc3F)c(F)c2F)C1] |
| 25 | (2R)-4-(7-{4-[(cyclopropylamino)methyl]-2-fluorophenyl}-6-fluoro-4-oxo-3,4-dihydroquinazolin-3-yl)-N-hydroxy-2-methanesulfonyl-2-methylbutanamide | 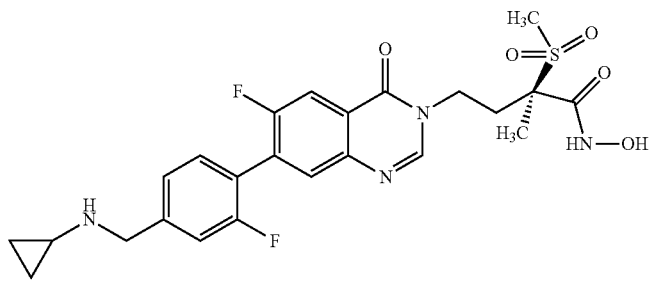 [SMILES: C[C@@](CCn1cnc2cc(-c3ccc(CNC4CC4)cc3F)c(F)cc2c1=O)(C(=O)NO)S(C)(=O)=O] |

| Ex. | Compound Name | Chemical Structure |
|---|---|---|
| 26 | (2R)-4-(6-fluoro-7-{2-fluoro-4-[(morpholin-4-yl)methyl]phenyl}-4-oxo-3,4-dihydroquinazolin-3-yl)-N-hydroxy-2-methanesulfonyl-2-methylbutanamide | 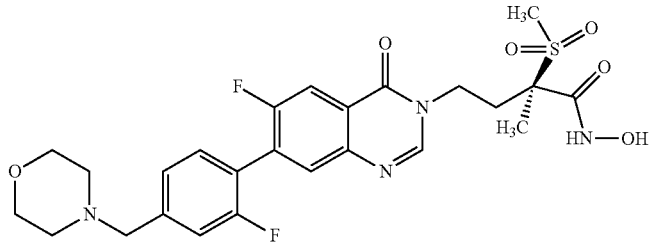 [SMILES: C[C@@](CCn1cnc2cc(-c3ccc(CN4CCOCC4)cc3F)c(F)cc2c1=O)(C(=O)NO)S(C)(=O)=O] |
| 27 | (2R)-4-{6-fluoro-7-[2-fluoro-4-(2-hydroxyethyl)phenyl]-4-oxo-3,4-dihydroquinazolin-3-yl}-N-hydroxy-2-methanesulfonyl-2-methylbutanamide | 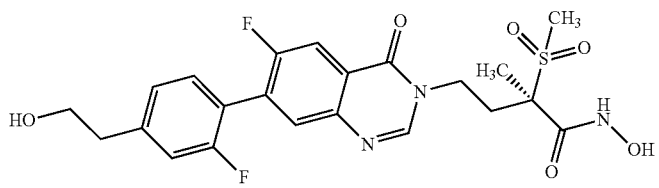 [SMILES: C[C@@](CCn1cnc2cc(-c3ccc(CCO)cc3F)c(F)cc2c1=O)(C(=O)NO)S(C)(=O)=O] |
| 28 | (2R)-4-{6-fluoro-7-[4-(2-hydroxyethyl)phenyl]-4-oxo-3,4-dihydroquinazolin-3-yl}-N-hydroxy-2-methanesulfonyl-2-methylbutanamide | 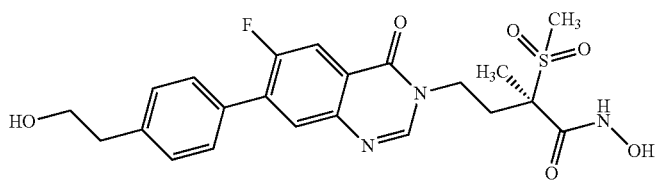 [SMILES: C[C@@](CCn1cnc2cc(-c3ccc(CCO)cc3)c(F)cc2c1=O)(C(=O)NO)S(C)(=O)=O] |
| 29 | (2R)-N-hydroxy-2-methanesulfonyl-2-methyl-4-(8-methyl-7-{4-[(morpholin-4-yl)methyl]phenyl}-4-oxo-3,4-dihydroquinazolin-3-yl)butanamide | 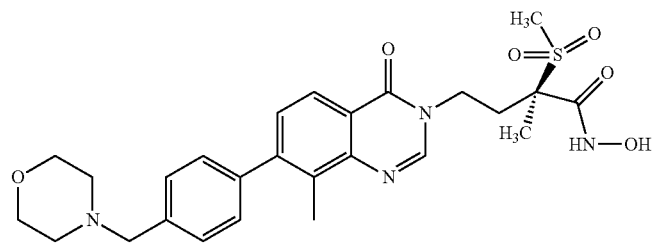 [SMILES: Cc1c(-c2ccc(CN3CCOCC3)cc2)ccc2c(=O)n(CC[C@](C)(C(=O)NO)S(C)(=O)=O)cnc12] |
| 30 | (2R)-4-[6-fluoro-7-(6-methoxypyridin-3-yl)-4-oxo-3,4-dihydroquinazolin-3-yl]-N-hydroxy-2-methanesulfonyl-2-methylbutanamide | 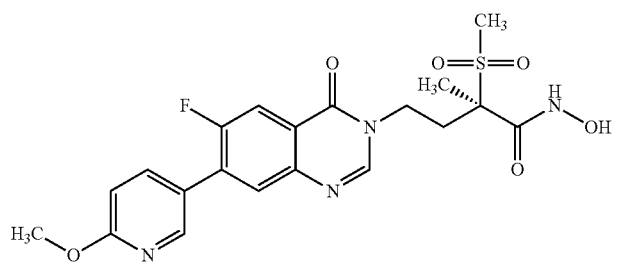 [SMILES: COc1ccc(-c2cc3ncn(CC[C@](C)(C(=O)NO)S(C)(=O)=O)c(=O)c3cc2F)cn1] |
| 32 | (2R)-4-[7-(1,3-dihydro-2-benzofuran-5-yl)-6-fluoro-4-oxo-3,4-dihydroquinazolin-3-yl]-N-hydroxy-2-methanesulfonyl-2-methylbutanamide | 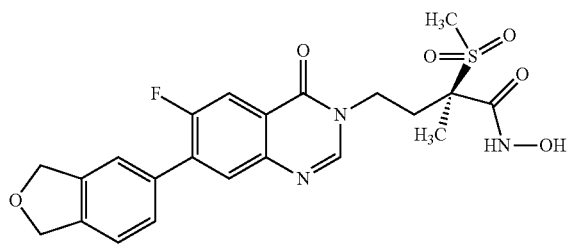 [SMILES: C[C@@](CCn1cnc2cc(-c3ccc4c(c3)COC4)c(F)cc2c1=O)(C(=O)NO)S(C)(=O)=O] |

-continued

| Ex. | Compound Name | Chemical Structure |
|---|---|---|
| 33 | (2R)-4-{7-[6-(dimethylamino)pyridin-3-yl]-6-fluoro-4-oxo-3,4-dihydroquinazolin-3-yl}-N-hydroxy-2-methanesulfonyl-2-methylbutanamide | 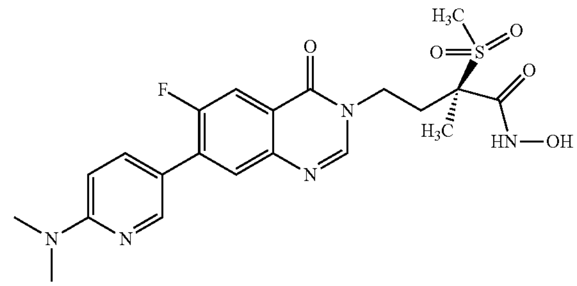 [SMILES: CN(C)c1ccc(-c2cc3ncn(CC[C@](C)(C(=O)NO)S(C)(=O)=O)c(=O)c3cc2F)cn1] |
| 34 | 2-(4-{6-fluoro-3-[(3R)-3-(hydroxycarbamoyl)-3-methanesulfonyl-3-methylpropyl]-4-oxo-3,4-dihydroquinazolin-7-yl}phenyl)ethyl acetate | 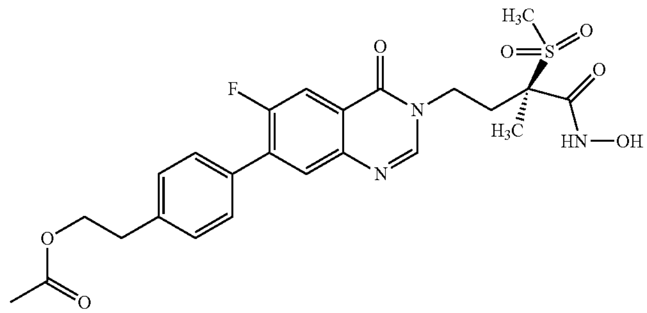 [SMILES: CC(=O)OCCc1ccc(-c2cc3ncn(CC[C@](C)(C(=O)NO)S(C)(=O)=O)c(=O)c3cc2F)cc1] |
| 35 | (2R)-N-hydroxy-2-methanesulfonyl-2-methyl-4-(7-{4-[(morpholin-4-yl)methyl]phenyl}-4-oxo-3,4-dihydroquinazolin-3-yl)butanamide | 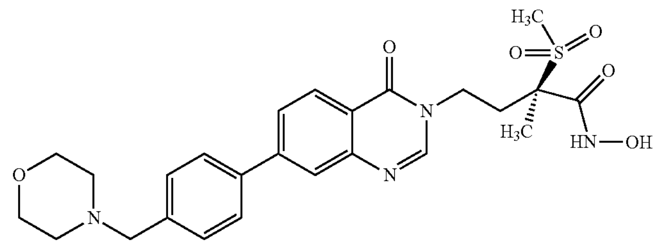 [SMILES: C[C@@](CCn1cnc2cc(-c3ccc(CN4CCOCC4)cc3)ccc2c1=O)(C(=O)NO)S(C)(=O)=O] |
| 36 | (2R)-4-[7-(2-fluoro-4-{[(2-methoxyethyl)(methyl)amino]methyl}phenyl)-4-oxo-3,4-dihydroquinazolin-3-yl]-N-hydroxy-2-methanesulfonyl-2-methylbutanamide | 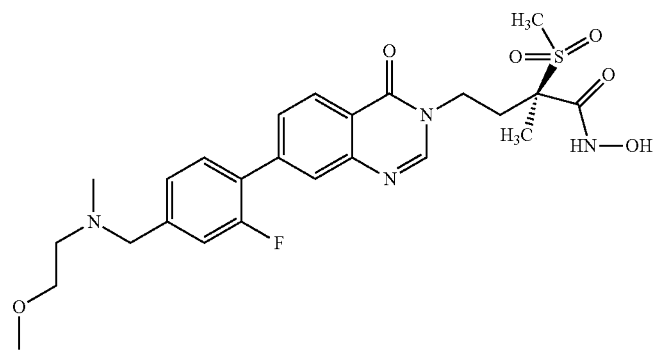 [SMILES: COCCN(C)Cc1ccc(-c2ccc3c(=O)n(CC[C@](C)(C(=O)NO)S(C)(=O)=O)cnc3c2)c(F)c1] |
| 37 | (2R)-4-(7-{2-fluoro-4-[(morpholin-4-yl)methyl]phenyl}-4-oxo-3,4-dihydroquinazolin-3-yl)-N-hydroxy-2-methanesulfonyl-2-methylbutanamide | 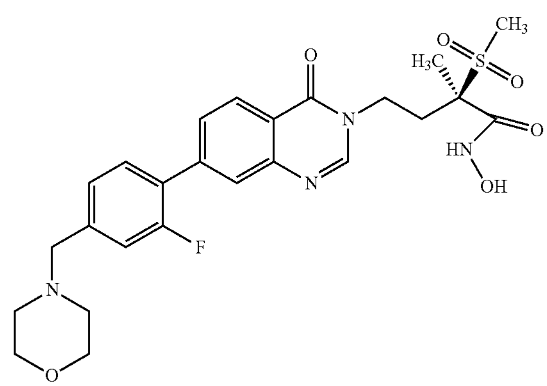 [SMILES: C[C@@](CCn1cnc2cc(-c3ccc(CN4CCOCC4)cc3F)ccc2c1=O)(C(=O)NO)S(C)(=O)=O] |

-continued

| Ex. | Compound Name | Chemical Structure |
|---|---|---|
| 38 | (2R)-4-[7-(2,3-difluoro-4-{[(2-methoxyethyl)(methyl)amino]methyl}phenyl)-4-oxo-3,4-dihydroquinazolin-3-yl]-N-hydroxy-2-methanesulfonyl-2-methylbutanamide | 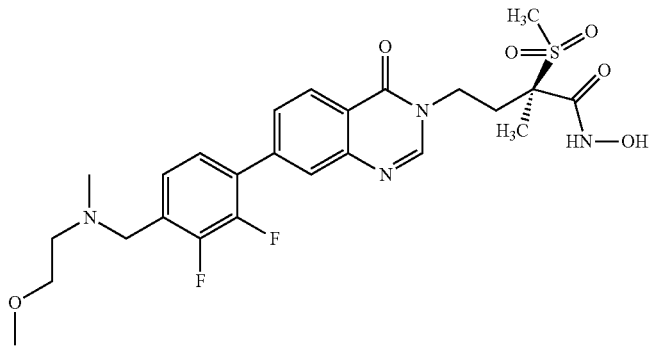 [SMILES: COCCN(C)Cc1ccc(-c2ccc3c(=O)n(CC[C@](C)(C(=O)NO)S(C)(=O)=O)cnc3c2)c(F)c1F] |
| 39 | (2R)-4-[7-(4-{[cyclopropyl(methyl)amino]methyl}-3-fluorophenyl)-4-oxo-3,4-dihydroquinazolin-3-yl]-N-hydroxy-2-methanesulfonyl-2-methylbutanamide | 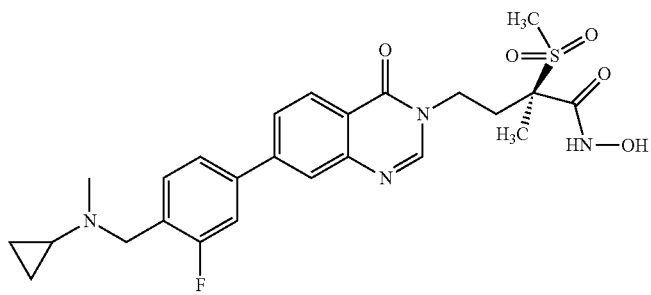 [SMILES: CN(Cc1ccc(-c2ccc3c(=O)n(CC[C@](C)(C(=O)NO)S(C)(=O)=O)cnc3c2)cc1F)C1CC1] |
| 40 | (2R)-4-(7-{4-[(3,3-difluoroazetidin-1-yl)methyl]-2-fluorophenyl}-4-oxo-3,4-dihydroquinazolin-3-yl)-N-hydroxy-2-methanesulfonyl-2-methylbutanamide | 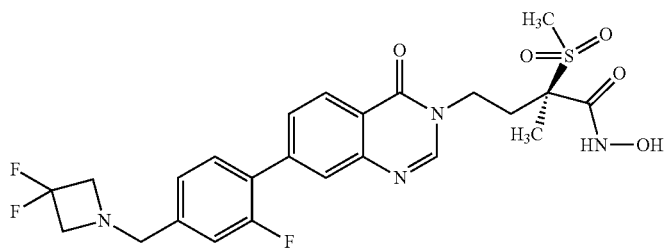 [SMILES: C[C@@](CCn1cnc2cc(-c3ccc(CN4CC(F)(F)C4)cc3F)ccc2c1=O)(C(=O)NO)S(C)(=O)=O] |
| 41 | (2R)-4-(7-{4-[(cyclopropylamino)methyl]-2-fluorophenyl}-4-oxo-3,4-dihydroquinazolin-3-yl)-N-hydroxy-2-methanesulfonyl-2-methylbutanamide | 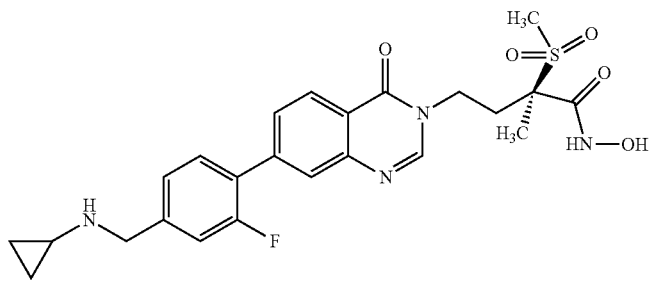 [SMILES: C[C@@](CCn1cnc2cc(-c3ccc(CNC4CC4)cc3F)ccc2c1=O)(C(=O)NO)S(C)(=O)=O] |
| 42 | (2R)-N-hydroxy-2-methanesulfonyl-2-methyl-4-(7-{4-[2-(morpholin-4-yl)ethyl]phenyl}-4-oxo-3,4-dihydroquinazolin-3-yl)butanamide | 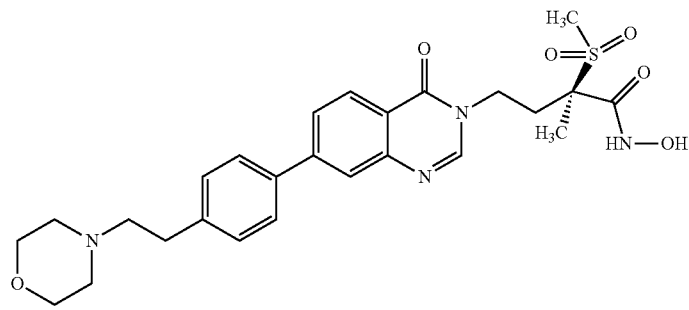 [SMILES: C[C@@](CCn1cnc2cc(-c3ccc(CCN4CCOCC4)cc3)ccc2c1=O)(C(=O)NO)S(C)(=O)=O] |

-continued

| Ex. | Compound Name | Chemical Structure |
|---|---|---|
| 43 | (2R)-4-(7-{2-fluoro-4-[2-(morpholin-4-yl)ethyl]phenyl}-4-oxo-3,4-dihydroquinazolin-3-yl)-N-hydroxy-2-ethanesulfonyl-2-methylbutanamide | 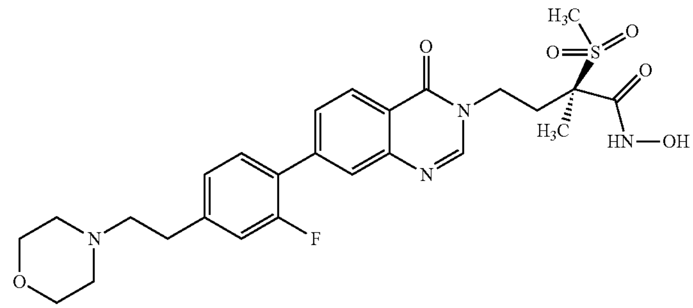 [SMILES: C[C@@](CCn1cnc2cc(-c3ccc(CCN4CCOCC4)cc3F)ccc2c1=O)(C(=O)NO)S(C)(=O)=O] |
| 44 | (2R)-N-hydroxy-4-{7-[4-(2-hydroxyethyl)phenyl]-4-oxo-3,4-dihydroquinazolin-3-yl}-2-methanesulfonyl-2-methylbutanamide | 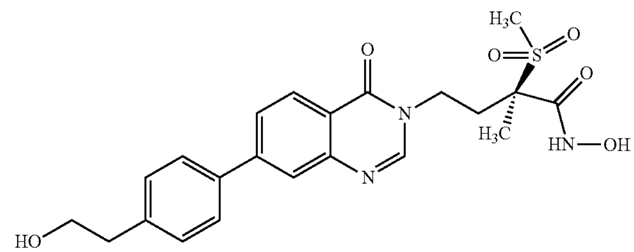 [SMILES: C[C@@](CCn1cnc2cc(-c3ccc(CCO)cc3)ccc2c1=O)(C(=O)NO)S(C)(=O)=O] |
| 45 | (2R)-4-{7-[2-fluoro-4-(2-hydroxyethyl)phenyl]-4-oxo-3,4-dihydroquinazolin-3-yl}-N-hydroxy-2-methanesulfonyl-2-methylbutanamide | 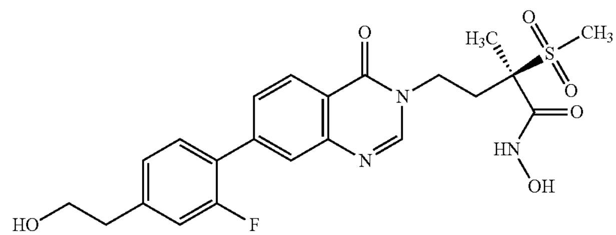 [SMILES: C[C@@](CCn1cnc2cc(-c3ccc(CCO)cc3F)ccc2c1=O)(C(=O)NO)S(C)(=O)=O] |
| 46 | (2R)-4-[7-(4-ethoxyphenyl)-4-oxo-3,4-dihydroquinazolin-3-yl]-N-hydroxy-2-methanesulfonyl-2-methylbutanamide | 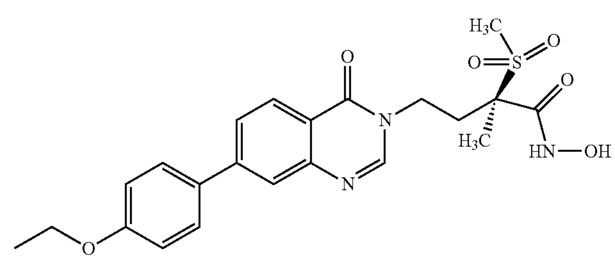 [SMILES: CCOc1ccc(-c2ccc3c(=O)n(CC[C@](C)(C(=O)NO)S(C)(=O)=O)cnc3c2)cc1] |
| 47 | (2R)-N-hydroxy-2-methanesulfonyl-4-{7-[4-(methoxymethyl)phenyl]-4-oxo-3,4-dihydroquinazolin-3-yl}-2-methylbutanamide | 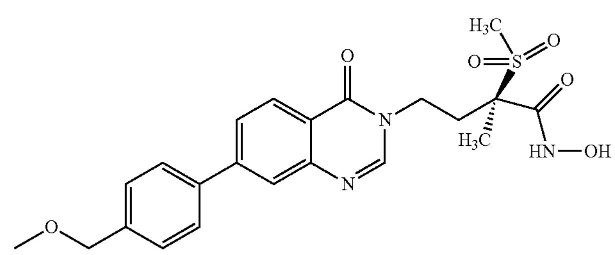 [SMILES: COCc1ccc(-c2ccc3c(=O)n(CC[C@](C)(C(=O)NO)S(C)(=O)=O)cnc3c2)cc1] |
| 48 | (2R)-4-{7-[2-fluoro-4-(2-methoxyethyl)phenyl]-4-oxo-3,4-dihydroquinazolin-3-yl}-N-hydroxy-2-methanesulfonyl-2-methylbutanamide | 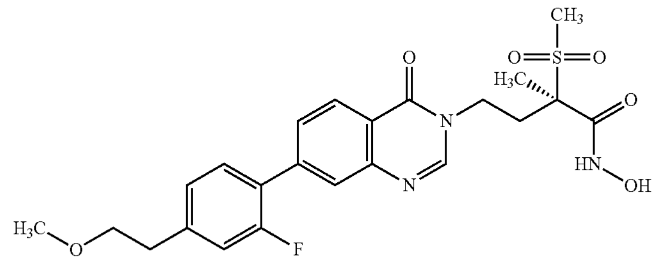 [SMILES: COCCc1ccc(-c2ccc3c(=O)n(CC[C@](C)(C(=O)NO)S(C)(=O)=O)cnc3c2)c(F)c1] |

| Ex. | Compound Name | Chemical Structure |
|---|---|---|
| 49 | (2R)-4-[7-(3-fluoro-4-{[methoxy(methyl)amino]methyl}phenyl)-4-oxo-3,4-dihydroquinazolin-3-yl]-N-hydroxy-2-methanesulfonyl-2-methylbutanamide | 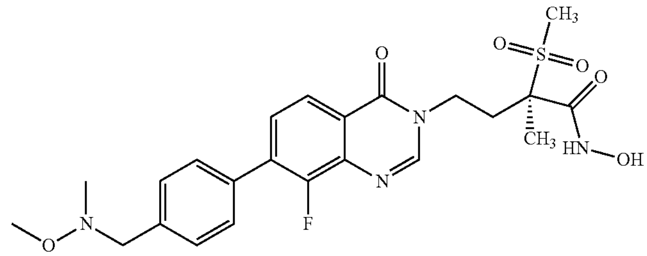 [SMILES: CON(C)Cc1ccc(-c2ccc3c(=O)n(CC[C@](C)(C(=O)NO)S(C)(=O)=O)cnc3c2F)cc1] |
| 50 | (2R)-4-(7-{2-fluoro-4-[(methoxyamino)methyl]phenyl}-4-oxo-3,4-dihydroquinazolin-3-yl)-N-hydroxy-2-methanesulfonyl-2-methylbutanamide | 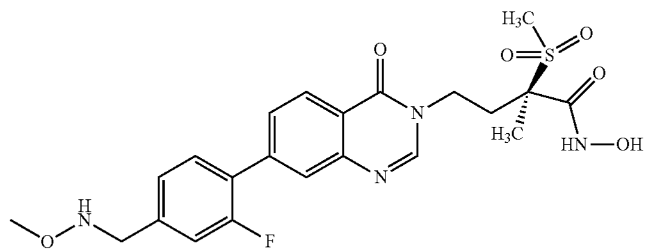 [SMILES: CONCc1ccc(-c2ccc3c(=O)n(CC[C@](C)(C(=O)NO)S(C)(=O)=O)cnc3c2)c(F)c1] |
| 51 | (2R)-4-(7-{4-[(ethoxyamino)methyl]-2-fluorophenyl}-4-oxo-3,4-dihydroquinazolin-3-yl)-N-hydroxy-2-methanesulfonyl-2-methylbutanamide | 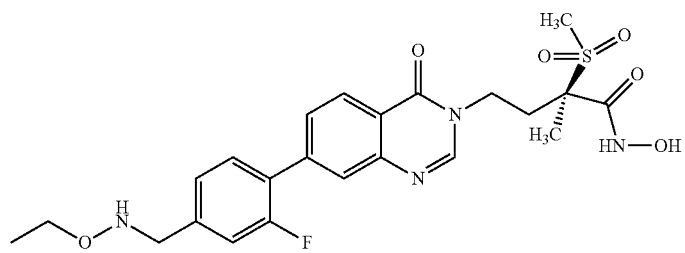 [SMILES: CCONCc1ccc(-c2ccc3c(=O)n(CC[C@](C)(C(=O)NO)S(C)(=O)=O)cnc3c2)c(F)c1] |
| 52 | (2R)-N-hydroxy-2-methanesulfonyl-4-[7-(4-{[methoxy(methyl)amino]methyl}phenyl)-4-oxo-3,4-dihydroquinazolin-3-yl]-2-methylbutanamide | | or a pharmaceutically acceptable salt thereof.

3. A compound which is (2R)-4-[7-(2-fluorophenyl)-4-oxo-3,4-dihydroquinazolin-3-yl]-N-hydroxy-2-methanesulfonyl-2-methylbutanamide:

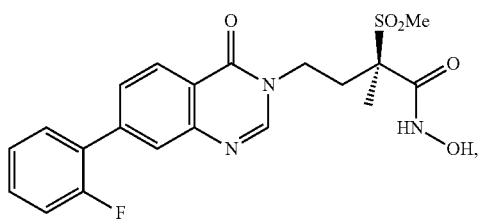 [SMILES: C[C@@](CCn1cnc2cc(-c3ccccc3F)ccc2c1=O)(C(=O)NO)S(C)(=O)=O]

or a pharmaceutically acceptable salt thereof.

4. The compound of claim 3 having the structure:

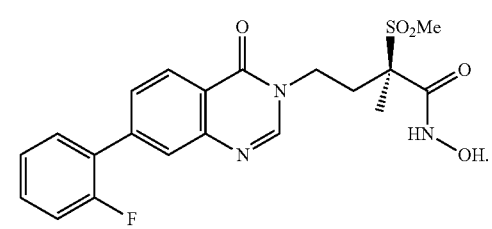 [SMILES: C[C@@](CCn1cnc2cc(-c3ccccc3F)ccc2c1=O)(C(=O)NO)S(C)(=O)=O]

* * * * *